US012404515B2

(12) United States Patent
Kelliher et al.

(10) Patent No.: US 12,404,515 B2
(45) Date of Patent: Sep. 2, 2025

(54) SIMULTANEOUS GENE EDITING AND HAPLOID INDUCTION

(71) Applicants: SYNGENTA PARTICIPATIONS AG, Basel (CH); SYNGENTA CROP PROTECTION, LLC, Greensboro, NC (US)

(72) Inventors: Timothy Kelliher, Durham, NC (US); Qiudeng Que, Durham, NC (US)

(73) Assignee: Syngenta Crop Protection AG, Basel (CH)

( * ) Notice: Subject to any disclaimer, the term of this patent is extended or adjusted under 35 U.S.C. 154(b) by 333 days.

(21) Appl. No.: 17/327,016

(22) PCT Filed: Dec. 17, 2019

(86) PCT No.: PCT/US2019/066719
§ 371 (c)(1),
(2) Date: May 21, 2021

(87) PCT Pub. No.: WO2020/131788
PCT Pub. Date: Jun. 25, 2020

(65) Prior Publication Data
US 2023/0060937 A1 Mar. 2, 2023

Related U.S. Application Data

(60) Provisional application No. 62/783,446, filed on Dec. 21, 2018.

(51) Int. Cl.
*C12N 15/82* (2006.01)
*A01H 1/02* (2006.01)
(Continued)

(52) U.S. Cl.
CPC ......... *C12N 15/8213* (2013.01); *A01H 1/021* (2021.01); *A01H 1/045* (2021.01);
(Continued)

(58) Field of Classification Search
None
See application file for complete search history.

(56) References Cited

U.S. PATENT DOCUMENTS 10,214,784 B2 * 2/2019 Ritchie et al. ....... C12Q 1/6895
2009/0070898 A1 3/2009 Allen et al.
(Continued)

FOREIGN PATENT DOCUMENTS

| WO | WO-2017004375 A1 * | 1/2017 | ............... A01H 1/06 |
| WO | WO-2017087682 A1 * | 5/2017 | ............... A01H 1/08 |
| WO | 2018/102816 A1 | 6/2018 | |

OTHER PUBLICATIONS

Gilles et al. "Quick Guide: Haploid Induction in Plants" 2017 Current Biology 27:R1089-R1107 Oct. 23, 2017; 3 total pages. (Year: 2017).*

(Continued)

*Primary Examiner* — Amjad Abraham
*Assistant Examiner* — Rebecca Stephens
(74) *Attorney, Agent, or Firm* — Amanda Bublitz

(57) ABSTRACT

The presently disclosed subject matter relates to using a haploid inducing line (whether existing or created) and transforming the haploid line so that it encodes cellular machinery capable of editing genes. The transformed haploid inducing line is used as a parent in a cross between two plants. During pollination, the parental gametes fuse to form an embryo; and the gene editing machinery is also delivered to the embryo at this time. During embryonic development, one set of parental chromosomes are lost, and the gene editing machinery operates on the remaining set of chromosomes. Thus, at least one haploid progeny with edited genes is produced from the cross. The disclosure is also directed to (Continued)

methods of testing an edited haploid plant progeny for the presence of a first plant's genomic material.

9 Claims, 24 Drawing Sheets

Specification includes a Sequence Listing.

(51) Int. Cl.
    *A01H 1/04*         (2006.01)
    *C12Q 1/6895*     (2018.01)

(52) U.S. Cl.
    CPC ....... *C12Q 1/6895* (2013.01); *C12Q 2600/13* (2013.01); *C12Q 2600/158* (2013.01); *C12Q 2600/172* (2013.01)

(56) References Cited

U.S. PATENT DOCUMENTS

| | | |
|---|---|---|
| 2009/0089901 A1 | 4/2009 | Miller et al. |
| 2010/0071097 A1 | 3/2010 | Bledig et al. |
| 2011/0191892 A1 | 8/2011 | Kishore et al. |

OTHER PUBLICATIONS

Nicolas et al., "Genetic Regulation of Meiotic Cross-Overs between Related Genomes in *Brassica napus* Haploids and Hybrids," The Plant Cell, vol. 21: pp. 373-385 (Feb. 2009).

International Search Report for International Application PCT/US2019/066719 mailed May 6, 2020.

Non-Final Rejection mailed Feb. 25, 2019, cited in U.S. Appl. No. 16/245,923, filed Jan. 11, 2019.

Amendment—Request for Reconsideration—Afer Non-Final Rejection filed on May 23, 2019, In U.S. Appl. No. 16/245,923, filed Jan. 11, 2019.

Examiner-Initiated Interview Summary dated Aug. 8, 2019, cited in U.S. Appl. No. 16/245,923, filed Jan. 11, 2019.

Notice of Allowance and Fees Due dated Aug. 9, 2019, cited in U.S. Appl. No. 16/245,923, filed Jan. 11, 2019.

Declaration of Timothy Kelliher pursuant to 37 C.F.R. 1.132 dated May 22, 2019, cited in U.S. Appl. No. 16/245,923, filed Jan. 11, 2019.

Alexandra A.M., et al., "Discovery and Development of Exome-Based, Co-dominant Single Nucleotide Polymorphism Markers in Hexaploid Wheat (*Triticum Aestivum* L.)," Plant Biotechnology Journal, Great Britain, Dec. 20, 2012, vol. 11, No. 3, pp. 279-295, DOI: 10.1111/pbi. 12009, ISSN 1467-7644, XP055951156.

Bertioli D.J., et al., "The Use of SNP Markers for Linkage Mapping in Diploid and Tetraploid Peanuts," G3 Genes, Genomes, Genetics, Nov. 8, 2013, vol. 4, No. 1, pp. 89-96, DOI: 10.1534/g3.113. 007617, XP055951153, Retrieved from URL: http://academic.oup.com/g3journal/article-pdf/4/1/89/37154970/g3journal0089.pdf.

Extended European Search Report for European Application No. 19898155.7, mailed Sep. 2, 2022, 08 Pages.

Mobashwer A., et al., "Ultra-High-Throughput Dartseq-Based Silicodart and Snp Markers for Genomic Studies in Macadamia", Plos One, Aug. 31, 2018, vol. 13, No. 8, p. e0203465, DOI: 10.1371/journal.pone.0203465, XP055951132.

\* cited by examiner

Figure 24.

SEQUENCE LISTING

<160> NUMBER OF SEQ ID NOS: 548

<210> SEQ ID NO 1
<211> LENGTH: 15722
<212> TYPE: DNA
<213> ORGANISM: Artificial Sequence
<220> FEATURE:
<223> OTHER INFORMATION: vector 23396
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)

```
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmVLHP
<220> FEATURE:
<221> NAME/KEY: misc_feature
<222> LOCATION: (6927)..(7032)
<223> OTHER INFORMATION: rsgRNAZmVLHP-01
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01

<400> SEQUENCE: 1
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc ccctcctcg      480 atatctccgc ggcgacctct ggcttttttcc gcggaattgc gcggtgggga cggattccac    540
gagaccgcga cgcaaccgcc tctcgccgct gggccccaca ccgctcggtg ccgtagcctc     600
acgggactct ttctccctcc tccccgtta taaattggct tcatccctc cttgcctcat       660 ccatccaaat cccagtcccc aatcccatcc cttcgtagga gaaattcatc gaagctaagc     720
gaatcctcgc gatcctctca aggtactgcg agttttcgat ccccctctcg accctcgta      780 tgtttgtgtt tgtcgtagcg tttgattagg tatgctttcc ctgtttgtgt tcgtcgtagc     840
gtttgattag gtatgctttc cctgttcgtg ttcatcgtag tgtttgatta ggtcgtgtga     900
ggcgatggcc tgctcgcgtc cttcgatctg tagtcgattt gcgggtcgtg gtgtagatct     960
gcgggctgtg atgaagttat ttggtgtgat ctgctcgcct gattctgcgg gttggctcga    1020
gtagatatga tggttggacc ggttggttcg tttaccgcgc tagggttggg ctgggatgat    1080
```

```
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttaccccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt atttttaaatg ctatatagtt   1920 ctggtacttg ttagaaagat ctgcttcata gtttagttgc ctatccctcg aattaggatg   1980
ctgagcagct gatcctatag cttttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg caccaacag    2160 cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca cgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg acccgaact tcaagagcaa   2880 cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct cgaccagag    3180 caagaacggc tacgccggct acatcgacgg cggcgccagc caggaggagt ctacaagtt    3240 catcaagccg atcctggaga gatggacgg caccgaggag ctgctggtga agctgaacag   3300
ggaggacctg ctgaggaagc agaggaccttt cgacaacggc agcatcccgc accagatcca   3360
cctgggcgag ctgcacgcca tcctgaggag gcaggaggac ttctaccgcgt tcctgaagga   3420
```

```
caacaggag   aagatcgaga   agatcctgac   cttccgcatc   ccgtactacg   tgggcccgct    3480
ggccaggggc   aacagcaggt   tcgcctggat   gaccaggaag   agcgaggaga   ccatcacccc    3540
gtggaacttc   gaggaggtgg   tggacaaggg   cgccagcgcc   cagagcttca   tcgagaggat    3600
gaccaacttc   gacaagaacc   tgccgaacga   gaaggtgctg   ccgaagcaca   gcctgctgta    3660
cgagtacttc   accgtgtaca   acgagctgac   caaggtgaag   tacgtgaccg   agggcatgag    3720
gaagccggcc   ttcctgagcg   gcgagcagaa   gaaggccatc   gtggacctgc   tgttcaagac    3780
caacaggaag   gtgaccgtga   agcagctgaa   ggaggactac   ttcaagaaga   tcgagtgctt    3840
cgacagcgtg   gagatcagcg   gcgtggagga   caggttcaac   gccagcctgg   gcacctacca    3900
cgacctgctg   aagatcatca   aggacaagga   cttcctggac   aacgaggaga   cgaggacat     3960
cctggaggac   atcgtgctga   ccctgaccct   gttcgaggac   agggagatga   tcgaggagag    4020
gctgaagacc   tacgcccacc   tgttcgacga   caaggtgatg   aagcagctga   agaggaggag    4080
gtacaccggc   tggggcaggc   tgagcaggaa   gctgatcaac   ggcatcaggg   acaagcagag    4140
cggcaagacc   atcctggact   tcctgaagag   cgacggcttc   gccaacagga   acttcatgca    4200
gctgatccac   gacgcagcc    tgaccttcaa   ggaggacatc   cagaaggccc   aggtgagcgg    4260
ccagggcgac   agcctgcacg   agcacatcgc   caacctggcc   ggcagcccgg   ccatcaagaa    4320
gggcatcctg   cagaccgtga   aggtggtgga   cgagctggtg   aaggtgatgg   gcaggcacaa    4380
gccggagaac   atcgtgatcg   agatggccag   ggagaaccag   accacccaga   agggccagaa    4440
gaacagcagg   gagaggatga   agaggatcga   ggagggcatc   aaggagctgg   gcagccagat    4500
cctgaaggag   caccccggtgg  agaacaccca   gctgcagaac   gagaagctgt   acctgtacta    4560
cctgcagaac   ggcagggaca   tgtacgtgga   ccaggagctg   gacatcaaca   ggctgagcga    4620
ctacgacgtg   gaccacatcg   tgccgcagag   cttcctgaag   gacgacagca   tcgacaacaa    4680
ggtgctgacc   aggagcgaca   agaacagggg   caagagcgac   aacgtgccga   gcgaggaggt    4740
ggtgaagaag   atgaaaaact   actggaggca   gctgctgaac   gccaagctga   tcacccagag    4800
gaagttcgac   aacctgacca   aggccgagag   gggcggcctg   agcgagctgg   acaaggccgg    4860
cttcattaaa   aggcagctgg   tggagaccag   gcagatcacc   aagcacgtgg   cccagatcct    4920
ggacagcagg   atgaacacca   agtacgacga   gaacgacaag   ctgatcaggg   aggtgaaggt    4980
gatcacctg   aagagcaagc   tggtgagcga   cttcaggaag   gacttccagt   tctacaaggt    5040
gagggagatc   aataattacc   accacgccca   cgacgcctac   ctgaacgccg   tggtgggcac    5100
cgccctgatt   aaaaagtacc   cgaagctgga   gagcgagttc   gtgtacgcgc   actacaaggt    5160
gtacgacgtg   aggaagatga   tcgccaagag   cgagcaggag   atcggcaagg   ccaccgccaa    5220
gtacttcttc   tacagcaaca   tcatgaactt   cttcaagacc   gagatcaccc   tggccaacgg    5280
cgagatcagg   aagaggccgc   tgatcgagac   caacggcgag   accggcgaga   tcgtgtggga    5340
caagggcagg   gacttcgcca   ccgtgaggaa   ggtgctgtcc   atgccgcagg   tgaacatcgt    5400
gaagaagacc   gaggtgcaga   ccggcggctt   cagcaaggag   agcatcctgc   cgaagaggaa    5460
cagcgacaag   ctgatcgcca   ggaagaagga   ctgggacccg   aagaagtacg   gcggcttcga    5520
cagcccgacc   gtggcctaca   gcgtgctggt   ggtggccaag   gtggagaagg   caagagcaa     5580
gaagctgaag   agcgtgaagg   agctggtggg   catcaccatc   atggagagga   gcagcttcga    5640
gaagaaccca   gtggacttcc   tggaggccaa   gggctacaag   gaggtgaaga   aggacctgat    5700
cattaaactg   ccgaagtaca   gcctgttcga   gctggagaac   ggcaggaaga   ggatgctggc    5760
cagcgccggc   gagctgcaga   agggcaacga   gctggccctg   ccgagcaagt   acgtgaactt    5820
```

```
cctgtacctg gccagccact acgagaagct gaagggcagc ccggaggaca acgagcagaa    5880
gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcaccct    6060
gaccaacctg ggcgccccgg ccgccttcaa gtacttcgac accaccatcg acaggaagag    6120
gtacaccagc accaaggagg tgctggacgc caccctgatc caccagagca tcaccggcct    6180
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag ggaccatagc    6660
acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagcag gaggcgtcga gcagcggttt tagagctaga    6960
aatagcaagt taaaataagg ctagtccgtt atcaacttga aaaagtggca ccgagtcggt    7020
gctttttttt tcggaccgcg cctgcagtgc agcgtgaccc ggtcgtgccc ctctctagag    7080
ataatgagca ttgcatgtct aagttataaa aaattaccac atatttttt tgtcacactt    7140 gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtatttga caacaggact ctacagtttt atcttttag     7320 tgtgcatgtg ttctcctttt tttttgcaaa tagcttcacc tatataatac ttcatccatt    7380
ttattagtac atccatttag ggtttagggt taatggtttt tatagactaa ttttttagt    7440 acatctattt tattctattt tagcctctaa attaagaaaa ctaaaactct attttagttt    7500
ttttatttaa taatttagat ataaaataga ataaataaa gtgactaaaa attaaacaaa     7560 tacccttttaa gaaattaaaa aaactaagga acatttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg accctctcg    7740 agagttccgc tccaccgttg gacttgctcc gctgtcggca tccagaaatt gcgtggcgga    7800
gcggcagacg tgagccggca cggcaggcgg cctcctcctc ctctcacggc accggcagct    7860 acggggatt cctttcccac cgctccttcg ctttcccttc ctcgcccgcc gtaataaata    7920 gacacccct ccacaccctc tttccccaac ctcgtgttgt tcggagcgca cacacacaca     7980
accagatctc ccccaaatcc acccgtcggc acctccgctt caaggtacgc cgctcgtcct    8040 ccccccccc cctctctacc ttctctagat cggcgttccg gtccatggtt agggcccggt    8100
agttctactt ctgttcatgt ttgtgttaga tccgtgtttg tgttagatcc gtgctgctag    8160
```

-continued

```
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280
ttttttttgt ttcgttgcat agggtttggt ttgcccttt cctttatttc aatatatgcc    8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gcttttgtt cgcttggttg tgatgatgtg gtgtggttgg gcggtcgttc    8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcacccca caagcacaa    9360 cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggcggcgc    9540 ccacccccgcc atcgcccact tcctgcagca gcccgacgcc gagcgcctga gcagctgtt    9600 cgccagcctg ctgaacatgc agggcgagga aagagccgc gccctggcca tcctgaagag    9660
cgccctggac agccagcagg gcgagccctg gcagaccatc cgcctgatca gcgagttcta   9720
ccccgaggac agcggcctgt tcagccccct gctgctgaac gtggtgaagc tgaaccccgg   9780
cgaggccatg ttcctgttcg ccgagacccc ccacgcctac ctgcagggcg tggccctgga   9840
ggtgatggcc aacagcgaca acgtgctgcg cgccggcctg accccaagt acatcgacat    9900 ccccgagctg gtggccaacg tgaagttcga ggccaagccc gccaaccagc tgctgaccca   9960
gcccgtgaag cagggcgccg agctggactt ccccatcccc gtggacgact cgccttcag   10020 cctgcacgac ctgagcgaca aggagaccac catcagccag cagagcgccg ccatcctgtt   10080
ctgcgtggag ggcgacgcca ccctgtggaa gggcagccag cagctgcagc tgaagcccgg   10140
cgagagcgcc ttcatcgccg ccaacgagag ccccgtgacc gtgaagggcc acggccgcct   10200
ggcccgcgtg tacaacaagc tgtgataggg gctcgatccg tcgacctgca gatcgttcaa   10260
acatttggca ataaagtttc ttaagattga atcctgttgc cggtcttgcg atgattcatca   10320 tataatttct gttgaattac gttaagcatg taataattaa catgtaatgc atgacgttat   10380
ttatgagatg ggttttatg attagagtcc gcaattata catttaatac gcgatagaaa     10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
```

```
aagttgtcta agcgtcaatt tgtttacacc acaatatatc ctgccaccag ccagccaaca   10620
gctccccgac cggcagctcg gcacaaaatc accactcgat acaggcagcc catcagaatt   10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg tttttgcgc cgacatcata acggttctgg    10860
caaatattct gaaatgagct gttgacaatt aatcatccgg ctcgtataat gtgtggaatt   10920
gtgagcggat aacaatttca cacaggaaac agaccatgag ggaagcgttg atcgccgaag   10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160 acctttttgga aacttcggct tcccctggag agagcgagat tctccgcgct gtagaagtca  11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcgc agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg gggcgagacc ataggcgatc   11820
tcctaaatca atagtagctg taacctcgaa gcgtttcact tgtaacaacg attgagaatt   11880
tttgtcataa aattgaaata cttggttcgc attttttgtca tccgcggtca gccgcaattc    11940
tgacgaactg cccatttagc tggagatgat tgtacatcct tcacgtgaaa atttctcaag   12000
cgctgtgaac aagggttcag attttagatt gaaaggtgag ccgttgaaac acgttcttct   12060
tgtcgatgac gacgtcgcta tgcggcatct tattattgaa taccttacga tccacgcctt   12120
caaagtgacc gcggtagccg acagcaccca gttcacaaga gtactctctt ccgcgacggt   12180
cgatgtcgtg gttgttgatc tagatttagg tcgtgaagat gggctcgagc taggagcaag   12240
tgattttatc gctaagccgt tcagtatcag agagtttcta gcacgcattc gggttgcctt   12300
gcgcgtgcgc cccaacgttg tccgctccaa agaccgacgg tcttttttgtt ttactgactg   12360 gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacagagga gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacgggggg   12660 gacgatggca gcctgagcca attcccagat ccccgaggaa tcggcgtgag cggtcgcaaa   12720
ccatccggcc cggtacaaat cggcgcggcg ctgggtgatg acctggtgga aagttgaag    12780 gccgcgcagg ccgcccagcg gcaacgcatc gaggcagaag cacgccccgg tgaatcgtgg   12840
caagcggccg ctgatcgaat ccgcaaagaa tcccggcaac cgccggcagc cggtgcgccg   12900
```

```
tcgattagga agccgcccaa gggcgacgag caaccagatt ttttcgttcc gatgctctat    12960
gacgtgggca cccgcgatag tcgcagcatc atggacgtgg ccgttttccg tctgtcgaag    13020
cgtgaccgac gagctggcga ggtgatccgc tacgagcttc cagacgggca cgtagaggtt    13080
tccgcagggc cggccggcat ggccagtgtg tgggattacg acctggtact gatgcggtt     13140 tcccatctaa ccgaatccat gaaccgatac cgggaaggga agggagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccgagggtga agccttgatt    13380
agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact ttttgatcga tcccggcatc ggccgttttc tctaccgcct ggcacgccgc    13560
gccgcaggca aggcagaagc cagatggttg ttcaagacga tctacgaacg cagtggcagc    13620
gccggagagt tcaagaagtt ctgttttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacgagca gatgctaggg     13800 caaattgccc tagcagggga aaaggtcga aaaggtctct ttcctgtgga tagcacgtac     13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctacccttcg gtcgctgcgc    14100
tccctacgcc ccgccgcttc gcgtcggcct atcgcggccg ctggccgctc aaaaatggct    14160
ggcctacggc caggcaatct accagggcgc ggacaagccg cgccgtcgcc actcgaccgc    14220
cggcgctgag gtctgcctcg tgaagaaggt gttgctgact cataccaggc ctgaatcgcc    14280
ccatcatcca gccagaaagt gagggagcca cggttgatga gagctttgtt gtaggtggac    14340
cagttggtga ttttgaactt ttgctttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatattttt    14580
gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga aatcaccatg agtgacgact gaatccggtg    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc gcctttctc     15180 ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
```

```
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg ttttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                   15722

<210> SEQ ID NO 2
<211> LENGTH: 20
<212> TYPE: DNA
<213> ORGANISM: Artificial Sequence
<220> FEATURE:
<223> OTHER INFORMATION: gRNA sequence for editing VLHP1

<400> SEQUENCE: 2
gcaggaggcg tcgagcagcg                                                20

<210> SEQ ID NO 3
<211> LENGTH: 15722
<212> TYPE: DNA
<213> ORGANISM: Artificial Sequence
<220> FEATURE:
<223> OTHER INFORMATION: vector 23399
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmGW2
<220> FEATURE:
<221> NAME/KEY: misc_feature
<222> LOCATION: (6927)..(7031)
<223> OTHER INFORMATION: rsgRNAZmGW2-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
```

```
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 3
attcctgtgg ttggcatgca catacaaatg gacgaacgga taaaccttt  cacgcccttt      60 taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccccgccg atgacgcggg acaagccgtt ttacgtttgg    240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc ccctcctcg     480 atatctccgc ggcgacctct ggcttttttcc gcggaattgc gcggtgggga cggattccac    540
gagaccgcga cgcaaccgcc tctcgccgct gggccccaca ccgctcggtg ccgtagcctc    600
acgggactct ttctccctcc tccccgtta taaattggct tcatccccctc cttgcctcat    660 ccatccaaat cccagtcccc aatcccatcc cttcgtagga gaaattcatc gaagctaagc    720
gaatcctcgc gatcctctca aggtactgcg agttttcgat ccccctctcg accccctgta    780
tgtttgtgtt tgtcgtagcg tttgattagg tatgctttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat tggtgtgat ctgctcgcct gattctgcgg gttggctcga   1020
gtagatatga tggttggacc ggttggttcg tttaccgcgc tagggttggg ctgggatgat   1080
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
```

```
tatattatat tggtaactta ttacccctat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt attttaaatg ctatatagtt   1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag ggggccactt cctgatcgag gcgacctgaa   2640
cccggacaac agcgacgtgg acaagctgtt catccagctg gtgcagacct acaaccagct   2700
gttcgaggag aacccgatca cgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg acccccgaact tcaagagcaa   2880 cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct tcgaccagag   3180
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggaccgtt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccaggggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga gaaggtgctg ccgaagcaca gcctgctgta   3660
cgagtacttc accgtgtaca acgagctgac caaggtgaag tacgtgaccg agggcatgag   3720
gaagccggcc ttcctgagcg gcgagcagaa gaaggccatc gtggacctgc tgttcaagac   3780
```

```
caacaggaag gtgaccgtga agcagctgaa ggaggactac ttcaagaaga tcgagtgctt    3840
cgacagcgtg gagatcagcg gcgtggagga caggttcaac gccagcctgg gcacctacca    3900
cgacctgctg aagatcatca aggacaagga cttcctggac aacgaggaga acgaggacat    3960
cctggaggac atcgtgctga ccctgaccct gttcgaggac agggagatga tcgaggagag    4020
gctgaagacc tacgcccacc tgttcgacga caaggtgatg aagcagctga agaggaggag    4080
gtacaccggc tggggcaggc tgagcaggaa gctgatcaac ggcatcaggg acaagcagag    4140
cggcaagacc atcctggact tcctgaagag cgacggcttc gccaacagga acttcatgca    4200
gctgatccac gacgcagcc tgaccttcaa ggaggacatc cagaaggccc aggtgagcgg    4260
ccagggcgac agcctgcacg agcacatcgc caacctggcc ggcagcccgg ccatcaagaa    4320
gggcatcctg cagaccgtga aggtggtgga cgagctggtg aaggtgatgg gcaggcacaa    4380
gccggagaac atcgtgatcg agatggccag ggagaaccag accacccaga gggccagaa    4440 gaacagcagg gagaggatga gaggatcga ggagggcatc aaggagctgg gcagccagat    4500
cctgaaggag cacccggtgg agaaccccca gctgcagaac gagaagctgt acctgtacta    4560
cctgcagaac ggcagggaca tgtacgtgga ccaggagctg gacatcaaca ggctgagcga    4620
ctacgacgtg gaccacatcg tgccgcagag cttcctgaag gacgacagca tcgacaacaa    4680
ggtgctgacc aggagcgaca gaacagggg caagagcgac aacgtgccga gcgaggaggt    4740
ggtgaagaag atgaaaaact actggaggca gctgctgaac gccaagctga tcacccagag    4800
gaagttcgac aacctgacca aggccgagag gggcggcctg agcgagctgg acaaggccgg    4860
cttcattaaa aggcagctgg tggagaccag gcagatcacc aagcacgtgg cccagatcct    4920
ggacagcagg atgaacacca gtacgacga aacgacaag ctgatcaggg aggtgaaggt    4980
gatcaccctg aagagcaagc tggtgagcga cttcaggaag gacttccagt tctacaaggt    5040
gagggagatc aataattacc accacgccca cgacgcctac ctgaacgccg tggtgggcac    5100
cgccctgatt aaaaagtacc cgaagctgga gagcgagttc gtgtacggcg actacaaggt    5160
gtacgacgtg aggaagatga tcgccaagag cgagcaggag atcggcaagg ccaccgccaa    5220
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
cagcgacaag ctgatcgcca ggaagaagga ctgggacccg aagaagtacg gcggcttcga    5520
cagcccgacc gtggcctaca gcgtgctggt ggtggccaag gtggagaagg gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga ggacctgat    5700 cattaaactg ccgaagtaca gcctgttcga gctggagaac ggcaggaaga gatgctggc    5760 cagcgccggc gagctgcaga agggcaacga gctggccctg ccgagcaagt acgtgaactt    5820
cctgtacctg gccagccact acgagaagct gaagggcagc ccggaggaca acgagcagaa    5880
gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcaccct    6060
gaccaacctg ggcgccccgg ccgccttcaa gtacttcgac accaccatcg acaggaagag    6120
gtacaccagc accaaggagg tgctggacgc caccctgatc caccagagca tcaccggcct    6180
```

```
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag ggaccatagc    6660
acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcaaagc tcgcgccctg ctaccgtttt tagagctaga    6960
aatagcaagt taaataagg ctagtccgtt atcaacttga aaaagtggca ccgagtcggt     7020 gcttttttt tcggaccgcg cctgcagtgc agcgtgaccc ggtcgtgccc ctctctagag     7080
ataatgagca ttgcatgtct aagttataaa aaattaccac atattttttt tgtcacactt    7140
gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtattttga caacaggact ctacagtttt atcttttag     7320 tgtgcatgtg ttctccttt ttttgcaaa tagcttcacc tatataatac ttcatccatt      7380
ttattagtac atccatttag ggtttagggt taatggtttt tatagactaa ttttttagt     7440 acatctattt tattctattt tagcctctaa attaagaaaa ctaaaactct attttagttt    7500
ttttatttaa taatttagat ataaaataga ataaaataaa gtgactaaaa attaaacaaa    7560
taccctttaa gaaattaaaa aaactaagga aacatttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg accccctctcg   7740 agagttccgc tccaccgttg gacttgctcc gctgtcggca tccagaaatt gcgtggcgga    7800
gcggcagacg tgagccggca cggcaggcgg cctcctcctc ctctcacggc accggcagct    7860 acggggatt cctttcccac cgctccttcg ctttcccttc ctcgcccgcc gtaataaata     7920
gacaccccct ccacccctc tttccccaac ctcgtgttgt tcggagcgca cacacaca      7980 accagatctc ccccaaatcc acccgtcggc acctccgctt caaggtacgc cgctcgtcct    8040 ccccccccc cctctctacc ttctctagat cggcgttccg gtccatggtt agggcccggt     8100
agttctactt ctgttcatgt ttgtgttaga tccgtgtttg tgttagatcc gtgctgctag    8160
cgttcgtaca cggatgcgac ctgtacgtca gacacgttct gattgctaac ttgccagtgt    8220 ttctcttgg ggaatcctgg gatggctcta gccgttccgc agacgggatc gatttcatga     8280 tttttttgt ttcgttgcat agggtttggt ttgccctttt cctttattc aatatatgcc      8340 gtgcacttgt ttgtcgggtc atcttttcat gctttttttt gtcttggttg tgatgatgtg    8400
gtctggttgg gcggtcgttc tagatcggag tagaattctg tttcaaacta cctggtggat    8460
ttattaattt tggatctgta tgtgtgtgcc atacatattc atagttacga attgaagatg    8520
```

```
atggatggaa atatcgatct aggataggta tacatgttga tgcgggtttt actgatgcat    8580
atacagagat gcttttttgtt cgcttggttg tgatgatgtg gtgtggttgg gcggtcgttc   8640
attcgttcta gatcggagta gaatactgtt tcaaactacc tggtgtattt attaattttg    8700
gaactgtatg tgtgtgtcat acatcttcat agttacgagt ttaagatgga tggaaatatc    8760
gatctaggat aggtatacat gttgatgtgg gttttactga tgcatataca tgatggcata    8820
tgcagcatct attcatatgc tctaaccttg agtacctatc tattataata aacaagtatg    8880
ttttataatt attttgatct tgatatactt ggatgatggc atatgcagca gctatatgtg    8940
gattttttta gccctgcctt catacgctat ttatttgctt ggtactgttt cttttgtcga    9000
tgctcaccct gttgtttggt gttacttctg cagggatccg gcagcagcca tgcagaagct    9060
gatcaacagc gtgcagaact acgcctgggg cagcaagacc gccctgaccg agctgtacgg    9120
catggagaac cccagcagcc agcccatggc cgagctgtgg atgggcgccc accccaagag    9180
cagcagccgc gtgcagaacg ccgccggcga catcgtgagc ctgcgcacg tgatcgagag    9240
cgacaagagc accctgctgg gcgaggccgt ggccaagcgc ttcggcgagc tgcccttcct    9300
gttcaaggtg ctgtgcgccg cccagcccct gagcatccag gtgcacccca caagcacaa    9360
cagcgagatc ggcttcgcca aggagaacgc cgccggcatc cccatggacg ccgccgagcg    9420
caactacaag accccaacc acaagcccga gctggtgttc gccctgaccc ccttcctggc    9480
catgaacgcc ttccgcgagt tcagcgagat cgtgagcctg ctgcagcccg tggccggcgc    9540
ccacccccgcc atcgcccact tcctgcagca gcccgacgcc gagcgcctga gcgagctgtt    9600
cgccagcctg ctgaacatgc agggcgagga gaagagccgc gccctggcca tcctgaagag    9660
cgccctggac agccagcagg gcgagccctg gcagaccatc cgcctgatca gcgagttcta    9720
ccccgaggac agcggcctgt tcagccccct gctgctgaac gtggtgaagc tgaacccgg    9780
cgaggccatg ttcctgttcg ccgagacccc ccacgcctac ctgcagggcg tggccctgga    9840
ggtgatggca aacagcgaca acgtgctgcg cgccggcctg accccaagt acatcgacat    9900
ccccgagctg gtggccaacg tgaagttcga ggccaagccc gccaaccagc tgctgaccca    9960
gcccgtgaag cagggcgccg agctggactt ccccatcccc gtggacgact cgcccttcag   10020
cctgcacgac ctgagcgaca aggagaccac catcagccag cagagcgccg ccatcctgtt   10080
ctgcgtggag ggcgacgcca ccctgtggaa gggcagccag cagctgcagc tgaagcccgg   10140
cgagagcgcc ttcatcgccg ccaacgagag ccccgtgacc gtgaagggcc acggccgcct   10200
ggcccgcgtg tacaacaagc tgtgatagga gctcgatccg tcgacctgca gatcgttcaa   10260
acatttggca ataaagtttc ttaagattga atcctgttgc cggtcttgcg atgattatca   10320
tataatttct gttgaattac gttaagcatg taataattaa catgtaatgc atgacgttat   10380
ttatgagatg gttttttatg attagagtcc cgcaattata catttaatac gcgatagaaa   10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
aagttgtcta agcgtcaatt tgtttacacc acaatatatc ctgccaccag ccagccaaca   10620
gctcccgac cggcagctcg gcacaaaatc accactcgat acaggcagcc catcagaatt   10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg ttttttgcgc cgacatcata acggttctgg   10860
caaatattct gaaatgagct gttgacaatt aatcatccgg ctcgtataat gtgtggaatt   10920
```

```
gtgagcggat aacaatttca cacaggaaac agaccatgag ggaagcgttg atcgccgaag   10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160
accttttgga aacttcggct tcccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcgc agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg gggcgagacc ataggcgatc   11820
tcctaaatca atagtagctg taacctcgaa gcgtttcact tgtaacaacg attgagaatt   11880
tttgtcataa aattgaaata cttggttcgc attttttgtca tccgcggtca gccgcaattc   11940
tgacgaactg cccatttagc tggagatgat tgtacatcct tcacgtgaaa atttctcaag   12000
cgctgtgaac aagggttcag attttagatt gaaaggtgag ccgttgaaac acgttcttct   12060
tgtcgatgac gacgtcgcta tgcggcatct tattattgaa taccttacga tccacgcctt   12120
caaagtgacc gcggtagccg acagcaccca gttcacaaga gtactctctt ccgcgacggt   12180
cgatgtcgtg gttgttgatc tagatttagg tcgtgaagat gggctcgagc taggagcaag   12240
tgattttatc gctaagccgt tcagtatcag agagtttcta gcacgcattc gggttgcctt   12300
gcgcgtgcgc cccaacgttg tccgctccaa agaccgacgg tcttttttgtt ttactgactg   12360 gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
gacgatggca gcctgagcca attcccagat ccccgaggaa tcggcgtgag cggtcgcaaa   12720
ccatccggcc cggtacaaat cggcgcgcg ctgggtgatg acctggtgga gaagttgaag   12780
gccgcgcagg ccgcccagcg gcaacgcatc gaggcagaag cacgccccgg tgaatcgtgg   12840
caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
cgtgaccgac gagctggcga ggtgatccgc tacgagcttc cagacgggca cgtagaggtt   13080
tccgcagggc cggccggcat ggccagtgtg tgggattacg acctggtact gatggcggtt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
```

```
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcagggga aaaggtcga aaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actcttttaaa acttattaaa actcttaaaa cccgcctggc ctgtgcataa   14040
ctgtctggcc agcgcacagc cgaagagctg caaaaagcgc ctacccttcg gtcgctgcgc   14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatatttttt   14580 gaaaaagccg tttctgtaat gaaggagaaa actcaccgag gcagttccat aggatggcaa   14640
gatcctggta tcggtctgcg attccgactc gtccaacatc aatacaacct attaatttcc   14700
cctcgtcaaa aataaggtta tcaagtgaga atcaccatg agtgacgact gaatccggtg   14760
agaatggcaa aagctctgca ttaatgaatc ggccaacgcg cggggagagg cggtttgcgt   14820 attggcgct cttccgcttc ctcgctcact gactcgctgc gctcggtcgt tcggctgcgg   14880
cgagcggtat cagctcactc aaaggcggta atacggttat ccacagaatc aggggataac   14940
gcaggaaaga acatgtgagc aaaaggccag caaaaggcca ggaaccgtaa aaaggccgcg   15000
ttgctggcgt ttttccatag gctccgcccc cctgacgagc atcacaaaaa tcgacgctca   15060
agtcagaggt ggcgaaaccc gacaggacta taaagatacc aggcgtttcc ccctggaagc   15120
tccctcgtgc gctctcctgt tccgaccctg ccgcttaccg gatacctgtc cgcctttctc   15180
ccttcgggaa gcgtggcgct ttctcatagc tcacgctgta ggtatctcag ttcggtgtag   15240
gtcgttcgct ccaagctggg ctgtgtgcac gaaccccccg ttcagcccga ccgctgcgcc   15300
ttatccggta actatcgtct tgagtccaac ccggtaagac acgacttatc gccactggca   15360
gcagccactg gtaacaggat tagcagagcg aggtatgtag cggtgctac agagttcttg   15420 aagtggtggc ctaactacgg ctacactaga agaacagtat ttggtatctg cgctctgctg   15480
aagccagtta ccttcggaaa aagagttggt agctcttgat ccggcaaaca aaccaccgct   15540
ggtagcggtg gtttttttgt ttgcaagcag cagattacgc gcagaaaaaa aggatctcaa   15600
gaagatcctt tgatcttttc tacggggtct gacgctcagt ggaacgaaaa ctcacgttaa   15660
```

```
gggattttgg tcatgagatt atcaaaaagg atcttcacct agatcctttt gatccggaat    15720
ta                                                                   15722
```

```
<210> SEQ ID NO 4
<211> LENGTH: 20
<212> TYPE: DNA
<213> ORGANISM: Artificial Sequence
<220> FEATURE:
<223> OTHER INFORMATION: for editing GW2-2

<400> SEQUENCE: 4
aagctcgcgc cctgctaccc                                                   20

<210> SEQ ID NO 5
<211> LENGTH: 19617
<212> TYPE: DNA
<213> ORGANISM: Artificial Sequence
<220> FEATURE:
<223> OTHER INFORMATION: vector 22808
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2119)..(5193)
<223> OTHER INFORMATION: cTNPLAIIAFw-01
<220> FEATURE:
<221> NAME/KEY: terminator
<222> LOCATION: (5200)..(5452)
<223> OTHER INFORMATION: tNOS-05-01
<220> FEATURE:
<221> NAME/KEY: promoter
<222> LOCATION: (5486)..(7478)
<223> OTHER INFORMATION: prUbi1-10
<220> FEATURE:
<221> NAME/KEY: gene
<222> LOCATION: (7492)..(10566)
<223> OTHER INFORMATION: cTNPLAIIARv-01
<220> FEATURE:
<221> NAME/KEY: terminator
<222> LOCATION: (10573)..(10825)
<223> OTHER INFORMATION: tNOS-05-01
<220> FEATURE:
<221> NAME/KEY: promoter
<222> LOCATION: (10844)..(12835)
<223> OTHER INFORMATION: prUbi1-04
<220> FEATURE:
<221> NAME/KEY: gene
<222> LOCATION: (12852)..(14030)
<223> OTHER INFORMATION: cPMI-09
<220> FEATURE:
<221> NAME/KEY: terminator
<222> LOCATION: (14053)..(14305)
<223> OTHER INFORMATION: tNOS-05-01
<220> FEATURE:
<221> NAME/KEY: misc_feature
<222> LOCATION: (14349)..(14478)
<223> OTHER INFORMATION: bNLB-03
<220> FEATURE:
<221> NAME/KEY: gene
<222> LOCATION: (14758)..(15546)
<223> OTHER INFORMATION: cSpec-03
<220> FEATURE:
<221> NAME/KEY: promoter
<222> LOCATION: (15641)..(15771)
<223> OTHER INFORMATION: prVirG-01
<220> FEATURE:
<221> NAME/KEY: gene
<222> LOCATION: (15846)..(16571)
```

```
<223> OTHER INFORMATION: cVirG-01
<220> FEATURE:
<221> NAME/KEY: gene
<222> LOCATION: (16601)..(17674)
<223> OTHER INFORMATION: cRepA-01
<220> FEATURE:
<221> NAME/KEY: misc_feature
<222> LOCATION: (17717)..(18121)
<223> OTHER INFORMATION: oVS1-02
<220> FEATURE:
<221> NAME/KEY: misc_feature
<222> LOCATION: (18799)..(19605)
<223> OTHER INFORMATION: oCOLE-06

<400> SEQUENCE: 5
attcctgtgg ttggcatgca catacaaatg gacgaacgga taaaccttt cacgcccttt      60 taaatatccg attattctaa taaacgctct tttctcttag gtttacccgc caatatatcc     120
tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg ccatttaaa caaagcttgg     300 taccattatg tggtctaggt aggttctata tataagaaaa cttgaaatgt tctaaaaaaa    360
aattcaagcc catgcatgat tgaagcaaac ggtatagcaa cggtgttaac ctgatctagt    420
gatctcttgc aatccttaac ggccacctac cgcaggtagc aaacggcgtc cccctcctcg    480
atatctccgc ggcgacctct ggcttttcc gcggaattgc gcggtgggga cggattccac     540
gagaccgcga cgcaaccgcc tctcgccgct gggccccaca ccgctcggtg ccgtagcctc    600
acgggactct ttctcctcc tccccgtta taaattggct tcatccctc cttgcctcat       660 ccatccaaat cccagtcccc aatcccatcc cttcgtagga gaaattcatc gaagctaagc    720
gaatcctcgc gatcctctca aggtactgcg agttttcgat ccccctctcg acccctcgta    780
tgtttgtgtt tgtcgtagcg tttgattagg tatgctttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga    1020
gtagatatga tggttggacc ggttggttcg tttaccgcgc tagggttggg ctgggatgat    1080
gttgcatgcg ccgttgcgcg tgatcccgca gcaggacttg cgtttgattg ccagatctcg    1140
ttacgattat gtgatttggt ttggactttt tagatctgta gcttctgctt atgtgccaga    1200
tgcgcctact gctcatatgc ctgatgataa tcataaatgg ctgtggaact aactagttga    1260
ttgcggagtc atgtatcagc tacaggtgta gggactagct acaggtgtag ggacttgcgt    1320
ctaattgttt ggtcctttac tcatgttgca attatgcaat ttagtttaga ttgtttgttc    1380
cactcatcta ggctgtaaaa gggacactgc ttagattgct gtttaatctt tttagtagat    1440
tatattatat tggtaactta ttaccctat tacatgccat acgtgacttc tgctcatgcc     1500
tgatgataat catagatcac tgtggaatta attagttgat tgttgaatca tgtttcatgt    1560
acataccacg gcacaattgc ttagttcctt aacaaatgca aatttactg atccatgtat     1620 gatttgcgtg gttctctaat gtgaaatact atagctactt gttagtaaga atcaggttcg    1680
tatgcttaat gctgtatgtg ccttctgctc atgcctgatg ataatcatat atcactggaa    1740
ttaattagtt gatcgtttaa tcatatatca agtacatacc atgccacaat ttttagtcac    1800
ttaacccatg cagattgaac tggtccctgc atgttttgct aaattgttct attctgatta    1860
gaccatatat catgtatttt tttttggtaa tggttctctt attttaaatg ctatatagtt    1920
```

```
ctggtacttg ttagaaagat ctgcttcata gtttagttgc ctatccctcg aattaggatg   1980
ctgagcagct gatcctatag cttttgtttca tgtatcaatt cttttgtgtt caacagtcag   2040
tttttgttag attcattgta acttatggtc gcttactctt ctggtcctca atgcttgcag   2100
gatcgcggcc gcgccaccat gggaaaacct attcctaatc ctctgctggg cctggattct   2160
accggaggca tggcccctaa gaaaaagcgg aaggtggacg gcggagtgga cctgagaaca   2220
ctgggatatt ctcagcagca gcaggagaag atcaagccca aggtgagatc tacagtggcc   2280
cagcaccacg aagccctggt gggacacgga tttacacacg cccacattgt ggccctgtct   2340
cagcaccctg ccgccctggg aacagtggcc gtgaaatatc aggatatgat tgccgccctg   2400
cctgaggcca cacgaagc cattgtggga gtgggaaaac agtggtctgg agccagagcc   2460
ctggaagccc tgctgacagt ggccggagaa ctgagaggac ctcctctgca gctggataca   2520
ggacagctgc tgaagattgc caaaaggggc ggagtgaccg cggtggaagc cgtgcacgcc   2580
tggagaaatg ccctgacagg agccctctg aacctgaccc ccgaacaggt ggtggccatt   2640
gccagccacg acggcggcaa gcaggccctg aaaccgtgc agagactgct gcccgtgctg   2700
tgccaggccc atggcctgac acctgaacag gtggtggcta tcgcctctca cgacggagga   2760
aaacaggctc tggaaacagt gcagcggctg ctgcctgtgc tgtgtcaggc tcacggcttg   2820
actccagaac aggtggtggc tattgcttcc aatattgggg ggaaacaggc cctgaaaact   2880
gtgcagcgcc tgctgccagt gctgtgccag gctcacggac tgaccccga acaggtggtg   2940 gccattgcca gcaacaacgg cggcaagcag gccctggaaa ccgtgcagag actgctgccc   3000
gtgctgtgcc aggcccatgg cctgacacct gaacaggtgg tggctatcgc ctctaacaac   3060
ggaggaaaac aggctctgga aacagtgcag cggctgctgc ctgtgctgtg tcaggctcac   3120
ggcttgactc cagaacaggt ggtggctatt gcttccaaca cgggggaa acaggccctg   3180 gaaactgtgc agcgcctgct gccagtgctg tgccaggctc acgggctgac ccccgaacag   3240
gtggtggcca ttgccagcaa cggcggcggc aagcaggccc tggaaaccgt gcagagactg   3300
ctgcccgtgc tgtgccaggc ccatggcctg acacctgaac aggtggtggc tatcgcctct   3360
cacgacggag gaaaacaggc tctggaaaca gtgcagcggc tgctgcctgt gctgtgtcag   3420
gctcacggct tgactccaga acaggtggtg gctattgctt ccaatattgg ggggaaacag   3480
gccctggaaa ctgtgcagcg cctgctgcca gtgctgtgcc aggctcacgg cctcactccc   3540
gaacaggtgg tggccattgc cagcaacatc ggcggcaagc aggccctgga accgtgcag   3600 agactgctgc ccgtgctgtg ccaggcccat ggcctgacac tgaacaggt ggtggctatc   3660 gcctctcacg acggaggaaa acaggctctg aaacagtgc agcggctgct gcctgtgctg   3720
tgtcaggctc acggcttgac tccagaacag gtggtggcta ttgcttccaa caacggggg   3780 aaacaggccc tggaaactgt gcagcgcctg ctgccagtgc tgtgccaggc tcacggactg   3840
acccccgaac aggtggtggc cattgccagc aacggcggcg caagcaggc cctgaaaccg   3900 gtgcagagac tgctgcccgt gctgtgccag gcccatggcc tgacacctga acaggtggtg   3960
gctatcgcct ctaacaacgg aggaaaacaa gcactcgaga cagtgcagcg gctgctgcct   4020
gtgctgtgtc aggctcacgg cttgactcca gaacaggtg tggctattgc ttccaacaac   4080 gggggaaac aggccctgga aactgtgcag cgcctgctgc cagtgctgtg ccaggctcac   4140
gggctgaccc ccgaacaggt ggtggccatt gccagcaaca tcggcggcaa gcaggccctg   4200
gaaaccgtgc agagactgct gcccgtgctg tgccaggccc atggcctgac acctgaacag   4260
```

```
gtggtggcta tcgcctctaa caacggagga aaacaggctc tggaaacagt gcagcggctg    4320
ctgcctgtgc tgtgtcaggc tcacggcttg actccacagc aggtcgtggc aattgctagc    4380
aatatcggcg gacggcccgc cctggagagc attgtggccc agctgtctag acctgatcct    4440
gccctggccg ccctgacaaa tgatcacctg gtggccctgg cctgtctggg aggcagacct    4500
gccctggatg ccgtgaaaaa aggactgcct cacgcccctg ccctgattaa agaacaaat     4560 agaagaatcc ccgagcggac ctctcacaga gtggccggat cccagctggt gaaatctgag    4620
ctggaggaga agaagtctga gctgagacac aagctgaagt acgtgcctca cgagtacatc    4680
gagctgatcg agatcgccag aaatagcacc caggatagaa tcctggagat gaaggtgatg    4740
gagttcttca tgaaagtgta cggctacaga ggaaagcatc tgggaggaag cagaaaacct    4800
gacggagcca tttatacagt gggcagccct atcgattatg cgtgatcgt ggatacaaag     4860 gcctacagcg gaggctacaa tctgcctatt ggacaggccg atgagatgca gagatacgtg    4920
gaggagaacc aaaccaggaa caagcatatc aaccctaacg agtggtggaa ggtgtaccct    4980
tctagcgtga ccgagttcaa gttcctgttt gtgagcggcc acttcaaggg caattataag    5040
gcccagctga ccaggctgaa ccacatcaca aattgtaatg cgccgtgct gtctgtggag     5100 gaactgctga ttggaggaga gatgattaag gccggaacac tgacactgga ggaggtgaga    5160
agaaagttca caacggcga gatcaacttc tgaaagcttg atcgttcaaa catttggcaa     5220
taaagtttct taagattgaa tcctgttgcc ggtcttgcga tgattatcat ataatttctg    5280
ttgaattacg ttaagcatgt aataattaac atgtaatgca tgacgttatt tatgagatgg    5340
gtttttatga ttagagtccc gcaattatac atttaatacg cgatagaaaa caaaatatag    5400
cgcgcaaact aggataaatt atcgcgcgcg gtgtcatcta tgttactaga tcttcgaacc    5460
ctagtcgaag acaaccggtg catgcctgca gtgcagcgtg acccggtcgt gcccctctct    5520
agagataatg agcattgcat gtctaagtta taaaaaatta ccacatattt ttttttgtcac   5580 acttgtttga agtgcagttt atctatcttt atacatatat ttaaacttta ctctacgaat    5640
aatataatct atagtactac aataatatca gtgttttaga gaatcatata aatgaacagt    5700
tagacatggt ctaaaggaca attgagtatt ttgacaacag gactctacag ttttatcttt    5760
ttagtgtgca tgtgttctcc tttttttttg caaatagctt cacctatata atacttcatc    5820
cattttatta gtacatccat ttaggggttta gggttaatgg ttttttataga ctaatttttt   5880 tagtacatct atttttattct atttttagcct ctaaattaag aaaactaaaa ctctatttta   5940 gttttttttat ttaataatttt agatataaaa tagaataaaa taaagtgact aaaaattaaa   6000 caaatacccct ttaagaaatt aaaaaaacta aggaaacatt tttcttgttt cgagtagata    6060
atgccagcct gttaaacgcc gtcgacgagt ctaacggaca ccaaccagcg aaccagcagc    6120
gtcgcgtcgg gccaagcgaa gcagacggca cggcatctct gtcgctgcct ctggacccct    6180
ctcgagagtt ccgctccacc gttggacttg ctccgctgtc ggcatccaga aattgcgtgg    6240
cggagcggca gacgtgagcc ggcacggcag gcggcctcct cctcctctca ggcaccggc     6300 agctacgggg gattcctttc ccaccgctcc ttcgctttcc cttcctcgcc cgccgtaata    6360
aatagacacc cctccacac cctctttccc caacctcgtg ttgttcggag cgcacacaca     6420
cacaaccaga tctcccccaa atccacccgt cggcacctcc gcttcaaggt acgccgctcg    6480 tcctccccccc cccccctct ctaccttctc tagatcggcg ttccggtcca tggttagggc    6540
ccggtagttc tacttctgtt catgtttgtg ttagatccgt gtttgtgtta gatccgtgct    6600
gctagcgttc gtacacggat gcgacctgta cgtcagacac gttctgattg ctaacttgcc    6660
```

```
agtgtttctc tttggggaat cctgggatgg ctctagccgt tccgcagacg ggatcgattt    6720 catgatttt  tttgtttcgt tgcatagggt ttggtttgcc cttttccttt atttcaatat    6780
atgccgtgca cttgtttgtc gggtcatctt ttcatgcttt tttttgtctt ggttgtgatg    6840
atgtggtctg gttgggcggt cgttctagat cggagtagaa ttctgtttca aactacctgg    6900
tggatttatt aattttggat ctgtatgtgt gtgccataca tattcatagt tacgaattga    6960
agatgatgga tggaaatatc gatctaggat aggtatacat gttgatgcgg gttttactga    7020
tgcatataca gagatgcttt ttgttcgctt ggttgtgatg atgtggtgtg gttgggcggt    7080
cgttcattcg ttctagatcg gagtagaata ctgtttcaaa ctacctggtg tatttattaa    7140
ttttggaact gtatgtgtgt gtcatacatc ttcatagtta cgagtttaag atggatggaa    7200
atatcgatct aggataggta tacatgttga tgtgggtttt actgatgcat atacatgatg    7260
gcatatgcag catctattca tatgctctaa ccttgagtac ctatctatta taataaacaa    7320
gtatgtttta taattatttt gatcttgata tacttggatg atggcatatg cagcagctat    7380
atgtggattt ttttagcccc gccttcatac gctatttatt tgcttggtac tgtttcttt     7440 gtcgatgctc accctgttgt ttggtgttac ttctgcagcg gccgcgccac catgggaaaa    7500
cctattccta atcctctgct gggcctggat tctaccggag gcatggcccc taagaaaaag    7560
cggaaggtgg acgcggagt  ggacctgaga acactgggat attctcagca gcagcaggag    7620
aagatcaagc ccaaggtgag atctacagtg gcccagcacc acgaagccct ggtgggacac    7680
ggatttacac acgcccacat tgtggccctg tctcagcacc ctgccgccct gggaacagtg    7740
gccgtgaaat atcaggatat gattgccgcc ctgcctgagg ccacacacga agccattgtg    7800
ggagtgggaa acagtggtc  tggagccaga gccctggaag ccctgctgac agtggccgga    7860
gaactgagag acctcctct  gcagctggat acaggacagc tgctgaagat tgccaaaagg    7920 ggcgagtga  ccgcggtgga agccgtgcac gcctggagaa atgccctgac aggagcccct    7980
ctgaacctga cccccgaaca ggtggtggcc attgccagca caacggcgg  caagcaggcc    8040 ctggaaaccg tgcagagact gctgcccgtg ctgtgccagg cccatggcct gacacctgaa    8100
caggtggtgg ctatcgcctc tcacgacgga ggaaaacagg ctctggaaac agtgcagcgg    8160
ctgctgcctg tgctgtgtca ggctcacggc ttgactccag aacaggtggt ggctattgct    8220
tccaacggcg gggaaaca   ggccctggaa actgtgcagc gcctgctgcc agtgctgtgc    8280
caggctcacg gactgacccc cgaacaggtg gtggccattg ccagcaacgg cggcggcaag    8340
caggccctgg aaaccgtgca gagactgctg cccgtgctgt gccaggccca tggcctgaca    8400
cctgaacagg tggtggctat cgcctctcac gacggaggaa acaggctct  ggaaacagtg    8460 cagcggctgc tgcctgtgct gtgtcaggct cacggcttga ctccagaaca ggtggtggct    8520
attgcttccc acgacggggg gaaacaggcc ctggaaactg tgcagcgcct gctgccagtg    8580
ctgtgccagg ctcacgggct gaccccgaa  caggtggtgg ccattgccag caacggcggc    8640
ggcaagcagg ccctggaaac cgtgcagaga ctgctgcccg tgctgtgcca ggcccatggc    8700
ctgacacctg aacaggtggt ggctatcgcc tctaacggcg gagaaaaaca ggctctggaa    8760
acagtgcagc ggctgctgcc tgtgctgtgt caggctcacg gcttgactcc agaacaggtg    8820
gtggctattg cttcccacga cgggggaaa  caggccctgg aaactgtgca gcgcctgctg    8880
ccagtgctgt gccaggctca cggcctcact cccgaacagg tggtggccat tgccagcaac    8940
aacggcggca agcaggccct ggaaaccgtg cagagactgc tgcccgtgct gtgccaggcc    9000
```

```
catggcctga cacctgaaca ggtggtggct atcgcctctc acgacggagg aaaacaggct    9060
ctggaaacag tgcagcggct gctgcctgtg ctgtgtcagg ctcacggctt gactccagaa    9120
caggtggtgg ctattgcttc ccacgacggg gggaaacagg ccctggaaac tgtgcagcgc    9180
ctgctgccag tgctgtgcca ggctcacgga ctgaccccg aacaggtggt ggccattgcc     9240
agcaacatcg gcggcaagca ggccctggaa accgtgcaga gactgctgcc cgtgctgtgc    9300
caggcccatg gcctgacacc tgaacaggtg gtggctatcg cctctaacaa cggaggaaaa    9360
caagcactcg agacagtgca gcggctgctg cctgtgctgt gtcaggctca cggcttgact    9420
ccagaacagg tggtggctat tgcttccaac ggcgggggga acaggccct ggaaactgtg     9480
cagcgcctgc tgccagtgct gtgccaggct cacgggctga cccccgaaca ggtggtggcc    9540
attgccagcc acgacggcgg caagcaggcc ctggaaaccg tgcagagact gctgcccgtg    9600
ctgtgccagg cccatggcct gacacctgaa caggtggtgg ctatcgcctc taatatcgga    9660
ggaaaacagg ctctggaaac agtgcagcgg ctgctgcctg tgctgtgtca ggctcacggc    9720
ttgactccac agcaggtcgt ggcaattgct agccacgacg gcggacggcc cgccctggag    9780
agcattgtgg cccagctgtc tagacctgat cctgccctgg ccgccctgac aaatgatcac    9840
ctggtggccc tggcctgtct gggaggcaga cctgccctgg atgccgtgaa aaaggactg    9900
cctcacgccc ctgccctgat aaaagaaca aatagaagaa tccccgagcg gacctctcac     9960
agagtggccg atcccagct ggtgaaatct gagctggagg agaagaagtc tgagctgaga    10020
cacaagctga agtacgtgcc tcacgagtac atcgagctga tcgagatcgc cagaaatagc    10080
acccaggata gaatcctgga gatgaaggtg atggagttct tcatgaaagt gtacggctac    10140
agaggaaagc atctgggagg aagcagaaaa cctgacggag ccatttatac agtgggcagc    10200
cctatcgatt atgcgtgat cgtggataca aaggcctaca gcggaggcta caatctgcct    10260
attggacagg ccgatgagat gcagagatac gtggaggaga accaaaccag gaacaagcat    10320
atcaacccta cgagtggtg gaaggtgtac ccttctagcg tgaccgagtt caagttcctg    10380
tttgtgagcg gccacttcaa gggcaattat aaggcccagc tgaccaggct gaaccacatc    10440
acaaattgta atggcgccgt gctgtctgtg gaggaactgc tgattggagg agagatgatt    10500
aaggccggaa cactgacact ggaggaggtg agaagaaagt tcaacaacgg cgagatcaac    10560
ttctgaaagc ttgatcgttc aaacatttgg caataaagtt tcttaagatt gaatcctgtt    10620
gccggtcttg cgatgattat catataattt ctgttgaatt acgttaagca tgtaataatt    10680
aacatgtaat gcatgacgtt atttatgaga tgggttttta tgattagagt cccgcaatta    10740
tacatttaat acgcgataga aaacaaaata tagcgcgcaa actaggataa attatcgcgc    10800
gcggtgtcat ctatgttact agatcttcga agacggaccg cgcctgcagt gcagcgtgac    10860
ccggtcgtgc ccctctctag agataatgag cattgcatgt ctaagttata aaaaattacc    10920
acatattttt tttgtcacac ttgtttgaag tgcagtttat ctatctttat acatatattt    10980
aaactttact ctacgaataa tataatctat agtactacaa taatatcagt gttttagaga    11040
atcatataaa tgaacagtta gacatggtct aaaggacaat tgagtatttt gacaacagga    11100
ctctacagtt ttatcttttt agtgtgcatg tgttctcctt ttttttgca aatagcttca     11160
cctatataat acttcatcca ttttattagt acatccattt agggtttagg gttaatggtt    11220
tttatagact aatttttta gtacatctat tttattctat tttagcctct aaattaagaa    11280
aactaaaact ctatttagt ttttatttt aataatttag atataaaata gaataaaata     11340
aagtgactaa aaattaaaca atacccttt aagaattaa aaaaactaag gaaacatttt     11400
```

```
tcttgtttcg agtagataat gccagcctgt taaacgccgt cgacgagtct aacggacacc    11460
aaccagcgaa ccagcagcgt cgcgtcgggc caagcgaagc agacggcacg gcatctctgt    11520
cgctgcctct ggaccsctct cgagagttcc gctccaccgt tggacttgct ccgctgtcgg    11580
catccagaaa ttgcgtggcg gagcggcaga cgtgagccgg cacggcaggc ggcctcctcc    11640
tcctctcacg gcaccggcag ctacggggga ttcctttccc accgctcctt cgctttccct    11700
tcctcgcccg ccgtaataaa tagacacccc ctccacaccc tctttcccca acctcgtgtt    11760
gttcggagcg cacacacaca caaccagatc tcccccaaat ccacccgtcg gcacctccgc    11820
ttcaaggtac gccgctcgtc ctccccccc cccctctcta ccttctctag atcggcgttc    11880
cggtccatgg ttagggcccg gtagttctac ttctgttcat gtttgtgtta gatccgtgtt    11940
tgtgttagat ccgtgctgct agcgttcgta cacggatgcg acctgtacgt cagacacgtt    12000
ctgattgcta acttgccagt gtttctcttt ggggaatcct gggatggctc tagccgttcc    12060
gcagacggga tcgatttcat gatttttttt gtttcgttgc atagggtttg gtttgccctt    12120
ttcctttatt tcaatatatg ccgtgcactt gtttgtcggg tcatcttttc atgcttttt     12180 ttgtcttggt tgtgatgatg tggtctggtt gggcggtcgt tctagatcgg agtagaattc    12240
tgtttcaaac tacctggtgg atttattaat tttggatctg tatgtgtgtg ccatacatat    12300
tcatagttac gaattgaaga tgatggatgg aaatatcgat ctaggatagg tatacatgtt    12360
gatgcgggtt ttactgatgc atatacagag atgcttttg ttcgcttggt tgtgatgatg    12420
tggtgtggtt gggcggtcgt tcattcgttc tagatcggag tagaatactg tttcaaacta    12480
cctggtgtat ttattaattt tggaactgta tgtgtgtgtc atacatcttc atagttacga    12540
gtttaagatg gatggaaata tcgatctagg ataggtatac atgttgatgt gggttttact    12600
gatgcatata catgatggca tatgcagcat ctattcatat gctctaacct tgagtaccta    12660
tctattataa taaacaagta tgttttataa ttattttgat cttgatatac ttggatgatg    12720
gcatatgcag cagctatatg tggattttt tagccctgcc ttcatacgct atttatttgc    12780
ttggtactgt ttcttttgtc gatgctcacc ctgttgtttg gtgttacttc tgcagggatc    12840
cggcagcagc catgcagaag ctgatcaaca gcgtgcagaa ctacgcctgg ggcagcaaga    12900
ccgccctgac cgagctgtac ggcatggaga accccagcag ccagcccatg gccgagctgt    12960
ggatgggcgc ccaccccaag agcagcagcc gcgtgcagaa cgccgccggc gacatcgtga    13020
gcctgcgcga cgtgatcgag agcgacaaga gcaccctgct gggcgaggcc gtggccaagc    13080
gcttcggcga gctgccctc ctgttcaagg tgctgtgcgc cgcccagccc ctgagcatcc    13140
aggtgcaccc caacaagcac aacagcgaga tcggcttcgc caaggagaac gccgccggca    13200
tccccatgga cgccgccgag cgcaactaca aggaccccaa ccacaagccc gagctggtgt    13260
tcgccctgac ccccttcctg gccatgaacg ccttccgcga gttcagcgag atcgtgagcc    13320
tgctgcagcc cgtggccggc gcccacccg ccatcgccca cttcctgcag cagcccgacg    13380
ccgagcgcct gagcgagctg ttcgccagcc tgctgaacat gcagggcgag gagaagagcc    13440
gcgccctggc catcctgaag agcgccctgg acagccagca gggcgagccc tggcagacca    13500
tccgcctgat cagcgagttc taccccgagg acagcggcct gttcagcccc ctgctgctga    13560
acgtggtgaa gctgaacccc ggcgaggcca tgttcctgtt cgccgagacc ccccacgcct    13620
acctgcaggg cgtggccctg gaggtgatgg ccaacagcga caacgtgctg cgcgccggcc    13680
tgacccccaa gtacatcgac atccccgagc tggtggccaa cgtgaagttc gaggccaagc    13740
```

```
ccgccaacca gctgctgacc cagcccgtga agcagggcgc cgagctggac ttccccatcc  13800
ccgtggacga cttcgccttc agcctgcacg acctgagcga caaggagacc accatcagcc  13860
agcagagcgc cgccatcctg ttctgcgtgg agggcgacgc caccctgtgg aagggcagcc  13920
agcagctgca gctgaagccc ggcgagagcc ccttcatcgc cgccaacgag agccccgtga  13980
ccgtgaaggg ccacggccgc ctggcccgcg tgtacaacaa gctgtgatag gagctcgatc  14040
cgtcgacctg cagatcgttc aaacatttgg caataaagtt tcttaagatt gaatcctgtt  14100
gccggtcttg cgatgattat catataattt ctgttgaatt acgttaagca tgtaataatt  14160
aacatgtaat gcatgacgtt atttatgaga tgggttttta tgattagagt cccgcaatta  14220
tacatttaat acgcgataga aaacaaaata tagcgcgcaa actaggataa attatcgcgc  14280
gcggtgtcat ctatgttact agatcggcgc ccgcaattg aagtttgggc ggccagcatg  14340
gccgtatccg caatgtgtta ttaagttgtc taagcgtcaa tttgtttaca ccacaatata  14400
tcctgccacc agccagccaa cagctccccg accggcagct cggcacaaaa tcaccactcg  14460
atacaggcag cccatcagaa ttaattctca tgtttgacag cttatcatcg actgcacggt  14520
gcaccaatgc ttctggcgtc aggcagccat cggaagctgt ggtatggctg tgcaggtcgt  14580
aaatcactgc ataattcgtg tcgctcaagg cgcactcccg ttctggataa tgttttttgc  14640
gccgacatca taacggttct ggcaaatatt ctgaaatgag ctgttgacaa ttaatcatcc  14700
ggctcgtata atgtgtggaa ttgtgagcgg ataacaattt cacacaggaa acagaccatg  14760
agggaagcgt tgatcgccga agtatcgact caactatcag aggtagttgg cgtcatcgag  14820
cgccatctcg aaccgacgtt gctggccgta catttgtacg gctccgcagt ggatggcggc  14880
ctgaagccac acagtgatat tgatttgctg gttacggtga ccgtaaggct tgatgaaaca  14940
acgcggcgag ctttgatcaa cgaccttttg gaaacttcgg cttcccctgg agagagcgag  15000
attctccgcg ctgtagaagt caccattgtt gtgcacgacg acatcattcc gtggcgttat  15060
ccagctaagc gcgaactgca atttggagaa tggcagcgca atgacattct tgcaggtatc  15120
ttcgagccag ccacgatcga cattgatctg gctatcttgc tgacaaaagc aagagaacat  15180
agcgttgcct tggtaggtcc agcggcggag gaactctttg atccggttcc tgaacaggat  15240
ctatttgagg cgctaaatga aaccttaacg ctatggaact cgccgcccga ctgggctggc  15300
gatgagcgaa atgtagtgct tacgttgtcc cgcatttggt acagcgcagt aaccggcaaa  15360
atcgcgccga aggatgtcgc tgccgactgg gcaatggagc gcctgccggc ccagtatcag  15420
cccgtcatac ttgaagctag gcaggcttat cttggacaag aagatcgctt ggcctcgcgc  15480
gcagatcagt tggaagaatt tgttcactac gtgaaaggcg agatcaccaa agtagtcggc  15540
aaataaagct ctagtggatc tccgtacccg gggatctggc tcgcggcgga cgcacgacgc  15600
cggggcgaga ccataggcga tctcctaaat caatagtagc tgtaacctcg aagcgtttca  15660
cttgtaacaa cgattgagaa tttttgtcat aaaattgaaa tacttggttc gcattttgt  15720
catccgcggt cagccgcaat tctgacgaac tgcccattta gctggagatg attgtacatc  15780
cttcacgtga aaatttctca agcgctgtga caagggttc agattttaga ttgaaaggtg  15840
agccgttgaa acacgttctt cttgtcgatg acgacgtcgc tatgcggcat cttattattg  15900
aataccttac gatccacgcc ttcaaagtga ccgcggtagc cgacagcacc cagttcacaa  15960
gagtactctc ttccgcgacg gtcgatgtcg tggttgttga tctagattta ggtcgtgaag  16020
atgggctcga gatcgttcgt aatctggcgg caaagtctga tattccaatc ataattatca  16080
gtggcgaccg ccttgaggag acggataaag ttgttgcact cgagctagga gcaagtgatt  16140
```

```
ttatcgctaa gccgttcagt atcagagagt ttctagcacg cattcgggtt gccttgcgcg   16200
tgcgccccaa cgttgtccgc tccaaagacc gacggtcttt ttgttttact gactggacac   16260
ttaatctcag gcaacgtcgc ttgatgtccg aagctggcgg tgaggtgaaa cttacggcag   16320
gtgagttcaa tcttctcctc gcgttttag aaaaccccg cgacgttcta tcgcgcgagc    16380
aacttctcat tgccagtcga gtacgcgacg aggaggttta tgacaggagt atagatgttc   16440
tcattttgag gctgcgccgc aaacttgagg cagatccgtc aagccctcaa ctgataaaaa   16500
cagcaagagg tgccggttat ttctttgacg cggacgtgca ggtttcgcac gggggacga    16560
tggcagcctg agccaattcc cagatccccg aggaatcggc gtgagcggtc gcaaaccatc   16620
cggcccggta caaatcggcg cggcgctggg tgatgacctg gtggagaagt tgaaggccgc   16680
gcaggccgcc cagcggcaac gcatcgaggc agaagcacgc cccggtgaat cgtggcaagc   16740
ggccgctgat cgaatccgca aagaatcccg gcaaccgccg gcagccggtg cgccgtcgat   16800
taggaagccg cccaagggcg acgagcaacc agatttttc gttccgatgc tctatgacgt    16860
gggcacccgc gatagtcgca gcatcatgga cgtggccgtt ttccgtctgt cgaagcgtga   16920
ccgacgagct ggcgaggtga tccgctacga gcttccagac gggcacgtag aggttttccgc  16980
agggccggcc ggcatggcca gtgtgtggga ttacgacctg gtactgatgg cggtttccca   17040
tctaaccgaa tccatgaacc gataccggga agggaaggga gacaagcccg gccgcgtgtt   17100
ccgtccacac gttgcggacg tactcaagtt ctgccggcga gccgatggcg gaaagcagaa   17160
agacgacctg gtagaaacct gcattcggtt aaacaccacg cacgttgcca tgcagcgtac   17220
gaagaaggcc aagaacggcc gcctggtgac ggtatccgag ggtgaagcct tgattagccg   17280
ctacaagatc gtaaagagcg aaaccgggcg gccggagtac atcgagatcg agctagctga   17340
ttggatgtac cgcgagatca cagaaggcaa gaacccggac gtgctgacgg ttcaccccga   17400
ttacttttg atcgatcccg gcatcggccg ttttctctac cgcctggcac gccgcgccgc    17460
aggcaaggca gaagccagat ggttgttcaa gacgatctac gaacgcagtg gcagcgccgg   17520
agagttcaag aagttctgtt tcaccgtgcg caagctgatc gggtcaaatg acctgccgga   17580
gtacgatttg aaggaggagg cggggcaggc tggcccgatc ctagtcatgc gctaccgcaa   17640
cctgatcgag ggcgaagcat ccgccggttc ctaatgtacg gagcagatgc tagggcaaat   17700
tgccctagca ggggaaaaag gtcgaaaagg tctctttcct gtggatagca cgtacattgg   17760
gaacccaaag ccgtacattg ggaaccggaa cccgtacatt gggaaccaa agccgtacat    17820
tgggaaccgg tcacacatgt aagtgactga tataaaagag aaaaaaggcg attttccgc    17880
ctaaaactct ttaaaactta ttaaaactct taaaacccgc ctggcctgtg cataactgtc   17940
tggccagcgc acagccgaag agctgcaaaa agcgcctacc cttcggtcgc tgcgctccct   18000
acgccccgcc gcttcgcgtc ggcctatcgc ggccgctggc cgctcaaaaa tggctggcct   18060
acggccaggc aatctaccag ggcgcggaca agccgcgccg tcgccactcg accgccggcg   18120
ctgaggtctg cctcgtgaag aaggtgttgc tgactcatac caggcctgaa tcgccccatc   18180
atccagccag aaagtgaggg agccacggtt gatgagagct tgttgtagg tggaccagtt    18240
ggtgattttg aacttttgct ttgccacgga acggtctgcg ttgtcgggaa gatgcgtgat   18300
ctgatccttc aactcagcaa agttcgatt tattcaacaa agccgccgtc ccgtcaagtc    18360
agcgtaatgc tctgccagtg ttacaaccaa ttaaccaatt ctgattagaa aaactcatcg   18420
agcatcaaat gaaactgcaa tttattcata tcaggattat caataccata tttttgaaaa   18480
```

```
agccgtttct gtaatgaagg agaaaactca ccgaggcagt tccataggat ggcaagatcc    18540
tggtatcggt ctgcgattcc gactcgtcca acatcaatac aacctattaa tttcccctcg    18600
tcaaaaataa ggttatcaag tgagaaatca ccatgagtga cgactgaatc cggtgagaat    18660
ggcaaaagct ctgcattaat gaatcggcca acgcgcgggg agaggcggtt tgcgtattgg    18720
gcgctcttcc gcttcctcgc tcactgactc gctgcgctcg gtcgttcggc tgcggcgagc    18780
ggtatcagct cactcaaagg cggtaatacg gttatccaca gaatcagggg ataacgcagg    18840
aaagaacatg tgagcaaaag gccagcaaaa ggccaggaac cgtaaaaagg ccgcgttgct    18900
ggcgtttttc cataggctcc gcccccctga cgagcatcac aaaaatcgac gctcaagtca    18960
gaggtggcga acccgacag gactataaag ataccaggcg tttccccctg gaagctccct    19020
cgtgcgctct cctgttccga ccctgccgct taccggatac ctgtccgcct ttctcccttc    19080
gggaagcgtg gcgctttctc atagctcacg ctgtaggtat ctcagttcgg tgtaggtcgt    19140
tcgctccaag ctgggctgtg tgcacgaacc ccccgttcag cccgaccgct gcgccttatc    19200
cggtaactat cgtcttgagt ccaacccggt aagacacgac ttatcgccac tggcagcagc    19260
cactggtaac aggattagca gagcgaggta tgtaggcggt gctacagagt tcttgaagtg    19320
gtggcctaac tacggctaca ctagaagaac agtatttggt atctgcgctc tgctgaagcc    19380
agttaccttc ggaaaaagag ttggtagctc ttgatccggc aaacaaacca ccgctggtag    19440
cggtggtttt tttgtttgca agcagcagat tacgcgcaga aaaaaggat ctcaagaaga    19500 tcctttgatc ttttctacgg ggtctgacgc tcagtggaac gaaaactcac gttaagggat    19560
tttggtcatg agattatcaa aaaggatctt cacctagatc cttttgatcc ggaatta       19617
```

<210> SEQ ID NO 6
<211> LENGTH: 55
<212> TYPE: DNA
<213> ORGANISM: Artificial Sequence
<220> FEATURE:
<223> OTHER INFORMATION: target sequence for the TALEN of 22808

<400> SEQUENCE: 6

```
tccagggtca acgtggagac agggaggtac gaaccggtga ctggcgaagg aagca                55
```

<210> SEQ ID NO 7
<211> LENGTH: 15722
<212> TYPE: DNA
<213> ORGANISM: Artificial Sequence
<220> FEATURE:
<223> OTHER INFORMATION: vector 23123
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator

```
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmPLAIIA
<220> FEATURE:
<221> NAME/KEY: misc_feature
<222> LOCATION: (6927)..(7031)
<223> OTHER INFORMATION: rsgRNAZmPLAIIA02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 7
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc cccctcctcg     480
atatctccgc ggcgacctct ggcttttttcc gcggaattgc gcggtgggga cggattccac     540
gagaccgcga cgcaaccgcc tctcgccgct gggcccaca ccgctcggtg ccgtagcctc      600
acgggactct ttctccctcc tccccgtta taaattggct tcatcccctc cttgcctcat      660
ccatccaaat cccagtcccc aatcccatcc cttcgtagga gaaattcatc gaagctaagc     720
gaatcctcgc gatcctctca aggtactgcg agttttcgat ccccctctcg acccctcgta     780
```

```
tgtttgtgtt tgtcgtagcg tttgattagg tatgctttcc ctgtttgtgt tcgtcgtagc      840
gtttgattag gtatgctttc cctgttcgtg ttcatcgtag tgtttgatta ggtcgtgtga      900
ggcgatggcc tgctcgcgtc cttcgatctg tagtcgattt gcgggtcgtg gtgtagatct      960
gcgggctgtg atgaagttat ttggtgtgat ctgctcgcct gattctgcgg gttggctcga     1020
gtagatatga tggttggacc ggttggttcg tttaccgcgc tagggttggg ctgggatgat     1080
gttgcatgcg ccgttgcgcg tgatcccgca gcaggacttg cgtttgattg ccagatctcg     1140
ttacgattat gtgatttggt ttggactttt tagatctgta gcttctgctt atgtgccaga     1200
tgcgcctact gctcatatgc ctgatgataa tcataaatgg ctgtggaact aactagttga     1260
ttgcggagtc atgtatcagc tacaggtgta gggactagct acaggtgtag ggacttgcgt     1320
ctaattgttt ggtcctttac tcatgttgca attatgcaat ttagtttaga ttgtttgttc     1380
cactcatcta ggctgtaaaa gggacactgc ttagattgct gtttaatctt tttagtagat     1440
tatattatat tggtaactta ttaccccctat tacatgccat acgtgacttc tgctcatgcc     1500
tgatgataat catagatcac tgtggaatta attagttgat tgttgaatca tgtttcatgt     1560
acataccacg gcacaattgc ttagttcctt aacaaatgca aatttttactg atccatgtat     1620 gatttgcgtg gttctctaat gtgaaatact atagctactt gttagtaaga atcaggttcg     1680
tatgcttaat gctgtatgtg ccttctgctc atgcctgatg ataatcatat atcactggaa     1740
ttaattagtt gatcgtttaa tcatatatca agtacatacc atgccacaat ttttagtcac     1800
ttaacccatg cagattgaac tggtccctgc atgttttgct aaattgttct attctgatta     1860
gaccatatat catgtatttt ttttttggtaa tggttctctt attttaaatg ctatatagtt     1920
ctggtacttg ttagaaagat ctgcttcata gtttagttgc ctatccctcg aattaggatg     1980
ctgagcagct gatcctatag cttttgtttca tgtatcaatt cttttgtgtt caacagtcag     2040
tttttgttag attcattgta acttatggtc gcttactctt ctggtcctca atgcttgcag     2100
gatcgcggcc gctcatatgg acaagaagta cagcatcggc ctggacatcg gcaccaacag     2160
cgtgggctgg gccgtgatca ccgacgagta caaggtgccg agcaagaagt tcaaggtgct     2220
gggcaacacc gacaggcaca gcatcaagaa gaacctgatc ggcgccctgc tgttcgacag     2280
cggcgagacc gccgaggcca ccaggctgaa gaggaccgcc aggaggaggt acaccaggag     2340
gaagaacagg atctgctacc tgcaggagat cttcagcaac gagatggcca aggtggacga     2400
cagcttcttc cacaggctgg aggagagctt cctggtggag gaggacaaga agcacgagag     2460
gcacccgatc ttcggcaaca tcgtggacga ggtggcctac cacgagaagt acccgaccat     2520
ctaccacctg aggaagaagc tggtggacag caccgacaag gccgacctga ggctgatcta     2580
cctggccctg gcccacatga tcaagttcag gggccacttc ctgatcgagg gcgacctgaa     2640
cccggacaac agcgacgtgg acaagctgtt catccagctg gtgcagacct acaaccagct     2700
gttcgaggag aacccgatca cgcagcggcg cgtggacgcc aaggccatcc tgagcgccag     2760
gctgagcaag agcaggaggc tggagaacct gatcgcccag ctgccgggcg agaagaagaa     2820
cggcctgttc ggcaacctga tcgccctgag cctgggcctg acccccgaact tcaagagcaa     2880 cttcgacctg gccgaggacg ccaagctgca gctgagcaag gacacctacg acgacgacct     2940
ggacaacctg ctggcccaga tcggcgacca gtacgccgac ctgttcctgg ccgccaagaa     3000
cctgagcgac gccatcctgc tgagcgacat cctgagggtg aacaccgaga tcaccaaggc     3060
cccgctgagc gccagcatga tcaagaggta cgacgagcac caccaggacc tgaccctgct     3120
gaaggccctg gtgaggcagc agctgccgga gaagtacaag gagatcttct tcgaccagag     3180
```

```
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480
ggccagggc aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga aaggtgctg ccgaagcaca gcctgctgta   3660
cgagtacttc accgtgtaca acgagctgac caaggtgaag tacgtgaccg agggcatgag   3720
gaagccggcc ttcctgagcg cgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac aggagatga tcgaggagag   4020
gctgaagacc tacgccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga agggccagaa   4440
gaacagcagg gagaggatga agaggatcga ggagggcatc aaggagctgg gcagccagat   4500
cctgaaggag cacccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacagggg caagagcgac aacgtgccga gcgaggaggt   4740
ggtgaagaag atgaaaaact actgaggca gctgctgaac gccaagctga tcacccagag   4800
gaagttcgac aacctgacca aggccgagag ggcggcctg agcgagctgg acaaggccgg   4860
cttcattaaa aggcagctgg tggagaccag gcagatcacc aagcacgtgg cccagatcct   4920
ggacagcagg atgaacacca agtacgacga aacgacaag ctgatcaggg aggtgaaggt   4980
gatcacccg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaagtacc gaagctgga gagcgagttc gtgtacgcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
```

```
cagcccgacc gtggcctaca gcgtgctggt ggtggccaag gtggagaagg gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggccctg ccgagcaagt acgtgaactt    5820
cctgtacctg gccagccact acgagaagct gaagggcagc ccggaggaca cgagcagaa    5880 gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcaggagca ggccgagaac atcatccacc tgttcaccct    6060
gaccaacctg ggcgccccgg ccgccttcaa gtacttcgac accaccatcg acaggaagag    6120
gtacaccagc accaaggagg tgctggacgc caccctgatc accagagca tcaccggcct    6180 gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag gaccatagc    6660 acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagggt caacgtggag acaggggttt tagagctaga    6960
aatagcaagt taaaataagg ctagtccgtt atcaacttga aaaagtggca ccgagtcggt    7020
gctttttttt tcggaccgcg cctgcagtgc agcgtgaccc ggtcgtgccc ctctctagag    7080
ataatgagca ttgcatgtct aagttataaa aaattaccac atatttttt tgtcacactt    7140 gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtattttga caacaggact ctacagtttt atctttttag    7320
tgtgcatgtg ttctccttt tttttgcaaa tagcttcacc tatataatac ttcatccatt    7380
ttattagtac atccatttag ggtttagggt taatggtttt tatagactaa ttttttttagt    7440 acatctattt tattctattt tagcctctaa attaagaaaa ctaaaactct attttagttt    7500
ttttatttaa taatttagat ataaaataga ataaaataaa gtgactaaaa attaaacaaa    7560
taccctttaa gaaattaaaa aaactaagga acattttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg accccctctcg    7740 agagttccgc tccaccgttg gacttgctcc gctgtcggca tccagaaatt gcgtggcgga    7800
gcggcagacg tgagccggca cggcaggcgg cctcctcctc ctctcacggc accggcagct    7860 acggggatt cctttcccac cgctccttcg ctttccttc ctcgcccgcc gtaataaata    7920
```

```
gacaccccct ccacaccctc tttccccaac ctcgtgttgt tcggagcgca cacacacaca   7980
accagatctc ccccaaatcc acccgtcggc acctccgctt caaggtacgc cgctcgtcct   8040
cccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctctttgg ggaatcctgg gatggctcta gccgttccgc agacgggatc gatttcatga   8280 tttttttgt ttcgttgcat agggtttggt ttgccctttt cctttatttc aatatatgcc   8340
gtgcacttgt ttgtcgggtc atcttttcat gctttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gcttttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gattttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcacg tgatcgagag   9240 cgacaagagc accctgctgg gcgaggccgt ggccaagcgc ttcggcgagc tgcccttcct   9300
gttcaaggtg ctgtgcgccg cccagcccct gagcatccag gtgcaccca acaagcacaa   9360 cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
ccaccccgcc atcgcccact tcctgcagca gcccgacgcc gagcgcctga gcgagctgtt   9600
cgccagcctg ctgaacatgc agggcgagga gaagagccgc gccctggcca tcctgaagag   9660
cgccctggac agccagcagg gcgagccctg gcagaccatc gcctgatca gcgagttcta   9720 ccccgaggac agcggcctgt tcagcccct gctgctgaac gtggtgaagc tgaacccgg   9780 cgaggccatg ttcctgttcg ccgagacccc ccacgcctac ctgcagggcg tggccctgga   9840
ggtgatggca acagcgaca acgtgctgcg cgccggcctg accccaagt acatcgacat   9900 ccccgagctg gtggccaacg tgaagttcga ggccaagccc gccaaccagc tgctgaccca   9960
gcccgtgaag cagggcgccg agctggactt ccccatcccc gtggacgact cgccttcag  10020 cctgcacgac ctgagcgaca aggagaccac catcagccag cagagcgccg ccatcctgtt  10080
ctgcgtggag ggcgacgcca ccctgtggaa gggcagccag cagctgcagc tgaagcccgg  10140
cgagagcgcc ttcatcgccg ccaacgagag ccccgtgacc gtgaagggcc acggccgcct  10200
ggcccgcgtg tacaacaagc tgtgatagga gctcgatccg tcgacctgca gatcgttcaa  10260
```

```
acatttggca ataaagtttc ttaagattga atcctgttgc cggtcttgcg atgattatca   10320
tataatttct gttgaattac gttaagcatg taataattaa catgtaatgc atgacgttat   10380
ttatgagatg ggtttttatg attagagtcc cgcaattata catttaatac gcgatagaaa   10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
aagttgtcta agcgtcaatt tgtttacacc acaatatatc ctgccaccag ccagccaaca   10620 gctcccccgac cggcagctcg gcacaaaatc accactcgat acaggcagcc catcagaatt   10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg ttttttgcgc cgacatcata acggttctgg   10860
caaatattct gaaatgagct gttgacaatt aatcatccgg ctcgtataat gtgtggaatt   10920
gtgagcggat aacaatttca cacaggaaac agaccatgag ggaagcgttg atcgccgaag   10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160 acctttgga aacttcggct tcccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcgc agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg gggcgagacc ataggcgatc   11820
tcctaaatca atagtagctg taacctcgaa gcgtttcact tgtaacaacg attgagaatt   11880
tttgtcataa aattgaaata cttggttcgc attttttgtca tccgcggtca gccgcaattc   11940
tgacgaactg cccatttagc tggagatgat tgtacatcct tcacgtgaaa atttctcaag   12000
cgctgtgaac aagggttcag attttagatt gaaaggtgag ccgttgaaac acgttcttct   12060
tgtcgatgac gacgtcgcta tgcggcatct tattattgaa taccttacga tccacgcctt   12120
caaagtgacc gcggtagccg acagcaccca gttcacaaga gtactctctt ccgcgacggt   12180
cgatgtcgtg gttgttgatc tagatttagg tcgtgaagat gggctcgagc taggagcaag   12240 tgatttatc gctaagccgt tcagtatcag agagtttcta gcacgcattc gggttgcctt   12300
gcgcgtgcgc cccaacgttg tccgctccaa agaccgacgg tctttttgtt ttactgactg   12360
gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
```

```
gacgatggca gcctgagcca attcccagat ccccgaggaa tcggcgtgag cggtcgcaaa   12720
ccatccggcc cggtacaaat cggcgcggcg ctgggtgatg acctggtgga gaagttgaag   12780
gccgcgcagg ccgcccagcg gcaacgcatc gaggcagaag cacgcccgg tgaatcgtgg    12840 caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
cgtgaccgac gagctggcga ggtgatccgc tacgagcttc cagacgggca cgtagaggtt   13080
tccgcagggc cggccggcat ggccagtgtg tgggattacg acctggtact gatggcggtt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcagggga aaaggtcgaa aaggtctctt ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actctttaaa acttattaaa actcttaaaa cccgcctggc ctgtgcataa   14040
ctgtctggcc agcgcacagc cgaagagctg caaaaagcgc ctacccttcg gtcgctgcgc   14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acggaacggt ctgcgttgtc gggaagatgc   14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatattttt   14580 gaaaagccg tttctgtaat gaaggagaaa actcaccgag gcagttccat aggatggcaa    14640
gatcctggta tcggtctgcg attccgactc gtccaacatc aatacaacct attaatttcc   14700
cctcgtcaaa aataaggtta tcaagtgaga atcaccatg agtgacgact gaatccggtg    14760
agaatggcaa aagctctgca ttaatgaatc ggccaacgcg cggggagagg cggtttgcgt   14820
attgggcgct cttccgcttc ctcgctcact gactcgctgc gctcggtcgt tcggctgcgg   14880
cgagcggtat cagctcactc aaaggcggta atacggttat ccacagaatc agggggataac   14940 gcaggaaaga acatgtgagc aaaaggccag caaaaggcca ggaaccgtaa aaaggccgcg   15000
```

-continued

```
ttgctggcgt ttttccatag ctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                   15722
```

<210> SEQ ID NO 8
<211> LENGTH: 20
<212> TYPE: DNA
<213> ORGANISM: Artificial Sequence
<220> FEATURE:
<223> OTHER INFORMATION: for editing MTL

<400> SEQUENCE: 8
gggtcaacgt ggagacaggg                                                20

<210> SEQ ID NO 9
<211> LENGTH: 41
<212> TYPE: DNA
<213> ORGANISM: Zea mays

<400> SEQUENCE: 9
agggtcaacg tggagacagg gaggtacgaa ccggtgactg g                         41

<210> SEQ ID NO 10
<211> LENGTH: 45
<212> TYPE: DNA
<213> ORGANISM: Zea mays

<400> SEQUENCE: 10
agggtcaacg tggagacagg cgaggaggta cgaaccggtg actgg                     45

<210> SEQ ID NO 11
<211> LENGTH: 42
<212> TYPE: DNA
<213> ORGANISM: Artificial Sequence
<220> FEATURE:
<223> OTHER INFORMATION: mutated MTL

<400> SEQUENCE: 11
agggtcaacg tggagacaag ggaggtacga accggtgact gg                        42

<210> SEQ ID NO 12
<211> LENGTH: 28
<212> TYPE: DNA
<213> ORGANISM: Artificial Sequence
<220> FEATURE:
<223> OTHER INFORMATION: mutated MTL portion

<400> SEQUENCE: 12

```
agggtcaacg tggagaaccg gtgactgg                                    28

<210> SEQ ID NO 13
<211> LENGTH: 40
<212> TYPE: DNA
<213> ORGANISM: Artificial Sequence
<220> FEATURE:
<223> OTHER INFORMATION: mutated MTL portion

<400> SEQUENCE: 13
agggtcaacg tggagacggg aggtacgaac cggtgactgg                       40

<210> SEQ ID NO 14
<211> LENGTH: 28
<212> TYPE: DNA
<213> ORGANISM: Artificial Sequence
<220> FEATURE:
<223> OTHER INFORMATION: mutated MTL portion

<400> SEQUENCE: 14
agggtcaacg tggagaaccg gtgactgg                                    28

<210> SEQ ID NO 15
<211> LENGTH: 42
<212> TYPE: DNA
<213> ORGANISM: Artificial Sequence
<220> FEATURE:
<223> OTHER INFORMATION: mutated MTL portion

<400> SEQUENCE: 15
agggtcaacg tggagacaag ggaggtacga accggtgact gg                    42

<210> SEQ ID NO 16
<211> LENGTH: 40
<212> TYPE: DNA
<213> ORGANISM: Artificial Sequence
<220> FEATURE:
<223> OTHER INFORMATION: mutated MTL portion

<400> SEQUENCE: 16
agggtcaacg tggagacggg aggtacgaac cggtgactgg                       40

<210> SEQ ID NO 17
<211> LENGTH: 41
<212> TYPE: DNA
<213> ORGANISM: Artificial Sequence
<220> FEATURE:
<223> OTHER INFORMATION: unmutated MTL portion

<400> SEQUENCE: 17
agggtcaacg tggagacagg gaggtacgaa ccggtgactg g                     41

<210> SEQ ID NO 18
<211> LENGTH: 28
<212> TYPE: DNA
<213> ORGANISM: Artificial Sequence
<220> FEATURE:
<223> OTHER INFORMATION: mutated MTL portion

<400> SEQUENCE: 18
agggtcaacg tggagaaccg gtgactgg                                    28

<210> SEQ ID NO 19
<211> LENGTH: 1371
<212> TYPE: DNA
```

<213> ORGANISM: Zea mays

<400> SEQUENCE: 19

```
agttcatcac taatcacact tattgttccc tcgacgagta tctagctagc tcattaatcg      60
atcaatcggg gtgtgcggtc gaaggcggca atggcgagct actcgtcgcg cgtccatgc     120
aatacctgta gcacgaaggc gatggccggg agcgtggtcg gcgagcccgt cgtgctgggg    180
cagagggtga cggtgctgac ggtggacggc ggcggcgtcc ggggtctcat cccgggaacc    240
atcctcgcct tcctcgaggc caggctgcag gagctggacg gaccggaggc gaggctggcg    300
gactacttcg actacatcgc cggaaccagc accggcggtc tcatcaccgc catgctcacc    360
gcgcccggca aggacaagcg gcctctctac gctgccaagg acatcaacca cttttacatg    420
gagaactgcc cgcgcatctt ccctcagaag agcaggcttg cggccgccat gtccgcgctg    480
aggaagccaa agtacaacgg caagtgcatg cgcagcctga ttaggagcat cctcggcgag    540
acgagggcca agagcacgcc tctgaagaac gctctgctct cggacgtgtg cattggcacg    600
tccgccgcgc cgacctacct cccggcgcac tacttccaga ctgaagacgc caacggcaag    660
gagcgcgaat acaacctcat cgacggcggt gtggcggcca acaacccgac gatggttgcg    720
atgacgcaga tcaccaaaaa gatgcttgcc agcaaggaca aggccgagga gctgtaccca    780
gtgaagccgt cgaactgccg caggttcctg gtgctgtcca tcgggacggg gtcgacgtcc    840
gagcagggcc tctacacggc gcggcagtgc tcccggtggg gtatctgccg gtggctccgc    900
aacaacggca tggccccccat catcgacatc ttcatggcgg ccagctcgga cctggtggac    960
atccacgtcg ccgcgatgtt ccagtcgctc cacagcgacg cgactacct gcgcatccag    1020
gacaactcgc tccgtggcgc cgcggccacc gtggacgcgg cgacgccgga gaacatgcgg   1080
acgtcgtcg ggatcgggga gcggatgctg cacagagggg tgtccagggt caacgtggag   1140
acagggaggt acgaaccggt gactggcgaa ggaagcaatg ccgatgccct cggtgggctc   1200
gctaggcagc tctccgagga gaggagaaca aggctcgcgc gccgcgtgtc tgccatcaac   1260
ccaagaggct ctagatgtgc gtcgtacgat atctaagaca agtggcttta ctgtcagtca   1320
catgcttgta aataagtaga ctttatttta ataaacata aaaatatata t              1371
```

```
<210> SEQ ID NO 20
<211> LENGTH: 15722
<212> TYPE: DNA
<213> ORGANISM: Artificial Sequence
<220> FEATURE:
<223> OTHER INFORMATION: vector 23397
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
```

-continued

```
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmVLHP
<220> FEATURE:
<221> NAME/KEY: misc_feature
<222> LOCATION: (6927)..(7031)
<223> OTHER INFORMATION: rsgRNAZmVLHP-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 20
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc cccctcctcg     480
atatctccgc ggcgacctct ggcttttttcc gcggaattgc gcggtgggga cggattccac    540
gagaccgcga cgcaaccgcc tctcgccgct gggcccaca ccgctcggtg ccgtagcctc      600
acgggactct ttctccctcc tccccgtta taaattggct tcatcccctc cttgcctcat      660
ccatccaaat cccagtcccc aatcccatcc cttcgtagga gaaattcatc gaagctaagc     720
gaatcctcgc gatcctctca aggtactgcg agttttcgat ccccctctcg accctcgta     780
```

```
tgtttgtgtt tgtcgtagcg tttgattagg tatgctttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga   1020
gtagatatga tggttggacc ggttggttcg tttaccgcgc tagggttggg ctgggatgat   1080
gttgcatgcg ccgttgcgcg tgatcccgca gcaggacttg cgtttgattg ccagatctcg   1140
ttacgattat gtgatttggt ttggactttt tagatctgta gcttctgctt atgtgccaga   1200
tgcgcctact gctcatatgc ctgatgataa tcataaatgg ctgtggaact aactagttga   1260
ttgcggagtc atgtatcagc tacaggtgta gggactagct acaggtgtag ggacttgcgt   1320
ctaattgttt ggtcctttac tcatgttgca attatgcaat ttagtttaga ttgtttgttc   1380
cactcatcta ggctgtaaaa gggacactgc ttagattgct gtttaatctt tttagtagat   1440
tatattatat tggtaactta ttaccccttat tacatgccat acgtgacttc tgctcatgcc   1500
tgatgataat catagatcac tgtggaatta attagttgat tgttgaatca tgtttcatgt   1560
acataccacg gcacaattgc ttagttcctt aacaaatgca aattttactg atccatgtat   1620
gatttgcgtg gttctctaat gtgaaatact atagctactt gttagtaaga atcaggttcg   1680
tatgcttaat gctgtatgtg ccttctgctc atgcctgatg ataatcatat atcactggaa   1740
ttaattagtt gatcgtttaa tcatatatca agtacatacc atgccacaat ttttagtcac   1800
ttaacccatg cagattgaac tggtccctgc atgttttgct aaattgttct attctgatta   1860
gaccatatat catgtatttt tttttggtaa tggttctctt atttaaatg ctatatagtt    1920
ctggtacttg ttagaaagat ctgcttcata gtttagttgc ctatccctcg aattaggatg   1980
ctgagcagct gatcctatag ctttgtttca tgtatcaatt cttttgtgtt caacagtcag   2040
tttttgttag attcattgta acttatggtc gcttactctt ctggtcctca atgcttgcag   2100
gatcgcggcc gctcatatgg acaagaagta cagcatcggc ctggacatcg gcaccaacag   2160
cgtgggctgg gccgtgatca ccgacgagta caaggtgccg agcaagaagt tcaaggtgct   2220
gggcaacacc gacaggcaca gcatcaagaa gaacctgatc ggcgccctgc tgttcgacag   2280
cggcgagacc gccgaggcca ccaggctgaa gaggaccgcc aggaggaggt acaccaggag   2340
gaagaacagg atctgctacc tgcaggagat cttcagcaac gagatggcca aggtggacga   2400
cagcttcttc cacaggctgg aggagagctt cctggtggag gaggacaaga agcacgagag   2460
gcacccgatc ttcggcaaca tcgtggacga ggtggcctac cacgagaagt acccgaccat   2520
ctaccacctg aggaagaagc tggtggacag caccgacaag gccgacctga ggctgatcta   2580
cctggccctg gcccacatga tcaagttcag gggccacttc ctgatcgagg gcgacctgaa   2640
cccggacaac agcgacgtgg acaagctgtt catccagctg gtgcagacct acaaccagct   2700
gttcgaggag aacccgatca cgccagcgg cgtggacgcc aaggccatcc tgagcgccag   2760
gctgagcaag agcaggaggc tggagaacct gatcgcccag ctgccgggcg agaagaagaa   2820
cggcctgttc ggcaacctga tcgccctgag cctgggcctg acccctgaact tcaagagcaa   2880
cttcgacctg gccgaggacg ccaagctgca gctgagcaag gacacctacg acgacgacct   2940
ggacaacctg ctggcccaga tcggcgacca gtacgccgac ctgttcctgg ccgccaagaa   3000
cctgagcgac gccatcctgc tgagcgacat cctgagggtg aacaccgaga tcaccaaggc   3060
cccgctgagc gccagcatga tcaagaggta cgacgagcac caccaggacc tgaccctgct   3120
gaaggccctg gtgaggcagc agctgccgga gaagtacaag gagatcttct cgaccagag   3180
```

```
caagaacggc tacgccggct acatcgacgg cggcgccagc caggaggagt tctacaagtt   3240
catcaagccg atcctggaga agatggacgg caccgaggag ctgctggtga agctgaacag   3300
ggaggacctg ctgaggaagc agaggacctt cgacaacggc agcatcccgc accagatcca   3360
cctgggcgag ctgcacgcca tcctgaggag gcaggaggac ttctacccgt tcctgaagga   3420
caacagggag aagatcgaga agatcctgac cttccgcatc ccgtactacg tgggcccgct   3480 ggccagggge aacagcaggt tcgcctggat gaccaggaag agcgaggaga ccatcacccc   3540
gtggaacttc gaggaggtgg tggacaaggg cgccagcgcc cagagcttca tcgagaggat   3600
gaccaacttc gacaagaacc tgccgaacga aaggtgctg ccgaagcaca gcctgctgta   3660
cgagtacttc accgtgtaca acgagctgac caaggtgaag tacgtgaccg agggcatgag   3720
gaagccggcc ttcctgagcg cgagcagaa gaaggccatc gtggacctgc tgttcaagac   3780
caacaggaag gtgaccgtga agcagctgaa ggaggactac ttcaagaaga tcgagtgctt   3840
cgacagcgtg gagatcagcg gcgtggagga caggttcaac gccagcctgg gcacctacca   3900
cgacctgctg aagatcatca aggacaagga cttcctggac aacgaggaga acgaggacat   3960
cctggaggac atcgtgctga ccctgaccct gttcgaggac aggagatga tcgaggagag   4020 gctgaagacc tacgcccacc tgttcgacga caaggtgatg aagcagctga agaggaggag   4080
gtacaccggc tggggcaggc tgagcaggaa gctgatcaac ggcatcaggg acaagcagag   4140
cggcaagacc atcctggact tcctgaagag cgacggcttc gccaacagga acttcatgca   4200
gctgatccac gacgacagcc tgaccttcaa ggaggacatc cagaaggccc aggtgagcgg   4260
ccagggcgac agcctgcacg agcacatcgc caacctggcc ggcagcccgg ccatcaagaa   4320
gggcatcctg cagaccgtga aggtggtgga cgagctggtg aaggtgatgg gcaggcacaa   4380
gccggagaac atcgtgatcg agatggccag ggagaaccag accacccaga gggccagaa   4440 gaacagcagg gagaggatga agaggatcga ggagggcatc aaggagctgg gcagccagat   4500
cctgaaggag caccccggtgg agaacaccca gctgcagaac gagaagctgt acctgtacta   4560
cctgcagaac ggcagggaca tgtacgtgga ccaggagctg gacatcaaca ggctgagcga   4620
ctacgacgtg gaccacatcg tgccgcagag cttcctgaag gacgacagca tcgacaacaa   4680
ggtgctgacc aggagcgaca agaacaggg caagagcgac aacgtgccga gcgaggaggt   4740
ggtgaagaag atgaaaaact actggaggca gctgctgaac gccaagctga tcacccagag   4800
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca gtacgacga aacgacaag ctgatcaggg aggtgaaggt   4980 gatcacccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacgcg actacaaggt   5160 gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
```

```
cagcccgacc gtggcctaca gcgtgctggt ggtggccaag gtggagaagg gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggccctg ccgagcaagt acgtgaactt    5820
cctgtacctg gccagccact acgagaagct gaagggcagc ccggaggaca cgagcagaa     5880 gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcaccct    6060
gaccaacctg ggcgccccgg ccgccttcaa gtacttcgac accaccatcg acaggaagag    6120
gtacaccagc accaaggagg tgctggacgc caccctgatc caccagagca tcaccggcct    6180
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggttttat gattagagtc ccgcaattat acatttaata cgcgatagaa     6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag gaccatagc     6660 acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagctg gagctgagct tccggggttt tagagctaga    6960
aatagcaagt taaaataagg ctagtccgtt atcaacttga aaaagtggca ccgagtcggt    7020
gctttttttt tcggaccgcg cctgcagtgc agcgtgaccc ggtcgtgccc ctctctagag    7080
ataatgagca ttgcatgtct aagtataaa aaattaccac atatttttt tgtcacactt      7140 gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtattttga caacaggact ctacagtttt atctttttag    7320
tgtgcatgtg ttctcctttt tttttgcaaa tagcttcacc tatataatac ttcatccatt    7380
ttattagtac atccatttag ggtttagggt taatggtttt tatagactaa ttttttttagt   7440 acatctattt tattctattt tagcctctaa attaagaaaa ctaaaactct attttagttt    7500
ttttatttaa taatttagat ataaaataga ataaaataaa gtgactaaaa attaaacaaa    7560
taccctttaa gaaattaaaa aaactaagga acattttttc ttgtttcgag tagataatgc    7620
cagcctgtta aacgccgtcg acgagtctaa cggacaccaa ccagcgaacc agcagcgtcg    7680
cgtcgggcca agcgaagcag acggcacggc atctctgtcg ctgcctctgg acccctctcg    7740
agagttccgc tccaccgttg gacttgctcc gctgtcggca tccagaaatt gcgtggcgga    7800
gcggcagacg tgagccggca cggcaggcgg cctcctcctc ctctcacggc accggcagct    7860 acggggggatt cctttcccac cgctccttcg ctttcccttc ctcgcccgcc gtaataaata    7920
```

```
gacacccct   ccacaccctc   tttccccaac   ctcgtgttgt   tcggagcgca   cacacacaca    7980
accagatctc   ccccaaatcc   acccgtcggc   acctccgctt   caaggtacgc   cgctcgtcct    8040 ccccccccc   cctctctacc   ttctctagat   cggcgttccg   gtccatggtt   agggcccggt    8100
agttctactt   ctgttcatgt   ttgtgttaga   tccgtgtttg   tgttagatcc   gtgctgctag    8160
cgttcgtaca   cggatgcgac   ctgtacgtca   gacacgttct   gattgctaac   ttgccagtgt    8220 ttctcttttgg   ggaatcctgg   gatggctcta   gccgttccgc   agacgggatc   gatttcatga    8280
ttttttttgt   ttcgttgcat   agggtttggt   ttgcccttttt   cctttatttc   aatatatgcc    8340
gtgcacttgt   ttgtcgggtc   atcttttcat   gctttttttt   gtcttggttg   tgatgatgtg    8400
gtctggttgg   gcggtcgttc   tagatcggag   tagaattctg   tttcaaacta   cctggtggat    8460
ttattaattt   tggatctgta   tgtgtgtgcc   atacatattc   atagttacga   attgaagatg    8520
atggatggaa   atatcgatct   aggataggta   tacatgttga   tgcgggtttt   actgatgcat    8580
atacagagat   gcttttttgtt   cgcttggttg   tgatgatgtg   gtgtggttgg   gcggtcgttc    8640
attcgttcta   gatcggagta   gaatactgtt   tcaaactacc   tggtgtattt   attaattttg    8700
gaactgtatg   tgtgtgtcat   acatcttcat   agttacgagt   ttaagatgga   tggaaatatc    8760
gatctaggat   aggtatacat   gttgatgtgg   gttttactga   tgcatataca   tgatggcata    8820
tgcagcatct   attcatatgc   tctaaccttg   agtacctatc   tattataata   aacaagtatg    8880
ttttataatt   attttgatct   tgatatactt   ggatgatggc   atatgcagca   gctatatgtg    8940 gatttttta   gccctgcctt   catacgctat   ttatttgctt   ggtactgttt   cttttgtcga    9000
tgctcaccct   gttgtttggt   gttacttctg   cagggatccg   gcagcagcca   tgcagaagct    9060
gatcaacagc   gtgcagaact   acgcctgggg   cagcaagacc   gccctgaccg   agctgtacgg    9120
catggagaac   cccagcagcc   agcccatggc   cgagctgtgg   atgggcgccc   accccaagag    9180
cagcagccgc   gtgcagaacg   ccgccggcga   catcgtgagc   ctgcgcgacg   tgatcgagag    9240
cgacaagagc   accctgctgg   gcgaggccgt   ggccaagcgc   ttcggcgagc   tgcccttcct    9300
gttcaaggtg   ctgtgcgccg   cccagcccct   gagcatccag   gtgcacccca   acaagcacaa    9360
cagcgagatc   ggcttcgcca   aggagaacgc   cgccggcatc   cccatggacg   ccgccgagcg    9420
caactacaag   gaccccaacc   acaagcccga   gctggtgttc   gccctgaccc   ccttcctggc    9480
catgaacgcc   ttccgcgagt   tcagcgagat   cgtgagcctg   ctgcagcccg   tggccggcgc    9540
ccaccccgcc   atcgcccact   tcctgcagca   gcccgacgcc   gagcgcctga   gcgagctgtt    9600
cgccagcctg   ctgaacatgc   agggcgagga   gaagagccgc   gccctggcca   tcctgaagag    9660
cgccctggac   agccagcagg   gcgagccctg   gcagaccatc   gcctgatca   gcgagttcta    9720 ccccgaggac   agcggcctgt   tcagccccct   gctgctgaac   gtggtgaagc   tgaacccgg    9780 cgaggccatg   ttcctgttcg   ccgagacccc   ccacgcctac   ctgcagggcg   tggccctgga    9840
ggtgatggca   acagcgaca   acgtgctgcg   cgccggcctg   accccaagt   acatcgacat    9900 ccccgagctg   gtggccaacg   tgaagttcga   ggccaagccc   gccaaccagc   tgctgaccca    9960
gcccgtgaag   cagggcgccg   agctggactt   ccccatccc   gtggacgact   cgccttcag    10020 cctgcacgac   ctgagcgaca   aggagaccac   catcagccag   cagagcgccg   ccatcctgtt    10080
ctgcgtggag   ggcgacgcca   ccctgtggaa   gggcagccag   cagctgcagc   tgaagcccgg    10140
cgagagcgcc   ttcatcgccg   ccaacgagag   ccccgtgacc   gtgaagggcc   acggccgcct    10200
ggcccgcgtg   tacaacaagc   tgtgatagga   gctcgatccg   tcgacctgca   gatcgttcaa    10260
```

-continued

```
acatttggca ataaagtttc ttaagattga atcctgttgc cggtcttgcg atgattatca    10320
tataatttct gttgaattac gttaagcatg taataattaa catgtaatgc atgacgttat    10380
ttatgagatg ggtttttatg attagagtcc cgcaattata catttaatac gcgatagaaa    10440
acaaaatata gcgcgcaaac taggataaat tatcgcgcgc ggtgtcatct atgttactag    10500
atcggcgcgc cgcaattgaa gtttgggcgg ccagcatggc cgtatccgca atgtgttatt    10560
aagttgtcta agcgtcaatt tgtttacacc acaatatatc ctgccaccag ccagccaaca    10620 gctcccccgac cggcagctcg gcacaaaatc accactcgat acaggcagcc catcagaatt    10680
aattctcatg tttgacagct tatcatcgac tgcacggtgc accaatgctt ctggcgtcag    10740
gcagccatcg gaagctgtgg tatggctgtg caggtcgtaa atcactgcat aattcgtgtc    10800
gctcaaggcg cactcccgtt ctggataatg ttttttgcgc cgacatcata acggttctgg    10860
caaatattct gaaatgagct gttgacaatt aatcatccgg ctcgtataat gtgtggaatt    10920
gtgagcggat aacaatttca cacaggaaac agaccatgag ggaagcgttg atcgccgaag    10980
tatcgactca actatcagag gtagttggcg tcatcgagcg ccatctcgaa ccgacgttgc    11040
tggccgtaca tttgtacggc tccgcagtgg atggcggcct gaagccacac agtgatattg    11100
atttgctggt tacggtgacc gtaaggcttg atgaaacaac gcggcgagct ttgatcaacg    11160
acctttggga aacttcggct tcccctggag agagcgagat tctccgcgct gtagaagtca    11220
ccattgttgt gcacgacgac atcattccgt ggcgttatcc agctaagcgc gaactgcaat    11280
ttggagaatg gcagcgcaat gacattcttg caggtatctt cgagccagcc acgatcgaca    11340
ttgatctggc tatcttgctg acaaaagcaa gagaacatag cgttgccttg gtaggtccag    11400
cggcggagga actctttgat ccggttcctg aacaggatct atttgaggcg ctaaatgaaa    11460
ccttaacgct atggaactcg ccgcccgact gggctggcga tgagcgaaat gtagtgctta    11520
cgttgtcccg catttggtac agcgcagtaa ccggcaaaat cgcgccgaag gatgtcgctg    11580
ccgactgggc aatggagcgc ctgccggccc agtatcagcc cgtcatactt gaagctaggc    11640
aggcttatct tggacaagaa gatcgcttgg cctcgcgcgc agatcagttg gaagaatttg    11700
ttcactacgt gaaaggcgag atcaccaaag tagtcggcaa ataaagctct agtggatctc    11760
cgtacccggg gatctggctc gcggcggacg cacgacgccg gggcgagacc ataggcgatc    11820
tcctaaatca atagtagctg taacctcgaa gcgtttcact tgtaacaacg attgagaatt    11880
tttgtcataa aattgaaata cttggttcgc atttttgtca tccgcggtca gccgcaattc    11940
tgacgaactg cccatttagc tggagatgat tgtacatcct tcacgtgaaa atttctcaag    12000
cgctgtgaac aagggttcag attttagatt gaaaggtgag ccgttgaaac acgttcttct    12060
tgtcgatgac gacgtcgcta tgcggcatct tattattgaa taccttacga tcccacgcctt    12120 caaagtgacc gcggtagccg acagcaccca gttcacaaga gtactctctt ccgcgacggt    12180
cgatgtcgtg gttgttgatc tagatttagg tcgtgaagat gggctcgagc taggagcaag    12240
tgattttatc gctaagccgt tcagtatcag agagtttcta gcacgcattc gggttgcctt    12300
gcgcgtgcgc cccaacgttg tccgctccaa agaccgacgg tctttttgtt ttactgactg    12360
gacacttaat ctcaggcaac gtcgcttgat gtccgaagct ggcggtgagg tgaaacttac    12420
ggcaggtgag ttcaatcttc tcctcgcgtt tttagagaaa ccccgcgacg ttctatcgcg    12480
cgagcaactt ctcattgcca gtcgagtacg cgacgaggag gtttatgaca ggagtataga    12540
tgttctcatt ttgaggctgc gccgcaaact tgaggcagat ccgtcaagcc ctcaactgat    12600
aaaaacagca agaggtgccg gttatttctt tgacgcggac gtgcaggttt cgcacggggg    12660
```

```
gacgatggca gcctgagcca attcccagat ccccgaggaa tcggcgtgag cggtcgcaaa   12720
ccatccggcc cggtacaaat cggcgcggcg ctgggtgatg acctggtgga gaagttgaag   12780
gccgcgcagg ccgcccagcg gcaacgcatc gaggcagaag cacgcccgg tgaatcgtgg    12840 caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
cgtgaccgac gagctggcga ggtgatccgc tacgagcttc cagacgggca cgtagaggtt   13080
tccgcagggc cggccggcat ggccagtgtg tgggattacg acctggtact gatggcggtt   13140
tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacggttcac   13500
cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgtttcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcagggga aaaggtcga aaaggtctct ttcctgtgga tagcacgtac    13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actcttaaa acttattaaa actcttaaaa cccgcctggc ctgtgcataa    14040
ctgtctggcc agcgcacagc cgaagagctg caaaaagcgc ctacccttcg gtcgctgcgc   14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
ccatcatcca gccagaaagt gagggagcca cggttgatga gagctttgtt gtaggtggac   14340
cagttggtga ttttgaactt ttgctttgcc acgaacggt ctgcgttgtc gggaagatgc     14400
gtgatctgat ccttcaactc agcaaaagtt cgatttattc aacaaagccg ccgtcccgtc   14460
aagtcagcgt aatgctctgc cagtgttaca accaattaac caattctgat tagaaaaact   14520
catcgagcat caaatgaaac tgcaatttat tcatatcagg attatcaata ccatatttt    14580 gaaaaagccg tttctgtaat gaaggagaaa actcaccgag gcagttccat aggatggcaa   14640
gatcctggta tcggtctgcg attccgactc gtccaacatc aatacaacct attaatttcc   14700
cctcgtcaaa aataaggtta tcaagtgaga atcaccatg agtgacgact gaatccggtg   14760
agaatggcaa aagctctgca ttaatgaatc ggccaacgcg cggggagagg cggtttgcgt   14820
attgggcgct cttccgcttc ctcgctcact gactcgctgc gctcggtcgt tcggctgcgg   14880
cgagcggtat cagctcactc aaaggcggta atacggttat ccacagaatc agggggataac    14940 gcaggaaaga acatgtgagc aaaaggccag caaaaggcca ggaaccgtaa aaaggccgcg   15000
```

```
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gttttttgt ttgcaagcag cagattacgc gcagaaaaaa aggatctcaa    15600
gaagatcctt tgatctttc tacggggtct gacgctcagt ggaacgaaaa ctcacgttaa    15660
gggattttgg tcatgagatt atcaaaaagg atcttcacct agatccttt gatccggaat    15720 ta                                                                    15722

<210> SEQ ID NO 21
<211> LENGTH: 20
<212> TYPE: DNA
<213> ORGANISM: Artificial Sequence
<220> FEATURE:
<223> OTHER INFORMATION: for editing VLHP2

<400> SEQUENCE: 21
gctggagctg agcttccggg                                                    20

<210> SEQ ID NO 22
<211> LENGTH: 15722
<212> TYPE: DNA
<213> ORGANISM: Artificial Sequence
<220> FEATURE:
<223> OTHER INFORMATION: vector 23398
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: misc_feature
<222> LOCATION: (5606)..(5608)
<223> OTHER INFORMATION: L to V mutation
<220> FEATURE:
<221> NAME/KEY: misc_feature
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmGW2
<220> FEATURE:
<221> NAME/KEY: misc_feature
```

```
<222> LOCATION: (6927)..(7031)
<223> OTHER INFORMATION: rsgRNAZmGW2-01
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 22
attcctgtgg ttggcatgca catacaaatg gacgaacgga taaaccttt  cacgcccttt    60 taaatatccg attattctaa taaacgctct tttctcttag gtttacccgc caatatatcc   120
tgtcaaacac tgatagttta aactgaaggc gggaaacgac aatctgatca tgagcggaga   180
attaagggag tcacgttatg accccgccg atgacgcggg acaagccgtt ttacgtttgg    240
aactgacaga accgcaacgc tgcaggaatt ggccgcagcg gccatttaaa caaagcttgg   300
taccattatg tggtctaggt aggttctata tataagaaaa cttgaaatgt tctaaaaaaa   360
aattcaagcc catgcatgat tgaagcaaac ggtatagcaa cggtgttaac ctgatctagt   420
gatctcttgc aatccttaac ggccacctac cgcaggtagc aaacggcgtc ccctcctcg    480 atatctccgc ggcgacctct ggcttttcc gcggaattgc gcggtgggga cggattccac    540
gagaccgcga cgcaaccgcc tctcgccgct gggccccaca ccgctcggtg ccgtagcctc   600
acgggactct ttctccctcc tccccgtta taaattggct tcatcccctc cttgcctcat    660
ccatccaaat cccagtcccc aatcccatcc cttcgtagga gaaattcatc gaagctaagc   720
gaatcctcgc gatcctctca aggtactgcg agttttcgat cccctctcg accctcgta    780 tgtttgtgtt tgtcgtagcg tttgattagg tatgctttcc ctgtttgtgt tcgtcgtagc   840
gtttgattag gtatgctttc cctgttcgtg ttcatcgtag tgtttgatta ggtcgtgtga   900
ggcgatggcc tgctcgcgtc cttcgatctg tagtcgattt gcgggtcgtg gtgtagatct   960
gcgggctgtg atgaagttat ttggtgtgat ctgctcgcct gattctgcgg gttggctcga  1020
gtagatatga tggttggacc ggttggtcg tttaccgcgc tagggttggg ctgggatgat   1080
gttgcatgcg ccgttgcgcg tgatcccgca gcaggacttg cgtttgattg ccagatctcg  1140
```

```
ttacgattat gtgatttggt ttggactttt tagatctgta gcttctgctt atgtgccaga    1200
tgcgcctact gctcatatgc ctgatgataa tcataaatgg ctgtggaact aactagttga    1260
ttgcggagtc atgtatcagc tacaggtgta gggactagct acaggtgtag ggacttgcgt    1320
ctaattgttt ggtcctttac tcatgttgca attatgcaat ttagtttaga ttgtttgttc    1380
cactcatcta ggctgtaaaa gggacactgc ttagattgct gtttaatctt tttagtagat    1440
tatattatat tggtaactta ttaccccctat tacatgccat acgtgacttc tgctcatgcc    1500
tgatgataat catagatcac tgtggaatta attagttgat tgttgaatca tgtttcatgt    1560
acataccacg gcacaattgc ttagttcctt aacaaatgca aattttactg atccatgtat    1620
gatttgcgtg gttctctaat gtgaaatact atagctactt gttagtaaga atcaggttcg    1680
tatgcttaat gctgtatgtg ccttctgctc atgcctgatg ataatcatat atcactggaa    1740
ttaattagtt gatcgtttaa tcatatatca agtacatacc atgccacaat ttttagtcac    1800
ttaacccatg cagattgaac tggtccctgc atgttttgct aaattgttct attctgatta    1860
gaccatatat catgtatttt tttttggtaa tggttctctt atttttaaatg ctatatagtt    1920 ctggtacttg ttagaaagat ctgcttcata gtttagttgc ctatccctcg aattaggatg    1980
ctgagcagct gatcctatag cttgtttca tgtatcaatt cttttgtgtt caacagtcag    2040
tttttgttag attcattgta acttatggtc gcttactctt ctggtcctca atgcttgcag    2100
gatcgcggcc gctcatatgg acaagaagta cagcatcggc ctggacatcg gcaccaacag    2160
cgtgggctgg gccgtgatca ccgacgagta caaggtgccg agcaagaagt tcaaggtgct    2220
gggcaacacc gacaggcaca gcatcaagaa gaacctgatc ggcgccctgc tgttcgacag    2280
cggcgagacc gccgaggcca ccaggctgaa gaggaccgcc aggaggaggt acaccaggag    2340
gaagaacagg atctgctacc tgcaggagat cttcagcaac gagatggcca aggtggacga    2400
cagcttcttc cacaggctgg aggagagctt cctggtggag gaggacaaga gcacgagag    2460 gcacccgatc ttcggcaaca tcgtggacga ggtggcctac cacgagaagt acccgaccat    2520
ctaccacctg aggaagaagc tggtggacag caccgacaag gccgacctga ggctgatcta    2580
cctggccctg gcccacatga tcaagttcag gggccacttc ctgatcgagg gcgacctgaa    2640
cccggacaac agcgacgtgg acaagctgtt catccagctg gtgcagacct acaaccagct    2700
gttcgaggag aacccgatca cgccagcgg cgtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg accccgaact tcaagagcaa    2880
cttcgacctg gccgaggacg ccaagctgca gctgagcaag gacacctacg acgacgacct    2940
ggacaacctg ctggcccaga tcggcgacca gtacgccgac ctgttcctgg ccgccaagaa    3000
cctgagcgac gccatcctgc tgagcgacat cctgagggtg aacaccgaga tcaccaaggc    3060
cccgctgagc gccagcatga tcaagaggta cgacgagcac caccaggacc tgaccctgct    3120
gaaggccctg gtgaggcagc agctgccgga gaagtacaag gagatcttct tcgaccagag    3180
caagaacggc tacgccggct acatcgacgg cggcgccagc caggaggagt ctacaagtt    3240 catcaagccg atcctggaga agatggacgg caccgaggag ctgctggtga agctgaacag    3300
ggaggacctg ctgaggaagc agaggaccct cgacaacggc agcatcccgc accagatcca    3360
cctgggcgag ctgcacgcca tcctgaggag gcaggaggac ttctacccgt tcctgaagga    3420
caacagggag aagatcgaga gatcctgac cttccgcatc ccgtactacg tgggcccgct    3480
ggccaggggc aacagcaggt tcgcctggat gaccaggaag agcgaggaga ccatcacccc    3540
```

```
gtggaacttc gaggaggtgg tggacaaggg cgccagcgcc cagagcttca tcgagaggat    3600
gaccaacttc gacaagaacc tgccgaacga gaaggtgctg ccgaagcaca gcctgctgta    3660
cgagtacttc accgtgtaca acgagctgac caaggtgaag tacgtgaccg agggcatgag    3720
gaagccggcc ttcctgagcg cgcgagcagaa gaaggccatc gtggacctgc tgttcaagac    3780
caacaggaag gtgaccgtga agcagctgaa ggaggactac ttcaagaaga tcgagtgctt    3840
cgacagcgtg gagatcagcg cgtggagga caggttcaac gccagcctgg gcacctacca    3900
cgacctgctg aagatcatca aggacaagga cttcctggac aacgaggaga cgaggacat    3960 cctggaggac atcgtgctga ccctgaccct gttcgaggac aggagatga tcgaggagag    4020 gctgaagacc tacgcccacc tgttcgacga caaggtgatg aagcagctga agaggaggag    4080
gtacaccggc tggggcaggc tgagcaggaa gctgatcaac ggcatcaggg acaagcagag    4140
cggcaagacc atcctggact tcctgaagag cgacggcttc gccaacagga acttcatgca    4200
gctgatccac gacgacagcc tgaccttcaa ggaggacatc cagaaggccc aggtgagcgg    4260
ccagggcgac agcctgcacg agcacatcgc caacctggcc ggcagcccgg ccatcaagaa    4320
gggcatcctg cagaccgtga aggtggtgga cgagctggtg aaggtgatgg gcaggcacaa    4380
gccggagaac atcgtgatcg agatggccag ggagaaccag accacccaga agggccagaa    4440
gaacagcagg gagaggatga agaggatcga ggagggcatc aaggagctgg gcagccagat    4500
cctgaaggag cacccggtgg agaacaccca gctgcagaac gagaagctgt acctgtacta    4560
cctgcagaac ggcagggaca tgtacgtgga ccaggagctg gacatcaaca ggctgagcga    4620
ctacgacgtg gaccacatcg tgccgcagag cttcctgaag gacgacagca tcgacaacaa    4680
ggtgctgacc aggagcgaca agaacagggg caagagcgac aacgtgccga gcgaggaggt    4740
ggtgaagaag atgaaaaact actggaggca gctgctgaac gccaagctga tcacccagag    4800
gaagttcgac aacctgacca aggccgagag gggcggcctg agcgagctgg acaaggccgg    4860
cttcattaaa aggcagctgg tggagaccag gcagatcacc aagcacgtgg cccagatcct    4920
ggacagcagg atgaacacca gtacgacga gaacgacaag ctgatcaggg aggtgaaggt    4980 gatcacccctg aagagcaagc tggtgagcga cttcaggaag gacttccagt ctacaaggt    5040 gagggagatc aataattacc accacgccca cgacgcctac ctgaacgccg tggtgggcac    5100
cgccctgatt aaaaagtacc cgaagctgga gagcgagttc gtgtacgcg actacaaggt    5160 gtacgacgtg aggaagatga tcgccaagag cgagcaggag atcggcaagg ccaccgccaa    5220
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
cagcgacaag ctgatcgcca ggaagaagga ctgggaccg aagaagtacg gcggcttcga    5520
cagcccgacc gtggcctaca gcgtgctggt ggtggccaag gtggagaagg gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggcctg ccgagcaagt acgtgaactt    5820
cctgtacctg gccagccact acgagaagct gaagggcagc ccggaggaca acgagcagaa    5880
```

```
gcagctgttc gtggagcagc acaagcacta cctggacgag atcatcgagc agatcagcga    5940
gttcagcaag agggtgatcc tggccgacgc caacctggac aaggtgctga gcgcctacaa    6000
caagcacagg acaagccga tcagggagca ggccgagaac atcatccacc tgttcaccct     6060
gaccaacctg ggcgccccgg ccgccttcaa gtacttcgac accaccatcg acaggaagag    6120
gtacaccagc accaaggagg tgctggacgc caccctgatc caccagagca tcaccggcct    6180
gtacgagacc aggatcgacc tgagccagct gggcggcgac agcagcccgc cgaagaagaa    6240
gaggaaggtg agctggaagg acgccagcgg ctggagcagg atgtgaagct tgatcgttca    6300
aacatttggc aataaagttt cttaagattg aatcctgttg ccggtcttgc gatgattatc    6360
atataatttc tgttgaatta cgttaagcat gtaataatta acatgtaatg catgacgtta    6420
tttatgagat gggttttat gattagagtc ccgcaattat acatttaata cgcgatagaa    6480
aacaaaatat agcgcgcaaa ctaggataaa ttatcgcgcg cggtgtcatc tatgttacta    6540
gatcttcgaa gggatcttta aacatacgaa cagatcactt aaagttcttc tgaagcaact    6600
taaagttatc aggcatgcat ggatcttgga ggaatcagat gtgcagtcag ggaccatagc    6660
acaggacagg cgtcttctac tggtgctacc agcaaatgct ggaagccggg aacactgggt    6720
acgttggaaa ccacgtgatg tggagtaaga taaactgtag gagaaaagca tttcgtagtg    6780
ggccatgaag cctttcagga catgtattgc agtatgggcc ggcccattac gcaattggac    6840
gacaacaaag actagtatta gtaccacctc ggctatccac atagatcaaa gctggtttaa    6900
aagagttgtg cagatgatcc gtggcagagc ggttcacgcg ccgcagtttt tagagctaga    6960
aatagcaagt taaataagg ctagtccgtt atcaacttga aaaagtggca ccgagtcggt     7020
gcttttttt tcggaccgcg cctgcagtgc agcgtgaccc ggtcgtgccc ctctctagag     7080
ataatgagca ttgcatgtct aagttataaa aaattaccac atatttttt tgtcacactt    7140
gtttgaagtg cagtttatct atctttatac atatatttaa actttactct acgaataata    7200
taatctatag tactacaata atatcagtgt tttagagaat catataaatg aacagttaga    7260
catggtctaa aggacaattg agtattttga caacaggact ctacagtttt atctttttag    7320
tgtgcatgtg ttctccttt tttttgcaaa tagcttcacc tatataatac ttcatccatt     7380
ttattagtac atccatttag ggtttagggt taatggtttt tatagactaa ttttttttagt   7440
acatctattt tattctattt tagcctctaa attaagaaaa ctaaaactct attttagttt    7500
ttttatttaa taatttagat ataaaataga ataaaataaa gtgactaaaa attaaacaaa    7560
tacccttaaa gaaattaaaa aaactaagga aacattttc ttgtttcgag tagataatgc     7620
cagcctgtta aacgccgtcg acgagtctaa cggacaccaa ccagcgaacc agcagcgtcg    7680
cgtcgggcca agcgaagcag acggcacggc atctctgtcg ctgcctctgg acccctctcg    7740
agagttccgc tccaccgttg gacttgctcc gctgtcggca tccagaaatt gcgtggcgga    7800
gcggcagacg tgagccggca cggcaggcgg cctcctcctc ctctcacggc accggcagct    7860
acggggatt cctttcccac cgctccttcg ctttcccttc ctcgcccgcc gtaataaata     7920
gacacccct ccacccctc tttccccaac ctcgtgttgt tcggagcgca cacacaca      7980
accagatctc ccccaaatcc acccgtcggc acctccgctt caaggtacgc cgtcgtcct    8040
cccccccccc cctctctacc ttctctagat cggcgttccg gtccatggtt agggcccggt    8100
agttctactt ctgttcatgt ttgtgttaga tccgtgtttg tgttagatcc gtgctgctag    8160
cgttcgtaca cggatgcgac ctgtacgtca gacacgttct gattgctaac ttgccagtgt    8220
ttctctttgg ggaatcctgg gatggctcta gccgttccgc agacgggatc gatttcatga    8280
```

```
tttttttttgt tcgttgcat agggtttggt ttgccctttt cctttatttc aatatatgcc    8340
gtgcacttgt ttgtcgggtc atcttttcat gcttttttt gtcttggttg tgatgatgtg     8400
gtctggttgg gcggtcgttc tagatcggag tagaattctg tttcaaacta cctggtggat    8460
ttattaattt tggatctgta tgtgtgtgcc atacatattc atagttacga attgaagatg    8520
atggatggaa atatcgatct aggataggta tacatgttga tgcgggtttt actgatgcat    8580
atacagagat gcttttttgtt cgcttggttg tgatgatgtg gtgtggttgg gcggtcgttc    8640
attcgttcta gatcggagta gaatactgtt tcaaactacc tggtgtattt attaattttg    8700
gaactgtatg tgtgtgtcat acatcttcat agttacgagt ttaagatgga tggaaatatc    8760
gatctaggat aggtatacat gttgatgtgg gttttactga tgcatataca tgatggcata    8820
tgcagcatct attcatatgc tctaaccttg agtacctatc tattataata aacaagtatg    8880
ttttataatt attttgatct tgatatactt ggatgatggc atatgcagca gctatatgtg    8940
gatttttta gccctgcctt catacgctat ttatttgctt ggtactgttt cttttgtcga    9000
tgctcaccct gttgtttggt gttacttctg cagggatccg gcagcagcca tgcagaagct    9060
gatcaacagc gtgcagaact acgcctgggg cagcaagacc gccctgaccg agctgtacgg    9120
catggagaac cccagcagcc agcccatggc cgagctgtgg atgggcgccc accccaagag    9180
cagcagccgc gtgcagaacg ccgccggcga catcgtgagc ctgcgcgacg tgatcgagag    9240
cgacaagagc accctgctgg gcgaggccgt ggccaagcgc ttcggcgagc tgcccttcct    9300
gttcaaggtg ctgtgcgccg cccagcccct gagcatccag gtgcacccca acaagcacaa    9360
cagcgagatc ggcttcgcca aggagaacgc cgccggcatc cccatggacg ccgccgagcg    9420
caactacaag gaccccaacc acaagcccga gctggtgttc gccctgaccc ccttcctggc    9480
catgaacgcc ttccgcgagt tcagcgagat cgtgagcctg ctgcagcccg tggccggcgc    9540
ccacccgcc atcgcccact tcctgcagca gcccgacgcc gagcgcctga gcgagctgtt    9600
cgccagcctg ctgaacatgc agggcgagga gaagagccgc gccctggcca tcctgaagag    9660
cgccctggac agccagcagg gcgagccctg gcagaccatc cgcctgatca gcgagttcta    9720
ccccgaggac agcggcctgt tcagcccccc tgctgctgaac gtggtgaagc tgaacccccgg    9780
cgaggccatg ttcctgttcg ccagagaccc ccacgcctac ctgcagggcg tggccctgga    9840
ggtgatggcc aacagcgaca acgtgctgcg cgccggcctg accccaagt acatcgacat    9900
ccccgagctg gtggccaacg tgaagttcga ggccaagccc gccaaccagc tgctgaccca    9960
gcccgtgaag cagggcgccg agctggactt ccccatcccc gtggacgact cgccttcag   10020
cctgcacgac ctgagcgaca aggagaccac catcagccag cagagcgccg ccatcctgtt   10080
ctgcgtggag ggcgacgcca ccctgtgaa gggcagccag cagctgcagc tgaagcccgg   10140
cgagagcgcc ttcatcgccg ccaacgagag cccgtgacc gtgaagggcc acggccgcct   10200
ggcccgcgtg tacaacaagc tgtgatagga gctcgatccg tcgacctgca gatcgttcaa   10260
acatttggca ataaagtttc ttaagattga atcctgttgc cggtcttgcg atgattatca   10320
tataatttct gttgaattac gttaagcatg taataattaa catgtaatgc atgacgttat   10380
ttatgagatg ggtttttatg attagagtcc cgcaattata catttaatac gcgatagaaa   10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
aagttgtcta agcgtcaatt tgtttacacc acaatatatc ctgccaccag ccagccaaca   10620
```

```
gctccccgac cggcagctcg gcacaaaatc accactcgat acaggcagcc catcagaatt   10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg tttttttgcgc cgacatcata acggttctgg   10860
caaatattct gaaatgagct gttgacaatt aatcatccgg ctcgtataat gtgtggaatt   10920
gtgagcggat aacaatttca cacaggaaac agaccatgag ggaagcgttg atcgccgaag   10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160
acctttggaa aacttcggct tcccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcgc agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg gggcgagacc ataggcgatc   11820
tcctaaatca atagtagctg taacctcgaa gcgtttcact tgtaacaacg attgagaatt   11880
tttgtcataa aattgaaata cttggttcgc attttttgtca tccgcggtca gccgcaattc   11940
tgacgaactg cccatttagc tggagatgat tgtacatcct tcacgtgaaa atttctcaag   12000
cgctgtgaac aagggttcag attttagatt gaaaggtgag ccgttgaaac acgttcttct   12060
tgtcgatgac gacgtcgcta tgcggcatct tattattgaa taccttacga tccacgcctt   12120
caaagtgacc gcggtagccg acagcaccca gttcacaaga gtactctctt ccgcgacggt   12180
cgatgtcgtg gttgttgatc tagatttagg tcgtgaagat gggctcgagc taggagcaag   12240
tgattttatc gctaagccgt tcagtatcag agagtttcta gcacgcattc gggttgcctt   12300
gcgcgtgcgc cccaacgttg tccgctccaa agaccgacgg tctttttgtt ttactgactg   12360
gacacttaat ctcaggcaac gtcgcttgat gtccgaagct ggcggtgagg tgaaacttac   12420
ggcaggtgag ttcaatcttc tcctcgcgtt tttagaaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
gacgatggca gcctgagcca attcccagat ccccgaggaa tcggcgtgag cggtcgcaaa   12720
ccatccggcc cggtacaaat cggcgcggcg ctgggtgatg acctggtgga aagttgaag   12780 gccgcgcagg ccgcccagcg gcaacgcatc gaggcagaag cacgccccgg tgaatcgtgg   12840
caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
```

```
cgtgaccgac gagctggcga ggtgatccgc tacgagcttc cagacgggca cgtagaggtt    13080
tccgcagggc cggccggcat ggccagtgtg tgggattacg acctggtact gatggcggtt    13140
tcccatctaa ccgaatccat gaaccgatac cgggaaggga agggagacaa gcccggccgc    13200
gtgttccgtc cacacgttgc ggacgtactc aagttctgcc ggcgagccga tggcggaaag    13260
cagaaagacg acctggtaga aacctgcatt cggttaaaca ccacgcacgt tgccatgcag    13320
cgtacgaaga aggccaagaa cggccgcctg gtgacggtat ccagggtgaa gccttgatt    13380 agccgctaca agatcgtaaa gagcgaaacc gggcggccgg agtacatcga gatcgagcta    13440
gctgattgga tgtaccgcga gatcacagaa ggcaagaacc cggacgtgct gacggttcac    13500
cccgattact tttgatcga tcccggcatc ggccgttttc tctaccgcct ggcacgccgc    13560
gccgcaggca aggcagaagc cagatggttg ttcaagacga tctacgaacg cagtggcagc    13620
gccggagagt tcaagaagtt ctgtttcacc gtgcgcaagc tgatcgggtc aaatgacctg    13680
ccggagtacg atttgaagga ggaggcgggg caggctggcc cgatcctagt catgcgctac    13740
cgcaacctga tcgagggcga agcatccgcc ggttcctaat gtacggagca gatgctaggg    13800
caaattgccc tagcagggga aaaggtcgaa aaaggtctct ttcctgtgga tagcacgtac    13860
attgggaacc caaagccgta cattgggaac cggaacccgt acattgggaa cccaaagccg    13920
tacattggga accggtcaca catgtaagtg actgatataa aagagaaaaa aggcgatttt    13980
tccgcctaaa actctttaaa acttattaaa actcttaaaa cccgcctggc ctgtgcataa    14040
ctgtctggcc agcgcacagc cgaagagctg caaaaagcgc ctaccccttcg gtcgctgcgc    14100 tccctacgcc ccgccgcttc gcgtcggcct atcgcggccg ctggccgctc aaaaatggct    14160
ggcctacggc caggcaatct accagggcgc ggacaagccg cgccgtcgcc actcgaccgc    14220
cggcgctgag gtctgcctcg tgaagaaggt gttgctgact cataccaggc ctgaatcgcc    14280
ccatcatcca gccagaaagt gagggagcca cggttgatga gagctttgtt gtaggtggac    14340
cagttggtga ttttgaactt ttgctttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatatttt    14580 gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga atcaccatg agtgacgact gaatccggtg    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc cgcctttctc    15180
ccttcgggaa gcgtggcgct ttctcatagc tcacgctgta ggtatctcag ttcggtgtag    15240
gtcgttcgct ccaagctggg ctgtgtgcac gaacccccccg ttcagcccga ccgctgcgcc    15300
ttatccggta actatcgtct tgagtccaac ccggtaagac acgacttatc gccactggca    15360
```

```
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                  15722
```

```
<210> SEQ ID NO 23
<211> LENGTH: 20
<212> TYPE: DNA
<213> ORGANISM: Artificial Sequence
<220> FEATURE:
<223> OTHER INFORMATION: for editing GW2-1

<400> SEQUENCE: 23
gagcggttca cgcggccgca                                                20

<210> SEQ ID NO 24
<211> LENGTH: 15721
<212> TYPE: DNA
<213> ORGANISM: Artificial Sequence
<220> FEATURE:
<223> OTHER INFORMATION: vector 23763
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: misc_feature
<222> LOCATION: (6221)..(6283)
<223> OTHER INFORMATION: xSV40NLS-03
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6945)
<223> OTHER INFORMATION: xTaVLHP1
<220> FEATURE:
<221> NAME/KEY: misc_feature
<222> LOCATION: (6927)..(7030)
<223> OTHER INFORMATION: rsgRNA TaVLHP1-01
<220> FEATURE:
<221> NAME/KEY: promoter
<222> LOCATION: (7041)..(9032)
<223> OTHER INFORMATION: prUbi1-04
<220> FEATURE:
<221> NAME/KEY: gene
```

```
<222> LOCATION: (9049)..(10227)
<223> OTHER INFORMATION: cPMI-09
<220> FEATURE:
<221> NAME/KEY: terminator
<222> LOCATION: (10250)..(10502)
<223> OTHER INFORMATION: tNOS-05-01
<220> FEATURE:
<221> NAME/KEY: misc_feature
<222> LOCATION: (10546)..(10675)
<223> OTHER INFORMATION: bNLB-03
<220> FEATURE:
<221> NAME/KEY: gene
<222> LOCATION: (10955)..(11743)
<223> OTHER INFORMATION: cSpec-03
<220> FEATURE:
<221> NAME/KEY: promoter
<222> LOCATION: (11838)..(11968)
<223> OTHER INFORMATION: prVirG-01
<220> FEATURE:
<221> NAME/KEY: gene
<222> LOCATION: (12705)..(13778)
<223> OTHER INFORMATION: cRepA-01
<220> FEATURE:
<221> NAME/KEY: misc_feature
<222> LOCATION: (13821)..(14225)
<223> OTHER INFORMATION: oVS1-02
<220> FEATURE:
<221> NAME/KEY: misc_feature
<222> LOCATION: (14903)..(15709)
<223> OTHER INFORMATION: oCOLE-06

<400> SEQUENCE: 24
attcctgtgg ttggcatgca catacaaatg gacgaacgga taaaccttt  cacgcccttt      60 taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg  atgacgcggg acaagccgtt ttacgtttgg     240
aactgacaga accgcaacgc tgcaggaatt ggccgcagcg gccatttaaa caaagcttgg     300
taccattatg tggtctaggt aggttctata tataagaaaa cttgaaatgt tctaaaaaaa     360
aattcaagcc catgcatgat tgaagcaaac ggtatagcaa cggtgttaac ctgatctagt     420
gatctcttgc aatccttaac ggccacctac cgcaggtagc aaacggcgtc ccctcctcg      480 atatctccgc ggcgacctct ggcttttccc gcggaattgc gcggtgggga cggattccac     540
gagaccgcga cgcaaccgcc tctcgccgct gggccccaca ccgctcggtg ccgtagcctc     600
acgggactct ttctccctcc tccccgtta  taaattggct tcatccctc  cttgcctcat     660 ccatccaaat cccagtcccc aatcccatcc cttcgtagga gaaattcatc gaagctaagc     720
gaatcctcgc gatcctctca aggtactgcg agttttcgat cccctctcg  acccctcgta     780 tgtttgtgtt tgtcgtagcg tttgattagg tatgcttcc  ctgtttgtgt tcgtcgtagc     840
gtttgattag gtatgctttc cctgttcgtg ttcatcgtag tgtttgatta ggtcgtgtga     900
ggcgatggcc tgctcgcgtc cttcgatctg tagtcgattt gcgggtcgtg gtgtagatct     960
gcgggctgtg atgaagttat ttggtgtgat ctgctcgcct gattctgcgg gttggctcga    1020
gtagatatga tggttggacc ggttggttcg tttaccgcgc tagggttggg ctgggatgat    1080
gttgcatgcg ccgttgcgcg tgatcccgca gcaggacttg cgtttgattg ccagatctcg    1140
ttacgattat gtgatttggt ttggactttt tagatctgta gcttctgctt atgtgccaga    1200
tgcgcctact gctcatatgc ctgatgataa tcataaatgg ctgtggaact aactagttga    1260
ttgcggagtc atgtatcagc tacaggtgta gggactagca acaggtgtag ggacttgcgt    1320
ctaattgttt ggtcctttac tcatgttgca attatgcaat ttagtttaga ttgtttgttc    1380
```

```
cactcatcta ggctgtaaaa gggacactgc ttagattgct gtttaatctt tttagtagat    1440
tatattatat tggtaactta ttaccnctat tacatgccat acgtgacttc tgctcatgcc    1500
tgatgataat catagatcac tgtggaatta attagttgat tgttgaatca tgtttcatgt    1560
acataccacg gcacaattgc ttagttcctt aacaaatgca aattttactg atccatgtat    1620
gatttgcgtg gttctctaat gtgaaatact atagctactt gttagtaaga atcaggttcg    1680
tatgcttaat gctgtatgtg ccttctgctc atgcctgatg ataatcatat atcactggaa    1740
ttaattagtt gatcgtttaa tcatatatca agtacatacc atgccacaat ttttagtcac    1800
ttaacccatg cagattgaac tggtccctgc atgttttgct aaattgttct attctgatta    1860
gaccatatat catgtatttt tttttggtaa tggttctctt attttaaatg ctatatagtt    1920
ctggtacttg ttagaaagat ctgcttcata gtttagttgc ctatccctcg aattaggatg    1980
ctgagcagct gatcctatag ctttgtttca tgtatcaatt cttttgtgtt caacagtcag    2040
tttttgttag attcattgta acttatggtc gcttactctt ctggtcctca atgcttgcag    2100
gatcgcggcc gctcatatgg acaagaagta cagcatcggc ctggacatcg gcaccaacag    2160
cgtgggctgg gccgtgatca ccgacgagta caaggtgccg agcaagaagt tcaaggtgct    2220
gggcaacacc gacaggcaca gcatcaagaa gaacctgatc ggcgccctgc tgttcgacag    2280
cggcgagacc gccgaggcca ccaggctgaa gaggaccgcc aggaggaggt acaccaggag    2340
gaagaacagg atctgctacc tgcaggagat cttcagcaac gagatggcca aggtggacga    2400
cagcttcttc cacaggctgg aggagagctt cctggtggag gaggacaaga agcacgagag    2460
gcacccgatc ttcggcaaca tcgtggacga ggtggcctac cacgagaagt acccgaccat    2520
ctaccacctg aggaagaagc tggtggacag caccgacaag gccgacctga ggctgatcta    2580
cctggccctg gcccacatga tcaagttcag gggccacttc ctgatcgagg gcgacctgaa    2640
cccggacaac agcgacgtgg acaagctgtt catccagctg gtgcagacct acaaccagct    2700
gttcgaggag aacccgatca cgccagcggc gtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg accccgaact tcaagagcaa    2880
cttcgacctg gccgaggacg ccaagctgca gctgagcaag gacacctacg acgacgacct    2940
ggacaacctg ctggcccaga tcggcgacca gtacgccgac ctgttcctgg ccgccaagaa    3000
cctgagcgac gccatcctgc tgagcgacat cctgagggtg aacaccgaga tcaccaaggc    3060
cccgctgagc gccagcatga tcaagaggta cgacgagcac caccaggacc tgaccctgct    3120
gaaggccctg gtgaggcagc agctgccgga gaagtacaag gagatcttct cgaccagag    3180
caagaacggc tacgccggct acatcgacgg cggcgccagc caggaggagt ctacaagtt    3240
catcaagccg atcctggaga gatggacgg caccgaggag ctgctggtga agctgaacag    3300
ggaggacctg ctgaggaagc agaggacctt cgacaacggc agcatcccgc accagatcca    3360
cctgggcgag ctgcacgcca tcctgaggag gcaggaggac ttctacccgt tcctgaagga    3420
caacagggag aagatcgaga agatcctgac cttccgcatc ccgtactacg tgggcccgct    3480
ggccagggga acagcaggt cgcctggat gaccaggaag agcgaggaga ccatcacccc    3540
gtggaacttc gaggaggtgg tggacaaggg cgccagcgcc cagagcttca tcgagaggat    3600
gaccaacttc gacaagaacc tgccgaacga gaaggtgctg ccgaagcaca gcctgctgta    3660
cgagtacttc accgtgtaca acgagctgac caaggtgaag tacgtgaccg agggcatgag    3720
gaagccggcc ttcctgagcg gcgagcagaa gaaggccatc gtggacctgc tgttcaagac    3780
```

```
caacaggaag gtgaccgtga agcagctgaa ggaggactac ttcaagaaga tcgagtgctt    3840
cgacagcgtg gagatcagcg gcgtggagga caggttcaac gccagcctgg gcacctacca    3900
cgacctgctg aagatcatca aggacaagga cttcctggac aacgaggaga acgaggacat    3960
cctggaggac atcgtgctga ccctgaccct gttcgaggac agggagatga tcgaggagag    4020
gctgaagacc tacgccacc tgttcgacga caaggtgatg aagcagctga agaggaggag    4080
gtacaccggc tggggcaggc tgagcaggaa gctgatcaac ggcatcaggg acaagcagag    4140
cggcaagacc atcctggact tcctgaagag cgacggcttc gccaacagga acttcatgca    4200
gctgatccac gacgacagcc tgaccttcaa ggaggacatc cagaaggccc aggtgagcgg    4260
ccagggcgac agcctgcacg agcacatcgc caacctggcc ggcagcccgg ccatcaagaa    4320
gggcatcctg cagaccgtga aggtggtgga cgagctggtg aaggtgatgg gcaggcacaa    4380
gccggagaac atcgtgatcg agatggccag ggagaaccag accacccaga gggccagaa    4440
gaacagcagg gagaggatga agaggatcga ggagggcatc aaggagctgg gcagccagat    4500
cctgaaggag cacccggtgg agaacaccca gctgcagaac agaagctgt acctgtacta    4560
cctgcagaac ggcagggaca tgtacgtgga ccaggagctg gacatcaaca ggctgagcga    4620
ctacgacgtg gaccacatcg tgccgcagag cttcctgaag gacgacagca tcgacaacaa    4680
ggtgctgacc aggagcgaca gaacaggggc aagagcgac aacgtgccga gcgaggaggt    4740
ggtgaagaag atgaaaaact actggaggca gctgctgaac gccaagctga tcacccagag    4800
gaagttcgac aacctgacca aggccgagag gggcggcctg agcgagctgg acaaggccgg    4860
cttcattaaa aggcagctgg tggagaccag gcagatcacc aagcacgtgg cccagatcct    4920
ggacagcagg atgaacacca agtacgacga gaacgacaag ctgatcaggg aggtgaaggt    4980
gatcacctg aagagcaagc tggtgagcga cttcaggaag gacttccagt tctacaaggt    5040
gagggagatc aataattacc accacgccca cgacgcctac ctgaacgccg tggtgggcac    5100
cgccctgatt aaaaagtacc cgaagctgga gagcgagttc gtgtacggcg actacaaggt    5160
gtacgacgtg aggaagatga tcgccaagag cgagcaggag atcggcaagg ccaccgccaa    5220
gtacttcttc tacagcaaca tcatgaactt cttcaagacc gagatcaccc tggccaacgg    5280
cgagatcagg aagaggccgc tgatcgagac caacggcgag accggcgaga tcgtgtggga    5340
caagggcagg gacttcgcca ccgtgaggaa ggtgctgtcc atgccgcagg tgaacatcgt    5400
gaagaagacc gaggtgcaga ccggcggctt cagcaaggag agcatcctgc cgaagaggaa    5460
cagcgacaag ctgatcgcca ggaagaagga ctgggacccg aagaagtacg gcggcttcga    5520
cagcccgacc gtggcctaca gcgtgctggt ggtggccaag gtggagaagg gcaagagcaa    5580
gaagctgaag agcgtgaagg agctggtggg catcaccatc atggagagga gcagcttcga    5640
gaagaaccca gtggacttcc tggaggccaa gggctacaag gaggtgaaga aggacctgat    5700
cattaaactg ccgaagtaca gcctgttcga gctggagaac ggcaggaaga ggatgctggc    5760
cagcgccggc gagctgcaga agggcaacga gctggccctg ccgagcaagt acgtgaactt    5820
cctgtacctg gccagccact acgagaagct gaagggcagc ccggaggaca acgagcagaa    5880
gcagctgttc gtggagcagc acaagcacta cctggacgca atcatcgagc agatcagcga    5940
gttcagcaag agggtgatcc tggccgacgc caacctggac aaggtgctga gcgcctacaa    6000
caagcacagg gacaagccga tcagggagca ggccgagaac atcatccacc tgttcaccct    6060
gaccaacctg ggcgcccgg ccgccttcaa gtacttcgac accaccatcg acaggaagag    6120
```

```
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggttttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag ggaccatagc   6660
acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag cctttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagacg agcaggcgca gttccgtttt agagctagaa   6960
atagcaagtt aaaataaggc tagtccgtta tcaacttgaa aaagtggcac cgagtcggtg   7020 ctttttttt cggaccgcgc ctgcagtgca gcgtgacccg tcgtgccccc tctctagaga   7080
taatgagcat tgcatgtcta agttataaaa aattaccaca tattttttt gtcacacttg   7140 tttgaagtgc agtttatcta tcttatataca tatatttaaa ctttactcta cgaataatat   7200
aatctatagt actacaataa tatcagtgtt ttagagaatc atataaatga acagttagac   7260
atggtctaaa ggacaattga gtattttgac aacaggactc tacagtttta tcttttagt   7320 gtgcatgtgt tctcctttt ttttgcaaat agcttcacct atataatact tcatccattt   7380
tattagtaca tccatttagg gtttagggtt aatggttttt atagactaat ttttttagta   7440
catctatttt attctatttt agcctctaaa ttaagaaaac taaaactcta ttttagtttt   7500
tttatttaat aatttagata taaaatagaa taaaataaag tgactaaaaa ttaaacaaat   7560 acccttaag aaattaaaaa aactaaggaa acatttttct tgtttcgagt agataatgcc   7620
agcctgttaa acgccgtcga cgagtctaac ggacaccaac cagcgaacca gcagcgtcgc   7680
gtcgggccaa gcgaagcaga cggcacggca tctctgtcgc tgcctctgga cccctctcga   7740
gagttccgct ccaccgttgg acttgctccg ctgtcggcat ccagaaattg cgtggcggag   7800
cggcagacgt gagccggcac ggcaggcggc ctcctcctcc tctcacggca ccggcagcta   7860
cgggggattc ctttcccacc gctccttcgc tttcccttcc tcgcccgccg taataaatag   7920 acacccctc cacacctct ttccccaacc tcgtgttgtt cggagcgcac acacacacaa   7980
ccagatctcc cccaaatcca cccgtcggca cctccgcttc aaggtacgcc gctcgtcctc   8040 ccccccccc ctctctacct tctctagatc ggcgttccgg tccatggtta gggcccggta   8100
gttctacttc tgttcatgtt tgtgttagat ccgtgtttgt gttagatccg tgctgctagc   8160
gttcgtacac ggatgcgacc tgtacgtcag acacgttctg attgctaact tgccagtgtt   8220
tctctttggg gaatcctggg atggctctag ccgttccgca gacgggatcg atttcatgat   8280
tttttttgtt tcgttgcata gggtttggtt tgcccttttc ctttattttca atatatgccg   8340 tgcacttgtt tgtcgggtca tcttttcatg ctttttttg tcttggttgt gatgatgtgg   8400
tctggttggg cggtcgttct agatcggagt agaattctgt ttcaaactac ctggtggatt   8460
tattaatttt ggatctgtat gtgtgtgcca tacatattca tagttacgaa ttgaagatga   8520
```

```
tggatggaaa tatcgatcta ggataggtat acatgttgat gcgggtttta ctgatgcata   8580
tacagagatg cttttgttc gcttggttgt gatgatgtgg tgtggttggg cggtcgttca    8640
ttcgttctag atcggagtag aatactgttt caaactacct ggtgtattta ttaattttgg   8700
aactgtatgt gtgtgtcata catcttcata gttacgagtt taagatggat ggaaatatcg   8760
atctaggata ggtatacatg ttgatgtggg ttttactgat gcatatacat gatggcatat   8820
gcagcatcta ttcatatgct ctaaccttga gtacctatct attataataa acaagtatgt   8880
tttataatta ttttgatctt gatatacttg gatgatggca tatgcagcag ctatatgtgg   8940 attttttag ccctgccttc atacgctatt tatttgcttg gtactgtttc ttttgtcgat    9000
gctcaccctg ttgtttggtg ttacttctgc agggatccgg cagcagccat gcagaagctg   9060
atcaacagcg tgcagaacta cgcctggggc agcaagaccg ccctgaccga gctgtacggc   9120
atggagaacc ccagcagcca gcccatggcc gagctgtgga tgggcgccca ccccaagagc   9180
agcagccgcg tgcagaacgc cgccggcgac atcgtgagcc tgcgcgacgt gatcgagagc   9240
gacaagagca ccctgctggg cgaggccgtg gccaagcgct cggcgagct gcccttcctg    9300 ttcaaggtgc tgtgcgccgc ccagcccctg agcatccagg tgcaccccaa caagcacaac   9360
agcgagatcg gcttcgccaa ggagaacgcc gccggcatcc ccatggacgc cgccgagcgc   9420
aactacaagg accccaacca caagcccgag ctggtgttcg ccctgacccc cttcctggcc   9480
atgaacgcct tccgcgagtt cagcgagatc gtgagcctgc tgcagcccgt ggccggcgcc   9540
caccccgcca tcgcccactt cctgcagcag cccgacgccg agcgcctgag cgagctgttc   9600
gccagcctgc tgaacatgca gggcgaggag aagagccgcg ccctggccat cctgaagagc   9660
gccctggaca gccagcaggg cgagccctgg cagaccatcc gcctgatcag cgagttctac   9720
cccgaggaca gcggcctgtt cagcccctg ctgctgaacg tggtgaagct gaaccccggc    9780
gaggccatgt tcctgttcgc cgagaccccc cacgcctacc tgcagggcgt ggccctggag   9840
gtgatggcca acagcgacaa cgtgctgcgc gccggcctga ccccaagta catcgacatc    9900 cccgagctgg tggccaacgt gaagttcgag gccaagcccg ccaaccagct gctgacccag   9960
cccgtgaagc agggcgccga gctggacttc cccatccccg tggacgactt cgccttcagc  10020
ctgcacgacc tgagcgacaa ggagaccacc atcagccagc agagcgccgc catcctgttc  10080
tgcgtggagg gcgacgccac cctgtggaag ggcagccagc agctgcagct gaagcccggc  10140
gagagcgcct tcatcgccgc caacgagagc cccgtgaccg tgaagggcca cggccgcctg  10200
gcccgcgtgt acaacaagct gtgataggag ctcgatccgt cgacctgcag atcgttcaaa  10260
catttggcaa taaagtttct taagattgaa tcctgttgcc ggtcttgcga tgattatcat  10320
ataatttctg ttgaattacg ttaagcatgt aataattaac atgtaatgca tgacgttatt  10380
tatgagatgg gttttatga ttagagtccc gcaattatac atttaatacg cgatagaaaa   10440
caaaatatag cgcgcaaact aggataaatt atcgcgcgcg gtgtcatcta tgttactaga  10500
tcggcgcgcc gcaattgaag tttgggcggc cagcatggcc gtatccgcaa tgtgttatta  10560
agttgtctaa gcgtcaattt gtttacacca caatatatcc tgccaccagc cagccaacag  10620
ctccccgacc ggcagctcgg cacaaaatca ccactcgata caggcagccc atcagaatta  10680
attctcatgt ttgacagctt atcatcgact gcacggtgca ccaatgcttc tggcgtcagg  10740
cagccatcgg aagctgtggt atggctgtgc aggtcgtaaa tcactgcata attcgtgtcg  10800
ctcaaggcgc actcccgttc tggataatgt tttttgcgcc gacatcataa cggttctggc  10860
```

```
aaatattctg aaatgagctg ttgacaatta atcatccggc tcgtataatg tgtggaattg   10920
tgagcggata acaatttcac acaggaaaca gaccatgagg gaagcgttga tcgccgaagt   10980
atcgactcaa ctatcagagg tagttggcgt catcgagcgc catctcgaac cgacgttgct   11040
ggccgtacat ttgtacggct ccgcagtgga tggcggcctg aagccacaca gtgatattga   11100
tttgctggtt acggtgaccg taaggcttga tgaaacaacg cggcgagctt tgatcaacga   11160
ccttttggaa acttcggctt cccctggaga gagcgagatt ctccgcgctg tagaagtcac   11220
cattgttgtg cacgacgaca tcattccgtg gcgttatcca gctaagcgcg aactgcaatt   11280
tggagaatgg cagcgcaatg acattcttgc aggtatcttc gagccagcca cgatcgacat   11340
tgatctggct atcttgctga caaaagcaag agaacatagc gttgccttgg taggtccagc   11400
ggcggaggaa ctctttgatc cggttcctga acaggatcta tttgaggcgc taaatgaaac   11460
cttaacgcta tggaactcgc cgcccgactg ggctggcgat gagcgaaatg tagtgcttac   11520
gttgtcccgc atttggtaca gcgcagtaac cggcaaaatc gcgccgaagg atgtcgctgc   11580
cgactgggca atggagcgcc tgccggccca gtatcagccc gtcatacttg aagctaggca   11640
ggcttatctt ggacaagaag atcgcttggc ctcgcgcgca gatcagttgg aagaatttgt   11700
tcactacgtg aaaggcgaga tcaccaaagt agtcggcaaa taaagctcta gtggatctcc   11760
gtacccgggg atctggctcg cggcggacgc acgacgccgg ggcgagacca taggcgatct   11820
cctaaatcaa tagtagctgt aacctcgaag cgtttcactt gtaacaacga ttgagaattt   11880
ttgtcataaa attgaaatac ttggttcgca tttttgtcat ccgcggtcag ccgcaattct   11940
gacgaactgc ccatttagct ggagatgatt gtacatcctt cacgtgaaaa tttctcaagc   12000
gctgtgaaca agggttcaga ttttagattg aaaggtgagc cgttgaaaca cgttcttctt   12060
gtcgatgacg acgtcgctat gcggcatctt attattgaat accttacgat ccacgccttc   12120
aaagtgaccg cggtagccga cagcacccag ttcacaagag tactctcttc cgcgacggtc   12180
gatgtcgtgt tgttgatct agatttaggt cgtgaagatg ggctcgagct aggagcaagt   12240
gattttatcg ctaagccgtt cagtatcaga gagtttctag cacgcattcg ggttgccttg   12300
cgcgtgcgcc caacgttgt ccgctccaaa gaccgacggt cttttgttt tactgactgg   12360
acacttaatc tcaggcaacg tcgcttgatg tccgaagctg gcggtgaggt gaaacttacg   12420
gcaggtgagt tcaatcttct cctcgcgttt ttagagaaac cccgcgacgt tctatcgcgc   12480
gagcaacttc tcattgccag tcgagtacgc gacgaggagg tttatgacag gagtatagat   12540
gttctcattt tgaggctgcg ccgcaaactt gaggcagatc cgtcaagccc tcaactgata   12600
aaaacagcaa gaggtgccgg ttatttcttt gacgcggacg tgcaggtttc gcacgggggg   12660
acgatgcag cctgagccaa ttcccagatc cccgaggaat cggcgtgagc ggtcgcaaac   12720
catccggccc ggtacaaatc ggcgcggcgc tgggtgatga cctggtggag aagttgaagg   12780
ccgcgcaggc cgcccagcgg caacgcatcg aggcagaagc acgccccggt gaatcgtggc   12840
aagcggccgc tgatcgaatc cgcaaagaat cccggcaacc gccggcagcc ggtgcgccgt   12900
cgattaggaa gccgcccaag ggcgacgagc aaccagattt tttcgttccg atgctctatg   12960
acgtgggcac ccgcgatagt cgcagcatca tggacgtggc cgttttccgt ctgtcgaagc   13020
gtgaccgacg agctggcgag gtgatccgct acgagcttcc agacgggcac gtagaggttt   13080
ccgcaggcc ggccggcatg gccagtgtgt gggattacga cctggtactg atggcggttt   13140
cccatctaac cgaatccatg aaccgatacc gggaagggaa gggagacaag cccggccgcg   13200
tgttccgtcc acacgttgcg gacgtactca agttctgccg gcgagccgat ggcggaaagc   13260
```

```
agaaagacga cctggtagaa acctgcattc ggttaaacac cacgcacgtt gccatgcagc   13320
gtacgaagaa ggccaagaac ggccgcctgg tgacggtatc cgagggtgaa gccttgatta   13380
gccgctacaa gatcgtaaag agcgaaaccg ggcggccgga gtacatcgag atcgagctag   13440
ctgattggat gtaccgcgag atcacagaag gcaagaaccc ggacgtgctg acggttcacc   13500
ccgattactt tttgatcgat cccggcatcg gccgttttct ctaccgcctg cacgccgcg    13560
ccgcaggcaa ggcagaagcc agatggttgt tcaagacgat ctacgaacgc agtggcagcg   13620
ccggagagtt caagaagttc tgtttcaccg tgcgcaagct gatcgggtca aatgacctgc   13680
cggagtacga tttgaaggag gaggcggggc aggctggccc gatcctagtc atgcgctacc   13740
gcaacctgat cgagggcgaa gcatccgccg gttcctaatg tacggagcag atgctagggc   13800
aaattgccct agcaggggaa aaaggtcgaa aaggtctctt tcctgtggat agcacgtaca   13860
ttgggaaccc aaagccgtac attgggaacc ggaacccgta cattgggaac ccaaagccgt   13920
acattgggaa ccggtcacac atgtaagtga ctgatataaa agagaaaaaa ggcgattttt   13980
ccgcctaaaa ctcttttaaaa cttattaaaa ctcttaaaac ccgcctggcc tgtgcataac   14040
tgtctggcca gcgcacagcc gaagagctgc aaaaagcgcc taccctttcgg tcgctgcgct   14100
ccctacgccc cgccgcttcg cgtcggccta tcgcggccgc tggccgctca aaaatggctg   14160
gcctacggcc aggcaatcta ccagggcgcg gacaagccgc gccgtcgcca ctcgaccgcc   14220
ggcgctgagg tctgcctcgt gaagaaggtg ttgctgactc ataccaggcc tgaatcgccc   14280
catcatccag ccagaaagtg agggagccac ggttgatgag agctttgttg taggtggacc   14340
agttggtgat tttgaacttt tgcttttgcca cggaacggtc tgcgttgtcg ggaagatgcg   14400
tgatctgatc cttcaactca gcaaaagttc gatttattca acaaagccgc cgtcccgtca   14460
agtcagcgta atgctctgcc agtgttacaa ccaattaacc aattctgatt agaaaaactc   14520
atcgagcatc aaatgaaact gcaatttatt catatcagga ttatcaatac catattttg    14580
aaaaagccgt ttctgtaatg aaggagaaaa ctcaccgagg cagttccata ggatggcaag   14640
atcctggtat cggtctgcga ttccgactcg tccaacatca atacaaccta ttaatttccc   14700
ctcgtcaaaa ataaggttat caagtgagaa atcaccatga gtgacgactg aatccggtga   14760
gaatggcaaa agctctgcat taatgaatcg gccaacgcgc ggggagaggc ggtttgcgta   14820
ttgggcgctc ttccgcttcc tcgctcactg actcgctgcg ctcggtcgtt cggctgcggc   14880
gagcggtatc agctcactca aaggcggtaa tacggttatc cacagaatca ggggataacg   14940
caggaaagaa catgtgagca aaaggccagc aaaaggccag gaaccgtaaa aaggccgcgt   15000
tgctggcgtt tttccatagg ctccgccccc ctgacgagca tcacaaaaat cgacgctcaa   15060
gtcagaggtg gcgaaacccg acaggactat aaagatacca ggcgtttccc cctggaagct   15120
ccctcgtgcg ctctcctgtt ccgaccctgc cgcttaccgg atacctgtcc gcctttctcc   15180
cttcgggaag cgtggcgctt tctcatagct cacgctgtag gtatctcagt tcggtgtagg   15240
tcgttcgctc caagctgggc tgtgtgcacg aaccccccgt tcagcccgac cgctgcgcct   15300
tatccggtaa ctatcgtctt gagtccaacc cggtaagaca cgacttatcg ccactggcag   15360
cagccactgg taacaggatt agcagagcga ggtatgtagg cggtgctaca gagttcttga   15420
agtggtggcc taactacggc tacactagaa gaacagtatt tggtatctgc gctctgctga   15480
agccagttac cttcggaaaa agagttggta gctcttgatc cggcaaacaa accaccgctg   15540
gtagcggtgg tttttttgtt tgcaagcagc agattacgcg cagaaaaaaa ggatctcaag   15600
```

-continued

```
aagatccttt gatcttttct acggggtctg acgctcagtg gaacgaaaac tcacgttaag    15660
ggattttggt catgagatta tcaaaaagga tcttcaccta gatccttttg atccggaatt    15720
a                                                                    15721
```

<210> SEQ ID NO 25
<211> LENGTH: 19
<212> TYPE: DNA
<213> ORGANISM: Artificial Sequence
<220> FEATURE:
<223> OTHER INFORMATION: for editing VLHP1 in wheat

<400> SEQUENCE: 25

```
gacgagcagg cgcagttcc                                                 19
```

<210> SEQ ID NO 26
<211> LENGTH: 20
<212> TYPE: DNA
<213> ORGANISM: Triticum aestivum

<400> SEQUENCE: 26

```
gctggagctg agcttccggg                                                20
```

<210> SEQ ID NO 27
<211> LENGTH: 20
<212> TYPE: DNA
<213> ORGANISM: Triticum aestivum

<400> SEQUENCE: 27

```
tctggagctg agcttccggg                                                20
```

<210> SEQ ID NO 28
<211> LENGTH: 20
<212> TYPE: DNA
<213> ORGANISM: Zea mays

<400> SEQUENCE: 28

```
aggcgtcgag cagcgaggtg                                                20
```

<210> SEQ ID NO 29
<211> LENGTH: 20
<212> TYPE: DNA
<213> ORGANISM: Artificial Sequence
<220> FEATURE:
<223> OTHER INFORMATION: edited ZmVLHP-03 portion

<400> SEQUENCE: 29

```
aggcgttgag cagcgaggtg                                                20
```

<210> SEQ ID NO 30
<211> LENGTH: 75
<212> TYPE: DNA
<213> ORGANISM: Artificial Sequence
<220> FEATURE:
<223> OTHER INFORMATION: repair donor template for creating E149L
      mutation in ZmPYL-D

<400> SEQUENCE: 30

```
ccttggtgtt gccgtcgggg acgtcgacga cgaatgacag gatgacgagc gtccctggcc    60
ggccgtcgat gacct                                                     75
```

<210> SEQ ID NO 31
<211> LENGTH: 15722
<212> TYPE: DNA

```
<213> ORGANISM: Artificial Sequence
<220> FEATURE:
<223> OTHER INFORMATION: vector 23136
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (304)..(2100)
<223> OTHER INFORMATION: prSoUbi4-04
<220> FEATURE:
<221> NAME/KEY: gene
<222> LOCATION: (2117)..(6286)
<223> OTHER INFORMATION: cCas9-01
<220> FEATURE:
<221> NAME/KEY: mutation
<222> LOCATION: (5606)..(5608)
<223> OTHER INFORMATION: L to V mutation
<220> FEATURE:
<221> NAME/KEY: mutation
<222> LOCATION: (5651)..(5653)
<223> OTHER INFORMATION: I to V mutation
<220> FEATURE:
<221> NAME/KEY: terminator
<222> LOCATION: (6292)..(6544)
<223> OTHER INFORMATION: tNOS-05-01
<220> FEATURE:
<221> NAME/KEY: promoter
<222> LOCATION: (6551)..(6925)
<223> OTHER INFORMATION: prOsU3-01
<220> FEATURE:
<221> NAME/KEY: misc_feature
<222> LOCATION: (6927)..(6946)
<223> OTHER INFORMATION: xZmPYL-D
<220> FEATURE:
<221> NAME/KEY: misc_feature
<222> LOCATION: (6927)..(7031)
<223> OTHER INFORMATION: rsgRBAZmPYLd-02
<220> FEATURE:
<221> NAME/KEY: promoter
<222> LOCATION: (7042)..(9033)
<223> OTHER INFORMATION: prUbi1-04
<220> FEATURE:
<221> NAME/KEY: gene
<222> LOCATION: (9050)..(10228)
<223> OTHER INFORMATION: cPMI-09
<220> FEATURE:
<221> NAME/KEY: terminator
<222> LOCATION: (10251)..(10503)
<223> OTHER INFORMATION: tNOS-05-01
<220> FEATURE:
<221> NAME/KEY: misc_feature
<222> LOCATION: (10547)..(10676)
<223> OTHER INFORMATION: bNLB-03
<220> FEATURE:
<221> NAME/KEY: gene
<222> LOCATION: (10956)..(11744)
<223> OTHER INFORMATION: cSpec-03
<220> FEATURE:
<221> NAME/KEY: promoter
<222> LOCATION: (11839)..(11969)
<223> OTHER INFORMATION: prVirG-01
<220> FEATURE:
<221> NAME/KEY: gene
<222> LOCATION: (12706)..(13779)
<223> OTHER INFORMATION: cRepA-01
<220> FEATURE:
<221> NAME/KEY: misc_feature
<222> LOCATION: (13822)..(14226)
<223> OTHER INFORMATION: oVS1-02
<220> FEATURE:
<221> NAME/KEY: misc_feature
<222> LOCATION: (14904)..(15710)
<223> OTHER INFORMATION: oCOLE-06

<400> SEQUENCE: 31
attcctgtgg ttggcatgca catacaaatg gacgaacgga taaaccttttt cacgcccttt    60
```

```
taaatatccg attattctaa taaacgctct tttctcttag gtttaccogc caatatatcc    120 tgtcaaacac tgatagttta aactgaaggc gggaaacgac aatctgatca tgagcggaga    180
attaagggag tcacgttatg acccccgccg atgacgcggg acaagccgtt ttacgtttgg    240
aactgacaga accgcaacgc tgcaggaatt ggccgcagcg gccatttaaa caaagcttgg    300
taccattatg tggtctaggt aggttctata tataagaaaa cttgaaatgt tctaaaaaaa    360
aattcaagcc catgcatgat tgaagcaaac ggtatagcaa cggtgttaac ctgatctagt    420
gatctcttgc aatccttaac ggccacctac cgcaggtagc aaacggcgtc ccctcctcg     480 atatctccgc ggcgacctct ggctttttcc gcggaattgc gcggtgggga cggattccac    540
gagaccgcga cgcaaccgcc tctcgccgct gggccccaca ccgctcggtg ccgtagcctc    600
acgggactct ttctccctcc tccccgttta taaattggct tcatcccctc cttgcctcat    660
ccatccaaat cccagtcccc aatcccatcc cttcgtagga gaaattcatc gaagctaagc    720
gaatcctcgc gatcctctca aggtactgcg agttttcgat cccctctcg accoctcgta     780 tgtttgtgtt tgtcgtagcg tttgattagg tatgcttttcc ctgtttgtgt tcgtcgtagc    840
gtttgattag gtatgctttc cctgttcgtg ttcatcgtag tgtttgatta ggtcgtgtga    900
ggcgatggcc tgctcgcgtc cttcgatctg tagtcgattt gcgggtcgtg gtgtagatct    960
gcgggctgtg atgaagttat ttggtgtgat ctgctcgcct gattctgcgg gttggctcga    1020
gtagatatga tggttggacc ggttggttcg tttaccgcgc tagggttggg ctgggatgat    1080
gttgcatgcg ccgttgcgcg tgatcccgca gcaggacttg cgtttgattg ccagatctcg    1140
ttacgattat gtgatttggt ttggactttt tagatctgta gcttctgctt atgtgccaga    1200
tgcgcctact gctcatatgc ctgatgataa tcataaatgg ctgtggaact aactagttga    1260
ttgcggagtc atgtatcagc tacaggtgta gggactagct acaggtgtag ggacttgcgt    1320
ctaattgttt ggtcctttac tcatgttgca attatgcaat ttagtttaga ttgtttgttc    1380
cactcatcta ggctgtaaaa gggacactgc ttagattgct gtttaatctt tttagtagat    1440
tatattatat tggtaactta ttaccccctat tacatgccat acgtgacttc tgctcatgcc    1500
tgatgataat catagatcac tgtggaatta attagttgat tgttgaatca tgtttcatgt    1560
acataccacg gcacaattgc ttagttcctt aacaaatgca aattttactg atccatgtat    1620
gatttgcgtg gttctctaat gtgaaatact atagctactt gttagtaaga atcaggttcg    1680
tatgcttaat gctgtatgtg ccttctgctc atgcctgatg ataatcatat atcactggaa    1740
ttaattagtt gatcgtttaa tcatatatca agtacatacc atgccacaat ttttagtcac    1800
ttaacccatg cagattgaac tggtccctgc atgttttgct aaattgttct attctgatta    1860
gaccatatat catgtatttt tttttggtaa tggttctctt atttaaatg ctatatagtt     1920 ctggtacttg ttagaaagat ctgcttcata gtttagttgc ctatccctcg aattaggatg    1980
ctgagcagct gatcctatag cttgttttca tgtatcaatt cttttgtgtt caacagtcag    2040 ttttttgttag attcattgta acttatggtc gcttactctt ctggtcctca atgcttgcag    2100
gatcgcggcc gctcatatgg acaagaagta cagcatcggc ctggacatcg gcaccaacag    2160
cgtgggctgg gccgtgatca ccgacgagta caaggtgccg agcaagaagt tcaaggtgct    2220
gggcaacacc gacaggcaca gcatcaagaa gaacctgatc ggcgccctgc tgttcgacag    2280
cggcgagacc gccgaggcca ccaggctgaa gaggaccgcc aggaggaggt acaccaggag    2340
gaagaacagg atctgctacc tgcaggagat cttcagcaac gagatggcca aggtggacga    2400
```

-continued

```
cagcttcttc cacaggctgg aggagagctt cctggtggag gaggacaaga agcacgagag    2460
gcacccgatc ttcggcaaca tcgtggacga ggtggcctac cacgagaagt acccgaccat    2520
ctaccacctg aggaagaagc tggtggacag caccgacaag gccgacctga ggctgatcta    2580
cctggccctg gcccacatga tcaagttcag gggccacttc ctgatcgagg gcgacctgaa    2640
cccggacaac agcgacgtgg acaagctgtt catccagctg gtgcagacct acaaccagct    2700
gttcgaggag aacccgatca acgccagcgg cgtggacgcc aaggccatcc tgagcgccag    2760
gctgagcaag agcaggaggc tggagaacct gatcgcccag ctgccgggcg agaagaagaa    2820
cggcctgttc ggcaacctga tcgccctgag cctgggcctg accccgaact tcaagagcaa    2880
cttcgacctg gccgaggacg ccaagctgca gctgagcaag gacacctacg acgacgacct    2940
ggacaacctg ctggcccaga tcggcgacca gtacgccgac ctgttcctgg ccgccaagaa    3000
cctgagcgac gccatcctgc tgagcgacat cctgagggtg aacaccgaga tcaccaaggc    3060
cccgctgagc gccagcatga tcaagaggta cgacgagcac caccaggacc tgaccctgct    3120
gaaggccctg gtgaggcagc agctgccgga gaagtacaag gagatcttct tcgaccagag    3180
caagaacggc tacgccggct acatcgacgg cggcgccagc caggaggagt ctacaagtt     3240
catcaagccg atcctggaga gatggacgg caccgaggag ctgctggtga agctgaacag     3300
ggaggacctg ctgaggaagc agaggacctt cgacaacggc agcatcccgc accagatcca    3360
cctgggcgag ctgcacgcca tcctgaggag gcaggaggac ttctacccgt tcctgaagga    3420
caacagggag aagatcgaga agatcctgac cttccgcatc ccgtactacg tgggcccgct    3480
ggccagggc aacagcaggt cgcctggat gaccaggaag agcgaggaga ccatcacccc     3540
gtggaacttc gaggaggtgg tggacaaggg cgccagcgcc cagagcttca tcgagaggat    3600
gaccaacttc gacaagaacc tgccgaacga gaaggtgctg ccgaagcaca gcctgctgta    3660
cgagtacttc accgtgtaca acgagctgac caaggtgaag tacgtgaccg agggcatgag    3720
gaagccggcc ttcctgagcg gcgagcagaa gaaggccatc gtggacctgc tgttcaagac    3780
caacaggaag gtgaccgtga agcagctgaa ggaggactac ttcaagaaga tcgagtgctt    3840
cgacagcgtg gagatcagcg gcgtggagga caggttcaac gccagcctgg gcacctacca    3900
cgacctgctg aagatcatca aggacaagga cttcctggac aacgaggaga cgaggacat     3960
cctggaggac atcgtgctga ccctgaccct gttcgaggac aggagatga tcgaggagag     4020
gctgaagacc tacgcccacc tgttcgacga caaggtgatg aagcagctga agaggaggag    4080
gtacaccggc tggggcaggc tgagcaggaa gctgatcaac ggcatcaggg acaagcagag    4140
cggcaagacc atcctggact tcctgaagag cgacggcttc gccaacagga acttcatgca    4200
gctgatccac gacgacagcc tgaccttcaa ggaggacatc cagaaggccc aggtgagcgg    4260
ccagggcgac agcctgcacg agcacatcgc caacctggcc ggcagcccgg ccatcaagaa    4320
gggcatcctg cagaccgtga aggtggtgga cgagctggtg aaggtgatgg gcaggcacaa    4380
gccggagaac atcgtgatcg agatggccag ggagaaccag accacccaga gggccagaa     4440
gaacagcagg gagaggatga gaggatcga ggagggcatc aaggagctgg gcagccagat     4500
cctgaaggag cacccggtgg agaacaccca gctgcagaac gagaagctgt acctgtacta    4560
cctgcagaac ggcagggaca tgtacgtgga ccaggagctg gacatcaaca ggctgagcga    4620
ctacgacgtg gaccacatcg tgccgcagag cttcctgaag gacgcagca tcgacaacaa     4680
ggtgctgacc aggagcgaca agaacagggg caagagcgac aacgtgccga gcgaggaggt    4740
ggtgaagaag atgaaaaact actggaggca gctgctgaac gccaagctga tcacccagag    4800
```

```
gaagttcgac aacctgacca aggccgagag gggcggcctg agcgagctgg acaaggccgg   4860
cttcattaaa aggcagctgg tggagaccag gcagatcacc aagcacgtgg cccagatcct   4920
ggacagcagg atgaacacca agtacgacga gaacgacaag ctgatcaggg aggtgaaggt   4980
gatcaccctg aagagcaagc tggtgagcga cttcaggaag gacttccagt tctacaaggt   5040
gagggagatc aataattacc accacgccca cgacgcctac ctgaacgccg tggtgggcac   5100
cgccctgatt aaaaagtacc cgaagctgga gagcgagttc gtgtacggcg actacaaggt   5160
gtacgacgtg aggaagatga tcgccaagag cgagcaggag atcggcaagg ccaccgccaa   5220
gtacttcttc tacagcaaca tcatgaactt cttcaagacc gagatcaccc tggccaacgg   5280
cgagatcagg aagaggccgc tgatcgagac caacggcgag accggcgaga tcgtgtggga   5340
caagggcagg gacttcgcca ccgtgaggaa ggtgctgtcc atgccgcagg tgaacatcgt   5400
gaagaagacc gaggtgcaga ccggcggctt cagcaaggag agcatcctgc cgaagaggaa   5460
cagcgacaag ctgatcgcca ggaagaagga ctgggacccg aagaagtacg gcggcttcga   5520
cagcccgacc gtggcctaca gcgtgctggt ggtggccaag gtggagaagg caagagcaa   5580 gaagctgaag agcgtgaagg agctggtggg catcaccatc atggagagga gcagcttcga   5640
gaagaaccca gtggacttcc tggaggccaa gggctacaag gaggtgaaga aggacctgat   5700
cattaaactg ccgaagtaca gcctgttcga gctggagaac ggcaggaaga ggatgctggc   5760
cagcgccggc gagctgcaga agggcaacga gctggccctg ccgagcaagt acgtgaactt   5820
cctgtacctg gccagccact acgagaagct gaagggcagc ccggaggaca cgagcagaa   5880 gcagctgttc gtggagcagc acaagcacta cctggacgag atcatcgagc agatcagcga   5940
gttcagcaag agggtgatcc tggccgacgc caacctggac aaggtgctga gcgcctacaa   6000
caagcacagg gacaagccga tcagggagca ggccgagaac atcatccacc tgttcaccct   6060
gaccaacctg ggcgccccgg ccgccttcaa gtacttcgac accaccatcg acaggaagag   6120
gtacaccagc accaaggagg tgctggacgc caccctgatc caccagagca tcaccggcct   6180
gtacgagacc aggatcgacc tgagccagct gggcggcgac agcagcccgc cgaagaagaa   6240
gaggaaggtg agctggaagg acgccagcgg ctggagcagg atgtgaagct tgatcgttca   6300
aacatttggc aataaagttt cttaagattg aatcctgttg ccggtcttgc gatgattatc   6360
atataatttc tgttgaatta cgttaagcat gtaataatta acatgtaatg catgacgtta   6420
tttatgagat gggtttttat gattagagtc ccgcaattat acatttaata cgcgatagaa   6480
aacaaaatat agcgcgcaaa ctaggataaa ttatcgcgcg cggtgtcatc tatgttacta   6540
gatcttcgaa gggatcttta aacatacgaa cagatcactt aaagttcttc tgaagcaact   6600
taaagttatc aggcatgcat ggatcttgga ggaatcagat gtgcagtcag gaccatagc   6660 acaggacagg cgtcttctac tggtgctacc agcaaatgct ggaagccggg aacactgggt   6720
acgttggaaa ccacgtgatg tggagtaaga taaactgtag gagaaaagca tttcgtagtg   6780
ggccatgaag ccttcagga catgtattgc agtatgggcc ggcccattac gcaattggac   6840
gacaacaaag actagtatta gtaccacctc ggctatccac atagatcaaa gctggtttaa   6900
aagagttgtg cagatgatcc gtggcagtcg gggacgtcga cgacgagttt tagagctaga   6960
aatagcaagt taaaataagg ctagtccgtt atcaacttga aaagtggca ccgagtcggt   7020 gctttttttt tcggaccgcg cctgcagtgc agcgtgaccc ggtcgtgccc ctctctagag   7080
ataatgagca ttgcatgtct aagttataaa aaattaccac atatttttt tgtcacactt   7140
```

-continued

```
gtttgaagtg cagtttatct atctttatac atatatttaa actttactct acgaataata   7200
taatctatag tactacaata atatcagtgt tttagagaat catataaatg aacagttaga   7260
catggtctaa aggacaattg agtattttga caacaggact ctacagtttt atctttttag   7320
tgtgcatgtg ttctccttt tttttgcaaa tagcttcacc tatataatac ttcatccatt   7380
ttattagtac atccatttag ggtttagggt taatggtttt tatagactaa tttttttagt   7440
acatctattt tattctattt tagcctctaa attaagaaaa ctaaaactct attttagttt   7500
ttttatttaa taatttagat ataaaataga ataaaataaa gtgactaaaa attaaacaaa   7560
tacccttttaa gaaattaaaa aaactaagga aacatttttc ttgtttcgag tagataatgc   7620
cagcctgtta aacgccgtcg acgagtctaa cggacaccaa ccagcgaacc agcagcgtcg   7680
cgtcgggcca agcgaagcag acggcacggc atctctgtcg ctgcctctgg acccctctcg   7740
agagttccgc tccaccgttg gacttgctcc gctgtcggca tccagaaatt gcgtggcgga   7800
gcggcagacg tgagccggca cggcaggcgg cctcctcctc ctctcacggc accggcagct   7860
acgggggatt cctttcccac cgctccttcg ctttcccttc ctcgcccgcc gtaataaata   7920
gacaccccct ccacccctc tttccccaac ctcgtgttgt tcggagcgca cacacacaca   7980
accagatctc ccccaaatcc acccgtcggc acctccgctt caaggtacgc cgctcgtcct   8040
ccccccccc cctctctacc ttctctagat cggcgttccg gtccatggtt agggcccggt   8100
agttctactt ctgttcatgt ttgtgttaga tccgtgtttg tgttagatcc gtgctgctag   8160
cgttcgtaca cggatgcgac ctgtacgtca gacacgttct gattgctaac ttgccagtgt   8220
ttctcttgg ggaatcctgg gatggctcta gccgttccgc agacgggatc gatttcatga   8280
ttttttttgt ttcgttgcat agggtttggt ttgccctttt cctttatttc aatatatgcc   8340
gtgcacttgt ttgtcgggtc atcttttcat gcttttttt gtcttggttg tgatgatgtg   8400
gtctggttgg gcggtcgttc tagatcggag tagaattctg tttcaaacta cctggtggat   8460
ttattaattt tggatctgta tgtgtgtgcc atacatattc atagttacga attgaagatg   8520
atggatggaa atatcgatct aggataggta tacatgttga tgcgggtttt actgatgcat   8580
atacagagat gctttttgtt cgcttggttg tgatgatgtg gtgtggttgg gcggtcgttc   8640
attcgttcta gatcggagta gaatactgtt tcaaactacc tggtgtattt attaattttg   8700
gaactgtatg tgtgtgtcat acatcttcat agttacgagt ttaagatgga tggaaatatc   8760
gatctaggat aggtatacat gttgatgtgg gttttactga tgcatataca tgatggcata   8820
tgcagcatct attcatatgc tctaaccttg agtacctatc tattataata aacaagtatg   8880
ttttataatt attttgatct tgatatactt ggatgatggc atatgcagca gctatatgtg   8940
gatttttta gccctgcctt catacgctat ttatttgctt ggtactgttt cttttgtcga   9000
tgctcaccct gttgtttggt gttacttctg cagggatccg gcagcagcca tgcagaagct   9060
gatcaacagc gtgcagaact acgcctgggg cagcaagacc gccctgaccg agctgtacgg   9120
catggagaac cccagcagcc agcccatggc cgagctgtgg atgggcgccc accccaagag   9180
cagcagccgc gtgcagaacg ccgccggcga catcgtgagc ctgcgcgacg tgatcgagag   9240
cgacaagagc accctgctgg gcgaggccgt ggccaagcgc ttcggcgagc tgcccttcct   9300
gttcaaggtg ctgtgcgccg cccagcccct gagcatccag gtgcaccca acaagcacaa   9360
cagcgagatc ggcttcgcca aggagaacgc cgccggcatc cccatggacg ccgccgagcg   9420
caactacaag gaccccaacc acaagcccga gctggtgttc gccctgaccc ccttcctggc   9480
catgaacgcc ttccgcgagt tcagcgagat cgtgagcctg ctgcagcccg tggccggcgc   9540
```

```
ccaccccgcc atcgcccact tcctgcagca gcccgacgcc gagcgcctga gcgagctgtt    9600
cgccagcctg ctgaacatgc agggcgagga gaagagccgc gccctggcca tcctgaagag    9660
cgccctggac agccagcagg gcgagccctg gcagaccatc cgcctgatca gcgagttcta    9720
ccccgaggac agcggcctgt tcagccccct gctgctgaac gtggtgaagc tgaacccgg     9780
cgaggccatg ttcctgttcg ccgagacccc ccacgcctac ctgcagggcg tggccctgga    9840
ggtgatggcc aacagcgaca acgtgctgcg cgccggcctg accccaagt acatcgacat     9900
ccccgagctg gtggccaacg tgaagttcga ggccaagccc gccaaccagc tgctgaccca    9960
gcccgtgaag cagggcgccg agctggactt ccccatcccc gtggacgact cgcccttcag   10020
cctgcacgac ctgagcgaca aggagaccac catcagccag cagagcgccg ccatcctgtt   10080
ctgcgtggag ggcgacgcca ccctgtggaa gggcagccag cagctgcagc tgaagcccgg   10140
cgagagcgcc ttcatcgccg ccaacgagag ccccgtgacc gtgaagggcc acggccgcct   10200
ggcccgcgtg tacaacaagc tgtgataggc gctcgatccg tcgacctgca gatcgttcaa   10260
acatttggca ataaagtttc ttaagattga atcctgttgc cggtcttgcg atgattatca   10320
tataatttct gttgaattac gttaagcatg taataattaa catgtaatgc atgacgttat   10380
ttatgagatg ggtttttatg attagagtcc cgcaattata catttaatac gcgatagaaa   10440
acaaaatata gcgcgcaaac taggataaat tatcgcgcgc ggtgtcatct atgttactag   10500
atcggcgcgc cgcaattgaa gtttgggcgg ccagcatggc cgtatccgca atgtgttatt   10560
aagttgtcta agcgtcaatt tgtttacacc acaatatatc ctgccaccag ccagccaaca   10620
gctccccgac cggcagctcg gcacaaaatc accactcgat acaggcagcc catcagaatt   10680
aattctcatg tttgacagct tatcatcgac tgcacggtgc accaatgctt ctggcgtcag   10740
gcagccatcg gaagctgtgg tatggctgtg caggtcgtaa atcactgcat aattcgtgtc   10800
gctcaaggcg cactcccgtt ctggataatg ttttttgcgc cgacatcata acggttctgg   10860
caaatattct gaaatgagct gttgacaatt aatcatccgg ctcgtataat gtgtggaatt   10920
gtgagcggat aacaatttca cacaggaaac agaccatgag ggaagcgttg atcgccgaag   10980
tatcgactca actatcagag gtagttggcg tcatcgagcg ccatctcgaa ccgacgttgc   11040
tggccgtaca tttgtacggc tccgcagtgg atggcggcct gaagccacac agtgatattg   11100
atttgctggt tacggtgacc gtaaggcttg atgaaacaac gcggcgagct ttgatcaacg   11160
accttttgga aacttcggct tcccctggag agagcgagat tctccgcgct gtagaagtca   11220
ccattgttgt gcacgacgac atcattccgt ggcgttatcc agctaagcgc gaactgcaat   11280
ttggagaatg gcagcgcaat gacattcttg caggtatctt cgagccagcc acgatcgaca   11340
ttgatctggc tatcttgctg acaaaagcaa gagaacatag cgttgccttg gtaggtccag   11400
cggcggagga actctttgat ccggttcctg aacaggatct atttgaggcg ctaaatgaaa   11460
ccttaacgct atggaactcg ccgcccgact gggctggcga tgagcgaaat gtagtgctta   11520
cgttgtcccg catttggtac agcgcagtaa ccggcaaaat cgcgccgaag gatgtcgctg   11580
ccgactgggc aatggagcgc ctgccggccc agtatcagcc cgtcatactt gaagctaggc   11640
aggcttatct tggacaagaa gatcgcttgg cctcgcgcgc agatcagttg gaagaatttg   11700
ttcactacgt gaaaggcgag atcaccaaag tagtcggcaa ataaagctct agtggatctc   11760
cgtacccggg gatctggctc gcggcggacg cacgacgccg gggcgagacc ataggcgatc   11820
tcctaaatca atagtagctg taacctcgaa gcgtttcact tgtaacaacg attgagaatt   11880
```

```
tttgtcataa aattgaaata cttggttcgc attttttgtca tccgcggtca gccgcaattc   11940
tgacgaactg cccatttagc tggagatgat tgtacatcct tcacgtgaaa atttctcaag   12000
cgctgtgaac aagggttcag attttagatt gaaaggtgag ccgttgaaac acgttcttct   12060
tgtcgatgac gacgtcgcta tgcggcatct tattattgaa taccttacga tccacgcctt   12120
caaagtgacc gcggtagccg acagcaccca gttcacaaga gtactctctt ccgcgacggt   12180
cgatgtcgtg gttgttgatc tagatttagg tcgtgaagat gggctcgagc taggagcaag   12240
tgattttatc gctaagccgt tcagtatcag agagtttcta gcacgcattc gggttgcctt   12300
gcgcgtgcgc cccaacgttg tccgctccaa agaccgacgg tctttttgtt ttactgactg   12360
gacacttaat ctcaggcaac gtcgcttgat gtccgaagct ggcggtgagg tgaaacttac   12420
ggcaggtgag ttcaatcttc tcctcgcgtt tttagagaaa ccccgcgacg ttctatcgcg   12480
cgagcaactt ctcattgcca gtcgagtacg cgacgaggag gtttatgaca ggagtataga   12540
tgttctcatt ttgaggctgc gccgcaaact tgaggcagat ccgtcaagcc ctcaactgat   12600
aaaaacagca agaggtgccg gttatttctt tgacgcggac gtgcaggttt cgcacggggg   12660
gacgatggca gcctgagcca attcccagat ccccgaggaa tcggcgtgag cggtcgcaaa   12720
ccatccggcc cggtacaaat cggcgcgcg ctgggtgatg acctggtgga gaagttgaag   12780
gccgcgcagg ccgcccagcg gcaacgcatc gaggcagaag cacgccccgg tgaatcgtgg   12840
caagcggccg ctgatcgaat ccgcaaagaa tcccggcaac cgccggcagc cggtgcgccg   12900
tcgattagga agccgcccaa gggcgacgag caaccagatt ttttcgttcc gatgctctat   12960
gacgtgggca cccgcgatag tcgcagcatc atggacgtgg ccgttttccg tctgtcgaag   13020
cgtgaccgac gagctggcga ggtgatccgc tacgagcttc cagacgggca cgtagaggtt   13080
tccgcagggc cggccggcat ggccagtgtg tgggattacg acctggtact gatgcggtt   13140 tcccatctaa ccgaatccat gaaccgatac cgggaaggga agggagacaa gcccggccgc   13200
gtgttccgtc cacacgttgc ggacgtactc aagttctgcc ggcgagccga tggcggaaag   13260
cagaaagacg acctggtaga aacctgcatt cggttaaaca ccacgcacgt tgccatgcag   13320
cgtacgaaga aggccaagaa cggccgcctg gtgacggtat ccgagggtga agccttgatt   13380
agccgctaca agatcgtaaa gagcgaaacc gggcggccgg agtacatcga gatcgagcta   13440
gctgattgga tgtaccgcga gatcacagaa ggcaagaacc cggacgtgct gacgttcac   13500 cccgattact ttttgatcga tcccggcatc ggccgttttc tctaccgcct ggcacgccgc   13560
gccgcaggca aggcagaagc cagatggttg ttcaagacga tctacgaacg cagtggcagc   13620
gccggagagt tcaagaagtt ctgttctcacc gtgcgcaagc tgatcgggtc aaatgacctg   13680
ccggagtacg atttgaagga ggaggcgggg caggctggcc cgatcctagt catgcgctac   13740
cgcaacctga tcgagggcga agcatccgcc ggttcctaat gtacggagca gatgctaggg   13800
caaattgccc tagcagggga aaaggtcga aaaggtctct ttcctgtgga tagcacgtac   13860
attgggaacc caaagccgta cattgggaac cggaacccgt acattgggaa cccaaagccg   13920
tacattggga accggtcaca catgtaagtg actgatataa aagagaaaaa aggcgatttt   13980
tccgcctaaa actctttaaa acttattaaa actcttaaaa cccgcctggc ctgtgcataa   14040
ctgtctggcc agcgcacagc cgaagagctg caaaaagcgc ctaccctccg gtcgctgcgc   14100
tccctacgcc ccgccgcttc gcgtcggcct atcgcggccg ctggccgctc aaaaatggct   14160
ggcctacggc caggcaatct accagggcgc ggacaagccg cgccgtcgcc actcgaccgc   14220
cggcgctgag gtctgcctcg tgaagaaggt gttgctgact cataccaggc ctgaatcgcc   14280
```

```
ccatcatcca gccagaaagt gagggagcca cggttgatga gagctttgtt gtaggtggac    14340
cagttggtga ttttgaactt ttgctttgcc acggaacggt ctgcgttgtc gggaagatgc    14400
gtgatctgat ccttcaactc agcaaaagtt cgatttattc aacaaagccg ccgtcccgtc    14460
aagtcagcgt aatgctctgc cagtgttaca accaattaac caattctgat tagaaaaact    14520
catcgagcat caaatgaaac tgcaatttat tcatatcagg attatcaata ccatatttt    14580 gaaaaagccg tttctgtaat gaaggagaaa actcaccgag gcagttccat aggatggcaa    14640
gatcctggta tcggtctgcg attccgactc gtccaacatc aatacaacct attaatttcc    14700
cctcgtcaaa aataaggtta tcaagtgaga atcaccatg agtgacgact gaatccggtg    14760
agaatggcaa aagctctgca ttaatgaatc ggccaacgcg cggggagagg cggtttgcgt    14820
attgggcgct cttccgcttc ctcgctcact gactcgctgc gctcggtcgt tcggctgcgg    14880
cgagcggtat cagctcactc aaaggcggta atacggttat ccacagaatc aggggataac    14940
gcaggaaaga acatgtgagc aaaaggccag caaaaggcca ggaaccgtaa aaaggccgcg    15000
ttgctggcgt ttttccatag gctccgcccc cctgacgagc atcacaaaaa tcgacgctca    15060
agtcagaggt ggcgaaaccc gacaggacta taaagatacc aggcgtttcc ccctggaagc    15120
tccctcgtgc gctctcctgt tccgaccctg ccgcttaccg gatacctgtc gcctttctc    15180 ccttcgggaa gcgtggcgct ttctcatagc tcacgctgta ggtatctcag ttcggtgtag    15240
gtcgttcgct ccaagctggg ctgtgtgcac gaaccccccg ttcagcccga ccgctgcgcc    15300
ttatccggta actatcgtct tgagtccaac ccggtaagac acgacttatc gccactggca    15360
gcagccactg gtaacaggat tagcagagcg aggtatgtag gcggtgctac agagttcttg    15420
aagtggtggc ctaactacgg ctacactaga agaacagtat ttggtatctg cgctctgctg    15480
aagccagtta ccttcggaaa aagagttggt agctcttgat ccggcaaaca aaccaccgct    15540
ggtagcggtg gtttttttgt ttgcaagcag cagattacgc gcagaaaaaa aggatctcaa    15600
gaagatcctt tgatcttttc tacggggtct gacgctcagt ggaacgaaaa ctcacgttaa    15660
gggattttgg tcatgagatt atcaaaaagg atcttcacct agatcctttt gatccggaat    15720
ta                                                                  15722
```

<210> SEQ ID NO 32
<211> LENGTH: 20
<212> TYPE: DNA
<213> ORGANISM: Artificial Sequence
<220> FEATURE:
<223> OTHER INFORMATION: encoding gRNA for vector 23136

<400> SEQUENCE: 32

```
gtcggggacg tcgacgacga                                                20
```

<210> SEQ ID NO 33
<211> LENGTH: 1823
<212> TYPE: DNA
<213> ORGANISM: Oryza sativa

<400> SEQUENCE: 33

```
acagtgacta gtgacaaacg atcgatcgat ccctccatcc acaaaccctc ctcgatctca      60
tcttccttcg tctcgtcaat ggcggcgagc tactcgtgcc ggcggacatg cgaggcgtgc     120
agcacgaggg cgatggccgg gtgcgtggtg ggcgagccgg cgtcggcgcc ggggcagcgg     180
gtgacgttgc tggcgatcga cggcggcggc atcagggggcc tcatcccggg caccatcctc     240
```

```
gccttcctcg aggccaggct gcaggagctg gatggccccg acgcgcgcct cgccgattac    300
ttcgactgca tcgccgggac cagcaccggc ggcctcatca ccgccatgct cgccgcgccc    360
ggcgaccacg gccgcccgct cttcgccgcc agcgacatca accgcttcta cctcgacaac    420
ggcccactca tcttcccaca aaagtaactg atcacctcga attcgatctc ctctcttcga    480
tctctgcatt atttgatttg attggggatt gtgggcggcg tggcgtggcg tccaggaggt    540
gcggcatggc ggcggccatg gcggcgctga cgaggccgag gtacaacggc aagtacctgc    600
aggggaagat caggaagatg ctgggcgaga cgagggtgcg cgacacgctg acgaacgtcg    660
tcatccccac gttcgacgtc aggctgctcc agccaaccat cttctccaca tacgacgtgc    720
gtgcgttgat tccatccgca ttggcgttgg aatcagctga ttgtttgatt gatcgaacaa    780
ttgatcggtt aaaattttgc aggcgaagag catgccgctc aagaacgcgc tcctctccga    840
catctgcatc agcacatccg cggcgccgac ctacctcccc gcgcactgct tccagaccac    900
cgacgacgcc accggcaagg tccgcgagtt cgacctcatc gacggcggcg tcgccgccaa    960
caacccggta actaatcaat caagcaatcc atcaaacgaa gatccacatg tgcattcctg   1020
tggtacaaat gctgatcgat cgatggatgg atcgattttc gcgagaacgt acagacgatg   1080
gtggccatga cgcagatcac caagaagata atggtgaagg acaaggagga gctgtacccg   1140
gtaaagccgt cggactgcgg taagttcctg gtgctgtccg tgggcaccgg gtcgacgtcg   1200
gaccagggga tgtacacggc gaggcagtgc tcgcggtggg ggatcgtccg gtggctgcgc   1260
aacaagggga tggcgcccat catcgacatc ttcatggcgg ccagctccga cctcgtcgac   1320
atccacgccg ccgtcatgtt ccagtcgctg cacagcgacg gcgactacct ccgcatccag   1380
gacaacacgc tccacggcga cgccgccacg gtggacgccg ccaccaggga caacatgcgg   1440
gcgctcgtcg ggatcggcga gcggatgctg gcgcagcggg tgtcgagggt caacgtcgag   1500
accggcaggt acgtcgaggt gcccggcgcc ggcagcaacg ccgacgcgct gaggggcttc   1560
gccaggcagc tctccgagga gaggagggcg aggctaggtc ggcgaaacgc tgcggcggc   1620
ggcggcgaag gagagcccag cggcgtggcg tgcaagcgtt agtaactgta cacgcatcat   1680
gctgacgcga tctttttat ttttcttttt ttttttac ctttctagcg gacatgggga    1740
ataacaagac gtgacagtag tgcaatcggt ttgtaacgtg cgtataccaa cattgatcca   1800
tttcttcatc acagtttcag ttc                                           1823
```

<210> SEQ ID NO 34
<211> LENGTH: 15921
<212> TYPE: DNA
<213> ORGANISM: Artificial Sequence
<220> FEATURE:
<223> OTHER INFORMATION: Vector 24038
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (313)..(1149)
<223> OTHER INFORMATION: prZmGRMZM5G876285-01
<220> FEATURE:
<221> NAME/KEY: gene
<222> LOCATION: (1152)..(5412)
<223> OTHER INFORMATION: cCas9-12
<220> FEATURE:
<221> NAME/KEY: terminator
<222> LOCATION: (5419)..(6736)
<223> OTHER INFORMATION: tZmGRMZM5G876285-01
<220> FEATURE:
<221> NAME/KEY: promoter

```
<222> LOCATION: (6750)..(7124)
<223> OTHER INFORMATION: prOsU3-01
<220> FEATURE:
<221> NAME/KEY: misc_feature
<222> LOCATION: (7126)..(7145)
<223> OTHER INFORMATION: xZmVLHP2
<220> FEATURE:
<221> NAME/KEY: misc_feature
<222> LOCATION: (7126)..(7230)
<223> OTHER INFORMATION: rsgRNAZmVLHP-02
<220> FEATURE:
<221> NAME/KEY: misc_feature
<222> LOCATION: (7146)..(7157)
<223> OTHER INFORMATION: rCrRNA-01
<220> FEATURE:
<221> NAME/KEY: misc_feature
<222> LOCATION: (7146)..(7230)
<223> OTHER INFORMATION: rsgRNAbase-01
<220> FEATURE:
<221> NAME/KEY: misc_feature
<222> LOCATION: (7162)..(7230)
<223> OTHER INFORMATION: rTracrRNA-01
<220> FEATURE:
<221> NAME/KEY: promoter
<222> LOCATION: (7241)..(9232)
<223> OTHER INFORMATION: prUbi-04
<220> FEATURE:
<221> NAME/KEY: gene
<222> LOCATION: (9249)..(10427)
<223> OTHER INFORMATION: cPMI-09
<220> FEATURE:
<221> NAME/KEY: terminator
<222> LOCATION: (10450)..(10702)
<223> OTHER INFORMATION: tNOS-05-01
<220> FEATURE:
<221> NAME/KEY: misc_feature
<222> LOCATION: (10746)..(10875)
<223> OTHER INFORMATION: bNLB-03
<220> FEATURE:
<221> NAME/KEY: gene
<222> LOCATION: (11155)..(11943)
<223> OTHER INFORMATION: cSpec-03
<220> FEATURE:
<221> NAME/KEY: promoter
<222> LOCATION: (12038)..(12168)
<223> OTHER INFORMATION: prVirG-01
<220> FEATURE:
<221> NAME/KEY: gene
<222> LOCATION: (12243)..(12875)
<223> OTHER INFORMATION: cVirG-09
<220> FEATURE:
<221> NAME/KEY: gene
<222> LOCATION: (12905)..(13978)
<223> OTHER INFORMATION: cRepA-01
<220> FEATURE:
<221> NAME/KEY: misc_feature
<222> LOCATION: (14021)..(14425)
<223> OTHER INFORMATION: oVA1-02
<220> FEATURE:
<221> NAME/KEY: misc_feature
<222> LOCATION: (15103)..(15909)
<223> OTHER INFORMATION: oCOLE-06

<400> SEQUENCE: 34
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg     240
aactgacaga accgcaacgc tgcaggaatt ggccgcagcg gccatttaaa caaagcttgg     300
taccgggacc ctaagtaatc ttgtgctaca aatttatttt tcagacagaa aaatctatttt     360 agctaactaa ttaatacaaa ttaataccaa gcaacgatag atgaacatct agttgtctaa     420
```

```
ttagctaact aattaataca aattaagtag aatccttacc gtggggagat ggggcgcgac    480
gaagtgctcg agcttggggc gcggcgaccg gcgacgtgaa gcttggggc gcggggggccg     540 gacggcgctg cgggcggcat ggcgggcggc tgcgggcggc ggcgcgggcg caggaaacaa    600
acgacgggag tgggaggaag gagaaagcgg cgcgccggtt tagtcctagc tcggcgccaa    660
gatctgtggc gccgagctag gtgccacgat ggccgccgcg tcagcaaagc tcggcgccaa    720
ggcatgttgc gccgagccgt gttagctcgg cgtcatagct catggtgccg agttttgggt    780
ctaaaattgc gtttaagtat tctagggatc taaacgcaaa tattttcga aaatagggcc     840 gaaaaacaaa aaaaatcgg tcgtttcgtc gagcacatcg tccagcctat cttgcatgtc      900
catcctctct atggttcgcg agccgcgcgc atggcgctcc aaaggagggg cgaggttgaa     960
tatagacaga tggaatgggt ggttctctat ttatagcgca tgcagtcgtc ccctggcaca    1020
cctatttata tgtgagcgtt cctggcacta gagagatcga tcgatcgagc ttaattgcgc    1080
cactgctcgt tatcctcctc ttgcattgca ttgcaggtcg tagttgagca gcagcaacca    1140
ctgcacaggc catggacaag aagtacagca tcggcctgga catcggcacc aacagcgtgg    1200
gctgggccgt gatcaccgac gagtacaagg tgataccaat ttgcatgatc cttgttcgtt    1260
ctagctcttg catgccgatc agttgaatca cgcggtttcc ttctgcgcat ttgcatccag    1320
gtgccgagca agaagttcaa ggtgctgggc aacaccgaca ggcacagcat caagaagaac    1380
ctgatcggcg ccctgctgtt cgacagcggc gagaccgccg aggccaccag gctgaagagg    1440
accgccagga ggaggtacac caggaggaag aacaggatct gctacctgca ggagatcttc    1500
agcaacgaga tggccaaggt ggacgacagc ttcttccaca ggctggagga gagcttcctg    1560
gtggaggagg acaagaagca cgagaggcac ccgatcttcg gcaacatcgt ggacgaggtg    1620
gcctaccacg agaagtaccc gaccatctac cacctgagga agaagctggt ggacagcacc    1680
gacaaggccg acctgaggct gatctacctg gccctggccc acatgatcaa gttcaggggc    1740
cacttcctga tcgagggcga cctgaacccc gacaacagcg acgtggacaa gctgttcatc    1800
cagctggtgc agacctacaa ccagctgttc gaggagaacc cgatcaacgc agcggcgtg    1860 gacgccaagg ccatcctgag cgccaggctg agcaagagca ggaggctgga gaacctgatc    1920
gcccagctgc cgggcgagaa gaagaacggc ctgttcggca acctgatcgc cctgagcctg    1980
ggcctgaccc cgaacttcaa gagcaacttc gacctggccg aggacgccaa gctgcagctg    2040
agcaaggaca cctacgacga cgacctggac aacctgctgg cccagatcgg cgaccagtac    2100
gccgacctgt tcctggccgc caagaacctg agcgacgcca tcctgctgag cgacatcctg    2160
agggtgaaca ccgagatcac caaggccccg ctgagcgcca gcatgatcaa gaggtacgac    2220
gagcaccacc aggacctgac cctgctgaag gccctggtga ggcagcagct gccggagaag    2280
tacaaggaga tcttcttcga ccagagcaag aacggctacg ccggctacat cgacggcggc    2340
gccagccagg aggagttcta caagttcatc aagccgatcc tggagaagat ggacggcacc    2400
gaggagctgc tggtgaagct gaacagggag gacctgctga ggaagcagag gaccttcgac    2460
aacggcagca tcccgcacca gatccacctg ggcgagctgc acgccatcct gaggaggcag    2520
gaggacttct acccgttcct gaaggacaac agggagaaga tcgagaagat cctgaccttc    2580
cgcatcccgt actacgtggg cccgctggcc aggggcaaca gcaggttcgc ctggatgacc    2640
aggaagagcg aggagaccat caccccgtgg aacttcgagg aggtggtgga caagggcgcc    2700
agcgcccaga gcttcatcga gaggatgacc aacttcgaca gaacctgcc gaacgagaag    2760 gtgctgccga agcacagcct gctgtacgag tacttcaccg tgtacaacga gctgaccaag    2820
```

```
gtgaagtacg tgaccgaggg catgaggaag ccggccttcc tgagcggcga gcagaagaag    2880
gccatcgtgg acctgctgtt caagaccaac aggaaggtga ccgtgaagca gctgaaggag    2940
gactacttca agaagatcga gtgcttcgac agcgtggaga tcagcggcgt ggaggacagg    3000
ttcaacgcca gcctgggcac ctaccacgac ctgctgaaga tcatcaagga caaggacttc    3060
ctggacaacg aggagaacga ggacatcctg gaggacatcg tgctgaccct gaccctgttc    3120
gaggacaggg agatgatcga ggagaggctg aagacctacg cccacctgtt cgacgacaag    3180
gtgatgaagc agctgaagag gaggaggtac accggctggg gcaggctgag caggaagctg    3240
atcaacggca tcagggacaa gcagagcggc aagaccatcc tggacttcct gaagagcgac    3300
ggcttcgcca acaggaactt catgcagctg atccacgacg acagcctgac cttcaaggag    3360
gacatccaga aggcccaggt gagcggccag ggcgacagcc tgcacgagca catcgccaac    3420
ctggccggca gcccggccat caagaagggc atcctgcaga ccgtgaaggt ggtggacgag    3480
ctggtgaagg tgatgggcag gcacaagccg agaacatcg tgatcgagat ggccaggag    3540 aaccagacca cccagaaggg ccagaagaac agcagggaga ggatgaagag gatcgaggag    3600
ggcatcaagg agctgggcag ccagatcctg aaggagcacc cggtggagaa cacccagctg    3660
cagaacgaga agctgtacct gtactacctg cagaacggca gggacatgta cgtggaccag    3720
gagctggaca tcaacaggct gagcgactac gacgtggacc acatcgtgcc gcagagcttc    3780
ctgaaggacg acagcatcga caacaaggtg ctgaccagga gcgacaagaa caggggcaag    3840
agcgacaacg tgccgagcga ggaggtggtg aagaagatga aaaactactg gaggcagctg    3900
ctgaacgcca agctgatcac ccagaggaag ttcgacaacc tgaccaaggc cgagaggggc    3960
ggcctgagcg agctggacaa ggccggcttc attaaaaggc agctggtgga gaccaggcag    4020
atcaccaagc acgtggccca gatcctggac agcaggatga acaccaagta cgacgagaac    4080
gacaagctga tcagggaggt gaaggtgatc acccctgaaga gcaagctggt gagcgacttc    4140
aggaaggact ccagttcta caaggtgagg gagatcaata attaccacca cgcccacgac    4200
gcctacctga cgccgtggt gggcaccgcc ctgattaaaa agtacccgaa gctggagagc    4260
gagttcgtgt acggcgacta caaggtgtac gacgtgagga gatgatcgc caagagcgag    4320 caggagatcg gcaaggccac cgccaagtac ttcttctaca gcaacatcat gaacttcttc    4380
aagaccgaga tcaccctggc caacggcgag atcaggaaga gccgctgat cgagaccaac    4440 ggcgagaccg cgagatcgt gtgggacaag ggcagggact cgccaccgt gaggaaggtg    4500 ctgtccatgc cgcaggtgaa catcgtgaag aagaccgagg tgcagaccgg cggcttcagc    4560
aaggagagca tcctgccgaa gaggaacagc gacaagctga tcgccaggaa gaaggactgg    4620
gacccgaaga agtacggcgg cttcgacagc ccgaccgtgg cctacagcgt gctggtggtg    4680
gccaaggtgg agaagggcaa gagcaagaag ctgaagagcg tgaaggagct ggtgggcatc    4740
accatcatgg agaggagcag cttcgagaag aacccagtgg acttcctgga ggccaagggc    4800
tacaaggagg tgaagaagga cctgatcatt aaactgccga agtacagcct gttcgagctg    4860
gagaacggca ggaagaggat gctggccagc gccggcgagc tgcagaaggg caacgagctg    4920
gccctgccga gcaagtacgt gaacttcctg tacctggcca ccactacga aagctgaag    4980 ggcagcccgg aggacaacga gcagaagcag ctgttcgtgg agcagcacaa gcactacctg    5040
gacgagatca tcgagcagat cagcgagttc agcaagaggg tgatcctggc cgacgccaac    5100
ctggacaagg tgctgagcgc ctacaacaag cacagggaca agccgatcag ggagcaggcc    5160
```

```
gagaacatca tccacctgtt caccctgacc aacctgggcg ccccggccgc cttcaagtac    5220
ttcgacacca ccatcgacag gaagaggtac accagcacca aggaggtgct ggacgccacc    5280
ctgatccacc agagcatcac cggcctgtac gagaccagga tcgacctgag ccagctgggc    5340
ggcgacagca gcccgccgaa gaagaagagg aaggtgagct ggaaggacgc cagcggctgg    5400
agcaggatgt gagctctaat gcatccaaac aacgacacca acgccaacat taattaatta    5460
gtagtctcca tgccctggga ttgtgcgtgg ccgctccgtt gaacaccacc catccttcgt    5520
tcggcatttt ttcccccctt gtttatataa ttttattgta tcgttttggc aaataatttt    5580
gtgattcgac cccaaagcaa gtttggttgt cttacgattt gtaaacctgg aacaatatat    5640
aatgtgattg aactgctttg tctattcttt ttgtagtacg ataatatgta tatgtattcc    5700
atgcgatctc ttctagggcg acgactaatg tgcaagtgtg tgtttgcatg cgctgagcac    5760
ggagtttgta ttcaggggtc aatatctttc gattccttta tctaaaaagg tgttgcatat    5820
atctaaaaaa aagaaaaaaa aggcttacaa ctgttgaaaa aataagcatt tttagtttta    5880
atttaattca gaaaatcata gtgatatatg tgacgatatg catgtgcata tgtatcacta    5940
ctcacataaa cagtaaacaa cagtaaaata tgtataaata caaaaataac aaagtgtacc    6000
ctgcggaggg accgatgttc aaggcatctg tggctccatt cacacgagac atctcgtgtg    6060
tatgttcgat gtagtcatac gcagtcgagg cagtcagatg tacgcagtgc agtccctcga    6120
tcggcgccgg cgacgaggaa cttgatcagt gctggtcgag cggacgaagc gagcagtcgc    6180
gagtacgctc ccgaaaaaca tgatcgctcg cacacccatg caagtgtcgc tctgcggacg    6240
acgatttcgg aagcctacgc gtatgagaat gtttgtatgt gtgttctctc gtaaccagaa    6300
gcctcatctc ctccgtatat atacacgcgc agagggaggc caacagatag taacggtgga    6360
aggaatactc ggaccaaggt ccgatctacc atggccacgg cccggcctgg ccagcggcgc    6420
gtgcgtgtgg cagtccttca tccttttatc agcttatcaa tagatgcacc aaagatccac    6480
ctatttaagt tgattgaatt gtctcttgta cttccggtat gttactaaag taataataca    6540
ccgtagcatt aaattgggcc tttagcattg gctattattg aatattaatt tgagccagac    6600
ccaccaccag atgctaagtc acaccaaaat gctctcatca tctcaaacat ttcatatact    6660
ggtgtttcga tggagactat taagttgaac atccacctag aatctagatt acacttgacc    6720
acaactacat aatggacgga ccgttcgaag ggatctttaa acatacgaac agatcactta    6780
aagttcttct gaagcaactt aaagttatca ggcatgcatg gatcttggag gaatcagatg    6840
tgcagtcagg gaccatagca caggacaggc gtcttctact ggtgctacca gcaaatgctg    6900
gaagccggga acactgggta cgttggaaac cacgtgatgt ggagtaagat aaactgtagg    6960
agaaaagcat ttcgtagtgg gccatgaagc cttccaggac atgtattgca gtatgggccg    7020
gcccattacg caattggacg acaacaaaga ctagtattag taccacctcg gctatccaca    7080
tagatcaaag ctggtttaaa agagttgtgc agatgatccg tggcagctgg agctgagctt    7140
ccggggtttt agagctagaa atagcaagtt aaaataaggc tagtccgtta tcaacttgaa    7200
aaagtggcac cgagtcggtg ctttttttt cggaccgcgc ctgcagtgca gcgtgacccg    7260
gtcgtgcccc tctctagaga taatgagcat tgcatgtcta agttataaaa aattaccaca    7320
tatttttttt gtcacacttg tttgaagtgc agtttatcta tctttataca tatatttaaa    7380
ctttactcta cgaataatat aatctatagt actacaataa tatcagtgtt ttagagaatc    7440
atataaatga acagttagac atggtctaaa ggacaattga gtattttgac aacaggactc    7500
tacagtttta tcttttagt gtgcatgtgt tctccttttt ttttgcaaat agcttcacct    7560
```

```
atataatact tcatccattt tattagtaca tccatttagg gtttagggtt aatggttttt    7620
atagactaat ttttttagta catctatttt attctatttt agcctctaaa ttaagaaaac    7680
taaaactcta ttttagtttt tttatttaat aatttagata taaaatagaa taaaataaag    7740
tgactaaaaa ttaaacaaat acccttaag aaattaaaaa aactaaggaa acatttttct    7800
tgtttcgagt agataatgcc agcctgttaa acgccgtcga cgagtctaac ggacaccaac    7860
cagcgaacca gcagcgtcgc gtcgggccaa gcgaagcaga cggcacggca tctctgtcgc    7920
tgcctctgga cccctctcga gagttccgct ccaccgttgg acttgctccg ctgtcggcat    7980
ccagaaattg cgtggcggag cggcagacgt gagccggcac ggcaggcggc ctcctcctcc    8040
tctcacggca ccggcagcta cggggattc ctttcccacc gctccttcgc tttcccttcc    8100
tcgcccgccg taataaatag acaccccctc cacaccctct ttccccaacc tcgtgttgtt    8160
cggagcgcac acacacacaa ccagatctcc cccaaatcca cccgtcggca cctccgcttc    8220
aaggtacgcc gctcgtcctc ccccccccc ctctctacct tctctagatc ggcgttccgg    8280
tccatggtta gggcccggta gttctacttc tgttcatgtt tgtgttagat ccgtgtttgt    8340
gttagatccg tgctgctagc gttcgtacac ggatgcgacc tgtacgtcag acacgttctg    8400
attgctaact tgccagtgtt tctctttggg gaatcctggg atggctctag ccgttccgca    8460
gacgggatcg atttcatgat ttttttttgtt tcgttgcata gggtttggtt tgcccttttc    8520
ctttatttca atatatgccg tgcacttgtt tgtcgggtca tcttttcatg ctttttttg    8580
tcttggttgt gatgatgtgg tctggttggg cggtcgttct agatcggagt agaattctgt    8640
ttcaaactac ctggtggatt tattaatttt ggatctgtat gtgtgtgcca tacatattca    8700
tagttacgaa ttgaagatga tggatggaaa tatcgatcta ggataggtat acatgttgat    8760
gcgggttta ctgatgcata tacagagatg cttttttgttc gcttggttgt gatgatgtgg    8820
tgtggttggg cggtcgttca ttcgttctag atcggagtag aatactgttt caaactacct    8880
ggtgtattta ttaattttgg aactgtatgt gtgtgtcata catcttcata gttacgagtt    8940
taagatggat ggaaatatcg atctaggata ggtatacatg ttgatgtggg ttttactgat    9000
gcatatacat gatggcatat gcagcatcta ttcatatgct ctaaccttga gtacctatct    9060
attataataa acaagtatgt tttataatta ttttgatctt gatatacttg gatgatggca    9120
tatgcagcag ctatatgtgg attttttag ccctgccttc atacgctatt tatttgcttg    9180
gtactgtttc ttttgtcgat gctcaccctg ttgtttggtg ttacttctgc agggatccgg    9240
cagcagccat gcagaagctg atcaacagcg tgcagaacta cgcctggggc agcaagaccg    9300
ccctgaccga gctgtacggc atggagaacc ccagcagcca gcccatggcc gagctgtgga    9360
tgggcgccca cccaagagc agcagccgcg tgcagaacgc cgccggcgac atcgtgagcc    9420
tgcgcgacgt gatcgagagc gacaagagca ccctgctggg cgaggccgtg gccaagcgct    9480
tcggcgagct gcccttcctg ttcaaggtgc tgtgcgccgc ccagccctg agcatccagg    9540
tgcaccccaa caagcacaac agcgagatcg gcttcgccaa ggagaacgcc gccggcatcc    9600
ccatggacgc cgccgagcgc aactacaagg accccaacca caagcccgag ctggtgttcg    9660
ccctgacccc cttcctggcc atgaacgcct tccgcgagtt cagcgagatc gtgagcctgc    9720
tgcagcccgt ggccggcgcc cacccgcca tcgccacctt cctgcagcag cccgacgccg    9780
agcgcctgag cgagctgttc gccagcctgc tgaacatgca gggcgaggag aagagccgcg    9840
ccctggccat cctgaagagc gccctggaca gccagcaggg cgagccctgg cagaccatcc    9900
```

```
gcctgatcag cgagttctac cccgaggaca gcggcctgtt cagcccctg ctgctgaacg    9960
tggtgaagct gaaccccggc gaggccatgt tcctgttcgc cgagacccc cacgcctacc   10020
tgcagggcgt ggccctggag gtgatggcca acagcgacaa cgtgctgcgc gccggcctga   10080
cccccaagta catcgacatc cccgagctgg tggccaacgt gaagttcgag gccaagcccg   10140
ccaaccagct gctgacccag cccgtgaagc agggcgccga gctggacttc cccatccccg   10200
tggacgactt cgccttcagc ctgcacgacc tgagcgacaa ggagaccacc atcagccagc   10260
agagcgccgc catcctgttc tgcgtggagg gcgacgccac cctgtggaag ggcagccagc   10320
agctgcagct gaagcccggc gagagcgcct catcgccgc caacgagagc cccgtgaccg   10380
tgaagggcca cggccgcctg gcccgcgtgt acaacaagct gtgataggag ctcgatccgt   10440
cgacctgcag atcgttcaaa catttggcaa taaagtttct taagattgaa tcctgttgcc   10500
ggtcttgcga tgattatcat ataatttctg ttgaattacg ttaagcatgt aataattaac   10560
atgtaatgca tgacgttatt tatgagatgg gttttatga ttagagtccc gcaattatac   10620
atttaatacg cgatagaaaa caaaatatag cgcgcaaact aggataaatt atcgcgcgcg   10680
gtgtcatcta tgttactaga tcggcgcgcc gcaattgaag tttgggcggc cagcatggcc   10740
gtatccgcaa tgtgttatta agttgtctaa gcgtcaattt gtttacacca caatatatcc   10800
tgccaccagc cagccaacag ctccccgacc ggcagctcgg cacaaaatca ccactcgata   10860
caggcagccc atcagaatta ttctcatgt ttgacagctt atcatcgact gcacggtgca   10920
ccaatgcttc tggcgtcagg cagccatcgg aagctgtggt atggctgtgc aggtcgtaaa   10980
tcactgcata attcgtgtcg ctcaaggcgc actcccgttc tggataatgt tttttgcgcc   11040
gacatcataa cggttctggc aaatattctg aaatgagctg ttgacaatta atcatccggc   11100
tcgtataatg tgtggaattg tgagcggata acaatttcac acaggaaaca gaccatgagg   11160
gaagcgttga tcgccgaagt atcgactcaa ctatcagagg tagttggcgt catcgagcgc   11220
catctcgaac cgacgttgct ggccgtacat ttgtacggct ccgcagtgga tggcggcctg   11280
aagccacaca gtgatattga tttgctggtt acggtgaccg taaggcttga tgaaacaacg   11340
cggcgagctt tgatcaacga ccttttggaa acttcggctt ccctggaga gagcgagatt   11400
ctccgcgctg tagaagtcac cattgttgtg cacgacgaca tcattccgtg gcgttatcca   11460
gctaagcgcg aactgcaatt tggagaatgg cagcgcaatg acattcttgc aggtatcttc   11520
gagccagcca cgatcgacat tgatctggct atcttgctga caaaagcaag agaacatagc   11580
gttgccttgg taggtccagc ggcggaggaa ctctttgatc cggttcctga acaggatcta   11640
tttgaggcgc taaatgaaac cttaacgcta tggaactcgc cgcccgactg ggctggcgat   11700
gagcgaaatg tagtgcttac gttgtcccgc atttggtaca gcgcagtaac cggcaaaatc   11760
gcgccgaagg atgtcgctgc cgactgggca atggagcgcc tgccggccca gtatcagccc   11820
gtcatacttg aagctaggca ggcttatctt ggacaagaag atcgcttggc ctcgcgcgca   11880
gatcagttgg aagaatttgt tcactacgtg aaaggcgaga tcaccaaagt agtcggcaaa   11940
taaagctcta gtggatctcc gtacccgggg atctggctcg cggcggacgc acgacgccgg   12000
ggcgagacca taggcgatct cctaaatcaa tagtagctgt aacctcgaag cgtttcactt   12060
gtaacaacga ttgagaattt tgtcataaa attgaaatac ttggttcgca ttttgtcat    12120
ccgcggtcag ccgcaattct gacgaactgc ccatttagct ggagatgatt gtacatcctt   12180
cacgtgaaaa tttctcaagc gctgtgaaca agggttcaga ttttagattg aaaggtgagc   12240
cgttgaaaca cgttcttctt gtcgatgacg acgtcgctat gcggcatctt attattgaat   12300
```

```
accttacgat ccacgccttc aaagtgaccg cggtagccga cagcacccag ttcacaagag   12360
tactctcttc cgcgacggtc gatgtcgtgg ttgttgatct agatttaggt cgtgaagatg   12420
ggctcgagct aggagcaagt gattttatcg ctaagccgtt cagtatcaga gagtttctag   12480
cacgcattcg ggttgccttg cgcgtgcgcc caacgttgt ccgctccaaa gaccgacggt    12540 cttttgttt tactgactgg acacttaatc tcaggcaacg tcgcttgatg tccgaagctg    12600
gcggtgaggt gaaacttacg gcaggtgagt tcaatcttct cctcgcgttt ttagagaaac   12660
cccgcgacgt tctatcgcgc gagcaacttc tcattgccag tcgagtacgc gacgaggagg   12720
tttatgacag gagtatagat gttctcattt tgaggctgcg ccgcaaactt gaggcagatc   12780
cgtcaagccc tcaactgata aaaacagcaa gaggtgccgg ttatttcttt gacgcggacg   12840
tgcaggtttc gcacgggggg acgatggcag cctgagccaa ttcccagatc cccgaggaat   12900
cggcgtgagc ggtcgcaaac catccggccc ggtacaaatc ggcgcggcgc tgggtgatga   12960
cctggtggag aagttgaagg ccgcgcaggc cgcccagcgg caacgcatcg aggcagaagc   13020 acgcccggt gaatcgtggc aagcggccgc tgatcgaatc cgcaaagaat cccggcaacc    13080
gccggcagcc ggtgcgccgt cgattaggaa gccgcccaag ggcgacgagc aaccagattt   13140
tttcgttccg atgctctatg acgtgggcac ccgcgatagt cgcagcatca tggacgtggc   13200
cgttttccgt ctgtcgaagc gtgaccgacg agctggcgag gtgatccgct acgagcttcc   13260
agacgggcac gtagaggttt ccgcagggcc ggccggcatg gccagtgtgt gggattacga   13320
cctggtactg atggcggttt cccatctaac cgaatccatg aaccgatacc gggaagggaa    13380
gggagacaag cccggccgcg tgttccgtcc acacgttgcg gacgtactca agttctgccg   13440
gcgagccgat ggcggaaagc agaaagacga cctggtagaa acctgcattc ggttaaacac   13500
cacgcacgtt gccatgcagc gtacgaagaa ggccaagaac ggccgcctgg tgacggtatc   13560
cgagggtgaa gccttgatta gccgctacaa gatcgtaaag agcgaaaccg ggcggccgga   13620
gtacatcgag atcgagctag ctgattggat gtaccgcgag atcacagaag caagaaccc    13680 ggacgtgctg acggttcacc ccgattactt tttgatcgat cccggcatcg ccgttttct    13740 ctaccgcctg gcacgccgcg ccgcaggcaa ggcagaagcc agatggttgt tcaagacgat   13800
ctacgaacgc agtggcagcg ccggagagtt caagaagttc tgtttcaccg tgcgcaagct   13860
gatcgggtca aatgacctgc cggagtacga tttgaaggag gaggcggggc aggctggccc   13920
gatcctagtc atgcgctacc gcaacctgat cgagggcgaa gcatccgccg gttcctaatg   13980
tacggagcag atgctagggc aaattgccct agcaggggaa aaaggtcgaa aaggtctctt   14040
tcctgtggat agcacgtaca ttgggaaccc aaagccgtac attgggaacc ggaacccgta   14100
cattgggaac ccaaagccgt acattgggaa ccggtcacac atgtaagtga ctgatataaa   14160
agagaaaaaa ggcgattttt ccgcctaaaa ctctttaaaa cttattaaaa ctcttaaaac   14220
ccgcctggcc tgtgcataac tgtctggcca gcgcacagcc gaaagctgc aaaaagcgcc    14280 taccccttcgg tcgctgcgct ccctacgccc cgccgcttcg cgtcggccta tcgcggccgc   14340
tggccgctca aaaatggctg gcctacggcc aggcaatcta ccagggcgcg gacaagccgc   14400
gccgtcgcca ctcgaccgcc ggcgctgagg tctgcctcgt gaagaaggtg ttgctgactc   14460
ataccaggcc tgaatcgccc catcatccag ccagaaagtg agggagccac ggttgatgag   14520
agctttgttg taggtggacc agttggtgat tttgaacttt tgctttgcca cggaacggtc   14580
tgcgttgtcg ggaagatgcg tgatctgatc cttcaactca gcaaaagttc gatttattca   14640
```

```
acaaagccgc cgtcccgtca agtcagcgta atgctctgcc agtgttacaa ccaattaacc   14700
aattctgatt agaaaaactc atcgagcatc aaatgaaact gcaatttatt catatcagga   14760
ttatcaatac catatttttg aaaagccgt ttctgtaatg aaggagaaaa ctcaccgagg   14820
cagttccata ggatggcaag atcctggtat cggtctgcga ttccgactcg tccaacatca   14880
atacaaccta ttaatttccc ctcgtcaaaa ataaggttat caagtgagaa atcaccatga   14940
gtgacgactg aatccggtga gaatggcaaa agctctgcat taatgaatcg gccaacgcgc   15000
ggggagaggc ggtttgcgta ttgggcgctc ttccgcttcc tcgctcactg actcgctgcg   15060
ctcggtcgtt cggctgcggc gagcggtatc agctcactca aaggcggtaa tacggttatc   15120
cacagaatca ggggataacg caggaaagaa catgtgagca aaaggccagc aaaaggccag   15180
gaaccgtaaa aaggccgcgt tgctggcgtt tttccatagg ctccgccccc ctgacgagca   15240
tcacaaaaat cgacgctcaa gtcagaggtg gcgaaacccg acaggactat aaagatacca   15300
ggcgtttccc cctggaagct ccctcgtgcg ctctcctgtt ccgaccctgc cgcttaccgg   15360
atacctgtcc gcctttctcc cttcgggaag cgtggcgctt tctcatagct cacgctgtag   15420
gtatctcagt tcggtgtagg tcgttcgctc caagctgggc tgtgtgcacg aaccccccgt   15480
tcagcccgac cgctgcgcct tatccggtaa ctatcgtctt gagtccaacc cggtaagaca   15540
cgacttatcg ccactggcag cagccactgg taacaggatt agcagagcga ggtatgtagg   15600
cggtgctaca gagttcttga agtggtggcc taactacggc tacactagaa gaacagtatt   15660
tggtatctgc gctctgctga agccagttac cttcggaaaa agagttggta gctcttgatc   15720
cggcaaacaa accaccgctg gtagcggtgg tttttttgtt tgcaagcagc agattacgcg   15780
cagaaaaaaa ggatctcaag aagatccttt gatcttttct acggggtctg acgctcagtg   15840
gaacgaaaac tcacgttaag ggattttggt catgagatta tcaaaaagga tcttcaccta   15900
gatccttttg atccggaatt a                                             15921
```

<210> SEQ ID NO 35
<211> LENGTH: 17954
<212> TYPE: DNA
<213> ORGANISM: artificial sequence
<220> FEATURE:
<223> OTHER INFORMATION: vector 24039
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (315)..(1729)
<223> OTHER INFORMATION: prZmGRMZM2G020852-01
<220> FEATURE:
<221> NAME/KEY: gene
<222> LOCATION: (1731)..(5979)
<223> OTHER INFORMATION: cCas9-13
<220> FEATURE:
<221> NAME/KEY: terminator
<222> LOCATION: (5989)..(8769)
<223> OTHER INFORMATION: tZmGRMZM2G020852-01
<220> FEATURE:
<221> NAME/KEY: promoter
<222> LOCATION: (8783)..(9157)
<223> OTHER INFORMATION: prOsU3-01
<220> FEATURE:
<221> NAME/KEY: misc_feature
<222> LOCATION: (9159)..(9178)
<223> OTHER INFORMATION: xZmVLHP2
<220> FEATURE:
<221> NAME/KEY: misc_feature
<222> LOCATION: (9159)..(9263)
<223> OTHER INFORMATION: rsgRNAZmVLHP-02

```
<220> FEATURE:
<221> NAME/KEY: misc_feature
<222> LOCATION: (9179)..(9190)
<223> OTHER INFORMATION: rCrRNA-01
<220> FEATURE:
<221> NAME/KEY: misc_feature
<222> LOCATION: (9195)..(9263)
<223> OTHER INFORMATION: rTracrRNA-01
<220> FEATURE:
<221> NAME/KEY: promoter
<222> LOCATION: (9274)..(11265)
<223> OTHER INFORMATION: prUbi1-04
<220> FEATURE:
<221> NAME/KEY: gene
<222> LOCATION: (11282)..(12460)
<223> OTHER INFORMATION: cPMI-09
<220> FEATURE:
<221> NAME/KEY: terminator
<222> LOCATION: (12483)..(12735)
<223> OTHER INFORMATION: tNOS-05-01
<220> FEATURE:
<221> NAME/KEY: misc_feature
<222> LOCATION: (12779)..(12908)
<223> OTHER INFORMATION: bNLB-03
<220> FEATURE:
<221> NAME/KEY: gene
<222> LOCATION: (13188)..(13976)
<223> OTHER INFORMATION: cSpec-03
<220> FEATURE:
<221> NAME/KEY: promoter
<222> LOCATION: (14071)..(14201)
<223> OTHER INFORMATION: prVirG-01
<220> FEATURE:
<221> NAME/KEY: gene
<222> LOCATION: (14276)..(14908)
<223> OTHER INFORMATION: cVirG-09
<220> FEATURE:
<221> NAME/KEY: gene
<222> LOCATION: (14938)..(16011)
<223> OTHER INFORMATION: cRepA-01
<220> FEATURE:
<221> NAME/KEY: misc_feature
<222> LOCATION: (16054)..(16458)
<223> OTHER INFORMATION: oVS1-02
<220> FEATURE:
<221> NAME/KEY: misc_feature
<222> LOCATION: (17136)..(17942)
<223> OTHER INFORMATION: oCOLE-o6

<400> SEQUENCE: 35
attcctgtgg ttggcatgca catacaaatg gacgaacgga taaacctttt cacgcccttt       60
taaatatccg attattctaa taaacgctct tttctcttag gtttacccgc caatatatcc      120
tgtcaaacac tgatagttta aactgaaggc gggaaacgac aatctgatca tgagcggaga      180
attaagggag tcacgttatg accccgccg atgacgcggg acaagccgtt ttacgtttgg       240
aactgacaga accgcaacgc tgcaggaatt ggccgcagcg gccatttaaa caaagcttgg      300
taccggaccg ttataacagt gaatacaaaa atgacattcg tgttatttag cacaagttac      360
gatctatttc aggaacatgc cggaattttc gaacaccatt ctcacaaaac atgaccttga      420
acttgcgatc cagttgtttt aaaattatat aaaacaaaaa caaagtcaga aaatcatgaa      480
acttgtcgac atgtcatgat atcatatgta gagactctaa taaaaagttg agattgtttc      540
atgaaagttg tcacacacta tgtgtagaaa cttagcccgt ctacattgaa gttctatgat      600
ttcatgtgaa ggacacctag gcatcgatgt ttatgataat atcttatgtt tgtttggaca      660
aaatattaaa aacaaataaa aggggtccct gatcactttg acgagcattg cattcagcaa      720
agggtgcctt tgttgagtgc aatggtcata gaactcggta gaaaagacat acataaacat      780
cgggaaactt gctttaccgc acgctatggc caagacactc ggcaaactag gctccttgt       840
```

```
tgagtgccat ctcaagcact cgacattgga actacgacta ggcctcacgg aagctttctt      900
tgccgagtgc cactaagcga ggaactcgga cactcagcaa cagctctgtc atcgtcacga      960
tgtcttttct ttgtcgtgta ccagttggca ctcggttaag actttactga gtgcccgata     1020
gaaagtactc ggcaaagaga ccgttgccga cgtttggttc actgagggct ctttgctgcc     1080
ttttggactt gacaaagaag tcatctccag tactgtctcc taggacgcag gatttatgtt     1140
ttttcccgga gctcgatctg tgggacatca cagatggtcc aatctggtga tctaaaatgg     1200
acggtttgcc aagcccacag agaagtcttt aagatcttcc acgatgcacg catgctttaa     1260
ggttagatag tgtttggtcc aaaaaagcgt caacaatcag gaaattagaa ctaaaattat     1320
taaaggacag atcaaaaggc atgcatgttc ttcttctata gtgtgtgttg agcctgagtt     1380
ttgattttag ctttattag gggactcgca gtctagctaa ggagttgtat tgatgttctg      1440
acaaatatta tgttcgatcg tcacagtggt cttgtgcgga tcgattaggc ccgatcatgg     1500
tgaaataaac taaccaccgg taagcccggg cagccctaga gcatgcagcg gcctacgtga     1560
agcccgcgtg tcgcatcgtc gtccgtcaga cgctaacggc aggccgctgc atgcgttgcc     1620
ggcgaactct ctcctgagcc actcgtcatc catataagta gacatcccat cactgtcgtc     1680
tatcaacaac acacagagcg acatttcgaa taacacagtt gagcgcgacc atggacaaga     1740
agtacagcat cggcctggac atcggcacca acagcgtggg ctgggccgtg atcaccgacg     1800
agtacaaggt acgagcggga tacatgttta tactcctcct gtaggtcgct ccttcatgta     1860
atgtgttgcg attaaaacgg tgcgcaggtg ccgagcaaga agttcaaggt gctgggcaac     1920
accgacaggc acagcatcaa gaagaacctg atcggcgccc tgctgttcga cagcggcgag     1980
accgccgagg ccaccaggct gaagaggacc gccaggagga ggtacaccag gaggaagaac     2040
aggatctgct acctgcagga gatcttcagc aacgagatgg ccaaggtgga cgacagcttc     2100
ttccacaggc tggaggagag cttcctggtg gaggaggaca agaagcacga gaggcacccg     2160
atcttcggca acatcgtgga cgaggtggcc taccacgaga gtacccgac catctaccac      2220 ctgaggaaga gctggtgga cagcaccgac aaggccgacc tgaggctgat ctacctggcc      2280
ctggcccaca tgatcaagtt caggggccac ttcctgatcg agggcgacct gaacccggac     2340
aacagcgacg tggacaagct gttcatccag ctggtgcaga cctacaacca gctgttcgag     2400
gagaacccga tcaacgccag cggcgtggac gccaaggcca tcctgagcgc caggctgagc     2460
aagagcagga ggctggagaa cctgatcgcc cagctgccgg gcgagaagaa gaacggcctg     2520
ttcggcaacc tgatcgccct gagcctgggc ctgaccccga acttcaagag caacttcgac     2580
ctggccgagg acgccaagct gcagctgagc aaggacacct acgacgacga cctggacaac     2640
ctgctggccc agatcggcga ccagtacgcc gacctgttcc tggccgccaa gaacctgagc     2700
gacgccatcc tgctgagcga catcctgagg gtgaacaccg agatcaccaa ggccccgctg     2760
agcgccagca tgatcaagag gtacgacgag caccaccagg acctgaccct gctgaaggcc     2820
ctggtgaggc agcagctgcc ggagaagtac aaggagatct cttcgacca gagcaagaac     2880 ggctacgccg gctacatcga cggcggcgcc agccaggagg agttctacaa gttcatcaag     2940
ccgatcctgg agaagatgga cggcaccgag gagctgctgg tgaagctgaa cagggaggac     3000
ctgctgagga agcagaggac cttcgacaac ggcagcatcc cgcaccagat ccacctgggc     3060
gagctgcacg ccatcctgag gaggcaggag gacttctacc cgttcctgaa ggacaacagg     3120
gagaagatca gagaagatcct gaccttccgc atcccgtact acgtgggccc gctggccagg     3180
ggcaacagca ggttcgcctg gatgaccagg aagagcgagg agaccatcac cccgtggaac     3240
```

```
ttcgaggagg tggtggacaa gggcgccagc gcccagagct tcatcgagag gatgaccaac    3300
ttcgacaaga acctgccgaa cgagaaggtg ctgccgaagc acagcctgct gtacgagtac    3360
ttcaccgtgt acaacgagct gaccaaggtg aagtacgtga ccgagggcat gaggaagccg    3420
gccttcctga gcggcgagca gaagaaggcc atcgtggacc tgctgttcaa gaccaacagg    3480
aaggtgaccg tgaagcagct gaaggaggac tacttcaaga agatcgagtg cttcgacagc    3540
gtggagatca gcggcgtgga ggacaggttc aacgccagcc tgggcaccta ccacgacctg    3600
ctgaagatca tcaaggacaa ggacttcctg gacaacgagg agaacgagga catcctggag    3660
gacatcgtgc tgaccctgac cctgttcgag gacaggagga tgatcgagga gaggctgaag    3720
acctacgccc acctgttcga cgacaaggtg atgaagcagc tgaagaggag gaggtacacc    3780
ggctggggca ggctgagcag gaagctgatc aacggcatca gggacaagca gagcggcaag    3840
accatcctgg acttcctgaa gagcgacggc ttcgccaaca ggaacttcat gcagctgatc    3900
cacgacgaca gcctgacctt caaggaggac atccagaagg cccaggtgag cggccagggc    3960
gacagcctgc acgagcacat cgccaacctg gccggcagcc cggccatcaa gaagggcatc    4020
ctgcagaccg tgaaggtggt ggacgagctg gtgaaggtga tgggcaggca caagccggag    4080
aacatcgtga tcgagatggc cagggagaac cagaccaccc agaagggcca gaagaacagc    4140
agggagagga tgaagaggat cgaggagggc atcaaggagc tgggcagcca gatcctgaag    4200
gagcacccgg tggagaacac ccagctgcag aacgagaagc tgtacctgta ctacctgcag    4260
aacggcaggg acatgtacgt ggaccaggag ctggacatca acaggctgag cgactacgac    4320
gtggaccaca tcgtgccgca gagcttcctg aaggacgaca gcatcgacaa caaggtgctg    4380
accaggagcg acaagaacag gggcaagagc gacaacgtgc cgagcgagga ggtggtgaag    4440
aagatgaaaa actactggag gcagctgctg aacgccaagc tgatcaccca gaggaagttc    4500
gacaacctga ccaaggccga gaggggcggc ctgagcgagc tggacaaggc cggcttcatt    4560
aaaaggcagc tggtggagac caggcagatc accaagcacg tggcccagat cctggacagc    4620
aggatgaaca ccaagtacga cgagaacgac aagctgatca gggaggtgaa ggtgatcacc    4680
ctgaagagca agctggtgag cgacttcagg aaggacttcc agttctacaa ggtgagggag    4740
atcaataatt accaccacgc ccacgacgcc tacctgaacg ccgtggtggg caccgccctg    4800
attaaaaagt acccgaagct ggagagcgag ttcgtgtacg gcgactacaa ggtgtacgac    4860
gtgaggaaga tgatcgccaa gagcgagcag gagatcggca aggccaccgc caagtacttc    4920
ttctacagca acatcatgaa cttcttcaag accgagatca ccctggccaa cggcgagatc    4980
aggaagaggc cgctgatcga gaccaacggc gagaccggcg agatcgtgtg ggacaagggc    5040
agggacttcg ccaccgtgag gaaggtgctg tccatgccgc aggtgaacat cgtgaagaag    5100
accgaggtgc agaccggcgg cttcagcaag gagagcatcc tgccgaagag gaacagcgac    5160
aagctgatcg ccaggaagaa ggactgggac ccgaagaagt acggcggctt cgacagcccg    5220
accgtggcct acagcgtgct ggtggtggcc aaggtggaga gggcaagag caagaagctg    5280
aagagcgtga aggagctggt gggcatcacc atcatggaga ggagcagctt cgagaagaac    5340
ccagtggact tcctggaggc caagggctac aaggaggtga agaaggacct gatcattaaa    5400
ctgccgaagt acagcctgtt cgagctggag aacggcagga agaggatgct ggccagcgcc    5460
ggcgagctgc agaagggcaa cgagctggcc ctgccgagca gtacgtgaa cttcctgtac    5520
ctggccagcc actacgagaa gctgaagggc agcccggagg acaacgagca gaagcagctg    5580
```

```
ttcgtggagc agcacaagca ctacctggac gagatcatcg agcagatcag cgagttcagc    5640
aagagggtga tcctggccga cgccaacctg acaaggtgc tgagcgccta caacaagcac     5700
agggacaagc cgatcaggga gcaggccgag aacatcatcc acctgttcac cctgaccaac    5760
ctgggcgccc cggccgcctt caagtacttc gacaccacca tcgacaggaa gaggtacacc    5820
agcaccaagg aggtgctgga cgccaccctg atccaccaga gcatcaccgg cctgtacgag    5880
accaggatcg acctgagcca gctgggcggc gacagcagcc cgccgaagaa gaagaggaag    5940
gtgagctgga aggacgccag cggctggagc aggatgtgag ctcaattaac tttgaattcc    6000
cttcgattca tccggcgcgg tgggctatgg acctgcagca gcaagctaat taagtttata    6060
tatattgcat gagagagcat gcaccgctaa ccatatatac tactgagact tctgaattct    6120
agtatatgta atccttttgt ttgggtttag gaggcaattc taatcatgta tgccgaattc    6180
caaagagtgg aaaacaagca aaatgttaaa tatacatgcc attttcggag gcaatttttt    6240
tcatgagggc atgttgctat aattccgggg accttggact tcttggagca ccttcctgtg    6300
acttaggcat acatgattag attataatcc aattagttaa gtcatagaaa attacctcat    6360
tctcatctcc atctccattt ctctatttct tctcaatcaa ggaccaaaat agcacttttg    6420
ctaaaaaaca agttagattg caaaccaaag tgcacaatac atagtaaaag gtatatgcaa    6480
catatttgaa tactcaaacc tctcatactt acattttcca tcattttgtt ccatttagcc    6540
tgtttgagct cggggttgga ctccaaaacc tcatgtcaac ataacttgat cctttttagca   6600 aactatgagc tctaacacca tacaatggtc aacaagaact attccaaaca taggaatgac    6660
ccaaactaca agtcaaagta tacttagctc tttgggcact tacaggttct aactttgata    6720
attctgtact tcttgtgacc atgactctgc tcgagctagg atcttgagcc ttatgactta    6780
aacaattaaa ccacaaacat tacctcaatg gttgtaagcc acgtccatat atcacagact    6840
tcaatgcatt cagactattc acagcttgac caaccttgac ctcttgcaag aacctcttct    6900
tctttgtgac cttaggtact ttagtcttct tgaccttctc ccttgctctt catacccttga   6960 agtccttctt gccttcacct tagttcaatc agctatctcc aagtcatgca cattgagttc    7020
cacttagtca atgtccatcc ttcaacttga cttgtgatgt ccacaattca tagtcatctc    7080
agtctatggg tccatcatgc ttgactccat gtgatgaacc ttgtaaggtt ttcactaagt    7140
acatgctcag acctttaatt gtgttgccat ccaaaaaaac caaaacctag attggaccat    7200
tcattatatt catcaatcat tgtacttgca agagtgatca aggtcatatt atttctctca    7260
actactccat tttgttgagg ggtgtcagtt gtggagactt cttgtttgat cccaacctca    7320
tcacaatact catgaatata gttgttgtca aattcatttc cattgtcact tcttattttt    7380
cttgattttg caatcaaact cattttgtac tttcatggta aatttattca atgttgatgc    7440
aacttttgac ttttcttgaa gaaagaacac tcaattacat ctagagaaat catcaacaac    7500
gaccaaacaa tacaggtttc ccccaacact agcatattat gtaggaccaa ataaatccat    7560
gtgaagtaac tctagtggtc ttggtgttga cataaaagcg tttgtaggat gtgtattggc    7620
aacttgtttt ccagcttgac atgcactata aagatttttc cttttttcaaa cacaacatct   7680 ttcaaatctc taaccatttc tttctttgga agcttcttgt tggggaaatg atccccggac    7740
cctaggaccc accggtcaga gagcgcgagg aagagccccc ggtcgctggg accgttggt     7800 ccgctggaaa atgtggttac gtcaaccctg aaagaacccg ccctggttg agcccgtgg      7860 caccgagcct agggtcgagc gcggtggaat ctgacaggag gggccagaca tgttggaggg    7920
gaaccactca agtggatccc gcgcctggcc ccagaatgac ccgtcattaa tacccaacca    7980
```

```
cattaaccat gcctggcacc gagccatagc acggacgtcg gtccacttcc cactcatgac   8040
ctacgaacca gttgggctgc atagcactca tgaccgatag gttgaaggct tggcttcgca   8100
gagtgaaagg cgctgcatac atgtgaaggc tcgacttctt tttcttttcc tttcttttct   8160
tttctatttt taggtttcca atttaaattc catttttttt gtggagttca tatttggatc   8220
aaatagacaa attcacctat cagtatgaat agatgcattt attttgttta tatctatttt   8280
cttcatattt atatagtatt tcccttattc tttatatcat tttcaatttg taattggtaa   8340
gtttggtctt aaattcccca tttgggcact aatatatttt tattaatatt attattatta   8400
ttattattat tatttataga tgcacaaaca cataaactcc gacatgatgc atagattatt   8460
ttagatgtca ctagttaatg gttcacttta aatatggtta ttcccatgtt ctaatgagta   8520
gagggcaaag catatattga ggtcaactct ttccttatta tttacaaatt ggggaaattc   8580
tattcataac tcttcttctc tctcccaagt agcttaatct tcaccatggt gatttcattg   8640
cactttgcac attttgatca ctttattcct tgtaacccga gtcaaagtgt caatgatctt   8700
gataggatac tccgtgcagg ttagatcacc ttgcacactg agttcttcca ttggtaactg   8760
ttcctctggc ggaccgttcg aagggatctt taaacatacg aacagatcac ttaaagttct   8820
tctgaagcaa cttaaagtta tcaggcatgc atggatcttg gaggaatcag atgtgcagtc   8880
agggaccata gcacaggaca ggcgtcttct actggtgcta ccagcaaatg ctggaagccg   8940
ggaacactgg gtacgttgga aaccacgtga tgtggagtaa gataaactgt aggagaaaag   9000
catttcgtag tgggccatga agcctttcag gacatgtatt gcagtatggg ccggcccatt   9060
acgcaattgg acgacaacaa agactagtat tagtaccacc tcggctatcc acatagatca   9120
aagctggttt aaaagagttg tgcagatgat ccgtggcagc tggagctgag cttccgggt    9180 tttagagcta gaaatagcaa gttaaaataa ggctagtccg ttatcaactt gaaaaagtgg   9240
caccgagtcg gtgctttttt tttcggaccg cgcctgcagt gcagcgtgac ccggtcgtgc   9300
ccctctctag agataatgag cattgcatgt ctaagttata aaaaattacc acatatttt    9360 tttgtcacac ttgttgaag tgcagtttat ctatctttat acatatattt aaactttact    9420
ctacgaataa tataatctat agtactacaa taatatcagt gttttagaga atcatataaa   9480
tgaacagtta gacatggtct aaaggacaat tgagtatttt gacaacagga ctctacagtt   9540 ttatctttt agtgtgcatg tgttctcctt ttttttgca aatagcttca cctatataat     9600
acttcatcca ttttattagt acatccattt agggtttagg gttaatggtt tttatagact   9660
aattttttta gtcatctat tttattctat tttagcctct aaattaagaa aactaaaact    9720
ctattttagt ttttttattt aataatttag atataaaata gaataaaata aagtgactaa   9780
aaattaaaca aataccctt aagaaattaa aaaaactaag gaaacatttt tcttgtttcg    9840
agtagataat gccagcctgt taaacgccgt cgacgagtct aacggacacc aaccagcgaa   9900
ccagcagcgt cgcgtcgggc caagcgaagc agacggcacg gcatctctgt cgctgcctct   9960 ggaccctct cgagagttcc gctccaccgt tggacttgct ccgctgtcgg catccagaaa   10020
ttgcgtggcg gagcggcaga cgtgagccgg cacggcaggc ggcctcctcc tcctctcacg  10080
gcaccggcag ctacggggga ttccttccc accgctcctt cgctttccct tcctcgcccg   10140
ccgtaataaa tagacacccc ctccacaccc tctttcccca acctcgtgtt gttcggagcg  10200
cacacacaca caaccagatc tcccccaaat ccaccgtcg gcacctccgc ttcaaggtac   10260
gccgctcgtc ctcccccccc ccctctctcta ccttctctag atcggcgttc cggtccatgg  10320
```

-continued

```
ttagggcccg gtagttctac ttctgttcat gtttgtgtta gatccgtgtt tgtgttagat    10380
ccgtgctgct agcgttcgta cacggatgcg acctgtacgt cagacacgtt ctgattgcta    10440
acttgccagt gtttctcttt ggggaatcct gggatggctc tagccgttcc gcagacggga    10500
tcgatttcat gattttttt gtttcgttgc atagggtttg gtttgccctt ttcctttatt    10560
tcaatatatg ccgtgcactt gtttgtcggg tcatctttc atgcttttt ttgtcttggt    10620
tgtgatgatg tggtctggtt gggcggtcgt tctagatcgg agtagaattc tgtttcaaac    10680
tacctggtgg atttattaat tttggatctg tatgtgtgtg ccatacatat tcatagttac    10740
gaattgaaga tgatggatgg aaatatcgat ctaggatagg tatacatgtt gatgcgggtt    10800
ttactgatgc atatacagag atgcttttg ttcgcttggt tgtgatgatg tggtgtggtt    10860
gggcggtcgt tcattcgttc tagatcggag tagaatactg tttcaaacta cctggtgtat    10920
ttattaattt tggaactgta tgtgtgtgtc atacatcttc atagttacga gtttaagatg    10980
gatgaaata tcgatctagg ataggtatac atgttgatgt gggttttact gatgcatata    11040
catgatggca tatgcagcat ctattcatat gctctaacct tgagtaccta tctattataa    11100
taaacaagta tgttttataa ttattttgat cttgatatac ttggatgatg gcatatgcag    11160
cagctatatg tggattttt tagccctgcc ttcatacgct atttatttgc ttggtactgt    11220
ttcttttgtc gatgctcacc ctgttgtttg gtgttacttc tgcagggatc cggcagcagc    11280
catgcagaag ctgatcaaca gcgtgcagaa ctacgcctgg ggcagcaaga ccgccctgac    11340
cgagctgtac ggcatggaga ccccagcag ccagcccatg ccgagctgt ggatgggcgc    11400
ccaccccaag agcagcagcc gcgtgcagaa cgccgccggc gacatcgtga gcctgcgcga    11460
cgtgatcgag agcgacaaga gcaccctgct gggcgaggcc gtggccaagc gcttcggcga    11520
gctgcccttc ctgttcaagg tgctgtgcgc cgcccagccc ctgagcatcc aggtgcaccc    11580
caacaagcac aacagcgaga tcggcttcgc caaggagaac gccgccggca tccccatgga    11640
cgccgccgag cgcaactaca aggaccccaa ccacaagccc gagctggtgt cgccctgac    11700
ccccttcctg gccatgaacg ccttccgcga gttcagcgag atcgtgagcc tgctgcagcc    11760
cgtggccggc gcccacccg ccatcgccca cttcctgcag cagcccgacg ccgagcgcct    11820
gagcgagctg ttcgccagcc tgctgaacat gcagggcgag gagaagagcc gcgccctggc    11880
catcctgaag agcgccctgg acagccagca gggcgagccc tggcagacca tccgcctgat    11940
cagcgagttc taccccgagg acagcggcct gttcagcccc ctgctgctga acgtggtgaa    12000
gctgaacccc ggcgaggcca tgttcctgtt cgccagacc ccacgcct acctgcaggg    12060
cgtggccctg gaggtgatgg ccaacagcga caacgtgctg cgcgccggcc tgaccccaa    12120
gtacatcgac atcccgagc tggtggccaa cgtgaagttc gaggcaagc ccgccaacca    12180
gctgctgacc cagcccgtga agcagggcgc cgagctggac ttccccatcc ccgtggacga    12240
cttcgccttc agcctgcacg acctgagcga caaggagacc accatcagcc agcagagcgc    12300
cgccatcctg ttctgcgtgg agggcgacgc caccctgtgg aagggcagcc agcagctgca    12360
gctgaagccc ggcgagagcg ccttcatcgc cgccaacgag agcccgtga ccgtgaaggg    12420
ccacggccgc ctgccgcg tgtacaacaa gctgtgatag agctcgatc cgtcgacctg    12480
cagatcgttc aaacatttgg caataaagtt tcttaagatt gaatcctgtt gccggtcttg    12540
cgatgattat catataattt ctgttgaatt acgttaagca tgtaataatt aacatgtaat    12600
gcatgacgtt atttatgaga tgggttttta tgattagagt cccgcaatta tacatttaat    12660
acgcgataga aaacaaaata tagcgcgcaa actaggataa attatcgcgc gcggtgtcat    12720
```

```
ctatgttact agatcggcgc gccgcaattg aagtttgggc ggccagcatg gccgtatccg  12780
caatgtgtta ttaagttgtc taagcgtcaa tttgtttaca ccacaatata tcctgccacc  12840
agccagccaa cagctccccg accggcagct cggcacaaaa tcaccactcg atacaggcag  12900
cccatcagaa ttaattctca tgtttgacag cttatcatcg actgcacggt gcaccaatgc  12960
ttctggcgtc aggcagccat cggaagctgt ggtatggctg tgcaggtcgt aaatcactgc  13020
ataattcgtg tcgctcaagg cgcactcccg ttctggataa tgttttttgc gccgacatca  13080
taacggttct ggcaaatatt ctgaaatgag ctgttgacaa ttaatcatcc ggctcgtata  13140
atgtgtggaa ttgtgagcgg ataacaattt cacacaggaa acagaccatg agggaagcgt  13200
tgatcgccga agtatcgact caactatcag aggtagttgg cgtcatcgag cgccatctcg  13260
aaccgacgtt gctggccgta catttgtacg gctccgcagt ggatggcggc ctgaagccac  13320
acagtgatat tgatttgctg gttacggtga ccgtaaggct tgatgaaaca cgcggcgag   13380
ctttgatcaa cgaccttttg gaaacttcgg cttcccctgg agagagcgag attctccgcg  13440
ctgtagaagt caccattgtt gtgcacgacg acatcattcc gtggcgttat ccagctaagc  13500
gcgaactgca atttggagaa tggcagcgca atgacattct tgcaggtatc ttcgagccag  13560
ccacgatcga cattgatctg gctatcttgc tgacaaaagc aagagaacat agcgttgcct  13620
tggtaggtcc agcggcggag gaactcttg atccggttcc tgaacaggat ctatttgagg  13680
cgctaaatga aaccttaacg ctatggaact cgccgcccga ctgggctggc gatgagcgaa  13740
atgtagtgct tacgttgtcc cgcatttggt acagcgcagt aaccggcaaa atcgcgccga  13800
aggatgtcgc tgccgactgg gcaatggagc gcctgccggc ccagtatcag cccgtcatac  13860
ttgaagctag gcaggcttat cttgacaag aagatcgctt ggcctcgcgc gcagatcagt  13920
tggaagaatt tgttcactac gtgaaaggcg agatcaccaa agtagtcggc aaataaagct  13980
ctagtggatc tccgtacccg gggatctggc tcgcggcgga cgcacgacgc cggggcgaga  14040
ccataggcga tctcctaaat caatagtagc tgtaacctcg aagcgtttca cttgtaacaa  14100
cgattgagaa tttttgtcat aaaattgaaa tacttggttc gcattttgt catccgcggt   14160
cagccgcaat tctgacgaac tgcccattta gctggagatg attgtacatc cttcacgtga  14220
aaatttctca agcgctgtga acaagggttc agattttaga ttgaaaggtg agccgttgaa  14280
acacgttctt cttgtcgatg acgacgtcgc tatgcggcat cttattattg aataccttac  14340
gatccacgcc ttcaaagtga ccgcggtagc cgacagcacc cagttcacaa gagtactctc  14400
ttccgcgacg gtcgatgtcg tggttgttga tctagattta ggtcgtgaag atgggctcga  14460
gctaggagca agtgatttta tcgctaagcc gttcagtatc agagagtttc tagcacgcat  14520
tcgggttgcc ttgcgcgtgc gccccaacgt tgtccgctcc aaagaccgac ggtctttttg  14580
ttttactgac tggacactta atctcaggca acgtcgcttg atgtccgaag ctggcggtga  14640
ggtgaaactt acggcaggtg agttcaatct tctcctcgcg ttttagaga aaccccgcga   14700
cgttctatcg cgcgagcaac ttctcattgc cagtcgagta cgcgacgagg aggtttatga  14760
caggagtata gatgttctca tttttgaggct gcgccgcaaa cttgaggcag atccgtcaag  14820
ccctcaactg ataaaaacag caagaggtgc cggttatttc tttgacgcgg acgtgcaggt  14880
ttcgcacggg gggacgatgg cagcctgagc caattcccag atccccgagg aatcggcgtg  14940
agcggtcgca aaccatccgg cccggtacaa atcggcgcgg cgctgggtga tgacctggtg  15000
gagaagttga aggccgcgca ggccgcccag cggcaacgca tcgaggcaga agcacgcccc  15060
```

```
ggtgaatcgt ggcaagcggc cgctgatcga atccgcaaag aatcccggca accgccggca    15120
gccggtgcgc cgtcgattag gaagccgccc aagggcgacg agcaaccaga ttttttcgtt    15180
ccgatgctct atgacgtggg cacccgcgat agtcgcagca tcatggacgt ggccgttttc    15240
cgtctgtcga agcgtgaccg acgagctggc gaggtgatcc gctacgagct tccagacggg    15300
cacgtagagg tttccgcagg gccggccggc atggccagtg tgtgggatta cgacctggta    15360
ctgatggcgg tttcccatct aaccgaatcc atgaaccgat accgggaagg gaagggagac    15420
aagcccggcc gcgtgttccg tccacacgtt gcggacgtac tcaagttctg ccggcgagcc    15480
gatggcggaa agcagaaaga cgacctggta gaaacctgca ttcggttaaa caccacgcac    15540
gttgccatgc agcgtacgaa gaaggccaag aacggccgcc tggtgacggt atccgagggt    15600
gaagccttga ttagccgcta caagatcgta aagagcgaaa ccgggcggcc ggagtacatc    15660
gagatcgagc tagctgattg gatgtaccgc gagatcacag aaggcaagaa cccggacgtg    15720
ctgacggttc accccgatta cttttttgatc gatcccggca tcggccgttt tctctaccgc    15780
ctggcacgcc gcgccgcagg caaggcagaa gccagatggt tgttcaagac gatctacgaa    15840
cgcagtggca gcgccggaga gttcaagaag ttctgtttca ccgtgcgcaa gctgatcggg    15900
tcaaatgacc tgccggagta cgatttgaag gaggaggcgg ggcaggctgg cccgatccta    15960
gtcatgcgct accgcaacct gatcgagggc gaagcatccg ccggttccta atgtacggag    16020
cagatgctag ggcaaattgc cctagcaggg gaaaaaggtc gaaaggtct ctttcctgtg    16080
gatagcacgt acattgggaa cccaaagccg tacattggga accggaaccc gtacattggg    16140
aacccaaagc cgtacattgg gaaccggtca cacatgtaag tgactgatat aaaagagaaa    16200
aaaggcgatt tttccgccta aaactcttta aaacttatta aaactcttaa aacccgcctg    16260
gcctgtgcat aactgtctgg ccagcgcaca gccgaagagc tgcaaaaagc gcctacccttt   16320
cggtcgctgc gctccctacg ccccgccgct tcgcgtcggc ctatcgcggc cgctggccgc    16380
tcaaaaatgg ctggcctacg gccaggcaat ctaccagggc gcggacaagc cgcgccgtcg    16440
ccactcgacc gccggcgctg aggtctgcct cgtgaagaag gtgttgctga ctcataccag    16500
gcctgaatcg ccccatcatc cagccagaaa gtgagggagc cacggttgat gagagctttg    16560
ttgtaggtgg accagttggt gattttgaac ttttgctttg ccacggaacg gtctgcgttg    16620
tcgggaagat gcgtgatctg atccttcaac tcagcaaaag ttcgatttat tcaacaaagc    16680
cgccgtcccg tcaagtcagc gtaatgctct gccagtgtta caaccaatta accaattctg    16740
attagaaaaa ctcatcgagc atcaaatgaa actgcaattt attcatatca ggattatcaa    16800
taccatattt ttgaaaaagc cgtttctgta atgaaggaga aaactcaccg aggcagttcc    16860
ataggatggc aagatcctgg tatcggtctg cgattccgac tcgtccaaca tcaatacaac    16920
ctattaattt ccccctcgtca aaaataaggt tatcaagtga gaaatcacca tgagtgacga    16980
ctgaatccgg tgagaatggc aaaagctctg cattaatgaa tcggccaacg cgcgggaga    17040
ggcggtttgc gtattgggcg ctcttccgct tcctcgctca ctgactcgct gcgctcggtc    17100
gttcggctgc ggcgagcggt atcagctcac tcaaaggcgg taatacggtt atccacagaa    17160
tcagggggata acgcaggaaa gaacatgtga gcaaaaggcc agcaaaaggc caggaaccgt    17220
aaaaaggccg cgttgctggc gttttccat aggctccgcc cccctgacga gcatcacaaa    17280
aatcgacgct caagtcagag gtggcgaaac ccgacaggac tataaagata ccaggcgttt    17340
ccccctggaa gctccctcgt gcgctctcct gttccgaccc tgccgcttac cggatacctg    17400
tccgcctttc tcccttcggg aagcgtggcg ctttctcata gctcacgctg taggtatctc    17460
```

```
agttcggtgt aggtcgttcg ctccaagctg ggctgtgtgc acgaaccccc cgttcagccc   17520
gaccgctgcg ccttatccgg taactatcgt cttgagtcca acccggtaag acacgactta   17580
tcgccactgg cagcagccac tggtaacagg attagcagag cgaggtatgt aggcggtgct   17640
acagagttct tgaagtggtg gcctaactac ggctacacta gaagaacagt atttggtatc   17700
tgcgctctgc tgaagccagt taccttcgga aaaagagttg gtagctcttg atccggcaaa   17760
caaaccaccg ctggtagcgg tggtttttt gtttgcaagc agcagattac gcgcagaaaa   17820
aaaggatctc aagaagatcc tttgatcttt tctacggggt ctgacgctca gtggaacgaa   17880
aactcacgtt aagggatttt ggtcatgaga ttatcaaaaa ggatcttcac ctagatcctt   17940
ttgatccgga atta                                                     17954
```

<210> SEQ ID NO 36
<211> LENGTH: 17045
<212> TYPE: DNA
<213> ORGANISM: Artificial Sequence
<220> FEATURE:
<223> OTHER INFORMATION: vector 24079
<220> FEATURE:
<221> NAME/KEY: misc_feature
<222> LOCATION: (4)..(259)
<220> FEATURE:
<221> NAME/KEY: promoter
<222> LOCATION: (312)..(2356)
<223> OTHER INFORMATION: prGRMZM2G146551-01
<220> FEATURE:
<221> NAME/KEY: gene
<222> LOCATION: (2358)..(6527)
<223> OTHER INFORMATION: cCas9-01
<220> FEATURE:
<221> NAME/KEY: mutation
<222> LOCATION: (5847)..(5849)
<223> OTHER INFORMATION: L to V mutation
<220> FEATURE:
<221> NAME/KEY: mutation
<222> LOCATION: (5892)..(5894)
<223> OTHER INFORMATION: I to V mutation
<220> FEATURE:
<221> NAME/KEY: terminator
<222> LOCATION: (6542)..(7860)
<223> OTHER INFORMATION: tGRMZM2G146551-01
<220> FEATURE:
<221> NAME/KEY: promoter
<222> LOCATION: (7874)..(8248)
<223> OTHER INFORMATION: prOsU3-01
<220> FEATURE:
<221> NAME/KEY: misc_feature
<222> LOCATION: (8249)..(8354)
<223> OTHER INFORMATION: rsgRNAZmVLHP-02
<220> FEATURE:
<221> NAME/KEY: misc_feature
<222> LOCATION: (8250)..(8269)
<223> OTHER INFORMATION: ZmVLHP2 target
<220> FEATURE:
<221> NAME/KEY: misc_feature
<222> LOCATION: (8270)..(8281)
<223> OTHER INFORMATION: rCrRNA-01
<220> FEATURE:
<221> NAME/KEY: misc_feature
<222> LOCATION: (8286)..(8354)
<223> OTHER INFORMATION: rTracrRNA-01
<220> FEATURE:
<221> NAME/KEY: promoter
<222> LOCATION: (8365)..(10356)
<223> OTHER INFORMATION: prUbi1-04
<220> FEATURE:
<221> NAME/KEY: gene
<222> LOCATION: (10373)..(11551)
<223> OTHER INFORMATION: cPMI-09
<220> FEATURE:
<221> NAME/KEY: terminator

```
<222> LOCATION: (11574)..(11826)
<223> OTHER INFORMATION: tNOS-05-01
<220> FEATURE:
<221> NAME/KEY: misc_feature
<222> LOCATION: (11870)..(11999)
<223> OTHER INFORMATION: bNLB-03
<220> FEATURE:
<221> NAME/KEY: gene
<222> LOCATION: (12279)..(13067)
<223> OTHER INFORMATION: cSpec-03
<220> FEATURE:
<221> NAME/KEY: promoter
<222> LOCATION: (13162)..(13292)
<223> OTHER INFORMATION: prVirG-01
<220> FEATURE:
<221> NAME/KEY: gene
<222> LOCATION: (13367)..(13999)
<223> OTHER INFORMATION: cVirG-09
<220> FEATURE:
<221> NAME/KEY: gene
<222> LOCATION: (14029)..(15102)
<223> OTHER INFORMATION: cRepA-01
<220> FEATURE:
<221> NAME/KEY: misc_feature
<222> LOCATION: (15145)..(15549)
<223> OTHER INFORMATION: oVS1-02
<220> FEATURE:
<221> NAME/KEY: misc_feature
<222> LOCATION: (16227)..(17033)
<223> OTHER INFORMATION: oCOLE-06

<400> SEQUENCE: 36
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa caaagcttgg     300
taccgggacc catgtagtat cacatgagtg agtcaaggac taagtattat gcattttgtt     360
tctcactcac ggattagctc gcaatcatca tagtgaaatc tagctactgg cactatcgaa     420
atctagctct tgccgagtg cactttatcg agcactcgac aaagcattct ttatcgagtg      480
ccagtcttgg cgaaataaga ctctcgacaa agaccttgtt taccgaggga gaaacactcg     540
gcgtaaaaag acactcggca agaagactt tgctgagtgt caaaccctca gcgaaatgcg      600 acccctcggca aggaccgtc agcagccatc tatagttgat ggctattaac ttcgcgagtg     660
tcaggcgttg acacacgaca aaatatcttt tttgtcgagt gtcactgggc aaacacttgg     720
taaacctatg ttttgccgag tgtctttcct tgacactcga caaagtatat ttgtttttc      780 ttttttcccca aacttttgt ggtgtgtttc tacaatatat agacctattt gttcaatttt     840
ggcacaatta taaagtgtt tgctataact atcagattta gtttgcttaa ttggatttct      900
ttggataatt cagatttgaa ctacaagcca cttgaaaaat ggaaacagt gaatacaaaa      960 atgacattca tgttatttag cacaagttat gatctatttc aggaacatgc gagaattttc    1020
gaacaccatt ctcacaaaac atgattgcgg acttgtgatc aagttgtttt aaaattgtat    1080
aaaacaaaaa caaagtcaga aaatcatgaa acttgttgac atgtcatgat atcatatgta    1140
gagactctaa taaaaatttg agattgtttc atgaaagttg tcacgcgcta tgtgtagaaa    1200
cctagcccgt ctacattgag gttctatgat ttcatgtgaa ggacatctag gcatcaatgt    1260
ttatgataat atcttatgtt tgtttggacg aaatattaaa aacaaataaa aagggtcct    1320 tgatcacttt gacgagcatt gcactcagca aagggtgcct ttgctgagtg caatggtcat    1380
```

```
agaactcggt agaaaaacat acatagacat agggaaactt gctttaccgc gtgctatggc    1440
caagacactc ggcaaactag gctcctttgt cgagttccat cccaagcact cgacattgga    1500
actgcgactg ggcctcacag aagctttctt tgccgagtgc cactaagcga ggaactcgga    1560
tgctcagcaa aggctctgtc atcgtcacga tgtcttttgt ttgtcgtgta ccagttggca    1620
ctcggtaaag actttactga gtgcccgata gaaagtactc gacaaagaga ccgttgccaa    1680
cgtttggttc actgagggct ctttgctgcc ttttggactt gacaaagaag ccgtctccag    1740
tagtgtctcc tgggaggcgg gatttatgtt ttttcccgga gctctgtggg acatcatgga    1800
cggtccagtc tggtgatcta aaatagacgt tttgccaagc tcacagagaa gtctttaaga    1860
tcttccacga tgcacgcatg ctttaaggtt agttagtgtt tggtctgaaa aagcgtcaac    1920
aattaggaaa caagaactaa aattattaaa ggacagatca ggaagcatgc atgttcttct    1980
tctatagtgt gtgttgagcc tgagtttggc cttttaggct ttattagggg gctcacagtc    2040
taactaagga gttgtattga tgtgctgaca aatattatgt tcgatcgtca cagtgttctt    2100
atgcggatcg attaggcccg atcatggtga aataaactaa ccaccggtaa gcccgggcag    2160
ccctagagca tgcagcggcc tacgtgaagc ccgcacatcg catcgtcgtc cgtcaggcgc    2220
taacggccgg ccgctgcatg cgtcgccggc gaactctctg ctgagccacc cgtcctccct    2280
ataagtagct atcccagcac cgtcgtctat caaccacaca cagagcggca tttcgaataa    2340
cacaggtgag cgcgaccatg gacaagaagt acagcatcgg cctggacatc ggcaccaaca    2400
gcgtgggctg ggccgtgatc accgacgagt acaaggtgcc gagcaagaag ttcaaggtgc    2460
tgggcaacac cgacaggcac agcatcaaga gaaacctgat cggcgccctg ctgttcgaca    2520
gcggcgagac cgccgaggcc accaggctga agaggaccgc caggaggagg tacaccagga    2580
ggaagaacag gatctgctac ctgcaggaga tcttcagcaa cgagatggcc aaggtggacg    2640
acagcttctt ccacaggctg gaggagagct cctggtgga ggaggacaag aagcacgaga    2700
ggcacccgat cttcggcaac atcgtggacg aggtggccta ccacgagaag tacccgacca    2760
tctaccacct gaggaagaag ctggtggaca gcaccgacaa ggccgacctg aggctgatct    2820
acctggccct ggcccacatg atcaagttca ggggccactt cctgatcgag ggcgacctga    2880
acccggacaa cagcgacgtg gacaagctgt tcatccagct ggtgcagacc tacaaccagc    2940
tgttcgagga gaacccgatc aacgccagcg gcgtggacgc caaggccatc ctgagcgcca    3000
ggctgagcaa gagcaggagg ctggagaacc tgatcgccca gctgccgggc gagaagaaga    3060
acggcctgtt cggcaacctg atcgccctga gcctgggcct gacccgaac ttcaagagca    3120
acttcgacct ggccgaggac gccaagctgc agctgagcaa ggacacctac gacgacgacc    3180
tggacaacct gctggcccag atcggcgacc agtacgccga cctgttcctg gccgccaaga    3240
acctgagcga cgccatcctg ctgagcgaca tcctgagggt gaacaccgag atcaccaagg    3300
ccccgctgag cgccagcatg atcaagaggt acgacgagca ccaccaggac ctgacccctgc    3360
tgaaggccct ggtgaggcag cagctgccgg agaagtacaa ggagatcttc ttcgaccaga    3420
gcaagaacgg ctacgccggc tacatcgacg gcggcgccag ccaggaggag ttctacaagt    3480
tcatcaagcc gatcctggag aagatggacg gcaccgagga gctgctggtg aagctgaaca    3540
gggaggacct gctgaggaag cagaggacct cgacaacgg cagcatcccg caccagatcc    3600
acctgggcga gctgcacgcc atcctgagga ggcaggagga cttctacccg ttcctgaagg    3660
acaacaggga gaagatcgag aagatcctga ccttccgcat cccgtactac gtgggcccgc    3720
tggccagggg caacagcagg ttcgcctgga tgaccaggaa gagcgaggag accatcaccc    3780
```

-continued

```
cgtggaactt cgaggaggtg gtggacaagg gcgccagcgc ccagagcttc atcgagagga    3840
tgaccaactt cgacaagaac ctgccgaacg agaaggtgct gccgaagcac agcctgctgt    3900
acgagtactt caccgtgtac aacgagctga ccaaggtgaa gtacgtgacc gagggcatga    3960
ggaagccggc cttcctgagc ggcgagcaga agaaggccat cgtggacctg ctgttcaaga    4020
ccaacaggaa ggtgaccgtg aagcagctga aggaggacta cttcaagaag atcgagtgct    4080
tcgacagcgt ggagatcagc ggcgtggagg acaggttcaa cgccagcctg ggcacctacc    4140
acgacctgct gaagatcatc aaggacaagg acttcctgga caacgaggag aacgaggaca    4200
tcctggagga catcgtgctg accctgaccc tgttcgagga cagggagatg atcgaggaga    4260
ggctgaagac ctacgcccac ctgttcgacg acaaggtgat gaagcagctg aagaggagga    4320
ggtacaccgg ctggggcagg ctgagcagga agctgatcaa cggcatcagg gacaagcaga    4380
gcggcaagac catcctggac ttcctgaaga gcgacggctt cgccaacagg aacttcatgc    4440
agctgatcca cgacgacagc ctgaccttca aggaggacat ccagaaggcc caggtgagcg    4500
gccagggcga cagcctgcac gagcacatcg ccaacctggc cggcagcccg gccatcaaga    4560
agggcatcct gcagaccgtg aaggtggtgg acgagctggt gaaggtgatg ggcaggcaca    4620
agccggagaa catcgtgatc gagatggcca gggagaacca gaccacccag aagggccaga    4680
agaacagcag ggagaggatg aagaggatcg aggagggcat caaggagctg ggcagccaga    4740
tcctgaagga gcacccggtg gagaacaccc agctgcagaa cgagaagctg tacctgtact    4800
acctgcagaa cggcagggac atgtacgtgg accaggagct ggacatcaac aggctgagcg    4860
actacgacgt ggaccacatc gtgccgcaga gcttcctgaa ggacgacagc atcgacaaca    4920
aggtgctgac caggagcgac aagaacaggg gcaagagcga caacgtgccg agcgaggagg    4980
tggtgaagaa gatgaaaaac tactggaggc agctgctgaa cgccaagctg atcacccaga    5040
ggaagttcga caacctgacc aaggccgaga ggggcggcct gagcgagctg gacaaggccg    5100
gcttcattaa aaggcagctg gtggagacca ggcagatcac caagcacgtg gcccagatcc    5160
tggacagcag gatgaacacc aagtacgacg agaacgacaa gctgatcagg gaggtgaagg    5220
tgatcaccct gaagagcaag ctggtgagcg acttcaggaa ggacttccag ttctacaagg    5280
tgagggagat caataattac caccacgccc acgacgccta cctgaacgcc gtggtgggca    5340
ccgccctgat taaaaagtac ccgaagctgg agagcgagtt cgtgtacggc gactacaagg    5400
tgtacgacgt gaggaagatg atcgccaaga gcgagcagga gatcggcaag gccaccgcca    5460
agtacttctt ctacagcaac atcatgaact tcttcaagac cgagatcacc ctggccaacg    5520
gcgagatcag gaagaggccg ctgatcgaga ccaacggcga gaccggcgag atcgtgtggg    5580
acaagggcag ggacttcgcc accgtgagga aggtgctgtc catgccgcag gtgaacatcg    5640
tgaagaagac cgaggtgcag accggcggct tcagcaagga gagcatcctg ccgaagagga    5700
acagcgacaa gctgatcgcc aggaagaagg actgggaccc gaagaagtac ggcggcttcg    5760
acagcccgac cgtggcctac agcgtgctgg tggtggccaa ggtggagaag gcaagagca    5820
agaagctgaa gagcgtgaag gagctggtgg gcatcaccat catggagagg agcagcttcg    5880
agaagaaccc agtggacttc ctggaggcca agggctacaa ggaggtgaag aaggacctga    5940
tcattaaact gccgaagtac agcctgttcg agctggagaa cggcaggaag aggatgctgg    6000
ccagcgccgg cgagctgcag aagggcaacg agctggccct gccgagcaag tacgtgaact    6060
tcctgtacct ggccagccac tacgagaagc tgaagggcag cccggaggac aacgagcaga    6120
```

```
agcagctgtt cgtggagcag cacaagcact acctggacga gatcatcgag cagatcagcg    6180
agttcagcaa gagggtgatc ctggccgacg ccaacctgga caaggtgctg agcgcctaca    6240
acaagcacag ggacaagccg atcagggagc aggccgagaa catcatccac ctgttcaccc    6300
tgaccaacct gggcgccccg gccgccttca gtacttcga caccaccatc gacaggaaga     6360
ggtacaccag caccaaggag gtgctggacg ccaccctgat ccaccagagc atcaccggcc    6420
tgtacgagac caggatcgac ctgagccagc tgggcggcga cagcagcccg ccgaagaaga    6480
agaggaaggt gagctggaag gacgccagcg gctggagcag gatgtgacca tggagctcta    6540
aactttgaat tcccttcgat tcatccggca cagcgggcta tggaccttca gcagcaagct    6600
aattaagttg gcagcatgca ccgctaacct tatatactac tgagacttcc aaattctagt    6660
atatgtaatc cttttgttcg ggttcatgat cgaattccaa agagtggaaa acaagcaaaa    6720
ggttaaatat acatgccatt tttggaggca tttttttcat gagggcatgt ttcgatatat    6780
ggaccactaa atatacatat catttacttt cctacaaatt tgctcatccc ttggaaatgc    6840
atagtctgtc tccaagaaaa agatactctg attacatcac tagtacacac agcctctata    6900
gtggcggttc tagagacatt ttcactggcg cttttcagtg ccgccagtgt taggggccag    6960
tggaaatcgc catttccatt caataaccgc cagtggaaaa agcatttcca ctggcggttt    7020
tcttaagcaa ccgccagtgg aaatgtttcc cgtctttttt taaattttcg tactgaaatt    7080
tatatattta cacacacaaa catatatata tatatattga tattgataaa catgtagtat    7140
tgatactaaa agcaacatga aattaaattc tatcatacat ttatatacat caaagtcttg    7200
tttacaacca tgtatgcatc acacattata tacatcaaag ttttcactta agctctaata    7260
actatctcgg ctaagagata gtctactaat ttctgttagt attctaaact ctggcaaagc    7320
taatgttccg gaagcatcgt gatatttccc ttctgcggga atgacctctt tcaatatgaa    7380
tgtgcacagg tcctcaacta tgccatacaa tgcaccttca gtcaagttct ccgggcttcc    7440
tttttgaaat tgctgtaaag gaagtttata acatcatct atttatactc aataataaca    7500
catttgcatc tttaatgaca taaatacata cgtgactatt actaataata ccttgccagg    7560
gttcgtgatg tatcgtccat tcattctcat aaactcgcac acgtagaacc cacataggac    7620
cgatccgggt ggttgcttgt ggcactacat aacgggagat tggttattta gttgcaacat    7680
tgtcctatgt acgtacatgt atgatatgta ttcataaatt cacatactta ctggccagtt    7740
ataatggatg tctagtggca cacctttttt ggacgtgtcg tactttccac catgtagctt    7800
ataaaaccta aatgccctgt gatctcaaat agaatcacca tgttattcta caattctcat    7860
gggacccttc gaagggatct ttaaacatac gaacagatca cttaaagttc ttctgaagca    7920
acttaaagtt atcaggcatg catggatctt ggaggaatca gatgtgcagt cagggaccat    7980
agcacaggac aggcgtcttc tactggtgct accagcaaat gctggaagcc gggaacactg    8040
ggtacgttgg aaaccacgtg atgtggagta agataaactg taggagaaaa gcatttcgta    8100
gtgggccatg aagcctttca ggacatgtat tgcagtatgg gccggccat  tacgcaattg    8160
gacgacaaca aagactagta ttagtaccac ctcggctatc cacatagatc aaagctggtt    8220
taaaagagtt gtgcagatga tccgtggcag ctggagctga gcttccgggg ttttagagct    8280
agaaatagca agttaaaata aggctagtcc gttatcaact tgaaaaagtg gcaccgagtc    8340
ggtgcttttt tttcggacc gcgcctgcag tgcagcgtga cccggtcgtg ccctctctca    8400
gagataatga gcattgcatg tctaagttat aaaaaattac cacatatttt ttttgtcaca    8460
cttgtttgaa gtgcagttta tctatcttta tacatatatt taaactttac tctacgaata    8520
```

```
atataatcta tagtactaca ataatatcag tgttttagag aatcatataa atgaacagtt    8580
agacatggtc taaaggacaa ttgagtattt tgacaacagg actctacagt tttatctttt    8640
tagtgtgcat gtgttctcct ttttttttgc aaatagcttc acctatataa tacttcatcc    8700
attttattag tacatccatt tagggtttag ggttaatggt ttttatagac taattttttt    8760
agtacatcta ttttattcta ttttagcctc taaattaaga aaactaaaac tctattttag    8820
tttttttatt taataattta gatataaaat agaataaaat aaagtgacta aaaattaaac    8880
aaatacccct taagaaatta aaaaaactaa ggaaacattt ttcttgtttc gagtagataa    8940
tgccagcctg ttaaacgccg tcgacgagtc taacggacac caaccagcga accagcagcg    9000
tcgcgtcggg ccaagcgaag cagacggcac ggcatctctg tcgctgcctc tggacccctc    9060
tcgagagttc cgctccaccg ttggacttgc tccgctgtcg gcatccagaa attgcgtggc    9120
ggagcggcag acgtgagccg gcacggcagg cggcctcctc ctcctctcac ggcaccggca    9180
gctacggggg attcctttcc caccgctcct tcgctttccc ttcctcgccc gccgtaataa    9240
atagacaccc cctccacacc ctctttcccc aacctcgtgt tgttcggagc gcacacacac    9300
acaaccagat ctcccccaaa tccacccgtc ggcacctccg cttcaaggta cgccgctcgt    9360
cctccccccc cccctctct accttctcta gatcggcgtt ccggtccatg gttagggccc    9420
ggtagttcta cttctgttca tgtttgtgtt agatccgtgt ttgtgttaga tccgtgctgc    9480
tagcgttcgt acacggatgc gacctgtacg tcagacacgt tctgattgct aacttgccag    9540
tgtttctctt tggggaatcc tgggatggct ctagccgttc cgcagacggg atcgatttca    9600
tgattttttt tgtttcgttg catagggttt ggtttgccct ttttcctttat ttcaatatat    9660 gccgtgcact tgtttgtcgg gtcatctttt catgcttttt tttgtcttgg ttgtgatgat    9720
gtggtctggt tgggcggtcg ttctagatcg gagtagaatt ctgtttcaaa ctacctggtg    9780
gatttattaa ttttggatct gtatgtgtgt gccatacata ttcatagtta cgaattgaag    9840
atgatggatg gaaatatcga tctaggatag gtatacatgt tgatgcgggt tttactgatg    9900
catatacaga gatgcttttt gttcgcttgg ttgtgatgat gtggtgtggt tgggcggtcg    9960
ttcattcgtt ctagatcgga gtagaatact gtttcaaact acctggtgta tttattaatt    10020
ttggaactgt atgtgtgtgt catacatctt catagttacg agtttaagat ggatggaaat    10080
atcgatctag dataggtata catgttgatg tgggttttac tgatgcatat acatgatggc    10140
atatgcagca tctattcata tgctctaacc ttgagtacct atctattata ataaacaagt    10200
atgttttata attattttga tcttgatata cttggatgat ggcatatgca gcagctatat    10260
gtggattttt ttagccctgc cttcatacgc tatttatttg cttggtactg tttctttttgt    10320 cgatgctcac cctgttgttt ggtgttactt ctgcagggat ccggcagcag ccatgcagaa    10380
gctgatcaac agcgtgcaga actacgcctg gggcagcaag accgccctga ccgagctgta    10440
cggcatggag aacccagca gccagcccat ggccgagctg tggatgggcg cccacccaa    10500 gagcagcagc cgcgtgcaga acgccgccgg cgacatcgtg agcctgcgcg acgtgatcga    10560
gagcgacaag agcaccctgc tgggcgaggc cgtggccaag cgcttcggcg agctgcctt    10620 cctgttcaag gtgctgtgcg ccgcccagcc cctgagcatc caggtgcacc ccaacaagca    10680
caacagcgag atcggcttcg ccaaggagaa cgccgccggc atccccatgg acgccgccga    10740
gcgcaactac aaggacccca accacaagcc cgagctggtg ttcgccctga ccccttcct    10800 ggccatgaac gccttccgcg agttcagcga gatcgtgagc ctgctgcagc ccgtggccgg    10860
```

```
cgcccacccc gccatcgccc acttcctgca gcagcccgac gccgagcgcc tgagcgagct   10920
gttcgccagc ctgctgaaca tgcagggcga ggagaagagc cgcgccctgg ccatcctgaa   10980
gagcgccctg gacagccagc agggcgagcc ctggcagacc atccgcctga tcagcgagtt   11040
ctaccccgag gacagcggcc tgttcagccc cctgctgctg aacgtggtga agctgaaccc   11100
cggcgaggcc atgttcctgt cgccgagac ccccacgcc tacctgcagg gcgtggccct   11160
ggaggtgatg ccaacagcg acaacgtgct gcgcgccggc ctgacccca agtacatcga   11220
catccccgag ctggtggcca acgtgaagtt cgaggccaag cccgccaacc agctgctgac   11280
ccagcccgtg aagcagggcg ccgagctgga cttccccatc cccgtggacg acttcgcctt   11340
cagcctgcac gacctgagcg acaaggagac caccatcagc cagcagagcg ccgccatcct   11400
gttctgcgtg gagggcgacg ccaccctgtg gaagggcagc cagcagctgc agctgaagcc   11460
cggcgagagc gccttcatcg ccgccaacga gagcccgtg accgtgaagg gccacggccg   11520
cctggcccgc gtgtacaaca gctgtgata ggagctcgat ccgtcgacct gcagatcgtt   11580
caaacatttg gcaataaagt ttcttaagat tgaatcctgt tgccggtctt gcgatgatta   11640
tcatataatt tctgttgaat tacgttaagc atgtaataat taacatgtaa tgcatgacgt   11700
tatttatgag atgggttttt atgattagag tcccgcaatt atacatttaa tacgcgatag   11760
aaaacaaaat atagcgcgca aactaggata aattatcgcg cgcggtgtca tctatgttac   11820
tagatcggcg cgccgcaatt gaagtttggg cggccagcat ggccgtatcc gcaatgtgtt   11880
attaagttgt ctaagcgtca atttgtttac accacaatat atcctgccac cagccagcca   11940
acagctcccc gaccggcagc tcggcacaaa atcaccactc gatacaggca gcccatcaga   12000
attaattctc atgtttgaca gcttatcatc gactgcacgg tgcaccaatg cttctggcgt   12060
caggcagcca tcggaagctg tggtatggct gtgcaggtcg taaatcactg cataattcgt   12120
gtcgctcaag gcgcactccc gttctggata atgttttttg cgccgacatc ataacggttc   12180
tggcaaatat tctgaaatga gctgttgaca attaatcatc cggctcgtat aatgtgtgga   12240
attgtgagcg gataacaatt tcacacagga aacagaccat gagggaagcg ttgatcgccg   12300
aagtatcgac tcaactatca gaggtagttg gcgtcatcga gcgccatctc gaaccgacgt   12360
tgctggccgt acatttgtac ggctccgcag tggatggcgg cctgaagcca cacagtgata   12420
ttgatttgct ggttacggtg accgtaaggc ttgatgaaac aacgcggcga gctttgatca   12480
acgacctttt ggaaacttcg gcttcccctg gagagagcga gattctccgc gctgtagaag   12540
tcaccattgt tgtgcacgac gacatcattc cgtggcgtta tccagctaag cgcgaactgc   12600
aatttggaga atggcagcgc aatgacattc ttgcaggtat cttcgagcca gccacgatcg   12660
acattgatct ggctatcttg ctgacaaaag caagagaaca tagcgttgcc ttggtaggtc   12720
cagcggcgga ggaactcttt gatccggttc ctgaacagga tctatttgag gcgctaaatg   12780
aaaccttaac gctatggaac tcgccgcccg actgggctgg cgatgagcga aatgtagtgc   12840
ttacgttgtc ccgcatttgg tacagcgcag taaccggcaa aatcgcgccg aaggatgtcg   12900
ctgccgactg gcaatggag cgcctgccgg cccagtatca gcccgtcata cttgaagcta   12960
ggcaggctta tcttggacaa gaagatcgct tggcctcgcg cgcagatcag ttggaagaat   13020
ttgttcacta cgtgaaaggc gagatcacca agtagtcgg caaataaagc tctagtggat   13080
ctccgtaccc ggggatctgg ctcgcggcgg acgcacgacg ccggggcgag accataggcg   13140
atctcctaaa tcaatagtag ctgtaacctc gaagcgttc acttgtaaca acgattgaga   13200
atttttgtca taaaattgaa atacttggtt cgcatttttg tcatccgcgg tcagccgcaa   13260
```

```
ttctgacgaa ctgcccattt agctggagat gattgtacat ccttcacgtg aaaatttctc   13320
aagcgctgtg aacaagggtt cagattttag attgaaaggt gagccgttga aacacgttct   13380
tcttgtcgat gacgacgtcg ctatgcggca tcttattatt gaatacctta cgatccacgc   13440
cttcaaagtg accgcggtag ccgacagcac ccagttcaca agagtactct cttccgcgac   13500
ggtcgatgtc gtggttgttg atctagattt aggtcgtgaa gatgggctcg agctaggagc   13560
aagtgatttt atcgctaagc cgttcagtat cagagagttt ctagcacgca ttcgggttgc   13620
cttgcgcgtg cgccccaacg ttgtccgctc caaagaccga cggtcttttt gttttactga   13680
ctggacactt aatctcaggc aacgtcgctt gatgtccgaa gctggcggtg aggtgaaact   13740
tacggcaggt gagttcaatc ttctcctcgc gttttagag aaaccccgcg acgttctatc   13800
gcgcgagcaa cttctcattg ccagtcgagt acgcgacgag gaggtttatg acaggagtat   13860
agatgttctc attttgaggc tgcgccgcaa acttgaggca gatccgtcaa gccctcaact   13920
gataaaaaca gcaagaggtg ccggttattt ctttgacgcg gacgtgcagg tttcgcacgg   13980
ggggacgatg gcagcctgag ccaattccca gatccccgag aatcggcgt gagcggtcgc   14040 aaaccatccg gcccggtaca aatcggcgcg gcgctgggtg atgacctggt ggagaagttg   14100
aaggccgcgc aggccgccca gcggcaacgc atcgaggcag aagcacgccc cggtgaatcg   14160
tggcaagcgg ccgctgatcg aatccgcaaa gaatcccggc aaccgccggc agccggtgcg   14220
ccgtcgatta ggaagccgcc caagggcgac gagcaaccag attttttcgt tccgatgctc   14280
tatgacgtgg gcacccgcga tagtcgcagc atcatggacg tggccgtttt ccgtctgtcg   14340
aagcgtgacc gacgagctgg cgaggtgatc cgctacgagc ttccagacgg gcacgtagag   14400
gtttccgcag ggccggccgg catggccagt gtgtgggatt acgacctggt actgatggcg   14460
gtttcccatc taaccgaatc catgaaccga taccgggaag ggaagggaga caagcccggc   14520
cgcgtgttcc gtccacacgt tgcggacgta ctcaagttct gccggcgagc cgatggcgga   14580
aagcagaaag acgacctggt agaaacctgc attcggttaa acaccacgca cgttgccatg   14640
cagcgtacga agaaggccaa gaacggccgc ctggtgacgg tatccgaggg tgaagccttg   14700
attagccgct acaagatcgt aaagagcgaa accgggcggc cggagtacat cgagatcgag   14760
ctagctgatt ggatgtaccg cgagatcaca gaaggcaaga acccggacgt gctgacggtt   14820 cacccccgatt acttttttgat cgatcccggc atcggccgtt ttctctaccg cctggcacgc   14880
cgcgccgcag gcaaggcaga agccagatgg ttgttcaaga cgatctacga acgcagtggc   14940
agcgccggag agttcaagaa gttctgtttc accgtgcgca agctgatcgg gtcaaatgac   15000
ctgccggagt acgatttgaa ggaggaggcg gggcaggctg gcccgatcct agtcatgcgc   15060
taccgcaacc tgatcgaggg cgaagcatcc gccggttcct aatgtacgga gcagatgcta   15120
gggcaaattg ccctagcagg ggaaaaaggt cgaaaaggtc tctttcctgt ggatagcacg   15180 tacatttggga acccaaagcc gtacattggg aaccggaacc cgtacattgg gaacccaaag   15240
ccgtacattg gaaccggtc acacatgtaa gtgactgata taaaagagaa aaaaggcgat   15300
ttttccgcct aaaactcttt aaaacttatt aaaactctta aaaccgcct ggcctgtgca   15360 taactgtctg gccagcgcac agccgaagag ctgcaaaaag cgcctaccct tcggtcgctg   15420
cgctccctac gccccgccgc ttcgcgtcgg cctatcgcgg ccgctggccg ctcaaaaatg   15480
gctggcctac ggccaggcaa tctaccaggg cgcggacaag ccgcgccgtc gccactcgac   15540
cgccggcgct gaggtctgcc tcgtgaagaa ggtgttgctg actcatacca ggcctgaatc   15600
```

```
gccccatcat ccagccagaa agtgagggag ccacggttga tgagagcttt gttgtaggtg    15660
gaccagttgg tgattttgaa cttttgcttt gccacggaac ggtctgcgtt gtcgggaaga    15720
tgcgtgatct gatccttcaa ctcagcaaaa gttcgattta ttcaacaaag ccgccgtccc    15780
gtcaagtcag cgtaatgctc tgccagtgtt acaaccaatt aaccaattct gattagaaaa    15840
actcatcgag catcaaatga aactgcaatt tattcatatc aggattatca ataccatatt    15900
tttgaaaaag ccgtttctgt aatgaaggag aaaactcacc gaggcagttc cataggatgg    15960
caagatcctg gtatcggtct gcgattccga ctcgtccaac atcaatacaa cctattaatt    16020
tcccctcgtc aaaataagg ttatcaagtg agaaatcacc atgagtgacg actgaatccg    16080
gtgagaatgg caaaagctct gcattaatga atcggccaac gcgcggggag aggcggtttg    16140
cgtattgggc gctcttccgc ttcctcgctc actgactcgc tgcgctcggt cgttcggctg    16200
cggcgagcgg tatcagctca ctcaaaggcg gtaatacggt tatccacaga atcaggggat    16260
aacgcaggaa agaacatgtg agcaaaaggc cagcaaaagg ccaggaaccg taaaaaggcc    16320
gcgttgctgg cgtttttcca taggctccgc cccccctgacg agcatcacaa aaatcgacgc    16380
tcaagtcaga ggtggcgaaa cccgacagga ctataaagat accaggcgtt tcccccctgga    16440 agctccctcg tgcgctctcc tgttccgacc ctgccgctta ccggatacct gtccgccttt    16500
ctcccttcgg gaagcgtggc gctttctcat agctcacgct gtaggtatct cagttcggtg    16560
taggtcgttc gctccaagct gggctgtgtg cacgaacccc ccgttcagcc cgaccgctgc    16620
gccttatccg gtaactatcg tcttgagtcc aacccggtaa gacacgactt atcgccactg    16680
gcagcagcca ctggtaacag gattagcaga gcgaggtatg taggcggtgc tacagagttc    16740
ttgaagtggt ggcctaacta cggctacact agaagaacag tatttggtat ctgcgctctg    16800
ctgaagccag ttaccttcgg aaaaagagtt ggtagctctt gatccggcaa acaaaccacc    16860
gctggtagcg gtggtttttt tgtttgcaag cagcagatta cgcgcagaaa aaaggatct    16920 caagaagatc ctttgatctt ttctacgggg tctgacgctc agtggaacga aaactcacgt    16980
taagggattt tggtcatgag attatcaaaa aggatcttca cctagatcct tttgatccgg    17040
aatta                                                                17045
```

```
<210> SEQ ID NO 37
<211> LENGTH: 16776
<212> TYPE: DNA
<213> ORGANISM: artificial sequence
<220> FEATURE:
<223> OTHER INFORMATION: vector 24091
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (330)..(2417)
<223> OTHER INFORMATION: prZmGRMZM2G471240-01
<220> FEATURE:
<221> NAME/KEY: gene
<222> LOCATION: (2420)..(6589)
<223> OTHER INFORMATION: cCas9-01
<220> FEATURE:
<221> NAME/KEY: mutation
<222> LOCATION: (5909)..(5911)
<223> OTHER INFORMATION: L to V mutation
<220> FEATURE:
<221> NAME/KEY: mutation
<222> LOCATION: (5954)..(5956)
<223> OTHER INFORMATION: I to V mutation
<220> FEATURE:
<221> NAME/KEY: terminator
```

```
<222> LOCATION: (6596)..(7591)
<223> OTHER INFORMATION: tZmGRMZM2G471240-01
<220> FEATURE:
<221> NAME/KEY: promoter
<222> LOCATION: (7605)..(7979)
<223> OTHER INFORMATION: prOsU3-01
<220> FEATURE:
<221> NAME/KEY: misc_feature
<222> LOCATION: (7981)..(8085)
<223> OTHER INFORMATION: rsgRNAZmVLHP-02
<220> FEATURE:
<221> NAME/KEY: misc_feature
<222> LOCATION: (7981)..(8000)
<223> OTHER INFORMATION: xZmVLHP2
<220> FEATURE:
<221> NAME/KEY: misc_feature
<222> LOCATION: (8001)..(8012)
<223> OTHER INFORMATION: rCrRNA-01
<220> FEATURE:
<221> NAME/KEY: misc_feature
<222> LOCATION: (8017)..(8085)
<223> OTHER INFORMATION: rTracrRNA-01
<220> FEATURE:
<221> NAME/KEY: promoter
<222> LOCATION: (8096)..(10087)
<223> OTHER INFORMATION: prUbi1-04
<220> FEATURE:
<221> NAME/KEY: gene
<222> LOCATION: (10104)..(11282)
<223> OTHER INFORMATION: cPMI-09
<220> FEATURE:
<221> NAME/KEY: terminator
<222> LOCATION: (11305)..(11557)
<223> OTHER INFORMATION: tNOS-05-01
<220> FEATURE:
<221> NAME/KEY: misc_feature
<222> LOCATION: (11601)..(11730)
<223> OTHER INFORMATION: bNLB-03
<220> FEATURE:
<221> NAME/KEY: gene
<222> LOCATION: (12010)..(12798)
<223> OTHER INFORMATION: cSpec-03
<220> FEATURE:
<221> NAME/KEY: promoter
<222> LOCATION: (12893)..(13023)
<223> OTHER INFORMATION: prVirG-01
<220> FEATURE:
<221> NAME/KEY: gene
<222> LOCATION: (13098)..(13730)
<223> OTHER INFORMATION: cVirG-09
<220> FEATURE:
<221> NAME/KEY: gene
<222> LOCATION: (13760)..(14833)
<223> OTHER INFORMATION: cRepA-01
<220> FEATURE:
<221> NAME/KEY: misc_feature
<222> LOCATION: (14876)..(15280)
<223> OTHER INFORMATION: oVS1-02
<220> FEATURE:
<221> NAME/KEY: misc_feature
<222> LOCATION: (15958)..(16764)
<223> OTHER INFORMATION: oCOLE-06

<400> SEQUENCE: 37
attcctgtgg ttggcatgca catacaaatg gacgaacgga taaaccttt cacgccctt       60 taaatatccg attattctaa taaacgctct tttctcttag gtttacccgc caatatatcc    120
tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg gccattaaa caaagcttgg     300 tacctcgcga atgcatctag atgggaccct atttgtactc attccatgtc tcataaactt    360
tgggcaccat ccatccaaca catccaatct aaacacacca aacgatgggg aatggaaaga    420
```

```
gcagtattcg attcaacaat ggcaaacaaa tatcactgaa ttagaccaag aataaaccta        480
attagacaac gacctcccaa ccatcattcg tcaggctgta aagaagataa agctgccttg        540
gggcatggat caagcagaac accagagatg aatccaaaca cacagaaaat cacgcgcgct        600
gtctacaatg acaacaagcc ccacatttca ttgcagtaca ctgggctaca aaggcacgta        660
caacaaagag ctagggaaac attgcggagg gcacgagaga gcagctaact tgacaatata        720
gcagactgag cttgcactgt tagcaggcga ggaagggaat catggggacg agaatgggg        780 tccatgcccg cgaaggagaa ggcggacgcc gccacggtgg caccggcgca cgcgcacaca      840
gggaacccgc acaggcagcc aaggatgctg cctcgccatt cgccggtcg tctctgccac       900 gctcctctct ctctcccgct gcatcgccgt ggatggggca agcagagagc agggactgcg       960
acgatctggg cggaggactc gccttggaga gcgcggacgc agacgggatt ctagggagag      1020
agcgaagacg gggcgcgcgc ggcgctcgcg cggcgtggtg gcggcgagat tagcgggggt      1080
ggggggaggg cggagccgtg gtgagggtgt ggacgccctc cttaccctct taagtagtag      1140
tagagatata atccgttcca aaatatccat ccgttcaatt tatatttcgt ttgatctttt       1200
taccctaaat ttgattgact catcttatta aaaagttca taactattat taatctttat         1260
tgagatatca tttagcatat aatatacttt aagtgtggtt ttagattttt tttaaaaaaa        1320
aaaattcgca aaattaaat gaaacgaccc aatcaaactt gaaaagtaaa actaattata         1380
aatttgaacg gaaggagtaa gaggatgttt gaatgtacta gagctaatag ttggttgctt      1440
taaaatttgc tagtagaatt agctagctaa taaatatcta gataactatt agctaatttg       1500
ctaaaacagc taatagttga actattagct agattgtttg gatgtattcg gctaatttta       1560
atggctaact attagctata gtacaatatt caaacacctc ctaattaaaa tggacaaata      1620
tctcttcttt tggtcccttg cgttagattt ttcatatctc cttatttagt ataaaagaat       1680
catcaaaaag tggacaaccc ctagtggaac accattttag tagtggttgc atgaaacctt     1740
tcgcgcacca gtttctatgt gtcactctaa aaatgggaca gcatgtacgt agtgcctata      1800
tatatacaag tcatctatcg ttgcctcctc agttcatcac taatcacact tattgtgccc        1860
tcgacgagta tctatagcta gctcattaat cgattcgggg gtgtgttgtc gaaggcggca    1920
ttggcgagct actcgtcgcg gcgtccaagc aatacctgta gcacgaaggc gatcgccggg    1980
agcgtggtcg gcgagcccgt cgtgctgggg cagagggtga cggtgctgac ggtggacggc    2040
ggcggcgtcc ggggtctcat cccgggaacc atcctcgcct tcctggaggc caggctgcag    2100
gagctggacg caccggaggc gaggctggcg gactacttcg actacatcgc cggaaccagc    2160
accggcggtc tcatcaccgc cttgctgacc gcgcccggca aggacaagcg gcctctctag     2220
gctgccaagg acatcaacca cttttacatc cataactgcc cgcgcatctt tcctcagaag     2280
tgagtccgat gctgccgcca ttgttcttgc atccatccag catcgtacgt acgtcctcta       2340
tacatctgcg gatcatcatg tgcgcatgtt tgtggcatgc atgcatgcat gtgagcagga    2400
gcaggcttgc gaaaacccca tggacaagaa gtacagcatc ggcctggaca tcggcaccaa   2460
cagcgtgggc tgggccgtga tcaccgacga gtacaaggtg ccgagcaaga agttcaaggt    2520
gctgggcaac accgacaggc acagcatcaa gaagaacctg atcggcgccc tgctgttcga    2580
cagcggcgag accgccgagg ccaccaggct gaagaggacc gccaggagga ggtacaccag    2640
gaggaagaac aggatctgct acctgcagga gatcttcagc aacgagatgg ccaaggtgga   2700
cgacagcttc ttccacaggc tggaggagag cttcctggtg gaggaggaca agaagcacga    2760
gaggcacccg atcttcggca acatcgtgga cgaggtggcc taccacgaga agtacccgac    2820
```

```
catctaccac ctgaggaaga agctggtgga cagcaccgac aaggccgacc tgaggctgat  2880
ctacctggcc ctggcccaca tgatcaagtt caggggccac ttcctgatcg agggcgacct  2940
gaacccggac aacagcgacg tggacaagct gttcatccag ctggtgcaga cctacaacca  3000
gctgttcgag gagaacccga tcaacgccag cggcgtggac gccaaggcca tcctgagcgc  3060
caggctgagc aagagcagga ggctggagaa cctgatcgcc cagctgccgg gcgagaagaa  3120
gaacggcctg ttcggcaacc tgatcgccct gagcctgggc ctgacccga acttcaagag  3180
caacttcgac ctggccgagg acgccaagct gcagctgagc aaggacaccT acgacgacga  3240
cctggacaac ctgctggccc agatcggcga ccagtacgcc gacctgttcc tggccgccaa  3300
gaacctgagc gacgccatcc tgctgagcga catcctgagg gtgaacaccg agatcaccaa  3360
ggcccccgctg agcgccagca tgatcaagag gtacgacgag caccaccagg acctgaccct  3420
gctgaaggcc ctggtgaggc agcagctgcc ggagaagtac aaggagatct tcttcgacca  3480
gagcaagaac ggctacgccg ctacatcga cggcggcgcc agccaggagg agttctacaa  3540
gttcatcaag ccgatcctgg agaagatgga cggcaccgag gagctgctgg tgaagctgaa  3600
cagggaggac ctgctgagga agcagaggac cttcgacaac ggcagcatcc cgcaccagat  3660
ccacctgggc gagctgcacg ccatcctgag gaggcaggag gacttctacc cgttcctgaa  3720
ggacaacagg gagaagatcg agaagatcct gaccttccgc atcccgtact acgtgggccc  3780
gctggccagg ggcaacagca ggttcgcctg gatgaccagg aagagcgagg agaccatcac  3840
cccgtgaaac ttcgaggagg tggtggacaa gggcgccagc gcccagagct tcatcgagag  3900
gatgaccaac ttcgacaaga acctgccgaa cgagaaggtg ctgccgaagc acagcctgct  3960
gtacgagtac ttcaccgtgt acaacgagct gaccaaggtg aagtacgtga ccgagggcat  4020
gaggaagccg gccttcctga cggcgagca aagaaggcc atcgtggacc tgctgttcaa  4080
gaccaacagg aaggtgaccg tgaagcagct gaaggaggac tacttcaaga agatcgagtg  4140
cttcgacagc gtggagatca cgggcgtgga ggacaggttc aacgccagcc tgggcaccta  4200
ccacgacctg ctgaagatca tcaaggacaa ggacttcctg gacaacgagg agaacgagga  4260
catcctggag gacatcgtgc tgaccctgac cctgttcgag gacagggaga tgatcgagga  4320
gaggctgaag acctacgccc acctgttcga cgacaaggtg atgaagcagc tgaagaggag  4380
gaggtacacc ggctggggca ggctgagcag gaagctgatc aacggcatca gggacaagca  4440
gagcggcaag accatcctgg acttcctgaa gagcgacggc ttcgccaaca ggaacttcat  4500
gcagctgatc cacgacgaca gcctgacctt caaggaggac atccagaagg cccaggtgag  4560
cggccagggc gacagcctgc acgagcacat cgccaacctg gccggcagcc cggccatcaa  4620
gaagggcatc ctgcagaccg tgaaggtggt ggacgagctg gtgaaggtga tgggcaggca  4680
caagccggag aacatcgtga tcgagatggc cagggagaac cagaccaccc agaagggcca  4740
gaagaacagc agggagagga tgaagaggat cgaggagggc atcaaggagc tgggcagcca  4800
gatcctgaag gagcacccgg tggagaacac ccagctgcag aacgagaagc tgtacctgta  4860
ctacctgcag aacggcaggg acatgtacgt ggaccaggag ctggacatca acaggctgag  4920
cgactacgac gtggaccaca tcgtgccgca gagcttcctg aaggacgaca gcatcgacaa  4980
caaggtgctg accaggagcg acaagaacag gggcaagagc gacaacgtgc cgagcgagga  5040
ggtggtgaag aagatgaaaa actactggag gcagctgctg aacgccaagc tgatcaccca  5100
gaggaagttc gacaacctga ccaaggccga gaggggcggc ctgagcgagc tggacaaggc  5160
```

```
cggcttcatt aaaaggcagc tggtggagac caggcagatc accaagcacg tggcccagat    5220
cctggacagc aggatgaaca ccaagtacga cgagaacgac aagctgatca gggaggtgaa    5280
ggtgatcacc ctgaagagca agctggtgag cgacttcagg aaggacttcc agttctacaa    5340
ggtgagggag atcaataatt accaccacgc ccacgacgcc tacctgaacg ccgtggtggg    5400
caccgccctg attaaaaagt acccgaagct ggagagcgag ttcgtgtacg cgactacaa     5460 ggtgtacgac gtgaggaaga tgatcgccaa gagcgagcag gagatcggca aggccaccgc    5520
caagtacttc ttctacagca acatcatgaa cttcttcaag accgagatca ccctggccaa    5580
cggcgagatc aggaagaggc cgctgatcga gaccaacggc gagaccggcg agatcgtgtg    5640
ggacaagggc agggacttcg ccaccgtgag gaaggtgctg tccatgccgc aggtgaacat    5700
cgtgaagaag accgaggtgc agaccggcgg cttcagcaag gagagcatcc tgccgaagag    5760
gaacagcgac aagctgatcg ccaggaagaa ggactgggac ccgaagaagt acggcggctt    5820
cgacagcccg accgtggcct acagcgtgct ggtggtggcc aaggtggaga agggcaagag    5880
caagaagctg aagagcgtga aggagctggt ggcatcacc atcatggaga ggagcagctt    5940
cgagaagaac ccagtggact tcctggaggc caagggctac aaggaggtga agaaggacct    6000
gatcattaaa ctgccgaagt acagcctgtt cgagctggag aacggcagga gaggatgct    6060 ggccagcgcc ggcgagctgc agaagggcaa cgagctggcc ctgccgagca agtacgtgaa    6120
cttcctgtac ctggccagcc actacgaaga gctgaagggc agcccggagg acaacgagca    6180
gaagcagctg ttcgtggagc agcacaagca ctacctggac gagatcatcg agcagatcag    6240
cgagttcagc aagagggtga tcctggccga cgccaacctg gacaaggtgc tgagcgccta    6300
caacaagcac agggacaagc cgatcaggga gcaggccgag aacatcatcc acctgttcac    6360
cctgaccaac ctgggcgccc cggccgcctt caagtacttc gacaccacca tcgacaggaa    6420
gaggtacacc agcaccaagg aggtgctgga cgccaccctg atccaccaga gcatcaccgg    6480
cctgtacgag accaggatcg acctgagcca gctgggcggc gacagcagcc cgccgaagaa    6540
gaagaggaag gtgagctgga aggacgccag cggctggagc aggatgtgac catgggacaa    6600
gtggctttac tgtcagtcac atgcttgtaa ataagtagac tttatttaa taaaacataa     6660 aaatatatat atgttcttga atataaaatt gataaccaaa ttaaaattcg aaccatcact    6720
tatacataat tttactttat tttttataaa acgtgaacgg gaaggactac cgtgaatgac    6780
tatagaacca atcatactag tataaaatat atgatgacac tacgggagag acaaactttg    6840
tctggcgcta atattttgc cgagtgtgaa ttcacgggca ctaggcaaag atcttcttg      6900 ccgagtgtta cgctgggcaa agtaagacac taggtaaatc agtcatttgc cgagtgtccg    6960
ccactaggca aagcaaaaca ctggcaaatc aaaagtttac ctagtgccag acactaggca    7020
aaaaaaaaac gctcggcaaa tcggaagttt ccctagtgcc agacactaga caagaaaaa     7080 cacttgataa actagcgtcg tcagctaaca ccatccacca accgttaacg ttgccgagta    7140
tctgacttcg acactcggca agaaggtct ctttgcctag tgtcggtctg aacactagg      7200 caaagaggca cttacctag tgtcgtattt tgacactcag taaaataatt ttttttcttt     7260
ctgcttccaa acttttatg atgtgttcct atagcaccta gaactacatg tcaagttttg     7320
gtaaaatttt tgaagttttt gctatattta cttaattat ttattaat tgaatttctt       7380 ttgataattc aaatttgaac tcggcaaggt aagaagcgag ggtagcctgg aaacacactt    7440
tgcctagtgt tacactcggt acaggagcct ccctgccta gtgctgcact cgacaaaaga    7500
ttcgcctttg cctagcgctg cactcggcac aggagtcgcc tttgcctagt gctgcactag    7560
```

```
gcaaagcctc cgttaccgtg ccttccatcg tcggacccct cgaagggatc tttaaacata    7620
cgaacagatc acttaaagtt cttctgaagc aacttaaagt tatcaggcat gcatggatct    7680
tggaggaatc agatgtgcag tcagggacca tagcacagga caggcgtctt ctactggtgc    7740
taccagcaaa tgctggaagc cgggaacact gggtacgttg aaaccacgt gatgtggagt     7800 aagataaact gtaggagaaa agcatttcgt agtgggccat gaagcctttc aggacatgta    7860
ttgcagtatg ggccggccca ttacgcaatt ggacgacaac aaagactagt attagtacca    7920
cctcggctat ccacatagat caaagctggt ttaaagagt tgtgcagatg atccgtggca     7980
gctggagctg agcttccggg gttttagagc tagaaatagc aagttaaaat aaggctagtc    8040
cgttatcaac ttgaaaaagt ggcaccgagt cggtgctttt tttttcggac cgcgcctgca    8100
gtgcagcgtg acccggtcgt gcccctctct agagataatg agcattgcat gtctaagtta    8160
taaaaaatta ccacatattt ttttgtcac acttgtttga agtgcagttt atctatcttt     8220
atacatatat ttaaactta ctctacgaat aatataatct atagtactac aataatatca     8280
gtgttttaga gaatcatata aatgaacagt tagacatggt ctaaaggaca attgagtatt    8340
ttgacaacag gactctacag ttttatcttt ttagtgtgca tgtgttctcc tttttttttg    8400
caaatagctt cacctatata atacttcatc cattttatta gtacatccat ttagggttta    8460
gggttaatgg tttttataga ctaattttt tagtacatct attttattct attttagcct     8520
ctaaattaag aaaactaaaa ctctatttta gtttttttat ttaataattt agatataaaa    8580
tagaataaaa taaagtgact aaaaattaaa caaatacccct ttaagaaatt aaaaaaacta   8640
aggaaacatt tttcttgttt cgagtagata atgccagcct gttaaacgcc gtcgacgagt    8700
ctaacggaca ccaaccagcg aaccagcagc gtcgcgtcgg gccaagcgaa gcagacggca    8760
cggcatctct gtcgctgcct ctggaccccct ctcgagagtt ccgctccacc gttggacttg   8820
ctccgctgtc ggcatccaga aattgcgtgg cggagcggca gacgtgagcc ggcacggcag    8880
gcggcctcct cctcctctca cggcaccggc agctacgggg gattcctttc ccaccgctcc    8940
ttcgctttcc cttcctcgcc cgccgtaata aatagacacc ccctccacac cctctttccc    9000
caacctcgtg ttgttcggag cgcacacaca cacaaccaga tctcccccaa atccacccgt    9060
cggcacctcc gcttcaaggt acgccgctcg tcctccccccc cccccctctc taccttctct    9120
agatcggcgt tccggtccat ggttagggcc cggtagttct acttctgttc atgtttgtgt    9180
tagatccgtg tttgtgttag atccgtgctg ctagcgttcg tacacggatg cgacctgtac    9240
gtcagacacg ttctgattgc taacttgcca gtgtttctct ttggggaatc ctgggatggc    9300
tctagccgtt ccgcagacgg gatcgatttc atgattttt ttgtttcgtt gcatagggtt     9360
tggtttgccc ttttccttta tttcaatata tgccgtgcac ttgtttgtcg ggtcatcttt    9420
tcatgctttt ttttgtcttg gttgtgatga tgtggtctgg ttgggcggtc gttctagatc    9480
ggagtagaat tctgtttcaa actacctggt ggatttatta attttggatc tgtatgtgtg    9540
tgccatacat attcatagtt acgaattgaa gatgatggat ggaaatatcg atctaggata    9600
ggtatacatg ttgatgcggg ttttactgat gcatatacag agatgctttt tgttcgcttg    9660
gttgtgatga tgtggtgtgg ttgggcggtc gttcattcgt tctagatcgg agtagaatac    9720
tgtttcaaac tacctggtgt atttattaat tttggaactg tatgtgtgtg tcatacatct    9780
tcatagttac gagtttaaga tggatggaaa tatcgatcta ggataggtat acatgttgat    9840
gtgggtttta ctgatgcata tacatgatgg catatgcagc atctattcat atgctctaac    9900
```

```
cttgagtacc tatctattat aataaacaag tatgttttat aattattttg atcttgatat     9960
acttggatga tggcatatgc agcagctata tgtggatttt tttagccctg ccttcatacg    10020
ctatttattt gcttggtact gtttcttttg tcgatgctca ccctgttgtt tggtgttact    10080
tctgcaggga tccggcagca gccatgcaga agctgatcaa cagcgtgcag aactacgcct    10140
ggggcagcaa gaccgccctg accgagctgt acggcatgga gaaccccagc agccagccca    10200
tggccgagct gtggatgggc gcccacccca gagcagcag ccgcgtgcag aacgccgccg     10260
gcgacatcgt gagcctgcgc gacgtgatcg agagcgacaa gagcaccctg ctgggcgagg    10320
ccgtggccaa gcgcttcggc gagctgccct tcctgttcaa ggtgctgtgc gccgcccagc    10380
ccctgagcat ccaggtgcac cccaacaagc acaacagcga gatcggcttc gccaaggaga    10440
acgccgccgg catccccatg gacgccgccg agcgcaacta caaggacccc aaccacaagc    10500
ccgagctggt gttcgccctg acccccttcc tggccatgaa cgccttccgc gagttcagcg    10560
agatcgtgag cctgctgcag cccgtggccg gcgcccaccc cgccatcgcc cacttcctgc    10620
agcagcccga cgccgagcgc ctgagcgagc tgttcgccag cctgctgaac atgcaggggcg   10680
aggagaagag ccgcgccctg gccatcctga gagcgccct ggacagccag cagggcgagc     10740
cctggcagac catccgcctg atcagcgagt tctaccccga ggacagcggc ctgttcagcc    10800
ccctgctgct gaacgtggtg aagctgaacc ccggcgaggc catgttcctg ttcgccgaga    10860
ccccccacgc ctacctgcag ggcgtggccc tggaggtgat ggccaacagc gacaacgtgc    10920
tgcgcgccgg cctgaccccc aagtacatcg acatccccga gctggtggcc aacgtgaagt    10980
tcgaggccaa gcccgccaac cagctgctga cccagcccgt gaagcagggc gccgagctgg    11040
acttccccat ccccgtggac gacttcgcct tcagcctgca cgacctgagc gacaaggaga    11100
ccaccatcag ccagcagagc gccgccatcc tgttctgcgt ggagggcgac gccaccctgt    11160
ggaagggcag ccagcagctg cagctgaagc ccggcgagag cgccttcatc gccgccaacg    11220
agagccccgt gaccgtgaag ggccacggcc gcctggcccg cgtgtacaac aagctgtgat    11280
aggagctcga tccgtcgacc tgcagatcgt tcaaacattt ggcaataaag tttcttaaga    11340
ttgaatcctg ttgccggtct tgcgatgatt atcatataat ttctgttgaa ttacgttaag    11400
catgtaataa ttaacatgta atgcatgacg ttatttatga gatgggtttt tatgattaga    11460
gtcccgcaat tatacattta atacgcgata gaaaacaaaa tatagcgcgc aaactaggat    11520
aaattatcgc gcgcggtgtc atctatgtta ctagatcggc gcgccgcaat tgaagtttgg    11580
gcggccagca tggccgtatc cgcaatgtgt tattaagttg tctaagcgtc aatttgttta    11640
caccacaata tatcctgcca ccagccagcc aacagctccc cgaccggcag ctcggcacaa    11700
aatcaccact cgatacaggc agcccatcag aattaattct catgtttgac agcttatcat    11760
cgactgcacg gtgcaccaat gcttctggcg tcaggcagcc atcggaagct gtggtatggc    11820
tgtgcaggtc gtaaatcact gcataattcg tgtcgctcaa ggcgcactcc cgttctggat    11880
aatgtttttt gcgccgacat cataacggtt ctggcaaata ttctgaaatg agctgttgac    11940
aattaatcat ccggctcgta taatgtgtgg aattgtgagc ggataacaat ttcacacagg    12000
aaacagacca tgagggaagc gttgatcgcc gaagtatcga ctcaactatc agaggtagtt    12060
ggcgtcatcg agcgccatct cgaaccgacg ttgctggccg tacatttgta cggctccgca    12120
gtggatggcg gcctgaagcc acacagtgat attgatttgc tggttacggt gaccgtaagg    12180
cttgatgaaa caacgcggcg agctttgatc aacgaccttt tggaaacttc ggcttcccct    12240
ggagagagcg agattctccg cgctgtagaa gtcaccattg ttgtgcacga cgacatcatt    12300
```

```
ccgtggcgtt atccagctaa gcgcgaactg caatttggag aatggcagcg caatgacatt    12360
cttgcaggta tcttcgagcc agccacgatc gacattgatc tggctatctt gctgacaaaa    12420
gcaagagaac atagcgttgc cttggtaggt ccagcggcgg aggaactctt tgatccggtt    12480
cctgaacagg atctatttga ggcgctaaat gaaaccttaa cgctatggaa ctcgccgccc    12540
gactgggctg gcgatgagcg aaatgtagtg cttacgttgt cccgcatttg gtacagcgca    12600
gtaaccggca aaatcgcgcc gaaggatgtc gctgccgact gggcaatgga gcgcctgccg    12660
gcccagtatc agcccgtcat acttgaagct aggcaggctt atcttggaca agaagatcgc    12720
ttggcctcgc gcgcagatca gttggaagaa tttgttcact acgtgaaagg cgagatcacc    12780
aaagtagtcg gcaaataaag ctctagtgga tctccgtacc cggggatctg gctcgcggcg    12840
gacgcacgac gccggggcga gaccataggc gatctcctaa atcaatagta gctgtaacct    12900
cgaagcgttt cacttgtaac aacgattgag aattttgtc ataaaattga aatacttggt     12960
tcgcattttt gtcatccgcg gtcagccgca attctgacga actgcccatt tagctggaga    13020
tgattgtaca tccttcacgt gaaaatttct caagcgctgt gaacaagggt tcagatttta    13080
gattgaaagg tgagccgttg aaacacgttc ttcttgtcga tgacgacgtc gctatgcggc    13140
atcttattat tgaataccttt acgatccacg ccttcaaagt gaccgcggta gccgacagca    13200
cccagttcac aagagtactc tcttccgcga cggtcgatgt cgtggttgtt gatctagatt    13260
taggtcgtga agatgggctc gagctaggag caagtgattt tatcgctaag ccgttcagta    13320
tcagagagtt tctagcacgc attcggggtg ccttgcgcgt gcgccccaac gttgtccgct    13380
ccaaagaccg acggtctttt tgttttactg actggacact taatctcagg caacgtcgct    13440
tgatgtccga agctggcggt gaggtgaaac ttacggcagg tgagttcaat cttctcctcg    13500
cgttttttaga gaaaccccgc gacgttctat cgcgcgagca acttctcatt gccagtcgag    13560
tacgcgacga ggaggtttat gacaggagta tagatgttct cattttgagg ctgcgccgca    13620
aacttgaggc agatccgtca agccctcaac tgataaaaac agcaagaggt gccggttatt    13680
tctttgacgc ggacgtgcag gtttcgcacg gggggacgat ggcagcctga gccaattccc    13740
agatccccga ggaatcggcg tgagcggtcg caaaccatcc ggcccggtac aaatcggcgc    13800
ggcgctgggt gatgacctgg tggagaagtt gaaggccgcg caggccgccc agcggcaacg    13860
catcgaggca gaagcacgcc ccggtgaatc gtggcaagcg gccgctgatc gaatccgcaa    13920
agaatcccgg caaccgccgg cagccggtgc gccgtcgatt aggaagccgc caagggcga    13980
cgagcaacca gatttttttcg ttccgatgct ctatgacgtg gcacccgcg atagtcgcag     14040
catcatggac gtggccgttt ccgtctgtc gaagcgtgac cgacgagctg gcgaggtgat      14100
ccgctacgag cttccagacg ggcacgtaga ggtttccgca gggccggccg gcatggccag    14160
tgtgtgggat tacgacctgg tactgatggc ggtttcccat ctaaccgaat ccatgaaccg    14220
ataccgggaa gggaagggag acaagcccgg ccgcgtgttc cgtccacacg ttgcggacgt    14280
actcaagttc tgccggcgag ccgatggcgg aaagcagaaa gacgacctgg tagaaacctg    14340
cattcggtta aacaccacgc acgttgccat gcagcgtacg aagaaggcca agaacggccg    14400
cctggtgacg gtatccgagg gtgaagcctt gattagccgc tacaagatcg taaagagcga    14460
aaccgggcgg ccggagtaca tcgagatcga gctagctgat tggatgtacc gcgagatcac    14520
agaaggcaag aacccggacg tgctgacggt tcacccgat tacttttga tcgatccgg        14580
catcggccgt tttctctacc gcctggcacg ccgcgccgca ggcaaggcag aagccagatg    14640
```

```
gttgttcaag acgatctacg aacgcagtgg cagcgccgga gagttcaaga agttctgttt    14700
caccgtgcgc aagctgatcg ggtcaaatga cctgccggag tacgatttga aggaggaggc    14760
ggggcaggct ggcccgatcc tagtcatgcg ctaccgcaac ctgatcgagg gcgaagcatc    14820
cgccggttcc taatgtacgg agcagatgct agggcaaatt gccctagcag gggaaaaagg    14880
tcgaaaaggt ctcttttcctg tggatagcac gtacattggg aacccaaagc cgtacattgg    14940
gaaccggaac ccgtacattg gaacccaaa gccgtacatt gggaaccggt cacacatgta     15000
agtgactgat ataaaagaga aaaaggcga ttttccgcc taaaactctt taaaacttat      15060
taaaactctt aaaacccgcc tggcctgtgc ataactgtct ggccagcgca cagccgaaga    15120
gctgcaaaaa gcgcctaccc ttcggtcgct gcgctcccta cgccccgccg cttcgcgtcg    15180
gcctatcgcg gccgctggcc gctcaaaaat ggctggccta cggccaggca atctaccagg    15240
gcgcggacaa gccgcgccgt cgccactcga ccgccggcgc tgaggtctgc ctcgtgaaga    15300
aggtgttgct gactcatacc aggcctgaat cgccccatca tccagccaga agtgaggga    15360 gccacggttg atgagagctt tgttgtaggt ggaccagttg gtgattttga acttttgctt    15420
tgccacggaa cggtctgcgt tgtcgggaag atgcgtgatc tgatccttca actcagcaaa    15480
agttcgattt attcaacaaa gccgccgtcc cgtcaagtca gcgtaatgct ctgccagtgt    15540
tacaaccaat taaccaattc tgattagaaa aactcatcga gcatcaaatg aaactgcaat    15600
ttattcatat caggattatc aataccatat ttttgaaaaa gccgtttctg taatgaagga    15660
gaaaactcac cgaggcagtt ccataggatg gcaagatcct ggtatcggtc tgcgattccg    15720
actcgtccaa catcaataca acctattaat ttcccctcgt caaaaataag gttatcaagt    15780
gagaaatcac catgagtgac gactgaatcc ggtgagaatg gcaaaagctc tgcattaatg    15840
aatcggccaa cgcgcgggga gaggcggttt gcgtattggg cgctcttccg cttcctcgct    15900
cactgactcg ctgcgctcgg tcgttcggct gcggcgagcg gtatcagctc actcaaaggc    15960
ggtaatacgg ttatccacag aatcagggga taacgcagga agaacatgt gagcaaaagg    16020 ccagcaaaag gccaggaacc gtaaaaaggc cgcgttgctg gcgttttccc ataggctccg    16080
cccccctgac gagcatcaca aaaatcgacg ctcaagtcag aggtggcgaa acccgacagg    16140
actataaaga taccaggcgt ttccccctgg aagctccctc gtgcgctctc ctgttccgac    16200
cctgccgctt accggatacc tgtccgcctt tctcccttcg ggaagcgtgg cgctttctca    16260
tagctcacgc tgtaggtatc tcagttcggt gtaggtcgtt cgctccaagc tgggctgtgt    16320
gcacgaaccc cccgttcagc ccgaccgctg cgccttatcc ggtaactatc gtcttgagtc    16380
caacccggta agacacgact tatcgccact ggcagcagcc actggtaaca ggattagcag    16440
agcgaggtat gtaggcggtg ctacagagtt cttgaagtgg tggcctaact acggctacac    16500
tagaagaaca gtatttggta tctgcgctct gctgaagcca gttaccttcg gaaaaagagt    16560
tggtagctct tgatccggca acaaaccac cgctggtagc ggtggttttt ttgtttgcaa    16620
gcagcagatt acgcgcagaa aaaaggatc tcaagaagat cctttgatct tttctacggg    16680
gtctgacgct cagtggaacg aaaactcacg ttaagggatt ttggtcatga gattatcaaa    16740
aaggatcttc acctagatcc ttttgatccg gaatta                              16776
```

<210> SEQ ID NO 38
<211> LENGTH: 17475
<212> TYPE: DNA
<213> ORGANISM: Artificial Sequence
<220> FEATURE:
<223> OTHER INFORMATION: vector 24094

```
<220> FEATURE:
<221> NAME/KEY: misc_feature
<222> LOCATION: (4)..(259)
<223> OTHER INFORMATION: bNRB-05
<220> FEATURE:
<221> NAME/KEY: promoter
<222> LOCATION: (330)..(2417)
<223> OTHER INFORMATION: prZmGRMZM2G471240-01
<220> FEATURE:
<221> NAME/KEY: gene
<222> LOCATION: (2420)..(7288)
<223> OTHER INFORMATION: cAmCyanCas9-01
<220> FEATURE:
<221> NAME/KEY: terminator
<222> LOCATION: (7295)..(8290)
<223> OTHER INFORMATION: tZmGRMZM2G471240-01
<220> FEATURE:
<221> NAME/KEY: promoter
<222> LOCATION: (8304)..(8678)
<223> OTHER INFORMATION: prOsU3-01
<220> FEATURE:
<221> NAME/KEY: misc_feature
<222> LOCATION: (8679)..(8784)
<223> OTHER INFORMATION: rsgRNAZmVLHP-02
<220> FEATURE:
<221> NAME/KEY: misc_feature
<222> LOCATION: (8680)..(8699)
<223> OTHER INFORMATION: ZmVLHP2 target
<220> FEATURE:
<221> NAME/KEY: misc_feature
<222> LOCATION: (8700)..(8711)
<223> OTHER INFORMATION: rCrRNA-01
<220> FEATURE:
<221> NAME/KEY: misc_feature
<222> LOCATION: (8716)..(8784)
<223> OTHER INFORMATION: rTracrRNA-01
<220> FEATURE:
<221> NAME/KEY: promoter
<222> LOCATION: (8795)..(10786)
<223> OTHER INFORMATION: prUbi1-04
<220> FEATURE:
<221> NAME/KEY: gene
<222> LOCATION: (10803)..(11981)
<223> OTHER INFORMATION: cPMI-09
<220> FEATURE:
<221> NAME/KEY: terminator
<222> LOCATION: (12004)..(12256)
<223> OTHER INFORMATION: tNOS-05-01
<220> FEATURE:
<221> NAME/KEY: misc_feature
<222> LOCATION: (12300)..(12429)
<223> OTHER INFORMATION: bNLB-03
<220> FEATURE:
<221> NAME/KEY: gene
<222> LOCATION: (12709)..(13497)
<223> OTHER INFORMATION: cSpec-03
<220> FEATURE:
<221> NAME/KEY: promoter
<222> LOCATION: (13592)..(13722)
<223> OTHER INFORMATION: prVirG-01
<220> FEATURE:
<221> NAME/KEY: gene
<222> LOCATION: (13797)..(14429)
<223> OTHER INFORMATION: cVirG-09
<220> FEATURE:
<221> NAME/KEY: gene
<222> LOCATION: (14459)..(15532)
<223> OTHER INFORMATION: cRepA-01
<220> FEATURE:
<221> NAME/KEY: misc_feature
<222> LOCATION: (15575)..(15979)
<223> OTHER INFORMATION: oVS1-02
<220> FEATURE:
<221> NAME/KEY: misc_feature
<222> LOCATION: (16657)..(17463)
<223> OTHER INFORMATION: oCOLE-06

<400> SEQUENCE: 38
```

```
attcctgtgg ttggcatgca catacaaatg gacgaacgga taaaccttt cacgcccttt    60 taaatatccg attattctaa taaacgctct tttctcttag gtttacccgc caatatatcc   120
tgtcaaacac tgatagttta aactgaaggc gggaaacgac aatctgatca tgagcggaga   180
attaagggag tcacgttatg accccgccg atgacgcggg acaagccgtt ttacgtttgg    240
aactgacaga accgcaacgc tgcaggaatt ggccgcagcg gccatttaaa caaagcttgg   300
tacctcgcga atgcatctag atgggaccct atttgtactc attccatgtc tcataaactt   360
tgggcaccat ccatccaaca catccaatct aaacacacca aacgatgggg aatggaaaga   420
gcagtattcg attcaacaat ggcaaacaaa tatcactgaa ttagaccaag aataaaccta   480
attagacaac gacctcccaa ccatcattcg tcaggctgta aagaagataa agctgccttg   540
gggcatggat caagcagaac accagagatg aatccaaaca cacagaaaat cacgcgcgct   600
gtctacaatg acaacaagcc ccacatttca ttgcagtaca ctgggctaca aaggcacgta   660
caacaaagag ctagggaaac attgcggagg cacgagaga gcagctaact tgacaatata    720
gcagactgag cttgcactgt tagcaggcga ggaagggaat catggggacg gagaatgggg   780
tccatgcccg cgaaggagaa ggcggacgcc gccacggtgg caccggcgca cgcgcacaca   840
gggaacccgc acaggcagcc aaggatgctg cctcgccatt gcgccggtcg tctctgccac   900
gctcctctct ctctcccgct gcatcgccgt ggatgggca agcagagagc agggactgcg    960
acgatctggg cggaggactc gccttggaga gcgcggacgc agacgggatt ctagggagag  1020
agcgaagacg gggcgcgcgc ggcgctcgcg cggcgtggtg gcggcgagat tagcggggt   1080 gggggggaggg cggagccgtg gtgagggtgt ggacgccctc cttaccctct taagtagtag  1140
tagagatata atccgttcca aaatatccat ccgttcaatt tatatttcgt ttgatctttt   1200
taccctaaat ttgattgact catcttatta aaaagttca taactattat taatctttat   1260
tgagatatca tttagcatat aatatacttt aagtgtggtt ttagatttt tttaaaaaa    1320 aaaattcgca aaaattaaat gaaacgaccc aatcaaactt gaaagtaaa actaattata   1380 aatttgaacg gaaggagtaa gaggatgttt gaatgtacta gagctaatag ttggttgctt  1440
taaaatttgc tagtagaatt agctagctaa taaatatcta gataactatt agctaatttg   1500
ctaaaacagc taatagttga actattagct agattgtttg gatgtattcg gctaatttta  1560
atggctaact attagctata gtacaatatt caaacacctc ctaattaaaa tggacaaata   1620
tctcttcttt tggtccctg cgttagattt ttcatatctc cttatttagt ataaaagaat   1680
catcaaaaag tggacaaccc ctagtggaac accattttag tagtggttgc atgaaacctt   1740
tcgcgcacca gtttctatgt gtcactctaa aaatgggaca gcatgtacgt agtgcctata   1800
tatatacaag tcatctatcg ttgcctcctc agttcatcac taatcacact tattgtgccc   1860
tcgacgagta tctatagcta gctcattaat cgattcgggg gtgtgttgtc gaaggcggca   1920
ttggcgagct actcgtcgcg gcgtccaagc aatacctgta gcacgaaggc gatcgccggg   1980
agcgtggtcg gcgagcccgt cgtgctgggg cagagggtga cggtgctgac ggtggacggc  2040
ggcggcgtcc ggggtctcat cccgggaacc atcctcgcct tcctggaggc caggctgcag   2100
gagctggacg caccggaggc gaggctggcg gactacttcg actacatcgc cggaaccagc   2160
accggcggtc tcatcaccgc cttgctgacc gcgcccggca aggacaagcg gcctctctag   2220
gctgccaagg acatcaacca ctttacatc cataactgcc cgcgcatctt tcctcagaag   2280
tgagtccgat gctgccgcca ttgttcttgc atccatccag catcgtacgt acgtcctcta   2340
tacatctgcg gatcatcatg tgcgcatgtt tgtggcatgc atgcatgcat gtgagcagga   2400
```

```
gcaggcttgc gaaaacccca tggccctgtc caacaagttc atcggcgacg acatgaagat   2460
gacctaccac atggacggct gcgtgaacgg ccactacttc accgtgaagg gcagggcag    2520
cggcaagccc tacgagggca cccagacctc caccttcaag gtgaccatgg ccaacggcgg   2580
cccctggcc ttctccttcg acatcctgtc caccgtgttc atgtacgca accgctgctt     2640
caccgcctac cccaccagca tgcccgacta cttcaagcag gccttccccg acggcatgtc   2700
ctacgagaga accttcacct acgaggacgg cggcgtggcc accgccagct gggagatcag   2760
cctgaagggc aactgcttcg agcacaagtc caccttccac ggcgtgaact tccccgccga   2820
cggcccccgtg atggccaaga agaccaccgg ctgggacccc tccttcgaga agatgaccgt  2880
gtgcgacggc atcttgaagg gcgacgtgac cgccttcctg atgctgcagg gcggcggcaa   2940
ctacagatgc cagttccaca cctcctacaa gaccaagaag cccgtgacca tgccccccaa   3000
ccacgtggtg gagcaccgca tcgccagaac cgacctggac aagggcggca acagcgtgca   3060
gctgaccgag cacgccgtgg cccacatcac ctccgtggtg cccttcggcg gcggcggatc   3120
cgacaagaag tacagcatcg gcctggacat cggcaccaac agcgtgggct gggccgtgat   3180
caccgacgag tacaaggtgc cgagcaagaa gttcaaggtg ctgggcaaca ccgacaggca   3240
cagcatcaag aagaacctga tcggcgccct gctgttcgac agcggcgaga ccgccgaggc   3300
caccaggctg aagaggaccg ccaggaggag gtacaccagg aggaagaaca ggatctgcta   3360
cctgcaggag atcttcagca cgagatggc caaggtggac gacagcttct ccacaggct    3420
ggaggagagc ttcctggtgg aggaggacaa gaagcacgag aggcacccga tcttcggcaa   3480
catcgtggac gaggtggcct accacgagaa gtacccgacc atctaccacc tgaggaagaa   3540
gctggtggac agcaccgaca aggccgacct gaggctgatc tacctggccc tggcccacat   3600
gatcaagttc aggggccact tcctgatcga gggcgacctg aacccggaca cagcgacgt    3660
ggacaagctg ttcatccagc tggtgcagac ctacaaccag ctgttcgagg agaacccgat   3720
caacgccagc ggcgtggacg ccaaggccat cctgagcgcc aggctgagca agagcaggag   3780
gctggagaac ctgatcgccc agctgccggg cgagaagaag aacggcctgt tcggcaacct   3840
gatcgccctg agcctgggcc tgacccgcaa cttcaagagc aacttcgacc tggccgagga   3900
cgccaagctg cagctgagca aggacaccta cgacgacgac ctggacaacc tgctggccca   3960
gatcggcgac cagtacgccg acctgttcct ggccgccaag aacctgagcg acgccatcct   4020
gctgagcgac atcctgaggg tgaacaccga gatcaccaag gccccgctga cgccagcat    4080
gatcaagagg tacgacgagc accaccagga cctgaccctg ctgaaggccc tggtgaggca   4140
gcagctgccg gagaagtaca aggagatctt cttcgaccag agcaagaacg gctacgccgg   4200
ctacatcgac ggcggcgcca gccaggagga gttctacaag ttcatcaagc cgatcctgga   4260
gaagatggac ggcaccgagg agctgctggt gaagctgaac agggaggacc tgctgaggaa   4320
gcagaggacc ttcgacaacg gcagcatccc gcaccagatc cacctgggcg agctgcacgc   4380
catcctgagg aggcaggagg acttctaccc gttcctgaag gacaacaggg agaagatcga   4440
gaagatcctg accttccgca tcccgtacta cgtgggcccg ctggccaggg gcaacagcag   4500
gttcgcctgg atgaccagga agagcgagga gaccatcacc ccgtggaact tcgaggaggt   4560
ggtggacaag ggcgccagcg cccagagctt catcgagagg atgaccaact tcgacaagaa   4620
cctgccgaac gagaaggtgc tgccgaagca cagcctgctg tacgagtact tcaccgtgta   4680
caacgagctg accaaggtga agtacgtgac cgagggcatg aggaagccgg ccttcctgag   4740
```

```
cggcgagcag aagaaggcca tcgtggacct gctgttcaag accaacagga aggtgaccgt    4800
gaagcagctg aaggaggact acttcaagaa gatcgagtgc ttcgacagcg tggagatcag    4860
cggcgtggag gacaggttca acgccagcct gggcacctac cacgacctgc tgaagatcat    4920
caaggacaag gacttcctgg acaacgagga gaacgaggac atcctggagg acatcgtgct    4980
gaccctgacc ctgttcgagg acaggagat gatcgaggag aggctgaaga cctacgccca    5040
cctgttcgac gacaaggtga tgaagcagct gaagaggagg aggtacaccg gctggggcag    5100
gctgagcagg aagctgatca acggcatcag ggacaagcag agcggcaaga ccatcctgga    5160
cttcctgaag agcgacggct cgccaacag gaacttcatg cagctgatcc acgacgacag    5220
cctgaccttc aaggaggaca tccagaaggc ccaggtgagc ggccagggcg acagcctgca    5280
cgagcacatc gccaacctgg ccggcagccc ggccatcaag aagggcatcc tgcagaccgt    5340
gaaggtggtg gacgagctgg tgaaggtgat gggcaggcac aagccggaga acatcgtgat    5400
cgagatggcc agggagaacc agaccaccca gaagggccag aagaacagca gggagaggat    5460
gaagaggatc gaggagggca tcaaggagct gggcagccag atcctgaagg agcacccggt    5520
ggagaacacc cagctgcaga acgagaagct gtacctgtac tacctgcaga acggcaggga    5580
catgtacgtg gaccaggagc tggacatcaa caggctgagc gactacgacg tggaccacat    5640
cgtgccgcag agcttcctga aggacgacag catcgacaac aaggtgctga ccaggagcga    5700
caagaacagg ggcaagagcg acaacgtgcc gagcgaggag tggtgaaga gatgaaaaa    5760 ctactggagg cagctgctga acgccaagct gatcacccag aggaagttcg acaacctgac    5820
caaggccgag aggggcggcc tgagcagct ggacaaggcc ggcttcatta aaaggcagct    5880
ggtggagacc aggcagatca ccaagcacgt ggcccagatc ctggacagca ggatgaacac    5940
caagtacgac gagaacgaca agctgatcag ggaggtgaag gtgatcaccc tgaagagcaa    6000
gctggtgagc gacttcagga aggacttcca gttctacaag gtgagggaga tcaataatta    6060
ccaccacgcc cacgacgcct acctgaacgc cgtggtgggc accgccctga ttaaaaagta    6120
cccgaagctg gagagcgagt tcgtgtacgg cgactacaag gtgtacgacg tgaggaagat    6180
gatcgccaag agcgagcagg agatcggcaa ggccaccgcc aagtacttct tctacagcaa    6240
catcatgaac ttcttcaaga ccgagatcac cctggccaac ggcgagatca ggaagaggcc    6300
gctgatcgag accaacggcg agaccggcga gatcgtgtgg gacaagggca gggacttcgc    6360
caccgtgagg aaggtgctgt ccatgccgca ggtgaacatc gtgaagaaga ccgaggtgca    6420
gaccggcggc ttcagcaagg agagcatcct gccgaagagg aacagcgaca gctgatcgc    6480 caggaagaag gactgggacc cgaagaagta cggcggcttc gacagcccga ccgtggccta    6540
cagcgtgctg gtggtggcca agtggagaaa gggcaagagc aagaagctga gagcgtgaa    6600 ggagctggtg ggcatcacca tcatggagag gagcagcttc gagaagaacc cagtggactt    6660
cctggaggcc aagggctaca aggaggtgaa aaggacctg atcattaaac tgccgaagta    6720
cagcctgttc gagctggaga acggcaggaa gaggatgctg gccagcgccg cgagctgca    6780 gaagggcaac gagctggccc tgccgagcaa gtacgtgaac ttcctgtacc tggccagcca    6840
ctacgagaag ctgaagggca gccggagga caacgagcag aagcagctgt tcgtggagca    6900
gcacaagcac tacctggacg agatcatcga gcagatcagc gagttcagca agagggtgat    6960
cctggccgac gccaacctgg acaaggtgct gagcgcctac aacaagcaca gggacaagcc    7020
gatcagggag caggccgaga acatcatcca cctgttcacc ctgaccaacc tgggcgcccc    7080
ggccgccttc aagtacttcg acaccaccat cgacaggaag aggtacacca gcaccaagga    7140
```

```
ggtgctggac gccaccctga tccaccagag catcaccggc ctgtacgaga ccaggatcga   7200
cctgagccag ctgggcggcg acagcagccc gccgaagaag aagaggaagg tgagctggaa   7260
ggacgccagc ggctggagca ggatgtgacc atgggacaag tggctttact gtcagtcaca   7320
tgcttgtaaa taagtagact ttattttaat aaaacataaa aatatatata tgttcttgaa   7380
tataaaattg ataaccaaat taaaattcga accatcactt atacataatt ttactttatt   7440
ttttataaaa cgtgaacggg aaggactacc gtgaatgact atagaaccaa tcatactagt   7500
ataaaatata tgatgacact acgggagaga caaactttgt ctggcgctaa atattttgcc   7560
gagtgtgaat tcacgggcac taggcaaaga tcttctttgc cgagtgttac gctgggcaaa   7620
gtaagacact aggtaaatca gtcatttgcc gagtgtccgc cactaggcaa agcaaaacac   7680
tggcaaatca aaagtttacc tagtgccaga cactaggcaa aaaaaaaacg ctcggcaaat   7740
cggaagtttc cctagtgcca gacactagac aaagaaaaac acttgataaa ctagcgtcgt   7800
cagctaacac catccaccaa ccgttaacgt tgccgagtat ctgacttcga cactcggcaa   7860
agaaggtctc tttgcctagt gtcggtctgg aacactaggc aaagaggcac tttacctagt   7920
gtcgtatttt gacactcagt aaaataattt tttttcttc tgcttccaaa cttttatga   7980 tgtgttccta tagcacctag aactacatgt caagttttgg taaaattttt gaagttttg   8040 ctatatttac ttaatttatt ttatttaatt gaatttcttt tgataattca aatttgaact   8100
cggcaaggta agaagcgagg gtagcctgga aacacacttt gcctagtgtt acactcggta   8160
caggagcctc ccctgcctag tgctgcactc gacaaaagat tcgcctttgc ctagcgctgc   8220
actcggcaca ggagtcgcct ttgcctagtg ctgcactagg caaagcctcc gttaccgtgc   8280
cttccatcgt cggacccttc gaagggatct taaacatac gaacagatca cttaaagttc   8340
ttctgaagca acttaaagtt atcaggcatg catggatctt ggaggaatca gatgtgcagt   8400
cagggaccat agcacaggac aggcgtcttc tactggtgct accagcaaat gctggaagcc   8460
gggaacactg ggtacgttgg aaaccacgtg atgtggagta agataaactg taggagaaaa   8520
gcatttcgta gtgggccatg aagcctttca ggacatgtat tgcagtatgg gccggcccat   8580
tacgcaattg gacgacaaca aagactagta ttagtaccac ctcggctatc cacatagatc   8640
aaagctggtt taaagagtt gtgcagatga tccgtggcag ctggagctga gcttccgggg   8700
ttttagagct agaaatagca agttaaaata aggctagtcc gttatcaact tgaaaaagtg   8760
gcaccgagtc ggtgcttttt tttcggacc gcgcctgcag tgcagcgtga cccggtcgtg   8820
cccctctcta gagataatga gcattgcatg tctaagttat aaaaaattac cacatatttt   8880
ttttgtcaca cttgtttgaa gtgcagttta tctatcttta tacatatatt taaactttac   8940
tctacgaata atataatcta tagtactaca ataaatatcag tgttttagag aatcatataa   9000
atgaacagtt agacatggtc taaaggacaa ttgagtattt tgacaacagg actctacagt   9060
tttatctttt tagtgtgcat gtgttctcct tttttttgc aaatagcttc acctatataa   9120
tacttcatcc attttattag tacatccatt tagggtttag ggttaatggt ttttatagac   9180 taatttttt agtacatcta ttttattcta ttttagcctc taaattaaga aaactaaaac   9240
tctattttag ttttttttatt taataattta gatataaaat agaataaaat aaagtgacta   9300
aaaattaaac aaataccctt taagaaatta aaaaaactaa ggaaacattt tcttgtttc   9360 gagtagataa tgccagcctg ttaaacgccg tcgacgagtc taacgacac caaccagcga   9420 accagcagcg tcgcgtcggg ccaagcgaag cagacggcac ggcatctctg tcgctgcctc   9480
```

| | |
|---|---|
| tggacccctc tcgagagttc cgctccaccg ttggacttgc tccgctgtcg gcatccagaa | 9540 |
| attgcgtggc ggagcggcag acgtgagccg gcacggcagg cggcctcctc ctcctctcac | 9600 |
| ggcaccggca gctacggggg attcctttcc caccgctcct tcgctttccc ttcctcgccc | 9660 |
| gccgtaataa atagacaccc cctccacacc ctctttcccc aacctcgtgt tgttcggagc | 9720 |
| gcacacacac acaaccagat ctcccccaaa tccacccgtc ggcacctccg cttcaaggta | 9780 |
| cgccgctcgt cctccccccc ccccctctct accttctcta gatcggcgtt ccggtccatg | 9840 |
| gttagggccc ggtagttcta cttctgttca tgtttgtgtt agatccgtgt ttgtgttaga | 9900 |
| tccgtgctgc tagcgttcgt acacggatgc gacctgtacg tcagacacgt tctgattgct | 9960 |
| aacttgccag tgtttctctt tggggaatcc tgggatggct ctagccgttc cgcagacggg | 10020 |
| atcgatttca tgatttttttt tgtttcgttg catagggttt ggtttgccct tttcctttat | 10080 |
| ttcaatatat gccgtgcact tgtttgtcgg gtcatctttt catgctttttt tttgtcttgg | 10140 |
| ttgtgatgat gtggtctggt tgggcggtcg ttctagatcg gagtagaatt ctgtttcaaa | 10200 |
| ctacctggtg gatttattaa ttttggatct gtatgtgtgt gccatacata ttcatagtta | 10260 |
| cgaattgaag atgatggatg gaaatatcga tctaggatag gtatacatgt tgatgcgggt | 10320 |
| tttactgatg catatacaga gatgcttttt gttcgcttgg ttgtgatgat gtggtgtggt | 10380 |
| tgggcggtcg ttcattcgtt ctagatcgga gtagaatact gtttcaaact acctggtgta | 10440 |
| tttattaatt ttgaactgt atgtgtgtgt catacatctt catagttacg agtttaagat | 10500 |
| ggatggaaat atcgatctag gataggtata catgttgatg tgggttttac tgatgcatat | 10560 |
| acatgatggc atatgcagca tctattcata tgctctaacc ttgagtacct atctattata | 10620 |
| ataaacaagt atgttttata attattttga tcttgatata cttggatgat ggcatatgca | 10680 |
| gcagctatat gtggattttt ttagccctgc cttcatacgc tatttatttg cttggtactg | 10740 |
| tttcttttgt cgatgctcac cctgttgttt ggtgttactt ctgcagggat ccggcagcag | 10800 |
| ccatgcagaa gctgatcaac agcgtgcaga actacgcctg gggcagcaag accgccctga | 10860 |
| ccgagctgta cggcatggag aaccccagca gccagcccat ggccgagctg tggatgggcg | 10920 |
| cccaccccaa gagcagcagc cgcgtgcaga acgccgccgg cgacatcgtg agcctgcgcg | 10980 |
| acgtgatcga gagcgacaag agcaccctgc tgggcgaggc cgtggccaag cgcttcggcg | 11040 |
| agctgccctt cctgttcaag gtgctgtgcg ccgcccagcc cctgagcatc caggtgcacc | 11100 |
| ccaacaagca caacagcgag atcggcttcg ccaaggagaa cgccgccggc atccccatgg | 11160 |
| acgccgccga gcgcaactac aaggacccca ccacaagcc cgagctggtg ttcgccctga | 11220 |
| ccccccttcct ggccatgaac gccttccgcg agttcagcga gatcgtgagc ctgctgcagc | 11280 |
| ccgtggccgg cgcccacccc gccatcgccc acttcctgca gcagcccgac gccgagcgcc | 11340 |
| tgagcgagct gttcgccagc ctgctgaaca tgcagggcga ggagaagagc cgcgccctgg | 11400 |
| ccatcctgaa gagcgccctg gacagccagc agggcgagcc ctggcagacc atccgcctga | 11460 |
| tcagcgagtt ctaccccgag gacagcggcc tgttcagccc cctgctgctg aacgtggtga | 11520 |
| agctgaaccc cggcgaggcc atgttcctgt tcgccgagac ccccacgcc tacctgcagg | 11580 |
| gcgtggccct ggaggtgatg gccaacagcg acaacgtgct cgcgccggc ctgacccca | 11640 |
| agtacatcga catccccgag ctggtggcca acgtgaagtt cgaggccaag cccgccaacc | 11700 |
| agctgctgac ccagcccgtg aagcagggcg ccgagctgga cttccccatc ccgtggacg | 11760 |
| acttcgcctt cagcctgcac gacctgagcg acaaggagac caccatcagc cagcagagcc | 11820 |
| ccgccatcct gttctgcgtg gagggcgacg ccaccctgtg gaagggcagc cagcagctgc | 11880 |

```
agctgaagcc cggcgagagc gccttcatcg ccgccaacga gagcccgtg accgtgaagg   11940
gccacggccg cctggcccgc gtgtacaaca agctgtgata ggagctcgat ccgtcgacct   12000
gcagatcgtt caaacatttg gcaataaagt ttcttaagat tgaatcctgt tgccggtctt   12060
gcgatgatta tcatataatt tctgttgaat tacgttaagc atgtaataat taacatgtaa   12120
tgcatgacgt tatttatgag atgggttttt atgattagag tcccgcaatt atacatttaa   12180
tacgcgatag aaaacaaaat atagcgcgca aactaggata aattatcgcg cgcggtgtca   12240
tctatgttac tagatcggcg cgccgcaatt gaagtttggg cggccagcat ggccgtatcc   12300
gcaatgtgtt attaagttgt ctaagcgtca atttgtttac accacaatat atcctgccac   12360
cagccagcca acagctcccc gaccggcagc tcggcacaaa atcaccactc gatacaggca   12420
gcccatcaga attaattctc atgtttgaca gcttatcatc gactgcacgg tgcaccaatg   12480
cttctggcgt caggcagcca tcggaagctg tggtatggct gtgcaggtcg taaatcactg   12540
cataattcgt gtcgctcaag gcgcactccc gttctggata atgtttttg cgccgacatc   12600
ataacggttc tggcaaatat tctgaaatga gctgttgaca attaatcatc cggctcgtat   12660
aatgtgtgga attgtgagcg gataacaatt tcacacagga aacagaccat gagggaagcg   12720
ttgatcgccg aagtatcgac tcaactatca gaggtagttg gcgtcatcga gcgccatctc   12780
gaaccgacgt tgctggccgt acatttgtac ggctccgcag tggatggcgg cctgaagcca   12840
cacagtgata ttgatttgct ggttacggtg accgtaaggc ttgatgaaac aacgcggcga   12900
gctttgatca acgaccttt ggaaacttcg gcttccctg gagagagcga gattctccgc   12960
gctgtagaag tcaccattgt tgtgcacgac gacatcattc cgtggcgtta ccagctaag   13020
cgcgaactgc aatttggaga atggcagcgc aatgacattc ttgcaggtat cttcgagcca   13080
gccacgatcg acattgatct ggctatcttg ctgacaaaag caagagaaca tagcgttgcc   13140
ttggtaggtc cagcggcgga ggaactcttt gatccggttc ctgaacagga tctatttgag   13200
gcgctaaatg aaaccttaac gctatggaac tcgccgcccg actgggctgg cgatgagcga   13260
aatgtagtgc ttacgttgtc ccgcatttgg tacagcgcag taaccggcaa aatcgcgccg   13320
aaggatgtcg ctgccgactg ggcaatggag cgcctgccgg cccagtatca gcccgtcata   13380
cttgaagcta ggcaggctta tcttggacaa gaagatcgct tggcctcgcg cgcagatcag   13440
ttggaagaat ttgttcacta cgtgaaaggc gagatcacca agtagtcgg caaataaagc   13500
tctagtggat ctccgtaccc ggggatctgg ctcgcggcgg acgcacgacg ccggggcgag   13560
accataggcg atctcctaaa tcaatagtag ctgtaacctc gaagcgtttc acttgtaaca   13620
acgattgaga attttgtca taaaattgaa atacttggtt cgcattttg tcatccgcgg   13680
tcagccgcaa ttctgacgaa ctgcccattt agctggagat gattgtacat ccttcacgtg   13740
aaaatttctc aagcgctgtg aacaagggtt cagattttag attgaaaggt gagccgttga   13800
aacacgttct tcttgtcgat gacgacgtcg ctatgcggca tcttattatt gaataccta   13860
cgatccacgc cttcaaagtg accgcggtag ccgacagcac ccagttcaca agagtactct   13920
cttccgcgac ggtcgatgtc gtggttgttg atctagattt aggtcgtgaa gatgggctcg   13980
agctaggagc aagtgatttt atcgctaagc cgttcagtat cagagagttt ctagcacgca   14040
ttcgggttgc cttgcgcgtg cgccccaacg ttgtccgctc caaagaccga cggtctttt   14100
gttttactga ctggacactt aatctcaggc aacgtcgctt gatgtccgaa gctgcggtg   14160
aggtgaaact tacggcaggt gagttcaatc ttctcctcgc gttttagag aaaccccgcg   14220
```

-continued

| | |
|---|---|
| acgttctatc gcgcgagcaa cttctcattg ccagtcgagt acgcgacgag gaggtttatg | 14280 |
| acaggagtat agatgttctc attttgaggc tgcgccgcaa acttgaggca gatccgtcaa | 14340 |
| gccctcaact gataaaaaca gcaagaggtg ccggttattt ctttgacgcg acgtgcagg | 14400 |
| tttcgcacgg ggggacgatg gcagcctgag ccaattccca gatccccgag gaatcggcgt | 14460 |
| gagcggtcgc aaaccatccg gcccggtaca aatcggcgcg gcgctgggtg atgacctggt | 14520 |
| ggagaagttg aaggccgcgc aggccgccca gcggcaacgc atcgaggcag aagcacgccc | 14580 |
| cggtgaatcg tggcaagcgg ccgctgatcg aatccgcaaa gaatcccggc aaccgccggc | 14640 |
| agccggtgcg ccgtcgatta ggaagccgcc caagggcgac gagcaaccag attttttcgt | 14700 |
| tccgatgctc tatgacgtgg gcacccgcga tagtcgcagc atcatggacg tggccgtttt | 14760 |
| ccgtctgtcg aagcgtgacc gacgagctgg cgaggtgatc cgctacgagc ttccagacgg | 14820 |
| gcacgtagag gtttccgcag ggccggccgg catggccagt gtgtgggatt acgacctggt | 14880 |
| actgatggcg gtttcccatc taaccgaatc catgaaccga taccgggaag ggaagggaga | 14940 |
| caagcccggc cgcgtgttcc gtccacacgt tgcggacgta ctcaagttct gccgcgagc | 15000 |
| cgatggcgga aagcagaaag acgacctggt agaaacctgc attcggttaa acaccacgca | 15060 |
| cgttgccatg cagcgtacga agaaggccaa gaacggccgc ctggtgacgg tatccgaggg | 15120 |
| tgaagccttg attagccgct acaagatcgt aaagagcgaa accgggcggc cggagtacat | 15180 |
| cgagatcgag ctagctgatt ggatgtaccg cgagatcaca gaaggcaaga acccggacgt | 15240 |
| gctgacggtt caccccgatt acttttgat cgatcccggc atcggccgtt ttctctaccg | 15300 |
| cctggcacgc cgcgccgcag gcaaggcaga agccagatgg ttgttcaaga cgatctacga | 15360 |
| acgcagtggc agcgccggag agttcaagaa gttctgtttc accgtgcgca agctgatcgg | 15420 |
| gtcaaatgac ctgccggagt acgatttgaa ggaggaggcg gggcaggctg gcccgatcct | 15480 |
| agtcatgcgc taccgcaacc tgatcgaggg cgaagcatcc gccggttcct aatgtacgga | 15540 |
| gcagatgcta gggcaaattg ccctagcagg ggaaaaaggt cgaaaaggtc tctttcctgt | 15600 |
| ggatagcacg tacattggga acccaaagcc gtacattggg aaccggaacc cgtacattgg | 15660 |
| gaacccaaag ccgtacattg ggaaccggtc acacatgtaa gtgactgata taaaagagaa | 15720 |
| aaaaggcgat ttttccgcct aaaactcttt aaaacttatt aaaactctta aaacccgcct | 15780 |
| ggcctgtgca taactgtctg gccagcgcac agccgaagag ctgcaaaaag cgcctaccct | 15840 |
| tcggtcgctg cgctccctac gccccgccgc ttcgcgtcgg cctatcgcgg ccgctggccg | 15900 |
| ctcaaaaatg gctggcctac ggccaggcaa tctaccaggg cgcggacaag ccgcgccgtc | 15960 |
| gccactcgac cgccggcgct gaggtctgcc tcgtgaagaa ggtgttgctg actcatacca | 16020 |
| ggcctgaatc gccccatcat ccagccagaa agtgagggag ccacggttga tgagagcttt | 16080 |
| gttgtaggtg gaccagttgg tgattttgaa cttttgcttt gccacggaac ggtctgcgtt | 16140 |
| gtcgggaaga tgcgtgatct gatccttcaa ctcagcaaaa gttcgattta ttcaacaaag | 16200 |
| ccgccgtccc gtcaagtcag cgtaatgctc tgccagtgtt acaaccaatt aaccaattct | 16260 |
| gattagaaaa actcatcgag catcaaatga aactgcaatt tattcatatc aggattatca | 16320 |
| ataccatatt tttgaaaaag ccgtttctgt aatgaaggag aaaactcacc gaggcagttc | 16380 |
| cataggatgg caagatcctg gtatcggtct gcgattccga ctcgtccaac atcaatacaa | 16440 |
| cctattaatt tccctcgtc aaaaataagg ttatcaagtg agaaatcacc atgagtgacg | 16500 |
| actgaatccg gtgagaatgg caaaagctct gcattaatga atcggccaac gcgcggggag | 16560 |
| aggcggtttg cgtattgggc gctcttccgc ttcctcgctc actgactcgc tgcgctcggt | 16620 |

```
cgttcggctg cggcgagcgg tatcagctca ctcaaaggcg gtaatacggt tatccacaga    16680
atcaggggat aacgcaggaa agaacatgtg agcaaaaggc cagcaaaagg ccaggaaccg    16740
taaaaaggcc gcgttgctgg cgttttccca taggctccgc cccccgtacg agcatcacaa    16800
aaatcgacgc tcaagtcaga ggtggcgaaa cccgacagga ctataaagat accaggcgtt    16860
tccccctgga agctccctcg tgcgctctcc tgttccgacc ctgccgctta ccggatacct    16920
gtccgccttt ctcccttcgg gaagcgtggc gctttctcat agctcacgct gtaggtatct    16980
cagttcggtg taggtcgttc gctccaagct gggctgtgtg cacgaacccc ccgttcagcc    17040
cgaccgctgc gccttatccg gtaactatcg tcttgagtcc aacccggtaa gacacgactt    17100
atcgccactg gcagcagcca ctggtaacag gattagcaga gcgaggtatg taggcggtgc    17160
tacagagttc ttgaagtggt ggcctaacta cggctacact agaagaacag tatttggtat    17220
ctgcgctctg ctgaagccag ttaccttcgg aaaaagagtt ggtagctctt gatccggcaa    17280
acaaaccacc gctggtagcg gtggtttttt tgtttgcaag cagcagatta cgcgcagaaa    17340
aaaaggatct caagaagatc ctttgatctt ttctacgggg tctgacgctc agtggaacga    17400
aaactcacgt taagggattt tggtcatgag attatcaaaa aggatcttca cctagatcct    17460
tttgatccgg aatta                                                    17475

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ttgtgctgct ccacgaaca                                                     19

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
gccagccact acgagaagct                                                    20

<210> SEQ ID NO 41
<211> LENGTH: 24
<212> TYPE: DNA
<213> ORGANISM: Artificial Sequence
<220> FEATURE:
<223> OTHER INFORMATION: probe

<400> SEQUENCE: 41
ctgcttctgc tcgttgtcct ccgg                                               24

<210> SEQ ID NO 42
<211> LENGTH: 17
<212> TYPE: DNA
<213> ORGANISM: Artificial Sequence
<220> FEATURE:
<223> OTHER INFORMATION: promer

<400> SEQUENCE: 42
gcggatgctg gcacagc                                                       17
```

```
<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
ggcattgctt ccttctccg                                                    19

<210> SEQ ID NO 44
<211> LENGTH: 15
<212> TYPE: DNA
<213> ORGANISM: Artificial Sequence
<220> FEATURE:
<223> OTHER INFORMATION: probe

<400> SEQUENCE: 44
cagggagcga ggtac                                                        15

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
ctggtggcca acgtgaagtt                                                   20

<210> SEQ ID NO 46
<211> LENGTH: 17
<212> TYPE: DNA
<213> ORGANISM: Artificial Sequence
<220> FEATURE:
<223> OTHER INFORMATION: primer

<400> SEQUENCE: 46
gcttcacggg ctgggtc                                                      17

<210> SEQ ID NO 47
<211> LENGTH: 20
<212> TYPE: DNA
<213> ORGANISM: Artificial Sequence
<220> FEATURE:
<223> OTHER INFORMATION: probe

<400> SEQUENCE: 47
aggccaagcc cgccaaccag                                                   20

<210> SEQ ID NO 48
<211> LENGTH: 17
<212> TYPE: DNA
<213> ORGANISM: Artificial Sequence
<220> FEATURE:
<223> OTHER INFORMATION: primer

<400> SEQUENCE: 48
gcggatgctg gcacaga                                                      17

<210> SEQ ID NO 49
<211> LENGTH: 18
<212> TYPE: DNA
<213> ORGANISM: Artificial Sequence
<220> FEATURE:
<223> OTHER INFORMATION: primer
```

<400> SEQUENCE: 49
gcattgcttc cttcgcca                                                              18

<210> SEQ ID NO 50
<211> LENGTH: 16
<212> TYPE: DNA
<213> ORGANISM: Artificial Sequence
<220> FEATURE:
<223> OTHER INFORMATION: probe

<400> SEQUENCE: 50
cagggaggta cgaacc                                                                16

<210> SEQ ID NO 51
<211> LENGTH: 16
<212> TYPE: DNA
<213> ORGANISM: Artificial Sequence
<220> FEATURE:
<223> OTHER INFORMATION: primer

<400> SEQUENCE: 51
gcggcgaaga agcgaa                                                                16

<210> SEQ ID NO 52
<211> LENGTH: 17
<212> TYPE: DNA
<213> ORGANISM: Artificial Sequence
<220> FEATURE:
<223> OTHER INFORMATION: primer

<400> SEQUENCE: 52
gcggcgtctc cagcttc                                                               17

<210> SEQ ID NO 53
<211> LENGTH: 12
<212> TYPE: DNA
<213> ORGANISM: Artificial Sequence
<220> FEATURE:
<223> OTHER INFORMATION: probe

<400> SEQUENCE: 53
ccaggaactg cg                                                                    12

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
aagaaacgcc ggctgagt                                                              18

<210> SEQ ID NO 55
<211> LENGTH: 15
<212> TYPE: DNA
<213> ORGANISM: Artificial Sequence
<220> FEATURE:
<223> OTHER INFORMATION: primer

<400> SEQUENCE: 55
accttgcggg gcgtt                                                                 15

<210> SEQ ID NO 56

```
<211> LENGTH: 12
<212> TYPE: DNA
<213> ORGANISM: Artificial Sequence
<220> FEATURE:
<223> OTHER INFORMATION: probe

<400> SEQUENCE: 56
ccaggaactg cg                                                          12

<210> SEQ ID NO 57
<211> LENGTH: 18
<212> TYPE: DNA
<213> ORGANISM: Artificial Sequence
<220> FEATURE:
<223> OTHER INFORMATION: primer

<400> SEQUENCE: 57
aagaaacgcc ggctgagt                                                    18

<210> SEQ ID NO 58
<211> LENGTH: 14
<212> TYPE: DNA
<213> ORGANISM: Artificial Sequence
<220> FEATURE:
<223> OTHER INFORMATION: primer

<400> SEQUENCE: 58
ccttgcgcgg cgtc                                                        14

<210> SEQ ID NO 59
<211> LENGTH: 12
<212> TYPE: DNA
<213> ORGANISM: Artificial Sequence
<220> FEATURE:
<223> OTHER INFORMATION: probe

<400> SEQUENCE: 59
ccaggaactg cg                                                          12

<210> SEQ ID NO 60
<211> LENGTH: 19
<212> TYPE: DNA
<213> ORGANISM: Artificial Sequence
<220> FEATURE:
<223> OTHER INFORMATION: primer

<400> SEQUENCE: 60
tgatcctcga ggccaagct                                                   19

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
aggtcgaggt cccctcca                                                    18

<210> SEQ ID NO 62
<211> LENGTH: 14
<212> TYPE: DNA
<213> ORGANISM: Artificial Sequence
<220> FEATURE:
<223> OTHER INFORMATION: probe

<400> SEQUENCE: 62
```

```
cctgctaccc gggc                                              14

<210> SEQ ID NO 63
<211> LENGTH: 15
<212> TYPE: DNA
<213> ORGANISM: Artificial Sequence
<220> FEATURE:
<223> OTHER INFORMATION: primer

<400> SEQUENCE: 63
cgcgccctgc taccc                                             15

<210> SEQ ID NO 64
<211> LENGTH: 17
<212> TYPE: DNA
<213> ORGANISM: Artificial Sequence
<220> FEATURE:
<223> OTHER INFORMATION: primer

<400> SEQUENCE: 64
gcgcgtgctt accagga                                           17

<210> SEQ ID NO 65
<211> LENGTH: 13
<212> TYPE: DNA
<213> ORGANISM: Artificial Sequence
<220> FEATURE:
<223> OTHER INFORMATION: probe

<400> SEQUENCE: 65
tcgaggagtg ccc                                               13

<210> SEQ ID NO 66
<211> LENGTH: 16
<212> TYPE: DNA
<213> ORGANISM: Artificial Sequence
<220> FEATURE:
<223> OTHER INFORMATION: primer

<400> SEQUENCE: 66
caccgatgag caggcg                                            16

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
agatacacct tccggccg                                          18

<210> SEQ ID NO 68
<211> LENGTH: 14
<212> TYPE: DNA
<213> ORGANISM: Artificial Sequence
<220> FEATURE:
<223> OTHER INFORMATION: probe

<400> SEQUENCE: 68
ttcctcccgg aagc                                              14

<210> SEQ ID NO 69
<211> LENGTH: 16
<212> TYPE: DNA
```

```
<213> ORGANISM: Artificial Sequence
<220> FEATURE:
<223> OTHER INFORMATION: primer

<400> SEQUENCE: 69
caccgatgag caggcg                                                   16

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
agatacacct tccggccagt                                               20

<210> SEQ ID NO 71
<211> LENGTH: 14
<212> TYPE: DNA
<213> ORGANISM: Artificial Sequence
<220> FEATURE:
<223> OTHER INFORMATION: probe

<400> SEQUENCE: 71
ctcctcccgg aagc                                                     14

<210> SEQ ID NO 72
<211> LENGTH: 25
<212> TYPE: DNA
<213> ORGANISM: Artificial Sequence
<220> FEATURE:
<223> OTHER INFORMATION: primer

<400> SEQUENCE: 72
caagtttctg gacaaggaga ttctc                                         25

<210> SEQ ID NO 73
<211> LENGTH: 27
<212> TYPE: DNA
<213> ORGANISM: Artificial Sequence
<220> FEATURE:
<223> OTHER INFORMATION: primer

<400> SEQUENCE: 73
aagaattccc ttcttaatag ctggaga                                       27

<210> SEQ ID NO 74
<211> LENGTH: 26
<212> TYPE: DNA
<213> ORGANISM: Artificial Sequence
<220> FEATURE:
<223> OTHER INFORMATION: probe

<400> SEQUENCE: 74
cacgagcaca ttgctaacct tgctgg                                        26

<210> SEQ ID NO 75
<211> LENGTH: 17
<212> TYPE: DNA
<213> ORGANISM: Artificial Sequence
<220> FEATURE:
<223> OTHER INFORMATION: primer

<400> SEQUENCE: 75
tcaccgatga gcaggca                                                  17
```

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
atacaccttc cggccagc                                                       18

<210> SEQ ID NO 77
<211> LENGTH: 14
<212> TYPE: DNA
<213> ORGANISM: Artificial Sequence
<220> FEATURE:
<223> OTHER INFORMATION: probe

<400> SEQUENCE: 77
ttcctcccgg aagc                                                           14

<210> SEQ ID NO 78
<211> LENGTH: 24
<212> TYPE: DNA
<213> ORGANISM: Artificial Sequence
<220> FEATURE:
<223> OTHER INFORMATION: primer

<400> SEQUENCE: 78
gatagggcta agagatgtg ggaa                                                 24

<210> SEQ ID NO 79
<211> LENGTH: 26
<212> TYPE: DNA
<213> ORGANISM: Artificial Sequence
<220> FEATURE:
<223> OTHER INFORMATION: primer

<400> SEQUENCE: 79
ctttgttcac attagggctc aaataa                                              26

<210> SEQ ID NO 80
<211> LENGTH: 16
<212> TYPE: DNA
<213> ORGANISM: Artificial Sequence
<220> FEATURE:
<223> OTHER INFORMATION: probe

<400> SEQUENCE: 80
tagactgaga tggatg                                                         16

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
aaaaccaccg gagaagacga                                                     20

<210> SEQ ID NO 82
<211> LENGTH: 17
<212> TYPE: DNA
<213> ORGANISM: Artificial Sequence
<220> FEATURE:

<223> OTHER INFORMATION: primer

<400> SEQUENCE: 82
aggtgtggcg gcagtga                                                        17

<210> SEQ ID NO 83
<211> LENGTH: 14
<212> TYPE: DNA
<213> ORGANISM: Artificial Sequence
<220> FEATURE:
<223> OTHER INFORMATION: probe

<400> SEQUENCE: 83
caccgtcatt gttc                                                           14

<210> SEQ ID NO 84
<211> LENGTH: 25
<212> TYPE: DNA
<213> ORGANISM: Artificial Sequence
<220> FEATURE:
<223> OTHER INFORMATION: primer

<400> SEQUENCE: 84
caagtttctg gacaaggaga ttctc                                               25

<210> SEQ ID NO 85
<211> LENGTH: 27
<212> TYPE: DNA
<213> ORGANISM: Artificial Sequence
<220> FEATURE:
<223> OTHER INFORMATION: primer

<400> SEQUENCE: 85
aagaattccc ttcttaatag ctggaga                                             27

<210> SEQ ID NO 86
<211> LENGTH: 26
<212> TYPE: DNA
<213> ORGANISM: Artificial Sequence
<220> FEATURE:
<223> OTHER INFORMATION: probe

<400> SEQUENCE: 86
cacgagcaca ttgctaacct tgctgg                                              26

<210> SEQ ID NO 87
<211> LENGTH: 15
<212> TYPE: DNA
<213> ORGANISM: Artificial Sequence
<220> FEATURE:
<223> OTHER INFORMATION: primer

<400> SEQUENCE: 87
gcgacgccgg aaagg                                                          15

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
tggcgtggtt tcgtcttctt a                                                   21

```
<210> SEQ ID NO 89
<211> LENGTH: 25
<212> TYPE: DNA
<213> ORGANISM: Artificial Sequence
<220> FEATURE:
<223> OTHER INFORMATION: probe

<400> SEQUENCE: 89
aagagcggcg tctggaggtg actca                                         25

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
aaccgcatcg tcagaaaaac                                               20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
tcaacttaac cggccaaatc                                               20

<210> SEQ ID NO 92
<211> LENGTH: 21
<212> TYPE: DNA
<213> ORGANISM: Artificial Sequence
<220> FEATURE:
<223> OTHER INFORMATION: primer

<400> SEQUENCE: 92
catcccttct cttccctcct g                                             21

<210> SEQ ID NO 93
<211> LENGTH: 23
<212> TYPE: DNA
<213> ORGANISM: Artificial Sequence
<220> FEATURE:
<223> OTHER INFORMATION: primer

<400> SEQUENCE: 93
gccagtgtga gtgtgtatga gca                                           23

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
catcgttttc tcccctcctc a                                             21

<210> SEQ ID NO 95
<211> LENGTH: 19
<212> TYPE: DNA
<213> ORGANISM: Artificial Sequence
<220> FEATURE:
<223> OTHER INFORMATION: primer
```

```
<400> SEQUENCE: 95
actgatatgc acggcgcca                                                19

<210> SEQ ID NO 96
<211> LENGTH: 22
<212> TYPE: DNA
<213> ORGANISM: Artificial Sequence
<220> FEATURE:
<223> OTHER INFORMATION: primer

<400> SEQUENCE: 96
tgcagtagct tcattttcac cg                                            22

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
aggaattgat atgtacgccc gt                                            22

<210> SEQ ID NO 98
<211> LENGTH: 16279
<212> TYPE: DNA
<213> ORGANISM: Artificial Sequence
<220> FEATURE:
<223> OTHER INFORMATION: vector 24075
<220> FEATURE:
<221> NAME/KEY: misc_feature
<222> LOCATION: (1)..(517)
<223> OTHER INFORMATION: bNRB-07
<220> FEATURE:
<221> NAME/KEY: promoter
<222> LOCATION: (538)..(1697)
<223> OTHER INFORMATION: prAtEFaA1-02
<220> FEATURE:
<221> NAME/KEY: gene
<222> LOCATION: (1716)..(5885)
<223> OTHER INFORMATION: cCas9-05
<220> FEATURE:
<221> NAME/KEY: mutation
<222> LOCATION: (5205)..(5207)
<223> OTHER INFORMATION: L to V mutation
<220> FEATURE:
<221> NAME/KEY: mutation
<222> LOCATION: (5250)..(5252)
<223> OTHER INFORMATION: I to V mutation
<220> FEATURE:
<221> NAME/KEY: terminator
<222> LOCATION: (5894)..(6146)
<223> OTHER INFORMATION: tNOS-05-01
<220> FEATURE:
<221> NAME/KEY: promoter
<222> LOCATION: (6173)..(6620)
<223> OTHER INFORMATION: prAtU6-01
<220> FEATURE:
<221> NAME/KEY: misc_feature
<222> LOCATION: (6621)..(6640)
<223> OTHER INFORMATION: AtGL1 target1
<220> FEATURE:
<221> NAME/KEY: misc_feature
<222> LOCATION: (6621)..(6725)
<223> OTHER INFORMATION: rsgRNA AtGL1-01
<220> FEATURE:
<221> NAME/KEY: misc_feature
<222> LOCATION: (6641)..(6652)
<223> OTHER INFORMATION: rCrRNA-01
<220> FEATURE:
<221> NAME/KEY: misc_feature
<222> LOCATION: (6657)..(6725)
<223> OTHER INFORMATION: rTracrRNA-01
```

```
<220> FEATURE:
<221> NAME/KEY: promoter
<222> LOCATION: (6726)..(7173)
<223> OTHER INFORMATION: prAtU6-01
<220> FEATURE:
<221> NAME/KEY: misc_feature
<222> LOCATION: (7174)..(7193)
<223> OTHER INFORMATION: AtGl1 target 2
<220> FEATURE:
<221> NAME/KEY: misc_feature
<222> LOCATION: (7174)..(7278)
<223> OTHER INFORMATION: rsgRNA AtGL1-02
<220> FEATURE:
<221> NAME/KEY: misc_feature
<222> LOCATION: (7194)..(7205)
<223> OTHER INFORMATION: rCrRNA-01
<220> FEATURE:
<221> NAME/KEY: misc_feature
<222> LOCATION: (7210)..(7278)
<223> OTHER INFORMATION: rTracrRNA-01
<220> FEATURE:
<221> NAME/KEY: promoter
<222> LOCATION: (7295)..(7640)
<223> OTHER INFORMATION: prCMP-02
<220> FEATURE:
<221> NAME/KEY: gene
<222> LOCATION: (7653)..(8447)
<223> OTHER INFORMATION: cNpt2-10
<220> FEATURE:
<221> NAME/KEY: terminator
<222> LOCATION: (8476)..(8728)
<223> OTHER INFORMATION: tNOS-05-01
<220> FEATURE:
<221> NAME/KEY: promoter
<222> LOCATION: (8755)..(10752)
<223> OTHER INFORMATION: prGmUBI-01
<220> FEATURE:
<221> NAME/KEY: gene
<222> LOCATION: (10765)..(11454)
<223> OTHER INFORMATION: cAmCyan-06
<220> FEATURE:
<221> NAME/KEY: terminator
<222> LOCATION: (11477)..(12119)
<223> OTHER INFORMATION: tPsE9-01
<220> FEATURE:
<221> NAME/KEY: misc_feature
<222> LOCATION: (12193)..(12311)
<223> OTHER INFORMATION: bNLB-03
<220> FEATURE:
<221> NAME/KEY: gene
<222> LOCATION: (12928)..(13716)
<223> OTHER INFORMATION: cSpec-03
<220> FEATURE:
<221> NAME/KEY: gene
<222> LOCATION: (13751)..(14824)
<223> OTHER INFORMATION: cRepA-08
<220> FEATURE:
<221> NAME/KEY: misc_feature
<222> LOCATION: (14867)..(15271)
<223> OTHER INFORMATION: oVC1-04
<220> FEATURE:
<221> NAME/KEY: misc_feature
<222> LOCATION: (15441)..(16247)
<223> OTHER INFORMATION: oCOLE-06

<400> SEQUENCE: 98
gccaggacgt cggccgaaag agcgacaagc agatcacgct tttcgacagc gtcggatttg      60
cgatcgagga ttttcggcg ctgcgctacg tccgcgaccg cgttgaggga tcaagccaca     120
gcagcccact cgaccttcta gccgacccag acgagccaag ggatcttttt ggaatgctgc    180
tccgtcgtca ggctttccga cgtttgggtg gttgaacaga agtcattatc gcacggaatg    240
ccaagcactc ccgaggggaa ccctgtggtt ggcatgcaca tacaaatgga cgaacggata    300
aaccttttca cgcccttta aatatccgat tattctaata aacgctcttt tctcttaggt     360
```

-continued

```
ttacccgcca atatatcctg tcaaacactg atagtttaaa ctgaaggcgg gaaacgacaa   420
tctgatcatg agcggagaat aagggagtc acgttatgac ccccgccgat gacgcgggac    480
aagccgtttt acgtttggaa ctgacagaac cgcaacgttg aaggcgcgcc actcagcaag   540
cttgatatcg gaagtttctc tcttgaggga ggttgctcgt ggaatgggac acatatggtt   600
gttataataa accatttcca ttgtcatgag attttgaggt taatatatac tttacttgtt   660
cattatttta tttggtgttt gaataaatga tataaatggc tcttgataat ctgcattcat   720
tgagatatca aatatttact ctagagaaga gtgtcatata gattgatggt ccacaatcaa   780
tgaaattttt gggagacgaa catgtataac catttgcttg aataaccta attaaaaggt    840 gtgattaaat gatgtttgta acatgtagta ctaaacattc ataaaacaca accaacccaa   900
gaggtattga gtattcacgg ctaaacaggg gcataatggt aatttaaaga atgatattat   960
tttatgttaa accctaacat tggtttcgga ttcaacgcta taaataaaac cactctcgtt  1020
gctgattcca tttatcgttc ttattgaccc tagccgctac acactttct gcgatatctc   1080 tgaggtaagc gttaacgtac ccttagatcg ttcttttct ttttcgtctg ctgatcgttg    1140
ctcatattat ttcgatgatt gttggattcg atgctctttg ttgattgatc gttctgaaaa  1200
ttctgatctg ttgtttagat tttatcgatt gttaatatca acgtttcact gcttctaaac  1260
gataatttat tcatgaaact attttcccat tctgatcgat cttgttttga gattttaatt  1320
tgttcgattg attgttggtt ggtggatcta tacgagtg aacttgttga tttgcgtatt    1380
taagatgtat gtcgatttga attgtgattg ggtaattctg gagtagcata acaaatccag  1440
tgttcccttt ttctaagggt aattctcgga ttgtttgctt tatatctctt gaaattgccg  1500
atttgattga atttagctcg cttagctcag atgatagagc accacaattt tgtggtaga   1560 aatcggtttg actccgatag cggcttttta ctatgattgt tttgtgttaa agatgatttt  1620
cataatggtt atatatgtct actgttttta ttgattcaat atttgattgt tctttttttt  1680
gcagatttgt tgaccaggga tccgcggccg ctaaaatgga taagaagtat tctattggac  1740
ttgatattgg aaccaactct gtgggatggg ctgttattac tgacgagtat aaggttccat  1800
ctaagaagtt caaggttctt ggaaacactg atagacactc tattaagaag aaccttattg  1860
gtgctcttct tttcgattct ggagagactg ctgaggctac tagacttaag agaactgcta  1920
gaagaagata tactagaaga aagaacagaa tttgctatct tcaagagatt ttctctaacg  1980
agatggctaa ggttgacgat tctttcttcc acagacttga ggagtctttc cttgttgagg  2040
aggataagaa gcacgagaga cacccaattt tcggaaacat tgttgacgag ttgcttatc    2100 acgagaagta tccaactatt tatcaccta gaaagaagct cgttgattct actgataagg   2160
ctgatcttag acttatttat cttgctcttg ctcacatgat taagttcaga ggacacttcc  2220
ttattgaggg agatcttaac ccagataact ctgacgttga taagctcttc attcaacttg  2280
ttcaaactta taaccaactt ttcgaggaga acccaattaa cgcttctgga gttgacgcta  2340
aggctattct ttctgctaga ctttctaagt ctagaaggct tgagaacctt attgctcaac  2400
ttccaggaga gaagaagaac ggacttttcg gaaaccttat tgctctttct cttggactta  2460
ctccaaactt caagtctaac ttcgatcttg ctgaggacgc taagctccaa ctttctaagg  2520
atacttacga cgatgatctt gataaccttc ttgctcaaat tggagatcaa tacgctgatc  2580
ttttccttgc tgctaagaac cttctgacg ctattcttct ttctgatatt cttagagtta   2640
acactgagat tactaaggct ccacttttctg cttctatgat taagagatac gacgagcacc  2700
accaagatct tactcttctt aaggctcttg ttagacaaca acttccagag aagtataagg  2760
```

-continued

```
agattttctt cgatcaatct aagaacggat acgctggata tattgacgga ggagcttctc    2820
aagaggagtt ctataagttc attaagccaa ttcttgagaa gatggacgga actgaggagc    2880
ttcttgttaa gctcaacaga gaggatcttc ttagaaagca agaactttc gataacggat     2940 ctattccaca ccaaattcac cttggagagc ttcacgctat tcttagaagg caagaggatt    3000
tctatccatt ccttaaggat aacagagaga agattgagaa gattcttact ttccgtattc    3060
catattacgt tggaccactt gctagaggaa actctagatt cgcttggatg actagaaagt    3120
ctgaggagac tattactcct tggaacttcg aggaggttgt tgataaggga gcttctgctc    3180
aatctttcat tgagagaatg actaacttcg ataagaacct tccaaacgag aaggttcttc    3240
caaagcactc tcttctttac gagtatttca ctgtttataa cgagcttact aaggttaagt    3300
acgttactga gggaatgaga aagccagctt cctttctgg agagcaaaag aaggctattg      3360
ttgatcttct tttcaagact aacagaaagg ttactgttaa gcaacttaag gaggattatt    3420
tcaagaagat tgagtgcttc gattctgttg agtttctgg agttgaggat agattcaacg      3480
cttctcttgg aacttatcac gatcttctta agattattaa ggataaggat ttccttgata    3540
acgaggagaa cgaggatatt cttgaggata ttgttcttac tcttactctt ttcgaggata    3600
gagagatgat tgaggagaga cttaagactt acgctcacct tttcgacgat aaggttatga    3660
agcaacttaa gaagaagaga tatactggat ggggtagact ttctagaaag ctcattaacg    3720
gaattagaga taagcaatct ggaaagacta ttcttgattt ccttaagtct gacggattcg    3780
ctaacagaaa cttcatgcaa cttattcacg acgattctct tactttcaag gaggatattc    3840
aaaaggctca agtttctgga caaggagatt ctcttcacga gcacattgct aaccttgctg    3900
gatctccagc tattaagaag ggaattcttc aaactgttaa ggttgttgac gagcttgtta    3960
aggttatggg tagacacaag ccagagaaca ttgttattga gatggctaga gagaaccaaa    4020
ctactcaaaa gggacaaaag aactctagag agagaatgaa gagaattgag gagggaatta    4080
aggagcttgg atctcaaatt cttaaggagc acccagttga gaacactcaa cttcaaaacg    4140
agaagctcta tctttattat cttcaaaacg gaagagatat gtacgttgat caagagcttg    4200
atattaacag actttctgat tacgacgttg atcacattgt tccacaatct ttccttaagg    4260
acgattctat tgataacaag gttcttacta gatctgataa gaacagagga agtctgata     4320 acgttccatc tgaggaggtt gttaagaaga tgaagaacta ttggagacaa cttcttaacg    4380
ctaagctcat tactcaaaga aagttcgata accttactaa ggctgagaga ggaggacttt    4440
ctgagcttga taaggctgga ttcattaaga gacaacttgt tgagactaga caaattacta    4500
agcacgttgc tcaaattctt gattctagaa tgaacactaa gtacgacgag aacgataagc    4560
tcattagaga ggttaaggtt attactctta agtctaagct cgtttctgat ttcagaaagg    4620
atttccaatt ctataaggtt agagagatta caactatca ccacgctcac gacgcttatc     4680
ttaacgctgt tgttggaact gctcttatta agaagtatcc aaaacttgag tctgagttcg    4740
tttacggaga ttataaggtt tacgacgtta gaaagatgat tgctaagtct gagcaagaga    4800
ttggaaaggc tactgctaag tatttcttct attctaacat tatgaacttc ttcaagactg    4860
agattactct tgctaacgga gagattagaa agaggccact tattgagact aacgagagaa    4920
ctggagagat tgtttgggat aagggaagag atttcgctac tgttagaaag gttctttcta    4980
tgccacaagt taacattgtt aagaaaactg aggttcaaac tggaggattc tctaaggagt    5040
ctattcttcc aaagagaaac tctgataagc tcattgctag aaagaaggat tgggacccaa    5100
```

```
agaagtacgg aggattcgat tctccaactg ttgcttattc tgttcttgtt gttgctaagg    5160
ttgagaaggg aaagtctaag aagctcaagt ctgttaagga gcttgttgga attactatta    5220
tggagagatc ttctttcgag aagaacccag ttgatttcct tgaggctaag ggatataagg    5280
aggttaagaa ggatcttatt attaagctcc caaagtattc tcttttcgag cttgagaacg    5340
gaagaaagag aatgcttgct tctgctggag agcttcaaaa gggaaacgag cttgctcttc    5400
catctaagta cgttaacttc ctttatcttg cttctcacta cgagaagctc aagggatctc    5460
cagaggataa cgagcaaaag caacttttcg ttgagcaaca caagcactat cttgacgaga    5520
ttattgagca aatttctgag ttctctaaga gagttattct tgctgacgct aaccttgata    5580
aggttctttc tgcttataac aagcacagag ataagccaat tagagagcaa gctgagaaca    5640
ttattcacct tttcactctt actaaccttg gtgctccagc tgctttcaag tatttcgata    5700
ctactattga tagaaagaga tatacttcta ctaaggaggt tcttgacgct actcttattc    5760
accaatctat tactggactt tacgagacta gaattgatct ttctcaactt ggaggagatt    5820
cttctccacc aaagaagaag agaaaggttt cttggaagga cgcttctgga tggtctagaa    5880
tgtgacgtcg cgtgatcgtt caaacatttg gcaataaagt ttcttaagat tgaatcctgt    5940
tgccggtctt gcgatgatta tcatataatt tctgttgaat tacgttaagc atgtaataat    6000
taacatgtaa tgcatgacgt tatttatgag atgggttttt atgattagag tcccgcaatt    6060
atacatttaa tacgcgatag aaaacaaaat atagcgcgca aactaggata aattatcgcg    6120
cgcggtgtca tctatgttac tagatctgca gatcggaccc ctaattagct aaaagcttcg    6180
ttgaacaacg gaaactcgac ttgccttccg cacaatacat catttcttct tagcttttt    6240 tcttcttctt cgttcataca gtttttttt gtttatcagc ttcatttttc ttgaaccgta    6300
gctttcgttt tcttcttttt aactttccat tcggagtttt tgtatcttgt ttcatagttt    6360
gtcccaggat tagaatgatt aggcatcgaa ccttcaagaa tttgattgaa taaaacatct    6420
tcattcttaa gatatgaaga taatcttcaa aaggccctg ggaatctgaa agaagagaag    6480
caggcccatt tatatgggaa agaacaatag tatttcttat ataggcccat ttaagttgaa    6540
aacaatcttc aaaagtccca catcgcttag ataagaaaac gaagctgagt ttatatacag    6600
ctagagtcga agtagtgatt ggaaaagttg tagactgaga gttttagagc tagaaatagc    6660
aagttaaaat aaggctagtc cgttatcaac ttgaaaaagt ggcaccgagt cggtgctttt    6720
tttttaagct tcgttgaaca acggaaactc gacttgcctt ccgcacaata catcatttct    6780 tcttagctttt ttttcttctt cttcgttcat acagtttttt tttgtttatc agcttacatt    6840
ttcttgaacc gtagctttcg ttttcttctt tttaactttc cattcggagt ttttgtatct    6900
tgtttcatag tttgtcccag gattagaatg attaggcatc gaaccttcaa gaatttgatt    6960
gaataaaaca tcttcattct taagatatga agataatctt caaaaggccc ctgggaatct    7020
gaaagaagag aagcaggccc atttatatgg gaaagaacaa tagtatttct tatataggcc    7080
catttaagtt gaaaacaatc ttcaaaagtc ccacatcgct tagataagaa aacgaagctg    7140
agtttatata cagctagagt cgaagtagtg attgcagtga tgaacaatga cgggttttag    7200
agctagaaat agcaagttaa aataaggcta gtccgttatc aacttgaaaa agtggcaccg    7260
agtcggtgct tttttttggg cgcgcctaaa gcttctggca gacaaagtgg cagacatact    7320
gtcccacaaa tgaagatgga atctgtaaaa gaaaacgcgt gaaataatgc gtctgacaaa    7380
ggttaggtcg gctgcctta atcaataccc aagtggtccc taccacgatg gaaaaactgt    7440
gcagtcggtt tggcttttc tgacgaacaa ataagattcg tggccgacag gtggggtcc    7500
```

-continued

```
accatgtgaa ggcatcttca gactccaata atggagcaat gacgtaaggg cttacgaaat    7560
aagtaagggt agtttgggaa atgtccactc acccgtcagt ctataaatac ttagcccctc    7620
cctcattgtt aagggagcaa ggatcctaaa ccatgattga acaagatgga ttgcacgcag    7680
gttctccggc cgcttgggtg gagaggctat tcggctatga ctgggcacaa cagacaatcg    7740
gctgctctga tgccgccgtg ttccggctgt cagcgcaggg gcgcccggtt cttttttgtca   7800 agaccgacct gtccggtgcc ctgaatgaac tgcaggacga ggcagcgcgg ctatcgtggc    7860
tggccacgac gggcgttcct tgcgcagctg tgctcgacgt tgtcactgaa gcgggaaggg    7920
actggctgct attgggcgaa gtgccggggc aggatctcct gtcatctcac cttgctcctg    7980
ccgagaaagt atccatcatg gctgatgcaa tgcggcggct gcatacgctt gatccggcta    8040
cctgcccatt cgaccaccaa gcgaaacatc gcatcgagcg agcacgtact cggatggaag    8100
ccggtcttgt cgatcaggat gatctggacg aagagcatca ggggctcgcg ccagccgaac    8160
tgttcgccag gctcaaggcg cgcatgcccg acggcgagga tctcgtcgtg acccatggcg    8220
atgcctgctt gccgaatatc atggtggaaa atggccgctt ttctggattc atcgactgtg    8280
gccggctggg tgtggcggac cgctatcagg acatagcgtt ggctacccgt gatattgctg    8340
aagagcttgg cggcgaatgg gctgaccgct tcctcgtgct ttacggtatc gccgctcccg    8400
attcgcagcg catcgccttc tatcgccttc ttgacgagtt cttctgatga gagctctaga    8460
tccccgaatt tccccgatcg ttcaaacatt tggcaataaa gtttcttaag attgaatcct    8520
gttgccggtc ttgcgatgat tatcatataa tttctgttga attacgttaa gcatgtaata    8580
attaacatgt aatgcatgac gttatttatg agatgggttt ttatgattag agtcccgcaa    8640
ttatacattt aatacgcgat agaaaacaaa atatagcgcg caaactagga taaattatcg    8700
cgcgcggtgt catctatgtt actagatcgg gaattgggta ccctaattag ctaaattcca    8760
aaattttcag ttagtcctta ctaattatta aattatagta ttaatccaat gtgattgcgg    8820
ttacatcatg tacggaaaaa taattctaat ccttgattta aatttgatct tgactattta    8880
tttattcttt atttcatttt gtaaatcatt ttatgtatct cctggcaagc aattttatcc    8940
accttgcacc aacaccttcg ggttccataa tcaaaccacc ttaacttcac accatgctgt    9000
aactcacacc gcccagcatc tccaatgtga aagaagctaa aatttaataa acaatcatac    9060
gaagcagtga caaaatacca gatggtatta atgctttgat aaaattaatt ggaaagtata    9120
aaatggtaga aaataataaa ttataattaa tttaaataag ataaaaaata attaaaaact    9180
aaaatgttaa aattttaaaa aaattatttt aaataatatt taaaaacatt aaaaatcatt    9240
ttaaaaaatt tatttataga acaattaaat aaatatttca gctaataaaa acaaaagct    9300 tacctagcct tagaagacaa cttgtccaac aattagatga tacccattgc ccttacgttt    9360
tctttaacat caattattgt ttttgtcaac aagctatctt ttagttttat tttattggta    9420
aaaaatatgt cgccttcaag ttgcatcatt taacacatct cgtcattaga aaataaaac    9480 tcttccctaa acgattagta gaaaaaatca ttcgataata aataagaaag aaaaattaga    9540
aaaaaataac ttcattttaa aaaaatcatt aaggctatat ttttttaaatg actaatttta    9600 tatagactgt aactaaaagt atacaattta ttatgctatg tatcttaaag aattacttat    9660
aaaaatctac ggaagaatat cttacaaagt gaaaaacaaa tgagaaagaa tttagtggga    9720
tgattatgat tttatttgaa aattgaaaaa ataattatta aagactttag tggagtaaga    9780
aagctttcct attagtcttt tcttatccat aaaaaaaaaa aaaatctag cgtgacagct    9840
```

```
tttccataga ttttaataat gtaaaatact ggtagcagcc gaccgttcag gtaatggaca      9900
ctgtggtcct aacttgcaac gggtgcgggc ccaatttaat aacgccgtgg taacggataa      9960
agccaagcgt gaagcggtga aggtacatct ctgactccgt caagattacg aaaccgtcaa     10020
ctacgaagga ctccccgaaa tatcatctgt gtcataaaca ccaagtcaca ccatacatgg     10080
gcacgcgtca caatatgatt ggagaacggt tccaccgcat atgctataaa atgccccac      10140 accoctcgac cctaatcgca cttcaattgc aatcaaatta gttcattctc tttgcgcagt     10200
tccctacctc tcctttcaag gttcgtagat ttcttctgtt ttttttcctt cttctttatt     10260
gtttgttcta catcagcatg atgttgattt gattgtgttt tctatcgttt catcgattat     10320 aaatttcat aatcagaaga ttcagctttt attaatgcaa gaacgtcctt aattgatgat     10380
tttataaccg taaattaggt ctaattagag ttttttcat aaagattttc agatccgttt     10440
acaacaagcc ttaattgttg attctgtagt cgtagattaa ggttttttc atgaactact     10500 tcagatccgt taaacaacag ccttatttgt tgatacttca gtcgtttttc aagaaattgt     10560
tcagatccgt tgataaaagc cttattcgtt gattctgtat ggtatttcaa gagatattgc     10620
tcaggtcctt tagcaactac cttatttgtt gattctgtgg ccatagatta ggattttttt     10680
tcacgaaatt gcttcttgaa attacgtgat ggattttgat tctgatttat cttgtgattg     10740
ttgactctac agagatctaa aaaaatggcc ctgtccaaca agttcatcgg cgacgacatg     10800
aagatgacct accacatgga cggctgcgtg aacggccact acttcaccgt gaagggcgag     10860
ggcagcggca agcctacga gggcacccag acctccacct tcaaggtgac gatggccaac     10920
ggcggccccc tggccttctc cttcgacatc ctgtccaccg tgttcatgta cggcaaccgc     10980
tgcttcaccg cctaccccac cagcatgccc gactacttca gcaggcctt ccccgacggc     11040 atgtcctacg agagaacctt cacctacgag gacggcggcg tggccaccgc cagctgggag     11100
atcagcctga agggcaactg cttcgagcac aagtccacct tccacggcgt gaacttcccc     11160
gccgacggcc ccgtgatggc caagaagacc accggctggg atccctcctt cgagaagatg     11220
accgtgtgcg acggcatctt gaagggcgac gtgaccgcct tcctgatgct gcagggcggc     11280
ggcaactaca gatgccagtt ccacacctcc tacaagacca agaagcccgt gaccatgccc     11340
cccaaccacg tggtggagca ccgcatcgcc agaaccgacc tggacaaggg cggcaacagc     11400
gtgcagctga ccgagcacgc cgtggcccac atcacctccg tggtgccctt ctgatgaact     11460
agtgaattcg agctcaagct ttcgttcgta tcatcggttt cgacaacgtt cgtcaagttc     11520
aatgcatcag tttcattgcg cacacaccag aatcctactg agtttgagta ttatggcatt     11580
gggaaaactg ttttttcttgt accatttgtt gtgcttgtaa tttactgtgt ttttattcg      11640 gttttcgcta tcgaactgtg aaatggaaat ggatggagaa gagttaatga atgatatggt     11700
ccttttgttc attctcaaat taatattatt tgtttttct cttatttgtt gtgtgttgaa      11760
tttgaaatta taagagatat gcaaacattt tgttttgagt aaaaatgtgt caaatcgtgg     11820
cctctaatga ccgaagttaa tatgaggagt aaaacacttg tagttgtacc attatgctta     11880
ttcactaggc aacaaatata ttttcagacc tagaaaagct gcaaatgtta ctgaatacaa     11940
gtatgtcctc ttgtgtttta gacatttatg aactttcctt tatgtaattt tccagaatcc     12000
ttgtcagatt ctaatcattg ctttataatt atagttatac tcatggattt gtagttgagt     12060
atgaaaatat ttttaatgc attttatgac ttgccaattg attgacaaca tgcatcaatc     12120
ggaccgttaa ctagctagac ggccaggatc gccgcgtgag cctttagcaa ctagctagat     12180
taattaaacg tccgcaatgt gttattaagt tgtctaagcg tcaatttgtt tacaccacaa     12240
```

```
tatatcctgc caccagccag ccaacagctc cccgaccggc agctcggcac aaaatcacca  12300
ctcgatacag gcagcccatc agtccgggac ggcgtcagcg ggagagccgt tgtaaggcgg  12360
cagactttgc tcatgttacc gatgctattc ggaagaacgg caactaagct gccgggtttg  12420
aaacacggat gatctcgcgg agggtagcat gttgattgta acgatgacag agcgttgctg  12480
cctgtgatca aatatcatct ccctcgcaga gatccgaatt atcagccttc ttattcattt  12540
ctcgcttaac cgtgacaggc tgtcgatctt gagaactatg ccgacataat aggaaatcgc  12600
tggataaagc cgctgaggaa gctgagtggc gctatttctt tagaagtgaa cgtcgactca  12660
tgtttgacag cttatcatcg actgcacggt gcaccaatgc ttctggcgtc aggcagccat  12720
cggaagctgt ggtatggctg tgcaggtcgt aaatcactgc ataattcgtg tcgctcaagg  12780
cgcactcccg ttctggataa tgttttttgc gccgacatca taacggttct ggcaaatatt  12840
ctgaaatgag ctgttgacaa ttaatcatcc ggctcgtata atgtgtggaa ttgtgagcgg  12900
ataacaattt cacacaggaa acagaccatg agggaagcgt tgatcgccga agtatcgact  12960
caactatcag aggtagttgg cgtcatcgag cgccatctcg aaccgacgtt gctggccgta  13020
catttgtacg gctccgcagt ggatggcggc ctgaagccac acagtgatat tgatttgctg  13080
gttacggtga ccgtaaggct tgatgaaaca acgcggcgag ctttgatcaa cgacctttg   13140 gaaacttcgg cttcccctgg agagagcgag attctccgcg ctgtagaagt caccattgtt  13200
gtgcacgacg acatcattcc gtggcgttat ccagctaagc gcgaactgca atttggagaa  13260
tggcagcgca atgacattct tgcaggtatc ttcgagccag ccacgatcga cattgatctg  13320
gctatcttgc tgacaaaagc aagagaacat agcgttgcct tggtaggtcc agcggcggag  13380
gaactctttg atccggttcc tgaacaggat ctatttgagg cgctaaatga aaccttaacg  13440
ctatggaact cgccgcccga ctgggctggc gatgagcgaa atgtagtgct tacgttgtcc  13500
cgcatttggt acagcgcagt aaccggcaaa atcgcgccga aggatgtcgc tgccgactgg  13560
gcaatggagc gcctgccggc ccagtatcag cccgtcatac ttgaagctag gcaggcttat  13620
cttggacaag aagatcgctt ggcctcgcgc gcagatcagt tggaagaatt tgttcactac  13680
gtgaaaggcg agatcaccaa agtagtcggc aaataaagct ctagtggatc tccgtacccg  13740
aggaatcggc gtgagcggtc gcaaaccatc cggcccggta caaatcggcg cggcgctggg  13800
tgatgacctg gtggagaagt tgaaggccgc gcaggccgcc cagcggcaac gcatcgaggc  13860
agaagcacgc cccggtgaat cgtggcaagc ggccgctgat cgaatccgca aagaatcccg  13920
gcaaccgccg cagccggtg cgccgtcgat taggaagccg cccaagggcg acgagcaacc   13980 agatttttc gttccgatgc tctatgacgt gggcacccgc gatagtcgca gcatcatgga   14040
cgtggccgtt ttccgtctgt cgaagcgtga ccgacgagct ggcgaggtga tccgctacga  14100
gcttccagac gggcacgtag aggtttccgc agggccggcc ggcatggcca gtgtgtggga  14160
ttacgacctg gtactgatgg cggtttccca tctaaccgaa tccatgaacc gataccggga  14220
agggaaggga gacaagcccg ccgcgtgtt ccgtccacac gttgcggacg tactcaagtt    14280
ctgccggcga gccgatggcg gaaagcagaa agacgacctg gtagaaacct gcattcggtt  14340
aaacaccacg cacgttgcca tgcagcgtac caagaaggcc aagaacggcc gcctggtgac  14400
ggtatccgag ggtgaagcct tgattagccg ctacaagatc gtaaagagcg aaaccgggcg  14460
gccggagtac atcgagatcg agctggctga ttggatgtac cgcgagatca cagaaggcaa  14520
gaacccggac gtgctgacgg ttcaccccga ttacttttg atcgatcccg gcatcggccg  14580
```

```
ttttctctac cgcctggcac gccgcgccgc aggcaaggca gaagccagat ggttgttcaa    14640
gacgatctac gaacgcagtg gcagcgccgg agagttcaag aagttctgtt tcaccgtgcg    14700
caagctgatc gggtcaaatg acctgccgga gtacgatttg aaggaggagg cggggcaggc    14760
tggcccgatc ctagtcatgc gctaccgcaa cctgatcgag ggcgaagcat ccgccggttc    14820
ctaatgtacg gagcagatgc tagggcaaat tgccctagca ggggaaaaag gtcgaaaagg    14880
actctttcct gtggatagca cgtacattgg gaacccaaag ccgtacattg ggaaccggaa    14940
cccgtacatt gggaacccaa agccgtacat tgggaaccgg acacacatgt aagtgactga    15000
tataaaagag aaaaaggcg attttccgc ctaaaactct ttaaaactta ttaaaactct    15060
taaaacccgc ctggcctgtg cataactgtc tggccagcgc acagccgaag agctgcaaaa    15120
agcgcctacc cttcggtcgc tgcgctccct acgccccgcc gcttcgcgtc ggcctatcgc    15180
ggccgctggc cgctcaaaaa tggctggcct acggccaggc aatctaccag ggcgcggaca    15240
agccgcgccg tcgccactcg accgccggcg ctgaggtctg cctcgtgaag aaggtgttgc    15300
tgactcatac caggccatta atgaatcggc caacgcgcgg ggagaggcgg tttgcgtatt    15360
gggcgctctt ccgcttcctc gctcactgac tcgctgcgct cggtcgttcg gctgcggcga    15420
gcggtatcag ctcactcaaa ggcggtaata cggttatcca cagaatcagg gataacgca    15480 ggaaagaaca tgtgagcaaa aggccagcaa aaggccagga accgtaaaaa ggccgcgttg    15540
ctggcgtttt tccataggct ccgcccccct gacgagcatc acaaaaatcg acgctcaagt    15600
cagaggtggc gaaacccgac aggactataa agataccagg cgtttccccc tggaagctcc    15660
ctcgtgcgct ctcctgttcc gaccctgccg cttaccggat acctgtccgc ctttctccct    15720
tcgggaagcg tggcgctttc tcatagctca cgctgtaggt atctcagttc ggtgtaggtc    15780
gttcgctcca agctgggctg tgtgcacgaa ccccccgttc agcccgaccg ctgcgcctta    15840
tccggtaact atcgtcttga gtccaacccg gtaagacacg acttatcgcc actggcagca    15900
gccactggta acaggattag cagagcgagg tatgtaggcg gtgctacaga gttcttgaag    15960
tggtggccta actacggcta cactagaaga acagtatttg gtatctgcgc tctgctgaag    16020
ccagttacct tcggaaaaag agttggtagc tcttgatccg gcaaacaaac caccgctggt    16080
agcggtggtt ttttgtttg caagcagcag attacgcgca gaaaaaaagg atctcaagaa    16140
gatcctttga tcttttctac ggggtctgac gctcagtgga acgaaaactc acgttaaggg    16200
attttggtca tgagattatc aaaaaggatc ttcacctaga tccttttgat ccggacaaac    16260
aaacaaatac agtaattta                                                16279
```

<210> SEQ ID NO 99
<211> LENGTH: 104
<212> TYPE: DNA
<213> ORGANISM: Zea mays

<400> SEQUENCE: 99

```
gtggagaatg cagagccatg gatcgcattc atggagtagc cacagggttc aaagtcaaaa    60
tcgcagatct ccatctcggg gatgatttca gagatgccag agag                     104
```

<210> SEQ ID NO 100
<211> LENGTH: 202
<212> TYPE: DNA
<213> ORGANISM: Zea mays
<220> FEATURE:
<221> NAME/KEY: misc_feature
<222> LOCATION: (24)..(24)
<223> OTHER INFORMATION: n is a, c, g, or t

```
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (135)..(136)
<223> OTHER INFORMATION: n is a, c, g, or t

<400> SEQUENCE: 100
cgagagacca gatcaacagc ttcnggnggc atnccttttg tggaanacct gaaagataaa      60
atgtacaaaa agtaaattag taanacaaca gtaacagttt ttttagagta ttgtaacaaa     120
atgtagaaag atttnngcac cttgtgccat gggtgtgctt tgatttgtgg gaacttaaac     180
tctgtgtaat ttgggttcat gc                                              202

<210> SEQ ID NO 101
<211> LENGTH: 201
<212> TYPE: DNA
<213> ORGANISM: Zea mays ;

<400> SEQUENCE: 101
gtcttcaaac ttgcagtgac gaatttcaat gtgcgtgatt ggaaccttt cgatggtggc       60 ccttgaacca gagtggataa tctctccaaa atcagatgta gagcatctgg ttgacatacg     120
gaagactact acctgttttc tagatttaca attcattgtc agaaattatg ctatctgact     180
taatcttcca aatactccta t                                              201

<210> SEQ ID NO 102
<211> LENGTH: 185
<212> TYPE: DNA
<213> ORGANISM: Zea mays ;
<220> FEATURE:
<221> NAME/KEY: misc_feature
<222> LOCATION: (93)..(93)
<223> OTHER INFORMATION: n is a, c, g, or t

<400> SEQUENCE: 102
agcgtgccca tgccggagcc ggtgccgccg ccgagagagt ggcagacctg gaagcctgac      60
aggcgggcat aagatcccag tcagcaaacc aancaacctt gcagaaatgg aagacgagac     120
gagacaagca ataaccaac caaccttgca ggcagtcgca gttctcggcc tcctttcgca     180
ccacg                                                                185

<210> SEQ ID NO 103
<211> LENGTH: 201
<212> TYPE: DNA
<213> ORGANISM: Zea mays ;

<400> SEQUENCE: 103
tcgaccgcag ygtggaatgc actggcaaca tyaatgctat gatccaagct ttcgaatgtg      60
ttcatgatgt aagtatatgt atacactctc agctactttc attctccagg ttcccttcat    120
```

```
ccagacatgc atgttctaac ygccgcsctc gtgatccagg gctggggtgt tgcygtgctg      180
gtgggtgtgc crcataagga c                                               201

<210> SEQ ID NO 104
<211> LENGTH: 99
<212> TYPE: DNA
<213> ORGANISM: Zea mays ;

<400> SEQUENCE: 104
gcagtcgagc gacgactagg aagaggaggt gatcgatgag aacggcgaaa ttgtcaagag       60
gaagaagaag ggccttaagg agaaggtcaa ggagaagct                              99

<210> SEQ ID NO 105
<211> LENGTH: 231
<212> TYPE: DNA
<213> ORGANISM: Zea mays ;

<400> SEQUENCE: 105
cgcttccaca ccgggagcac attggacgcc gcgtcacaag aaggtataca cagcatggtc       60
aaattgtttg cctctgtggt cgtgcactcg tgcatgcatg cggacagtgc ccatgcttca      120
gtcatgttga gttgagttct gcttgccggc ctgtgatgtt atttgttctt gttcaatcat      180
atcgcaactg gcagtgctgt ccgacgagcg cgacgccgcg gccagcggcg g               231

<210> SEQ ID NO 106
<211> LENGTH: 101
<212> TYPE: DNA
<213> ORGANISM: Zea mays ;

<400> SEQUENCE: 106
gcgagcacat acgtcgtgga cacattcgaa ggcggatatc atggcgttga tgttaccggt       60
gcactccacg ctgcggtcga cgccgccgtt ggtcagctca a                          101

<210> SEQ ID NO 107
<211> LENGTH: 201
<212> TYPE: DNA
<213> ORGANISM: Zea mays ;

<400> SEQUENCE: 107
ggttgtcacc tttsaratcg agtagactgc catcagtgcc atgacttatt ggcaarttgg       60
agtcttttag ggtccacttg ttttccttga attctgcaag ctgaatttgc tttttttgttg     120 acttcaatam tccaaccart tctcgaayga cbrccatgcy attcttcgcc ttgtgctctc      180
tgagatagag tggagtcatg a                                                201

<210> SEQ ID NO 108
<211> LENGTH: 889
<212> TYPE: DNA
<213> ORGANISM: Zea mays ;

<400> SEQUENCE: 108
gaatattcat ggggcggtta caagatggca ggtgaggaca ggcaggaaga tgaacaagac       60
gacaagagcc gacgtagtcg tccaaggatt cgatcaggat attcctccaa gatgacaaag      120
accacaaaaa tagttgcttc ttcagacgtg aaccaatttt aaaactaatt gcataagagg      180
tgattaatta gcaagacaaa actattagct ctagttagct cttgaaggca tataataata     240
tagcatgata tgaactaatt atgggctaca tattcagaat taataggttt gtctcgtcaa      300
ttaatcactg tttacttgca cagtagagca agagcaagcg cagagaacag ggcataata      360
```

-continued

```
aactgctgcg ggtggtgtac ctaaaccatg atccaatatt acatcccctt atgctgactc    420
cagcagttca tcaaaacttt acccataaac aatgttttac actatagatt gcactattcg    480
taaaatagag tttgaatatg agtatgaata tgtataagct gttggagata gtcttaatac    540
ctagtttaat tactctagta taaacctcaa tctacatgta ttaaggtaga ttggagtgta    600
acttaaacta atttatatcc caatccacct caacatacat aactatagtc tatcgtacaa    660
tatctaaatg aagcctaaag acaacgttta ggataaggaa cgtgttaaac agcccaaaag    720
cattatgact ccatgagtcc aacggcccaa tagcacgaga catcgcaaca tgcccgctcc    780
ccaacaactg tagcacctga tttgattggt acaaaaatta tgatgacgtc ccatttgcag    840
acatcgagca tattgcccaa taccettgtt tgaaattcaa aatttgaat                 889
```

<210> SEQ ID NO 109
<211> LENGTH: 824
<212> TYPE: DNA
<213> ORGANISM: Zea mays ;
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (349)..(370)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (392)..(394)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (666)..(666)

```
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (752)..(752)
<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t

<400> SEQUENCE: 109
catatgaaaa atcnctggtt ccgctttcgt tttttnngca tacctaataa ccaacctctg      60
catctgcttc aggttcgtac ttttgaggcg caatgtgggt cgttggcgca gtatgggatg     120
aagcacatgc ggtccttcgc aaacatctgc aacgctggca tccttcctga ngcagtgtcg     180
aaggtcgctg ctcaggcttg caccagcatt ccttccaacc cctggagttc tatccacaag     240
ggttttagcg cctaagaatc ataaggtgag gcgaaatatt tcagccgctc caccgcaacg     300
aactggttta cattaccagt cctcagggggg gtcctagttc ttgaaccann nnnnnnnnn      360
nnnnnnnnnn ctantatagc tgttccaccg tnnntccaga ttacatagct atgcncaatt     420
tccggtgtac atatnatagt cggaaagtta tttggcaatt gtattggtcg ttgctgtata     480
tattccctat agtttgttag cagatgtgta gtttgtnatt ccataaaaat gaagaacgcg     540
ttactgctat ttctatgtag ccgactgntg ctcatgtgaa actttacccc attcttgttg     600
ggaaatgnac tatccgtggt ggaattctng catcgaaaac aattcccggg ngatcctta     660
ttcaangtga ancgtctgtc natttccatt tgaggntcgt attattttca nttgtaggct     720
tgtggctggt ggcatctgtt ccactatgnt tncaaacaag nnctatgggc agtttcattt     780
gtttcgttct ctatatncct gcagcaccta cccatggaaa aaat                     824

<210> SEQ ID NO 110
<211> LENGTH: 643
<212> TYPE: DNA
<213> ORGANISM: Zea mays ;
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
```

```
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (349)..(352)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
```

<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (464)..(465)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t

<400> SEQUENCE: 110

```
tcnngnangn angtgtttat ttnacctnca gattccacct ttgtttcttc tatatttaca    60
tggtaccttg naggttcttg ctctttgtga tnatccgtgc ctctnggaaa aagaggaaac   120
caaatcattg ttcaggtgaa tatcntcatc nttcaattta cagaactcct aaattcanag   180
atctagtgng tgatatcntg ctattttncc caacttnagt gtcaaagcaa cctaaaaatt   240
ctaaaaaata cagagatagg gcaatctgtc ttcctttaaa atcaaagctg tggcattttc   300
tttgaaatta gtaaacattt atataaatag taaaatntcn tggagatcnn nnaggtantt   360
aacnttttc ccttcaactt ccacagtaat taaacatacc taggaanata gttttngagt   420
tctcatgttt aattgatntg ttcatcanaa gaaccattac ntcnntgcct aattatgcat   480
gcccttnat ttttcctaaa atttcccttg ataccatttc aagttgcaaa gatgantttt   540
ttttncttcg tactgtttaa tatttttgtt agccataaac tttcaaaant agttcagtgt   600
cccatttata cataaatnct tatgtgtacn tgatgggtcg nct                     643
```

<210> SEQ ID NO 111
<211> LENGTH: 201

```
<212> TYPE: DNA
<213> ORGANISM: Zea mays ;
<220> FEATURE:
<221> NAME/KEY: misc_feature
<222> LOCATION: (189)..(191)
<223> OTHER INFORMATION: n is a, c, g, or t

<400> SEQUENCE: 111
atttatgtgc ctyyaggcga accacttyca tcygaacctg gcgagccgtt gagagtgaac      60
gtgctmttca agcatattca ggcaatgctg tcyggcgaca cggctgtcat cgcagagact     120
ggggactcgt ggtttaactg ccagaagctg aagctaccgg aaggmtgtgg gtaagctcct    180
ctttcgaann ntgrttttgc t                                               201

<210> SEQ ID NO 112
<211> LENGTH: 300
<212> TYPE: DNA
<213> ORGANISM: Zea mays ;

<400> SEQUENCE: 112
gcacagaact ctcccctgtc ctttcctggg gttttggtta cgtggtggta gtaagcttgg      60
atttgcacat ggataaagtt gttctaagct ccgtgggttg cttgagatct tgctgttatt    120
gcgtgccgtc ctcactttt tgcaatccg aggaatgaat ttgtcgttta ctcgttttgg     180
tggattatta gcgcgaaaaa aaaactcttt ttttttgtt cttttactac gaaaagcatc     240
ttcttggatt ttgctatctt cttttactac gaaaaactct tgagtctagg aatttgaatt    300

<210> SEQ ID NO 113
<211> LENGTH: 193
<212> TYPE: DNA
<213> ORGANISM: Zea mays ;

<400> SEQUENCE: 113
ggctattgta caacaacaag gcggcattgc catcrcagtt gcagtactas caattgccwt      60
cgkgattgcg gttgcggtgt tgcagtagta gtgctgtagt actatcaagt gagtctgatg    120
catgamcaga gcagayggag tagttaaacg gaggcgccgg tgagcttgcc gttgacgatg    180
tggtggttgt cgt                                                        193

<210> SEQ ID NO 114
<211> LENGTH: 201
<212> TYPE: DNA
<213> ORGANISM: Zea mays ;

<400> SEQUENCE: 114
rgacacggag gagcagtacg acttcgaccc gctggacgac accaagacgt ggccggagga      60
cctgctsccg ctcmgscccg tggggaggct ggtgctggac cggaacgtgg acaacttctt    120
caacgagaac gagcagctgg cgttcggscc ggggctggtg gtgccaggga tctactactc    180
ggacgacaag atgctgcagt g                                               201

<210> SEQ ID NO 115
<211> LENGTH: 199
<212> TYPE: DNA
<213> ORGANISM: Zea mays ;

<400> SEQUENCE: 115
atgaactatg aagaaccta tcactttgag ctagtctcaa gtccaagcaa agakaacaat       60
tcaccagtag taatggaaag agaagattag caataactat tgtttagtgg agcaataaat    120
```

```
atctttttca gtttcaagtm ttaagagaga aaatgataga tgtaaatggc aagcacctac    180
tgtacttgac aacgttaaa                                                 199
```

<210> SEQ ID NO 116
<211> LENGTH: 795
<212> TYPE: DNA
<213> ORGANISM: Zea mays ;
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (130)..(137)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature

```
<222> LOCATION: (677)..(677)
<223> OTHER INFORMATION: n is a, c, g, or t
<220> FEATURE:
<221> NAME/KEY: misc_feature
<222> LOCATION: (691)..(693)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t

<400> SEQUENCE: 116
atagtaaaag gttggaatgt tagttgaaaa caaggtgtaa gaaatgtatc atcttttgga      60
ctggacaaca gacctgaagt agaagcttct gggtttcctc ananntggcc ctcagcttnn     120
cnccnaangn nnnnnnntcc tntgaaacga ggagtttgtc atacagtgng gcaatgccag     180
gattacccct ggngaacncc atntccncca gatcaatagt caccctgaaa aatggccact     240
cattgtacat ttcctggagc atgtggaggt tcctgatgtc cttctggagg acattcttga     300
atgcggctcc aaatcctagc cagaccggga ggtggaaccg cgtntgtgtc caagcaaaga     360
tccatgggat tgctcggagt gagtcgatac ctccgctcgg cttctcttg gatggcctgc      420 ttcctatgtt catcctacca tactctgttt caggggttgc ctgtcaacac aaacatcaca     480
aagtaaatac tcgctaaatg tagggggtcaa atcgaatgct tcagtaacca ttttacttag    540
gcttgcaaaa gatagtttct ncagtaaatc attgtgctag attaatatta agtatcaggt     600
caganctatt tcaaaagttt gttttgcat cttatgttac tgtagtatct ctagacacca      660
ctcaggtggn agcctcnagt actggtctac nnncatcttt tnatgttact gtagtatggc     720
aatcgatggg atcaaggact tacaaggcgg aaatactcga caaagcgtgg ctctttgaag     780
acaatggacc gatat                                                      795

<210> SEQ ID NO 117
<211> LENGTH: 627
<212> TYPE: DNA
<213> ORGANISM: Zea mays ;
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
```

<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (613)..(624)
<223> OTHER INFORMATION: n is a, c, g, or t

<400> SEQUENCE: 117

```
atgctctggg gtcatctcat gtctgaattc tgatccaatt gaagggttgt agctttagtg      60
caatgttgct atntttatca tgcaaacccc tttacctttt gtaacatgtc accaaacaat     120
tcatttccat tgggttgttc aaggatcatg tattcccatg caatacaacn tggagaagtc     180
angctattcc tttactattt tacgtagcag tgttggccca cgattatatt gttttaatat     240
ctgtacttca gttgaggaaa ttatattttc tgagcgatca gntaatcact tattttggtt     300
ccactacttt cctatcaggt tcttgagtct cggaatattc agcttttntt gggatatttt     360
gtgagcngca tcaaagaggc tcctacatct gatgantcaa gtagcacagt tacatactct     420
gaagttgacg gtgatcatag gaaactaatt ttggaccttc aacctgctga aagaggcctc     480
aaaggncaga cnctcgatgc tgatttggtg ctgtggacag tgggttcaac atctcagatt     540
ccncggttac agcctcctga tgctccctan gttattcctc tgaatggtcg nggacaggng     600
gagacagagg aannnnnnnn nnnnaaa                                         627
```

<210> SEQ ID NO 118
<211> LENGTH: 772
<212> TYPE: DNA
<213> ORGANISM: Zea mays ;
<220> FEATURE:
<221> NAME/KEY: misc_feature
<222> LOCATION: (52)..(57)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(76)
<223> OTHER INFORMATION: n is a, c, g, or t
<220> FEATURE:
<221> NAME/KEY: misc_feature

```
<222> LOCATION: (88)..(97)
<223> OTHER INFORMATION: n is a, c, g, or t
<220> FEATURE:
<221> NAME/KEY: misc_feature
<222> LOCATION: (99)..(109)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(119)
<223> OTHER INFORMATION: n is a, c, g, or t
<220> FEATURE:
<221> NAME/KEY: misc_feature
<222> LOCATION: (122)..(131)
<223> OTHER INFORMATION: n is a, c, g, or t
<220> FEATURE:
<221> NAME/KEY: misc_feature
<222> LOCATION: (134)..(145)
<223> OTHER INFORMATION: n is a, c, g, or t
<220> FEATURE:
<221> NAME/KEY: misc_feature
<222> LOCATION: (147)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (163)..(166)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (180)..(184)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (376)..(377)
<223> OTHER INFORMATION: n is a, c, g, or t
<220> FEATURE:
<221> NAME/KEY: misc_feature
<222> LOCATION: (425)..(427)
<223> OTHER INFORMATION: n is a, c, g, or t
<220> FEATURE:
<221> NAME/KEY: misc_feature
<222> LOCATION: (446)..(447)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
```

```
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (715)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (733)..(734)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t

<400> SEQUENCE: 118
gcatagcata ctgcatgcat ggcgctgttg cattgcaggt tgcagctgca gnnnnnncng    60
```

```
nngacccngn tgnnnncgtg cagactgnnn nnnnnnnann nnnnnnnnnc anntnnnnnt    120
annnnnnnnn ngtnnnnnnn nnnnnannnn tanataaatn tannnnagta canttttgcn    180
nnnncctgct gcctgcccta gcactagcag ccaggcagca gggctggcgc ctntgctgcg    240
gtgcatgaaa aggcgacgag caaagaaggg gcgcgtggaa aactgcccgt cgcgcgctgc    300
taccgccgta tgattggatc gagtggagcg tgcggttggc ttttggatc ctttcggcac     360 gtcaagaaat aaaaanntaa ccagttcctt tatttcatcg gtctccgact ctccaaggcg    420
gcagnnncag caagctctcg tagctnngtg taaagctgtg gagcacacag cagctgtgag    480
cctgtgttgg tgttgcgagc aagagcanag ctggcaagcg cagcanagga nttgcacacg    540
gctttatacg aatgagcaga acanaggcat ctgtacatga ngacgggcac ggcacacaca    600
caggcctttg gttcgttgga nganngtgta ttggcctcct actatactga nactgnacac    660
ccctggacat ccgcatgncc gcatctacta cgcatngata gcagcgntnt gtaannnnnn    720
tgnantggnc tcnnangcag ccatgccatg nnanccagna nncccacagc ac            772

<210> SEQ ID NO 119
<211> LENGTH: 201
<212> TYPE: DNA
<213> ORGANISM: Zea mays ;

<400> SEQUENCE: 119
cacacataat tactccmatc ttctcagtgg aggtacatca gcaaccgagg tttataaagg     60
aacrctygag gacaacacga tggtggcggt gcatagattg gtctacgagg gctctgagga    120
ggcgttcatc aacggaggga tggtygtgtc caagatcgcc cacargaaca tcgtcagagt    180
tctgggctgc tgtctggaac c                                              201

<210> SEQ ID NO 120
<211> LENGTH: 220
<212> TYPE: DNA
<213> ORGANISM: Zea mays ;
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t

<400> SEQUENCE: 120
tggatccatc acggtagagc tgacnatgat atgtccaaan gcttctgctg ctagttgttg     60
gtcgtccgca agagacttga cccnacaggt tttttcgtt gggcctcaag aactgtaggt     120
gcattttcca tggagggtta tgatgcttaa ccccactctg gtttctgatg gctaaaacat    180
tctctccagt cggcttctac catgagccct ggcacttagt                          220

<210> SEQ ID NO 121
<211> LENGTH: 301
<212> TYPE: DNA
<213> ORGANISM: Zea mays ;
<220> FEATURE:
<221> NAME/KEY: misc_feature
<222> LOCATION: (59)..(59)
<223> OTHER INFORMATION: n is a, c, g, or t
<220> FEATURE:
```

<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (181)..(186)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (294)..(296)
<223> OTHER INFORMATION: n is a, c, g, or t

<400> SEQUENCE: 121
tggctttatc cgtccggatg ccccgccatg tgctccttgt ctcgggactc ggagacagnc    60
tgacagtcct gggttnttgt gctaatggcc ntggttaact tacgttaatc ntgcgcctta   120
ttatcatcat ctaggtgtaa ttacttccgt ctgtgctaat cacctcgtga ttgcctgcaa   180
nnnnnnggaa ccccagcccc ccnaccttgc tgatgccgtg cttttctaga gaagtaccct   240
gccgcgtcac gcttcgtcct cgcctgcttt ggattcaacg gnttttttgga gncnnnggcc   300 a                                                                   301

<210> SEQ ID NO 122
<211> LENGTH: 170
<212> TYPE: DNA
<213> ORGANISM: Zea mays ;
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t

<400> SEQUENCE: 122
ggtgccggaa gccgcctaca gcggcccgcc gctcagctat tacgtcacca agttccagcc    60
ggcggtggct gcgccggcgc agaccctcga ggccccgcc cccgncgagg cacaagacgg   120
cgccgccgcc ncgtcgngn ctccggaggt accggcaccg cagctgtcgt                170

<210> SEQ ID NO 123
<211> LENGTH: 190

```
<212> TYPE: DNA
<213> ORGANISM: Zea mays ;

<400> SEQUENCE: 123
rcataaaaya ttgcaaatgc tgaggaatat aagcacatag atacttagca tgtgtccgcc      60
agatggaaat acttttacca ttcccccaca actggattgc cagaaaggtc aatgcctatg     120
acaccttggt ccatyatttc cayggctaga ttaacctggc caggggaaay aaatsatttt    180
gtgcagattc                                                            190

<210> SEQ ID NO 124
<211> LENGTH: 201
<212> TYPE: DNA
<213> ORGANISM: Zea mays ;

<400> SEQUENCE: 124
acgsygtaag ggctctactg catgttcctg aggttgctct tgacaccctc aatttgctgg     60
aaatcatccc catctrggga cataaatgga gcaaaattgc tgtgagcttg aacaaatgga    120
aggtcactgt gatggttctg aatgccatca ggcagattct gtgatgtgtt tgcttctgat    180
gaagaaggga agttccagcg g                                              201

<210> SEQ ID NO 125
<211> LENGTH: 201
<212> TYPE: DNA
<213> ORGANISM: Zea mays ;

<400> SEQUENCE: 125
tctcaagctt atttaggttg actaaatttg gaacatcccc cgagatgcta ttgccggcaa     60
gcgcgagctc cgtaagcatg gcagctttgc caatcgatgc tggtatggac cccttcagct   120
ggttactctg caaccgaaga acartgaggt tcgagaatga gtcaagccag tctggcacac   180
ttccattgaa gtagttacca t                                              201

<210> SEQ ID NO 126
<211> LENGTH: 294
<212> TYPE: DNA
<213> ORGANISM: Zea mays ;

<400> SEQUENCE: 126
tactagcaca ctttgcctcc tgatagcttg taccattgtg accttgtttg gattttggga     60
ttccacccaa tgtcaaacat acccaaacag tgaccccgtka tcttttttctt cgtatttcta   120 tgtcaagcac tyaagcataa ctcatacact tgcctctaca ggtgtttctg aaacactagt   180
gctcaatatg tcaactctga catggtcagt tgttagcact gtggaaggac gtgttcctct   240
tgccagtgag gtatwtctct tgagcggttg agcagcattc cagttgttaa gatg         294

<210> SEQ ID NO 127
<211> LENGTH: 214
<212> TYPE: DNA
<213> ORGANISM: Zea mays ;

<400> SEQUENCE: 127
gcacaggtaa ctcttgcatg gcacctgtcc tgaaacaagt ttcgtgctaa caagggaaat    60
tatccttttt cgtggcacca atatctgttt tccattcaat gatgtactga tgtgttcacg   120
gagtcgttac ctagaaatct cgcttactgc gacatatcac accgagcatc attttatatc   180
tgctgtgygc cctccttgct aatgtaggca cctg                                214
```

<210> SEQ ID NO 128
<211> LENGTH: 300
<212> TYPE: DNA
<213> ORGANISM: Zea mays ;

<400> SEQUENCE: 128
rytkcaacmt gcgagaarta raaaatcact aaccttggct ttatcaagta tagcaaggtg      60
aamgcgaatg ccargaagaa gcagagtccr ccgacgrtga ggtacgcaag cccagaaaa     120 tcgttctttc ccccgagcca ggttgcggta gaaagcacca gcttcttctt gccaccaaag    180
ctataggtgt tgtagttgtt gtccarctgg actgtgattg trtcgttttc cttgagatca    240
acatatatcc ttccatacag cttctgaat gtcggaagtg ctgyagtccg catccaaaca     300

<210> SEQ ID NO 129
<211> LENGTH: 287
<212> TYPE: DNA
<213> ORGANISM: Zea mays ;

<400> SEQUENCE: 129
gcgctcgcca tgaatgcgcg tcgtctccrt tggaccatca accatttgca attgatgagg     60
agacgagaca ggagaaacgg cgagggcagy agtgttctgt agctgaaagc tgccgcgaat    120
cgactgccat tattggacgc cgtcccttgc ccgactgaga atcgggcggc cgcgtgcact    180
gcactrcmct accgccgccc gccaggcgcc agccrrcctc gtggtacaaa attcatccag    240
aattcgcacg aggccaccag ctcggctccg gcctgcgagg atttcaa                  287

<210> SEQ ID NO 130
<211> LENGTH: 288
<212> TYPE: DNA
<213> ORGANISM: Zea mays ;

<400> SEQUENCE: 130
tcatggaatt gcttcaaacc cgagagcggc aagataatag acgaacgatc agctccagcc     60
acctgtaagt acaatcacaa ayrgtaagag caatggatca ctygtggagg cttgtgttta    120
caaataatrg ccaacaacag gttacctcag aaatcctcaa ataatggccc ctgttgttgc    180
tgcccaggtc gaagaagaac cttttctgat ctgccctrat maccttagac atacccatgc    240
cactaatttc ttcttgagga ggcagatcaa ccaagcgttc sacatcta                 288

<210> SEQ ID NO 131
<211> LENGTH: 284
<212> TYPE: DNA
<213> ORGANISM: Zea mays ;

<400> SEQUENCE: 131
tayaagcaat attaagagat ggaaatgtcg cctctgtacc acaagttagt aagttactaa     60
cttgattgtt aaaacaccat cgaaatgtgt gacatgtagg acctggtccc acatgtcaga    120
caaagccaat gctattttgg cattcatgtt gcaatgtagt gctataattt ccacaaaaaa    180
wacaagacag gtcaaatact gygtaaacat tcgatccaaa aaacagagat gctttgtcat    240
aaaaaatcta gccaaaagaa ttggagctat tgagatacaa tgra                     284

<210> SEQ ID NO 132
<211> LENGTH: 256
<212> TYPE: DNA
<213> ORGANISM: Zea mays ;

<400> SEQUENCE: 132

```
acgttccttg tcgaccatta tcattcgcta tctatttttg aacgaacgca ttcgctatct    60
atggccacat ctccacttcg tctttgccga agcttcagta cgcggtgcgg gtgtctcctg   120
gtgtgtatgc tgttctttc  tcggtccata ttatccccg  tttgacgcgc ctctgtcaat   180
ctgctgtact gtgaatttta tttgacgtgc ataaatyatt ctggaaacgc tcttggtacg   240
tcacgtacct ygagaa                                                   256

<210> SEQ ID NO 133
<211> LENGTH: 267
<212> TYPE: DNA
<213> ORGANISM: Zea mays ;

<400> SEQUENCE: 133
atcsggcacc tgatccwgaa tgtgagwcsg agtgcgacct atacccgtcc ccaaccgccc    60
ccattgaatc caccggtgaa tctatcgctc cgccaccacg aggccctata ttaactccac   120
agcatccatg tgtccgagtc tgtctgtata cctgtcactc acgctaccgc cgtgccgatc   180
gttcgttcct tccctccctt cgcgggccgc gcgcctatkw twtttactac tstattcrta   240
tcattatayt ktttggtttc cwtccck                                       267

<210> SEQ ID NO 134
<211> LENGTH: 297
<212> TYPE: DNA
<213> ORGANISM: Zea mays ;

<400> SEQUENCE: 134
ttctcgtaat ctctatggaa attrccrtta ctagagataa atggcatcct tgcaatgtcc    60
caaattctca ccgaagaaca caagkaaaag araagaaaat attgagcaag cacagcacag   120
gcaggcagca tgaatccaca cagaaccagt ggtttttagc acagyasgyt gacagccaag   180
ggttacagta cataatcaga cggggcaaca cgaacgaagc agccgcatca rcagcagcct   240
asaacccatt aattgacaca cagcgtatat atatatatrt agtacttgtc ttttagc      297

<210> SEQ ID NO 135
<211> LENGTH: 231
<212> TYPE: DNA
<213> ORGANISM: Zea mays ;

<400> SEQUENCE: 135
aagtccagat gactttcaga aagaaaatcg agaacttcag acaccttctg accgctgaag    60
cacgaacgac aatggccata ctgcacgatg ttgcacgttt ygtagaagtt tgtatcttcg   120
ttaaaaatta tagcagtaca aatsatagcr cattctgtag gtgtaggata cagtaacaca   180
gcagcagaac atcaaacccr tctcctgcca ggctctgagc aacgccaaag c            231

<210> SEQ ID NO 136
<211> LENGTH: 301
<212> TYPE: DNA
<213> ORGANISM: Zea mays ;

<400> SEQUENCE: 136
ccrtrcaaca ttagstcgtt ytgtttctat ttsttgacca agacatggtt gytgttctga    60
tggcagattt gaacctgaca tgcttgcytt ttctgggtgc tattatggtg gtggagaaaa   120
ggagaggaga gaattagctg caattcgcag acgatggaga accttgcatg tacaagctgt   180
gtgatgtgta atcattactc gcttactgag atagaattay cttttgctaa aagttttcat   240
```

```
attctagata cgtgacccgg agaaaggaag acggcaaggc aggtgtccac taactcctga    300
g                                                                    301

<210> SEQ ID NO 137
<211> LENGTH: 282
<212> TYPE: DNA
<213> ORGANISM: Zea mays ;
<220> FEATURE:
<221> NAME/KEY: misc_feature
<222> LOCATION: (1)..(1)
<223> OTHER INFORMATION: n is a, c, g, or t

<400> SEQUENCE: 137
ncgcgtgttc gtgcggatgc waykcatgca gaggyagcar arctagctag yaagcacgwa     60
ckyacgtagc acatgataag aaggctgcrt tgagacagta agacgaagaa tggcargcag    120
aagagcacgt cagcatgctc cccgcggctt atagcttaga ggcacttgaa tccggtgggc    180
ackctcttgc cgcagtggtt gaggatragg ctgaggtcga csggyaggtt gagcttgatt    240
cckaggacct ctcccttgat ggcggtgcag aggcacacgg cg                       282

<210> SEQ ID NO 138
<211> LENGTH: 301
<212> TYPE: DNA
<213> ORGANISM: Zea mays ;

<400> SEQUENCE: 138
atggatgctt ytgtagcatt aaacgtgaga gtttaatcts accacaacaa gcatgggtga     60
tcacaagaaa tacaaaacag ccaactaacc aaamawkata ttagcaaatg caacttactt    120
ataacatggc aaccaaacac aaacacattg tgcacactta tgctggctta gtctatcctg    180
cattagaccc aatgcagtga attgctagtg caagcaacca attgctcccg tagtgtttcc    240
ttttgcttct atgaaggcta tgaactgtca gggtttattc tagtgatcta tttatctayc    300
a                                                                    301

<210> SEQ ID NO 139
<211> LENGTH: 216
<212> TYPE: DNA
<213> ORGANISM: Zea mays ;

<400> SEQUENCE: 139
tggaaaccrt taataattga agtttctya gtacagrtct gcatagcatt gaactggaca      60
gcttgctgcg ttactctgtr taasgaacga tctactgctg atctgtactg ttccttgatt    120
tttyyyycwc ttttcttctt tgatggcaa gcaggactga agataagatg gctgccttrc     180
cattggccac cgcagaagca tgtgatgcta atgctg                              216

<210> SEQ ID NO 140
<211> LENGTH: 301
<212> TYPE: DNA
<213> ORGANISM: Zea mays ;

<400> SEQUENCE: 140
ggaaatcttg acaaggatat ggagagaagg tttagctacg ccctaagcag agaagacatc     60
gagaacgcca tactcggagg accttaasct gaacacatgg ccaagggct cakagctagg    120 aattgcttag tcgaggttgg cactgaagaa ataatcgctc cagtgatctg cgtgctacca    180
ttacgccatt gtaagagcaa atggatcatg tgtcagaaaa taatattcat gagcaataat    240
ctcgaactag gctggaaatg ttggawgcct cctggtgaca tgcgyytggt ttgttggcmt    300
``` c                                                                    301

<210> SEQ ID NO 141
<211> LENGTH: 301
<212> TYPE: DNA
<213> ORGANISM: Zea mays ;

<400> SEQUENCE: 141
mtaggaaggt caaggtgcct ttggaccccg gcagcaacta caccttcgac ctgagctact      60
accgccacgt rctcgccacg ggcgggctgt tccagtccga cggcagcctc ctgcacgacc     120
ccgtcaccag aggctacgtc gagaaggtgg ccaaggcgtc gtcgcccgac gagtactacg     180
cggacttcgc crcggcgatg gtcaagatgg gccgcaccga cgtgcttgtc ggcgatcatg     240
gggagatcag gccaacgtgt ggcatttttg ttgactaggt tcaggaktgg gttgaaratg     300
c                                                                    301

<210> SEQ ID NO 142
<211> LENGTH: 294
<212> TYPE: DNA
<213> ORGANISM: Zea mays ;

<400> SEQUENCE: 142
gtcaacaagc accagacttt ccaggacact cggtgctttt tcgtggtctc cacagatgga      60
tcccaggcag ayttctccta cctgaagtgc ctggagaact tgtgaggaa gagctacacg      120 gaggacgysg acacattctg catgaagtac ttaaggcccc gtcgcaggca ggcaccacca     180
gctgatgttg ggacagcatc aggcrccccg gatgaggttc caccgtcaac cgcagctgag     240
acagagcaag gcactcctcc agcccctcag gcagaggttc crcaagagay ttgg          294

<210> SEQ ID NO 143
<211> LENGTH: 285
<212> TYPE: DNA
<213> ORGANISM: Zea mays ;

<400> SEQUENCE: 143
attacaccwa acttgtcctt ataagttaga aytcctacaa tatttattag actctgtagg      60
agaatctctt ctagatacaa acccacatcc tttactgtaa aaaaggccca ttgttagcta     120
caatgactta acatctacgg agggaccaaa tctctggtct gaaacccaaa cttttcaaggt    180 tcactaggtt cgtccactgg cagataaaac aaatcctcat ttaygatcat aagttgacat     240
actggacaaa gaatacttgt aagacgatcc cttcttatct gatga                    285

<210> SEQ ID NO 144
<211> LENGTH: 297
<212> TYPE: DNA
<213> ORGANISM: Zea mays ;

<400> SEQUENCE: 144
agtgtagaga tactcacaag aacaattttg aactgccttg cagagccagg taccacgaat      60
aagtgttcaa ccttactctc atgcctcaat ttcaagaaca cctgaacaca tttgctaaat     120
gatgtaagaa aaaagttgcc atcatggtag cagatacgag gtgagtagca acctggtgag     180
gtttaaatgt gtgcccmagc ggtgtgstta gttgaaaaga taaacrcagt ttctgcagat     240
ggtttgcaga aagagacact tttgtatctt tcagaagatc taacctgaaa tgaagca       297

<210> SEQ ID NO 145

```
<211> LENGTH: 301
<212> TYPE: DNA
<213> ORGANISM: Zea mays ;

<400> SEQUENCE: 145
ccatgcgcta ctaccaggcc ggytcctcgg agatgttygg ctccacgccg ccgccgcagc      60
gcgaggacac gcccttccac ccgcgctcgc cctacgccgc cgccaaggtc gccgcgcact     120
ggtacacsgt caactaccgc gaggcctacg acgtattcgc ctgcaacggc gtgctyttca     180
accacgagtc cccgcgccgc ggcgagaact tcgtcacgcg caagatcacg cgcgccgtcg     240
gccgcatcaa ggtcgggctg cagaccaggg tcttcctcgg caacctctcg gccgccaggg     300
a                                                                    301

<210> SEQ ID NO 146
<211> LENGTH: 255
<212> TYPE: DNA
<213> ORGANISM: Zea mays ;

<400> SEQUENCE: 146
tacatacctt gcagcatgtc aaatgcacaa ggatgaagag agagggaaag ttgcagcaaa      60
gaaacttgtt gagatggaac cacaaagctc atccacgtac gtgttcctdt caagcttrca     120
tgctgcggct ggtaactggg ttgaagccaa agtagccaga gaagcaatgc gagaaaaagg     180
ggtgatgaaa tttccagggt gtagttggat cacagtgggk aacaaacara gygtatttgt     240
tgtacaggac acaca                                                     255

<210> SEQ ID NO 147
<211> LENGTH: 299
<212> TYPE: DNA
<213> ORGANISM: Zea mays ;

<400> SEQUENCE: 147
actcaaattg agtcaagaaa tgctaaggga aagcccgtga acaatataa tcgaactttt       60 acattttatt gatgtggcct tyttaaaaat gacgccataa accwctatac tgaaaacggc     120
ctcggcgctt aaaccagtag cattcgtagg ttcatttctg atttgggact tcaaaccaat     180
agtgtttgag actcacaggt ttagaaccga ttggtggctg ccttcaatca agagcgaaac     240
caacatgtta ttgcccacct taaaatcaca gattttgtat tatcgtgtac aataaaaat      299

<210> SEQ ID NO 148
<211> LENGTH: 301
<212> TYPE: DNA
<213> ORGANISM: Zea mays ;

<400> SEQUENCE: 148
ycagatcatc actggaatca acagcagttc tctggttcat tgttcagat gcttckgtgt       60 caactgcttc tgaaygatgg tttaagctta taacatcatc arcatttttg ttaattattg     120
cactgttctc gttgtccttt accacgctat ccaaawtttc tggctcctca gatactacaa     180
gatcagatrt ctgcccgttc tgagtaagag tggtttcagg actgacaccc ataccttgtg     240
caagtgctac ataccgaagt actagwtgct tgtacgaatt caataggctc tctacatcag     300
c                                                                    301

<210> SEQ ID NO 149
<211> LENGTH: 274
<212> TYPE: DNA
<213> ORGANISM: Zea mays ;
```

<400> SEQUENCE: 149

```
ctttagtagc tagtcytata gctcataggt tctcagttcg gtatatrtyg gtgayatatt        60
tcatgaactt astttwaam cmatttaaaa mgcamacgca acaacgaagg gagtgatatt       120
gaccatgggc ctttcgtagc ttttcaatca aacgtcacat aaaaaaagaa acawccaaaa      180
gwtcataata cacagattkr aamskkkaga caaaaatacg agtacaagac attggaccttt    240
caatwwtttt tttktgtttt ctgagacatg aaaa                                  274
```

<210> SEQ ID NO 150
<211> LENGTH: 319
<212> TYPE: DNA
<213> ORGANISM: Zea mays ;

<400> SEQUENCE: 150

```
ttgcaccacc catagtttaa gaggcagttg ctttcacaca ctttatttg catggcacag        60
ccaactgtcc ccatcattct aaaccaggct gcaactgagc cactacagaa actgctaata     120
ttagatattc cagcaaatag tcttgacact agagtgctag gtccctaaac acgaaagaca     180
tttgtcagga gacccgtatt gagtactagc agagtatact accgctagat attccagtat    240
aatcgtgcag cagctccggt caatggcagt ggcacttgaa gtctgcaacc tcagccaaca    300
gatccacatg agaaccaac                                                  319
```

<210> SEQ ID NO 151
<211> LENGTH: 283
<212> TYPE: DNA
<213> ORGANISM: Zea mays ;

<400> SEQUENCE: 151

```
tacactatac taattagaat gtctggaaag gctgggaaga ccactaaatt tgtctcattk      60
ttggaggaaa tggtgtccra aggatgtgtt cttartctga ttgcttataa tactgttatt    120
gaggctcttg gtaagaacaa gatggttgac gaggcgattt ttatgctttc taaaatgatt    180
gagagtgact gtcggcccaa tcaattcaca tatagcatta tgctggatgt tttatcaaca    240
gggggacaac tccacaggtt gaatgagatt ctagatattt gta                       283
```

<210> SEQ ID NO 152
<211> LENGTH: 193
<212> TYPE: DNA
<213> ORGANISM: Zea mays ;

<400> SEQUENCE: 152

```
cctttctcca gttggtaata tgcttcatgt aaggtacctg aaggtggtaa gcracatgat      60
agtcaaactc ccactcatta ttcgaggcct gcgacactta gagacactcg aggtggatgc    120
agaaraagtc gctgttccac tggatgtttt catcttgaag agcctgttgc atctccgact    180
tccgagcaag gct                                                        193
```

<210> SEQ ID NO 153
<211> LENGTH: 298
<212> TYPE: DNA
<213> ORGANISM: Zea mays ;

<400> SEQUENCE: 153

```
tgcatatgag aaactacaag gttggcaggg tcctttcctg tgcccgagct gtcatgaaaa      60
gaaagaagca atggaaggga aacgccggcc aaaaggtatc attaaatagt atttacctga    120
```

| | |
|---|---|
| actacattct ktagttaacc ctcagacagc tcattcgttt ctgggttcct atttgtcttt | 180 |
| ccaggatctt catcaaacgt ctttggtcac atgtgctagg cctgcctacc actaaagatt | 240 |
| cttttattga ttsttagctg gaaataatag kcagcccata acaattcatt ggctagaa | 298 |

<210> SEQ ID NO 154
<211> LENGTH: 360
<212> TYPE: DNA
<213> ORGANISM: Zea mays ;

<400> SEQUENCE: 154

| | |
|---|---|
| aagcacccgc atgcagactt ccaaactatc cagtgtccac aaatagcagt tttgcaaact | 60 |
| aaatacatat atgaaatgat gacacaggcc acccaaacaa caagccctag agaatcagac | 120 |
| caaccaaccg agcaattcgc agtgctccat atcttctagc attcacaacc tgacgaacgt | 180 |
| tgttgccttc cagcgccccc aacatcaatc gtatcaggaa gatacctgca aaagttggta | 240 |
| aaacatagat caagttacac cacaaggctg cctgcatgta tgatacatat atgtgagcta | 300 |
| tatactattc aaacttacat atcttcttct ggctcatttt ttacagcatt cctcgctata | 360 |

<210> SEQ ID NO 155
<211> LENGTH: 299
<212> TYPE: DNA
<213> ORGANISM: Zea mays ;

<400> SEQUENCE: 155

| | |
|---|---|
| agaygctact ctgctaccat tttgagaatc tattgacaag aactttacag gaggrgtctc | 60 |
| atccccagga gccttgctga taactggaga tggagaagat atgcacatat ccactcgtga | 120 |
| atgcyttttc ctggacttat ttctgtcctt cagcagttgt tttccctagc aaacaaaagg | 180 |
| agatacacat agcatgagaa agaagaaasa aactgaaaca ttytataatg agaaaaaaac | 240 |
| atggggagtt ggggacaaag caactcacca atgcttctac aaatgttttg aacctccga | 299 |

<210> SEQ ID NO 156
<211> LENGTH: 262
<212> TYPE: DNA
<213> ORGANISM: Zea mays ;

<400> SEQUENCE: 156

| | |
|---|---|
| tgcttctgtc gaattgctgc gggcagarca tgctttggtg gyggctttgc agtgtgaaac | 60 |
| gttatgaatc tgagaacctc gatgcatgcy agggacaggg aatacctgaa caggggccaa | 120 |
| gatgacatga acaggacgcc ggacagcacg tgcacaacct tcctgctcaa gctctgcctt | 180 |
| cattgatggc atggatcagt acagagttcg gaagccaacg acgtgaacar ctgaacataa | 240 |
| gcaaatgtaa tggccgttct aa | 262 |

<210> SEQ ID NO 157
<211> LENGTH: 301
<212> TYPE: DNA
<213> ORGANISM: Zea mays ;

<400> SEQUENCE: 157

| | |
|---|---|
| aggtcgacaa ggctgctagt aacatgtctg agccgacatc aggggagatg caggatgctg | 60 |
| ctttccagtc tgacgaagag gaggaagatg aagatgttga tgaaacagta ttcggtcaag | 120 |
| attcagattc gtcacaraat agcggcaccg acgacgatgc aaagtagact cactgctggt | 180 |
| attcatcatt atggtgattg tattgttttt aattaaattg ccaagcttga tttttgtcaa | 240 |
| ggcgacgytg gaaggttgca cagaattttg ayagtgtctc tggtttcatt ttgaaagcac | 300 | t                                                                               301

<210> SEQ ID NO 158
<211> LENGTH: 271
<212> TYPE: DNA
<213> ORGANISM: Zea mays ;

<400> SEQUENCE: 158
agaaaacgag gccttcgtcg tcttagcgcg crggggcgta ggacggcggc agcggcagcc    60
ccacgacctt gccgcagcgg agggcgttgt cgggcatgtt gtactcgtcg cgcagtgatc   120
gcgccggcga gacgacgctg atgtagaact gctccccgag gtagtaccgc tcccagatgt   180
tggaatgcac gctccacatg cccgcgttgt cgaacgtcag catgattgcc gtccatgacc   240
gcgggtacac ctggatcgtg tgccggctca c                                  271

<210> SEQ ID NO 159
<211> LENGTH: 286
<212> TYPE: DNA
<213> ORGANISM: Zea mays ;

<400> SEQUENCE: 159
ttctggtact tgcggatctc gcgcagmgcc acsgtsccgg gcctgtacct gtggggcttc    60
ttcacgccgc cggtcgtcgg cgcmgacttc ctcgccgcct gcaacraray aacaaccgcc   120
gccgcgtcag crccgtctta caacgggaac catcgagggg atcggaacak cagatcggta   180
cgggtaggta gagacgaacc ttggtkgcga gctgcttgcg cggggccttg cctccggtgg   240
acttgcgggc ggtctgcttc gtacgagcca tcttctcctc tccttg                  286

<210> SEQ ID NO 160
<211> LENGTH: 252
<212> TYPE: DNA
<213> ORGANISM: Zea mays ;

<400> SEQUENCE: 160
ctgcgttagt ttcaccccctt ctagctgcga gtgaaagaaa cwtgataaca gctwsctgct    60
agtttctatg ryrgccatcg aatctgacat ggctayctcc tgtgmcmacg caggtccgca   120
ggtactacca gccgaggaag agccaccgga cggtgacggc ggtgatccac ggcgagaagg   180
tgccgctgta cggcgccggg ggcggcctga cgctgtcsac gagcgcgggc gggggsgcgg   240
tgcccctgac gc                                                       252

<210> SEQ ID NO 161
<211> LENGTH: 301
<212> TYPE: DNA
<213> ORGANISM: Zea mays ;

<400> SEQUENCE: 161
agcaccacga ttcacaccta cacatattca gacacaaaat tgggcagcga tgggcatgga    60
catttcattg atagatggta tttagctgcc tactytggca tttgattcga gcagcgaagc   120
ttcaagagct gcagaatcgc tacayatatt tctgtgggta cacatgcttc ttgttctcca   180
ctcgacccag atcattgtga tggactacta actgscagta caaaagcaga catctatcaa   240
acttacacaa aaggcgtgca caacgagaya gyctgcttgc gcatctccaa gtctagtcta   300
g                                                                   301

<210> SEQ ID NO 162

```
<211> LENGTH: 237
<212> TYPE: DNA
<213> ORGANISM: Zea mays ;

<400> SEQUENCE: 162
awwttkkwag ygcarraata aacaaggcac tgtwrattgt acagagcaag ctctctgcat    60
ttttcaatgc cgcagcatct gcaactgcaa gcagagtttc tagaggccaa ggccgactgt   120
cctgccatct ctcctgcgga ggcctgctat gtaatgtttc tccaggttgg tgtcgagctc   180
ctccagtttc ttggcttctt ccgccgagct cccgaccttg ttctcgaccg tgtttaa      237

<210> SEQ ID NO 163
<211> LENGTH: 278
<212> TYPE: DNA
<213> ORGANISM: Zea mays ;

<400> SEQUENCE: 163
tcaatttgtg atttcatcca caatttcttc atatgtgagg aatgccgcac rcacttctat    60
gaaatgtgtt caargtttgg aaaaactact ctagccatat attgccacag aaatcaastg   120
catgtytaat agttaccgtt cacctgtagt gtatcagtcc ccttcaaatc tgcccgtgac   180
cttgccctct ggctatggrc cgcgcataac aaagttaacg agaggttgat gaaagaagaa   240
aaggagttag acaatgctga tccttcattt cctaagat                          278

<210> SEQ ID NO 164
<211> LENGTH: 263
<212> TYPE: DNA
<213> ORGANISM: Zea mays ;

<400> SEQUENCE: 164
ttgcatacaa acttgatcma aatgtttrca amccatgctt gaacrratat acaaacccgt    60
tgyggcagga acatyttagc ttwgkammmt ygywvagcaa caatagcttc aatagagatt   120
gttgtaagtg tagagtgttg ctgcgatgga ractatgcaa atcacaaggg atgggagaag   180
agtgacattc agaaggaggt ccgtgccgag ataaccggct gcagtaatcg tggcatctgc   240
aactacacgg gccaacgtcc cgg                                          263

<210> SEQ ID NO 165
<211> LENGTH: 266
<212> TYPE: DNA
<213> ORGANISM: Zea mays ;

<400> SEQUENCE: 165
acaagtccaa atcaaaggtg ttgtcccgcc aatgcttacc ccccatgscy ccccraaata    60
gcatctgaat ccattttttt gtcygatctt tttkkctcct cttctgacag ggaaatgctg   120
cttgagttgg acgaggaaca gactggaatg caaatgcacg tgcaggttgc aaattcttat   180
gttrwttttt gkggcctatc artrcacagt actcatagca tgacaaatgg cgttgcaggt   240
tttggttttt accsgttttg gtttcc                                       266

<210> SEQ ID NO 166
<211> LENGTH: 197
<212> TYPE: DNA
<213> ORGANISM: Zea mays ;

<400> SEQUENCE: 166
aacctcgact ccactataas tgcaggacgc acgrcaygca caactgaaac atccggacca    60
acaggcagag tagtagccca aggatgacc cgtctcatgc aaaaacagtc agcttgataa   120
```
acttatcgag aaggcaacaa cggygcccaa gtactggttg aaatacagag cagacattga    180
agtgccaaag aggggggg                                                 197

<210> SEQ ID NO 167
<211> LENGTH: 301
<212> TYPE: DNA
<213> ORGANISM: Zea mays ;

<400> SEQUENCE: 167
gtctagaaaa gtcaaaacgt catatacttg aacrggagt agatatgaca aaaagagcat     60
gcaagtgatg ttcttacaga agaatatata tatttcatgg caagctagta cctaaacttc   120
agatggagtc tttgcatcga ttgacagggc atgcaacccg gtcttgagct cctcctgcag   180
gagatcatag acagccctgt gcctcttrag caagctcttc ccctcaaact ccttggacac   240
caccctcaca ttgaaatgtg tctccccatt ggtcccagcc acgccagcat ggcccttgtg   300
g                                                                   301

<210> SEQ ID NO 168
<211> LENGTH: 291
<212> TYPE: DNA
<213> ORGANISM: Zea mays ;

<400> SEQUENCE: 168
attttaccat actgcattca agttttaca agattggaca ttattagtat aaaacatgaa     60
acttttcaag tgaacaasaa ctataarcaa cgtccgcaag cgcaatccac agcttgaggt   120
tacattgtga gtgtagtaga aaaactaggt ggtcccaaat agcacaagat tatccaagct   180
acccagtttt ctacgattat gggcacracc ataagagcat agmagtgctt cgcatcctgt   240
tgcattaaga aagtagtata ggcatcggag gtgctgaatc taagcacacg g            291

<210> SEQ ID NO 169
<211> LENGTH: 299
<212> TYPE: DNA
<213> ORGANISM: Zea mays ;

<400> SEQUENCE: 169
taaaccagay tagatgccac ctagktttct gacacaaatc aygaacaaaa cacgagaaga    60
aagcyaatca tacacggatg ayggatggac tcagcggagc ccttatttgc taccattcct   120
catgtcttat tgcagaaatc catctattgc cactcaactt camtcagtct ctggaactct   180
gtatcaacag gggatgggaa atgtgtcatg ttcaatgttt agcycatgaa acatagaaga   240
ccmcattaga agctattatg tgcttacatt tgattttttt atccaagact caagtgtat    299

<210> SEQ ID NO 170
<211> LENGTH: 300
<212> TYPE: DNA
<213> ORGANISM: Zea mays ;

<400> SEQUENCE: 170
rrhytkrtgg aggtcggggg aagaaaccct aagaacgatg tctcaccaaa ttgattcctt    60
ccgcccgaga gatttagaag ctagatctgt ccagatttag tggattgata ggttttgtga   120
atttgtcatt ctccaactaa tctacttaca gccagatttt acatcagacc tgatgaaaca   180
ctgtttcctt gacacgaaac tggtggacgc tgcctttgca tcaagaatca agaaattgat   240
ttrcgtttta tgtytctggt agcyccagac acctcatact ctcctctgtt gcctgtsatg   300

<210> SEQ ID NO 171
<211> LENGTH: 232
<212> TYPE: DNA
<213> ORGANISM: Zea mays ;

<400> SEQUENCE: 171

```
aacggctaag agtcaggcga ttctgtttgt acagagacaa tcgcagcact tgrmtgctwc      60
gcatgcgstt cagagggcct tcagctcagg cttgacagat ctagttttgg ycgccacgcy     120
rctcttcggc gagcactgya ctctgctggc atctttagaa gccccgatgc tgtgacgatg     180
tggccgggtg gtagatgttg cgttggtgtt ttttccctcg ggtgtctgtg gt             232
```

<210> SEQ ID NO 172
<211> LENGTH: 201
<212> TYPE: DNA
<213> ORGANISM: Zea mays ;
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(31)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

<400> SEQUENCE: 172

```
aaacaanact cagtggactc gcngaaannn nataatgaaa ggtgctccat ccatacccat      60
gagaangttc cgatgctcgc agtctcatgt ttcccagtca gtcttctttc atttccttct    120
ccgtatgcac taatatgcag atcatggcgc agagaaaggt tcaggattgc tctcttgatc    180
tcttcaaacc cgccgtcttc g                                              201
```

<210> SEQ ID NO 173
<211> LENGTH: 301
<212> TYPE: DNA
<213> ORGANISM: Zea mays ;
<220> FEATURE:
<221> NAME/KEY: misc_feature
<222> LOCATION: (239)..(281)
<223> OTHER INFORMATION: n is a, c, g, or t

<400> SEQUENCE: 173

```
aaaattactg aaggcaggtg ggttgcagtt gtgtgttcgt tactgtttac tgtawyatgt      60
caagctgtcg gctgcaattt ctttgctggc aagccgcagg cactggtgaa gtgctgataa    120
atacatcata ttctgttgac ctgtgaagaa acttgttcwa ggtrgattcc attgtactag    180
ctctgttgcy cagcatctcc ttgtttggga acattaacaa ccagcyctcr mccctcaann    240
nnnnnnnnnn nnnnnnnnnn nnnnnnnnnn nnnnnnnnnn ntaaaatagt cgcatcatgt    300
a                                                                    301
```

<210> SEQ ID NO 174
<211> LENGTH: 19
<212> TYPE: DNA
<213> ORGANISM: Artificial ;Primer
<220> FEATURE:
<223> OTHER INFORMATION: Assay component

<400> SEQUENCE: 174
gccatggatc gcattcatg                                                    19

<210> SEQ ID NO 175
<211> LENGTH: 24
<212> TYPE: DNA
<213> ORGANISM: Artificial ;Primer
<220> FEATURE:
<223> OTHER INFORMATION: Assay component

<400> SEQUENCE: 175
ctctctggca tctctgaaat catc                                              24

<210> SEQ ID NO 176
<211> LENGTH: 18
<212> TYPE: DNA
<213> ORGANISM: Artificial ;Probe
<220> FEATURE:
<223> OTHER INFORMATION: Assay component

<400> SEQUENCE: 176
cgattttgac tttgaacc                                                     18

<210> SEQ ID NO 177
<211> LENGTH: 17
<212> TYPE: DNA
<213> ORGANISM: Artificial ;Probe
<220> FEATURE:
<223> OTHER INFORMATION: Assay component

<400> SEQUENCE: 177
cgattttgac ttcgaac                                                      17

<210> SEQ ID NO 178
<211> LENGTH: 18
<212> TYPE: DNA
<213> ORGANISM: Artificial ;Primer
<220> FEATURE:
<223> OTHER INFORMATION: Assay component

<400> SEQUENCE: 178
acacccatgg cacaaggt                                                     18

<210> SEQ ID NO 179
<211> LENGTH: 22
<212> TYPE: DNA
<213> ORGANISM: Artificial ;Primer
<220> FEATURE:
<223> OTHER INFORMATION: Assay component

<400> SEQUENCE: 179
cgagagacca gatcaacagc tt                                                22

<210> SEQ ID NO 180
<211> LENGTH: 19
<212> TYPE: DNA
<213> ORGANISM: Artificial ;Probe
<220> FEATURE:
<223> OTHER INFORMATION: Assay component

<400> SEQUENCE: 180
caatactcta aaaaaactg                                                    19

<210> SEQ ID NO 181

```
<211> LENGTH: 19
<212> TYPE: DNA
<213> ORGANISM: Artificial ;Probe
<220> FEATURE:
<223> OTHER INFORMATION: Assay component

<400> SEQUENCE: 181
caatactcta agaaaactg                                                    19

<210> SEQ ID NO 182
<211> LENGTH: 25
<212> TYPE: DNA
<213> ORGANISM: Artificial ;Primer
<220> FEATURE:
<223> OTHER INFORMATION: Assay component

<400> SEQUENCE: 182
cccttgaacc agagtggata atctc                                             25

<210> SEQ ID NO 183
<211> LENGTH: 26
<212> TYPE: DNA
<213> ORGANISM: Artificial ;Primer
<220> FEATURE:
<223> OTHER INFORMATION: Assay component

<400> SEQUENCE: 183
caggtagtag tcttccgtat gtcaac                                            26

<210> SEQ ID NO 184
<211> LENGTH: 17
<212> TYPE: DNA
<213> ORGANISM: Artificial ;Probe
<220> FEATURE:
<223> OTHER INFORMATION: Assay component

<400> SEQUENCE: 184
atcagatgta aagcatc                                                      17

<210> SEQ ID NO 185
<211> LENGTH: 19
<212> TYPE: DNA
<213> ORGANISM: Artificial ;Probe
<220> FEATURE:
<223> OTHER INFORMATION: Assay component

<400> SEQUENCE: 185
aaatcagatg tagagcatc                                                    19

<210> SEQ ID NO 186
<211> LENGTH: 19
<212> TYPE: DNA
<213> ORGANISM: Artificial ;Primer
<220> FEATURE:
<223> OTHER INFORMATION: Assay component

<400> SEQUENCE: 186
actgcctgca aggttggtt                                                    19

<210> SEQ ID NO 187
<211> LENGTH: 20
<212> TYPE: DNA
<213> ORGANISM: Artificial ;Primer
<220> FEATURE:
<223> OTHER INFORMATION: Assay component

<400> SEQUENCE: 187
```
cgggcataag atcccagtca                                              20

<210> SEQ ID NO 188
<211> LENGTH: 16
<212> TYPE: DNA
<213> ORGANISM: Artificial ;Probe
<220> FEATURE:
<223> OTHER INFORMATION: Assay component

<400> SEQUENCE: 188
caaaccaaac aacctt                                                  16

<210> SEQ ID NO 189
<211> LENGTH: 15
<212> TYPE: DNA
<213> ORGANISM: Artificial ;Probe
<220> FEATURE:
<223> OTHER INFORMATION: Assay component

<400> SEQUENCE: 189
aaaccaagca acctt                                                   15

<210> SEQ ID NO 190
<211> LENGTH: 17
<212> TYPE: DNA
<213> ORGANISM: Artificial ;Primer
<220> FEATURE:
<223> OTHER INFORMATION: Assay component

<400> SEQUENCE: 190
ccccagccct ggatcac                                                 17

<210> SEQ ID NO 191
<211> LENGTH: 27
<212> TYPE: DNA
<213> ORGANISM: Artificial ;Primer
<220> FEATURE:
<223> OTHER INFORMATION: Assay component

<400> SEQUENCE: 191
gctttcgaat gtgttcatga tgtaagt                                      27

<210> SEQ ID NO 192
<211> LENGTH: 17
<212> TYPE: DNA
<213> ORGANISM: Artificial ;Probe
<220> FEATURE:
<223> OTHER INFORMATION: Assay component

<400> SEQUENCE: 192
cctggagaat gaaagta                                                 17

<210> SEQ ID NO 193
<211> LENGTH: 16
<212> TYPE: DNA
<213> ORGANISM: Artificial ;Probe
<220> FEATURE:
<223> OTHER INFORMATION: Assay component

<400> SEQUENCE: 193
ctggagaagg aaagta                                                  16

<210> SEQ ID NO 194
<211> LENGTH: 25
<212> TYPE: DNA

```
<213> ORGANISM: Artificial ;Primer
<220> FEATURE:
<223> OTHER INFORMATION: Assay component

<400> SEQUENCE: 194
agcttctcct tgaccttctc cttaa                                          25

<210> SEQ ID NO 195
<211> LENGTH: 23
<212> TYPE: DNA
<213> ORGANISM: Artificial ;Primer
<220> FEATURE:
<223> OTHER INFORMATION: Assay component

<400> SEQUENCE: 195
aggaagagga ggtgatcgat gag                                            23

<210> SEQ ID NO 196
<211> LENGTH: 17
<212> TYPE: DNA
<213> ORGANISM: Artificial ;Probe
<220> FEATURE:
<223> OTHER INFORMATION: Assay component

<400> SEQUENCE: 196
aacggcgaaa ttgtcaa                                                   17

<210> SEQ ID NO 197
<211> LENGTH: 15
<212> TYPE: DNA
<213> ORGANISM: Artificial ;Probe
<220> FEATURE:
<223> OTHER INFORMATION: Assay component

<400> SEQUENCE: 197
cggcgagatt gtcaa                                                     15

<210> SEQ ID NO 198
<211> LENGTH: 16
<212> TYPE: DNA
<213> ORGANISM: Artificial ;Primer
<220> FEATURE:
<223> OTHER INFORMATION: Assay component

<400> SEQUENCE: 198
gcgtcacaag aaggta                                                    16

<210> SEQ ID NO 199
<211> LENGTH: 16
<212> TYPE: DNA
<213> ORGANISM: Artificial ;Primer
<220> FEATURE:
<223> OTHER INFORMATION: Assay component

<400> SEQUENCE: 199
gcaagcagaa ctcaac                                                    16

<210> SEQ ID NO 200
<211> LENGTH: 17
<212> TYPE: DNA
<213> ORGANISM: Artificial ;Probe
<220> FEATURE:
<223> OTHER INFORMATION: Assay component

<400> SEQUENCE: 200
tcaacatgac tgaatca                                                   17
```

```
<210> SEQ ID NO 201
<211> LENGTH: 17
<212> TYPE: DNA
<213> ORGANISM: Artificial ;Probe
<220> FEATURE:
<223> OTHER INFORMATION: Assay component

<400> SEQUENCE: 201
caacatgact gaagcat                                                  17

<210> SEQ ID NO 202
<211> LENGTH: 15
<212> TYPE: DNA
<213> ORGANISM: Artificial ;Primer
<220> FEATURE:
<223> OTHER INFORMATION: Assay component

<400> SEQUENCE: 202
cgcagcgtgg agtgc                                                    15

<210> SEQ ID NO 203
<211> LENGTH: 24
<212> TYPE: DNA
<213> ORGANISM: Artificial ;Primer
<220> FEATURE:
<223> OTHER INFORMATION: Assay component

<400> SEQUENCE: 203
acacattcga aggcggatat catg                                          24

<210> SEQ ID NO 204
<211> LENGTH: 15
<212> TYPE: DNA
<213> ORGANISM: Artificial ;Probe
<220> FEATURE:
<223> OTHER INFORMATION: Assay component

<400> SEQUENCE: 204
ccggtaacat caacg                                                    15

<210> SEQ ID NO 205
<211> LENGTH: 15
<212> TYPE: DNA
<213> ORGANISM: Artificial ;Probe
<220> FEATURE:
<223> OTHER INFORMATION: Assay component

<400> SEQUENCE: 205
ccggtaacgt caacg                                                    15

<210> SEQ ID NO 206
<211> LENGTH: 25
<212> TYPE: DNA
<213> ORGANISM: Artificial ;Primer
<220> FEATURE:
<223> OTHER INFORMATION: Assay component

<400> SEQUENCE: 206
ggagtctttt agggtccact tgttt                                         25

<210> SEQ ID NO 207
<211> LENGTH: 21
<212> TYPE: DNA
<213> ORGANISM: Artificial ;Primer
<220> FEATURE:
```

-continued

<223> OTHER INFORMATION: Assay component

<400> SEQUENCE: 207
agagagcaca aggcgaagaa t                                            21

<210> SEQ ID NO 208
<211> LENGTH: 17
<212> TYPE: DNA
<213> ORGANISM: Artificial ;Probe
<220> FEATURE:
<223> OTHER INFORMATION: Assay component

<400> SEQUENCE: 208
ttctgcaagt tgaattt                                                 17

<210> SEQ ID NO 209
<211> LENGTH: 14
<212> TYPE: DNA
<213> ORGANISM: Artificial ;Probe
<220> FEATURE:
<223> OTHER INFORMATION: Assay component

<400> SEQUENCE: 209
tgcaagctga attt                                                    14

<210> SEQ ID NO 210
<211> LENGTH: 19
<212> TYPE: DNA
<213> ORGANISM: Artificial ;Primer
<220> FEATURE:
<223> OTHER INFORMATION: Assay component

<400> SEQUENCE: 210
gagcaagcgc agagaacag                                               19

<210> SEQ ID NO 211
<211> LENGTH: 18
<212> TYPE: DNA
<213> ORGANISM: Artificial ;Primer
<220> FEATURE:
<223> OTHER INFORMATION: Assay component

<400> SEQUENCE: 211
cgggcatgtt gcgatgtc                                                18

<210> SEQ ID NO 212
<211> LENGTH: 20
<212> TYPE: DNA
<213> ORGANISM: Artificial ;Probe
<220> FEATURE:
<223> OTHER INFORMATION: Assay component

<400> SEQUENCE: 212
aaaactttac ccataaacaa                                              20

<210> SEQ ID NO 213
<211> LENGTH: 17
<212> TYPE: DNA
<213> ORGANISM: Artificial ;Probe
<220> FEATURE:
<223> OTHER INFORMATION: Assay component

<400> SEQUENCE: 213
actttacccg taaacaa                                                 17

```
<210> SEQ ID NO 214
<211> LENGTH: 21
<212> TYPE: DNA
<213> ORGANISM: Artificial ;Primer
<220> FEATURE:
<223> OTHER INFORMATION: Assay component

<400> SEQUENCE: 214
cccgggaatt gttttcgatg c                                              21

<210> SEQ ID NO 215
<211> LENGTH: 29
<212> TYPE: DNA
<213> ORGANISM: Artificial ;Primer
<220> FEATURE:
<223> OTHER INFORMATION: Assay component

<400> SEQUENCE: 215
ccctatagtt tgttagcaga tgtgtagtt                                      29

<210> SEQ ID NO 216
<211> LENGTH: 17
<212> TYPE: DNA
<213> ORGANISM: Artificial ;Probe
<220> FEATURE:
<223> OTHER INFORMATION: Assay component

<400> SEQUENCE: 216
taacgcgttc ttcattt                                                   17

<210> SEQ ID NO 217
<211> LENGTH: 15
<212> TYPE: DNA
<213> ORGANISM: Artificial ;Probe
<220> FEATURE:
<223> OTHER INFORMATION: Assay component

<400> SEQUENCE: 217
acgcgtcctt cattt                                                     15

<210> SEQ ID NO 218
<211> LENGTH: 35
<212> TYPE: DNA
<213> ORGANISM: Artificial ;Primer
<220> FEATURE:
<223> OTHER INFORMATION: Assay component

<400> SEQUENCE: 218
gcaacctaaa aattctaaaa aatacagaga taggg                               35

<210> SEQ ID NO 219
<211> LENGTH: 29
<212> TYPE: DNA
<213> ORGANISM: Artificial ;Primer
<220> FEATURE:
<223> OTHER INFORMATION: Assay component

<400> SEQUENCE: 219
actaatttca aagaaaatgc cacagcttt                                      29

<210> SEQ ID NO 220
<211> LENGTH: 21
<212> TYPE: DNA
<213> ORGANISM: Artificial ;Probe
<220> FEATURE:
<223> OTHER INFORMATION: Assay component
```

```
<400> SEQUENCE: 220
attttaaagg aagatagatt g                                      21

<210> SEQ ID NO 221
<211> LENGTH: 19
<212> TYPE: DNA
<213> ORGANISM: Artificial ;Probe
<220> FEATURE:
<223> OTHER INFORMATION: Assay component

<400> SEQUENCE: 221
tttaaaggaa gacagattg                                         19

<210> SEQ ID NO 222
<211> LENGTH: 19
<212> TYPE: DNA
<213> ORGANISM: Artificial ;Primer
<220> FEATURE:
<223> OTHER INFORMATION: Assay component

<400> SEQUENCE: 222
gcgagccgtt gagagtgaa                                         19

<210> SEQ ID NO 223
<211> LENGTH: 19
<212> TYPE: DNA
<213> ORGANISM: Artificial ;Primer
<220> FEATURE:
<223> OTHER INFORMATION: Assay component

<400> SEQUENCE: 223
ccacgagtcc ccagtctct                                         19

<210> SEQ ID NO 224
<211> LENGTH: 14
<212> TYPE: DNA
<213> ORGANISM: Artificial ;Probe
<220> FEATURE:
<223> OTHER INFORMATION: Assay component

<400> SEQUENCE: 224
acagccatgt cgcc                                              14

<210> SEQ ID NO 225
<211> LENGTH: 14
<212> TYPE: DNA
<213> ORGANISM: Artificial ;Probe
<220> FEATURE:
<223> OTHER INFORMATION: Assay component

<400> SEQUENCE: 225
acagccgtgt cgcc                                              14

<210> SEQ ID NO 226
<211> LENGTH: 25
<212> TYPE: DNA
<213> ORGANISM: Artificial ;Primer
<220> FEATURE:
<223> OTHER INFORMATION: Assay component

<400> SEQUENCE: 226
ccaccaaaac gagtaaacga caaat                                  25

<210> SEQ ID NO 227
<211> LENGTH: 25
```

```
<212> TYPE: DNA
<213> ORGANISM: Artificial ;Primer
<220> FEATURE:
<223> OTHER INFORMATION: Assay component

<400> SEQUENCE: 227
ggttgcttga gatcttgctg ttatt                                    25

<210> SEQ ID NO 228
<211> LENGTH: 15
<212> TYPE: DNA
<213> ORGANISM: Artificial ;Probe
<220> FEATURE:
<223> OTHER INFORMATION: Assay component

<400> SEQUENCE: 228
agtgagcacg gcacg                                               15

<210> SEQ ID NO 229
<211> LENGTH: 15
<212> TYPE: DNA
<213> ORGANISM: Artificial ;Probe
<220> FEATURE:
<223> OTHER INFORMATION: Assay component

<400> SEQUENCE: 229
agtgaggacg gcacg                                               15

<210> SEQ ID NO 230
<211> LENGTH: 18
<212> TYPE: DNA
<213> ORGANISM: Artificial ;Primer
<220> FEATURE:
<223> OTHER INFORMATION: Assay component

<400> SEQUENCE: 230
acaacaaggc ggcattgc                                            18

<210> SEQ ID NO 231
<211> LENGTH: 21
<212> TYPE: DNA
<213> ORGANISM: Artificial ;Primer
<220> FEATURE:
<223> OTHER INFORMATION: Assay component

<400> SEQUENCE: 231
ggcgcctccg tttaactact c                                        21

<210> SEQ ID NO 232
<211> LENGTH: 20
<212> TYPE: DNA
<213> ORGANISM: Artificial ;Probe
<220> FEATURE:
<223> OTHER INFORMATION: Assay component

<400> SEQUENCE: 232
ttgcagtagt agtactgtag                                          20

<210> SEQ ID NO 233
<211> LENGTH: 20
<212> TYPE: DNA
<213> ORGANISM: Artificial ;Probe
<220> FEATURE:
<223> OTHER INFORMATION: Assay component

<400> SEQUENCE: 233
```
ttgcagtagt agtgctgtag                                              20

<210> SEQ ID NO 234
<211> LENGTH: 21
<212> TYPE: DNA
<213> ORGANISM: Artificial ;Primer
<220> FEATURE:
<223> OTHER INFORMATION: Assay component

<400> SEQUENCE: 234
gctgctcgtt ctcgttgaag a                                            21

<210> SEQ ID NO 235
<211> LENGTH: 18
<212> TYPE: DNA
<213> ORGANISM: Artificial ;Primer
<220> FEATURE:
<223> OTHER INFORMATION: Assay component

<400> SEQUENCE: 235
cgctggacga caccaaga                                                18

<210> SEQ ID NO 236
<211> LENGTH: 17
<212> TYPE: DNA
<213> ORGANISM: Artificial ;Probe
<220> FEATURE:
<223> OTHER INFORMATION: Assay component

<400> SEQUENCE: 236
tccacgttcc tgtccag                                                 17

<210> SEQ ID NO 237
<211> LENGTH: 15
<212> TYPE: DNA
<213> ORGANISM: Artificial ;Probe
<220> FEATURE:
<223> OTHER INFORMATION: Assay component

<400> SEQUENCE: 237
cacgttccgg tccag                                                   15

<210> SEQ ID NO 238
<211> LENGTH: 24
<212> TYPE: DNA
<213> ORGANISM: Artificial ;Primer
<220> FEATURE:
<223> OTHER INFORMATION: Assay component

<400> SEQUENCE: 238
gctagtctca agtccaagca aaga                                         24

<210> SEQ ID NO 239
<211> LENGTH: 24
<212> TYPE: DNA
<213> ORGANISM: Artificial ;Primer
<220> FEATURE:
<223> OTHER INFORMATION: Assay component

<400> SEQUENCE: 239
agtaggtgct tgccatttac atct                                         24

<210> SEQ ID NO 240
<211> LENGTH: 22
<212> TYPE: DNA
<213> ORGANISM: Artificial ;Probe -continued

```
<220> FEATURE:
<223> OTHER INFORMATION: Assay component

<400> SEQUENCE: 240
aagattagca ataactattg tt                                            22

<210> SEQ ID NO 241
<211> LENGTH: 22
<212> TYPE: DNA
<213> ORGANISM: Artificial ;Probe
<220> FEATURE:
<223> OTHER INFORMATION: Assay component

<400> SEQUENCE: 241
aagattagca ataactgttg tt                                            22

<210> SEQ ID NO 242
<211> LENGTH: 20
<212> TYPE: DNA
<213> ORGANISM: Artificial ;Primer
<220> FEATURE:
<223> OTHER INFORMATION: Assay component

<400> SEQUENCE: 242
cggtctggct aggatttgga                                               20

<210> SEQ ID NO 243
<211> LENGTH: 21
<212> TYPE: DNA
<213> ORGANISM: Artificial ;Primer
<220> FEATURE:
<223> OTHER INFORMATION: Assay component

<400> SEQUENCE: 243
gagcatgtgg aggttcctga t                                             21

<210> SEQ ID NO 244
<211> LENGTH: 17
<212> TYPE: DNA
<213> ORGANISM: Artificial ;Probe
<220> FEATURE:
<223> OTHER INFORMATION: Assay component

<400> SEQUENCE: 244
cattcaagaa tgtcctc                                                  17

<210> SEQ ID NO 245
<211> LENGTH: 17
<212> TYPE: DNA
<213> ORGANISM: Artificial ;Probe
<220> FEATURE:
<223> OTHER INFORMATION: Assay component

<400> SEQUENCE: 245
cattcaagca tgtcctc                                                  17

<210> SEQ ID NO 246
<211> LENGTH: 25
<212> TYPE: DNA
<213> ORGANISM: Artificial ;Primer
<220> FEATURE:
<223> OTHER INFORMATION: Assay component

<400> SEQUENCE: 246
gaatctgaga tgttgaaccc actgt                                         25
```

-continued

<210> SEQ ID NO 247
<211> LENGTH: 21
<212> TYPE: DNA
<213> ORGANISM: Artificial ;Primer
<220> FEATURE:
<223> OTHER INFORMATION: Assay component

<400> SEQUENCE: 247
tgctgaaaga ggcctcaaag g                                             21

<210> SEQ ID NO 248
<211> LENGTH: 16
<212> TYPE: DNA
<213> ORGANISM: Artificial ;Probe
<220> FEATURE:
<223> OTHER INFORMATION: Assay component

<400> SEQUENCE: 248
caccaaatca gcatcg                                                   16

<210> SEQ ID NO 249
<211> LENGTH: 16
<212> TYPE: DNA
<213> ORGANISM: Artificial ;Probe
<220> FEATURE:
<223> OTHER INFORMATION: Assay component

<400> SEQUENCE: 249
caccaaatcg gcatcg                                                   16

<210> SEQ ID NO 250
<211> LENGTH: 21
<212> TYPE: DNA
<213> ORGANISM: Artificial ;Primer
<220> FEATURE:
<223> OTHER INFORMATION: Assay component

<400> SEQUENCE: 250
ttcttgacgt gccgaaagga t                                             21

<210> SEQ ID NO 251
<211> LENGTH: 20
<212> TYPE: DNA
<213> ORGANISM: Artificial ;Primer
<220> FEATURE:
<223> OTHER INFORMATION: Assay component

<400> SEQUENCE: 251
ccgccgtatg attggatcga                                               20

<210> SEQ ID NO 252
<211> LENGTH: 17
<212> TYPE: DNA
<213> ORGANISM: Artificial ;Probe
<220> FEATURE:
<223> OTHER INFORMATION: Assay component

<400> SEQUENCE: 252
aaaaagccaa ccgcacg                                                  17

<210> SEQ ID NO 253
<211> LENGTH: 17
<212> TYPE: DNA
<213> ORGANISM: Artificial ;Probe
<220> FEATURE:
<223> OTHER INFORMATION: Assay component

<400> SEQUENCE: 253
aaaaagccag ccgcacg                                                  17

<210> SEQ ID NO 254
<211> LENGTH: 25
<212> TYPE: DNA
<213> ORGANISM: Artificial ;Primer
<220> FEATURE:
<223> OTHER INFORMATION: Assay component

<400> SEQUENCE: 254
ggtacatcag caaccgaggt ttata                                         25

<210> SEQ ID NO 255
<211> LENGTH: 21
<212> TYPE: DNA
<213> ORGANISM: Artificial ;Primer
<220> FEATURE:
<223> OTHER INFORMATION: Assay component

<400> SEQUENCE: 255
gttgatgaac gcctcctcag a                                             21

<210> SEQ ID NO 256
<211> LENGTH: 15
<212> TYPE: DNA
<213> ORGANISM: Artificial ;Probe
<220> FEATURE:
<223> OTHER INFORMATION: Assay component

<400> SEQUENCE: 256
ctcgtagagc aatct                                                    15

<210> SEQ ID NO 257
<211> LENGTH: 16
<212> TYPE: DNA
<213> ORGANISM: Artificial ;Probe
<220> FEATURE:
<223> OTHER INFORMATION: Assay component

<400> SEQUENCE: 257
cctcgtagac caatct                                                   16

<210> SEQ ID NO 258
<211> LENGTH: 23
<212> TYPE: DNA
<213> ORGANISM: Artificial ;Primer
<220> FEATURE:
<223> OTHER INFORMATION: Assay component

<400> SEQUENCE: 258
gaagccgact ggagagaatg ttt                                           23

<210> SEQ ID NO 259
<211> LENGTH: 25
<212> TYPE: DNA
<213> ORGANISM: Artificial ;Primer
<220> FEATURE:
<223> OTHER INFORMATION: Assay component

<400> SEQUENCE: 259
ttttccatgg agggttatga tgctt                                         25

<210> SEQ ID NO 260

```
<211> LENGTH: 19
<212> TYPE: DNA
<213> ORGANISM: Artificial ;Probe
<220> FEATURE:
<223> OTHER INFORMATION: Assay component

<400> SEQUENCE: 260
ctctggtttc tgatggcta                                               19

<210> SEQ ID NO 261
<211> LENGTH: 18
<212> TYPE: DNA
<213> ORGANISM: Artificial ;Probe
<220> FEATURE:
<223> OTHER INFORMATION: Assay component

<400> SEQUENCE: 261
tctggtttct ggtggcta                                                18

<210> SEQ ID NO 262
<211> LENGTH: 27
<212> TYPE: DNA
<213> ORGANISM: Artificial ;Primer
<220> FEATURE:
<223> OTHER INFORMATION: Assay component

<400> SEQUENCE: 262
gcgccttatt atcatcatct aggtgta                                      27

<210> SEQ ID NO 263
<211> LENGTH: 20
<212> TYPE: DNA
<213> ORGANISM: Artificial ;Primer
<220> FEATURE:
<223> OTHER INFORMATION: Assay component

<400> SEQUENCE: 263
gaaaagcacg gcatcagcaa                                              20

<210> SEQ ID NO 264
<211> LENGTH: 18
<212> TYPE: DNA
<213> ORGANISM: Artificial ;Probe
<220> FEATURE:
<223> OTHER INFORMATION: Assay component

<400> SEQUENCE: 264
attagcacaa acggaagt                                                18

<210> SEQ ID NO 265
<211> LENGTH: 18
<212> TYPE: DNA
<213> ORGANISM: Artificial ;Probe
<220> FEATURE:
<223> OTHER INFORMATION: Assay component

<400> SEQUENCE: 265
attagcacag acggaagt                                                18

<210> SEQ ID NO 266
<211> LENGTH: 15
<212> TYPE: DNA
<213> ORGANISM: Artificial ;Primer
<220> FEATURE:
<223> OTHER INFORMATION: Assay component

<400> SEQUENCE: 266
```
cggcgccgtc ttgtg                                                          15

<210> SEQ ID NO 267
<211> LENGTH: 17
<212> TYPE: DNA
<213> ORGANISM: Artificial ;Primer
<220> FEATURE:
<223> OTHER INFORMATION: Assay component

<400> SEQUENCE: 267
ccggaagccg cctacag                                                        17

<210> SEQ ID NO 268
<211> LENGTH: 18
<212> TYPE: DNA
<213> ORGANISM: Artificial ;Probe
<220> FEATURE:
<223> OTHER INFORMATION: Assay component

<400> SEQUENCE: 268
aacttggtga cgtaatag                                                       18

<210> SEQ ID NO 269
<211> LENGTH: 18
<212> TYPE: DNA
<213> ORGANISM: Artificial ;Probe
<220> FEATURE:
<223> OTHER INFORMATION: Assay component

<400> SEQUENCE: 269
aacttggtga cgtagtag                                                       18

<210> SEQ ID NO 270
<211> LENGTH: 23
<212> TYPE: DNA
<213> ORGANISM: Artificial ;Primer
<220> FEATURE:
<223> OTHER INFORMATION: Assay component

<400> SEQUENCE: 270
gaccaaggtg tcataggcat tga                                                 23

<210> SEQ ID NO 271
<211> LENGTH: 26
<212> TYPE: DNA
<213> ORGANISM: Artificial ;Primer
<220> FEATURE:
<223> OTHER INFORMATION: Assay component

<400> SEQUENCE: 271
gcaaatgctg aggaatataa gcacat                                              26

<210> SEQ ID NO 272
<211> LENGTH: 15
<212> TYPE: DNA
<213> ORGANISM: Artificial ;Probe
<220> FEATURE:
<223> OTHER INFORMATION: Assay component

<400> SEQUENCE: 272
cccccacaac tggat                                                          15

<210> SEQ ID NO 273
<211> LENGTH: 14
<212> TYPE: DNA

```
<213> ORGANISM: Artificial ;Probe
<220> FEATURE:
<223> OTHER INFORMATION: Assay component

<400> SEQUENCE: 273
ccccacgact ggat                                                    14

<210> SEQ ID NO 274
<211> LENGTH: 24
<212> TYPE: DNA
<213> ORGANISM: Artificial ;Primer
<220> FEATURE:
<223> OTHER INFORMATION: Assay component

<400> SEQUENCE: 274
ccatcacagt gaccttccat ttgt                                         24

<210> SEQ ID NO 275
<211> LENGTH: 23
<212> TYPE: DNA
<213> ORGANISM: Artificial ;Primer
<220> FEATURE:
<223> OTHER INFORMATION: Assay component

<400> SEQUENCE: 275
tgacaccctc aatttgctgg aaa                                          23

<210> SEQ ID NO 276
<211> LENGTH: 15
<212> TYPE: DNA
<213> ORGANISM: Artificial ;Probe
<220> FEATURE:
<223> OTHER INFORMATION: Assay component

<400> SEQUENCE: 276
aagctcacag caatt                                                   15

<210> SEQ ID NO 277
<211> LENGTH: 15
<212> TYPE: DNA
<213> ORGANISM: Artificial ;Probe
<220> FEATURE:
<223> OTHER INFORMATION: Assay component

<400> SEQUENCE: 277
aagctcacgg caatt                                                   15

<210> SEQ ID NO 278
<211> LENGTH: 22
<212> TYPE: DNA
<213> ORGANISM: Artificial ;Primer
<220> FEATURE:
<223> OTHER INFORMATION: Assay component

<400> SEQUENCE: 278
gttgcagagt aaccagctga ag                                           22

<210> SEQ ID NO 279
<211> LENGTH: 18
<212> TYPE: DNA
<213> ORGANISM: Artificial ;Primer
<220> FEATURE:
<223> OTHER INFORMATION: Assay component

<400> SEQUENCE: 279
cgcgagctcc gtaagcat                                                18
```

```
<210> SEQ ID NO 280
<211> LENGTH: 15
<212> TYPE: DNA
<213> ORGANISM: Artificial ;Probe
<220> FEATURE:
<223> OTHER INFORMATION: Assay component

<400> SEQUENCE: 280
tccataccag catcg                                                      15

<210> SEQ ID NO 281
<211> LENGTH: 15
<212> TYPE: DNA
<213> ORGANISM: Artificial ;Probe
<220> FEATURE:
<223> OTHER INFORMATION: Assay component

<400> SEQUENCE: 281
tccataccgg catcg                                                      15

<210> SEQ ID NO 282
<211> LENGTH: 27
<212> TYPE: DNA
<213> ORGANISM: Artificial ;Primer
<220> FEATURE:
<223> OTHER INFORMATION: Assay component

<400> SEQUENCE: 282
cagagttgac atattgagca ctagtgt                                         27

<210> SEQ ID NO 283
<211> LENGTH: 25
<212> TYPE: DNA
<213> ORGANISM: Artificial ;Primer
<220> FEATURE:
<223> OTHER INFORMATION: Assay component

<400> SEQUENCE: 283
ccaatgtcaa acatacccaa acagt                                           25

<210> SEQ ID NO 284
<211> LENGTH: 17
<212> TYPE: DNA
<213> ORGANISM: Artificial ;Probe
<220> FEATURE:
<223> OTHER INFORMATION: Assay component

<400> SEQUENCE: 284
tgtagaggca aatgtat                                                    17

<210> SEQ ID NO 285
<211> LENGTH: 18
<212> TYPE: DNA
<213> ORGANISM: Artificial ;Probe
<220> FEATURE:
<223> OTHER INFORMATION: Assay component

<400> SEQUENCE: 285
ctgtagaggc aagtgtat                                                   18

<210> SEQ ID NO 286
<211> LENGTH: 27
<212> TYPE: DNA
<213> ORGANISM: Artificial ;Primer
<220> FEATURE:
```

<223> OTHER INFORMATION: Assay component

<400> SEQUENCE: 286
ggcaccaata tctgttttcc attcaat                                            27

<210> SEQ ID NO 287
<211> LENGTH: 26
<212> TYPE: DNA
<213> ORGANISM: Artificial ;Primer
<220> FEATURE:
<223> OTHER INFORMATION: Assay component

<400> SEQUENCE: 287
acagcagata taaaatgatg ctcggt                                             26

<210> SEQ ID NO 288
<211> LENGTH: 18
<212> TYPE: DNA
<213> ORGANISM: Artificial ;Probe
<220> FEATURE:
<223> OTHER INFORMATION: Assay component

<400> SEQUENCE: 288
tgatatgtca cagtaagc                                                      18

<210> SEQ ID NO 289
<211> LENGTH: 16
<212> TYPE: DNA
<213> ORGANISM: Artificial ;Probe
<220> FEATURE:
<223> OTHER INFORMATION: Assay component

<400> SEQUENCE: 289
atatgtcgca gtaagc                                                        16

<210> SEQ ID NO 290
<211> LENGTH: 16
<212> TYPE: DNA
<213> ORGANISM: Artificial ;Primer
<220> FEATURE:
<223> OTHER INFORMATION: Assay component

<400> SEQUENCE: 290
tcccccgagc caggtt                                                        16

<210> SEQ ID NO 291
<211> LENGTH: 25
<212> TYPE: DNA
<213> ORGANISM: Artificial ;Primer
<220> FEATURE:
<223> OTHER INFORMATION: Assay component

<400> SEQUENCE: 291
cctatagctt tggtggcaag aagaa                                              25

<210> SEQ ID NO 292
<211> LENGTH: 16
<212> TYPE: DNA
<213> ORGANISM: Artificial ;Probe
<220> FEATURE:
<223> OTHER INFORMATION: Assay component

<400> SEQUENCE: 292
ctggtgcttt ctaccg                                                        16

```
<210> SEQ ID NO 293
<211> LENGTH: 16
<212> TYPE: DNA
<213> ORGANISM: Artificial ;Probe
<220> FEATURE:
<223> OTHER INFORMATION: Assay component

<400> SEQUENCE: 293
ctggtgcttt cgaccg                                                  16

<210> SEQ ID NO 294
<211> LENGTH: 17
<212> TYPE: DNA
<213> ORGANISM: Artificial ;Primer
<220> FEATURE:
<223> OTHER INFORMATION: Assay component

<400> SEQUENCE: 294
gccgcccgat tctcagt                                                 17

<210> SEQ ID NO 295
<211> LENGTH: 18
<212> TYPE: DNA
<213> ORGANISM: Artificial ;Primer
<220> FEATURE:
<223> OTHER INFORMATION: Assay component

<400> SEQUENCE: 295
cgcgaatcga ctgccatt                                                18

<210> SEQ ID NO 296
<211> LENGTH: 14
<212> TYPE: DNA
<213> ORGANISM: Artificial ;Probe
<220> FEATURE:
<223> OTHER INFORMATION: Assay component

<400> SEQUENCE: 296
acgccatccc ttgc                                                    14

<210> SEQ ID NO 297
<211> LENGTH: 13
<212> TYPE: DNA
<213> ORGANISM: Artificial ;Probe
<220> FEATURE:
<223> OTHER INFORMATION: Assay component

<400> SEQUENCE: 297
cgccgtccct tgc                                                     13

<210> SEQ ID NO 298
<211> LENGTH: 25
<212> TYPE: DNA
<213> ORGANISM: Artificial ;Primer
<220> FEATURE:
<223> OTHER INFORMATION: Assay component

<400> SEQUENCE: 298
agccacctgt aagtacaatc acaaa                                        25

<210> SEQ ID NO 299
<211> LENGTH: 18
<212> TYPE: DNA
<213> ORGANISM: Artificial ;Primer
<220> FEATURE:
<223> OTHER INFORMATION: Assay component
```

<400> SEQUENCE: 299
cctgggcagc aacaacag                                                 18

<210> SEQ ID NO 300
<211> LENGTH: 16
<212> TYPE: DNA
<213> ORGANISM: Artificial ;Probe
<220> FEATURE:
<223> OTHER INFORMATION: Assay component

<400> SEQUENCE: 300
ccaacaacat gttacc                                                   16

<210> SEQ ID NO 301
<211> LENGTH: 16
<212> TYPE: DNA
<213> ORGANISM: Artificial ;Probe
<220> FEATURE:
<223> OTHER INFORMATION: Assay component

<400> SEQUENCE: 301
ccaacaacag gttacc                                                   16

<210> SEQ ID NO 302
<211> LENGTH: 25
<212> TYPE: DNA
<213> ORGANISM: Artificial ;Primer
<220> FEATURE:
<223> OTHER INFORMATION: Assay component

<400> SEQUENCE: 302
catgtcagac aaagccaatg ctatt                                         25

<210> SEQ ID NO 303
<211> LENGTH: 30
<212> TYPE: DNA
<213> ORGANISM: Artificial ;Primer
<220> FEATURE:
<223> OTHER INFORMATION: Assay component

<400> SEQUENCE: 303
tggctagatt ttttatgaca aagcatctct                                    30

<210> SEQ ID NO 304
<211> LENGTH: 19
<212> TYPE: DNA
<213> ORGANISM: Artificial ;Probe
<220> FEATURE:
<223> OTHER INFORMATION: Assay component

<400> SEQUENCE: 304
cattcatgtt acaatgtag                                                19

<210> SEQ ID NO 305
<211> LENGTH: 16
<212> TYPE: DNA
<213> ORGANISM: Artificial ;Probe
<220> FEATURE:
<223> OTHER INFORMATION: Assay component

<400> SEQUENCE: 305
tcatgttgca atgtag                                                   16

<210> SEQ ID NO 306
<211> LENGTH: 17

```
<212> TYPE: DNA
<213> ORGANISM: Artificial ;Primer
<220> FEATURE:
<223> OTHER INFORMATION: Assay component

<400> SEQUENCE: 306
cagaggcgcg tcaaacg                                                    17

<210> SEQ ID NO 307
<211> LENGTH: 24
<212> TYPE: DNA
<213> ORGANISM: Artificial ;Primer
<220> FEATURE:
<223> OTHER INFORMATION: Assay component

<400> SEQUENCE: 307
cctggtgtgt atgctgttct tttc                                            24

<210> SEQ ID NO 308
<211> LENGTH: 15
<212> TYPE: DNA
<213> ORGANISM: Artificial ;Probe
<220> FEATURE:
<223> OTHER INFORMATION: Assay component

<400> SEQUENCE: 308
tcggtccata ttatc                                                      15

<210> SEQ ID NO 309
<211> LENGTH: 14
<212> TYPE: DNA
<213> ORGANISM: Artificial ;Probe
<220> FEATURE:
<223> OTHER INFORMATION: Assay component

<400> SEQUENCE: 309
cggtccatct tatc                                                       14

<210> SEQ ID NO 310
<211> LENGTH: 24
<212> TYPE: DNA
<213> ORGANISM: Artificial ;Primer
<220> FEATURE:
<223> OTHER INFORMATION: Assay component

<400> SEQUENCE: 310
ttgaatccac cggtgaatct atcg                                            24

<210> SEQ ID NO 311
<211> LENGTH: 18
<212> TYPE: DNA
<213> ORGANISM: Artificial ;Primer
<220> FEATURE:
<223> OTHER INFORMATION: Assay component

<400> SEQUENCE: 311
gcggtagcgt gagtgaca                                                   18

<210> SEQ ID NO 312
<211> LENGTH: 18
<212> TYPE: DNA
<213> ORGANISM: Artificial ;Probe
<220> FEATURE:
<223> OTHER INFORMATION: Assay component

<400> SEQUENCE: 312
```

|  |  |
|---|---|
| atacagacag actcggac | 18 |

<210> SEQ ID NO 313
<211> LENGTH: 18
<212> TYPE: DNA
<213> ORGANISM: Artificial ;Probe
<220> FEATURE:
<223> OTHER INFORMATION: Assay component

<400> SEQUENCE: 313

|  |  |
|---|---|
| atacagacag gctcggac | 18 |

<210> SEQ ID NO 314
<211> LENGTH: 22
<212> TYPE: DNA
<213> ORGANISM: Artificial ;Primer
<220> FEATURE:
<223> OTHER INFORMATION: Assay component

<400> SEQUENCE: 314

|  |  |
|---|---|
| gtactgtaac ccttggctgt ca | 22 |

<210> SEQ ID NO 315
<211> LENGTH: 18
<212> TYPE: DNA
<213> ORGANISM: Artificial ;Primer
<220> FEATURE:
<223> OTHER INFORMATION: Assay component

<400> SEQUENCE: 315

|  |  |
|---|---|
| ggcaggcagc atgaatcc | 18 |

<210> SEQ ID NO 316
<211> LENGTH: 17
<212> TYPE: DNA
<213> ORGANISM: Artificial ;Probe
<220> FEATURE:
<223> OTHER INFORMATION: Assay component

<400> SEQUENCE: 316

|  |  |
|---|---|
| acagaaccaa tggtttt | 17 |

<210> SEQ ID NO 317
<211> LENGTH: 16
<212> TYPE: DNA
<213> ORGANISM: Artificial ;Probe
<220> FEATURE:
<223> OTHER INFORMATION: Assay component

<400> SEQUENCE: 317

|  |  |
|---|---|
| cagaaccagt ggtttt | 16 |

<210> SEQ ID NO 318
<211> LENGTH: 23
<212> TYPE: DNA
<213> ORGANISM: Artificial ;Primer
<220> FEATURE:
<223> OTHER INFORMATION: Assay component

<400> SEQUENCE: 318

|  |  |
|---|---|
| ctgctgctgt gttactgtat cct | 23 |

<210> SEQ ID NO 319
<211> LENGTH: 18
<212> TYPE: DNA
<213> ORGANISM: Artificial ;Primer
<220> FEATURE:
<223> OTHER INFORMATION: Assay component

<400> SEQUENCE: 319
tgaccgctga agcacgaa                                                 18

<210> SEQ ID NO 320
<211> LENGTH: 17
<212> TYPE: DNA
<213> ORGANISM: Artificial ;Probe
<220> FEATURE:
<223> OTHER INFORMATION: Assay component

<400> SEQUENCE: 320
atggccatac agcacga                                                  17

<210> SEQ ID NO 321
<211> LENGTH: 18
<212> TYPE: DNA
<213> ORGANISM: Artificial ;Probe
<220> FEATURE:
<223> OTHER INFORMATION: Assay component

<400> SEQUENCE: 321
aatggccata ctgcacga                                                 18

<210> SEQ ID NO 322
<211> LENGTH: 23
<212> TYPE: DNA
<213> ORGANISM: Artificial ;Primer
<220> FEATURE:
<223> OTHER INFORMATION: Assay component

<400> SEQUENCE: 322
catcacacag cttgtacatg caa                                           23

<210> SEQ ID NO 323
<211> LENGTH: 25
<212> TYPE: DNA
<213> ORGANISM: Artificial ;Primer
<220> FEATURE:
<223> OTHER INFORMATION: Assay component

<400> SEQUENCE: 323
gtggagaaaa ggagaggaga gaatt                                         25

<210> SEQ ID NO 324
<211> LENGTH: 17
<212> TYPE: DNA
<213> ORGANISM: Artificial ;Probe
<220> FEATURE:
<223> OTHER INFORMATION: Assay component

<400> SEQUENCE: 324
caattcgcag acgatgg                                                  17

<210> SEQ ID NO 325
<211> LENGTH: 15
<212> TYPE: DNA
<213> ORGANISM: Artificial ;Probe
<220> FEATURE:
<223> OTHER INFORMATION: Assay component

<400> SEQUENCE: 325
attcgcaggc gatgg                                                    15

<210> SEQ ID NO 326
<211> LENGTH: 25
<212> TYPE: DNA
<213> ORGANISM: Artificial ;Primer
<220> FEATURE:
<223> OTHER INFORMATION: Assay component

<400> SEQUENCE: 326
cggattcaag tgcctctaag ctata						25

<210> SEQ ID NO 327
<211> LENGTH: 24
<212> TYPE: DNA
<213> ORGANISM: Artificial ;Primer
<220> FEATURE:
<223> OTHER INFORMATION: Assay component

<400> SEQUENCE: 327
gagacagtaa gacgaagaat ggca						24

<210> SEQ ID NO 328
<211> LENGTH: 14
<212> TYPE: DNA
<213> ORGANISM: Artificial ;Probe
<220> FEATURE:
<223> OTHER INFORMATION: Assay component

<400> SEQUENCE: 328
cacgtcagca tgct							14

<210> SEQ ID NO 329
<211> LENGTH: 14
<212> TYPE: DNA
<213> ORGANISM: Artificial ;Probe
<220> FEATURE:
<223> OTHER INFORMATION: Assay component

<400> SEQUENCE: 329
cacgtcggca tgct							14

<210> SEQ ID NO 330
<211> LENGTH: 27
<212> TYPE: DNA
<213> ORGANISM: Artificial ;Primer
<220> FEATURE:
<223> OTHER INFORMATION: Assay component

<400> SEQUENCE: 330
gcaacttact tataacatgg caaccaa						27

<210> SEQ ID NO 331
<211> LENGTH: 25
<212> TYPE: DNA
<213> ORGANISM: Artificial ;Primer
<220> FEATURE:
<223> OTHER INFORMATION: Assay component

<400> SEQUENCE: 331
gcaattcact gcattgggtc taatg						25

<210> SEQ ID NO 332
<211> LENGTH: 17
<212> TYPE: DNA
<213> ORGANISM: Artificial ;Probe
<220> FEATURE:
<223> OTHER INFORMATION: Assay component

```
<400> SEQUENCE: 332
ataagtgtgc acaatgt                                                   17

<210> SEQ ID NO 333
<211> LENGTH: 17
<212> TYPE: DNA
<213> ORGANISM: Artificial ;Probe
<220> FEATURE:
<223> OTHER INFORMATION: Assay component

<400> SEQUENCE: 333
ataagtgtgc gcaatgt                                                   17

<210> SEQ ID NO 334
<211> LENGTH: 24
<212> TYPE: DNA
<213> ORGANISM: Artificial ;Primer
<220> FEATURE:
<223> OTHER INFORMATION: Assay component

<400> SEQUENCE: 334
tctgcatagc attgaactgg acag                                           24

<210> SEQ ID NO 335
<211> LENGTH: 25
<212> TYPE: DNA
<213> ORGANISM: Artificial ;Primer
<220> FEATURE:
<223> OTHER INFORMATION: Assay component

<400> SEQUENCE: 335
aggaacagta cagatcagca gtaga                                          25

<210> SEQ ID NO 336
<211> LENGTH: 18
<212> TYPE: DNA
<213> ORGANISM: Artificial ;Probe
<220> FEATURE:
<223> OTHER INFORMATION: Assay component

<400> SEQUENCE: 336
acagagtaac acagcaag                                                  18

<210> SEQ ID NO 337
<211> LENGTH: 17
<212> TYPE: DNA
<213> ORGANISM: Artificial ;Probe
<220> FEATURE:
<223> OTHER INFORMATION: Assay component

<400> SEQUENCE: 337
cagagtaacg cagcaag                                                   17

<210> SEQ ID NO 338
<211> LENGTH: 23
<212> TYPE: DNA
<213> ORGANISM: Artificial ;Primer
<220> FEATURE:
<223> OTHER INFORMATION: Assay component

<400> SEQUENCE: 338
gtaatggtag cacgcagatc act                                            23

<210> SEQ ID NO 339
```

```
<211> LENGTH: 24
<212> TYPE: DNA
<213> ORGANISM: Artificial ;Primer
<220> FEATURE:
<223> OTHER INFORMATION: Assay component

<400> SEQUENCE: 339
gctaggaatt gcttagtcga ggtt                                          24

<210> SEQ ID NO 340
<211> LENGTH: 17
<212> TYPE: DNA
<213> ORGANISM: Artificial ;Probe
<220> FEATURE:
<223> OTHER INFORMATION: Assay component

<400> SEQUENCE: 340
actgaagaaa taatcgc                                                  17

<210> SEQ ID NO 341
<211> LENGTH: 16
<212> TYPE: DNA
<213> ORGANISM: Artificial ;Probe
<220> FEATURE:
<223> OTHER INFORMATION: Assay component

<400> SEQUENCE: 341
ctgaagaagt aatcgc                                                   16

<210> SEQ ID NO 342
<211> LENGTH: 20
<212> TYPE: DNA
<213> ORGANISM: Artificial ;Primer
<220> FEATURE:
<223> OTHER INFORMATION: Assay component

<400> SEQUENCE: 342
gcgaagtccg cgtagtactc                                               20

<210> SEQ ID NO 343
<211> LENGTH: 18
<212> TYPE: DNA
<213> ORGANISM: Artificial ;Primer
<220> FEATURE:
<223> OTHER INFORMATION: Assay component

<400> SEQUENCE: 343
cgtcaccaga ggctacgt                                                 18

<210> SEQ ID NO 344
<211> LENGTH: 15
<212> TYPE: DNA
<213> ORGANISM: Artificial ;Probe
<220> FEATURE:
<223> OTHER INFORMATION: Assay component

<400> SEQUENCE: 344
acgccttgac cacct                                                    15

<210> SEQ ID NO 345
<211> LENGTH: 15
<212> TYPE: DNA
<213> ORGANISM: Artificial ;Probe
<220> FEATURE:
<223> OTHER INFORMATION: Assay component

<400> SEQUENCE: 345
```

```
acgccttggc cacct                                                     15

<210> SEQ ID NO 346
<211> LENGTH: 25
<212> TYPE: DNA
<213> ORGANISM: Artificial ;Primer
<220> FEATURE:
<223> OTHER INFORMATION: Assay component

<400> SEQUENCE: 346
agaactttgt gaggaagagc tacac                                          25

<210> SEQ ID NO 347
<211> LENGTH: 20
<212> TYPE: DNA
<213> ORGANISM: Artificial ;Primer
<220> FEATURE:
<223> OTHER INFORMATION: Assay component

<400> SEQUENCE: 347
gcctgatgct gtcccaacat                                                20

<210> SEQ ID NO 348
<211> LENGTH: 18
<212> TYPE: DNA
<213> ORGANISM: Artificial ;Probe
<220> FEATURE:
<223> OTHER INFORMATION: Assay component

<400> SEQUENCE: 348
catgaagtat ttaaggcc                                                  18

<210> SEQ ID NO 349
<211> LENGTH: 18
<212> TYPE: DNA
<213> ORGANISM: Artificial ;Probe
<220> FEATURE:
<223> OTHER INFORMATION: Assay component

<400> SEQUENCE: 349
catgaagtac ttaaggcc                                                  18

<210> SEQ ID NO 350
<211> LENGTH: 25
<212> TYPE: DNA
<213> ORGANISM: Artificial ;Primer
<220> FEATURE:
<223> OTHER INFORMATION: Assay component

<400> SEQUENCE: 350
ctgtaaaaaa ggcccattgt tagct                                          25

<210> SEQ ID NO 351
<211> LENGTH: 23
<212> TYPE: DNA
<213> ORGANISM: Artificial ;Primer
<220> FEATURE:
<223> OTHER INFORMATION: Assay component

<400> SEQUENCE: 351
tgggtttcag accagagatt tgg                                            23

<210> SEQ ID NO 352
<211> LENGTH: 17
<212> TYPE: DNA
```

```
<213> ORGANISM: Artificial ;Probe
<220> FEATURE:
<223> OTHER INFORMATION: Assay component

<400> SEQUENCE: 352
ccctccgtaa atgttaa                                                    17

<210> SEQ ID NO 353
<211> LENGTH: 17
<212> TYPE: DNA
<213> ORGANISM: Artificial ;Probe
<220> FEATURE:
<223> OTHER INFORMATION: Assay component

<400> SEQUENCE: 353
ccctccgtag atgttaa                                                    17

<210> SEQ ID NO 354
<211> LENGTH: 24
<212> TYPE: DNA
<213> ORGANISM: Artificial ;Primer
<220> FEATURE:
<223> OTHER INFORMATION: Assay component

<400> SEQUENCE: 354
caagaacacc tgaacacatt tgct                                            24

<210> SEQ ID NO 355
<211> LENGTH: 21
<212> TYPE: DNA
<213> ORGANISM: Artificial ;Primer
<220> FEATURE:
<223> OTHER INFORMATION: Assay component

<400> SEQUENCE: 355
acctcaccag gttgctactc a                                               21

<210> SEQ ID NO 356
<211> LENGTH: 18
<212> TYPE: DNA
<213> ORGANISM: Artificial ;Probe
<220> FEATURE:
<223> OTHER INFORMATION: Assay component

<400> SEQUENCE: 356
ccatcatggt atcagata                                                   18

<210> SEQ ID NO 357
<211> LENGTH: 18
<212> TYPE: DNA
<213> ORGANISM: Artificial ;Probe
<220> FEATURE:
<223> OTHER INFORMATION: Assay component

<400> SEQUENCE: 357
ccatcatggt agcagata                                                   18

<210> SEQ ID NO 358
<211> LENGTH: 16
<212> TYPE: DNA
<213> ORGANISM: Artificial ;Primer
<220> FEATURE:
<223> OTHER INFORMATION: Assay component

<400> SEQUENCE: 358
ccgcgcactg gtacac                                                     16
```

<210> SEQ ID NO 359
<211> LENGTH: 18
<212> TYPE: DNA
<213> ORGANISM: Artificial ;Primer
<220> FEATURE:
<223> OTHER INFORMATION: Assay component

<400> SEQUENCE: 359
gcgcgtgacg aagttctc                                                    18

<210> SEQ ID NO 360
<211> LENGTH: 15
<212> TYPE: DNA
<213> ORGANISM: Artificial ;Probe
<220> FEATURE:
<223> OTHER INFORMATION: Assay component

<400> SEQUENCE: 360
cctacgacgt attcg                                                       15

<210> SEQ ID NO 361
<211> LENGTH: 13
<212> TYPE: DNA
<213> ORGANISM: Artificial ;Probe
<220> FEATURE:
<223> OTHER INFORMATION: Assay component

<400> SEQUENCE: 361
tacggcgtat tcg                                                         13

<210> SEQ ID NO 362
<211> LENGTH: 18
<212> TYPE: DNA
<213> ORGANISM: Artificial ;Primer
<220> FEATURE:
<223> OTHER INFORMATION: Assay component

<400> SEQUENCE: 362
tgctgcggct ggtaactg                                                    18

<210> SEQ ID NO 363
<211> LENGTH: 25
<212> TYPE: DNA
<213> ORGANISM: Artificial ;Primer
<220> FEATURE:
<223> OTHER INFORMATION: Assay component

<400> SEQUENCE: 363
ccctggaaat ttcatcaccc ctttt                                            25

<210> SEQ ID NO 364
<211> LENGTH: 19
<212> TYPE: DNA
<213> ORGANISM: Artificial ;Probe
<220> FEATURE:
<223> OTHER INFORMATION: Assay component

<400> SEQUENCE: 364
ttgaagccaa agtagccag                                                   19

<210> SEQ ID NO 365
<211> LENGTH: 16
<212> TYPE: DNA
<213> ORGANISM: Artificial ;Probe
<220> FEATURE:

-continued

<223> OTHER INFORMATION: Assay component

<400> SEQUENCE: 365
aagccaaggt agccag                                                        16

<210> SEQ ID NO 366
<211> LENGTH: 17
<212> TYPE: DNA
<213> ORGANISM: Artificial ;Primer
<220> FEATURE:
<223> OTHER INFORMATION: Assay component

<400> SEQUENCE: 366
gcctcggcgc ttaaacc                                                       17

<210> SEQ ID NO 367
<211> LENGTH: 25
<212> TYPE: DNA
<213> ORGANISM: Artificial ;Primer
<220> FEATURE:
<223> OTHER INFORMATION: Assay component

<400> SEQUENCE: 367
cctgtgagtc tcaaacacta ttggt                                              25

<210> SEQ ID NO 368
<211> LENGTH: 19
<212> TYPE: DNA
<213> ORGANISM: Artificial ;Probe
<220> FEATURE:
<223> OTHER INFORMATION: Assay component

<400> SEQUENCE: 368
tagcattcgt aagttcatt                                                     19

<210> SEQ ID NO 369
<211> LENGTH: 16
<212> TYPE: DNA
<213> ORGANISM: Artificial ;Probe
<220> FEATURE:
<223> OTHER INFORMATION: Assay component

<400> SEQUENCE: 369
cattcgtagg ttcatt                                                        16

<210> SEQ ID NO 370
<211> LENGTH: 29
<212> TYPE: DNA
<213> ORGANISM: Artificial ;Primer
<220> FEATURE:
<223> OTHER INFORMATION: Assay component

<400> SEQUENCE: 370
ttgttaatta ttgcactgtt ctcgttgtc                                          29

<210> SEQ ID NO 371
<211> LENGTH: 25
<212> TYPE: DNA
<213> ORGANISM: Artificial ;Primer
<220> FEATURE:
<223> OTHER INFORMATION: Assay component

<400> SEQUENCE: 371
tcagtcctga aaccactctt actca                                              25

-continued

```
<210> SEQ ID NO 372
<211> LENGTH: 17
<212> TYPE: DNA
<213> ORGANISM: Artificial ;Probe
<220> FEATURE:
<223> OTHER INFORMATION: Assay component

<400> SEQUENCE: 372
ttaccacgct attcaaa                                                        17

<210> SEQ ID NO 373
<211> LENGTH: 18
<212> TYPE: DNA
<213> ORGANISM: Artificial ;Probe
<220> FEATURE:
<223> OTHER INFORMATION: Assay component

<400> SEQUENCE: 373
tttaccacgc tatccaaa                                                       18

<210> SEQ ID NO 374
<211> LENGTH: 25
<212> TYPE: DNA
<213> ORGANISM: Artificial ;Primer
<220> FEATURE:
<223> OTHER INFORMATION: Assay component

<400> SEQUENCE: 374
gcaacaacga agggagtgat attga                                               25

<210> SEQ ID NO 375
<211> LENGTH: 25
<212> TYPE: DNA
<213> ORGANISM: Artificial ;Primer
<220> FEATURE:
<223> OTHER INFORMATION: Assay component

<400> SEQUENCE: 375
gaaggtccaa tgtcttgtac tcgta                                               25

<210> SEQ ID NO 376
<211> LENGTH: 15
<212> TYPE: DNA
<213> ORGANISM: Artificial ;Probe
<220> FEATURE:
<223> OTHER INFORMATION: Assay component

<400> SEQUENCE: 376
ccatgggtct ttcgt                                                          15

<210> SEQ ID NO 377
<211> LENGTH: 15
<212> TYPE: DNA
<213> ORGANISM: Artificial ;Probe
<220> FEATURE:
<223> OTHER INFORMATION: Assay component

<400> SEQUENCE: 377
ccatgggcct ttcgt                                                          15

<210> SEQ ID NO 378
<211> LENGTH: 24
<212> TYPE: DNA
<213> ORGANISM: Artificial ;Primer
<220> FEATURE:
<223> OTHER INFORMATION: Assay component
```

<400> SEQUENCE: 378
gctgctgcac gattatactg gaat                                            24

<210> SEQ ID NO 379
<211> LENGTH: 23
<212> TYPE: DNA
<213> ORGANISM: Artificial ;Primer
<220> FEATURE:
<223> OTHER INFORMATION: Assay component

<400> SEQUENCE: 379
ctgagccact acagaaactg cta                                             23

<210> SEQ ID NO 380
<211> LENGTH: 18
<212> TYPE: DNA
<213> ORGANISM: Artificial ;Probe
<220> FEATURE:
<223> OTHER INFORMATION: Assay component

<400> SEQUENCE: 380
ctagagtgct aagtccct                                                   18

<210> SEQ ID NO 381
<211> LENGTH: 18
<212> TYPE: DNA
<213> ORGANISM: Artificial ;Probe
<220> FEATURE:
<223> OTHER INFORMATION: Assay component

<400> SEQUENCE: 381
ctagagtgct aggtccct                                                   18

<210> SEQ ID NO 382
<211> LENGTH: 21
<212> TYPE: DNA
<213> ORGANISM: Artificial ;Primer
<220> FEATURE:
<223> OTHER INFORMATION: Assay component

<400> SEQUENCE: 382
gaaaggctgg gaagaccact a                                               21

<210> SEQ ID NO 383
<211> LENGTH: 19
<212> TYPE: DNA
<213> ORGANISM: Artificial ;Primer
<220> FEATURE:
<223> OTHER INFORMATION: Assay component

<400> SEQUENCE: 383
ggccgacagt cactctcaa                                                  19

<210> SEQ ID NO 384
<211> LENGTH: 17
<212> TYPE: DNA
<213> ORGANISM: Artificial ;Probe
<220> FEATURE:
<223> OTHER INFORMATION: Assay component

<400> SEQUENCE: 384
aaaatcgcct tgtcaac                                                    17

<210> SEQ ID NO 385
<211> LENGTH: 16

```
<212> TYPE: DNA
<213> ORGANISM: Artificial ;Probe
<220> FEATURE:
<223> OTHER INFORMATION: Assay component

<400> SEQUENCE: 385
aaaatcgcct cgtcaa                                                    16

<210> SEQ ID NO 386
<211> LENGTH: 19
<212> TYPE: DNA
<213> ORGANISM: Artificial ;Primer
<220> FEATURE:
<223> OTHER INFORMATION: Assay component

<400> SEQUENCE: 386
ctccagttgg taatatgct                                                 19

<210> SEQ ID NO 387
<211> LENGTH: 19
<212> TYPE: DNA
<213> ORGANISM: Artificial ;Primer
<220> FEATURE:
<223> OTHER INFORMATION: Assay component

<400> SEQUENCE: 387
gagtgggagt ttgactatc                                                 19

<210> SEQ ID NO 388
<211> LENGTH: 17
<212> TYPE: DNA
<213> ORGANISM: Artificial ;Probe
<220> FEATURE:
<223> OTHER INFORMATION: Assay component

<400> SEQUENCE: 388
cttaccactt tcaggta                                                   17

<210> SEQ ID NO 389
<211> LENGTH: 16
<212> TYPE: DNA
<213> ORGANISM: Artificial ;Probe
<220> FEATURE:
<223> OTHER INFORMATION: Assay component

<400> SEQUENCE: 389 ttaccaccttt caggta                                                   16

<210> SEQ ID NO 390
<211> LENGTH: 24
<212> TYPE: DNA
<213> ORGANISM: Artificial ;Primer
<220> FEATURE:
<223> OTHER INFORMATION: Assay component

<400> SEQUENCE: 390
cctggaaaga caaataggaa ccca                                           24

<210> SEQ ID NO 391
<211> LENGTH: 16
<212> TYPE: DNA
<213> ORGANISM: Artificial ;Primer
<220> FEATURE:
<223> OTHER INFORMATION: Assay component

<400> SEQUENCE: 391
```

-continued

```
ggaaacgccg gccaaa                                          16

<210> SEQ ID NO 392
<211> LENGTH: 18
<212> TYPE: DNA
<213> ORGANISM: Artificial ;Probe
<220> FEATURE:
<223> OTHER INFORMATION: Assay component

<400> SEQUENCE: 392
aacgaatgag ctgtctga                                        18

<210> SEQ ID NO 393
<211> LENGTH: 18
<212> TYPE: DNA
<213> ORGANISM: Artificial ;Probe
<220> FEATURE:
<223> OTHER INFORMATION: Assay component

<400> SEQUENCE: 393
aaacgaatga gcagtctg                                        18

<210> SEQ ID NO 394
<211> LENGTH: 25
<212> TYPE: DNA
<213> ORGANISM: Artificial ;Primer
<220> FEATURE:
<223> OTHER INFORMATION: Assay component

<400> SEQUENCE: 394
gtgctccata tcttctagca ttcac                                25

<210> SEQ ID NO 395
<211> LENGTH: 19
<212> TYPE: DNA
<213> ORGANISM: Artificial ;Primer
<220> FEATURE:
<223> OTHER INFORMATION: Assay component

<400> SEQUENCE: 395
ggcagccttg tggtgtaac                                       19

<210> SEQ ID NO 396
<211> LENGTH: 17
<212> TYPE: DNA
<213> ORGANISM: Artificial ;Probe
<220> FEATURE:
<223> OTHER INFORMATION: Assay component

<400> SEQUENCE: 396
aacctgacga acgttgt                                         17

<210> SEQ ID NO 397
<211> LENGTH: 15
<212> TYPE: DNA
<213> ORGANISM: Artificial ;Probe
<220> FEATURE:
<223> OTHER INFORMATION: Assay component

<400> SEQUENCE: 397
ctgacgaacg ctgtt                                           15

<210> SEQ ID NO 398
<211> LENGTH: 23
<212> TYPE: DNA
<213> ORGANISM: Artificial ;Primer
```

<220> FEATURE:
<223> OTHER INFORMATION: Assay component

<400> SEQUENCE: 398
tgcacatatc cactcgtgaa tgc                                               23

<210> SEQ ID NO 399
<211> LENGTH: 24
<212> TYPE: DNA
<213> ORGANISM: Artificial ;Primer
<220> FEATURE:
<223> OTHER INFORMATION: Assay component

<400> SEQUENCE: 399 atctccttt gtttgctagg gaaa                                               24

<210> SEQ ID NO 400
<211> LENGTH: 19
<212> TYPE: DNA
<213> ORGANISM: Artificial ;Probe
<220> FEATURE:
<223> OTHER INFORMATION: Assay component

<400> SEQUENCE: 400
tatttctgtc ctttagcag                                                    19

<210> SEQ ID NO 401
<211> LENGTH: 16
<212> TYPE: DNA
<213> ORGANISM: Artificial ;Probe
<220> FEATURE:
<223> OTHER INFORMATION: Assay component

<400> SEQUENCE: 401
ttctgtcctt cagcag                                                       16

<210> SEQ ID NO 402
<211> LENGTH: 20
<212> TYPE: DNA
<213> ORGANISM: Artificial ;Primer
<220> FEATURE:
<223> OTHER INFORMATION: Assay component

<400> SEQUENCE: 402
gggccaagat gacatgaaca                                                   20

<210> SEQ ID NO 403
<211> LENGTH: 21
<212> TYPE: DNA
<213> ORGANISM: Artificial ;Primer
<220> FEATURE:
<223> OTHER INFORMATION: Assay component

<400> SEQUENCE: 403
cagagcttga gcaggaaggt t                                                 21

<210> SEQ ID NO 404
<211> LENGTH: 14
<212> TYPE: DNA
<213> ORGANISM: Artificial ;Probe
<220> FEATURE:
<223> OTHER INFORMATION: Assay component

<400> SEQUENCE: 404
acgccggata gcac                                                         14

```
<210> SEQ ID NO 405
<211> LENGTH: 13
<212> TYPE: DNA
<213> ORGANISM: Artificial ;Probe
<220> FEATURE:
<223> OTHER INFORMATION: Assay component

<400> SEQUENCE: 405
ccggacagca cgt                                                          13

<210> SEQ ID NO 406
<211> LENGTH: 24
<212> TYPE: DNA
<213> ORGANISM: Artificial ;Primer
<220> FEATURE:
<223> OTHER INFORMATION: Assay component

<400> SEQUENCE: 406
ctgacgaaga ggaggaagat gaag                                              24

<210> SEQ ID NO 407
<211> LENGTH: 22
<212> TYPE: DNA
<213> ORGANISM: Artificial ;Primer
<220> FEATURE:
<223> OTHER INFORMATION: Assay component

<400> SEQUENCE: 407
accagcagtg agtctacttt gc                                                22

<210> SEQ ID NO 408
<211> LENGTH: 14
<212> TYPE: DNA
<213> ORGANISM: Artificial ;Probe
<220> FEATURE:
<223> OTHER INFORMATION: Assay component

<400> SEQUENCE: 408
atcgtcgtcg gtgc                                                         14

<210> SEQ ID NO 409
<211> LENGTH: 13
<212> TYPE: DNA
<213> ORGANISM: Artificial ;Probe
<220> FEATURE:
<223> OTHER INFORMATION: Assay component

<400> SEQUENCE: 409
atcgtcgccg gtg                                                          13

<210> SEQ ID NO 410
<211> LENGTH: 21
<212> TYPE: DNA
<213> ORGANISM: Artificial ;Primer
<220> FEATURE:
<223> OTHER INFORMATION: Assay component

<400> SEQUENCE: 410
gagcgtgcat tccaacatct g                                                 21

<210> SEQ ID NO 411
<211> LENGTH: 19
<212> TYPE: DNA
<213> ORGANISM: Artificial ;Primer
<220> FEATURE:
<223> OTHER INFORMATION: Assay component
```

<400> SEQUENCE: 411
gtactcgtcg cgcagtgat                                                  19

<210> SEQ ID NO 412
<211> LENGTH: 18
<212> TYPE: DNA
<213> ORGANISM: Artificial ;Probe
<220> FEATURE:
<223> OTHER INFORMATION: Assay component

<400> SEQUENCE: 412
agacgacgct gatataga                                                   18

<210> SEQ ID NO 413
<211> LENGTH: 16
<212> TYPE: DNA
<213> ORGANISM: Artificial ;Probe
<220> FEATURE:
<223> OTHER INFORMATION: Assay component

<400> SEQUENCE: 413
acgacgctga tgtaga                                                     16

<210> SEQ ID NO 414
<211> LENGTH: 23
<212> TYPE: DNA
<213> ORGANISM: Artificial ;Primer
<220> FEATURE:
<223> OTHER INFORMATION: Assay component

<400> SEQUENCE: 414
accaaggttc gtctctacct acc                                             23

<210> SEQ ID NO 415
<211> LENGTH: 16
<212> TYPE: DNA
<213> ORGANISM: Artificial ;Primer
<220> FEATURE:
<223> OTHER INFORMATION: Assay component

<400> SEQUENCE: 415
cctcgccgcc tgcaac                                                     16

<210> SEQ ID NO 416
<211> LENGTH: 18
<212> TYPE: DNA
<213> ORGANISM: Artificial ;Probe
<220> FEATURE:
<223> OTHER INFORMATION: Assay component

<400> SEQUENCE: 416
cttacaacgg gaacaatc                                                   18

<210> SEQ ID NO 417
<211> LENGTH: 17
<212> TYPE: DNA
<213> ORGANISM: Artificial ;Probe
<220> FEATURE:
<223> OTHER INFORMATION: Assay component

<400> SEQUENCE: 417
cttacaacgg gaaccat                                                    17

<210> SEQ ID NO 418

```
<211> LENGTH: 18
<212> TYPE: DNA
<213> ORGANISM: Artificial ;Primer
<220> FEATURE:
<223> OTHER INFORMATION: Assay component

<400> SEQUENCE: 418
gcaggtccgc aggtacta                                                18

<210> SEQ ID NO 419
<211> LENGTH: 19
<212> TYPE: DNA
<213> ORGANISM: Artificial ;Primer
<220> FEATURE:
<223> OTHER INFORMATION: Assay component

<400> SEQUENCE: 419
ccttctcgcc gtggatcac                                               19

<210> SEQ ID NO 420
<211> LENGTH: 14
<212> TYPE: DNA
<213> ORGANISM: Artificial ;Probe
<220> FEATURE:
<223> OTHER INFORMATION: Assay component

<400> SEQUENCE: 420
accgtccgtt ggct                                                    14

<210> SEQ ID NO 421
<211> LENGTH: 13
<212> TYPE: DNA
<213> ORGANISM: Artificial ;Probe
<220> FEATURE:
<223> OTHER INFORMATION: Assay component

<400> SEQUENCE: 421
accgtccggt ggc                                                     13

<210> SEQ ID NO 422
<211> LENGTH: 20
<212> TYPE: DNA
<213> ORGANISM: Artificial ;Primer
<220> FEATURE:
<223> OTHER INFORMATION: Assay component

<400> SEQUENCE: 422
gcatttgatt cgagcagcga                                              20

<210> SEQ ID NO 423
<211> LENGTH: 20
<212> TYPE: DNA
<213> ORGANISM: Artificial ;Primer
<220> FEATURE:
<223> OTHER INFORMATION: Assay component

<400> SEQUENCE: 423
tgggtcgagt ggagaacaag                                              20

<210> SEQ ID NO 424
<211> LENGTH: 17
<212> TYPE: DNA
<213> ORGANISM: Artificial ;Probe
<220> FEATURE:
<223> OTHER INFORMATION: Assay component

<400> SEQUENCE: 424
```
tgtgtaccca cagaaat                                                   17

<210> SEQ ID NO 425
<211> LENGTH: 18
<212> TYPE: DNA
<213> ORGANISM: Artificial ;Probe
<220> FEATURE:
<223> OTHER INFORMATION: Assay component

<400> SEQUENCE: 425
atgtgtaccc acaggaat                                                  18

<210> SEQ ID NO 426
<211> LENGTH: 20
<212> TYPE: DNA
<213> ORGANISM: Artificial ;Primer
<220> FEATURE:
<223> OTHER INFORMATION: Assay component

<400> SEQUENCE: 426
tttcaatgcc gcagcatctg                                                20

<210> SEQ ID NO 427
<211> LENGTH: 19
<212> TYPE: DNA
<213> ORGANISM: Artificial ;Primer
<220> FEATURE:
<223> OTHER INFORMATION: Assay component

<400> SEQUENCE: 427
tcgacaccaa cctggagaa                                                 19

<210> SEQ ID NO 428
<211> LENGTH: 17
<212> TYPE: DNA
<213> ORGANISM: Artificial ;Probe
<220> FEATURE:
<223> OTHER INFORMATION: Assay component

<400> SEQUENCE: 428
cagagtttct agaggcc                                                   17

<210> SEQ ID NO 429
<211> LENGTH: 18
<212> TYPE: DNA
<213> ORGANISM: Artificial ;Probe
<220> FEATURE:
<223> OTHER INFORMATION: Assay component

<400> SEQUENCE: 429
caagcagagt ttctacag                                                  18

<210> SEQ ID NO 430
<211> LENGTH: 18
<212> TYPE: DNA
<213> ORGANISM: Artificial ;Primer
<220> FEATURE:
<223> OTHER INFORMATION: Assay component

<400> SEQUENCE: 430
gcaaggtcac gggcagat                                                  18

<210> SEQ ID NO 431
<211> LENGTH: 24
<212> TYPE: DNA

```
<213> ORGANISM: Artificial ;Primer
<220> FEATURE:
<223> OTHER INFORMATION: Assay component

<400> SEQUENCE: 431
agccatatat tgccacagaa atca                                          24

<210> SEQ ID NO 432
<211> LENGTH: 19
<212> TYPE: DNA
<213> ORGANISM: Artificial ;Probe
<220> FEATURE:
<223> OTHER INFORMATION: Assay component

<400> SEQUENCE: 432
caggtgaacg gtaactatt                                                19

<210> SEQ ID NO 433
<211> LENGTH: 19
<212> TYPE: DNA
<213> ORGANISM: Artificial ;Probe
<220> FEATURE:
<223> OTHER INFORMATION: Assay component

<400> SEQUENCE: 433
caggtgaacg gtaacaatt                                                19

<210> SEQ ID NO 434
<211> LENGTH: 21
<212> TYPE: DNA
<213> ORGANISM: Artificial ;Primer
<220> FEATURE:
<223> OTHER INFORMATION: Assay component

<400> SEQUENCE: 434
gcaacaatag cttcaataga g                                             21

<210> SEQ ID NO 435
<211> LENGTH: 19
<212> TYPE: DNA
<213> ORGANISM: Artificial ;Primer
<220> FEATURE:
<223> OTHER INFORMATION: Assay component

<400> SEQUENCE: 435
cccttgtgat ttgcatagt                                                19

<210> SEQ ID NO 436
<211> LENGTH: 14
<212> TYPE: DNA
<213> ORGANISM: Artificial ;Probe
<220> FEATURE:
<223> OTHER INFORMATION: Assay component

<400> SEQUENCE: 436
ccatcgcagc aaca                                                     14

<210> SEQ ID NO 437
<211> LENGTH: 13
<212> TYPE: DNA
<213> ORGANISM: Artificial ;Probe
<220> FEATURE:
<223> OTHER INFORMATION: Assay component

<400> SEQUENCE: 437
tcgcagcagc act                                                      13
```

<210> SEQ ID NO 438
<211> LENGTH: 19
<212> TYPE: DNA
<213> ORGANISM: Artificial ;Primer
<220> FEATURE:
<223> OTHER INFORMATION: Assay component

<400> SEQUENCE: 438
gtcatgctat gagtactgt                                                    19

<210> SEQ ID NO 439
<211> LENGTH: 17
<212> TYPE: DNA
<213> ORGANISM: Artificial ;Primer
<220> FEATURE:
<223> OTHER INFORMATION: Assay component

<400> SEQUENCE: 439
atgctgcttg agttgga                                                      17

<210> SEQ ID NO 440
<211> LENGTH: 17
<212> TYPE: DNA
<213> ORGANISM: Artificial ;Probe
<220> FEATURE:
<223> OTHER INFORMATION: Assay component

<400> SEQUENCE: 440
cacgtgcatt tgtattc                                                      17

<210> SEQ ID NO 441
<211> LENGTH: 15
<212> TYPE: DNA
<213> ORGANISM: Artificial ;Probe
<220> FEATURE:
<223> OTHER INFORMATION: Assay component

<400> SEQUENCE: 441
cacgtgcatt tgcat                                                        15

<210> SEQ ID NO 442
<211> LENGTH: 22
<212> TYPE: DNA
<213> ORGANISM: Artificial ;Primer
<220> FEATURE:
<223> OTHER INFORMATION: Assay component

<400> SEQUENCE: 442
ggcacttcaa tgtctgctct gt                                                22

<210> SEQ ID NO 443
<211> LENGTH: 20
<212> TYPE: DNA
<213> ORGANISM: Artificial ;Primer
<220> FEATURE:
<223> OTHER INFORMATION: Assay component

<400> SEQUENCE: 443
gatgacccgt ctcatgcaaa                                                   20

<210> SEQ ID NO 444
<211> LENGTH: 16
<212> TYPE: DNA
<213> ORGANISM: Artificial ;Probe
<220> FEATURE:

<223> OTHER INFORMATION: Assay component

<400> SEQUENCE: 444
cgagaaggca acaacg                                                          16

<210> SEQ ID NO 445
<211> LENGTH: 15
<212> TYPE: DNA
<213> ORGANISM: Artificial ;Probe
<220> FEATURE:
<223> OTHER INFORMATION: Assay component

<400> SEQUENCE: 445
agaaggcaac accgg                                                           15

<210> SEQ ID NO 446
<211> LENGTH: 23
<212> TYPE: DNA
<213> ORGANISM: Artificial ;Primer
<220> FEATURE:
<223> OTHER INFORMATION: Assay component

<400> SEQUENCE: 446
tcatggcaag ctagtaccta aac                                                  23

<210> SEQ ID NO 447
<211> LENGTH: 20
<212> TYPE: DNA
<213> ORGANISM: Artificial ;Primer
<220> FEATURE:
<223> OTHER INFORMATION: Assay component

<400> SEQUENCE: 447
ctgcaggagg agctcaagac                                                      20

<210> SEQ ID NO 448
<211> LENGTH: 18
<212> TYPE: DNA
<213> ORGANISM: Artificial ;Probe
<220> FEATURE:
<223> OTHER INFORMATION: Assay component

<400> SEQUENCE: 448
atcgattgac agggcatg                                                        18

<210> SEQ ID NO 449
<211> LENGTH: 14
<212> TYPE: DNA
<213> ORGANISM: Artificial ;Probe
<220> FEATURE:
<223> OTHER INFORMATION: Assay component

<400> SEQUENCE: 449
ttgacagggc gtgc                                                            14

<210> SEQ ID NO 450
<211> LENGTH: 25
<212> TYPE: DNA
<213> ORGANISM: Artificial ;Primer
<220> FEATURE:
<223> OTHER INFORMATION: Assay component

<400> SEQUENCE: 450
cacctccgat gcctatacta ctttc                                                25

```
<210> SEQ ID NO 451
<211> LENGTH: 18
<212> TYPE: DNA
<213> ORGANISM: Artificial ;Primer
<220> FEATURE:
<223> OTHER INFORMATION: Assay component

<400> SEQUENCE: 451
gcgcaatcca cagcttga                                                 18

<210> SEQ ID NO 452
<211> LENGTH: 19
<212> TYPE: DNA
<213> ORGANISM: Artificial ;Probe
<220> FEATURE:
<223> OTHER INFORMATION: Assay component

<400> SEQUENCE: 452
ttgtgagtgt agtagaaaa                                                19

<210> SEQ ID NO 453
<211> LENGTH: 19
<212> TYPE: DNA
<213> ORGANISM: Artificial ;Probe
<220> FEATURE:
<223> OTHER INFORMATION: Assay component

<400> SEQUENCE: 453
ttgtgagtgt agtagagaa                                                19

<210> SEQ ID NO 454
<211> LENGTH: 24
<212> TYPE: DNA
<213> ORGANISM: Artificial ;Primer
<220> FEATURE:
<223> OTHER INFORMATION: Assay component

<400> SEQUENCE: 454 cggagcccctt atttgctacc attc                                         24

<210> SEQ ID NO 455
<211> LENGTH: 23
<212> TYPE: DNA
<213> ORGANISM: Artificial ;Primer
<220> FEATURE:
<223> OTHER INFORMATION: Assay component

<400> SEQUENCE: 455
ccctgttgat acagagttcc aga                                           23

<210> SEQ ID NO 456
<211> LENGTH: 19
<212> TYPE: DNA
<213> ORGANISM: Artificial ;Probe
<220> FEATURE:
<223> OTHER INFORMATION: Assay component

<400> SEQUENCE: 456
aaatccatct attgctact                                                19

<210> SEQ ID NO 457
<211> LENGTH: 16
<212> TYPE: DNA
<213> ORGANISM: Artificial ;Probe
<220> FEATURE:
<223> OTHER INFORMATION: Assay component
```

```
<400> SEQUENCE: 457
catctattgc cactca                                                   16

<210> SEQ ID NO 458
<211> LENGTH: 22
<212> TYPE: DNA
<213> ORGANISM: Artificial ;Primer
<220> FEATURE:
<223> OTHER INFORMATION: Assay component

<400> SEQUENCE: 458
ttccgcccga gagatttaga ag                                            22

<210> SEQ ID NO 459
<211> LENGTH: 20
<212> TYPE: DNA
<213> ORGANISM: Artificial ;Primer
<220> FEATURE:
<223> OTHER INFORMATION: Assay component

<400> SEQUENCE: 459
caccagtttc gtgtcaagga                                               20

<210> SEQ ID NO 460
<211> LENGTH: 19
<212> TYPE: DNA
<213> ORGANISM: Artificial ;Probe
<220> FEATURE:
<223> OTHER INFORMATION: Assay component

<400> SEQUENCE: 460
tgtaaaatct ggctgtaag                                                19

<210> SEQ ID NO 461
<211> LENGTH: 17
<212> TYPE: DNA
<213> ORGANISM: Artificial ;Probe
<220> FEATURE:
<223> OTHER INFORMATION: Assay component

<400> SEQUENCE: 461
tgtaaaatct ggccgta                                                  17

<210> SEQ ID NO 462
<211> LENGTH: 19
<212> TYPE: DNA
<213> ORGANISM: Artificial ;Primer
<220> FEATURE:
<223> OTHER INFORMATION: Assay component

<400> SEQUENCE: 462
ggccacatcg tcacagcat                                                19

<210> SEQ ID NO 463
<211> LENGTH: 19
<212> TYPE: DNA
<213> ORGANISM: Artificial ;Primer
<220> FEATURE:
<223> OTHER INFORMATION: Assay component

<400> SEQUENCE: 463
tcagctcagg cttgacaga                                                19

<210> SEQ ID NO 464
<211> LENGTH: 17
```

```
<212> TYPE: DNA
<213> ORGANISM: Artificial ;Probe
<220> FEATURE:
<223> OTHER INFORMATION: Assay component

<400> SEQUENCE: 464
cttctaaaga tgccagc                                                    17

<210> SEQ ID NO 465
<211> LENGTH: 15
<212> TYPE: DNA
<213> ORGANISM: Artificial ;Probe
<220> FEATURE:
<223> OTHER INFORMATION: Assay component

<400> SEQUENCE: 465
tctaaagacg ccagc                                                      15

<210> SEQ ID NO 466
<211> LENGTH: 25
<212> TYPE: DNA
<213> ORGANISM: Artificial ;Primer
<220> FEATURE:
<223> OTHER INFORMATION: Assay component

<400> SEQUENCE: 466
gcatattagt gcatacggag aagga                                           25

<210> SEQ ID NO 467
<211> LENGTH: 21
<212> TYPE: DNA
<213> ORGANISM: Artificial ;Primer
<220> FEATURE:
<223> OTHER INFORMATION: Assay component

<400> SEQUENCE: 467
cgatgctcgc agtctcatgt t                                               21

<210> SEQ ID NO 468
<211> LENGTH: 16
<212> TYPE: DNA
<213> ORGANISM: Artificial ;Probe
<220> FEATURE:
<223> OTHER INFORMATION: Assay component

<400> SEQUENCE: 468
cccagtcaat cttctt                                                     16

<210> SEQ ID NO 469
<211> LENGTH: 15
<212> TYPE: DNA
<213> ORGANISM: Artificial ;Probe
<220> FEATURE:
<223> OTHER INFORMATION: Assay component

<400> SEQUENCE: 469
ccagtcagtc ttctt                                                      15

<210> SEQ ID NO 470
<211> LENGTH: 27
<212> TYPE: DNA
<213> ORGANISM: Artificial ;Primer
<220> FEATURE:
<223> OTHER INFORMATION: Assay component

<400> SEQUENCE: 470
```

```
cactggtgaa gtgctgataa atacatc                                             27

<210> SEQ ID NO 471
<211> LENGTH: 23
<212> TYPE: DNA
<213> ORGANISM: Artificial ;Primer
<220> FEATURE:
<223> OTHER INFORMATION: Assay component

<400> SEQUENCE: 471
atgttcccaa acaaggagat gct                                                 23

<210> SEQ ID NO 472
<211> LENGTH: 18
<212> TYPE: DNA
<213> ORGANISM: Artificial ;Probe
<220> FEATURE:
<223> OTHER INFORMATION: Assay component

<400> SEQUENCE: 472
cctgtgaaga aacttgtt                                                       18

<210> SEQ ID NO 473
<211> LENGTH: 17
<212> TYPE: DNA
<213> ORGANISM: Artificial ;Probe
<220> FEATURE:
<223> OTHER INFORMATION: Assay component

<400> SEQUENCE: 473
ctgtgaagaa gcttgtt                                                        17

<210> SEQ ID NO 474
<211> LENGTH: 104
<212> TYPE: DNA
<213> ORGANISM: Zea mays

<400> SEQUENCE: 474
gtggagaatg cagagccatg gatcgcattc atggagtagc cacagggttc gaagtcaaaa         60
tcgcagatct ccatctcggg gatgatttca gagatgccag agag                         104

<210> SEQ ID NO 475
<211> LENGTH: 202
<212> TYPE: DNA
<213> ORGANISM: Zea mays
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (135)..(136)
<223> OTHER INFORMATION: n is a, c, g, or t
```

<400> SEQUENCE: 475
cgagagacca gatcaacagc ttcnggnggc atnccttttg tggaanacct gaaagataaa    60
atgtacaaaa agtaaattag taanacaaca gtaacagttt tcttagagta ttgtaacaaa   120
atgtagaaag atttnngcac cttgtgccat gggtgtgctt tgatttgtgg gaacttaaac   180
tctgtgtaat ttgggttcat gc                                            202

<210> SEQ ID NO 476
<211> LENGTH: 201
<212> TYPE: DNA
<213> ORGANISM: Zea mays

<400> SEQUENCE: 476
gtcttcaaac ttgcagtgac gaatttcaat gtgcgtgatt ggaaccttt cgatggtggc    60 ccttgaacca gagtggataa tctctccaaa atcagatgta aagcatctgg ttgacatacg   120
gaagactact acctgttttc tagatttaca attcattgtc agaaattatg ctatctgact   180
taatcttcca aatactccta t                                             201

<210> SEQ ID NO 477
<211> LENGTH: 185
<212> TYPE: DNA
<213> ORGANISM: Zea mays

<400> SEQUENCE: 477
agcgtgccca tgccggagcc ggtgccgccg ccgagagagt ggcagacctg gaagcctgac    60
aggcgggcat aagatcccag tcagcaaacc aagcaacctt gcagaaatgg aagacgagac   120
gagacaagca aataaccaac caaccttgca ggcagtcgca gttctcggcc tcctttcgca   180
ccacg                                                               185

<210> SEQ ID NO 478
<211> LENGTH: 201
<212> TYPE: DNA
<213> ORGANISM: Zea mays

<400> SEQUENCE: 478
tcgaccgcag ygtggaatgc actggcaaca tyaatgctat gatccaagct ttcgaatgtg    60
ttcatgatgt aagtatatgt atacactctc agctactttc cttctccagg ttcccttcat   120
ccagacatgc atgttctaac ygccgcsctc gtgatccagg gctggggtgt tgcygtgctg   180
gtgggtgtgc crcataagga c                                             201

<210> SEQ ID NO 479
<211> LENGTH: 99
<212> TYPE: DNA
<213> ORGANISM: Zea mays

<400> SEQUENCE: 479
gcagtcgagc gacgactagg aagaggaggt gatcgatgag aacggcgaga ttgtcaagag    60
gaagaagaag ggccttaagg agaaggtcaa ggagaagct                           99

<210> SEQ ID NO 480
<211> LENGTH: 231
<212> TYPE: DNA
<213> ORGANISM: Zea mays

<400> SEQUENCE: 480

```
cgcttccaca ccgggagcac attggacgcc gcgtcacaag aaggtataca cagcatggtc    60
aaattgtttg cctctgtggt cgtgcactcg tgcatgcatg cggacagtgc ccatgattca   120
gtcatgttga gttgagttct gcttgccggc ctgtgatgtt atttgttctt gttcaatcat   180
atcgcaactg gcagtgctgt ccgacgagcg cgacgccgcg gccagcggcg g            231
```

<210> SEQ ID NO 481
<211> LENGTH: 101
<212> TYPE: DNA
<213> ORGANISM: Zea mays

<400> SEQUENCE: 481

```
gcgagcacat acgtcgtgga cacattcgaa ggcggatatc atggcgttga cgttaccggt    60
gcactccacg ctgcggtcga cgccgccgtt ggtcagctca a                       101
```

<210> SEQ ID NO 482
<211> LENGTH: 201
<212> TYPE: DNA
<213> ORGANISM: Zea mays

<400> SEQUENCE: 482

```
ggttgtcacc tttsaratcg agtagactgc catcagtgcc atgacttatt ggcaarttgg    60
agtcttttag ggtccacttg ttttccttga attctgcaag ttgaatttgc ttttttgttg   120
acttcaatam tccaaccart tctcgaayga cbrccatgcy attcttcgcc ttgtgctctc   180
tgagatagag tggagtcatg a                                             201
```

<210> SEQ ID NO 483
<211> LENGTH: 889
<212> TYPE: DNA
<213> ORGANISM: Zea mays

<400> SEQUENCE: 483

```
gaatattcat ggggcggtta caagatggca ggtgaggaca ggcaggaaga tgaacaagac    60
gacaagagcc gacgtagtcg tccaaggatt cgatcaggat attcctccaa gatgacaaag   120
accacaaaaa tagttgcttc ttcagacgtg aaccaatttt aaaactaatt gcataagagg   180
tgattaatta gcaagacaaa actattagct ctagttagct cttgaaggca tataataata   240
tagcatgata tgaactaatt atgggctaca tattcagaat taataggttt gtctcgtcaa   300
ttaatcactg tttacttgca cagtagagca agagcaagcg cagagaacag ggcataata    360 aactgctgcg ggtggtgtac ctaaaccatg atccaatatt acatcccctt atgctgactc   420
cagcagttca tcaaaacttt acccgtaaac aatgttttac actatagatt gcactattcg   480
taaaatagag tttgaatatg agtatgaata tgtataagct gttggagata gtcttaatac   540
ctagtttaat tactctagta taaacctcaa tctacatgta ttaaggtaga ttggagtgta   600 acttaaaacta atttatatcc caatccacct caacatacat aactatagtc tatcgtacaa   660
tatctaaatg aagcctaaag acaacgttta ggataaggaa cgtgttaaac agcccaaaag   720
cattatgact ccatgagtcc aacggcccaa tagcacgaga catcgcaaca tgcccgctcc   780
ccaacaactg tagcacctga tttgattggt acaaaaatta tgatgacgtc ccatttgcag   840
acatcgagca tattgcccaa taccccttgtt tgaaattcaa aatttgaat              889
```

<210> SEQ ID NO 484
<211> LENGTH: 824
<212> TYPE: DNA
<213> ORGANISM: Zea mays

-continued

```
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (349)..(370)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (392)..(394)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (568)..(568)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (752)..(752)
```

<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t
<220> FEATURE:
<221> NAME/KEY: misc_feature
<222> LOCATION: (797)..(797)
<223> OTHER INFORMATION: n is a, c, g, or t

<400> SEQUENCE: 484

```
catatgaaaa atcnctggtt ccgctttcgt tttttnngca tacctaataa ccaacctctg      60
catctgcttc aggttcgtac ttttgaggcg caatgtgggt cgttggcgca gtatgggatg     120
aagcacatgc ggtccttcgc aaacatctgc aacgctggca tccttcctga ngcagtgtcg    180
aaggtcgctg ctcaggcttg caccagcatt ccttccaacc cctggagttc tatccacaag    240
ggttttagcg cctaagaatc ataaggtgag gcgaaatatt tcagccgctc caccgcaacg    300
aactggttta cattaccagt cctcagggg gtcctagttc ttgaaccann nnnnnnnnnn     360
nnnnnnnnn ctantatagc tgttccaccg tnnntccaga ttacatagct atgcncaatt     420
tccggtgtac atatnatagt cggaaagtta tttggcaatt gtattggtcg ttgctgtata    480
tattccctat agtttgttag cagatgtgta gtttgtnatt cataaaaat gaaggacgcg     540
ttactgctat ttctatgtag ccgactgntg ctcatgtgaa actttacccc attcttgttg    600
ggaaatgnac tatccgtggt ggaattctng catcgaaaac aattcccggg ngatcctta     660
ttcaangtga ancgtctgtc natttccatt tgaggntcgt attattttca nttgtaggct    720
tgtggctggt ggcatctgtt ccactatgnt tncaaacaag nnctatgggc agtttcattt    780
gtttcgttct ctatatncct gcagcaccta cccatggaaa aaat                     824
```

<210> SEQ ID NO 485
<211> LENGTH: 643
<212> TYPE: DNA
<213> ORGANISM: Zea mays
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature

```
<222> LOCATION: (92)..(92)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (349)..(352)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (464)..(465)
<223> OTHER INFORMATION: n is a, c, g, or t
<220> FEATURE:
```

```
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t

<400> SEQUENCE: 485
tcnngnangn angtgtttat ttnacctnca gattccacct ttgtttcttc tatatttaca      60
tggtaccttg naggttcttg ctctttgtga tnatccgtgc ctctnggaaa aagaggaaac     120
caaatcattg ttcaggtgaa tatcntcatc nttcaattta cagaactcct aaattcanag     180
atctagtgng tgatatcntg ctattttncc caacttnagt gtcaaagcaa cctaaaaatt     240
ctaaaaaata cagagatagg gcaatctatc ttcctttaaa atcaaagctg tggcattttc     300
tttgaaatta gtaaacattt atataaatag taaaatntcn tggagatcnn nnaggtantt     360 aacnttttc ccttcaactt ccacagtaat taaacatacc taggaanata gttttngagt      420
tctcatgttt aattgatntg ttcatcanaa gaaccattac ntcnntgcct aattatgcat     480 gcccttnat ttttcctaaa atttcccttg ataccatttc aagttgcaaa gatganttt      540 ttttncttcg tactgtttaa tatttttgtt agccataaac tttcaaaant agttcagtgt     600
cccatttata cataaatnct tatgtgtacn tgatgggtcg nct                       643

<210> SEQ ID NO 486
<211> LENGTH: 201
<212> TYPE: DNA
<213> ORGANISM: Zea mays
<220> FEATURE:
<221> NAME/KEY: misc_feature
<222> LOCATION: (189)..(191)
<223> OTHER INFORMATION: n is a, c, g, or t

<400> SEQUENCE: 486
atttatgtgc ctyyaggcga accacttyca tcygaacctg gcgagccgtt gagagtgaac      60
gtgctmttca agcatattca ggcaatgctg tcyggcgaca tggctgtcat cgcagagact    120
ggggactcgt ggtttaactg ccagaagctg aagctaccgg aaggmtgtgg gtaagctcct    180
ctttcgaann ntgrttttgc t                                               201

<210> SEQ ID NO 487
<211> LENGTH: 300
<212> TYPE: DNA
<213> ORGANISM: Zea mays

<400> SEQUENCE: 487
```

```
gcacagaact ctcccctgtc ctttcctggg gttttggtta cgtggtggta gtaagcttgg    60
atttgcacat ggataaagtt gttctaagct ccgtgggttg cttgagatct tgctgttatt   120
gcgtgccgtg ctcactttt ttgcaatccg aggaatgaat tgtcgttta ctcgttttgg    180 tggattatta gcgcgaaaaa aaaactcttt ttttttgtt cttttactac gaaaagcatc    240
ttcttggatt ttgctatctt cttttactac gaaaaactct tgagtctagg aatttgaatt   300
```

<210> SEQ ID NO 488
<211> LENGTH: 193
<212> TYPE: DNA
<213> ORGANISM: Zea mays

<400> SEQUENCE: 488

```
ggctattgta caacaacaag gcggcattgc catcrcagtt gcagtactas caattgccwt    60
cgkgattgcg gttgcggtgt tgcagtagta gtactgtagt actatcaagt gagtctgatg   120
catgamcaga gcagayggag tagttaaacg gaggcgccgg tgagcttgcc gttgacgatg   180
tggtggttgt cgt                                                      193
```

<210> SEQ ID NO 489
<211> LENGTH: 201
<212> TYPE: DNA
<213> ORGANISM: Zea mays

<400> SEQUENCE: 489

```
rgacacggag gagcagtacg acttcgaccc gctggacgac accaagacgt ggccggagga    60
cctgctsccg ctcmgscccg tggggaggct ggtgctggac aggaacgtgg acaacttctt   120
caacgagaac gagcagctgg cgttcggscc ggggctggtg gtgccaggga tctactactc   180
ggacgacaag atgctgcagt g                                             201
```

<210> SEQ ID NO 490
<211> LENGTH: 199
<212> TYPE: DNA
<213> ORGANISM: Zea mays

<400> SEQUENCE: 490

```
atgaactatg aagaaccta tcactttgag ctagtctcaa gtccaagcaa agakaacaat    60
tcaccagtag taatggaaag agaagattag caataactgt tgtttagtgg agcaataaat   120 atcttttca gtttcaagtm ttaagagaga aaatgataga tgtaaatggc aagcacctac   180
tgtacttgac aacgttaaa                                               199
```

<210> SEQ ID NO 491
<211> LENGTH: 795
<212> TYPE: DNA
<213> ORGANISM: Zea mays
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(122)

```
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (130)..(137)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (691)..(693)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t

<400> SEQUENCE: 491
atagtaaaag gttggaatgt tagttgaaaa caaggtgtaa gaaatgtatc atcttttgga      60
ctggacaaca gacctgaagt agaagcttct gggtttcctc ananntggcc ctcagcttnn     120
cnccnaangn nnnnnnntcc tntgaaacga ggagtttgtc atacagtgng gcaatgccag     180
gattacccct gggnaacncc atntccncca gatcaatagt caccctgaaa atggccact     240 cattgtacat ttcctggagc atgtggaggt tcctgatgtc cttctggagg acatgcttga    300
atgcggctcc aaatcctagc cagaccggga ggtggaaccg cgtntgtgtc caagcaaaga    360
```

-continued

```
tccatgggat tgctcggagt gagtcgatac ctccgctcgg ctttctcttg gatggcctgc    420
ttcctatgtt catcctacca tactctgttt caggggttgc ctgtcaacac aaacatcaca    480
aagtaaatac tcgctaaatg tagggtcaa atcgaatgct tcagtaacca ttttacttag     540
gcttgcaaaa gatagtttct ncagtaaatc attgtgctag attaatatta agtatcaggt    600
caganctatt tcaaaagttt gttttttgcat cttatgttac tgtagtatct ctagacacca   660
ctcaggtggn agcctcnagt actggtctac nnncatcttt tnatgttact gtagtatggc    720
aatcgatggg atcaaggact tacaaggcgg aaatactcga caaagcgtgg ctctttgaag    780
acaatggacc gatat                                                     795
```

```
<210> SEQ ID NO 492
<211> LENGTH: 627
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (613)..(624)
<223> OTHER INFORMATION: n is a, c, g, or t
```

<400> SEQUENCE: 492

```
atgctctggg gtcatctcat gtctgaattc tgatccaatt gaagggttgt agctttagtg    60
caatgttgct atntttatca tgcaaacccc tttacctttt gtaacatgtc accaaacaat   120
tcatttccat tgggttgttc aaggatcatg tattcccatg caatacaacn tggagaagtc   180
angctattcc tttactattt tacgtagcag tgttggccca cgattatatt gttttaatat   240
ctgtacttca gttgaggaaa ttatattttc tgagcgatca gntaatcact tattttggtt   300
ccactacttt cctatcaggt tcttgagtct cggaatattc agcttttntt gggatatttt   360
gtgagcngca tcaaagaggc tcctacatct gatgantcaa gtagcacagt tacatactct   420
gaagttgacg gtgatcatag gaaactaatt ttggaccttc aacctgctga aagaggcctc   480
aaaggncaga cnctcgatgc cgatttggtg ctgtggacag tgggttcaac atctcagatt   540
ccncggttac agcctcctga tgctccctan gttattcctc tgaatggtcg nggacaggng   600
gagacagagg aannnnnnnn nnnnaaa                                        627
```

<210> SEQ ID NO 493
<211> LENGTH: 772
<212> TYPE: DNA
<213> ORGANISM: Zea mays
<220> FEATURE:
<221> NAME/KEY: misc_feature
<222> LOCATION: (52)..(57)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(76)
<223> OTHER INFORMATION: n is a, c, g, or t
<220> FEATURE:
<221> NAME/KEY: misc_feature
<222> LOCATION: (88)..(97)
<223> OTHER INFORMATION: n is a, c, g, or t
<220> FEATURE:
<221> NAME/KEY: misc_feature
<222> LOCATION: (99)..(109)
<223> OTHER INFORMATION: n is a, c, g, or t
<220> FEATURE:
<221> NAME/KEY: misc_feature
<222> LOCATION: (112)..(113)
<223> OTHER INFORMATION: n is a, c, g, or t
<220> FEATURE:
<221> NAME/KEY: misc_feature
<222> LOCATION: (115)..(119)
<223> OTHER INFORMATION: n is a, c, g, or t
<220> FEATURE:
<221> NAME/KEY: misc_feature
<222> LOCATION: (122)..(131)
<223> OTHER INFORMATION: n is a, c, g, or t
<220> FEATURE:
<221> NAME/KEY: misc_feature
<222> LOCATION: (134)..(145)
<223> OTHER INFORMATION: n is a, c, g, or t
<220> FEATURE:
<221> NAME/KEY: misc_feature -continued

```
<222> LOCATION: (147)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (163)..(166)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (180)..(184)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (376)..(377)
<223> OTHER INFORMATION: n is a, c, g, or t
<220> FEATURE:
<221> NAME/KEY: misc_feature
<222> LOCATION: (425)..(427)
<223> OTHER INFORMATION: n is a, c, g, or t
<220> FEATURE:
<221> NAME/KEY: misc_feature
<222> LOCATION: (446)..(447)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
```

```
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (715)..(720)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (725)..(725)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (733)..(734)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (751)..(752)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (761)..(762)
<223> OTHER INFORMATION: n is a, c, g, or t

<400> SEQUENCE: 493
gcatagcata ctgcatgcat ggcgctgttg cattgcaggt tgcagctgca gnnnnnncng      60
nngacccngn tgnnnncgtg cagactgnnn nnnnnnnann nnnnnnnnnc anntnnnnnt     120
annnnnnnnn ngtnnnnnnn nnnnnannnn tanataaatn tannnnagta canttttgcn     180
nnnncctgct gcctgcccta gcactagcag ccaggcagca gggctggcgc ctntgctgcg     240
gtgcatgaaa aggcgacgag caaagaaggg gcgcgtggaa aactgcccgt cgcgcgctgc     300
taccgccgta tgattggatc gagtggagcg tgccggctgg ctttttggatc ctttcggcac    360 gtcaagaaat aaaaannntaa ccagttcctt tatttcatcg gtctccgact ctccaaggcg    420
gcagnnncag caagctctcg tagctnngtg taaagctgtg gagcacacag cagctgtgag     480
cctgtgttgg tgttgcgagc aagagcanag ctggcaagcg cagcanagga nttgcacacg     540
gctttatacg aatgagcaga acanaggcat ctgtacatga ngacgggcac ggcacacaca     600
caggcctttg gttcgttgga nganngtgta ttggcctcct actatactga nactgnacac     660
ccctggacat ccgcatgncc gcatctacta cgcatngata gcagcgntnt gtaannnnnn     720
tgnantggnc tcnnangcag ccatgccatg nnanccagna nncccacagc ac             772
```

<210> SEQ ID NO 494
<211> LENGTH: 201
<212> TYPE: DNA
<213> ORGANISM: Zea mays

<400> SEQUENCE: 494
cacacataat tactccmatc ttctcagtgg aggtacatca gcaaccgagg tttataaagg    60
aacrctygag gacaacacga tggtggcggt gcatagattg ctctacgagg gctctgagga   120
ggcgttcatc aacggaggga tggtygtgtc caagatcgcc cacargaaca tcgtcagagt   180
tctgggctgc tgtctggaac c                                             201

<210> SEQ ID NO 495
<211> LENGTH: 220
<212> TYPE: DNA
<213> ORGANISM: Zea mays
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t

<400> SEQUENCE: 495
tggatccatc acggtagagc tgacnatgat atgtccaaan gcttctgctg ctagttgttg    60
gtcgtccgca agagacttga cccnacaggt tttttttcgtt gggcctcaag aactgtaggt  120
gcattttcca tggagggtta tgatgcttaa ccccactctg gttctggtg gctaaaacat    180 tctctccagt cggcttctac catgagccct ggcacttagt                         220

<210> SEQ ID NO 496
<211> LENGTH: 301
<212> TYPE: DNA
<213> ORGANISM: Zea mays
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (181)..(186)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:

```
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (294)..(296)
<223> OTHER INFORMATION: n is a, c, g, or t

<400> SEQUENCE: 496
tggctttatc cgtccggatg ccccgccatg tgctccttgt ctcgggactc ggagacagnc      60
tgacagtcct gggttnttgt gctaatggcc ntggttaact tacgttaatc ntgcgcctta    120
ttatcatcat ctaggtgtaa ttacttccgt ttgtgctaat cacctcgtga ttgcctgcaa    180
nnnnnnggaa ccccagcccc ccnaccttgc tgatgccgtg cttttctaga gaagtaccct    240
gccgcgtcac gcttcgtcct cgcctgcttt ggattcaacg gnttttggga gncnnnggcc    300
a                                                                    301

<210> SEQ ID NO 497
<211> LENGTH: 170
<212> TYPE: DNA
<213> ORGANISM: Zea mays
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t

<400> SEQUENCE: 497
ggtgccggaa gccgcctaca gcggcccgcc gctcagctac tacgtcacca agttccagcc      60
ggcggtggct gcgccggcgc agaccctcga ggccccgcc cccgncgagg cacaagacgg    120
cgccgccgcc nccgtcgngn ctccggaggt accggcaccg cagctgtcgt              170

<210> SEQ ID NO 498
<211> LENGTH: 190
<212> TYPE: DNA
<213> ORGANISM: Zea mays

<400> SEQUENCE: 498
rcataaaaya ttgcaaatgc tgaggaatat aagcacatag atacttagca tgtgtccgcc      60
agatggaaat acttttacca ttcccccacg actggattgc agaaaggtc aatgcctatg    120 acaccttggt ccatyatttc cayggctaga ttaacctggc caggggaaay aaatsatttt    180
gtgcagattc                                                           190

<210> SEQ ID NO 499
<211> LENGTH: 201
<212> TYPE: DNA
<213> ORGANISM: Zea mays

<400> SEQUENCE: 499
acgsygtaag ggctctactg catgttcctg aggttgctct tgacaccctc aatttgctgg      60
aaatcatccc catctrggga cataaatgga gcaaaattgc cgtgagcttg aacaaatgga    120
```

```
aggtcactgt gatggttctg aatgccatca ggcagattct gtgatgtgtt tgcttctgat    180
gaagaaggga agttccagcg g                                              201

<210> SEQ ID NO 500
<211> LENGTH: 201
<212> TYPE: DNA
<213> ORGANISM: Zea mays

<400> SEQUENCE: 500
tctcaagctt atttaggttg actaaatttg aacatcccc cgagatgcta ttgccggcaa     60
gcgcgagctc cgtaagcatg gcagctttgc caatcgatgc cggtatggac cccttcagct   120
ggttactctg caaccgaaga acartgaggt tcgagaatga gtcaagccag tctggcacac   180
ttccattgaa gtagttacca t                                             201

<210> SEQ ID NO 501
<211> LENGTH: 294
<212> TYPE: DNA
<213> ORGANISM: Zea mays

<400> SEQUENCE: 501
tactagcaca ctttgcctcc tgatagcttg taccattgtg accttgtttg gattttggga    60
ttccacccaa tgtcaaacat acccaaacag tgaccgtka tcttttttctt cgtatttcta   120 tgtcaagcac tyaagcataa ctcatacatt tgcctctaca ggtgtttctg aaacactagt   180
gctcaatatg tcaactctga catggtcagt tgttagcact gtggaaggac gtgttcctct   240
tgccagtgag gtatwtctct tgagcggttg agcagcattc cagttgttaa gatg         294

<210> SEQ ID NO 502
<211> LENGTH: 214
<212> TYPE: DNA
<213> ORGANISM: Zea mays

<400> SEQUENCE: 502
gcacaggtaa ctcttgcatg gcacctgtcc tgaaacaagt ttcgtgctaa caagggaaat    60
tatccttttt cgtggcacca atatctgttt tccattcaat gatgtactga tgtgttcacg   120
gagtcgttac ctagaaatct cgcttactgt gacatatcac accgagcatc attttatatc   180
tgctgtgygc cctccttgct aatgtaggca cctg                               214

<210> SEQ ID NO 503
<211> LENGTH: 300
<212> TYPE: DNA
<213> ORGANISM: Zea mays

<400> SEQUENCE: 503
rytkcaacmt gcgagaarta raaaatcact aaccttggct ttatcaagta tagcaaggtg    60
aamgcgaatg ccargaagaa gcagagtccr ccgacgrtga ggtacgcaag cccagaaaa   120 tcgttctttc ccccgagcca ggttgcggtc gaaagcacca gcttcttctt gccaccaaag   180
ctataggtgt tgtagttgtt gtccarctgg actgtgattg trtcgttttc cttgagatca   240
acatatatcc ttccatacag ctttctgaat gtcggaagtg ctgyagtccg catccaaaca   300

<210> SEQ ID NO 504
<211> LENGTH: 287
<212> TYPE: DNA
<213> ORGANISM: Zea mays
```

<400> SEQUENCE: 504

```
gcgctcgcca tgaatgcgcg tcgtctccrt tggaccatca accatttgca attgatgagg    60
agacgagaca ggagaaacgg cgagggcagy agtgttctgt agctgaaagc tgccgcgaat   120
cgactgccat tattggacgc catcccttgc ccgactgaga atcgggcggc cgcgtgcact   180
gcactrcmct accgccgccc gccaggcgcc agccrrcctc gtggtacaaa attcatccag   240
aattcgcacg aggccaccag ctcggctccg gcctgcgagg atttcaa                287
```

<210> SEQ ID NO 505
<211> LENGTH: 288
<212> TYPE: DNA
<213> ORGANISM: Zea mays

<400> SEQUENCE: 505

```
tcatggaatt gcttcaaacc cgagagcggc aagataatag acgaacgatc agctccagcc    60
acctgtaagt acaatcacaa ayrgtaagag caatggatca ctygtggagg cttgtgttta   120
caaataatrg ccaacaacat gttacctcag aaatcctcaa ataatggccc ctgttgttgc   180
tgcccaggtc gaagaagaac cttttctgat ctgccctrat maccttagac atacccatgc   240
cactaatttc ttcttgagga ggcagatcaa ccaagcgttc sacatcta                288
```

<210> SEQ ID NO 506
<211> LENGTH: 284
<212> TYPE: DNA
<213> ORGANISM: Zea mays

<400> SEQUENCE: 506

```
tayaagcaat attaagagat ggaaatgtcg cctctgtacc acaagttagt aagttactaa    60
cttgattgtt aaaacaccat cgaaatgtgt gacatgtagg acctggtccc acatgtcaga   120
caaagccaat gctattttgg cattcatgtt acaatgtagt gctataattt ccacaaaaaa   180
wacaagacag gtcaaatact gygtaaacat tcgatccaaa aaacagagat gctttgtcat   240
aaaaaatcta gccaaaagaa ttggagctat tgagatacaa tgra                    284
```

<210> SEQ ID NO 507
<211> LENGTH: 256
<212> TYPE: DNA
<213> ORGANISM: Zea mays

<400> SEQUENCE: 507

```
acgttccttg tcgaccatta tcattcgcta tctattttg aacgaacgca ttcgctatct     60
atggccacat ctccacttcg tctttgccga agcttcagta cgcggtgcgg gtgtctcctg   120
gtgtgtatgc tgttcttttc tcggtccatc ttatcccccg tttgacgcgc tctgtcaat   180
ctgctgtact gtgaatttta tttgacgtgc ataaatyatt ctggaaacgc tcttggtacg   240
tcacgtacct ygagaa                                                   256
```

<210> SEQ ID NO 508
<211> LENGTH: 267
<212> TYPE: DNA
<213> ORGANISM: Zea mays

<400> SEQUENCE: 508

```
atcsggcacc tgatccwgaa tgtgagwcsg agtgcgacct ataccgtcc ccaaccgccc     60
ccattgaatc caccggtgaa tctatcgctc cgccaccacg aggccctata ttaactccac   120
agcatccatg tgtccgagcc tgtctgtata cctgtcactc acgctaccgc cgtgccgatc   180
```

-continued

```
gttcgttcct tccctccctt cgcgggccgc gcgcctatkw twtttactac tstattcrta    240
tcattatayt ktttggtttc cwtccck                                        267

<210> SEQ ID NO 509
<211> LENGTH: 297
<212> TYPE: DNA
<213> ORGANISM: Zea mays

<400> SEQUENCE: 509
ttctcgtaat ctctatggaa attrccrtta ctagagataa atggcatcct tgcaatgtcc    60
caaattctca ccgaagaaca caagkaaaag araagaaaat attgagcaag cacagcacag   120
gcaggcagca tgaatccaca cagaaccaat ggtttttagc acagyasgyt gacagccaag   180
ggttacagta cataatcaga cggggcaaca cgaacgaagc agccgcatca rcagcagcct   240
asaacccatt aattgacaca cagcgtatat atatatatrt agtacttgtc ttttagc      297

<210> SEQ ID NO 510
<211> LENGTH: 231
<212> TYPE: DNA
<213> ORGANISM: Zea mays

<400> SEQUENCE: 510
aagtccagat gactttcaga agaaaatcg agaacttcag acaccttctg accgctgaag    60
cacgaacgac aatggccata cagcacgatg ttgcacgttt ygtagaagtt tgtatcttcg   120
ttaaaaatta tagcagtaca aatsatagcr cattctgtag gtgtaggata cagtaacaca   180
gcagcagaac atcaaacccr tctcctgcca ggctctgagc aacgccaaag c            231

<210> SEQ ID NO 511
<211> LENGTH: 301
<212> TYPE: DNA
<213> ORGANISM: Zea mays

<400> SEQUENCE: 511
ccrtrcaaca ttagstcgtt ytgtttctat ttsttgacca agacatggtt gytgttctga    60
tggcagattt gaacctgaca tgcttgcytt ttctgggtgc tattatggtg gtggagaaaa   120
ggagaggaga gaattagctg caattcgcag gcgatggaga accttgcatg tacaagctgt   180
gtgatgtgta atcattactc gcttactgag atagaattay cttttgctaa aagttttcat   240
attctagata cgtgacccgg agaaaggaag acggcaaggc aggtgtccac taactcctga   300
g                                                                   301

<210> SEQ ID NO 512
<211> LENGTH: 282
<212> TYPE: DNA
<213> ORGANISM: Zea mays
<220> FEATURE:
<221> NAME/KEY: misc_feature
<222> LOCATION: (1)..(1)
<223> OTHER INFORMATION: n is a, c, g, or t

<400> SEQUENCE: 512
ncgcgtgttc gtgcggatgc waykcatgca gaggyagcar arctagctag yaagcacgwa    60
ckyacgtagc acatgataag aaggctgcrt tgagacagta agacgaagaa tggcargcag   120
aagagcacgt cggcatgctc cccgcggctt atagcttaga ggcacttgaa tccggtgggc   180
ackctcttgc cgcagtggtt gaggatragg ctgaggtcga csggyaggtt gagcttgatt   240
```

```
cckaggacct ctcccttgat ggcggtgcag aggcacacgg cg              282
```

<210> SEQ ID NO 513
<211> LENGTH: 301
<212> TYPE: DNA
<213> ORGANISM: Zea mays

<400> SEQUENCE: 513

```
atggatgctt ytgtagcatt aaacgtgaga gtttaatcts accacaacaa gcatgggtga   60
tcacaagaaa tacaaaacag ccaactaacc aaamawkata ttagcaaatg caacttactt  120
ataacatggc aaccaaacac aaacacattg cgcacactta tgctggctta gtctatcctg  180
cattagaccc aatgcagtga attgctagtg caagcaacca attgctcccg tagtgtttcc  240
ttttgcttct atgaaggcta tgaactgtca gggtttattc tagtgatcta tttatctayc  300
a                                                                  301
```

<210> SEQ ID NO 514
<211> LENGTH: 216
<212> TYPE: DNA
<213> ORGANISM: Zea mays

<400> SEQUENCE: 514

```
tggaaaccrt taataattga agttttctya gtacagrtct gcatagcatt gaactggaca   60
gcttgctgtg ttactctgtr taasgaacga tctactgctg atctgtactg ttccttgatt  120
tttyyyycwc ttttcttctt ttgatggcaa gcaggactga agataagatg gctgccttrc  180
cattggccac cgcagaagca tgtgatgcta atgctg                            216
```

<210> SEQ ID NO 515
<211> LENGTH: 301
<212> TYPE: DNA
<213> ORGANISM: Zea mays

<400> SEQUENCE: 515

```
ggaaatcttg acaaggatat ggagagaagg tttagctacg ccctaagcag agaagacatc   60
gagaacgcca tactcggagg accttaasct gaacacatgg ccaaggggct cakagctagg  120
aattgcttag tcgaggttgg cactgaagaa gtaatcgctc cagtgatctg cgtgctacca  180
ttacgccatt gtaagagcaa atggatcatg tgtcgagaaa taatattcat gagcaataat  240
ctcgaactag gctggaaatg ttggawgcct cctggtgaca tgcgyytggt ttgttggcmt  300
c                                                                  301
```

<210> SEQ ID NO 516
<211> LENGTH: 301
<212> TYPE: DNA
<213> ORGANISM: Zea mays

<400> SEQUENCE: 516

```
mtaggaaggt caaggtgcct ttggaccccg gcagcaacta caccttcgac ctgagctact   60
accgccacgt rctcgccacg ggcgggctgt tccagtccga cggcagcctc ctgcacgacc  120
ccgtcaccag aggctacgtc gagaaggtgg tcaaggcgtc gtcgcccgac gagtactacg  180
cggacttcgc crcggcgatg gtcaagatgg gccgcaccga cgtgcttgtc ggcgatcatg  240
gggagatcag gccaacgtgt ggcatttttg ttgactaggt tcaggaktgg gttgaaratg  300
c                                                                  301
```

<210> SEQ ID NO 517
<211> LENGTH: 294
<212> TYPE: DNA
<213> ORGANISM: Zea mays

<400> SEQUENCE: 517

| | | |
|---|---|---|
| gtcaacaagc accagacttt ccaggacact cggtgctttt tcgtggtctc cacagatgga | 60 |
| tcccaggcag ayttctccta cctgaagtgc ctggagaact tgtgaggaa gagctacacg | 120 |
| gaggacgysg acacattctg catgaagtat ttaaggcccc gtcgcaggca ggcaccacca | 180 |
| gctgatgttg ggacagcatc aggcrccccg gatgaggttc caccgtcaac cgcagctgag | 240 |
| acagagcaag gcactcctcc agcccctcag gcagaggttc crcaagagay ttgg | 294 |

<210> SEQ ID NO 518
<211> LENGTH: 285
<212> TYPE: DNA
<213> ORGANISM: Zea mays

<400> SEQUENCE: 518

| | | |
|---|---|---|
| attacaccwa acttgtcctt ataagttaga aytcctacaa tatttattag actctgtagg | 60 |
| agaatctctt ctagatacaa acccacatcc tttactgtaa aaaaggccca ttgttagcta | 120 |
| caatgactta acatttacgg agggaccaaa tctctggtct gaaacccaaa ctttcaaggt | 180 |
| tcactaggtt cgtccactgg cagataaaac aaatcctcat ttaygatcat aagttgacat | 240 |
| actggacaaa gaatacttgt aagacgatcc cttcttatct gatga | 285 |

<210> SEQ ID NO 519
<211> LENGTH: 297
<212> TYPE: DNA
<213> ORGANISM: Zea mays

<400> SEQUENCE: 519

| | | |
|---|---|---|
| agtgtagaga tactcacaag aacaattttg aactgccttg cagagccagg taccacgaat | 60 |
| aagtgttcaa ccttactctc atgcctcaat ttcaagaaca cctgaacaca tttgctaaat | 120 |
| gatgtaagaa aaaagttgcc atcatggtat cagatacgag gtgagtagca acctggtgag | 180 |
| gtttaaatgt gtgcccmagc ggtgtgstta gttgaaaaga taaacrcagt ttctgcagat | 240 |
| ggtttgcaga aagagacact tttgtatctt tcagaagatc taacctgaaa tgaagca | 297 |

<210> SEQ ID NO 520
<211> LENGTH: 301
<212> TYPE: DNA
<213> ORGANISM: Zea mays

<400> SEQUENCE: 520

| | | |
|---|---|---|
| ccatgcgcta ctaccaggcc ggytcctcgg agatgttygg ctccacgccg ccgccgcagc | 60 |
| gcgaggacac gcccttccac ccgcgctcgc cctacgccgc cgccaaggtc gccgcgcact | 120 |
| ggtacacsgt caactaccgc gaggcctacg gcgtattcgc ctgcaacggc gtgctyttca | 180 |
| accacgagtc cccgcgccgc ggcgagaact tcgtcacgcg caagatcacg cgcgccgtcg | 240 |
| gccgcatcaa ggtcgggctg cagaccaggg tcttcctcgg caacctctcg gccgccaggg | 300 |
| a | 301 |

<210> SEQ ID NO 521
<211> LENGTH: 255
<212> TYPE: DNA
<213> ORGANISM: Zea mays

<400> SEQUENCE: 521

```
tacatacctt gcagcatgtc aaatgcacaa ggatgaagag agagggaaag ttgcagcaaa    60
gaaacttgtt gagatggaac cacaaagctc atccacgtac gtgttcctdt caagcttrca   120
tgctgcggct ggtaactggg ttgaagccaa ggtagccaga gaagcaatgc gagaaaaagg   180
ggtgatgaaa tttccagggt gtagttggat cacagtgggk aacaaacara gygtatttgt   240
tgtacaggac acaca                                                    255
```

<210> SEQ ID NO 522
<211> LENGTH: 299
<212> TYPE: DNA
<213> ORGANISM: Zea mays

<400> SEQUENCE: 522

```
actcaaattg agtcaagaaa tgctaaggga agcccgtgaa acaatataa tcgaacttttt    60 acattttatt gatgtggcct tyttaaaaat gacgccataa accwctatac tgaaaacggc   120
ctcggcgctt aaaccagtag cattcgtaag ttcattctg atttgggact tcaaaccaat    180
agtgtttgag actcacaggt ttagaaccga ttggtggctg ccttcaatca agagcgaaac   240
caacatgtta ttgcccacct taaaatcaca gattttgtat tatcgtgtac aataaaaat    299
```

<210> SEQ ID NO 523
<211> LENGTH: 301
<212> TYPE: DNA
<213> ORGANISM: Zea mays

<400> SEQUENCE: 523

```
ycagatcatc actggaatca acagcagttc tctggttcat tgttcagat gcttckgtgt     60 caactgcttc tgaaygatgg tttaagctta taacatcatc arcattttg ttaattattg    120 cactgttctc gttgtccttt accacgctat tcaaawtttc tggctcctca gatactacaa   180
gatcagatrt ctgcccgttc tgagtaagag tggtttcagg actgacaccc ataccttgtg   240
caagtgctac ataccgaagt actagwtgct tgtacgaatt caataggctc tctacatcag   300
c                                                                    301
```

<210> SEQ ID NO 524
<211> LENGTH: 274
<212> TYPE: DNA
<213> ORGANISM: Zea mays

<400> SEQUENCE: 524

```
ctttagtagc tagtcytata gctcataggt tctcagttcg gtatatrtyg gtgayatatt    60
tcatgaactt asttttwaam cmatttaaaa mgcamacgca acaacgaagg gagtgatatt   120
gaccatgggt ctttcgtagc ttttcaatca aacgtcacat aaaaaaagaa acawccaaaa   180
gwtcataata cacagattkr aamskkkaga caaaaatacg agtacaagac attggaccttt   240 caatwwtttt tttktgtttt ctgagacatg aaaa                                274
```

<210> SEQ ID NO 525
<211> LENGTH: 319
<212> TYPE: DNA
<213> ORGANISM: Zea mays

<400> SEQUENCE: 525

```
ttgcaccacc catagtttaa gaggcagttg ctttcacaca ctttattttg catggcacag    60
ccaactgtcc ccatcattct aaaccaggct gcaactgagc cactacagaa actgctaata   120
```

```
ttagatattc cagcaaatag tcttgacact agagtgctaa gtccctaaac acgaaagaca    180
tttgtcagga gacccgtatt gagtactagc agagtatact accgctagat attccagtat    240
aatcgtgcag cagctccggt caatggcagt ggcacttgaa gtctgcaacc tcagccaaca    300
gatccacatg agaaccaac                                                  319

<210> SEQ ID NO 526
<211> LENGTH: 283
<212> TYPE: DNA
<213> ORGANISM: Zea mays

<400> SEQUENCE: 526
tacactatac taattagaat gtctggaaag gctgggaaga ccactaaatt tgtctcattk     60
ttggaggaaa tggtgtccra aggatgtgtt cttartctga ttgcttataa tactgttatt    120
gaggctcttg gtaagaacaa gatggttgac aaggcgattt ttatgctttc taaaatgatt    180
gagagtgact gtcggcccaa tcaattcaca tatagcatta tgctggatgt tttatcaaca    240
gggggacaac tccacaggtt gaatgagatt ctagatattt gta                      283

<210> SEQ ID NO 527
<211> LENGTH: 193
<212> TYPE: DNA
<213> ORGANISM: Zea mays

<400> SEQUENCE: 527
cctttctcca gttggtaata tgcttcatgt aaggtacctg aaagtggtaa gcracatgat     60
agtcaaactc ccactcatta ttcgaggcct gcgacactta gagacactcg aggtggatgc    120
agaaraagtc gctgttccac tggatgtttt catcttgaag agcctgttgc atctccgact    180
tccgagcaag gct                                                        193

<210> SEQ ID NO 528
<211> LENGTH: 298
<212> TYPE: DNA
<213> ORGANISM: Zea mays

<400> SEQUENCE: 528
tgcatatgag aaactacaag gttggcaggg tcctttcctg tgcccgagct gtcatgaaaa     60
gaaagaagca atggaaggga aacgccggcc aaaaggtatc attaaatagt atttacctga    120
actacattct ktagttaacc ctcagactgc tcattcgttt ctgggttcct atttgtcttt    180
ccaggatctt catcaaacgt ctttggtcac atgtgctagg cctgcctacc actaaagatt    240
cttttattga ttsttagctg gaaataatag kcagcccata acaattcatt ggctagaa      298

<210> SEQ ID NO 529
<211> LENGTH: 360
<212> TYPE: DNA
<213> ORGANISM: Zea mays

<400> SEQUENCE: 529
aagcacccgc atgcagactt ccaaactatc cagtgtccac aaatagcagt tttgcaaact     60
aaatacatat atgaaatgat gacacaggcc acccaaacaa caagccctag agaatcagac    120
caaccaaccg agcaattcgc agtgctccat atcttctagc attcacaacc tgacgaacgc    180
tgttgccttc cagcgcccccc aacatcaatc gtatcaggaa gatacctgca aaagttggta    240
aaacatagat caagttacac cacaaggctg cctgcatgta tgatacatat atgtgagcta    300
```

```
tatactattc aaacttacat atcttcttct ggctcatttt ttacagcatt cctcgctata    360

<210> SEQ ID NO 530
<211> LENGTH: 299
<212> TYPE: DNA
<213> ORGANISM: Zea mays

<400> SEQUENCE: 530
agaygctact ctgctaccat tttgagaatc tattgacaag aactttacag gaggrgtctc     60
atccccagga gccttgctga taactggaga tggagaagat atgcacatat ccactcgtga    120 atgcytttc ctggacttat ttctgtcctt tagcagttgt tttccctagc aaacaaaagg     180
agatacacat agcatgagaa agaagaaasa aactgaaaca ttytataatg agaaaaaaac    240
atggggagtt ggggacaaag caactcacca atgcttctac aaatgttttg aacctccga    299

<210> SEQ ID NO 531
<211> LENGTH: 262
<212> TYPE: DNA
<213> ORGANISM: Zea mays

<400> SEQUENCE: 531
tgcttctgtc gaattgctgc gggcagarca tgctttggtg gyggctttgc agtgtgaaac     60
gttatgaatc tgagaacctc gatgcatgcy agggacaggg aatacctgaa caggggccaa    120
gatgacatga acaggacgcc ggatagcacg tgcacaacct tcctgctcaa gctctgcctt    180
cattgatggc atggatcagt acagagttcg gaagccaacg acgtgaacar ctgaacataa    240
gcaaatgtaa tggccgttct aa                                             262

<210> SEQ ID NO 532
<211> LENGTH: 301
<212> TYPE: DNA
<213> ORGANISM: Zea mays

<400> SEQUENCE: 532
aggtcgacaa ggctgctagt aacatgtctg agccgacatc aggggagatg caggatgctg     60
ctttccagtc tgacgaagag gaggaagatg aagatgttga tgaaacagta ttcggtcaag    120
attcagattc gtcacaraat agcggcaccg gcgacgatgc aaagtagact cactgctggt    180
attcatcatt atggtgattg tattgttttt aattaaattg ccaagcttga ttttgtcaa     240 ggcgacgytg gaaggttgca cagaattttg ayagtgtctc tggtttcatt ttgaaagcac    300
t                                                                    301

<210> SEQ ID NO 533
<211> LENGTH: 271
<212> TYPE: DNA
<213> ORGANISM: Zea mays

<400> SEQUENCE: 533
agaaaacgag gccttcgtcg tcttagcgcg crggggcgta ggacggcggc agcggcagcc     60
ccacgacctt gccgcagcgg agggcgttgt cgggcatgtt gtactcgtcg cgcagtgatc    120
gcgccggcga gacgacgctg atatagaact gctcccgag gtagtaccgc tcccagatgt     180
tggaatgcac gctccacatg cccgcgttgt cgaacgtcag catgattgcc gtccatgacc    240
gcgggtacac ctggatcgtg tgccggctca c                                   271

<210> SEQ ID NO 534
<211> LENGTH: 286
```

```
<212> TYPE: DNA
<213> ORGANISM: Zea mays

<400> SEQUENCE: 534
ttctggtact tgcggatctc gcgcagmgcc acsgtsccgg gcctgtacct gtggggcttc      60
ttcacgccgc cggtcgtcgg cgcmgacttc ctcgccgcct gcaacraray aacaaccgcc     120
gccgcgtcag crccgtctta aacgggaac aatcgagggg atcggaacak cagatcggta     180
cgggtaggta gagacgaacc ttggtkgcga gctgcttgcg cggggccttg cctccggtgg     240
acttgcgggc ggtctgcttc gtacgagcca tcttctcctc tccttg                    286

<210> SEQ ID NO 535
<211> LENGTH: 252
<212> TYPE: DNA
<213> ORGANISM: Zea mays

<400> SEQUENCE: 535
ctgcgttagt ttcaccccctt ctagctgcga gtgaaagaaa cwtgataaca gctwsctgct     60
agtttctatg ryrgccatcg aatctgacat ggctayctcc tgtgmcmacg caggtccgca    120
ggtactacca gccgaggaag agccaacgga cggtgacggc ggtgatccac ggcgagaagg    180
tgccgctgta cggcgccggg gcggcctga cgctgtcsac gagcgcgggc gggggsgcgg    240
tgcccctgac gc                                                        252

<210> SEQ ID NO 536
<211> LENGTH: 301
<212> TYPE: DNA
<213> ORGANISM: Zea mays

<400> SEQUENCE: 536
agcaccacga ttcacaccta cacatattca gacacaaaat tgggcagcga tgggcatgga     60
catttcattg atagatggta tttagctgcc tactytggca tttgattcga gcagcgaagc    120
ttcaagagct gcagaatcgc tacayatatt cctgtgggta cacatgcttc ttgttctcca   180
ctcgacccag atcattgtga tggactacta actgscagta caaaagcaga catctatcaa   240
acttacacaa aaggcgtgca caacgagaya gyctgcttgc gcatctccaa gtctagtcta   300
g                                                                    301

<210> SEQ ID NO 537
<211> LENGTH: 237
<212> TYPE: DNA
<213> ORGANISM: Zea mays

<400> SEQUENCE: 537
awwttkkwag ygcarraata aacaaggcac tgtwrattgt acagagcaag ctctctgcat    60
ttttcaatgc cgcagcatct gcaactgcaa gcagagtttc tacaggccaa ggccgactgt   120
cctgccatct ctcctgcgga ggcctgctat gtaatgtttc tccaggttgg tgtcgagctc   180
ctccagtttc ttggcttctt ccgccgagct cccgaccttg ttctcgaccg tgtttaa      237

<210> SEQ ID NO 538
<211> LENGTH: 278
<212> TYPE: DNA
<213> ORGANISM: Zea mays

<400> SEQUENCE: 538
tcaatttgtg atttcatcca caatttcttc atatgtgagg aatgccgcac rcacttctat    60
```

-continued

| | |
|---|---|
| gaaatgtgtt caargtttgg aaaaactact ctagccatat attgccacag aaatcaastg | 120 |
| catgtytaat tgttaccgtt cacctgtagt gtatcagtcc ccttcaaatc tgcccgtgac | 180 |
| cttgccctct ggctatggrc cgcgcataac aaagttaacg agaggttgat gaaagaagaa | 240 |
| aaggagttag acaatgctga tccttcattt cctaagat | 278 |

<210> SEQ ID NO 539
<211> LENGTH: 263
<212> TYPE: DNA
<213> ORGANISM: Zea mays

<400> SEQUENCE: 539

| | |
|---|---|
| ttgcatacaa acttgatcma aatgttttrca amccatgctt gaacrratat acaaacccgt | 60 |
| tgyggcagga acatyttagc ttwgkammmt ygywvagcaa caatagcttc aatagagatt | 120 |
| gttgtaagtg tagagtgctg ctgcgatgga ractatgcaa atcacaaggg atgggagaag | 180 |
| agtgacattc agaaggaggt ccgtgccgag ataaccggct gcagtaatcg tggcatctgc | 240 |
| aactacacgg gccaacgtcc cgg | 263 |

<210> SEQ ID NO 540
<211> LENGTH: 266
<212> TYPE: DNA
<213> ORGANISM: Zea mays

<400> SEQUENCE: 540

| | |
|---|---|
| acaagtccaa atcaaaggtg ttgtcccgcc aatgcttacc ccccatgscy ccccraaata | 60 |
| gcatctgaat ccattttttt gtcygatctt tttkkctcct cttctgacag ggaaatgctg | 120 |
| cttgagttgg acgaggaaca gactggaata caaatgcacg tgcaggttgc aaattcttat | 180 |
| gttrwttttt gkggcctatc artrcacagt actcatagca tgacaaatgg cgttgcaggt | 240 |
| tttggttttt accsgttttg gtttcc | 266 |

<210> SEQ ID NO 541
<211> LENGTH: 197
<212> TYPE: DNA
<213> ORGANISM: Zea mays

<400> SEQUENCE: 541

| | |
|---|---|
| aacctcgact ccactataas tgcaggacgc acgrcaygca caactgaaac atccggacca | 60 |
| acaggcagag tagtagccca aaggatgacc cgtctcatgc aaaaacagtc agcttgataa | 120 |
| acttatcgag aaggcaacac cggygcccaa gtactggttg aaatacagag cagacattga | 180 |
| agtgccaaag aggggggg | 197 |

<210> SEQ ID NO 542
<211> LENGTH: 301
<212> TYPE: DNA
<213> ORGANISM: Zea mays

<400> SEQUENCE: 542

| | |
|---|---|
| gtctagaaaa gtcaaaacgt catatacttg gaacrggagt agatatgaca aaaagagcat | 60 |
| gcaagtgatg ttcttacaga agaatatata tatttcatgg caagctagta cctaaacttc | 120 |
| agatggagtc tttgcatcga ttgacagggc gtgcaacccg gtcttgagct cctcctgcag | 180 |
| gagatcatag acagccctgt gcctcttrag caagctcttc ccctcaaact ccttggacac | 240 |
| caccctcaca ttgaaatgtg tctccccatt ggtcccagcc acgccagcat ggcccttgtg | 300 |
| g | 301 |

<210> SEQ ID NO 543
<211> LENGTH: 291
<212> TYPE: DNA
<213> ORGANISM: Zea mays

<400> SEQUENCE: 543
attttaccat actgcattca aagttttaca agattggaca ttattagtat aaaacatgaa    60
acttttcaag tgaacaasaa ctataarcaa cgtccgcaag cgcaatccac agcttgaggt   120
tacattgtga gtgtagtaga gaaactaggt ggtcccaaat agcacaagat tatccaagct   180
acccagtttt ctacgattat gggcacracc ataagcagat agmagtgctt cgcatcctgt   240
tgcattaaga aagtagtata ggcatcggag gtgctgaatc taagcacacg g            291

<210> SEQ ID NO 544
<211> LENGTH: 299
<212> TYPE: DNA
<213> ORGANISM: Zea mays

<400> SEQUENCE: 544
taaaccagay tagatgccac ctagktttct gacacaaatc aygaacaaaa cacgagaaga    60
aagcyaatca tacacggatg ayggatggac tcagcggagc ccttatttgc taccattcct   120
catgtcttat tgcagaaatc catctattgc tactcaactt camtcagtct ctggaactct   180
gtatcaacag gggatgggaa atgtgtcatg ttcaatgttt agcycatgaa acatagaaga   240
ccmcattaga agctattatg tgcttacatt tgattttttt atccaagact caagtgtat    299

<210> SEQ ID NO 545
<211> LENGTH: 300
<212> TYPE: DNA
<213> ORGANISM: Zea mays

<400> SEQUENCE: 545
rrhytkrtgg aggtcggggg aagaaaccct aagaacgatg tctcaccaaa ttgattcctt    60
ccgcccgaga gatttagaag ctagatctgt ccagatttag tggattgata ggttttgtga   120
atttgtcatt ctccaactaa tctacttacg gccagatttt acatcagacc tgatgaaaca   180
ctgtttcctt gacacgaaac tggtggacgc tgcctttgca tcaagaatca agaaattgat   240
ttrcgtttta tgtytctggt agcyccagac acctcatact ctcctctgtt gcctgtsatg   300

<210> SEQ ID NO 546
<211> LENGTH: 232
<212> TYPE: DNA
<213> ORGANISM: Zea mays

<400> SEQUENCE: 546
aacggctaag agtcaggcga ttctgtttgt acagagacaa tcgcagcact tgrmtgctwc    60
gcatgcgstt cagagggcct tcagctcagg cttgacagat ctagttttgg ycgccacgcy   120
rctcttcggc gagcactgya ctctgctggc gtctttagaa gccccgatgc tgtgacgatg   180
tggccgggtg gtagatgttg cgttggtgtt ttttccctcg ggtgtctgtg gt           232

<210> SEQ ID NO 547
<211> LENGTH: 201
<212> TYPE: DNA
<213> ORGANISM: Zea mays
<220> FEATURE:
<221> NAME/KEY: misc_feature
<222> LOCATION: (7)..(7)

```
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(31)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t

<400> SEQUENCE: 547
aaacaanact cagtggactc gcngaaannn nataatgaaa ggtgctccat ccatacccat      60
gagaangttc cgatgctcgc agtctcatgt ttcccagtca atcttctttc atttccttct    120
ccgtatgcac taatatgcag atcatggcgc agagaaaggt tcaggattgc tctcttgatc    180
tcttcaaacc cgccgtcttc g                                              201

<210> SEQ ID NO 548
<211> LENGTH: 301
<212> TYPE: DNA
<213> ORGANISM: Zea mays
<220> FEATURE:
<221> NAME/KEY: misc_feature
<222> LOCATION: (239)..(281)
<223> OTHER INFORMATION: n is a, c, g, or t

<400> SEQUENCE: 548
aaaattactg aaggcaggtg ggttgcagtt gtgtgttcgt tactgtttac tgtawyatgt     60
caagctgtcg gctgcaattt ctttgctggc aagccgcagg cactggtgaa gtgctgataa    120
atacatcata ttctgttgac ctgtgaagaa gcttgttcwa ggtrgattcc attgtactag    180
ctctgttgcy cagcatctcc ttgtttggga acattaacaa ccagcyctcr mccctcaann    240
nnnnnnnnnn nnnnnnnnnn nnnnnnnnnn nnnnnnnnnn ntaaaatagt cgcatcatgt    300
a                                                                    301
```

SIMULTANEOUS GENE EDITING AND HAPLOID INDUCTION

FIELD OF THE INVENTION

This invention is related to the field of plant biotechnology, specifically agriculture biotechnology and gene editing, as well as plant breeding. The presently disclosed subject matter relates to using a haploid inducing line (whether existing or created) and transforming the haploid inducing line so that it contains DNA coding for cellular machinery capable of editing genes.

STATEMENT REGARDING ELECTRONIC SUBMISSION OF A SEQUENCE LISTING

A Sequence Listing entitled "81771-US-ST26.xml", 1,001 kilo bytes in size, generated on Oct. 25, 2024 and filed via EFS-Web, is provided in lieu of a paper copy. This Sequence Listing is hereby incorporated by reference into the specification for its disclosures.

BACKGROUND

Targeted mutagenesis (also known as "gene editing") is a very important technology to crop breeding. There are numerous methods to edit specific gene targets now, including CRISPR, TALEN, meganucleases, and zinc fingers. One method to introduce editing machinery into plants is to use *Agrobacterium* or biolistic transformation of plant tissue. In transformation, DNA coding for the editing machinery (e.g., CAS9 and guide RNA) is introduced into plant callus, seed or embryonic tissue. Stably-transformed plants ("events") are then recovered, optionally with the help of a selectable marker. But because tissue culture is genotype-dependent, this route will not work for all crops, or even all varieties of the crops for which it does work. These are known as transformation-recalcitrant crops or varieties. These crops or varieties may be valued for their performance but it is a challenge for biotechnology that they cannot be transformed and thus cannot be directly edited via transformation. For recalcitrant varieties, one of two alternative approaches could be used to introduce desirable mutations. First, one could introduce the edits via trait introgression. This route is expensive, laborious, and time-consuming. It also means impurity of the final product because of genetic linkage—that is, there will be a linked block surrounding the introgressed edits, containing genes and alleles from the transformable donor line. This linkage can be an issue if any of those genes or alleles impact the performance of the transformation-recalcitrant line (may also be referred to as an "elite line"). Secondly, one could introduce the editing machinery transiently to the growing plant without tissue culture, such as floral dipping for *Arabidopsis* transformation. The challenge is ensuring edits end up in cells that contribute to the germ-line, so they are passed on to progeny seed. There are few established or routine methods to do this in crops.

We have previously shown new methods to transiently introduce editing machinery during haploid induction in U.S. patent application Ser. No. 15/901,464, which was the national phase of PCT/US2017/064512 (the entire contents of both are incorporated herein by reference). Haploid induction ("HI") is a class of plant phenomena characterized by loss of one parent's set of chromosomes (the chromosomes from the haploid inducer parent) from the embryo at some time during or after fertilization, often during early embryo development. Haploid induction is also known as gynogenesis if the inducer line is used as the male in the cross, or androgenesis if the inducer line is used as the female in the cross. Haploid induction has been observed in numerous plant species, such as sorghum, barley, wheat, maize, *Arabidopsis*, and many other species.

Commonly, during haploid induction, both parent lines used in the induction cross are both diploids, so their gametes (egg cells and sperm cells) are haploids. Haploid induction is frequently a medium to low penetrance trait of the inducer line, so the resulting progeny, depending on the species or situation, may be either diploid (if no genome loss takes place) or haploids (if genome loss does indeed take place). If the parent line that is crossed to the haploid inducer is not diploid, but rather a tetraploid, hexaploid, or other plant of higher ploidy, the term haploid induction is something of a misnomer, because the "haploid" progeny produced will have a gametic chromosome number, and thus would not really be haploids, but rather diploids (if the parent is tetraploid) or triploids (if the parent is hexaploid) and so on. Therefore, as used herein, "haploids" possess half the number of chromosomes of either parent; thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy.

Haploid induction can occur during self-pollination or intercrossing of two lines within the same species, or it can occur during wide crosses, where it can be viewed as a hybridization barrier, preventing the formation of interspecific hybrids. In maize, the most commonly employed method of inducing haploids is through the use of an intraspecific haploid inducer male line, which is primarily triggered by rearrangements of, mutations in, and/or recombinations, insertion, or deletions within a region of chromosome 1, specifically the MATRILINEAL (MATL) gene, also known as NOT LIKE DAD1 (NLD1) and PHOSPHOLIPASE Al (PLA1) (with the notable exception of the ig type haploid induction, which is a result of a mutation in the INDETERMINATE GAMETOPHYTE1 gene on chromosome 3). In wheat, the most common method of inducting haploids is by wide cross to maize pollen—regardless of parent genotype or lineage, this works with almost any wheat crossed by almost any maize pollen.

HI maize lines contain a quantitative trait locus ("QTL") on Chromosome 1 responsible for at least 66% of the variation in haploid induction. The QTL causes haploid induction at different rates when it is introgressed into various backgrounds. All maize haploid inducer lines used in the seed industry are derivatives of the founding HI line, known as Stock6, and all have the haploid inducer chromosome 1 QTL mutation.

In maize, haploid seed or embryos are specifically produced by making crosses between a haploid inducer male (i.e., "haploid inducer pollen") and virtually any ear that one chooses—the ear could be of any inbred, hybrid, or other germplasm. Haploids are produced when the haploid inducer pollen DNA is not fully transmitted and/or maintained through the first cell divisions of the embryos. The resulting phenotype is not fully penetrant, with some ovules containing haploid embryos, and others containing diploid embryos, 2fricana22 embryos, chimeric embryos, or aborted embryos. The haploid kernels have embryos that contain only the maternal DNA plus normal triploid endosperm. After haploid induction, haploid embryos or seed are typically segregated from diploid and 2fricana22 siblings using a phenotypic or genetic marker screen and grown or cultured into haploid plants. These plants are then converted either naturally or via chemical manipulation (e.g., using an anti-microtubule agent such as colchicine) into doubled haploid ("DH") plants which then produce inbred seed.

Plant breeding is facilitated by the use of doubled haploid (DH) plants. The production of DH plants enables plant breeders to obtain inbred lines without multi-generational inbreeding, thus decreasing the time required to produce homozygous plants. DH plants provide an invaluable tool to plant breeders, particularly for generating inbred lines, QTL mapping, cytoplasmic conversions, trait introgression, and F2 screening for high throughput trait improvement. A great deal of time is spared as homozygous lines are essentially generated in one generation, negating the need for multi-generational single-seed decent (conventional inbreeding). In particular, because DH plants are entirely homozygous, they are very amenable to quantitative genetics studies. The production of haploid seed is critical for the doubled haploid breeding process. Haploid seed are produced on maternal germplasm when fertilized with pollen from a gynogenetic inducer, such as Stock 6 and Stock 6-derivative lines.

We previously described a novel method in which the in vivo haploid induction process can be co-opted to transiently introduce editing machinery into any germplasm by including it in the haploid inducer parent, either stably integrated as a transgene, or transiently expressed. Simultaneous editing plus haploid induction can be done in almost any crop via wide cross or de novo haploid induction for instance via CENH3 mutation (i.e., CENH3-modified haploid inducer; see, e.g., WO 2017/004375, incorporated herein by reference in its entirety) or via lipid spray (see P.C.T. Patent Application No. PCT/US2016/62548, incorporated herein by reference in its entirety). We showed examples of HI in maize, both field corn and sweet corn, using a haploid inducer male as the editing donor line. Further, we showed examples of HI in *Arabidopsis* using CENH3-modified haploid inducer lines.

We also provided examples of HI in wheat using maize pollen as the editing donor line in a wide cross. In wheat, rice, barley, *Brassica*, and other crops, the route to haploid induction would be to use a pollen donor that induces haploids via wide cross. For example, one could use corn pollen on wheat, millet pollen on wheat, barley pollen on other barley species, or any other wide crossing method. In those cases of gynogenetic haploid induction it would be preferable for the male line to contain the editing machinery, because it is the male (pollen-derived) DNA that is eliminated in the haploid induction process. In cases of androgenic haploid induction, for instance in the ig1 system in maize or via altered CENH3 in any crop (which can work via either the male or the female), the editing machinery would be optimally present in the female parent, because the female chromosomes are eliminated in the haploid induction process.

In simultaneous editing plus haploid induction, the goal is to rapidly and cost-effectively edit crops and elite lines ("editing destination lines") without tissue culture. The line that receives the edits could be elite germplasm, and the editing machinery itself would be eliminated during the haploid induction process. At the same time, edited doubled haploid lines are produced.

Here we teach, inter alia, new methods for confirming the presence of haloid progeny, for example, edited haploid progeny, for the presence of haploid inducer genome.

SUMMARY

Tissue culture recalcitrance is a major challenge to rapid elite line editing across crops. Using haploid inducing lines to deliver the targeted mutagenesis machinery to elite lines and simultaneously induce haploids represents the surmounting of this major obstacle. Next-generation breeding programs may come to depend on this process.

The editing machinery is delivered via the inducer line. The editing machinery is most often DNA-binding proteins combined in some cases with RNA and in some cases also with DNA. The DNA, RNA, and proteins that make up the editing machinery are encoded by and are present in the inducer line because they have been stably inserted in the inducer, for example, via bombardment or agrobacterium mediated transformation. In other examples, the editing machinery is transiently introduced (through exogenous application) or transiently expressed in the gametophyte prior to fertilization. After fertilization, edits are made by the editing machinery in the non-inducer target genes prior to or during elimination of the inducer chromosomes. The result is a haploid embryo or plant or seed that contains the chromosome set only from the non-inducer parent, where that chromosome set contains DNA sequences that have been edited. Haploids may be further tested for evidence of the haploid inducer parent. These edited haploids can be identified, grown, and their chromosomes doubled, preferably by colchicine or other mitotic inhibitor. This line can then be directly used in downstream breeding programs.

In one embodiment, the invention provides a method of editing a plant's genomic DNA. This is done by taking a first plant—which is a haploid inducing plant and which also has encoded into its DNA the machinery necessary for accomplishing the editing (for example, a Cas9 enzyme and a guide RNA)—and using that first plant's pollen to pollinate a second plant. The second plant is the plant to be edited. From that pollination event, progeny (e.g., embryos or seeds) are produced; at least one of which will be a haploid seed. This haploid seed will only contain the chromosomes of the second plant; the first plant's chromosomes have vanished (having been eliminated, lost or degraded), but before doing so, the first plant's chromosomes permitted the gene-editing machinery to be expressed. Alternately, and without wishing to be bound by theory, the first plant delivers the already-expressed editing machinery upon pollination via the pollen tube. Or, in the case that the haploid inducer line is the female in the cross, the haploid inducing plant's egg cell contains the editing machinery that is present and perhaps already being expressed, upon fertilization with the "wild type" or non-haploid inducing pollen grain. Through any of these routes, the haploid progeny obtained by the cross will also have had its genome edited. The haploids may be further tested for evidence of the inducer parent genome.

In one aspect, the editing machinery is any DNA modification enzyme, but is preferably a site-directed nuclease. The site-directed nuclease is preferably CRISPR-based, but could also be a meganuclease, a transcription-activator like effector nuclease (TALEN), or a zinc finger nuclease. The nuclease used in this invention could be Cas9, Cfp1, dCas9-FokI, chimeric FEN1-FokI. In one aspect, the DNA modification enzyme is a site-directed base editing enzyme such as Cas9-cytidine deaminase or Cas9-adeninie deaminase, wherein the Cas9 can have one or both of its nuclease activity inactivated, i.e. chimeric Cas9 nickase (nCas9) or deactivated Cas9 (dCas9) fused to cytidine deaminase or adenine deaminase. The optional guide RNA targets the genome at the specific site intended to be edited. In one aspect, the optional guide RNA comprises an 18-21 nucleotide sequence with homology to any of SEQ ID NOs: 2, 4, 8, 21, 23, 25, 29, 32, and 33.

Once the edited haploid progeny is obtained, it may optionally have its chromosomes doubled by a chromosome doubling agent (for example colchicine, pronamide, dithipyr, trifluralin, or another known anti-microtubule agent).

In one embodiment, the first plant is a monocot or a dicot. Aspects of the first plant include maize, wheat, rice, barley, oats, triticale, sorghum, pearl millet, teosinte, bamboo, sugar cane, asparagus, onion, and garlic. In one embodiment, the second plant is a monocot or a dicot. Aspects of the second plant include maize, wheat, rice, barley, oats, triticale, sorghum, pearl millet, teosinte, bamboo, sugar cane, asparagus, onion, and garlic. In one embodiment, the first plant is a monocot or a dicot of a different species than the second plant. For example, in one aspect, the first plant is maize and the second plant is wheat. In another aspect, the first plant is wheat and the second plant is maize. In another embodiment, the first plant is a maize plant selected and/or derived from the lines Stock 6, RWK, RWS, UH400, AX5707RS, NP2222-matl, or any of the several other known HI lines. In yet another embodiment, the first plant comprises a mutation in a CENH3 gene, an ig1 gene, or another mutation conferring paternal-haploid inducing systems. In another embodiment, the first plant is a rice plant with the MATL gene modified or knocked out which makes it a haploid inducer line.

In another embodiment, the first plant is not necessarily a haploid inducer, yet the first plant comprises the genes necessary for encoding the gene editing machinery. In this embodiment, haploid induction is produced by administering a compound during, immediately before, or immediately following pollination. In one aspect, the composition comprises a lipid or a phospholipase inhibitor. In another aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AACOCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11€-conjugated Linoleic acid, or 2-oleoyl-1-palmitoyl-sn-glycero-3-phospho-ethanolamine.

The disclosure also includes methods of testing an edited haploid plant progeny for the presence of a first plant's genomic material, wherein the first plant is a haploid inducer line of the plant. In one embodiment, a method comprises isolating a nucleic acid from the edited haploid progeny, and detecting in the nucleic acid the presence of a plurality of codominant markers, wherein the codominant markers have a distinct haplotype for a second plant and wherein the second plant comprises the source of genomic DNA in the edited haploid plant progeny.

The edited haploid may be obtained, for example, by a method comprising: (a) obtaining the first plant, wherein the first plant is capable of expressing a DNA modification enzyme and optionally at least one guide nucleic acid; (b) obtaining the second plant, wherein the second plant comprises the plant genomic DNA which is to be edited; (c) pollinating the second plant with pollen from the first plant; and selecting at least one haploid progeny produced by the pollination of step (c) wherein the haploid progeny comprises the genome of the second plant but not the first plant, and the genome of the haploid progeny has been modified by the DNA modification enzyme and optional at least one guide nucleic acid delivered by the first plant. The DNA modification enzyme and guide nucleic acids can be those described herein. Typically, the edited haploid progeny will be treated with a chromosome doubling agent, e.g. colchicine, pronamide, dithipyr, trifluralin, or another known anti-microtubule agent, after testing, thereby creating an edited doubled haploid progeny.

Plants may vary by embodiment and may include those described herein, e.g. in some embodiments, the first plant is a maize plant selected and/or derived from the lines Stock 6, RWK, RWS, UH400, AX5707RS, NP2222-matl, or any of the several other known HI lines, and the first plant acts as the male and the second plant acts as the female.

The plurality of codominant markers include at least one of at least 5, at least 10, at least 15, at least 20, at least 25, at least 30, at least 35, at least 40, at least 45, at least 50, at least at 55, at least 60, at least 65, and at least 70 markers. Typically, the plurality of codominant markers will include at least two markers selected from the group consisting of the markers in Table 12. Detecting may include the use of at least one assay component in Table 13.

BRIEF DESCRIPTION OF THE SEQUENCES IN THE SEQUENCE LISTING

SEQ ID NO: 1 is a nucleotide sequence for vector 23396.

SEQ ID NO: 2 is the nucleotide sequence encoding the gRNA sequence for editing VLHP1 in maize.

SEQ ID NO: 3 is a nucleotide sequence for vector 23399.

SEQ ID NO: 4 is the gRNA sequence for editing GW2-2 in maize.

SEQ ID NO: 5 is the nucleotide sequence for vector 22808, comprising a TALEN construct.

SEQ ID NO: 6 is the target sequence for the TALEN of 22808.

SEQ ID NO: 7 is the nucleotide sequence for vector 23123 comprising a Cas9 construct.

SEQ ID NO: 8 is the gRNA for editing MATL in maize.

SEQ ID NO: 9 is nucleotide sequence for the relevant portion of MATL in NP2222.

SEQ ID NO: 10 is nucleotide sequence for the relevant portion of MATL in Stock6.

SEQ ID NO: 11 is nucleotide sequence for the relevant portion of MATL in USR01350333-3 Allele SEQ ID NO: 12 is nucleotide sequence for the relevant portion of MATL in USR01350333-3 Allele 2.

SEQ ID NO: 13 is nucleotide sequence for the relevant portion of MATL in USR01350344-2 Allele 1.

SEQ ID NO: 14 is nucleotide sequence for the relevant portion of MATL in USR01350344-2 Allele 2.

SEQ ID NO: 15 is nucleotide sequence for the relevant portion of MATL in USR01350343-1 Allele 1.

SEQ ID NO: 16 is nucleotide sequence for the relevant portion of MATL in USR01350328-1 Allele 1.

SEQ ID NO: 17 is nucleotide sequence for the relevant portion of MATL in USR01350337-2 Allele 1.

SEQ ID NO: 18 is nucleotide sequence for the relevant portion of MATL in USR01350337-2 Allele 2.

SEQ ID NO: 19 is the nucleotide sequence of cDNA wildtype MATL.

SEQ ID NO: 20 is the nucleotide sequence for vector 23397.

SEQ ID NO: 21 is the gRNA sequence for editing VLHP2 in maize.

SEQ ID NO: 22 is the nucleotide sequence for vector 23398.

SEQ ID NO: 23 is the gRNA sequence for editing GW2-1 in maize.

SEQ ID NO: 24 is the nucleotide sequence for vector 23763.

SEQ ID NO: 25 is the gRNA sequence for VLHP1 in wheat.

SEQ ID NO: 26 is the wheat VLHP target sequence for TaVLHP2.

SEQ ID NO: 27 is the wheat VLHP target sequence for TaVLHP3.

SEQ ID NO: 28 is the target sequence in ZmVLHP2-03 for editing.

SEQ ID NO: 29 is the edited sequence in ZmVLHP2-03.

SEQ ID NO: 30 is the repair donor template sequence for creating E149L mutation in ZmPYL-D.

SEQ ID NO: 31 is the nucleotide sequence for vector 23136.

SEQ ID NO: 32 is the gRNA of vector 23136.

SEQ ID NO: 33 is the nucleotide sequence of rice PLA gene 0503g27610.

SEQ ID NO: 34 is the nucleotide sequence for vector 24038.

SEQ ID NO: 35 is the nucleotide sequence for vector 24039.

SEQ ID NO: 36 is the nucleotide sequence for vector 24079.

SEQ ID NO: 37 is the nucleotide sequence for vector 24091.

SEQ ID NO: 38 is the nucleotide sequence for vector 24094.

SEQ ID NOs: 39 through 97 are primers and probes used in the identified PCR Taqman assays.

SEQ ID NO: 98 is the nucleotide sequence for vector 24075.

SEQ ID NOs: 99-173 are nucleotide sequences containing codominant markers as described in Table 12.

SEQ ID NOs: 174-473 are nucleotide sequences of assay components described in Table 13.

BRIEF DESCRIPTION OF THE FIGURES

FIG. 24 shows the GL1 target site sequence mutations in the parent #USR01424135 and all of the sequenced edited haploids from outcrosses by *Landsberg erecta* pollen. It is clear that the precise edit made is different in the different haploids.

DEFINITIONS

Figure 1:
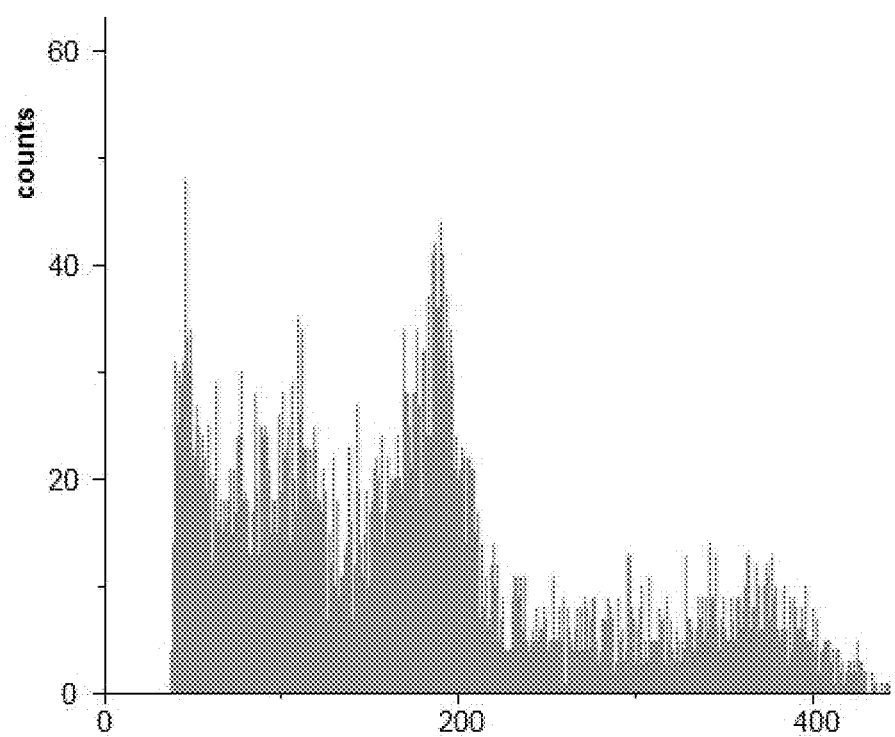
FIG. 1 shows the ploidy analysis (flow cytometry) data for USR01350334-3: DIPLOID (major peak at 200, secondary peak at 400).
Figure 2:
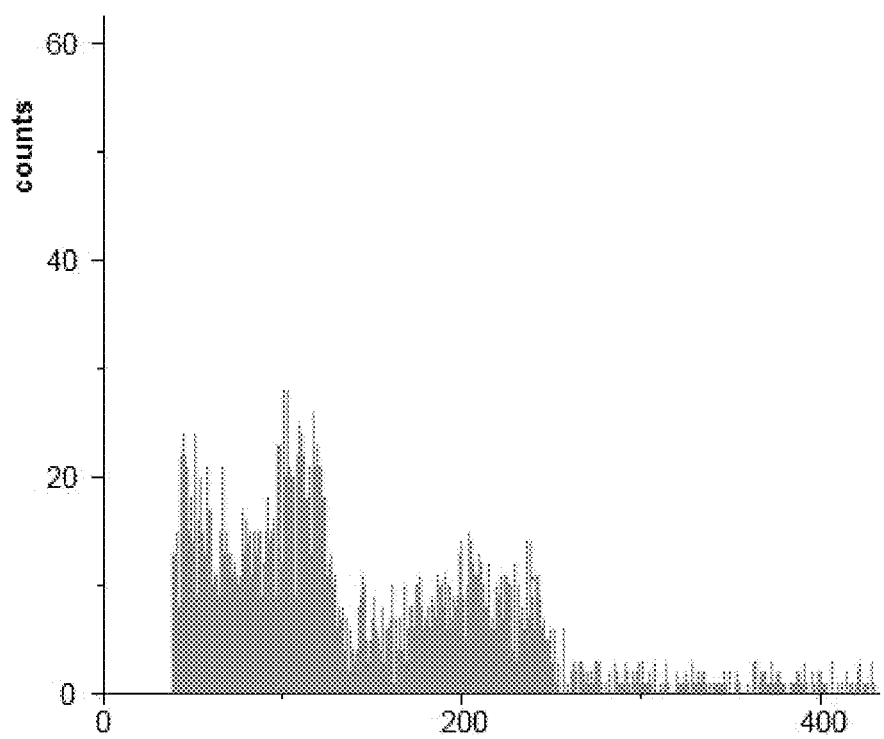
FIG. 2 shows the ploidy analysis (flow cytometry) data for USR01350333-3: HAPLOID (major peak at 100, secondary peak at 200).
Figure 3:
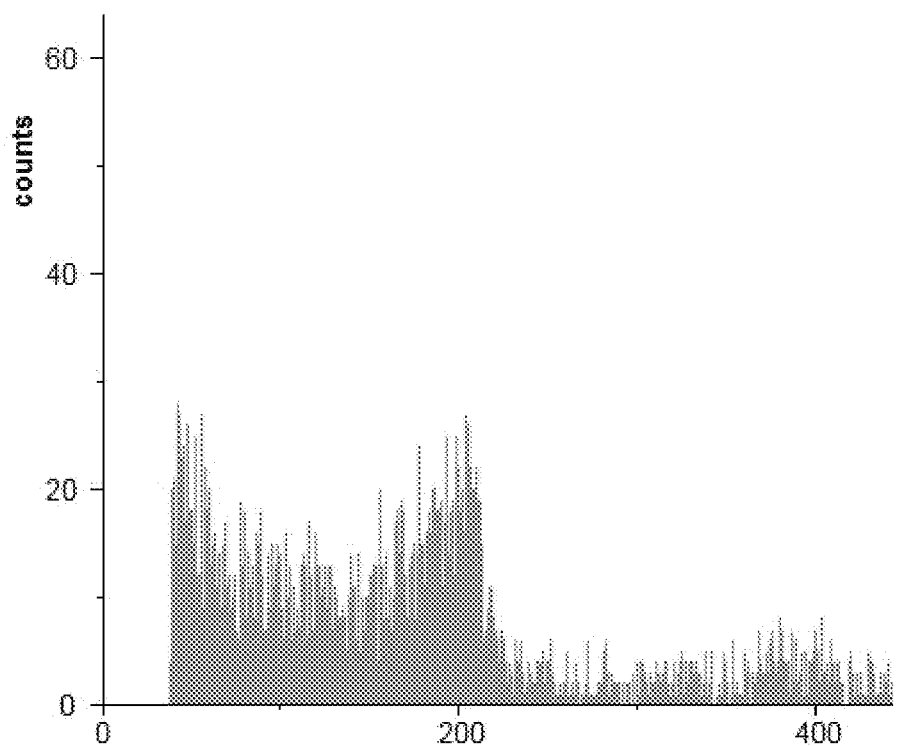
FIG. 3 shows the ploidy analysis (flow cytometry) data for USR01350333-10: DIPLOID (major peak at 200, secondary peak at 400).
Figure 4:
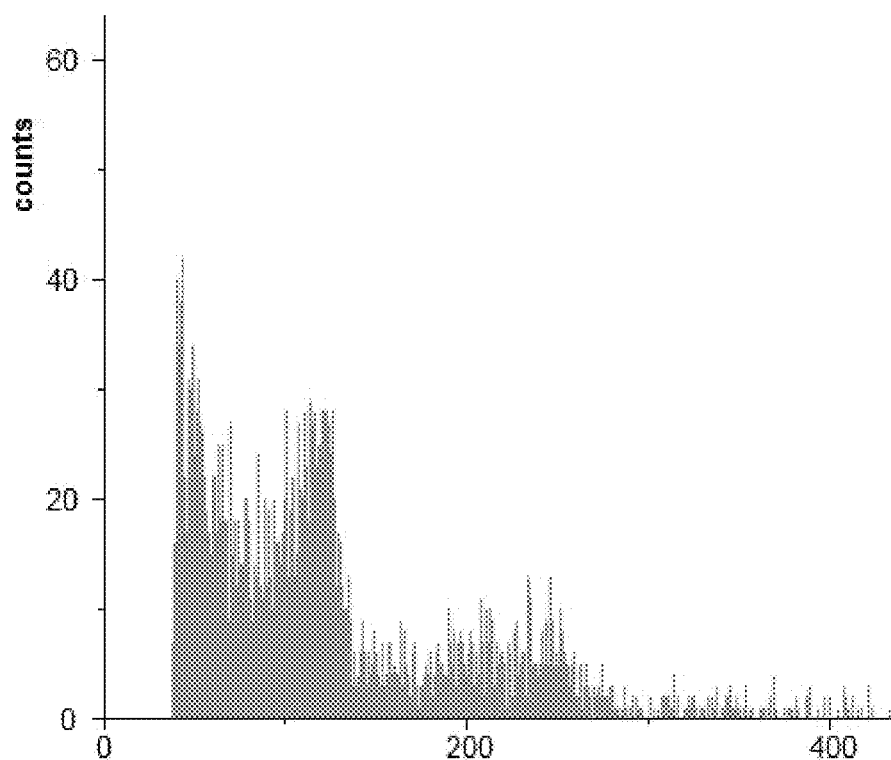
FIG. 4 shows the ploidy analysis (flow cytometry) data for USR01350344-2: HAPLOID (major peak at 100, secondary peak at 200).
Figure 5:
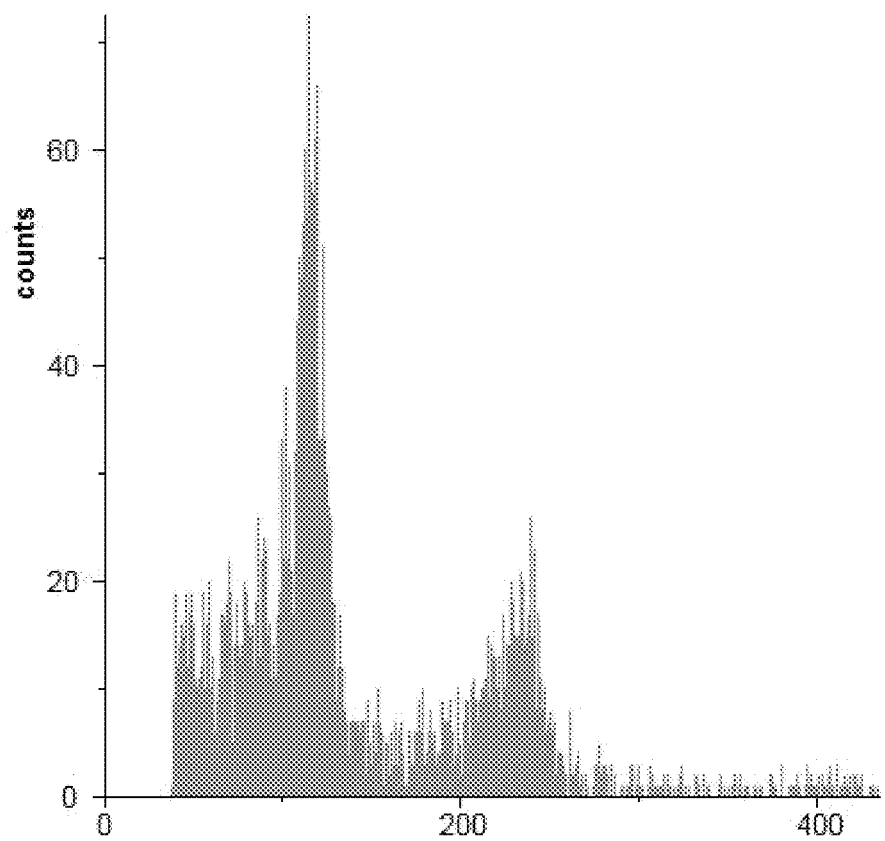
FIG. 5 shows the ploidy analysis (flow cytometry) data for USR01350343-1: HAPLOID (major peak at 100, secondary peak at 200).
Figure 6:
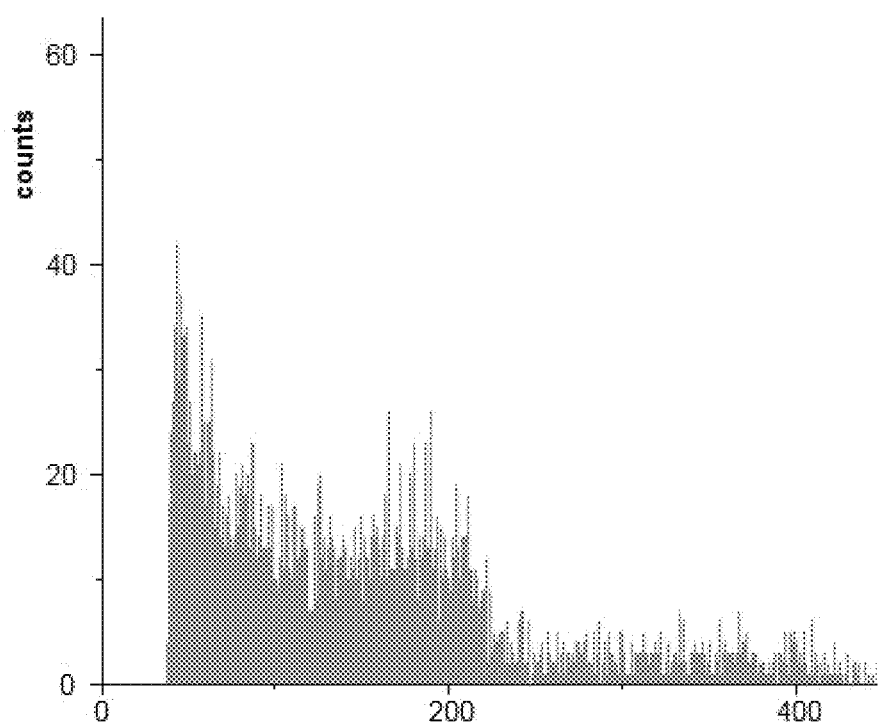
FIG. 6 shows the ploidy analysis (flow cytometry) data for USR01350341-1: DIPLOID (major peak at 200, secondary peak at 400).
Figure 7:
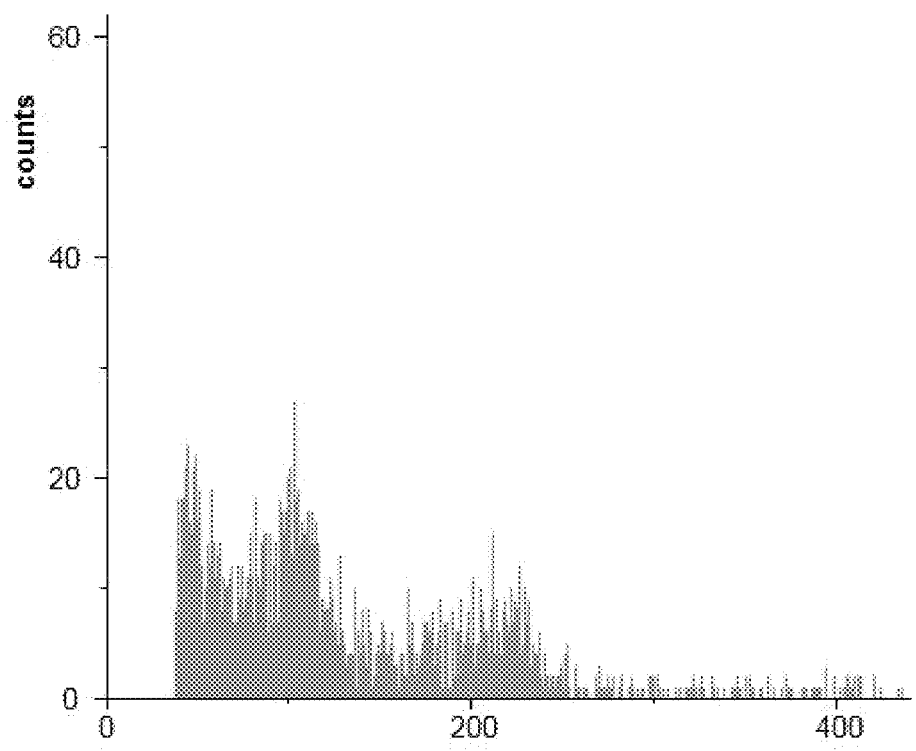
FIG. 7 shows the ploidy analysis (flow cytometry) data for USR01350328-1: HAPLOID (major peak at 100, secondary peak at 200).
Figure 8:
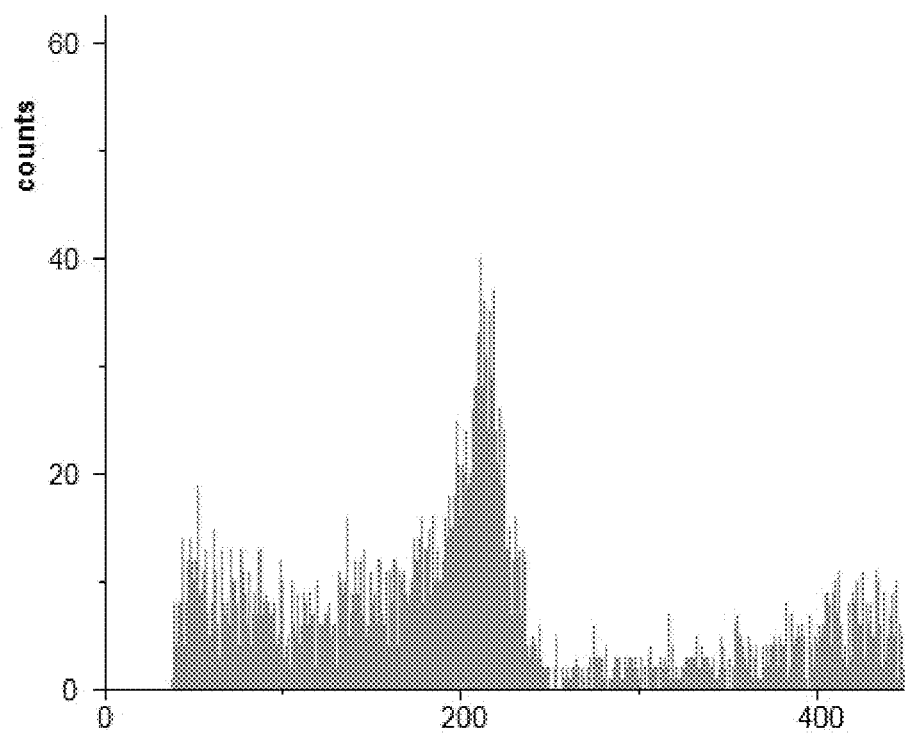
FIG. 8 shows the ploidy analysis (flow cytometry) data for USR01350321-3: DIPLOID (major peak at 200, secondary peak at 400).

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a," "an," and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about." The term "about," as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising," which is synonymous with "including," "containing," and "characterized by," is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising," "consisting essentially of," and "consisting of," where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 9 or 19. It is understood that the disclosed subject matter thus also encompasses nucleic acids that encode polypeptides that in some embodiments consist essentially of amino acid sequences that are at least 95% identical to that SEQ ID NO: 9 or 19 as well as nucleic acids that encode polypeptides that in some embodiments consist of amino acid sequences that are at least 95% identical to that SEQ ID NO: 9 or 19. Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "de novo haploid induction" refers to the triggering of haploid induction by the introduction of a spontaneous haploid inducing agent. Such introduction can be achieved by topical spray, hand-pollination, mutagenesis, or transgenic methods. The terms "de novo haploid induction," "de novo HI," and "haploid induction de novo" are used interchangeably throughout this specification.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form.

As used herein, a plant referred to as "haploid" has a reduced number of chromosomes (n) in the haploid plant, and its chromosome set is equal to that of the gamete. In a haploid organism, only half of the normal number of chromosomes are present. Thus haploids of diploid organisms (e.g., maize) exhibit monoploidy; haploids of tetraploid organisms (e.g., ryegrasses) exhibit diploidy; haploids of hexaploid organisms (e.g., wheat) exhibit triploidy; etc. As used herein, a plant referred to as "doubled haploid" is developed by doubling the haploid set of chromosomes. A plant or seed that is obtained from a doubled haploid plant that is selfed to any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes; that is, a plant will be considered doubled haploid if it contains viable gametes, even if it is chimeric in vegetative tissues.

As used herein, the term "human-induced mutation" refers to any mutation that occurs as a result of either direct or indirect human action. This term includes, but is not limited to, mutations obtained by any method of targeted mutagenesis.

As used herein, "introduced" means delivered, expressed, applied, transported, transferred, permeated, or other like term to indicate the delivery, whether of nucleic acid or protein or combination thereof, of a desired object to an object. For example, nucleic acids encoding a site directed nuclease and optionally at least one guide RNA may be introduced into a haploid embryo upon haploid induction. Likewise, extant editing machinery (comprising a site directed nuclease protein and optionally at least one guide RNA) may be introduced to a haploid embryo upon application of appropriate cell-penetrating peptides.

As used herein, the terms "marker probe" and "probe" refer to a nucleotide sequence or nucleic acid molecule that can be used to detect the presence or absence of a sequence within a larger sequence, e.g., a nucleic acid probe that is complementary to all of or a portion of the marker or marker locus, through nucleic acid hybridization. Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence," "polynucleotide," "nucleic acid sequence," "nucleic acid molecule," and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, California, U.S.A. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 1 being compared. In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon (i.e., start codon), a translation termination (i.e., stop codon), and the nucleic acid sequence there between that encodes the amino acids present in the polypeptide. The terms "initiation codon" and "termination codon" refer to a unit of three adjacent nucleotides (i.e., a codon) in a coding sequence that specifies initiation and chain termination, respectively, of protein synthesis (mRNA translation).

Patatin-like phospholipase A2a may also be known as PLA, pPLA, pPLAIIA pPLAIIα, PLA2alpha, or PLA2, or other similar variation. Patatin-like phospholipase AIIα is also referred to as MATRILINEAL (MATL). These terms are used interchangeably throughout. A MATRILINEAL gene comprising a four basepair frameshift mutation is referred to as matrilineal (matl).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from vegetative or sexual reproduction from one or more parent plants. In gynogenesis-mediated haploid induction, the haploid embryo on the female parent comprises female chromosomes to the exclusion of male chromosomes—thus it is not a progeny of the male haploid-inducing line. The haploid corn seed typically still has normal triploid endosperm that contains the male genome. The edited haploid progeny and subsequent edited doubled haploid plants and subsequent seed is not the only desired progeny. There is also the seed from the haploid inducer line itself, often carrying the Cas9 transgene, and subsequent plant and seed progeny of the haploid inducing plant. Both the haploid seed and the haploid inducer (self-pollination-derived) seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the F1 or F2 or still further generations. An F1 is a first-generation progeny produced from parents at least one of which is used for the first time as donor of a trait, while progeny of second generation (F2) or subsequent generations (F3, F4, and the like) are specimens produced from selfings, intercrosses, backcrosses, and/or other crosses of F1s, F2s, and the like. An F1 can thus be (and in some embodiments is) a hybrid resulting from a cross between two true breeding parents (i.e., parents that are true-breeding are each homozygous for a trait of interest or an allele thereof), while an F2 can be (and in some embodiments is) a progeny resulting from self-pollination of the F1 hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 2, 4, 8, 21, 23, 25, 29, 32, and 33 can serve as a reference sequence for comparing to other sequences obtained from plants.

As used herein, the term "regenerate," and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point € for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene (e.g., matl in maize or Os03g27610 in rice) that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell." It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

As used herein, the term "targeted mutagenesis" or "mutagenesis strategy" refers to any method of mutagenesis that results in the intentional mutagenesis of a chosen gene. Targeted mutagenesis includes the methods CRISPR, TILLING, TALEN, and other methods not yet discovered but which may be used to achieve the same outcome.

As used herein, haploid induction rate ("HIR") means the number of surviving haploid kernels over the total number of kernels after an ear is pollinated with haploid inducer pollen.

Particular problems plague that haploid induction: increased embryo abortion rates and increased fertilization failure rates (reduced seed set rates). For these reasons, there exists a need to successfully determine the cause of HI, and to use that knowledge to determine methods of stably or increasingly creating haploid plants while simultaneously reducing fertilization failure and embryo abortions.

It is specifically contemplated that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the promoter via mutation. It is further contemplated that one could mutagenize these sequences in order to enhance their expression of transgenes in a particular species. The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory sequence. In particular, site-specific mutagenesis is a technique useful in the preparation of promoter mutants, through specific mutagenesis of the underlying DNA. RNA-guided endonucleases ("RGEN," e.g., CRISPR/Cas9) may also be used. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

Where a clone comprising a promoter has been isolated in accordance with the instant invention, one may wish to delimit the essential promoter regions within the clone. One efficient, targeted means for preparing mutagenized promoters relies upon the identification of putative regulatory elements within the promoter sequence. This can be initiated by comparison with promoter sequences known to be expressed in similar tissue specific or developmentally unique patterns. Sequences which are shared among promoters with similar expression patterns are likely candidates for the binding of transcription factors and are thus likely elements which confer expression patterns. Confirmation of these putative regulatory elements can be achieved by deletion analysis of each putative regulatory sequence followed by functional analysis of each deletion construct by assay of a reporter gene which is functionally attached to each construct. As such, once a starting promoter sequence is provided, any of a number of different deletion mutants of the starting promoter could be readily prepared.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus the design, construction, and use of chimeric regulatory elements is one embodiment of this invention. Promoters of the present invention include homologues of cis elements known to affect gene regulation that show homology with the promoter sequences of the present invention.

Functional equivalent fragments of one of the transcription regulating nucleic acids described herein comprise at least 50, 100, 150, 200, 250, 300, 350, 400, 450, 500, 550, 600, 650, 700, 750, 800, 850, 900, 950, or 1000 base pairs of a transcription regulating nucleic acid. Equivalent fragments of transcription regulating nucleic acids, which are obtained by deleting the region encoding the 5'-untranslated region of the mRNA, would then only provide the (untranscribed) promoter region. The 5'-untranslated region can be easily determined by methods known in the art (such as 5'-RACE analysis). Accordingly, some of the transcription regulating nucleic acids, described herein, are equivalent fragments of other sequences.

As indicated above, deletion mutants of the promoter of the invention also could be randomly prepared and then assayed. Following this strategy, a series of constructs are prepared, each containing a different portion of the promoter (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette as described herein may comprise further regulatory elements. The term in this context is to be understood in the broad meaning comprising all sequences which may influence construction or function of the expression cassette. Regulatory elements may, for example, modify transcription and/or translation in prokaryotic or eukaryotic organisms. The expression cassette described herein may be downstream (in 3' direction) of the nucleic acid sequence to be expressed and optionally contain additional regulatory elements, such as transcriptional or translational enhancers. Each additional regulatory element may be operably liked to the nucleic acid sequence to be expressed (or the transcription regulating nucleotide sequence). Additional regulatory elements may comprise additional promoters, minimal promoters, promoter elements, or transposon elements which may modify or enhance the expression regulating properties. The expression cassette may also contain one or more introns, one or more exons and one or more terminators.

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell Nature 313: 810-812 (1985)), temporally regulated, spatially regulated, tissue specific, and spatial temporally regulated. Using the regulatory elements described herein, numerous agronomic genes can be expressed in transformed plants. More particularly, plants can be genetically engineered to express various phenotypes of agronomic interest.

DETAILED DESCRIPTION

One embodiment of the invention provides a method of editing plant genomic DNA, comprising: (i) obtaining a first plant, wherein the first plant is a haploid inducer line of the plant, and wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; and (iv) selecting at least one haploid progeny produced by the pollination of step € wherein the haploid progeny comprises the genome of the second plant but not the first plant, and the genome of the haploid progeny has been modified by the DNA modification enzyme and optional guide nucleic acid delivered by the first plant.

In one aspect of the method, the DNA modification enzyme is a site-directed nuclease selected from the group consisting of meganucleases (MNs), zinc-finger nucleases (ZFNs), transcription-activator like effector nucleases (TALENs), Cas9 nuclease, Cfp1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease; and further wherein the guide nucleic acid is a guide RNA.

In another aspect of the method, the edited haploid progeny is treated with a chromosome doubling agent, thereby creating an edited doubled haploid progeny. For example, the chromosome doubling agent is colchicine, pronamide, dithipyr, trifluralin, or another known anti-microtubule agent.

In another aspect of the method, the first plant is a monocot or a dicot. For example, the first plant is a monocot selected from the group consisting of maize, wheat, rice, barley, oats, triticale, sorghum, pearl millet, teosinte, bamboo, sugar cane, asparagus, onion, and garlic. In another aspect, the second plant is a monocot or a dicot. For example the second plant is a monocot selected from the group consisting of maize, wheat, rice, barley, oats, triticale, sorghum, pearl millet, teosinte, bamboo, sugar cane, asparagus, onion, and garlic.

In another aspect of the method, the optional guide RNA is an 18-21 nucleotide sequence and is homologous to a sequence selected from the group consisting of SEQ ID NOs: 2, 4, 8, 21, 23, 25, 29, 32, and 33. In another aspect, the first plant expresses a marker gene. For example, the marker gene is selected from the group consisting of GUS, PMI, PAT, GFP, RFP, CFP, B1, C1, R-nj, anthocyanin pigments, and any other marker gene.

In another aspect of the method, the first plant is a maize plant selected and/or derived from the lines Stock 6, RWK, RWS, UH400, AX5707RS, NP2222-matl, or any of the several other known HI lines.

In one embodiment, the first plant and the second plant are different species. In one aspect, first plant is a wheat plant and the second plant is a maize plant. In another aspect, first plant is a maize plant and the second plant is a wheat plant.

One object of the invention is a gene-edited plant produced by the method provided.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) pollinating the second plant with pollen from the first plant; (iv) applying a composition comprising a lipid or a phospholipase inhibitor immediately preceding, during, or following the pollination of step (iii); and (v) selecting at least one haploid progeny produced by the pollination of step (iii) wherein the haploid progeny comprises the genome of the second plant but not the first plant, and the genome of the haploid progeny has been modified by the DNA modification enzyme and optional guide nucleic acid delivered by the first plant. In one aspect, the composition comprises methyl alpha-linolenoyl fluorophosphonate (MALFP), linoleic acid ethyl ester (LLAEE), linoleic acid (LLA), corn oil, distearoyl-phosphatidyl choline (DSPC), methyl arachidonyl fluorophosphonate (MAFP), Palmityl trifluoromethylketone (PACOCF3), Arachidonyl trifluoromethylketone (AA-COCF3), Manoalide, Linolenic acid ethyl ester (LNAEE), Linolenic acid ethyl ester (LNAEE), Oleic acid methyl ester (OAME), Oleic acid ethyl ester (OAEE), Palmitic acid ethyl ester (PAEE), Palmitoleic acid ethyl ester (PLAEE), Linseed oil, corn oil, alpha-Linolenic acid (aLNA), gamma-Linolenic acid (gLNA), Oleic acid, Arachidonic acid, Stearic Acid, 9(Z)-11€-conjugated Linoleic acid, or 2-oleoyl-1-palmitoyl-sn-glycero-3-phospho-ethanolamine.

In another embodiment, the invention provides a method of editing plant genomic DNA, comprising: (i) obtaining a first plant, wherein said first plant is capable of expressing a DNA modification enzyme and optionally a guide nucleic acid; (ii) obtaining a second plant, wherein the second plant comprises the plant genomic DNA which is to be edited; (iii) crossing the first plant with the second plant; and (iv) selecting at least one haploid progeny produced by the crossing of step (iii) wherein the haploid progeny comprises the genome of the second plant but not the first plant, and the genome of the haploid progeny has been modified by the DNA modification enzyme and optional guide nucleic acid delivered by the first plant. In one aspect, the first plant acts as the female parent in the cross of step (iii). In another aspect, the first plant comprises a mutation in a CENH3 gene, an ig1 gene, or another mutation conferring paternal-haploid inducing systems.

EXAMPLES

I. Producing New Haploid Inducer Lines Comprising the Editing Machinery.

We transformed a transformable line of maize called NP2222 with a TALEN construct, and separately transformed this line with a Cas9 and guide RNA construct. The TALEN construct (pBSC22808 (SEQ ID NO: 5), with TALENs targeting cleavage within target sequence, 5'-TCCAGGGTCAACGTGGAGACAGGGAGGTACG-AACCGGTGACTGGCGAAGGAAGCA-3', SEQ ID NO: 6; TALEN recognition sequence underlined) and the Cas9 construct (pBSC23123 (SEQ ID NO: 7) with guide RNA sequence of xZmPLAIIA, 5'-GGGTCAACGTGGA-GACAGGG-3', SEQ ID NO: 8) were designed to target mutations into the fourth exon of maize gene called MATRI-LINEAL (MATL; GRAMENE ID: GRMZM2G471240). This gene, when mutated at the target site by the TALEN or by the Cas9 and guide RNA, is knocked out, resulting in a loss of function of the protein product. We previously established that lines that are homozygous for loss of function mutations in MATL are haploid inducer lines, meaning that when they are used as pollen donors in crosses, they induce the formation of haploids on the resulting ears (see P.C.T. Patent Application No. PCT/US2016/62548, filed Nov. 17, 2016, incorporated herein by reference in its entirety).

We produced several events and self-pollinated them to make T1 seed. We grew up T1 individuals from event MZET152408A042A. We recovered five T1 progeny that retained two copies of the Cas9 and guide RNA editing machinery stably transformed, and were also homozygous mutant for the MATL gene. See Table 1.

TABLE 1

New HI lines comprising the genome editing machinery.

| New HI Line Individual ID | wt MATL Presence | Cas9 Presence | Mutation in MATL |
|---|---|---|---|
| USR01283349 | − | + | 13 bp deletion, homozygous |
| USR01283378 | − | + | 13 bp deletion, homozygous |
| USR01283388 | − | + | 8 bp deletion, homozygous |
| USR01283391 | − | + | 8 bp deletion, homozygous |
| USR01283398 | − | + | 13 bp deletion, homozygous |

The MATL mutations are detected using a TaqMan assay, which amplifies the wildtype copy of MATL (referred to herein as MATL or wt-MATL; these terms are used interchangeably throughout). When both copies of MATL are mutated, this assays reads negative (i.e., "−"). The Cas9 and guide RNA editing machinery were stably inserted via Construct 23123 (SEQ ID NO: 7). We sequenced the mutations in MATL via PCR and subcloning. Four colonies of each PCR product was sequenced, and all of the colonies for a given individual had the same sequence, indicating these plants are all homozygous mutant for the MATL allele (also referred to herein as matl when referencing the 4 basepair insertion in MATRILINEAL found in Stock6 and other Stock6-derived lines, or pMATL when referencing any other human-induced mutation in MATRILINEAL). There were two plants that had 8 bp deletions, and three plants that had 13 bp deletions.

II. Using the New HI Lines as Male Parents and Progeny Analysis.

We crossed the above new HI plants as male pollen donors to a female tester line, which contained a recessive color marker but were wild type for the MATL gene. The male haploid inducer line is homozygous wild type for the same color marker. This female line was thus a non-haploid inducer and were homozygous wild-type for the MATL gene but homozygous mutant for the color marker. We recovered seeds from the crosses, and germinated seedlings therefrom.

Progeny seedlings were subjected to several assays. Progeny seedlings were scored as diploids if they do not exhibit the color marker (because the recessive marker is complemented by the male inducer DNA). Progeny seedlings were scored as putative haploids if they do exhibit the color marker because the recessive marker is not complemented. Of the 2656 seeds planted, we used the color assay and identified 90 seedlings as putative haploids.

We further analyzed the 90 putative haploids for presence of the wildtype MATL gene using a Taqman marker assay. Of these, 82 were positive for MATL, meaning they were not edited by the editing machinery provided by the male parent.

true haploid, putative edited individuals, specifically focusing on the sequence flanking the guide RNA target mutagenesis site. This was to determine the nature of the edits that may or may not have occurred there. We sub-cloned the PCR fragment using commercially-available TOPO Blunt IV kit, and sequenced at least four colonies each (forward and reverse sequencing). See Table 2, below, for comparisons of the edited alleles and the reference wt-MATL allele.

TABLE 2

Comparing the Edited Alleles against wt-MATL.

| Individual ID | Allele Type | Sequence (corresponds to 1126-1166 of SEQ ID NO: 19) | SEQ ID NO: |
|---|---|---|---|
| NP2222 | vit-MATL | AGGGTCAACGTGGAGACAGGGAGGTACGAACCGGTGACTGG | 9 |
| Stock6 | matl | AGGGTCAACGTGGAGACAGGCGAGGAGGTACGAACCGGTGACTGG | 10 |
| USR01350333-3 Allele 1 | edited | AGGGTCAACGTGGAGACAAGGGAGGTACGAACCGGTGACTGG | 11 |
| USR01350333-3 Allele 2 | PCR contamination | AGGGTCAACGTGGA::::::::::::GAACCGGTGACTGG | 12 |
| USR01350344-2 Allele 1 | edited | AGGGTCAACGTGGAGAC:GGGAGGTACGAACCGGTGACTGG | 13 |
| USR01350344-2 Allele 2 | PCR contamination | AGGGTCAACGTGGA::::::::::::GAACCGGTGACTGG | 14 |
| USR01350343-1 Allele 1 | edited | AGGGTCAACGTGGAGACAAGGGAGGTACGAACCGGTGACTGG | 15 |
| USR01350328-1 Allele 1 | edited | AGGGTCAACGTGGAGAC:GGGAGGTACGAACCGGTGACTGG | 16 |
| USR01350337-2 Allele 1 | not edited | AGGGTCAACGTGGAGACAGGGAGGTACGAACCGGTGACTGG | 17 |
| USR01350337-2 Allele 2 | PCR contamination | AGGGTCAACGTGGA::::::::::::GAACCGGTGACTGG | 18 |

The remaining 8 putative haploid seedlings were negative for wildtype MATL using the Taqman marker, indicating that they may have been edited by the editing machinery provided by the male parent.

We performed ploidy analysis via Flow Cytometry on these 8 putative, edited haploid seedlings using leaf tissue in a ploidy analyzer. See FIGS. 1-8. We found that four of them were true haploids, while the others were actually diploids. As we discuss below, we ran PCR and sequenced the mutations in the MATL gene in these four true haploids as well as for plant USR01350337-2 which, according to the MATL Taqman assay, was not edited by the genome editing machinery.

The finding that there were four diploids among the 90 putative haploids was not unexpected—the seedling assay is not perfect and there are occasional false positives. We tested the 90 haploids for the presence of the Cas9 construct (Construct 23123), and found it was missing in 86 out of 90, including the four true haploids above. In contrast, the four edited diploids that we found during the ploidy analysis all had the Cas9 construct present, confirming their status as hybrid diploids that were falsely identified by the haploid seedling assay as being haploids.

We then used the leaf tissue to isolate genomic DNA and ran a PCR reaction to sequence the MATL gene in those four Individual USR01350333-3 produced an edited MATL allele with an insertion of alanine at basepair 1143 of the cDNA sequence (underlined in Table 2). This would be sufficient to cause a frameshift in the coding sequence, which would produce a premature STOP codon. What we previously thought was Edited Allele #2 of USR01350333-3 (a 13 basepair deletion of GACAAGGGAGGTAC) was actually the result of PCR contamination. After resequencing, we confirmed that this plant only has one edited allele, and it was found in 6 out of 6 colonies.

This alleles is novel in that it is not in either the male or the female parent plant of this individual. The male parent ID for this individual was USR01283391, and that plant was found to be homozygous for an 8 bp deletion.

Individual USR01350344-2 provides a deletion of A (a deletion of basepair 1143 of the wild type cDNA sequence). This mutation would be sufficient to cause a frame-shift in the coding sequence, and produce a premature STOP codon. After resequencing and discovering the PCR contamination, we confirmed this was found in 6 out of 6 colonies. Previously identified as Edited Allele #2 of USR01350344-2, this was identified as PCR contamination.

Individual USR01350343-1 provides an insertion of A at basepair 1143 of the cDNA sequence. This would be sufficient to cause a frame-shift in the coding sequence, and produce a premature STOP codon. This was found in 4 out of 4 colonies.

Individual USR01350328-1 provides a deletion of A (a deletion of basepair 1143 from the wild type cDNA sequence). This mutation would be sufficient to cause a frame-shift in the coding sequence, and produce a premature STOP codon. It was found in 4 out of 4 colonies.

Individual USR01350337-2 had no change: its sequence was 100% identical to that of wt-MATL.

In summary, we found that 4 out of 86 confirmed haploids had mutations in the MATL gene. We have confirmed that these plants are haploids and do not contain any Cas9 DNA. It is clear that the Cas9 transgene has been eliminated along with the rest of the male-derived DNA during embryogenesis, and that edits have occurred to the female (egg cell-derived) genome in the process of embryogenesis.

We know that the edits are novel and occurred in the female genome in the process of embryogenesis because the haploid inducer line typically makes maternal haploids and we have confirmed that these are indeed haploids. One might try to argue that there is a chance that these are actually paternal haploids, and that the edits we are seeing are actually edits that were already present in the paternal DNA. However, we can prove that this is not the case. First, the mutations do not match those of the paternal parent. This can clearly be seen in Table 3 and 4 (shown below). The edited haploid plant USR01350343-1 was homozygous for an insertion of a single nucleotide (an "A"), but the male parent plant had a deletion of 13 nucleotides. Similarly, plant USR01350328-1 was homozygous for a deletion of an A, but the male parent had a deletion of 13 nucleotides. These examples, taken together, prove that during the haploid induction process, it is possible to have editing of the maternal genome occur, resulting in the formation of edited maternal haploids. According to these and based on the assay detecting MATL presence and the confirmation via ploidy analysis, and using the Cas9 transgene on the male side under control of the maize ubiquitin promoter, the rate of editing during the haploid induction process is about 4/86, or 4.65%.

Furthermore, the rate of editing during haploid induction may be very different when using different haploid inducer lines or using wide crosses. It appears that both haploid induction in maize using MATL mutant lines and wide crosses in barley, wheat, or other crops all work via similar mechanisms: fertilization is followed by genome elimination. It also appears that the time period between fertilization and genome elimination is long enough for the editing machinery to edit the target gene in the genome of the line to which the inducer line has been hybridized (the target germplasm). It is noted that the choice of promoter driving expression of the stably transformed editing proteins system may have a large impact on the rate of editing in haploids. We used a constitutive sugarcane promoter (prSoUbi4) but other promoters driving high or specific expression in the embryo sac, the egg cell, in the pollen, or in sperm cells might be more effective, particularly in the case of wide crosses, in which the male DNA is eliminated in a much more robust and rapid fashion than in intraspecific haploid inducer systems like the maize haploid inducer system or CENH3 type haploid inducer systems. In other words, during a wide cross, for instance when crossing maize pollen on to wheat ears, which is done in order to induce wheat maternal haploids, it might work best to have the editing machinery in the maize pollen driven by a promoter that has strong pollen or sperm cell expression, perhaps in addition to zygote expression, so that abundant editing machinery (RNA and protein) is delivered and present in the zygote cell and during the subsequent two, four, or eight cell embryo stage, even if the male DNA is eliminated or lost very quickly.

TABLE 3

Haploid Progeny Produced

| Individual Progeny ID code | wt MATL Presence | Ploidy Analysis | Cas9 Presence | Allele 1 |
|---|---|---|---|---|
| USR01350333-3 | − | Haploid | − | insertion of A |
| USR01350344-2 | − | Haploid | − | deletion of A |
| USR01350343-1 | − | Haploid | − | insertion of an A |
| USR01350328-1 | − | Haploid | − | deletion of A |
| USR01350337-2 | + | Haploid | − | no mutation |
| USR01350334-3 | − | Diploid | + | |
| USR01350333-10 | − | Diploid | + | |
| USR01350341-1 | − | Diploid | + | |
| USR01350321-3 | − | Diploid | + | |

TABLE 4

Male Parent Information and Their Progeny

| Male Parent ID | wt MATL Presence | Sequencing (# colonies) | Cas9 Presence | Progeny ID |
|---|---|---|---|---|
| USR01283391 | − | deletion of 8 nt (4) | + | USR01350333-3 and USR01350333-10 |
| USR01283349 | − | deletion of 13 nt (4) | + | USR01350344-2, USR01350328-1 and USR01350321-3 |
| USR01283378 | − | deletion of 13 nt (4) | + | USR01350343-1 and USR01350341-1 |
| USR01283398 | − | deletion of 13 nt (4) | + | USR01350337-2 |
| USR01283388 | − | deletion of 8 nt (4) | + | USR01350334-3 |

III. Simultaneous Haploid Induction and Editing in Elite Maize Inbred Lines.

A transformable haploid inducer line, NP2222-HI, RWK, RWS, or UH400 or Stock6 or any other haploid inducer line, all of which already have the mutant versions of MATL, is stably transformed with construct expressing genome modification system such as Cas9+guide RNA (Cong, L. et al. 2013. Multiplex genome engineering using CRISPR/Cas systems. *Science* 339, 819-823), dCas9-FokI+ guide RNA (Tsai, S. Q. et al. 2014, Dimeric CRISPR RNA-guided FokI nucleases for highly specific genome editing. *Nature Biotechnol.* 32, 569-576), TALEN (Li et al., 2012, High-efficiency TALEN-based gene editing produces disease-resistant rice. Nature Biotech. 30, 390-392), engineered meganuclease (Gao et al., 2010, Heritable targeted mutagenesis in maize using a designed endonuclease. *Plant Journal.* 61:176-187), zinc finger nuclease (Shukla et al. 2009. Precise genome modification in the crop species *Zea mays* using zinc-finger nucleases. Nature 459, 437-441), dCas9-cytidine deaminase (Komor et al. 2016, Programmable editing of a target base in genomic DNA without double-stranded DNA cleavage. Nature doi:10.1038/nature17946) or any other genome modification system. The transgenic haploid inducer line also expressing the editing machinery is then used as pollen donor to create mutations and haploids in target lines via outcrossing. Haploid embryos or seeds are then recovered, identified as haploids, and tested for the edits at the target site (whatever target site is chosen by virtue of the TALEN construct design or the Cas9 guide RNA design). Haploids containing the desired edits is chromosomally doubled using standard procedures using standard means such as colchicine, trifluralin or other chromosome doubling agent. Identification of the induced haploids can be simplified by using a color marker as is typically done in corn doubled haploid production—this color marker can display in the resulting embryos, seeds, seedlings, or adult plant. Presence of mutations at the target site can be checked by sequence analysis (DNA sequencing), by marker analysis, or by phenotype. Because there is only one copy of the DNA to mutate in haploid plants, recessive phenotypes should display so that could be another way to identify the haploids that were edited.

A. Mutagenesis of VLHP Targets in Elite Maize Inbred Line with Transgenic Editing Locus Generated Directly in a Haploid Inducer Line.

VLHP1 and VLHP2 are homeodomain-leucine zipper I-class homeobox genes and members of a class of proteins that is unique to plants. The HD domain is involved in D NA binding whereas the Zip domain is involved in protein homo- and hetero-dimerization. HD-Zip I proteins are generally involved in responses related to abiotic stress, abscisic acid (ABA), blue light, de-etiolation and embryogenesis (Elhiti and Stasolla, 2009. Structure and function of homodomain-leucine zipper (HD-Zip) proteins. Plant Signal Behav. 4: 86-88). VLHP1 and VLHP2 are in the same gene family as Grassy Tillers1 (GT1). GT1 promotes lateral bud dormancy and suppresses elongation of lateral ear branches in maize.

Figure 9:
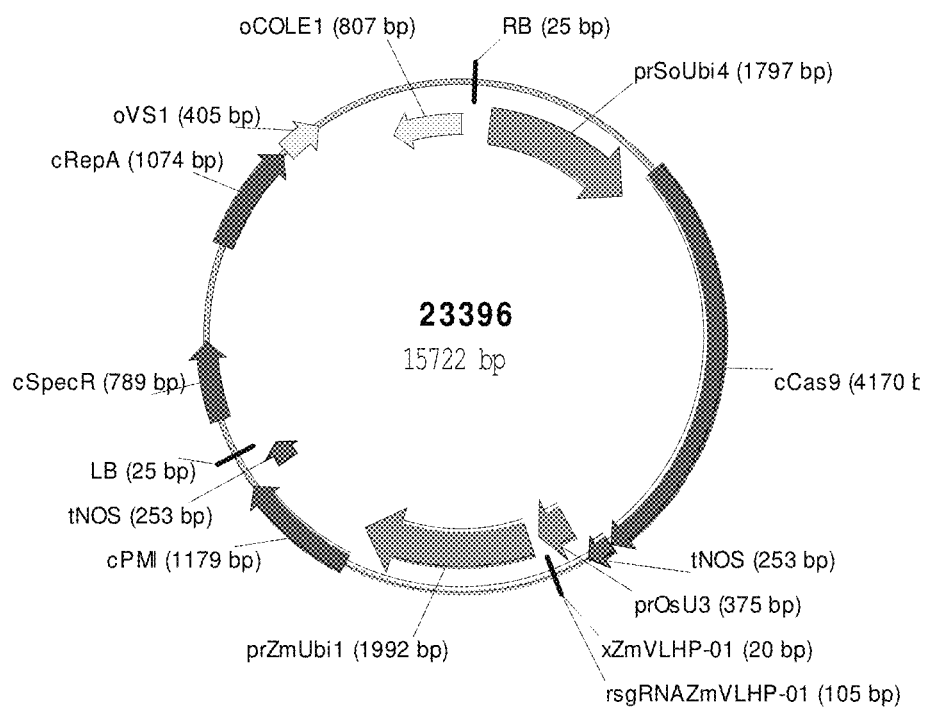
FIG. 9 is a schematic drawing of vector 23396 (SEQ ID NO: 1) used for *Agrobacterium*-mediated transformation of maize immature embryos to generate targeted mutations in ZmVLHP1 genes. xZmVLHP-01: guide RNA (gRNA) sequence (5'-GCAGGAGGCGTCGAGCAGCG-3', SEQ ID NO: 2); rsgRNAZmVLHP-01: single guide RNA (sgRNA) comprising of gRNA, tracRNA and PolIII termination sequences. cPMI: PMI selectable marker gene; cCas9: Cas9 nuclease gene; RB: T-DNA right border; LB: T-DNA left border; tNOS: Nopaline synthetase terminator. cSpec: Spectinomycin resistance gene.

In this example, vector 23396 (SEQ ID NO: 1; see also FIG. 9) for expressing Cas9 and single guide RNA (sgRNA) was made to target maize VLHP1 (GRMZM2G104204) and its homolog VLHP2 (GRMZM2G062244) genes. Vector 23396 expresses a sgRNA with 20-nucleotide targeting sequence xZmVLHP-01 (5'-GCAGGAGGCGTCGAG-CAGCG-3', SEQ ID NO: 2). xZmVLHP-01 targets both VLHP1 and VLHP2 genes at the second exon. Vector 23396 was introduced into a transformable haploid inducer line NP2222-HI using Agrobacterium-mediated transformation with mannose selection. NP2222-HI was derived from crossing of transformable maize inbred line NP2222 with Stock 6 derivative line RWKS to introgress the haploid induction (HI) locus. NP2222-HI has an average haploid induction rate of about 9.2%.

NP2222-HI transformants from vector 23396 were assayed for modification of genomic VLHP target sequences (5'-GCAGGAGGCGTCGAGCA/GCG-3'; SEQ ID NO: 2). The slash ("/") represents the Cas9 cleavage position. Target locus editing activity was determined using quantitative PCR Taqman method as described before (WO2016106121, incorporated herein by reference). Transgenic lines with high target site modification activities—i.e., both VLHP1 and VLHP2 genes were modified, and preferably containing single copy transgene—were selected for further studies and used for crossing or progeny production.

Pollen from T0 transformants of 23396 is used directly to pollinate ears of elite inbred line ID5829 or other maize lines including sweet corn lines to induce production of haploid embryos. Alternatively, T0 transformants of 23396 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the VLHP target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination ("DAP," extraction between 10-25 DAP is theoretically possible). DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining that mutation has occurred at the xZmVLHP-01 target sequence.

Alternate methods are available. One could allow the seed to mature and select haploids later by another phenotype. One could let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

B. Mutagenesis of GW2 Targets in Elite Maize Inbred Line with Transgenic Editing Locus Introduced Directly in a Haploid Inducer Line.

A mutation in DA2, an E3-ubiquitin ligase gene, in rice resulted in larger seeds (Song et al., 2007). Rice DA2 has 2 maize homologs, GW2-1 (GRMZM2G170088) and GW2-2 (GRMZM2G007288). The maize genes are 94% identical at the protein level and 90% identical at the DNA level. GRMZM2G170088 has a large 177 bp insert (59 aa) in comparison with GRMZM2G007288.

Figure 10:
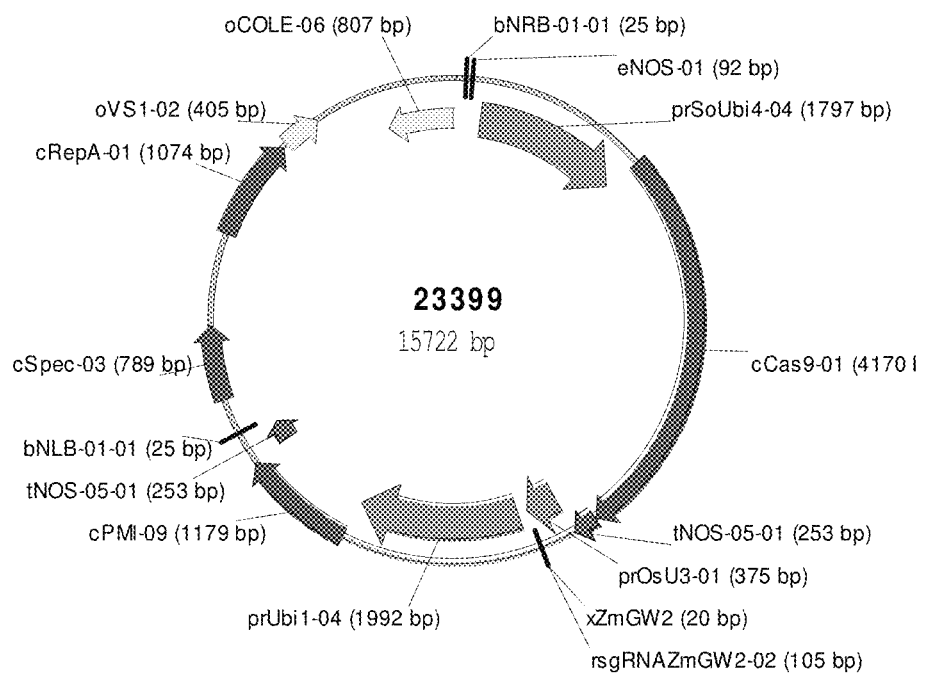
FIG. 10 is a schematic drawing of vector 23399 (SEQ ID NO: 3) used for *Agrobacterium*-mediated transformation of maize immature embryos to generate targeted mutations in ZmGW2 genes. xZmGW2-02: guide RNA (gRNA) sequence (5'-AAGCTCGCGCCCTGCTACCC-3', SEQ ID NO: 4); rsgRNAZmGW2-02: single guide RNA (sgRNA) comprising of gRNA, tracrRNA and PolIII termination sequences. cPMI-09: PMI selectable marker gene; cCas9-01: Cas9 nuclease gene; RB: T-DNA right border; LB: T-DNA left border; tNOS: Nopaline synthetase terminator. cSpec: Spectinomycin resistance gene.

In this example, vector 23399 (SEQ ID NO: 3, see also FIG. 10) was made for expression of Cas9 and sgRNA to target both maize GW2-1 (GRMZM2G170088) and its homolog GW2-2 (GRMZM2G007288) genes. Both GW2-1 and GW2-2 genes contain target sequence xZmGW2-02 (5'-AAGCTCGCGCCCTGCTACCC-3', SEQ ID NO: 4) in exon 1 and this sequence was used to design sgRNA expressed from vector 23399. Binary vector 23399 expresses single guide RNA (sgRNA) with 20-nucleotide targeting sequence xZmGW2-02 fused to single guide RNA scaffold comprising of both crRNA and tracrRNA. Vector 23399 was introduced into a transformable haploid inducer line NP2222-HI using Agrobacterium-mediated transformation with mannose selection. NP2222-HI was derived from crossing of transformable maize inbred line NP2222 with Stock 6 derivative line RWKS to introgress the haploid induction (HI) locus.

NP2222-HI transformants of vector 23399 were assayed for modification of genomic GW2-2 target sequences (5'-AAGCTCGCGCCCTGCTA/CCC-3', SEQ ID NO: 4; the slash ("/") indicates the Cas9 cleavage position). Target sequence editing activity was determined using quantitative PCR Taqman method as described before (WO2016106121). Transgenic lines with high target site modification activities—i.e. both GW2-1 and GW2-2 genes were modified, and preferably containing single copy transgene—were selected for further studies and used for crossing or progeny production.

Pollen from T0 transformants of 23399 is used directly to pollinate ears of elite inbred line ID5829 or other maize line including sweet corn lines to induce production of haploid embryos. Alternatively, T0 transformants of 23399 in NP2222-HI background are selfed to produce progeny lines carrying homozygous transgene and pollen from the progeny plants are used to pollinate other corn lines to induce haploid embryo formation. The induced haploid embryos are extracted from kernels and placed on embryo rescue media for direct germination or allowed to mature to form seeds. Tissues from the induced haploid embryos and the resulting plants are assayed to determine if editing has occurred in the maize GW2 target sequences. If the induced haploid embryos or plants contain desired mutations, chromosome doubling treatment is applied to produce doubled haploid lines from them. For example, using embryo rescue method, embryos are extracted from elite line ID5829 ears pollinated with transgenic haploid inducer line carrying 23396 editing locus at 18-22 days after pollination. DNA is isolated from germinated haploid seedlings and used for assay. Colchicine treatment is applied to seedling for chromosome doubling. Alternatively, chromosome doubling agent can be applied to the isolated embryos during germination. DNA is extracted from germinated seedlings and used for determining if mutation has occurred at the xZmGW2-02 target sequence. Alternately, one could allow the seed to mature and select haploids later by another phenotype. One could even let the seed dry down and at a later date germinate the seeds to determine haploids without a marker (e.g., using plant size rather than a gene conferring a color marker), at which point one would test for edits and apply chromosome doubling agents where appropriate. This method may have its advantages in that embryo screening and/or rescue is avoided.

IV. Simultaneous Haploid Induction and Editing in Corn, Rice, Sunflower, or Any Other Crop Via Chemical-Based Haploid Induction Any line of corn, rice, wheat, tomato, sunflower, barley, or any other crop is transformable with the editing construct (Cas9 plus guide RNAs designed to mutate a particular target site) and then optionally make the editing construct either heterozygous or homozygous (via self-pollination of the transformed event), and then using lipid or oil applications during outcrossing (pollination onto target lines) in order to induce de novo haploids and simultaneously edit the target sites in the target genomes. These lipid applications have the ability to induce haploids when applied to pollen, silks, flowers, or tassels of any plant—regardless of male parent. In particular, the male parent is not required to have any mutations in the MATL gene (i.e., it can be homozygous wild type for the MATRILINEAL gene). These lipid applications induce haploids de novo, without any genetic requirement on behalf of either parent. See P.C.T. Patent Application No. PCT/US2016/62548, incorporated herein by reference in its entirety. The mechanism of de novo haploid induction via lipid spray apparently works the same way as it does in matl mutant (genetic haploid inducer) lines: via chromosome elimination post-fertilization. Haploid progeny are isolated and checked for the induced mutations (caused via the editing process) and then doubled to make edited, doubled haploid plants.

V. Mutagenesis of Target Sequences in Elite Field Corn and Sweet Corn Inbred Lines with Transgenic Editing Locus Introgressed into a Haploid Inducer Line.

Transgenic locus expressing genome editing machinery can also be generated in conventional transformable maize line without haploid inducing activity such as A188, Hi-II or NP2222 and then introgressed into haploid inducer line such as NP2222-HI, RWK, RWKS, RWS, or UH400 or Stock6 or any other haploid inducer line.

In this example, maize inbred line NP2222 is transformed with VLHP Cas9-sgRNA vectors (23396 and 23397) and GW2 Cas9-sgRNA vectors (23398 and 23399). Vectors 23396 and 23399 have been described in previous examples (Example IIIA and Example IIIB). Vector 23397 (SEQ ID NO: 20) is identical to 23396 except the gRNA-coding sequence xZmVLHP-01 (5'-GCAGGAGGCGTCG-AGCAGCG-3', SEQ ID NO: 2) is replaced with xZmVLHP-02 (5'-GCTGGAGCTGAGCTTCCGGG-3', SEQ ID NO: 21). Vector 23398 (SEQ ID NO: 23) is identical to 23399 except the gRNA-coding sequence xZmGW2-02 (5'-AAGCTCGCGCCCTGCTACCC-3', SEQ ID NO: 4) in 23399 is replaced by xZmGW2-01 (5'-GAGCGGTT-CACGCGGCCGCA-3', SEQ ID NO: 23). These vectors were introduced into *Agrobacterium* strain LBA4404 (pVGW7). The resulting *Agrobacterium* strain containing vector 23396, 23397, 23398, or 23399 was used to transform immature embryos of transformable elite inbred line NP2222. Calli were induced from infected immature embryos and selected on mannose media to recover transgenic calli. Transgenic calli were placed on regeneration and rooting media to recover transgenic plants expressing the CRISPR-Cas9 editing machinery. Transgenic plants were assayed for transgene copy number and moved to greenhouse for seed production.

Single copy transformants of vector 23396 (MZET154902A004A, MZET154902B006A), 23397 (MZET154903B009A, MZET154903B012A), 23398 (MZET154904B005A, MZET154904B014A) and 23399 (MZET154905A002A, MZET154905A010A) were identified and backcrossed with non-transgenic NP2222. Ears of transgenic progeny plants containing T-DNA insert of each of the above vectors were pollinated with pollen of haploid inducer line RWKS to produce F1 progeny. F1 progeny containing transgenic locus and haploid induction locus were identified by genotyping assays and self-pollinated to produce F2 progeny seeds. F2 progeny seeds were planted and seedling plants assayed to identify plants homozygous for transgenic Cas9-sgRNA locus (assay #2540) and haploid induction locus (assay #2827) with qPCR Taqman assays.

Lines homozygous for the haploid induction locus and preferably homozygous transgenic 23396, 23397, 23398, and 23399 Cas9-sgRNA editing locus were used to pollinate ears from target elite field corn line ID5829 and sweet corn lines (SWC726 or SWC412F) for haploid induction. Induced haploid embryos were isolated from pollinated ID5829, SWC412F, SWC726 ears and germinated on embryo rescue media. Alternatively, pollinated ears were allowed to mature and kernels with haploid embryos were germinated. Leaf samples were collected and analyzed with Taqman assay to identify plants containing mutations in VLHP and GW2 genes but absence of genetic components from induction line such as transgenic Cas9-sgRNA or other non-transgenic marker gene sequences. Identified haploid plants with targeted GW2 or VLHP gene mutations were treated with colchicine for chromosome doubling to recover doubled haploid plants for seed production. Alternatively, extracted haploid embryos can be treated with chromosome doubling agent such as colchicine and the resulting plants are analyzed for ploidy level and presence of targeted mutations in GW2 or VLHP genes. Plants with targeted GW2 and VLHP gene mutations are grown to maturity for seed production and further progeny evaluation.

Figure 11:
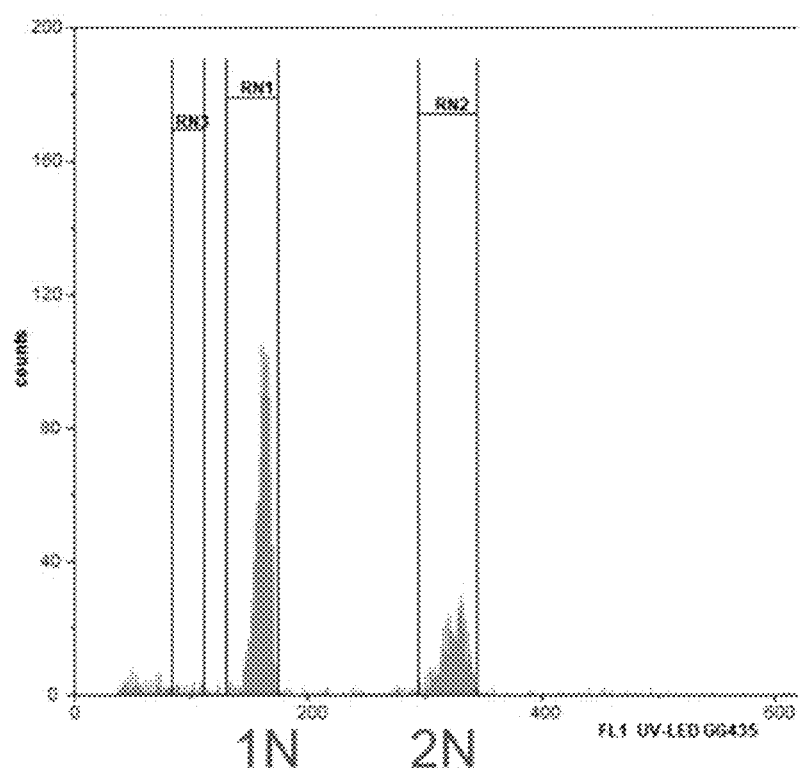
FIG. 11 shows ploidy assay of edited haploid sweet corn line JSER82A056.
Figure 12:
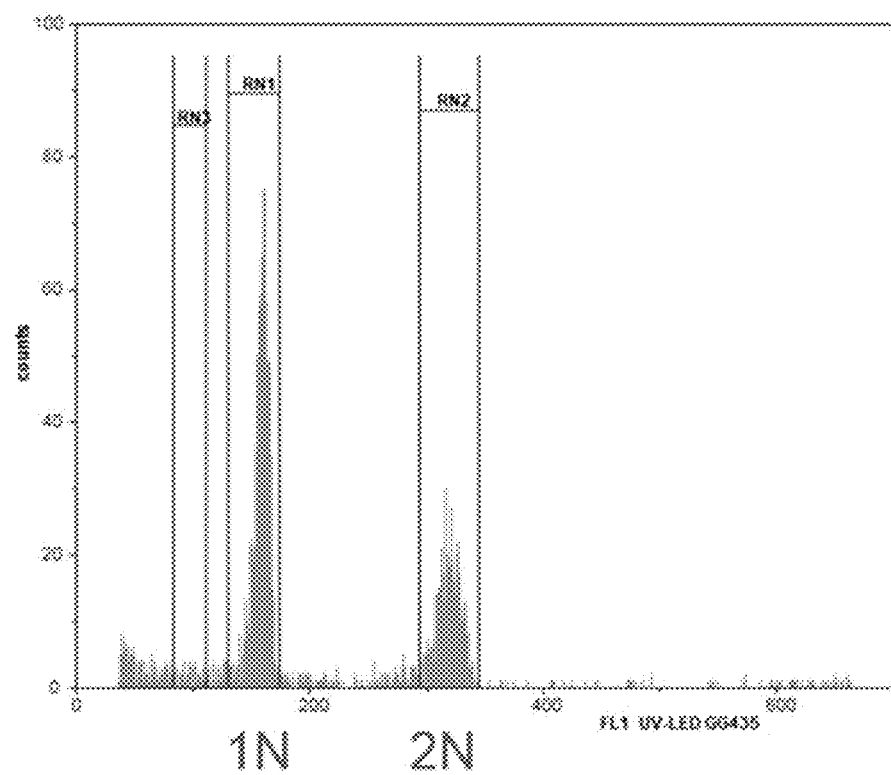
FIG. 12 shows the same for edited haploid sweet corn line JSER82A063. These lines were obtained through crossing with RWKS haploid induction line carrying transgene locus of CRISPR-Cas9 expression vector 23399.

For example, edited haploid lines (JSER82A056 and JSER82A063) were identified from crosses between sweet corn line SWC412F ears pollinated with haploid inducer containing 23399 Cas9-sgRNA transgene. Line JSER82A056 has both GW2-01 and GW2-02 target genes mutated, whereas line JSER82A063 only has GW2-02 gene mutated (See Table 5). Neither of these lines contain Cas9 transgene (assay #2540 for Cas9 or #1750 for PMI selectable marker gene) or haploid inducer gene (assay #2827) as the male genome has been eliminated from the haploids. Ploidy level analysis confirmed that both lines are haploids (FIGS. 11 and 12). Note that wildtype ("VVT") genes in the haploids have a copy number of "2" and mutant will be "0" since the copy call is relative to the endogenous ADH gene copy number. Therefore, haploid lines carrying VVT unedited GW2-01 or GW2-02 genes will have a copy call of "2." VVT haploid inducer locus will have copy call of "2" for assay #2826 and "0" for assay #2827 (haploid inducer variant). If a corn plant line is a diploid between sweet corn and transgenic inducer, it will be heterozygous for the haploid inducer gene and thus have copy call of "1" for both assay #2826 and assay #2827.

(Eder and Chalyk, 2002, In vivo haploid induction in maize. Theor. Appl. Genetics 104:703-708). Treated lines were planted in soil and grown in greenhouse for progeny seed production.

VI. Simultaneous Haploid Induction and Editing in Wheat and Other Monocots Via Wide Cross.

Haploid induction is also achieved using interspecific or intergeneric wide crosses (Kasha and Kao, 1970, High frequency haploid production in barley (*Hordeum vulgare* L.). Nature 225:874-886). For example, wheat haploids can be obtained by pollination with various intergeneric crosses with maize (Suenaga and Nakajima 1989), pearl millet (Inagaki and Mujeeb-Kazi 1995), teosinte (Ushiyama et al. 1991), *H. bulbosum* (Barclay 1975), and sorghum (Ohkawa et al. 1992). Barley haploids are obtained by pollination with *Hordeum bulbosum* pollen. Tobacco haploids can be obtained by crossing with N. 31fricana pollen. Many other examples exist in other crops.

Similar to examples above in introducing transgenic editing locus into Stock6 induction line, transgenic editing locus can be introduced into these lines used for wide crosses to induce haploid induction and targeted sequence mutation. Transgenic lines expressing editing machinery can be generated in any line of corn, wheat, barley, rye, pearl millet, rice, *Brassica*, lettuce, tomato, or any other crop by direct transformation or out-crossing. Preferably the transgenic locus is made homozygous and then the line is used as pollen

TABLE 5

Progeny zygosity analysis from crosses. Taqman analysis results showing the lines do not contain transgene or haploid inducer locus from pollen donor, but have edits in GW2-01 and/or GW2-02 targets.

| | | | | Allele: | | | |
|---|---|---|---|---|---|---|---|
| | | cCas9-01 | cPMI-09 | CRISPR target in GW2-01 (23399) | CRISPR target in GW2-02 (23399) | pPLAIIa WT allele | RWK (Haploid Inducer) allele of pPLAIIa |
| | | | | Assay ID: | | | |
| Plant ID | Construct ID | 2540 Copy# level | 1750 Copy# level | 3065 Copy# level | 3095 Copy# level | 2826 Copy# level | 2827 Copy# level |
| 1-copy control | | + | 1 | ND | ND | 1 | 1 |
| wild type control | | 0 | 0 | 2 | 2 | 2 | 0 |
| *JSER82A056* | *23399* | *0* | *0* | *0* | *0* | *2* | *0* |
| *JSER82A063* | *23399* | *0* | *0* | *1 or 2* | *0* | *2* | *0* |
| JSER85A021 | 23399 | 0 | 0 | 0 | >2 | 2 | 0 |
| JSER85A022 | 23399 | 0 | 0 | 0 | >2 | 2 | 0 |
| JSER85A024 | 23399 | 0 | 0 | 0 | >2 | 2 | 0 |
| JSER85A027 | 23399 | 0 | 0 | 0 | >2 | 2 | 0 |
| JSER85A037 | 23399 | 0 | 0 | 0 | >2 | 2 | 0 |
| JSER85A039 | 23399 | 0 | 0 | 0 | >2 | 2 | 0 |
| JSER85A044 | 23399 | 0 | 0 | 0 | >2 | 2 | 0 |
| JSER85A055 | 23399 | 0 | 0 | 0 | >2 | 2 | 0 |

Figure 13:
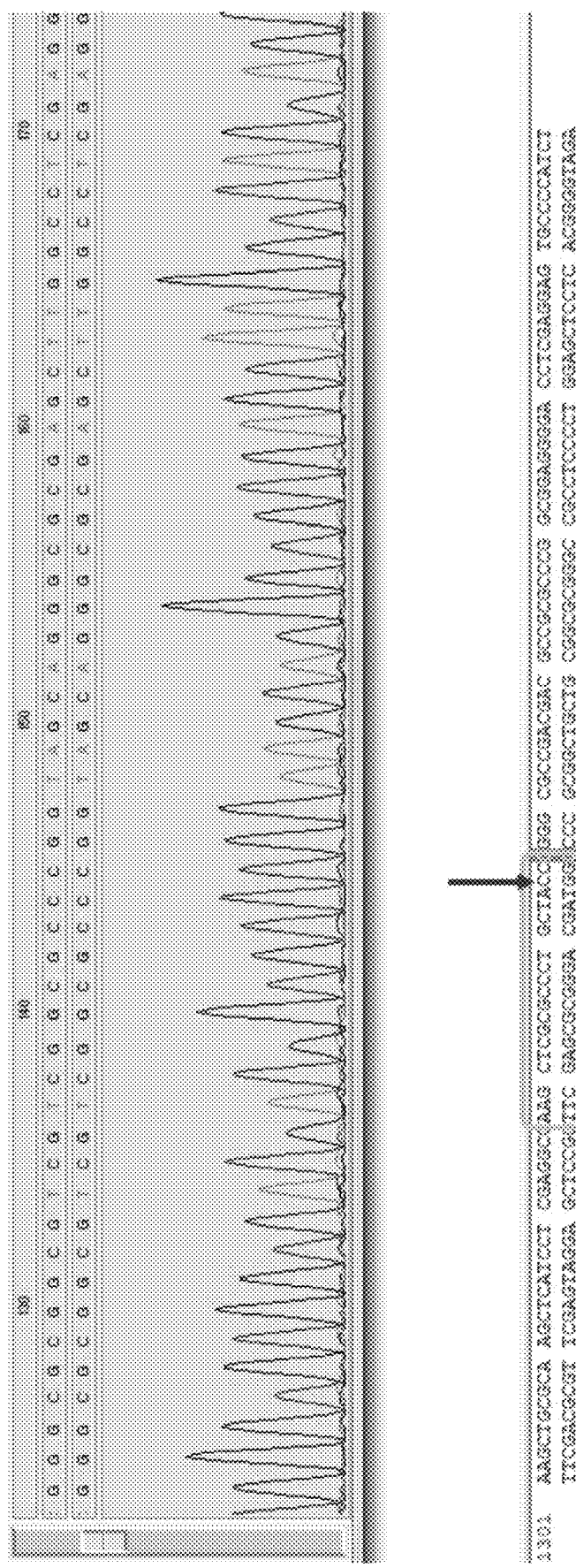
FIG. 13 shows sequencing confirmation of GW2-02 target site editing in haploid sweet corn line JSER82A063. A single base C next to the predicted Cas9 cleavage site was deleted.

To further confirm target-specific editing in these haploid lines, GW2-02 target region was amplified from JSER82A063 by PCR and the PCR product was sequenced. A single base C was deleted in JSER82A063 in comparison with the VVT sequence precisely at the Cas9 cleavage site (FIG. 13). These results clearly demonstrated that editing machinery brought into the egg cell from the male gametophyte can edit the female genome before the male genome is eliminated after double fertilization to form haploid embryo. Candidate edited haploid lines without transgene were treated with injection of 0.125% colchicine in 0.5% DMSO or seedling drenching in 0.06% colchicine solution donor in a wide cross with other compatible recipient crops to induce haploids to produce desired edits. The process of post-fertilization genome elimination in wide crosses is basically the same as the process in the maize MATL mutant system, although in some cases the foreign pollen-derived DNA and editing machinery may be eliminated slightly earlier in embryo development, which is why this method is preferably practiced using a promoter that drives expression of the editing machinery in the pollen, sperm cells, and/or zygote cell, so that the editing RNA and protein is present and able to edit the target genome even though the male DNA is eliminated rather quickly after fertilization.

To demonstrate feasibility of simultaneous haploid induction and editing via wide crosses, maize transgenic lines expressing Cas9 and sgRNA targeting wheat VLHP gene sequences were generated. Vector 23763 (SEQ ID NO: 24) contains expression cassettes for Cas9 and sgRNA containing protospacer sequence xTaVLHP1 (5'-GACGAGCAGGCGCAGTTCC-3', SEQ ID NO: 25) for guiding Cas9-mediated cleavage of TaVLHP1 target sites in wheat. The wheat genome has three xTaVLHP1 targets in total (TaVLHP1-4A, TaVLHP1-4B and TaVLHP1-4D), with each one in its three sub-genomes. The guide sequence in 23397 (SEQ ID NO: 20), xZmVLHP (5'-GCTGGAGCTGAGCTTCCGGG-3', SEQ ID NO: 21) will also direct cleavage of wheat VLHP target sequences, xTaVLHP2-1A (5'-GCTGGAGCTGAGCTTCCGGG-3', SEQ ID NO: 26) or xTaVLHP2-1B (5'-TCTGGAGCTGAGCTTCCGGG-3', SEQ ID NO: 27). There are three VLHP2A genes containing xTaVLHP2-1A and 3 VLHP2B genes containing xTaVLHP2-1B sequences in the Chinese Spring wheat genome. Vectors 23397 and 23763 were transformed into maize inbred line NP2222 using *Agrobacterium*-mediated transformation to generate transgenic lines expressing Cas9 and sgRNA. Transgenic maize lines were grown in greenhouse and selfed to produce T1 plants.

Pollen collected from transgenic maize T0 or progeny T1 plants carrying T-DNA of vector 23397 or 23763 were used to pollinate emasculated spring wheat line AC-Nanda. At one to two days before anthesis, wheat florets were emasculated and two days later are pollinated with fresh maize pollen carrying the editing machinery. For convenience, spikelets from a Syngenta elite cytoplasmic male sterile ("CMS") wheat line (16A300292) were also directly used as female donors to induce haploid embryo formation with transgenic maize pollen expressing 23397 or 23763 Cas9-sgRNA. Embryos were extracted from pollinated florets at 14-20 days after pollination for embryo rescue to recover haploid plantlets from the wheat x maize haploid induction system. Excised embryos were cultured on either full strength MS (Murashige and Skoog 1962) or ½ MS or B5 basal medium containing various modifications of organic supplements and grown in vitro for 3-5 weeks at 20-25° C. and 16-hour day length.

Figure 14:
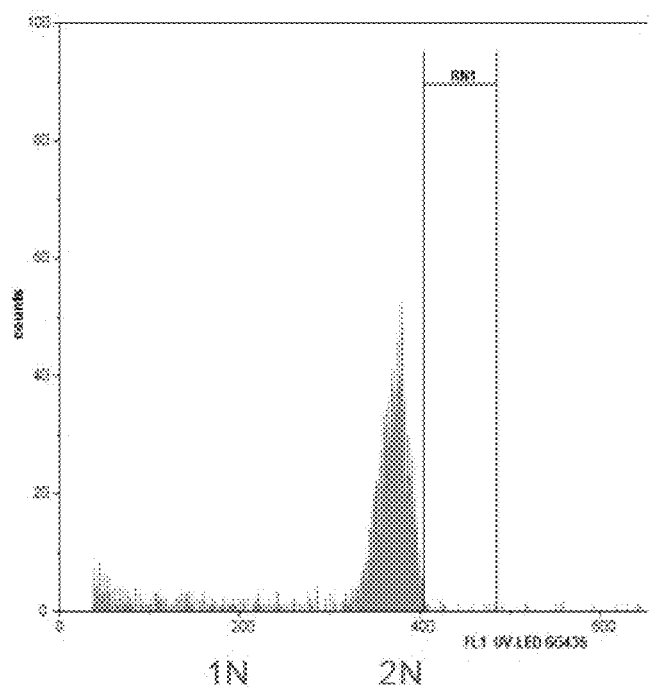
FIG. 14 shows ploidy analysis of wild type control.
Figure 15:
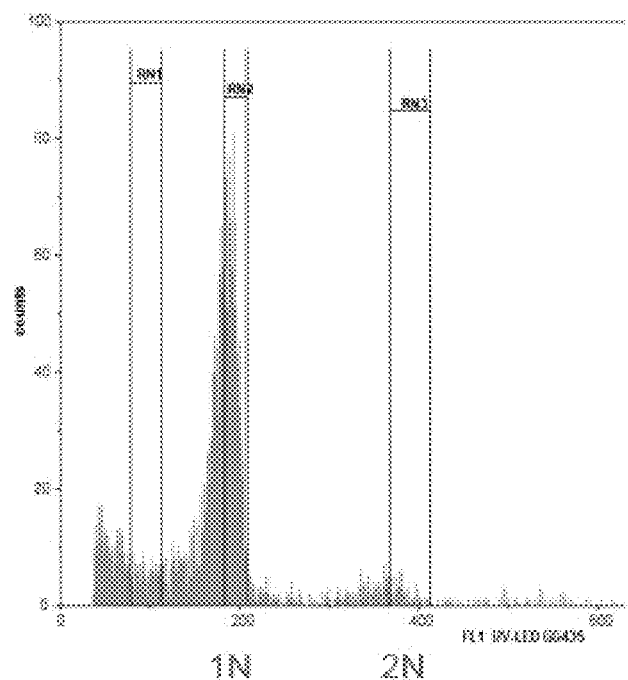
FIG. 15 shows ploidy analysis of edited haploid wheat line JSWER30A22.
Figure 16:
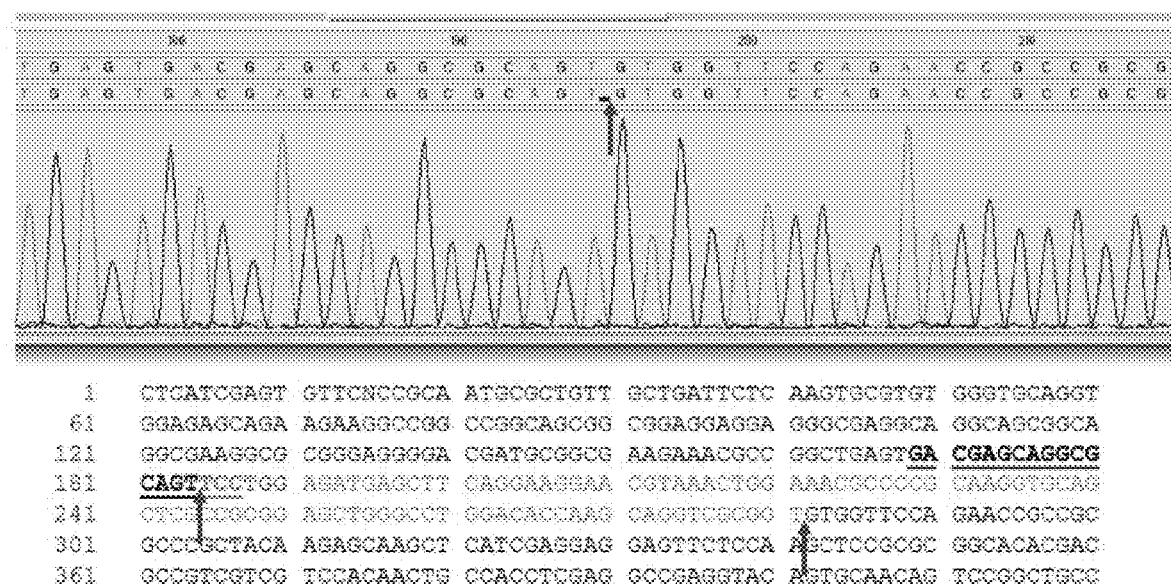
FIG. 16 shows sequencing confirmation of TaVLHP1-4B target site editing in haploid wheat line JSWER30A22. Lower panel showing 97 bp of TaVLHP1-4B sequence was deleted immediately downstream of the predicted Cas9 cleavage site. The 97 bp deleted sequences were marked by 2 arrows.

For example, pollen of T1 progeny from transgenic maize line MZET164902A044A containing vector 23763 was used to pollinate spikes of CMS line 16A300292 to induce wheat haploids. Haploid embryos were rescued and the resulting wheat haploid seedling were sampled for qPCR analysis to determine the copy number of VLHP target sequences (See Table 6). One of the haploid lines (JSWER30A22) was found to contain mutation in TaVLHP1-4B gene, but not in its orthologs TaVLHP1-4A and TaVLHP1-4D in the A and D sub-genomes. Ploidy level analysis confirmed that JSWER30A22 is a true haploid (See FIGS. 14 and 15). The mutation within the TaVLHP1-4B target region was further characterized by sequencing and was found to contain 97 bp deletion starting from the predicted Cas9 cleavage site (FIG. 16). We also identified another line JSW16A07 with "0" copy in TaVLHP1-4A gene (assay #3252), suggesting targeted editing in the target sequence. However, the deletion in this target gene is probably quite large in deleting the primer binding site(s) since we were not able to recover PCR product for sequencing. Haploid seedlings with an edited target site were transplanted to soil after 3-5 weeks in vitro culture. The transplanted seedlings were hardened for one week in a growth chamber under the same environmental regime. Colchicine was added after shoots had formed. However, the chromosome doubling treatment can be done earlier at embryo rescue in vitro culture stage or later after transplanting. When whole wheat seedlings are treated for doubling, roots of the haploid seedling are trimmed leaving a zone of 2-3 cm and then submerged in a 0.1% colchicine solution with 2% dimethyl sulfoxide (DMSO) and ca. 0.05% Tween-20 at 20° C. for 5 hours. After this treatment, the roots are washed to remove residual colchicine and potted in peat soil. Plant tissue samples can be removed from haploid seedlings for mutation detection to identify plants containing mutations in TaVLHP target gene sequences but with the maize chromosomes including sequences encoding the transgenic editing machinery completely eliminated. Since JSWER30A22 is from a CMS line, the plant is pollinated with a restorer to produce progeny seeds.

TABLE 6

Taqman analysis for wheat progeny from wide crosses. Line JSW30A22 is edited.

| | | Allele: | | | | |
|---|---|---|---|---|---|---|
| | | TAV_4A | TAV_4B | TAV_4D | PMI | CAS9 |
| | | | | Assay ID: | | |
| Plant ID | Construct ID | 3252 Copy# level | 3253 Copy# level | 3254 Copy# level | 1750 Copy# level | 2540 Copy# level |
| WT, AC-Nanda | N/A | >2 | 2 | >2 | 0 | 0 |
| WT, AC-Nanda | N/A | 2 | 2 | 2 | 0 | 0 |
| WT, CMS | N/A | 2 | 2 | 2 | 0 | 0 |
| WT, CMS | N/A | 2 | 2 | 2 | 0 | 0 |
| JSW29A01 | 23763 | 2 | 2 | 2 | 0 | 0 |
| JSW29A02 | 23763 | 2 | 2 | 2 | 0 | 0 |
| JSW29A03 | 23763 | 2 | 2 | 2 | 0 | 0 |
| JSW29A04 | 23763 | 2 | 2 | 2 | 0 | 0 |
| JSW29A05 | 23763 | 1 or 2 | 2 | 2 | 0 | 0 |
| JSW29A06 | 23763 | 2 | 2 | 2 | 0 | 0 |
| JSW29A07 | 23763 | 2 | 2 | 2 | 0 | 0 |
| JSW29A08 | 23763 | 2 | 2 | 2 | 0 | 0 |
| JSW29A09 | 23763 | 2 | 2 | 2 | 0 | 0 |
| JSW29A10 | 23763 | 2 | 2 | 2 | 0 | 0 |
| JSW29A11 | 23763 | 2 | 2 | 2 | 0 | 0 |

TABLE 6-continued

Taqman analysis for wheat progeny from wide crosses. Line JSW30A22 is edited.

| | | Allele: | | | | |
|---|---|---|---|---|---|---|
| | | TAV_4A | TAV_4B | TAV_4D | PMI | CAS9 |
| | | | | Assay ID: | | |
| Plant ID | Construct ID | 3252 Copy# level | 3253 Copy# level | 3254 Copy# level | 1750 Copy# level | 2540 Copy# level |
| JSW29A12 | 23763 | 2 | 2 | 2 | 0 | 0 |
| JSW29A13 | 23763 | 2 | 2 | 2 | 0 | 0 |
| JSW29A14 | 23763 | 2 | 2 | 2 | 0 | 0 |
| JSW29A15 | 23763 | 2 | 2 | 2 | 0 | 0 |
| JSW29A16 | 23763 | 2 | 2 | 2 | 0 | 0 |
| JSW30A01 | 23763 | 2 | 2 | 2 | 0 | 0 |
| JSW30A02 | 23763 | 2 | 1 or 2 | 2 | 0 | 0 |
| JSW30A03 | 23763 | 2 | 2 | 2 | 0 | 0 |
| JSW30A04 | 23763 | 2 | 2 | 2 | 0 | 0 |
| JSW30A05 | 23763 | 2 | 2 | 2 | 0 | 0 |
| JSW30A06 | 23763 | 2 | 2 | 2 | 0 | 0 |
| JSW30A07 | 23763 | 2 | 2 | 2 | 0 | 0 |
| JSW30A08 | 23763 | 2 | 2 | 2 | 0 | 0 |
| JSW30A09 | 23763 | 2 | 2 | 2 | 0 | 0 |
| JSW30A10 | 23763 | 2 | 2 | 2 | 0 | 0 |
| JSW30A11 | 23763 | 2 | 2 | 2 | 0 | 0 |
| JSW30A12 | 23763 | 2 | 2 | 2 | 0 | 0 |
| JSW30A13 | 23763 | 2 | 2 | 2 | 0 | 0 |
| JSW30A14 | 23763 | 2 | 2 | 2 | 0 | 0 |
| JSW30A15 | 23763 | 2 | 2 | 2 | 0 | 0 |
| JSW30A16 | 23763 | 2 | 2 | 2 | 0 | 0 |
| JSW30A17 | 23763 | 2 | 2 | 2 | 0 | 0 |
| JSW30A18 | 23763 | 2 | 2 | 2 | 0 | 0 |
| JSW30A19 | 23763 | >2 | 2 | 2 | 0 | 0 |
| JSW30A20 | 23763 | 2 | 2 | 2 | 0 | 0 |
| JSW30A21 | 23763 | 2 | 2 | 2 | 0 | 0 |
| *JSW30A22* | *23763* | *2* | *0* | *2* | *0* | *0* |
| JSW30A23 | 23763 | 2 | 2 | 1 or 2 | 0 | 0 |
| JSW30A24 | 23763 | 2 | 2 | 2 | 0 | 0 |
| JSW30A25 | 23763 | 2 | 2 | 2 | 0 | 0 |
| JSW30A26 | 23763 | 2 | 2 | 2 | 0 | 0 |
| JSW30A27 | 23763 | 2 | 2 | 2 | 0 | 0 |
| JSW30A28 | 23763 | 2 | 2 | 2 | 0 | 0 |
| JSW30A29 | 23763 | 2 | 2 | 2 | 0 | 0 |
| JSW30A30 | 23763 | 2 | 1 or 2 | 1 or 2 | 0 | 0 |
| JSW30A31 | 23763 | 2 | 2 | 2 | 0 | 0 |

To further demonstrate feasibility of simultaneous haploid induction and editing via wide crosses, maize transgenic lines expressing Cas9 from five promoters that have high and/or specific expression in pollen, along with sgRNA targeting wheat VLHP gene sequences, were generated. These five vectors were 24038 (SEQ ID NO: 34), 24039 (SEQ ID NO: 35), 24079 (SEQ ID NO: 36), 24091 (SEQ ID NO: 37), and 24094 (SEQ ID NO: 38). All five of these vectors utilized the same sgRNA containing protospacer sequence xTaVLHP2 (5'-GCTGGAGCTGAGCTTCCGGG -3', SEQ ID NO: 21) for guiding Cas9-mediated cleavage of TaVLHP2 target sites in wheat. The wheat genome has three xTaVLHP2 targets in total (TaVLHP2-2A, TaVLHP2-2B and TaVLHP2-2O), with each one in its three sub-genomes. The guide sequence in these five constructs also directs cleavage of wheat VLHP target sequences, xTaVLHP2 (5'-GCTGGAGCTGAGCTTCCGGG-3', SEQ ID NO: 26) or xTaVLHP3 (5'-TCTGGAGCTGAGCTTCCGGG-3', SEQ ID NO: 27). There are three TaVLHP2 genes containing xTaVLHP2 and 3 TaVLHP3 genes containing xTaVLHP2-1 B sequences in the Chinese Spring wheat genome.

Vector 24038 (SEQ ID NO: 34) contains expression cassettes for Cas9 under control of a pollen-preferred high expression promoter prZmGRMZM5G876285 and terminator tZmGRMZM5G876285 from the maize prf3 (34fricana34 homolog3) gene, which has an extremely high native expression at the RNA and protein level in pollen and which has evidence of high sperm cell expression.

Vector 24039 (SEQ ID NO: 35) contains expression cassettes for Cas9 under control of a pollen-preferred high expression promoter prZmGRMZM2G020852 and terminator tZmGRMZM2G020852 from the maize EXPB2 (BETA EXPANSIN2) gene, which has an extremely high native expression at the RNA and protein level in pollen and which has evidence of sperm cell expression.

Vector 24079 (SEQ ID NO: 36) contains expression cassettes for Cas9 under control of a pollen-preferred high expression promoter prZmGRMZM2G146551 and terminator tZmGRMZM2G146551 from the maize EXPB1 (BETA EXPANSIN1) gene, which has an extremely high native expression at the RNA and protein level in pollen and which has evidence of sperm cell expression.

Vector 24091 (SEQ ID NO: 37) contains expression cassettes for Cas9 under control of a pollen-preferred promoter prZmGRMZM2G471240 and terminator tZmGMRMZM2G471240 from the maize MATL (MATRILINEAL) gene, which shows evidence of pollen and possibly sperm cell expression at the RNA and protein level.

Vector 24094 (SEQ ID NO: 38) contains expression cassettes for Cas9 under control of a pollen-preferred promoter prZmGRMZM2G471240 and terminator tZmGMRMZM2G471240 from the maize MATL (MATRILINEAL) gene, which shows evidence of pollen and possibly sperm cell expression at the RNA and protein level. This construct additionally has an N-terminal fusion of AmCyan fluorescent protein on the Cas9 molecule for imaging and visualization of the Cas9 localization in pollen.

These five vectors (24038, 24039, 24079, 24091, and 24094) were transformed into maize inbred line NP2222 using *Agrobacterium*-mediated transformation to generate transgenic lines expressing Cas9 and sgRNA.

Figure 17:
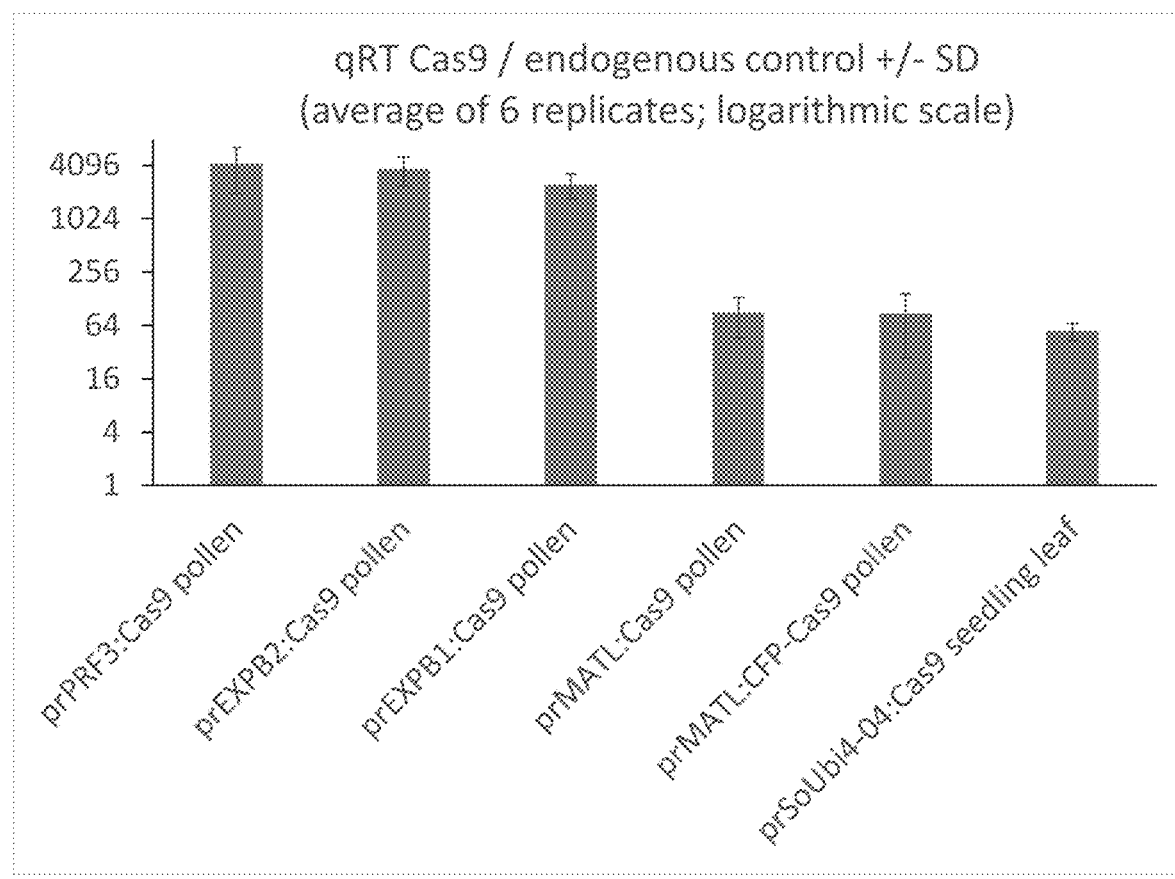
FIG. 17 shows pollen expression as measured by pollen collected from transgenic maize T0 plants carrying T-DNA of vector 24038, 24039, 24079, 24091, and 24094, which were used to pollinate emasculated spring wheat line AC-Nanda. The expression was high in the pollen, averaging about 100 fold higher in plants carrying T-DNA vectors 24038, 24039, and 24079 compared to the sugar cane ubiquitin promoter used in many of the corn and wheat examples. The expression was also higher in pollen from plants containing vectors 24038, 24039, and 24079 when compared to the pollen carrying the MATRILINEAL promoter constructs (24094 and 24091).
Figure 18:
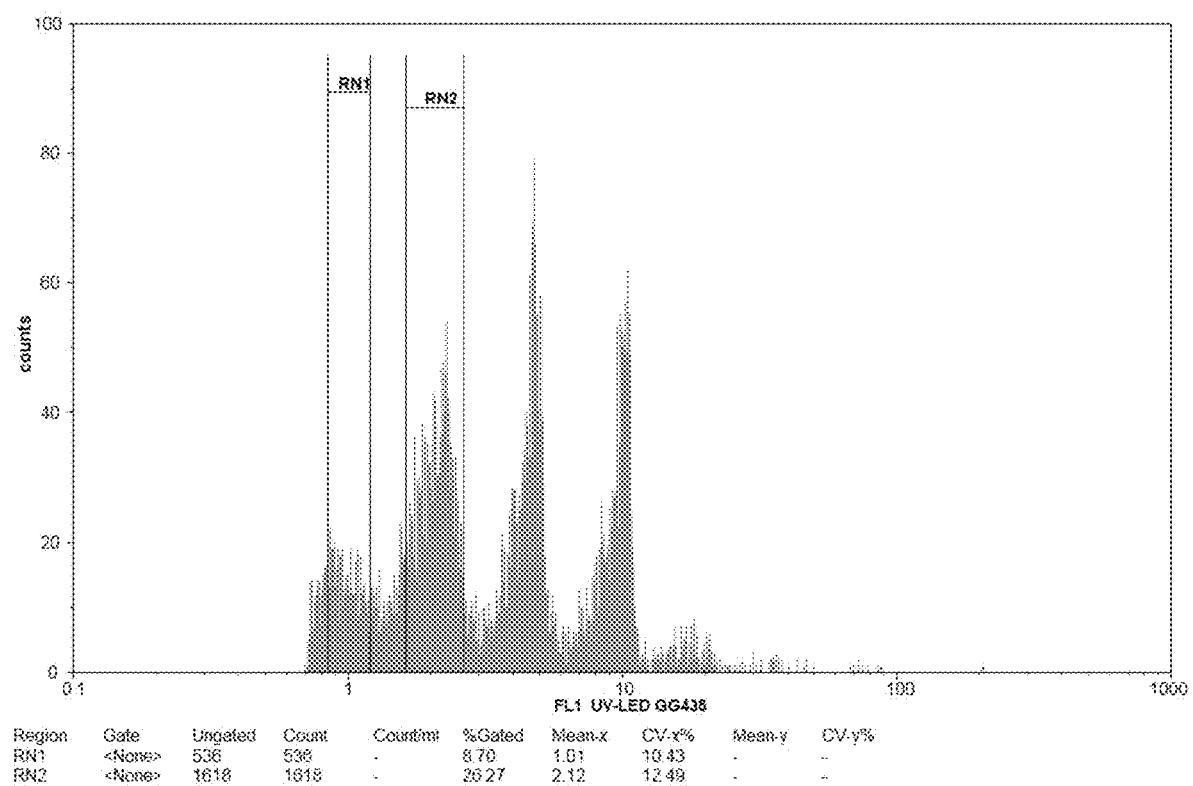
FIG. 18 shows the ploidy analysis histogram of a diploid control (parent USR01424135). The first peak is located at the "2" position on the logarithmic X-axis. Because this is leaf tissue from *Arabidopsis*, we see multiple peaks indicating the normal level of endoreduplication.
Figure 19:
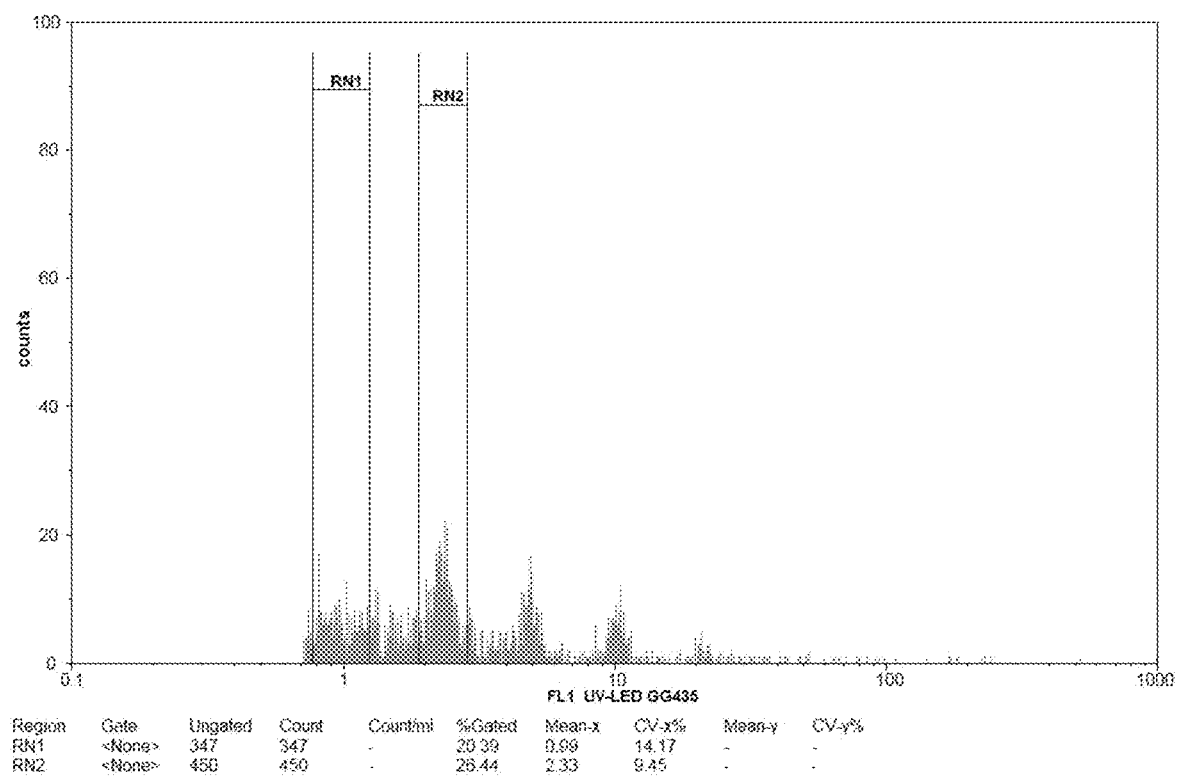
FIG. 19 shows the ploidy analysis histogram of a diploid control (parent USR01431603). The first peak is located at the "2" position on the logarithmic X-axis. Because this is leaf tissue from *Arabidopsis*, we see multiple peaks indicating the normal level of endoreduplication.
Figure 20:
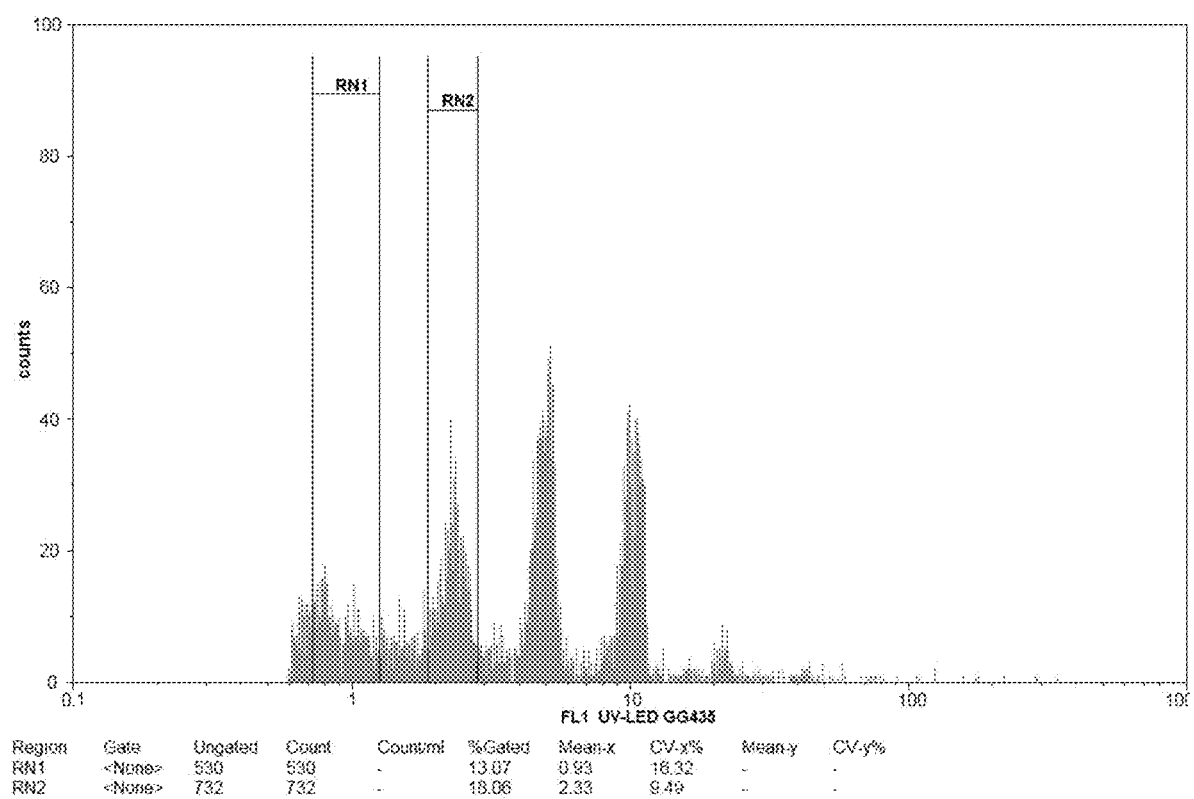
FIG. 20 shows the ploidy analysis histogram of a diploid control (parent USR01431609). The first peak is located at the "2" position on the logarithmic X-axis. Because this is leaf tissue from *Arabidopsis*, we see multiple peaks indicating the normal level of endoreduplication.
Figure 21:
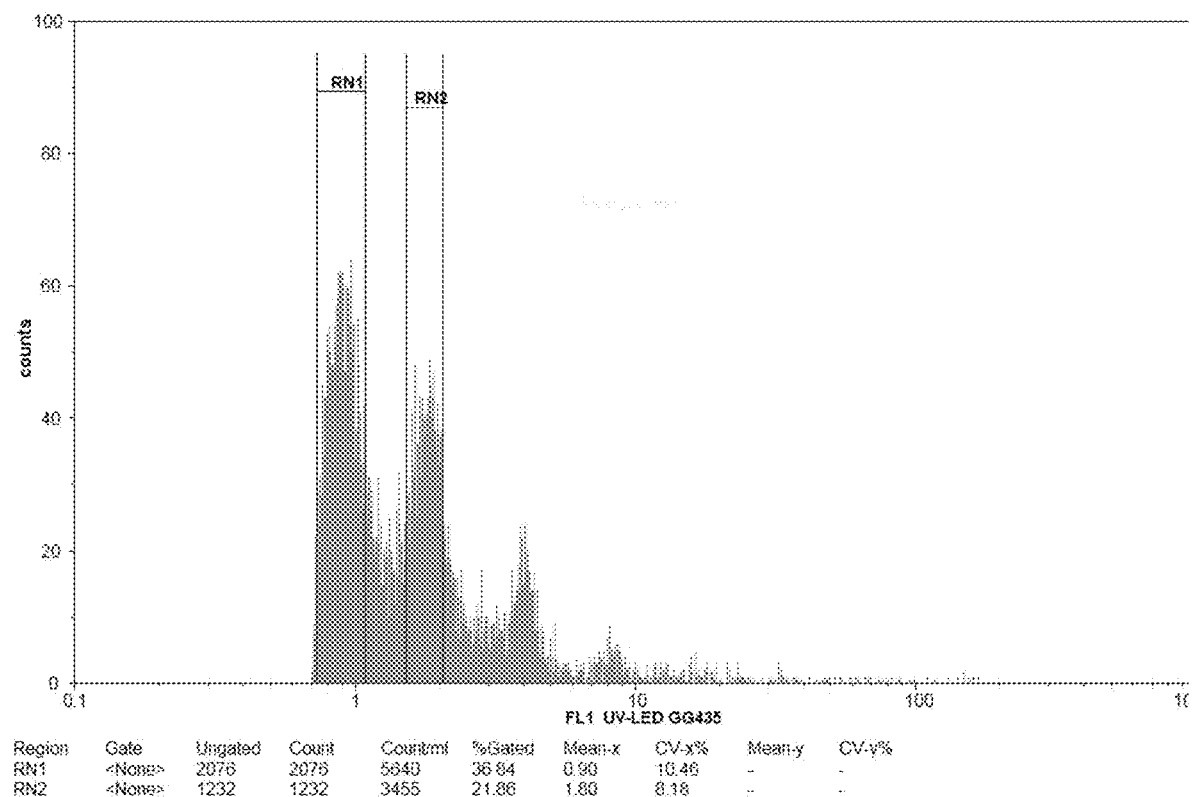
FIG. 21 shows the ploidy analysis histogram of an edited haploid from plate 1033, well C3 (USR01424135 X Ler- 427). The first peak is located at the "1" position on the logarithmic X-axis, indicating it is a haploid. Because this is leaf tissue from *Arabidopsis*, we see multiple peaks indicating the normal level of endoreduplication.
Figure 22:
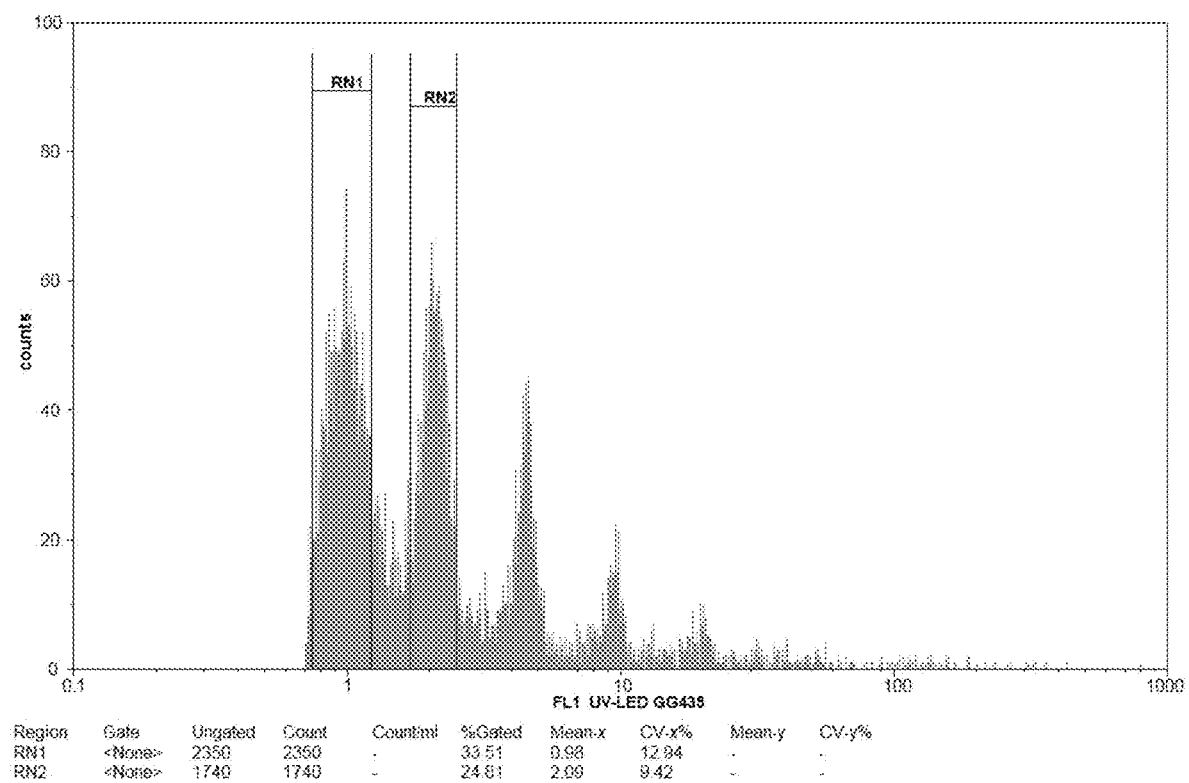
FIG. 22 shows the ploidy analysis histogram of an edited haploid from plate 1033, well E4 (USR01424135 X Ler-437). The first peak is located at the "1" position on the logarithmic X-axis, indicating it is a haploid. Because this is leaf tissue from *Arabidopsis*, we see multiple peaks indicating the normal level of endoreduplication.
Figure 23:
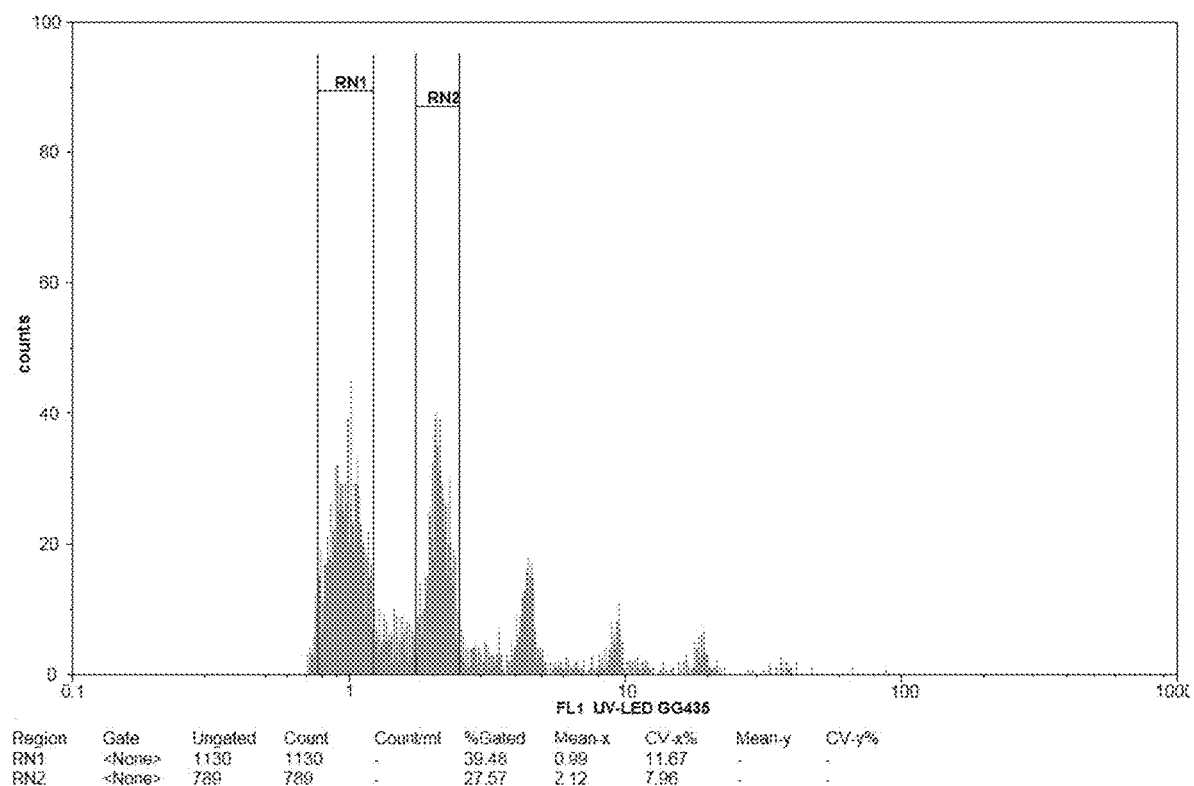
FIG. 23 shows the ploidy analysis histogram of an edited haploid from plate 1046, well H12 (USR01431609 X Ler-123). The first peak is located at the "1" position on the logarithmic X-axis, indicating it is a haploid. Because this is leaf tissue from *Arabidopsis*, we see multiple peaks indicating the normal level of endoreduplication.

Transgenic maize lines were grown in greenhouse and single and two-copy transgenic plants were outcrossed onto spring wheat and a CMS wheat line. Pollen collected from transgenic maize T0 plants carrying T-DNAs of one of the vectors 24038, 24039, 24079, 24091, and 24094 were used to pollinate emasculated spring wheat line AC-Nanda. Pollen was also used for a qRT experiment, in which the expression of the Cas9 was measured at the RNA level and compared to Cas9 expression in leaf samples when the Cas9 was driven by a sugar cane ubiquitin promoter used in many of the corn and wheat examples given above. As you can see in FIG. 17, the expression was high in the pollen, averaging about 100 fold higher in plants carrying the T-DNA vectors 24038, 24039, and 24079 compared to the Ubiquitin promoter. The expression was also higher in pollen from plants containing vectors 24038, 24039, and 24079 when compared to the pollen carrying the MATRILINEAL promoter constructs (24094 and 24091), which is known to have lower native gene expression. All five of these promoters have expression patterns that are restricted to pollen. As an indication that the promoters were working properly, we observed no T0 expression of Cas9 in callus seedling leaves, and there was no editing of the VLHP target sites in the T0 maize leaves (without wishing to be bound by theory, editing may happen at the maize target sites, in all likelihood, at the mature pollen stage, when the Cas9 is expressed for the first time).

At one to two days before anthesis, wheat florets were emasculated from the CMS line and the AC Nanda line. Two days later the florets were pollinated with fresh maize pollen carrying the editing machinery, Cas9-sgRNA, from either construct 24038, 24039, 24091, or 24094 (T0 plants transformed with construct 24079 were delayed, and not crossed to wheat in this manner). Wheat embryos were extracted from pollinated florets at 14-20 days after pollination for embryo rescue to recover haploid plantlets from the wheat x maize haploid induction system. Excised embryos were cultured on either full strength MS (Murashige and Skoog 1962) or ½ MS or B5 basal medium containing various modifications of organic supplements and grown in vitro for 1-5 weeks at 20-25° C. and 16-hour day length. For example, pollen of T0 progeny from transgenic maize line MZKE172601A100A containing vector 24039 was used to pollinate spikes of CMS line 16A300292 to induce wheat haploids. Haploid embryos were rescued and the resulting wheat haploid seedlings were sampled for qPCR analysis to determine the copy number of VLHP target sequences (Table 7). In this analysis, we tested for the Cas9 transgene using assay #2540. All wheat embryos rescued and tested lacked this transgene and gave scores of "0" for Cas9, because they do not have any corn DNA in the developing embryo and therefore do not have the transgene. The corn DNA is totally eliminated, kicked out or fails to be fully delivered in the first place during the haploid induction process, taking place during and/or after fertilization). In addition to Cas9, we test for assays #3332 and #3333, which give non-specific amplification of both VLHP2-2A and -2D alleles. These assays typically read as "2" or ">2" in haploid wheat, and the majority of the haploids we produced using the transgenic maize pollen scored 2 or >2 for these assays. We used these assays to look for putative edited haploids, by looking for scores of 0 or 1. A call of "1" might indicate that one of the two alleles, either VLHP2-2A, or -2D, was edited. Finally, we tested for assay 3255 in AC Nanda haploids, which detects VLHP2-2B specifically. The CMS line does not amplify this assay, even when it is wild-type, so we did not use it for the CMS haploids. The unedited haploids give a score of a "2," while putative edited haploids are found because they have a score of "0." A score of "1" might indicate a faulty reading or a chimeric, partially-edited sample.

As an example, one of the AC Nanda haploid plants 440-A5 was found to contain mutation in TaVLHP2-2B gene, but not in its orthologs TaVLHP2-2A and TaVLHP2-2D in the A and D sub-genomes (Table 7). The Taqman data also showed that it lacked the Cas9 transgene. The mutation within the TaVLHP2-2B target region was further characterized by sequencing, but although we were able to amplify the A and D alleles, we could no longer amplify the B allele, suggesting that there is a larger edit present, likely a large deletion, that results in the PCR product no longer amplifying.

As another example, one of the CMS haploid plants 450-D11 was found to contain mutation in either the TaVLHP2-2D or -2A homologues, according to the score of "1" for both assays 3332 and 3333. (Table 7). The taqman data showed that it lacked the Cas9 transgene. The TaVLHP2-2A, 2B and 2D target regions were further characterized by sequencing, but although we were able to amplify the A and B alleles, we could no longer amplify the D allele, suggesting that there is a larger edit present that led to PCR failure.

Considering the 2295 wheat haploids produced from crosses to maize pollen carrying one of the following five preferred-pollen expression constructs (24038, 24039, 24091, and 24094), we found 15 haploids that gave Taqman assay data that indicated possible editing at either the VLHP2-2A, VLHP2-2D, or VLHP2-2B target sites. After sequencing, seven of those haploids were found to have wild-type sequences at the target sites, and were called false positives due to Taqman error. These errors are thought to be either due to the fact that assays #3332 and #3333 gave non-specific amplification of both VLHP-2A and -2D alleles, leading to some missed calls, or due to low DNA quantity.

Of the remaining 8 putative edited haploids, six were AC Nanda (440-B3, 440-D3, 440-A5, 447-G8, 456-G9, 459-A2) where the editing transgene was from construct 24038. Four of those (440-B3, 440-D3, 440-A5, and 456-G9) contained edits in VLHP2-2B. These were found because they had a Taqman score of "0" for assay 3255. These plants lacked Cas9 (score of "0") but had wild-type "2" scores for VLHP2-2A or VLHP2-20 (assays #3332 and #3333) indicating they were not edited that those sites. These six plants were confirmed to be haploids by ploidy analysis. We attempted to sequence the edited alleles, but while the PCR and sequencing reactions worked well for 2A and 2D, we were not able to obtain a PCR product for 2B. We repeated the PCR several times using a range of reaction conditions but could not amplify the 2B homeologs from these haploid plants. This may indicate that the editing caused a large change in the 2B gene in these plants that may end up deleting the primer annealing site. We expect that many of the CMS plants also have edits at the VLHP2-2B target site, but we did not have an assay to detect the VLHP2-2B allele from the CMS line.

Considering AC Nanda alone, we calculate an overall editing rate at that allele of 0.7% for all constructs, but a particularly high editing rate of 1.4% for construct 24038.

In addition to these four edited haploids with scores of "0" for 3255, several other plants gave scores of "0 or 1" or "1" for 3255, which indicates possible chimerism (partial editing in certain cell lineages of the embryo or plantlet), but we did not follow up on those plants. For AC Nanda homolog VLHP2-2A, plant 447-G8 contained an edit which we were also not able to sequence because the PCR reaction failed, even though 2B and 2D did amplify and contained wild-type sequence. We repeated the PCR several times using a range of reaction conditions but could not amplify the 2A homolog. Similarly, for VLHP2-2D, plant 459-A2 contained an edit which we were not able to sequence because the PCR reaction failed. We repeated the PCR several times using a range of reaction conditions but could not amplify the 2D homolog. We also found putative edits in 447-H12 and 440-G6, but upon sequencing we found that these were false positives.

For the CMS haploids, plant 450-O11 gave scores of "1" for both assay #3332 and 3333 (Table 7). Upon sequencing, we found that the 2A homolog had wild-type sequence, but we could not PCR-amplify the 2D homolog, suggesting that a large edit had occurred. We repeated the PCR several times using a range of reaction conditions but could not amplify the 2D homolog. For plant 452-B11, the Taqman score was "0" for #3332 (VLHP2-2A), and we could not amplify that allele for sequencing, even though the 2D and 2B PCR products and sequences were normal. We repeated the PCR several times using a range of reaction conditions but could not amplify the 2A homolog. We also found five plants that had putative edits according to the Taqman data for assays 3332 and 3333, but PCR-sequencing showed these to be false positives; the sequence was wild-type (unedited).

In total, we found two edited CMS haploids and six edited AC Nanda haploids. There may be many more edited haploids that we were not able to detect because we did not have assays for the 2B gene for the CMS plants, nor for the VLHP3 gene target sites of the guide RNA in these five constructs.

The sequencing data from these edited haploids are consistent with the concept of a large deletion, inversion or rearrangement around the guide RNA target site, and extending far enough away to possibly include removal of one of the primer binding sites. This type of large change is not uncommon during editing by Cas9, especially in tissues where DNA repair via non-homologous end-joining is slower or inhibited—which may be the case in the just-fertilized zygote or early haploid wheat embryo.

TABLE 7

Sequencing data from edited wheat haploids.

| Plant ID | Construct ID | copy # | TAV 2A 3332 Raw Copy # | TAV 2A 3332 Copy # level | TAV_2D 3333 Raw Copy # | TAV_2D 3333 Copy # level | TAV_2B 3255 Raw Copy # | TAV_2B 3255 Copy # level | PMI 1750 Raw Copy # | PMI 1750 Copy # level | Cas9 2540 Raw Copy # | Cas9 2540 Copy # level | Sequencing result |
|---|---|---|---|---|---|---|---|---|---|---|---|---|---|
| | | | | | | | CMS | | | | | | |
| 427-A2 | WT | N/A | 2.44 | >2 | 2.38 | 2 | Not tested | | 0.00 | 0 | 0.00 | 0 | not sequenced |
| 427-B2 | WT | N/A | 1.99 | 2 | 1.99 | 2 | Not tested | | 0.00 | 0 | 0.00 | 0 | not sequenced |
| 427-C2 | WT | N/A | 2.02 | 2 | 2.07 | 2 | Not tested | | 0.00 | 0 | 0.00 | 0 | not sequenced |
| 427-D2 | WT | N/A | 2.31 | 2 | 2.16 | 2 | Not tested | | 0.00 | 0 | 0.00 | 0 | not sequenced |
| 427-A10 | 24091 | 2 | 2.07 | 2 | 1.66 | 2 | Not tested | | 0.00 | 0 | 0.00 | 0 | not sequenced |
| 427-B10 | 24091 | 2 | 1.95 | 2 | 1.84 | 2 | Not tested | | 0.00 | 0 | 0.00 | 0 | not sequenced |
| 427-C10 | 24091 | 2 | 1.93 | 2 | 2.28 | 2 | Not tested | | 0.00 | 0 | 0.00 | 0 | not sequenced |
| 427-D10 | 24091 | 2 | 2.59 | >2 | 2.48 | >2 | Not tested | | 0.00 | 0 | 0.00 | 0 | not sequenced |
| 427-E10 | 24091 | 2 | 1.90 | 2 | 1.78 | 2 | Not tested | | 0.00 | 0 | 0.00 | 0 | not sequenced |
| 427-F10 | 24091 | 2 | 2.03 | 2 | 1.96 | 2 | Not tested | | 0.00 | 0 | 0.00 | 0 | not sequenced |
| 427-G10 | 24091 | 2 | 2.08 | 2 | 2.25 | 2 | Not tested | | 0.00 | 0 | 0.00 | 0 | not sequenced |
| 427-H10 | 24091 | 2 | *0.58* | *1* | *0.81* | *1* | Not tested | | 0.00 | 0 | 0.00 | 0 | A and D were both WT |
| 427-A11 | 24091 | 2 | 1.57 | 1 or 2 | 1.93 | 2 | Not tested | | 0.00 | 0 | 0.00 | 0 | not sequenced |
| 427-B11 | 24091 | 2 | 1.41 | 1 or 2 | 1.63 | 2 | Not tested | | 0.00 | 0 | 0.00 | 0 | not sequenced |
| 427-C11 | 24091 | 2 | 1.06 | 1 | 1.21 | 1 | Not tested | | 0.01 | 0 | 0.01 | 0 | not sequenced |
| 427-D11 | 24091 | 2 | 1.98 | 2 | 2.03 | 2 | Not tested | | 0.00 | 0 | 0.00 | 0 | not sequenced |
| 427-E11 | 24091 | 2 | 1.94 | 2 | 1.94 | 2 | Not tested | | 0.00 | 0 | 0.00 | 0 | not sequenced |
| 427-F11 | 24091 | 2 | 1.84 | 2 | 1.84 | 2 | Not tested | | 0.00 | 0 | 0.00 | 0 | not sequenced |
| 427-G11 | 24091 | 2 | 1.54 | 1 or 2 | 1.76 | 2 | Not tested | | 0.00 | 0 | 0.00 | 0 | not sequenced |
| 427-H11 | 24091 | 2 | 1.75 | 2 | 1.76 | 2 | Not tested | | 0.00 | 0 | 0.00 | 0 | not sequenced |
| 427-A12 | 24091 | 2 | 1.99 | 2 | 2.15 | 2 | Not tested | | 0.00 | 0 | 0.00 | 0 | not sequenced |
| 427-B12 | 24091 | 2 | *0.72* | *1* | *1.26* | *1* | Not tested | | 0.00 | 0 | 0.00 | 0 | A and D were both WT |
| 427-C12 | 24091 | 2 | 1.69 | 2 | 1.50 | 1 or 2 | Not tested | | 0.00 | 0 | 0.01 | 0 | not sequenced |
| 427-D12 | 24091 | 1 | 2.34 | 2 | 2.03 | 2 | Not tested | | 0.00 | 0 | 0.00 | 0 | not sequenced |
| 427-E12 | 24091 | 1 | 1.98 | 2 | 2.04 | 2 | Not tested | | 0.00 | 0 | 0.00 | 0 | not sequenced |
| 427-F12 | 24091 | 1 | 1.89 | 2 | 1.97 | 2 | Not tested | | 0.00 | 0 | 0.00 | 0 | not sequenced |
| 427-G12 | 24091 | 1 | 1.56 | 1 or 2 | 1.77 | 2 | Not tested | | 0.00 | 0 | 0.00 | 0 | not sequenced |
| 427-H12 | 24091 | 1 | 1.57 | 1 or 2 | 2.36 | 2 | Not tested | | 0.00 | 0 | 0.00 | 0 | not sequenced |
| 428-A3 | 24091 | 1 | 2.12 | 2 | 1.75 | 2 | Not tested | | 0.00 | 0 | 0.00 | 0 | not sequenced |
| 428-B3 | 24091 | 1 | 2.69 | >2 | 1.89 | 2 | Not tested | | 0.00 | 0 | 0.00 | 0 | not sequenced |
| 428-C3 | 24091 | 1 | 2.09 | 2 | 2.44 | >2 | Not tested | | 0.00 | 0 | 0.00 | 0 | not sequenced |
| 428-D3 | 24091 | 1 | 2.05 | 2 | 2.39 | 2 | Not tested | | 0.00 | 0 | 0.00 | 0 | not sequenced |
| 428-E3 | 24091 | 1 | 2.48 | >2 | 2.87 | >2 | Not tested | | 0.00 | 0 | 0.00 | 0 | not sequenced |
| 428-F3 | 24091 | 1 | 2.33 | 2 | 2.76 | >2 | Not tested | | 0.00 | 0 | 0.00 | 0 | not sequenced |
| 428-G3 | 24091 | 1 | 2.84 | >2 | *0.22* | *0* | Not tested | | 0.00 | 0 | 0.00 | 0 | A and D were both WT |

TABLE 7-continued

Sequencing data from edited wheat haploids.

| Plant ID | Construct ID | copy # | TAV_2A 3332 Raw Copy # | TAV_2A 3332 Copy # level | TAV_2D 3333 Raw Copy # | TAV_2D 3333 Copy # level | TAV_2B 3255 Raw Copy # | TAV_2B 3255 Copy # level | PMI 1750 Raw Copy # | PMI 1750 Copy # level | Cas9 2540 Raw Copy # | Cas9 2540 Copy # level | Sequencing result |
|---|---|---|---|---|---|---|---|---|---|---|---|---|---|
| 428-H3 | 24091 | 1 | 2.83 | >2 | 2.60 | >2 | Not tested | | 0.00 | 0 | 0.00 | 0 | not sequenced |
| 450-A11 | 24094 | 1 | 1.97 | 2 | 2.24 | 2 | Not tested | | 0.00 | 0 | 0.00 | 0 | not sequenced |
| 450-B11 | 24094 | 1 | 2.13 | 2 | 2.04 | 2 | Not tested | | 0.00 | 0 | 0.00 | 0 | not sequenced |
| 450-C11 | 24094 | 1 | 2.15 | 2 | 2.18 | 2 | Not tested | | 0.00 | 0 | 0.00 | 0 | not sequenced |
| *450-D11* | *24094* | *1* | *1.04* | *1* | *0.99* | *1* | *Not tested* | | *0.00* | *0* | *0.00* | *0* | *A & B were WT; D failed* |
| 450-E11 | 24094 | 1 | 2.35 | 2 | 2.01 | 2 | Not tested | | 0.00 | 0 | 0.00 | 0 | not sequenced |
| 450-F11 | 24094 | 1 | 2.02 | 2 | 1.90 | 2 | Not tested | | 0.00 | 0 | 0.00 | 0 | not sequenced |
| 450-G11 | 24039 | 1 | 1.76 | 2 | 1.72 | 2 | Not tested | | 0.00 | 0 | 0.00 | 0 | not sequenced |
| 450-H11 | 24039 | 1 | 2.07 | 2 | 2.04 | 2 | Not tested | | 0.00 | 0 | 0.00 | 0 | not sequenced |
| 452-H4 | 24038 | 2 | *2.62* | *>2* | *0.01* | *0* | Not tested | | 0.00 | 0 | 0.00 | 0 | A and D were both WT |
| 452-A11 | 24038 | 2 | 2.24 | 2 | 2.28 | 2 | Not tested | | 0.00 | 0 | 0.00 | 0 | not sequenced |
| *452-B11* | *24038* | *2* | *0.00* | *0* | *2.22* | *2* | *Not tested* | | *0.00* | *0* | *0.00* | *0* | *B & D were WT; A failed* |
| 452-C11 | 24038 | 2 | 2.55 | >2 | 2.22 | 2 | Not tested | | 0.00 | 0 | 0.00 | 0 | not sequenced |
| 452-D11 | 24038 | 2 | *0.82* | *1* | *1.26* | *1* | Not tested | | 0.00 | 0 | 0.00 | 0 | A and D were both WT |
| 452-E11 | 24038 | 2 | 2.43 | >2 | 2.36 | 2 | Not tested | | 0.00 | 0 | 0.00 | 0 | not sequenced |
| 452-F11 | 24038 | 2 | 2.12 | 2 | 2.21 | 2 | Not tested | | 0.00 | 0 | 0.00 | 0 | not sequenced |
| 452-G11 | 24038 | 2 | 2.38 | 2 | 1.99 | 2 | Not tested | | 0.00 | 0 | 0.00 | 0 | not sequenced |
| 452-H11 | 24038 | 2 | 1.82 | 2 | 1.83 | 2 | Not tested | | 0.00 | 0 | 0.00 | 0 | not sequenced |
| | | | | | | | NANDA | | | | | | |
| 425-A2 | WT | N/A | 2.30 | 2 | 2.62 | >2 | 1.908 | 2 | 0.00 | 0 | 0.00 | 0 | not sequenced |
| 425-B2 | WT | N/A | 2.28 | 2 | 2.41 | >2 | 2.274 | 2 | 0.00 | 0 | 0.00 | 0 | not sequenced |
| 425-C2 | WT | N/A | 2.47 | >2 | 1.92 | 2 | 1.962 | 2 | 0.00 | 0 | 0.00 | 0 | not sequenced |
| 425-D2 | WT | N/A | 2.10 | 2 | 2.11 | 2 | 1.772 | 2 | 0.00 | 0 | 0.00 | 0 | not sequenced |
| 447-A12 | 24038 | 2 | 1.72 | 2 | 1.90 | 2 | 2.02 | 2 | 0.00 | 0 | 0.00 | 0 | not sequenced |
| 447-B12 | 24039 | 2 | 2.18 | 2 | 1.62 | 2 | 1.47 | 1 or 2 | 0.00 | 0 | 0.00 | 0 | not sequenced |
| 447-C12 | 24039 | 2 | 1.78 | 2 | 2.40 | 2 | 1.90 | 2 | 0.00 | 0 | 0.00 | 0 | not sequenced |
| 447-D12 | 24039 | 2 | 1.58 | 1 or 2 | 1.70 | 2 | 2.18 | 2 | 0.00 | 0 | 0.00 | 0 | not sequenced |
| 447-E12 | 24039 | 2 | 2.13 | 2 | 1.82 | 2 | 2.14 | 2 | 0.00 | 0 | 0.00 | 0 | not sequenced |
| 447-F12 | 24039 | 2 | 2.25 | 2 | 1.78 | 2 | 2.15 | 2 | 0.00 | 0 | 0.00 | 0 | not sequenced |
| 447-G12 | 24039 | 2 | 1.90 | 2 | 2.30 | 2 | 2.23 | 2 | 0.00 | 0 | 0.00 | 0 | not sequenced |
| 447-H12 | 24039 | 1 | 2.34 | 2 | 1.95 | 2 | *0.89* | *1* | 0.00 | 0 | 0.00 | 0 | WT |
| 440-A2 | 24039 | 1 | 1.72 | 2 | 1.71 | 2 | 1.24 | 1 | 0.00 | 0 | 0.00 | 0 | not sequenced |
| 440-B2 | 24039 | 1 | 2.30 | 2 | 2.56 | >2 | 1.77 | 2 | 0.00 | 0 | 0.00 | 0 | not sequenced |
| 440-C2 | 24039 | 1 | 3.05 | >2 | 1.85 | 2 | 2.01 | 2 | 0.00 | 0 | 0.00 | 0 | not sequenced |
| 440-D2 | 24039 | 1 | 1.66 | 2 | 1.70 | 2 | 1.44 | 1 or 2 | 0.00 | 0 | 0.00 | 0 | not sequenced |
| 440-E2 | 24039 | 1 | 2.23 | 2 | 1.91 | 2 | 2.04 | 2 | 0.00 | 0 | 0.00 | 0 | not sequenced |
| 440-F2 | 24039 | 1 | 2.63 | >2 | 2.07 | 2 | 2.28 | 2 | 0.00 | 0 | 0.00 | 0 | not sequenced |
| 440-G2 | 24038 | 11 | 1.91 | 2 | 1.87 | 2 | 2.10 | 2 | 0.00 | 0 | 0.00 | 0 | not sequenced |
| 440-H2 | 24038 | 1 | 1.85 | 2 | 1.80 | 2 | 1.97 | 2 | 0.00 | 0 | 0.00 | 0 | not sequenced |
| 440-A3 | 24038 | 1 | 2.52 | >2 | 2.05 | 2 | 1.99 | 2 | 0.00 | 0 | 0.00 | 0 | not sequenced |
| *440-B3* | *24038* | *1* | *2.16* | *2* | *2.19* | *2* | *0.00* | *0* | *0.00* | *0* | *0.00* | *0* | *A & D were WT; B failed* |
| 440-C3 | 24038 | 1 | 2.58 | >2 | 2.02 | 2 | 2.78 | >2 | 0.00 | 0 | 0.00 | 0 | not sequenced |
| *440-D3* | *24038* | *1* | *2.34* | *2* | *2.32* | *2* | *0.00* | *0* | *0.00* | *0* | *0.00* | *0* | *A & D were WT; B failed* |
| 440-E3 | 24038 | 1 | 2.49 | >2 | 2.23 | 2 | 2.47 | >2 | 0.00 | 0 | 0.00 | 0 | not sequenced |
| 440-F3 | 24038 | 1 | 2.08 | 2 | 2.10 | 2 | 2.17 | 2 | 0.00 | 0 | 0.00 | 0 | not sequenced |
| 440-F4 | 24038 | 1 | 1.73 | 2 | 1.47 | 1 or 2 | 1.41 | 1 or 2 | 0.00 | 0 | 0.00 | 0 | not sequenced |
| 440-G4 | 24038 | 1 | 1.53 | 1 or 2 | 2.02 | 2 | 1.99 | 2 | 0.00 | 0 | 0.00 | 0 | not sequenced |
| 440-H4 | 24038 | 1 | 2.22 | 2 | 1.90 | 2 | 0.00 | 0 | 0.00 | 0 | 0.00 | 0 | not sequenced |
| *440-A5* | *24038* | *1* | *2.22* | *2* | *1.90* | *2* | *0.00* | *0* | *0.00* | *0* | *0.00* | *0* | *A & D were WT; B failed* |
| 440-A6 | 24039 | 2 | 2.49 | >2 | 2.32 | 2 | 1.84 | 2 | 0.00 | 0 | 0.00 | 0 | not sequenced |
| 440-B6 | 24039 | 2 | 2.12 | 2 | 2.03 | 2 | 2.21 | 2 | 0.00 | 0 | 0.00 | 0 | not sequenced |
| 440-C6 | 24039 | 2 | 2.63 | >2 | 2.07 | 2 | 2.28 | 2 | 0.00 | 0 | 0.00 | 0 | not sequenced |
| 440-D6 | 24039 | 2 | 2.49 | >2 | 2.23 | 2 | 2.47 | >2 | 0.00 | 0 | 0.00 | 0 | not sequenced |
| 440-E6 | 24039 | 2 | 2.45 | >2 | 2.20 | 2 | 2.32 | 2 | 0.00 | 0 | 0.00 | 0 | not sequenced |
| 440-F6 | 24039 | 2 | 2.10 | 2 | 1.92 | 2 | 1.91 | 2 | 0.00 | 0 | 0.00 | 0 | not sequenced |
| 440-G6 | 24039 | 2 | *0.57* | *1* | *0.66* | *1* | *0.53* | *1* | 0.00 | 0 | 0.00 | 0 | A, B & D were all WT |
| 440-H6 | 24039 | 2 | 1.81 | 2 | 1.96 | 2 | 2.51 | >2 | 0.00 | 0 | 0.00 | 0 | not sequenced |
| 447-A8 | 24038 | 1 | 2.42 | >2 | 2.21 | 2 | 2.10 | 2 | 0.00 | 0 | 0.00 | 0 | not sequenced |
| 447-B8 | 24038 | 1 | 2.46 | >2 | 2.32 | 2 | 2.09 | 2 | 0.00 | 0 | 0.00 | 0 | not sequenced |
| 447-C8 | 24038 | 1 | 2.09 | 2 | 2.08 | 2 | 2.29 | 2 | 0.00 | 0 | 0.00 | 0 | not sequenced |
| 447-D8 | 24038 | 1 | 2.13 | 2 | 2.14 | 2 | 2.34 | 2 | 0.00 | 0 | 0.00 | 0 | not sequenced |
| 447-E8 | 24038 | 11 | 2.36 | 2 | 2.31 | 2 | 2.44 | >2 | 0.00 | 0 | 0.00 | 0 | not sequenced |
| 447-F8 | 24038 | 1 | 2.72 | >2 | 2.28 | 2 | 2.00 | 2 | 0.00 | 0 | 0.00 | 0 | not sequenced |

TABLE 7-continued

Sequencing data from edited wheat haploids.

| Plant ID | Con- struct ID | copy # | TAV 2A 3332 | | TAV_2D 3333 | | TAV_2B 3255 | | PMI 1750 | | Cas9 2540 | | Sequencing result |
|---|---|---|---|---|---|---|---|---|---|---|---|---|---|
| | | | Raw Copy # | Copy # level | Raw Copy # | Copy # level | Raw Copy # | Copy # level | Raw Copy # | Copy # level | Raw Copy # | Copy # level | |
| *447-G8* | *24038* | *1* | *0.71* | *1* | *1.34* | *1 or 2* | *2.33* | *2* | *0.00* | *0* | *0.00* | *0* | *B & D were WT; A failed* |
| 447-H8 | 24038 | 1 | 2.25 | 2 | 2.29 | 2 | 2.01 | 2 | 0.00 | 0 | 0.00 | 0 | not sequenced |
| 456-A9 | 24038 | 2 | 2.19 | 2 | 1.59 | 1 or 2 | 2.03 | 2 | 0.00 | 0 | 0.00 | 0 | not sequenced |
| 456-B9 | 24038 | 2 | 2.13 | 2 | 2.11 | 2 | 2.02 | 2 | 0.00 | 0 | 0.00 | 0 | not sequenced |
| 456-C9 | 24038 | 2 | 2.16 | 2 | 1.85 | 2 | 1.45 | 1 or 2 | 0.00 | 0 | 0.00 | 0 | not sequenced |
| 456-D9 | 24038 | 2 | 2.56 | >2 | 2.18 | 2 | 1.76 | 2 | 0.00 | 0 | 0.00 | 0 | not sequenced |
| 456-E9 | 24038 | 2 | 2.29 | 2 | 2.03 | 2 | 1.65 | 2 | 0.00 | 0 | 0.00 | 0 | not sequenced |
| 456-F9 | 24038 | 2 | 2.24 | 2 | 2.02 | 2 | 2.05 | 2 | 0.00 | 0 | 0.00 | 0 | not sequenced |
| *456-G9* | *24038* | *2* | *2.49* | *>2* | *2.03* | *2* | *0.00* | *0* | *0.00* | *0* | *0.00* | *0* | *A & D were WT; B failed* |
| 456-H9 | 24038 | 2 | 1.78 | 2 | 1.62 | 2 | 1.38 | 1 or 2 | 0.00 | 0 | 0.00 | 0 | not sequenced |
| *459-A2* | *24038* | *2* | *1.38* | *1 or 2* | *1.11* | *1* | *0.94* | *1* | *0.00* | *0* | *0.00* | *0* | *A & B were WT; D failed* |
| 459-B2 | 24038 | 2 | 1.86 | 2 | 1.91 | 2 | 2.12 | 2 | 0.00 | 0 | 0.00 | 0 | not sequenced |
| 459-C2 | 24038 | 2 | 1.94 | 2 | 2.09 | 2 | 1.42 | 1 or 2 | 0.00 | 0 | 0.00 | 0 | not sequenced |
| 459-D2 | 24038 | 2 | 2.09 | 2 | 2.05 | 2 | 1.91 | 2 | 0.00 | 0 | 0.00 | 0 | not sequenced |
| 459-E2 | 24038 | 2 | 2.18 | 2 | 2.12 | 2 | 2.12 | 2 | 0.00 | 0 | 0.00 | 0 | not sequenced |

Overall, we found that the editing frequency (number of edited haploids identified divided by the total number of haploids) for construct 24038 was 0.79%; for construct 24039 it was 0%; for construct 24091 it was 0%, and for construct 24094 it was 0.75%. However, this editing rate is certainly an under-estimate because we did not have assays to detect edits at many of the guide RNA target sites. Additionally, because we used T0 pollen that was either 1 or 2 copy, we know that with the 1-copy pollen, only 50% of the fertilizing pollen grains will contain the Cas9, and so only half of the embryos have the opportunity to be edited; similarly, for 2 copy parents, assuming random segregation of the transgenes in the male meiosis, we would expect about 75% of the pollen to contain Cas9, so 25% of the embryos cannot be edited. It is reasonable to conclude that, when one is trying to use this simultaneous editing plus haploid induction technology with the editing machinery carried by the pollen, it may in some cases be more optimal to use a promoter that express specifically or highly in pollen and in sperm cells, so that the Cas9 can be expressed at a higher level. In cases where the gene target might impact development of the haploid inducer plant, having a pollen or sperm-preferred promoter that does not express in leaves might be useful because it would avoid editing the target gene in the haploid inducer plant during development—perhaps editing it for the first time in pollen.

Because the sperm cells fertilize the egg, they have the potential to deliver Cas9 RNA and protein (as well as the transgene DNA itself, integrated into one of the male chromosomes that will be eliminated). As we demonstrated in the wide-cross work in this example, it may work well to have the Cas9 and/or guide RNA under the control of a promoter that specifically or highly expresses in pollen, and in particular in sperm cells, when using a haploid inducer as the male to edit elite lines. We do not know exactly whether MATRILINEAL, EXPB1, EXPB2, and PRF3 express in the vegetative nucleus, the sperm cells, or both, and whether there might be any expression in a zygote cell type, but these were chosen because they are supposedly highly and/or specifically expressed in pollen. The PRF3 promoter has a DUO1 binding motif in the promoter, which may indicate it expresses in sperm cells. This is consistent with that promoter having higher editing frequency. The fact that we found many edited wheat haploids after the wide cross makes it clear that when there is high expression of Cas9 in pollen, using these or any other promoter, that expression can lead to editing in the wheat embryos after the wide cross. There is a strong possibility that these promoters, as well as other promoters that drive expression in pollen, or in particular in the sperm cells, might increase the efficiency of the editing process during corn haploid induction, or rice haploid induction.

Similarly, in the next example below, we show haploid editing in a dicot using a CENH3-modified-haploid inducer line, and we use constitutive promoter to drive the Cas9. But in an attempt to increase the efficiency of the haploid editing, we could opt to use a promoter that drives high and/or specific expression in egg cells, such as the EGG APPARATUS1 gene's promoter ("prEA1") (see, e.g., Gray-Mitsumune, M. and Matton, D. P., The Egg apparatus 1 gene from maize is a member of a large gene family found in both monocots and dicots, Planta 223(3):618-625 (February 2006)) or EGG CELL1 (EC1) (see, e.g., Sprunck S, et al., Egg cell-secreted EC1 triggers sperm cell activation during double fertilization. Science 2012; 338:1093-97; PMID: 23180860; http://dx.doi.org/10.1126/science.1223944).

As an example of this, one could use a sperm-cell expressed promoter, such as the *Arabidopsis* sperm-specific DUO1 promoter (see, e.g., Engel, et al., Green Sperm. Identification of Male Gamete Promoters in *Arabidopsis*, Plant Physiology August 2005, 138 (4) 2124-2133; DOI: 10.1104/pp.104.054213), or homologs of DUO1 from other species (for instance, the maize genes GRMZM2G105137 and GRMZM2G046443 are both DUO1 homologs that share a similar pollen-specific expression pattern). If one used any of these to drive Cas9 expression in the sperm cells of a haploid inducer line like RWK, NP2222-HI, or an matl mutant, it might make a highly efficient haploid editor line for use in editing diverse elite maize or wheat germplasm, via intraspecific or wide cross, respectively.

Other suitable sperm-expressed promoters for this concept of driving high Cas9 expression in sperm cells would include the DUO1 homologs in wheat, rice, barley, tomato, sunflower, or other monocots or dicots. Other suitable promoters for this concept are shown in Table 8 below. These promoters, or their homologs in crop species—might be very useful for this concept. The principal at work is that gamete cell expression of the editing machinery can increase the rate or efficiency of this invention because it means that there will be abundant editing protein or RNA present or delivered to the embryo during fertilization so that editing can happen rapidly.

TABLE 8

Promoters List: promoters one can use in a transgene to drive high sperm cell expression of editing machinery to boost the efficiency of simultaneous editing and doubled-haploid induction ("SEDHI").

| Gene Name | Gene ID | Maize Ortholog | Rice Ortholog |
|---|---|---|---|
| DUO1 | At3G60460 | GRMZM2G105137, GRMZM2G046443 | LOC_Os04g46384 |
| MGH3 | At1G19890 | NA | NA |
| GEX1 | At5G55490 | GRMZM2G388045 | LOC_Os09g27040, LOC_Os07g47194 |
| GEX2 | At5G49150 | GRMZM2G036832 | LOC_Os09g25650 |
| GEX3 | At5G16020 | GRMZM2G458159 | LOC_Os01g42060 |
| HAP2/GSC1 | At4G11720 | GRMZM2G412911 | LOC_Os05g18730 |
| CycB1 | At4G37490 | NA | NA |
| DAZ1 | At2G17180 | GRMZM2G132057 | NA |
| DAZ2 | At4G35280 | NA | LOC_Os02g19180 |
| DAZ3 | At4G35700 | NA | NA |
| PCR11 | At1G68610 | NA | NA |
| DAN1 | At3G04620 | NA | NA |
| TIP1 | AT3G47440 | NA | LOC_Os04g46490 |
| MKKK20 | AT3G50310 | NA | NA |
| DAF1 | At3G62230 | NA | NA |
| DAW1 | At4G35560 | GRMZM2G176647 | NA |
| DAU2/DMP9 | At5G39650 | NA | NA |

VII. Simultaneous Haploid Induction and Editing in Dicots Via Wide Cross or Via Crosses to CENH3-Altered Lines or Other Haploid Inducing Lines.

In vivo haploid induction can also be achieved using interspecific or intergeneric wide crosses on dicot plant species, for example, in cotton (Turcotte et al. 1969, Semigametic production of haploids in pima cotton. Crop Sci. 9:653-655) and tobacco (Burke et al, 1979, Maternal haploids of Nicotiana tabacum L. Science 206:585; Wernsman et al. 1989, Androgenetic vs. gynogenetic doubled haploids of tobacco. Crop Sci. 29:1151-1155). Haploid Arabidopsis plants can be obtained by crossing with pollen from mutant CENH3 plant, or by crossing said plants as females to wild type pollen (Ravi and Chan, 2010, Haploid plants produced by centromere-mediated genome elimination. Nature 464: 615-618). Other candidate genes which may be modified to generate a haploid inducer and SEDHI editing line include KNL2 and CENPC (both of which may operate via centromere-mediated uniparental genome elimination) as well as MSI2 and sunflower PLA2. In this case, the haploid-inducing genome (be it the male or female in the cross) also contains the editing machinery, so that the editing can be achieved during the haploid induction process, with the result being an edited maternal or paternal haploid progeny plant without altered CENH3 or editing transgenes. See, e.g., WO 2017/004375, incorporated herein by reference in its entirety. Transgenic locus expressing editing machinery can be introduced into any dicot crops or their wild relatives of Brassica, tomato, pepper, lettuce, eggplant, soybean, sunflower, sugar beet, cotton, alfalfa, tobacco, and others. The transgenic lines expressing editing machinery are then used as pollen donors, or in the case of CENH3, either pollen donors or acceptors, in interspecific or intergeneric wide crosses for haploid induction and simultaneous genome editing. For example, N. 43fricana transgenic CRISPR-Cas9 lines expressing sgRNA targeting tobacco gibberellin 20-oxidase are created through Agrobacterium-mediated transformation and used to pollinate emasculated tobacco flowers to induce haploid plants with their genome edited at the gibberellin 20-oxidase locus. Preferably, an easily transformable line with large number of pollen is used as pollen donor for haploid induction and to provide the editing machinery transiently. The recipient plant for haploid production has flowers that are easy to emasculate or is male sterile. More preferably, a color or other visual marker is present in the induction line or is included in the editing locus to easily differentiate haploid embryos or plants from diploids resulted from normal zygote development.

We exemplified this by utilizing an Arabidopsis haploid inducer line in the Columbia ecotype, and transforming it with a construct encoding expression of Cas9 and a single guide RNA targeting the GLABROUS1 gene (GL1) which, when knocked out, gives a trichome-less phenotype. We crossed the T0s as females by Landsberg erecta (Ler) ecotype pollen, and recovered gl1 edited haploid progeny.

The haploid inducer materials were obtained from the Comai lab at UC Davis. These materials are typically utilized as paternal haploid inducer lines (causing androgenesis, when crossed as females to wild-type males) but can also act as maternal haploid inducers (causing gynogenesis, when crossed as males to wild-type females). These lines have been altered to become haploid inducers by replacing the native CENH3 gene with a Zea mays CENH3 transgene as reported in (Maheshwari, et al, 2017, Centromere location in Arabidopsis is unaltered by extreme divergence in CENH3 protein sequence. Genome Research 27(3)).

In particular, both copies of the native AtCENH3 gene was knocked out and complemented with the stably inserted ZmCENH3 transgene, which did not impact normal plant development, and did not produce haploids upon self-pollination, but did produce about 10% haploids upon outcross. This is a modification to the original concept of CENH3-tailswap described in detail in (Ravi and Chan, 2010, Haploid plants produced by centromere-mediated genome elimination. Nature 464: 615-618) and many subsequent publications.

After we obtained the CENH3* lines from UC Davis, we grew them up, confirmed that they had the ZmCENH3 transgene and were homozygous "null" for the native AtCENH3 gene. We did this by designing a taqman qPCR assay for ZmCENH3 (assay #2298) and by using PCR and gel electrophoresis to test 183 seedlings for the zygosity of the AtCENH3 genotype by running PCR using the XbaI forward and reverse primers (SEQ NO TKX and TKY) and Reddy mix at 60° C. annealing temperature and cutting with the XbaI restriction enzyme overnight at 37° C. The wild-type allele would be cut by this enzyme and produce two bands (189 bp, 25 bp) while the mutant would remain at 215 bp. These tests showed that all of the seed that UC Davis sent were homozygous for the mutant allele Atcenh3-1, and that there were multiple copies of the ZmCENH3 transgene present.

Confident that these acquired seeds were indeed haploid inducers, we kept 100 plants and initiated floral dip transformation with binary vector 24075 (SEQ ID NO: 98)

containing a sgRNA cassette targeting the *Arabidopsis* (GL1) gene (AT3G27920) at two target sites. The target sequences are 5'-GGAAAAGTTGTAGACTGAGA-3', and 5'-GCAGTGATGAACAATGACGG-3' (complementary strand). The disruption of the GL1 gene produces visible phenotypes of partially or completely glabrous plants (glabrous plants lack trichomes). The Cas9 gene (cCas9-05) in this vector was driven by the *Arabidopsis thaliana* elongation factor promoter. The vector also contains two selectable marker cassettes conferring Kan resistance and AmCyan florescence driven by the CMP-02 promoter and Glycine max UBI-01 promoter respectively. The vector was moved into the agrobacterium strain EHA101 and then floral dip transformed into the haploid inducer *Arabidopsis* plants.

The transformation protocol was as follows: In the morning we spread 24075 EHA101 RecA *Agrobacterium* obtained from plates to YPSpec100Kan50 plates. We cultured these in 28° C. dark for 24 hours. We prepared infiltration medium (4 L): ½ XMS salts (8.66 g), 1×gamborg's B5 vitamins (4 ml), 5% (W/V) sucrose (200 g), 0.044 µM BAP (12.5 mg-12.5 mlDMSO) 40 µL, followed by filter sterilization. We then added 250 µl 40 mg/ml AS (20 mg/L) and 25 µl Silwet L-77(50 µl/L) to 500 ml Infiltration media. Using a loop to collect the *Agrobacterium* and put in 50 ml tube with ~10 ml o the filter sterilization, we suspended the *Agrobacterium* until it produced 1 L with an optical density 600 of 0.54. We dipped the inflorescence shoot in to the suspension medium for 20-30 seconds and used the lid to cover the tray. We repeated this for a second time with another suspension of OD600 of 0.552.

About 4 weeks after transformation, approximately 100,000 self-pollinated seeds were harvested and incubated at 4° C. for two days vernalization, and then the seeds were sterilized by soaking in 70% ethanol for 1 minute and then soaking in 50% (V/V) bleach with 0.05% (v/v) Triton X-100 for a further 10 minutes, then washing the seeds in four changes of sterile water. The seeds were then placed on kanamycin (50 µg/ml) plates for germination-screening/selection in a plant tissue culture room (23° C. day, 24° C. night, 16 hours lighting). 38 positive transformants were identified because they were resistant to the kanamycin selection, and they were grown into seedlings before being transferred onto soil and sampled to test for the presence of the Cas9 T-DNA (assay #3049) as well as the status of the two guide RNA cut sites (assays #3321 and #3322). 10 single copy and 15 2-copy events were identified that had both alleles of GL1 mutated and that had a trichomeless phenotype. These plants were prioritized because they had shown evidence of Cas9 activity (by virtue of the mutated GL1 and the glabrous phenotype), they had the Cas9 transgene and they had the ZmCENH3 transgene by qPCR assay. These plants were induced to flower for a long period of time by keeping them in the following growth conditions: 16 hours light, 23° C. Day 20° C. night temperature, not >60% relative humidity.

At the same time as these haploid inducer plants that were transformed with the Cas9 construct were being identified, we were sowing and growing a population of *Landsberg erecta* (Ler) seed obtained from the *Arabidopsis* Biological Resource Center at Ohio State University (line #CS20). These are wild type seed and the sequence of the GL1 guide RNA target sites in CS20 match that of the guide RNA in our construct. We allowed both populations to flower and made about 2000 controlled crosses, using the wild-type Ler plants as the male pollen-donor, crossing onto the approximately 25 haploid inducers with the Cas9 construct, which was used as the female. We made up to 100 crosses per female, marking the crossed flowers with a black marker and removing flowers that we did not cross so as to limit the potential of harvesting self-pollinated siliques. In most cases, we emasculated the female flowers prior to pollination by removing the anthers with forceps, again to avoid contamination with self-pollinated seed, but in some cases this was not necessary because the anthers were young or mal-developed.

About 15 days we harvested the siliques which had developed a light brown color. Then we opened the siliques and planted the seeds in the soil. Then put them in the 6° C. (day and light), 8 hours day length, 200 umal/m2s lighting, 60% relative humidity growth chamber for 4 days. Then we transferred them to 16 hours light, 23° C. Day, 20° C. night temperature, not >60% humidity growth chamber for 7-10 days. We observed a high frequency of aborted seed in almost all of the siliques, averaging about 40-50% of the total seeds. This number of aborted embryos is very consistent with the performance of this haploid inducer material in published reports. Without wishing to be constrained by this theory, it has been speculated that the aborted seed is most likely caused by partial or complete genome elimination in the endosperm leading to endosperm imbalance and failure. This is a natural phenomenon in CENH3-type haploid inducer lines during outcross and is likely not connected with the presence of the Cas9 transgene. These aborted embryos do not germinate. Because of the steady and reliable rate of embryo abortion in every outcrossed silique, we ended up using the absence of that phenotype to screen away siliques that were accidental self-pollinations. That way we germinated siliques that had been outcrossed.

In total we recovered approximately 2000 germinated progeny, the majority of which were outcrossed. We identified the edited haploids via a combination of qPCR marker assays and/or phenotypic screening. The markers that we used to detect the edited haploids were as follows.

First, we looked for a "0" score for the ZmCENH3 assay. This indicates that the plant is a haploid because the maternal genome has been lost, and so the ZmCENH3 transgene, which is present in multiple copies of the mother haploid inducer plant, has also been lost. The diploids, in contrast, will be hybrids between the maternal and paternal genome, and will have a "1" or "2" or higher Taqman score for this assay, depending on the copy number of the mother plant. The key is that all diploids will show evidence of this transgene, but paternal haploids, having only the Ler genome, will not and will thus be a "0."

Second, we looked for a "0" score for the Cas9 assay, which indicates that it is non-transgenic. This can also be seen visually by using a fluorescent light and looking for the CFP fluorescent marker.

Third, we looked for a "0" score for one of the GL1 target site assays, which indicates that the plant has been edited. The diploid plants might show a "0," "1" or "2" for those assays, but the haploids either showed a "2" or a "0." The first of the two GL1 guide RNAs apparently had a much higher editing efficiency than the second, because assay 3321 had a high preponderance of "0"s and "1"s in the haploid inducer T0s, but 3322 had mostly "2"s.

Using these assays, we were able to identify unedited haploids (which were "0" for ZmCENH3 and Cas9, but had "2" scores for both GL1 target sites) and also edited haploids (which had a "0" for the ZmCENH3, Cas9 and GL1 (3321) assays). We were also able to identify diploid hybrids that had Cas9 (and often were edited at the GL1 sites) and diploid hybrids that did not have Cas9 (and often had one copy of GL1 edited (from the maternal parent) but not the other, and thus had a score of "1" for the GL1 assay. We were also able to identify several putative edited haploids because they had a score of "0" for the target site assay (3321), the ZmCENH3 (2298) and the Cas9 (3049). See Table 9 below for an example of progeny Taqman data from parent USR01424136 containing three putative edited haploids (plant 254 in well F2, plant 260 in well D3, and plant 261 in plant E3).

pollination of the fully-edited mother plant and production of null segregant, fully edited (and thus glabrous) progeny. The Taqman assays were able to detect and screen out these false positives, because they directly tested for the presence of not only the Cas9 transgene, but also the ZmCENH3 allele, which would certainly be present in any self-pollinated contaminating seed. We found several examples of self-pollinated seed that all came from one mother plant. The

TABLE 9

Progeny analysis from parent USR01424136.

| PLATE 1045 HI parent was single copy Cas9 Well | Plant ID | AtGL1-1 cut site 3321 | | AtGL1-2 cut site 3322 | | ZmCENH3 2298 | | Cas9 3049 | | Putative Haploid | Putative Edited |
|---|---|---|---|---|---|---|---|---|---|---|---|
| | | Raw Copy # | Copy# level | Raw Copy # | Copy# level | Raw Copy # | Copy# level | Raw Copy # | Copy# level | | |
| E2 | USR01424136 X Ler-253 | 0.06 | 0 | 0.87 | 1 | 4.30 | >2 | 2.93 | >2 | | X |
| *F2* | *USR01424136 X Ler-254* | *0.00* | *0* | *0.32* | *0 or 1* | *0.00* | *0* | *0.00* | *0* | *X* | *X* |
| G2 | USR01424136 X Ler-255 | 1.32 | 1 or 2 | 2.06 | 2 | 3.16 | >2 | 0.00 | 0 | | |
| H2 | USR01424136 X Ler-256 | 0.02 | 0 | 0.99 | 1 | 2.51 | >2 | 2.99 | >2 | | X |
| A3 | USR01424136 X Ler-257 | 0.04 | 0 | 0.87 | 1 | 2.40 | 2 | 2.84 | >2 | | X |
| B3 | USR01424136 X Ler-258 | 0.03 | 0 | 1.64 | 2 | 2.99 | >2 | 3.17 | >2 | | X |
| C3 | USR01424136 X Ler-259 | 0.03 | 0 | 1.21 | 1 | 5.28 | >2 | 5.28 | >2 | | X |
| *D3* | *USR01424136 X Ler-260* | *0.06* | *0* | *2.01* | *2* | *0.00* | *0* | *0.00* | *0* | *X* | *X* |
| *E3* | *USR01424136 X Ler-261* | *0.00* | *0* | *2.01* | *2* | *0.01* | *0* | *0.00* | *0* | *X* | *X* |
| F3 | USR01424136 X Ler-262 | 2.04 | 2 | 2.10 | 2 | 0.00 | 0 | 0.00 | 0 | X | |
| G3 | USR01424136 X Ler-263 | 1.36 | 1 or 2 | 1.25 | 1 | 0.00 | 0 | 0.00 | 0 | X | |
| H3 | USR01424136 X Ler-264 | 1.75 | 2 | 1.71 | 2 | 0.00 | 0 | 0.00 | 0 | X | |
| A4 | USR01424136 X Ler-265 | 0.00 | 0 | 1.67 | 2 | 3.06 | >2 | 3.16 | >2 | | X |
| B4 | USR01424136 X Ler-266 | 1.66 | 2 | 2.32 | 2 | 0.00 | 0 | 0.00 | 0 | X | |
| C4 | USR01424136 X Ler-267 | 2.09 | 2 | 1.94 | 2 | 3.99 | >2 | 0.00 | 0 | | |
| D4 | USR01424136 X Ler-268 | 1.47 | 1 or 2 | 2.08 | 2 | 6.34 | >2 | 1.51 | 1 or 2 | | |
| E4 | USR01424136 X Ler-269 | 1.95 | 2 | 1.76 | 2 | 3.19 | >2 | 0.00 | 0 | | |
| F4 | USR01424136 X Ler-270 | 1.92 | 2 | 2.17 | 2 | 4.28 | >2 | 0.02 | 0 | | |
| G4 | USR01424136 X Ler-271 | 2.02 | 2 | 1.85 | 2 | 4.31 | >2 | 0.00 | 0 | | |
| H4 | USR01424136 X Ler-272 | 0.00 | 0 | 1.71 | 2 | 1.65 | 2 | 1.12 | 1 | | X |

Simply by germinating seeds and sampling for qPCR Taqman analysis, we were able to identify 8 putative edited haploids. Edited haploids were also identified by phenotypic visual screening, and then confirmed later by Taqman assay. We screened for the edited haploids by looking for trichome-less, or glabrous, plants, which indicated that they did not have any wild-type alleles for the GL1 gene, and by looking for a lack of cyan fluorescent protein ("CFP") expression in the embryo or seedling root. This indicated that they lacked the Cas9 T-DNA. We observed several of these plants, and submitted them for Taqman assays. For three such plants that we identified phenotypically, we were able to confirm that they were truly edited haploids by the Taqman assays. We were aware of the fact that it is possible that some of these glabrous plants that lack CFP were false positives, either because the CFP was silent or because of self-pollination notes for that mother indicated that there was highly abundant pollen that may have resulted in some self-pollination. We excluded these progeny from the total analysis.

Figure 24:
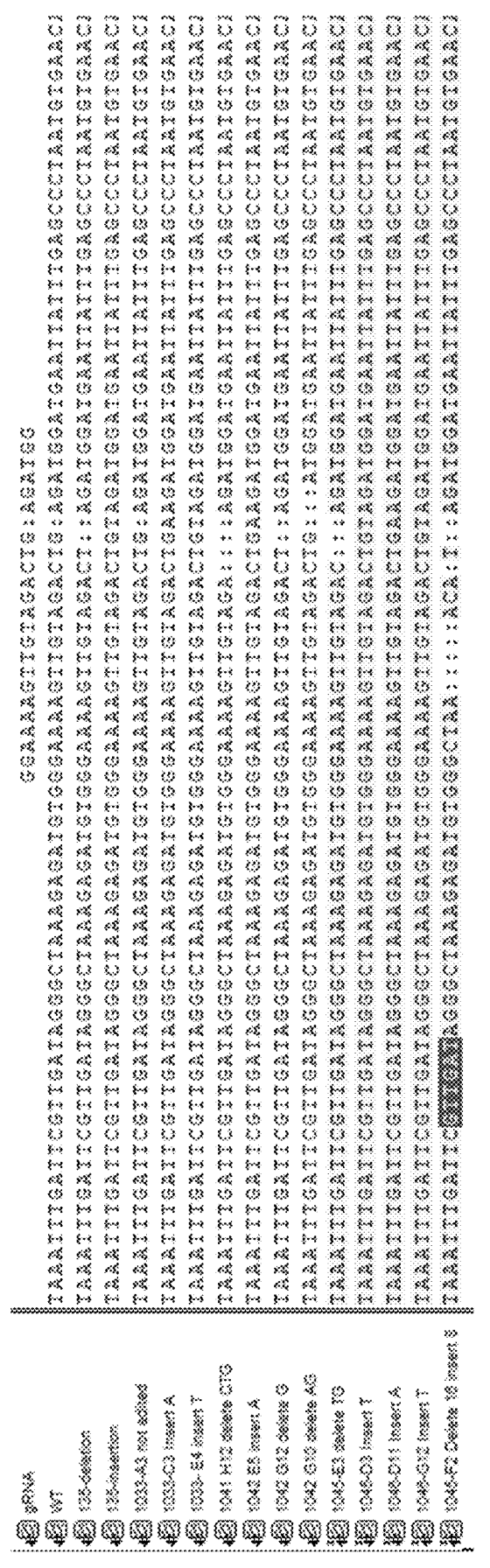

All of the putative edited haploids identified by Taqman assay were sequenced. We used PCR to amplify the edited alleles, and then subcloned and sequenced at least 8 colonies for each putative edited allele. See Table 10 for the sequence changes we found in the edited haploids at the first guide RNA (assay #3321) target site, as well as the Taqman data from the T0 parents. In total, we found 19 putative edited haploids, and we confirmed that the 3321 target sites had mutations in 11 of the 12 edited haploids that we attempted to sequence. Whether the other 7 would also have mutations will be confirmed upon sequencing. See the sequence alignment for these edits in FIG. 24.

TABLE 10

Taqman and sequence data from 19 edited haploids.

| Plate | Well | Plant ID | AtGL1-1 cut site 3321 | | AtGL1-2 cut site 3322 | | ZmCENH3 2298 | | Cas9 3049 | | Target site mutation | PA confirm? |
|---|---|---|---|---|---|---|---|---|---|---|---|---|
| | | | Raw Copy # | Copy# level | Raw Copy # | Copy# level | Raw Copy # | Copy# level | Raw Copy # | Copy# level | | |
| 1033 | A3 | USR01424135 X Ler-425 | 0.00 | 0 | 1.67 | 2 | 0.04 | 0 | 0.00 | 0 | wild type | Not done |
| 1033 | C3 | USR01424135 X Ler-427 | 0.21 | 0 | 2.43 | >2 | 0.01 | 0 | 0.00 | 0 | insert A | Yes |

TABLE 10-continued

Taqman and sequence data from 19 edited haploids.

| Plate | Well | Plant ID | AtGL1-1 cut site 3321 Raw Copy # | AtGL1-1 cut site 3321 Copy# level | AtGL1-2 cut site 3322 Raw Copy # | AtGL1-2 cut site 3322 Copy# level | ZmCENH3 2298 Raw Copy # | ZmCENH3 2298 Copy# level | Cas9 3049 Raw Copy # | Cas9 3049 Copy# level | Target site mutation | PA confirm? |
|---|---|---|---|---|---|---|---|---|---|---|---|---|
| 1033 | E4 | USR01424135 X Ler-437 | 0.08 | 0 | 2.04 | 2 | 0.00 | 0 | 0.00 | 0 | insert T | Yes |
| 1042 | E5 | USR01424136 X Ler-25 | 0.16 | 0 | 2.95 | >2 | 0.00 | 0 | 0.00 | 0 | insert A | Not done |
| 1042 | G10 | USR01424136 X Ler-67 | 0.00 | 0 | 2.19 | 2 | 0.00 | 0 | 0.00 | 0 | delete AG | Not done |
| 1042 | G12 | USR01424136 X Ler-83 | 0.00 | 0 | 1.86 | 2 | 0.00 | 0 | 0.00 | 0 | delete G | Not done |
| 1043 | B11 | USR01424136 X Ler-154 | 0.16 | 0 | 1.59 | 1 or 2 | 0.01 | 0 | 0.00 | 0 | Not done | Not done |
| 1045 | F2 | USR01424136 X Ler-254 | 0.00 | 0 | 0.32 | 0 or1 | 0.00 | 0 | 0.00 | 0 | delete 8 nt* | Not done |
| 1045 | D3 | USR01424136 X Ler-260 | 0.06 | 0 | 2.01 | 2 | 0.00 | 0 | 0.00 | 0 | insert T | Not done |
| 1045 | E3 | USR01424136 X Ler-261 | 0.00 | 0 | 2.01 | 2 | 0.01 | 0 | 0.00 | 0 | delete TG | Not done |
| 1046 | D11 | USR01431609 X Ler-111 | 0.09 | 0 | 1.59 | 1 or 2 | 0.02 | 0 | 0.01 | 0 | insert A | Not done |
| 1046 | G12 | USR01431609 X Ler-122 | 0.02 | 0 | 1.62 | 2 | 0.00 | 0 | 0.00 | 0 | insert T | Not done |
| 1046 | H12 | USR01431609 X Ler-123 | 0.00 | 0 | 0.00 | 0 | 0.00 | 0 | 0.00 | 0 | delete CTG | Yes |
| 0583 | D12 | USR01431603 X Ler-80 | 0.00 | 0 | 1.50 | 1 or 2 | 0.00 | 0 | 0.00 | 0 | Not done | Not done |
| 0584 | A9 | USR01431603 X Ler-137 | 0.00 | 0 | 1.87 | 2 | 0.00 | 0 | 0.00 | 0 | Not done | Not done |
| 0584 | C11 | USR01431603 X Ler-155 | 0.05 | 0 | 2.06 | 2 | 0.00 | 0 | 0.17 | 0 | Not done | Not done |
| 0584 | G11 | USR01431603 X Ler-159 | 0.09 | 0 | 2.15 | 2 | 0.00 | 0 | 0.00 | 0 | Not done | Not done |
| 0584 | C12 | USR01431603 X Ler-163 | 0.00 | 0 | 1.35 | 1 or 2 | 0.00 | 0 | 0.11 | 0 | Not done | Not done |
| 0584 | F12 | USR01431603 X Ler-166 | 0.00 | 0 | 1.65 | 2 | 0.00 | 0 | 0.00 | 0 | Not done | Not done |
| 0585 | H7 | USR01431603 X Ler-212 | 0.06 | 0 | 2.05 | 2 | 0.00 | 0 | 0.01 | 0 | Not done | Not done |
| Female Parent T0 Plants | | USR01424135 | 0.03 | 0 | 1.42 | 1 or 2 | 4.46 | >2 | 2.98 | >2 | ΔG, +T chimera | Diploid |
| | | USR01424136 | 0.03 | 0 | 1.13 | 1 | 3.59 | >2 | 2.76 | >2 | Not done | Diploid |
| | | USR01431603 | 0.14 | 0 | 1.25 | 1 | 2.48 | >2 | 3.42 | >2 | Not done | Diploid |
| | | USR01431609 | 0.18 | 0 | 1.1 | 1 | 4.75 | >2 | 5.57 | >2 | Not done | Diploid |

*delete 16 nt insert CTAAACAT

We further ran leaf samples from three edited haploid plants through ploidy analysis, along with three diploid controls (tissue sampled from the maternal parent plants), which showed that they were true haploids (FIGS. 18-23). This served to reconfirm their status as edited haploids.

In three parental lines where we were confident that there was no self-pollination contamination, we did not do any phenotypic pre-screening, but instead sampled all germinated progeny for Taqman analysis (Table 11). The three female parents for these progeny were USR01431603, USR01431609, and USR01431604. We found a haploid induction rate of about 9.7% calculated by dividing the number of progeny that lack the ZmCENH3 and Cas9 transgenes (59) by the total number of progeny sampled (605). Of the 59 haploids we found that 10 were edited. That means 16.9% of haploids, on average, were edited by the maternal Cas9, prior to elimination of the maternal genome. Without wishing to be constrained by this final number, this means that, using this system, as a percentage of total progeny, 9.7%*16.9%=1.64% of all germinated progeny were edited haploids.

TABLE 11

Haploid induction rate and editing rate data from three sets of progeny, each derived from a different SEDHI inducer female parent crossed by Landsberg erecta pollen.

| ID | Parent plant Cas9-05 | Parent plant cNpt2-10 | Total samples | Haploid number | Haploid rate | Edited Haploid | Edited Haploid rate |
|---|---|---|---|---|---|---|---|
| USR01431603 X Landsberg erecta | >2 | >2 | 230 | 36 | 15.65 | 7 | 19.44 |
| USR01431609 X Landsberg erecta | >2 | >2 | 123 | 14 | 11.38 | 3 | 21.43 |
| USR01431804 X Landsberg erecta | 2 | 1 | 252 | 9 | 3.57 | 0 | 0.00 |

The rate of CENH3* type haploid editing or other paternal haploid editing (using a maternal haploid inducer line) might be increased through the use of a promoter that drives the expression of Cas9 and/or the guide RNA to a higher level in the egg cell before fertilization and/or in the zygote cell during or after fertilization. An example of such a promoter would be the promoter for EA1 (EGG APPARATUS1) (GRMZM2G456746), although there are many other examples. One could also express the Cas9 in the context of an egg apparatus—specific enhancer (EASE), which is a 77-bp sequence that stimulates expression of adjoining genes in the egg cell or the very early zygote (see, e.g., Yang, et al. An Egg Apparatus-Specific Enhancer of *Arabidopsis*, Identified by Enhancer Detection, PLANT PHYSIOLOGY November 2005, 139 (3) 1421-1432; DOI: https://doi.org/10.1104/pp.105.068262).

VIII. Simultaneous Haploid Induction and Editing by Directly Modifying a Target Base in Genomic DNA Sequence.

Targeted mutagenesis of DNA sequence can also be achieved through direct conversion of one DNA base to another without requiring double stranded breaks (DSBs). For example, cytidine deaminase APOBEC1, adenine deaminase, and other enhancing components like Uracil DNA glycosylase (UDG) can be fused to Cas9 (A840H) nickase or nuclease-inactivated dead Cas9 (dCa9) to direct editing of DNA sequence without introducing double strand DNA breaks (Komor et al. 2016. Programmable editing of a target base in genomic DNA without double-stranded DNA cleavage. Nature doi:10.1038/nature17946; Gaudelli et al. 2017. Programmable base editing of A:T to G:C in genomic DNA without DNA cleavage. Nature doi:10.1038/nature24644; Komor et al. 2017. Improved base excision repair inhibition and bacteriophage Mu Gam protein yields C:G-to-T:A base editors with higher efficiency and product purity. Science Advances, Vol. 3, no. 8, eaao4774, DOI: 10.1126/sciadv.aao4774). This kind of base editor machinery can also be delivered through haploid induction line to induce base editing in target sequences directly in other varieties. For example, a guide RNA sequence, xZmVLHP-03 (5'-AGGCGTCGAGCAGCGAGGTG-3', SEQ ID NO: 28) is designed to target the cytidine deaminase base editor system to convert ZmVLHP gene exon 2 genomic sequence 5'-AGGCGTCGAGCAGCGAGGTG-3' (SEQ ID NO: 28) into 5'-AGGCGTTGAGCAGCGAGGTG-3' (SEQ ID NO: 29), thus changing the arginine codon CGA into a stop codon (TGA) in the coding sequence and causing premature termination of the protein sequence and functional gene knock-out. The C to T mutation is underlined. Similarly, chimeric nCas9- or dCas9-adenine deaminase base editing system can be used to mutate the coding region, splicing junction or promoter sequence of ZmVLHP or other genes to generate variants that have altered gene activity. Both cytidine and adenine deaminase are particularly useful for altering transcript splicing site since canonical splicing junction has 5'- . . . AG/GT . . . 3' sequence (or 5'- . . . AC/CT . . . 3' in the opposite strand).

IX. Simultaneous Haploid Induction and Editing by Allele Replacement with DNA Template Not only can in vivo haploid induction system be used to introduce protein, RNA or DNA for cleavage or conversion of target sequence, it can also be used to deliver DNA template for homology-dependent repair for precise sequence replacement in the target region in the form of transgenic DNA. The template DNA can be inserted into the inducer line genome carrying genome editing machinery such as CRISPR-Cas9 system, either in the same transgenic locus or different locus. When both Cas9-sgRNA and template DNA are present in the induced haploid embryos, cleavage of the target sequence will result in repair of the chromosomal break with the homologous transgenic DNA sequence as template. For example, for creating E149L mutation in ZmPYL-D gene (GRMZM2G048733_P02) (see WO16033230, incorporated herein by reference), DNA fragment containing donor sequence (5'-CCTTGGTG TTGCCGTCGGGGACGTCGACGACGAATGACAGGA TGACGAGCGTCCCTGGCCGGCCG TCGATGACCT-3', SEQ ID NO: 30) is used as repair donor. It should be noted that additional homology sequences can be added to flank this core repair donor sequence. One or more copies of this repair donor sequence are inserted into Cas9-sgRNA expression vector 23136 (SEQ ID NO: 31) which expresses guide RNA 5'-GTCGGGGACGTCGACGACGA-3' (SEQ ID NO: 32) to form allele modification vector pBSC23136-AMD. It should be noted that the potential PAM site has been removed from the donor DNA sequences so that the integrated donor sequence will not be cleaved by the Cas9-sgRNA complex expressed from pBSC23136-AMD. pBSC23136-AMD is transformed into haploid inducer line NP2222-HI to generate transgenic editing line. Transgenic editing-haploid induction lines are selfed to produce progeny lines homozygous editing loci. These homozygous lines are used to pollinate target elite maize inbred lines to induce haploid formation and also introduce modified alleles by expressed Cas9-sgRNA using donor DNA present transiently before pollen donor chromosomes are eliminated.

X. Inducing Haploids and Simultaneous Gene Editing in Rice

A HI-rice line is obtained. For example, the rice MATL ortholog, Os03g27610 (SEQ ID NO: 33, is mutated to create a new rice HI line. This line is transformed with a vector comprising a site-directed mutagenesis system for editing the rice genome, for example the CRISPR/Cas9 system.

The rice HI line is crossed with a different rice line, preferably an elite line, to produce at least one progeny haploid embryo. During the cross to produce at least one progeny haploid embryo, the HI parent rice plant also causes the genome editing machinery, e.g., Cas9 plus a guide RNA, to be delivered to the embryo. At that point, the editing machinery operates to edit the genome of the haploid embryo, and thus an edited, haploid progeny plant is obtained.

XI. Taqman Assays and Conditions.

Several assays are mentioned by number or by target name. Provided below is a table of assays mentioned above and the sequences of the relevant primers and probes. Conditions for PCR are standard for all assays and are as follows: Denature at 98° C. for 2 minutes; followed by 35 cycles of (i) denature at 98° C. for 30 seconds, (ii) anneal at 60° C. for 30 seconds, (iii)extension at 72° C. for 1 minute; followed by final extension at 72° C. for 10 minutes with a hold at 4° C. until ready. Assays are carried out at these conditions unless otherwise noted below.

TABLE 11

Assay primers and probes.

| Target | Cas9-in corn | | SEQ ID |
|---|---|---|---|
| Assay No. | 2540 | Sequence | NO: |
| Forward Primer | FE09340 | TTGTGCTGCTCCACGAACA | 39 |
| Reverse Primer | FE09341 | GCCAGCCACTACGAGAAGCT | 40 |
| Probe | FE09342 | CTGCTTCTGCTCGTTGTCCTCCGG | 41 |
| Target | mat1 | | SEQ ID |
| Assay No. | 2827 | Sequence | NO: |
| Forward Primer | FE10299 | GCGGATGCTGGCACAGC | 42 |
| Reverse Primer | FE10300 | GGCATTGCTTCCTTCTCCG | 43 |
| Probe | FE10301 | CAGGGAGCGAGGTAC | 44 |
| Target | PMI | | SEQ ID |
| Assay No. | 1750 | Sequence | NO: |
| Forward Primer | FE07390 | CTGGTGGCCAACGTGAAGTT | 45 |
| Reverse Primer | FE07391 | GCTTCACGGGCTGGGTC | 46 |
| Probe | FE07392 | AGGCCAAGCCCGCCAACCAG | 47 |
| Target | MATL-WT | | SEQ ID |
| Assay No. | 2826 | Sequence | NO: |
| Forward Primer | FE10297 | GCGGATGCTGGCACAGA | 48 |
| Reverse Primer | FE10298 | GCATTGCTTCCTTCGCCA | 49 |
| Probe | FE10299 | CAGGGAGGTACGAACC | 50 |
| Target | TAV_4A | | SEQ ID |
| Assay No. | 3252 | Sequence | NO: |
| Forward Primer | FE11306 | GCGGCGAAGAAGCGAA | 51 |
| Reverse Primer | FE11307 | GCGGCGTCTCCAGCTTC | 52 |
| Probe | FE11308 | CCAGGAACTGCG | 53 |
| Target | TAV_4B | | SEQ ID |
| Assay No. | 3253 | Sequence | NO: |
| Forward Primer | FE11309 | AAGAAACGCCGGCTGAGT | 54 |
| Reverse Primer | FE11310 | ACCTTGCGGGGCGTT | 55 |
| Probe | FE11308 | CCAGGAACTGCG | 56 |
| Target | TAV_4D | | SEQ ID |
| Assay No. | 3254 | Sequence | NO: |
| Forward Primer | FE11309 | AAGAAACGCCGGCTGAGT | 57 |
| Reverse Primer | FE11311 | CCTTGCGCGGCGTC | 58 |
| Probe | FE11308 | CCAGGAACTGCG | 59 |
| Target | GW2-01 | | SEQ ID |
| Assay No. | 3065 | Sequence | NO: |
| Forward Primer | FE10799 | TGATCCTCGAGGCCAAGCT | 60 |
| Reverse Primer | FE10800 | AGGTCGAGGTCCCCTCCA | 61 |
| Probe | FE10801 | CCTGCTACCCGGGC | 62 |

TABLE 11-continued

Assay primers and probes.

| | | | |
|---|---|---|---|
| Target Assay No. | GW2-02 3095 | Sequence | SEQ ID NO: |
| Forward Primer | FE10991 | CGCGCCCTGCTACCC | 63 |
| Reverse Primer | FE10992 | GCGCGTGCTTACCAGGA | 64 |
| Probe | FE10993 | TCGAGGAGTGCCC | 65 |
| Target Assay No. | TaVHLP2-2A 3332 | Sequence | SEQ ID NO: |
| Forward Primer | FE11312 | CACCGATGAGCAGGCG | 66 |
| Reverse Primer | FE11313 | AGATACACCTTCCGGCCG | 67 |
| Probe | FE11314 | TTCCTCCCGGAAGC | 68 |
| Target Assay No. | TaVHLP2-2D 3333 | Sequence | SEQ ID NO: |
| Forward Primer | FE11312 | CACCGATGAGCAGGCG | 69 |
| Reverse Primer | FE11313 | AGATACACCTTCCGGCCAGT | 70 |
| Probe | FE11314 | CTCCTCCCGGAAGC | 71 |
| Target Assay No. | 3049 | Sequence | SEQ ID NO: |
| Forward Primer | FE10730 | CAAGTTTCTGGACAAGGAGATTCTC | 72 |
| Reverse Primer | FE10731 | AAGAATTCCCTTCTTAATAGCTGGAGA | 73 |
| Probe | FE10732 | CACGAGCACATTGCTAACCTTGCTGG | 74 |
| Target Assay No. | TaVHLP2-2B 3255 | Sequence | SEQ ID NO: |
| Forward Primer | FE11315 | TCACCGATGAGCAGGCA | 75 |
| Reverse Primer | FE11316 | ATACACCTTCCGGCCAGC | 76 |
| Probe | FE11317 | TTCCTCCCGGAAGC | 77 |
| Target Assay No. | 3321 | Sequence | SEQ ID NO: |
| Forward Primer | FE11540 | GATAGGGCTAAAGAGATGTGGGAA | 78 |
| Reverse Primer | FE11541 | CTTTGTTCACATTAGGGCTCAAATAA | 79 |
| Probe | FE11542 | TAGACTGAGATGGATG | 80 |
| Target Assay No. | 3322 | Sequence | SEQ ID NO: |
| Forward Primer | FE11543 | AAAACCACCGGAGAAGACGA | 81 |
| Reverse Primer | FE11544 | AGGTGTGGCGGCAGTGA | 82 |
| Probe | FE11545 | CACCGTCATTGTTC | 83 |
| Target Assay No. | Cas9-in Arabidopsis 3049 | Sequence | SEQ ID NO: |
| Forward Primer | FE10730 | CAAGTTTCTGGACAAGGAGATTCTC | 84 |
| Reverse Primer | FE10731 | AAGAATTCCCTTCTTAATAGCTGGAGA | 85 |
| Probe | FE10732 | CACGAGCACATTGCTAACCTTGCTGG | 86 |

TABLE 11-continued

Assay primers and probes.

| Target Assay No. | ZmCENH3 2298 | Sequence | SEQ ID NO: |
|---|---|---|---|
| Forward Primer | FE08737 | GCGACGCCGGAAAGG | 87 |
| Reverse Primer | FE08738 | TGGCGTGGTTTCGTCTTCTTA | 88 |
| Probe | FE08739 | AAGAGCGGCGTCTGGAGGTGACTCA | 89 |

| Target | GL1 3321 target site (PCR) | Sequence | SEQ ID NO: |
|---|---|---|---|
| Forward Primer | 3321F | AACCGCATCGTCAGAAAAAC | 90 |
| Reverse Primer | 3321R | TCAACTTAACCGGCCAAATC | 91 |
| Annealing Temp. | 60 °C | | |

| Target | VLHP2-2A target site (PCR) | Sequence | SEQ ID NO: |
|---|---|---|---|
| Forward Primer | FE4117 | CATCCCTTCTCTTCCCTCCTG | 92 |
| Reverse Primer | FE4118 | GCCAGTGTGAGTGTGTATGAGCA | 93 |
| Annealing Temp. | 61 °C | | |

| Target | VLHP2-2B target site (PCR) | Sequence | SEQ ID NO: |
|---|---|---|---|
| Forward Primer | FE4120 | CATCGTTTTCTCCCCTCCTCA | 94 |
| Reverse Primer | FE4121 | ACTGATATGCACGGCGCCA | 95 |
| Annealing Temp. | 62 °C | | |

| Target | VLHP2-2D target site (PCR) | Sequence | SEQ ID NO: |
|---|---|---|---|
| Forward Primer | FE4121 | TGCAGTAGCTTCATTTTCACCG | 96 |
| Reverse Primer | FE4122 | AGGAATTGATATGTACGCCCGT | 97 |
| Annealing Temp. | 61 °C | | |

XII. Use of Codominant Markers for Haploid Testing.

The invention includes methods of testing a haploid plant progeny, e.g. an edited haploid, for the presence of the inducer parent's genomic material. In one embodiment, the method comprises isolating a nucleic acid from the edited haploid progeny, and detecting in the nucleic acid the presence of a plurality of codominant markers. As used herein, codominant markers are markers where the two parents have different alleles at a genetic locus. For example, one parent is a "G" at one locus and the other parent is an "A" at the same locus. The markers will create a distinct haplotype for the first plant, which is the haploid inducer parent, and a distinct haplotype for the second plant which is the source of genomic DNA in the haploid progeny. Haploids may be obtained, for example, by any of the methods described above.

Any number of codominant markers may be used, for example, the plurality of codominant markers include of at least 5, at least 10, at least 15, at least 20, at least 25, at least 30, at least 35, at least 40, at least 45, at least 50, at least at 55, at least 60, at least 65, and at least 70 markers. Table 12 provides 74 codominant markers to distinguish between NP2222 and B14 genetics following a cross (marker position identified using brackets), for illustrative purposes, but other may prefer more or less. Similarly, it should be clear that those of ordinary skill in the art may design their own codominant markers as desired. SEQ ID NOs: 99-173 represent the sequence when the male line (inducer line NP2222) is detected. SEQ ID NOs: 474-548 represent the sequence when the female line (inbred line, B14) is detected. The SNP position is indicated by brackets.

TABLE 12

| SEQ ID NO. | Sequence (Codominant Marker Position shown in Brackets) |
|---|---|
| 99 | GTGGAGAATGCAGAGCCATGGATCGCATTCATGGAGTAGCCACAGGGTTC[A]AAGTCAAAATCGCAGATCTCCATCTCGGGGATGATTTCAGAGATGCCAGAGAG |
| 100 | CGAGAGACCAGATCAACAGCTTCNGGNGGCATNCCTTTTGTGGAANACCTGAAAGATAAAATGTACAAAAAGTAAATTAGTAANACAACAGTAACAGTTTT[T]TTAGAGTATTGTAACAAAATGTAGAAAGATTTNNGCACCTTGTGCCATGGGTGTGCTTTGATTTGTGGGAACTTAAACTCTGTGTAATTTGGGTTCATGC |
| 101 | GTCTTCAAACTTGCAGTGACGAATTTCAATGTGCGTGATTGGAACCTTTTCGATGGTGGCCCTTGAACCAGAGTGGATAATCTCTCCAAAATCAGATGTA[G]AGCATCTGGTTGACATACGGAAGACTACTACCTGTTTTCTAGATTTACAATTCATTGTCAGAAATTATGCTATCTGACTTAATCTTCCAAATACTCCTAT |
| 102 | AGCGTGCCCATGCCGGAGCCGGTGCCGCCGCCGAGAGAGTGGCAGACCTGGAAGCCTGACAGGCGGGCATAAGATCCCAGTCAGCAAACCAA[A]CAACCTTGCAGAAATGGAAGACGAGACGAGACAAGCAAATAACCAACCAACCTTGCAGGCAGTCGCAGTTCTCGGCCTCCTTTCGCACCACG |
| 103 | TCGACCGCAGYGTGGAATGCACTGGCAACATYAATGCTATGATCCAAGCTTTCGAATGTGTTCATGATGTAAGTATATGTATACACTCTCAGCTACTTTC[A]TTCTCCAGGTTCCCTTCATCCAGACATGCATGTTCTAACYGCCGCSCTCGTGATCCAGGGCTGGGGTGTTGCYGTGCTGGTGGGTGTGCCRCATAAGGAC |
| 104 | GCAGTCGAGCGACGACTAGGAAGAGGAGGTGATCGATGAGAACGGCGA[A]ATTGTCAAGAGGAAGAAGAAGGGCCTTAAGGAGAAGGTCAAGGAGAAGCT |
| 105 | CGCTTCCACACCGGGAGCACATTGGACGCCGCGTCACAAGAAGGTATACACAGCATGGTCAAATTGTTTGCCTCTGTGGTCGTGCACTCGTGCATGCATGCGGACAGTGCCCATG[C]TTCAGTCATGTTGAGTTGAGTTCTGCTTGCCGGCCTGTGATGTTATTTGTTCTTGTTCAATCATATCGCAACTGGCAGTGCTGTCCGACGAGCGCGACGCCGCGGCCAGCGGCGG |
| 106 | GCGAGCACATACGTCGTGGACACATTCGAAGGCGGATATCATGGCGTTGA[T]GTTACCGGTGCACTCCACGCTGCGGTCGACGCCGCCGTTGGTCAGCTCAA |
| 107 | GGTTGTCACCTTTSARATCGAGTAGACTGCCATCAGTGCCATGACTTATTGGCAARTTGGAGTCTTTTAGGGTCCACTTGTTTTCCTTGAATTCTGCAAG[C]TGAATTTGCTTTTTTGTTGACTTCAATAMTCCAACCARTTCTCGAAYGACBRCCATGCYATTCTTCGCCTTGTGCTCTCTGAGATAGAGTGGAGTCATGA |
| 108 | GAATATTCATGGGGCGGTTACAAGATGGCAGGTGAGGACAGGCAGGAAGATGAACAAGACGACAAGAGCCGACGTAGTCGTCCAAGGATTCGATCAGGATATTCCTCCAAGATGACAAAGACCACAAAAATAGTTGCTTCTTCAGACGTGAACCAATTTTAAAACTAATTGCATAAGAGGTGATTAATTAGCAAGACAAAACTATTAGCTCTAGTTAGCTCTTGAAGGCATATAATAATATAGCATGATATGAACTAATTATGGGCTACATATTCAGAATTAATAGGTTTGTCTCGTCAATTAATCACTGTTTACTTGCACAGTAGAGCAAGAGCAAGCGCAGAGAACAGGGGCATAATAAACTGCTGCGGGTGGTGTACCTAAACCATGATCCAATATTACATCCCCTTATGCTGACTCCAGCAGTTCATCAAAACTTTACCC[A]TAAACAATGTTTTACACTATAGATTGCACTATTCGTAAAATAGAGTTTGAATATGAGTATGAATATGTATAAGCTGTTGGAGATAGTCTTAATACCTAGTTTAATTACTCTAGTATAAACCTCAATCTACATGTATTAAGGTAGATTGGAGTGTAACTTAAACTAATTTATATCCCAATCCACCTCAACATACATAACTATAGTCTATCGTACAATATCTAAATGAAGCCTAAAGACAACGTTTAGGATAAGGAACGTGTTAAACAGCCCAAAAGCATTATGACTCCATGAGTCCAACGGCCCAATAGCACGAGACATCGCAACATGCCCGCTCCCCAACAACTGTAGCACCTGATTTGATTGGTACAAAAATTATGATGACGTCCCATTTGCAGACATCGAGCATATTGCCCAATACCCTTGTTTGAAATTCAAAATTTGAAT |
| 109 | CATATGAAAAATCNCTGGTTCCGCTTTCGTTTTTTNNGCATACCTAATAACCAACCTCTGCATCTGCTTCAGGTTCGTACTTTTGAGGCGCAATGTGGGTCGTTGGCGCAGTATGGGATGAAGCACATGCGGTCCTTCGCAAACATCTGCAACGCTGGCATCCTTCCTGANGCAGTGTCGAAGGTCGCTGCTCAGGCTTGCACCAGCATTCCTTCCAACCCCTGGAGTTCTATCCACAAGGGTTTTAGCGCCTAAGAATCATAAGGTGAGGCGAAATATTTCAGCCGCTCCACCGCAACGAACTGGTTTACATTACCAGTCCTCAGGGGGGTCCTAGTTCTTGAACCANNNNNNNNNNNNNNNNNNNNNNNCTANTATAGCTGTTCCACCGTNNNTCCAGATTACATAGCTATGCNCAATTTCCGGTGTACATATNATAGTCGGAAAGTTATTTGGCAATTGTATTGGTCGTTGCTGTATATATTCCCTATAGTTTGTTAGCAGATGTGTAGTTTGTNATTCCATAAAAATGAAG[A]ACGCGTTACTGCTATTTCTATGTAGCCGACTGNT |

TABLE 12-continued

| SEQ ID NO. | Sequence (Codominant Marker Position shown in Brackets) |
|---|---|
| | GCTCATGTGAAACTTTACCCCATTCTTGTTGGGAAATGNACTATCCGTGGTG<br>GAATTCTNGCATCGAAAACAATTCCCGGGNGATCCTTTATTCAANGTGAANC<br>GTCTGTCNATTTCCATTTGAGGNTCGTATTATTTTCANTTGTAGGCTTGTGGC<br>TGGTGGCATCTGTTCCACTATGNTTNCAAACAAGNNCTATGGGCAGTTTCAT<br>TTGTTTCGTTCTCTATATNCCTGCAGCACCTACCCATGGAAAAAAT |
| 110 | TCNNGNANGNANGTGTTTATTTNACCTNCAGATTCCACCTTTGTTTCTTCTAT<br>ATTTACATGGTACCTTGNAGGTTCTTGCTCTTTGTGATNATCCGTGCCTCTNG<br>GAAAAAGAGGAAACCAAATCATTGTTCAGGTGAATATCNTCATCNTTCAATT<br>TACAGAACTCCTAAATTCANAGATCTAGTGNGTGATATCNTGCTATTTTNCC<br>CAACTTNAGTGTCAAAGCAACCTAAAAATTCTAAAAAATACAGAGATAGGG<br>CAATCT[G]TCTTCCTTTAAAATCAAAGCTGTGGCATTTTCTTTGAAATTAG<br>TAAACATTTATATAAATAGTAAAATNTCNTGGAGATCNNNNAGGTANTTAA<br>CNTTTTTCCCTTCAACTTCCACAGTAATTAAACATACCTAGGAANATAGTTTT<br>NGAGTTCTCATGTTTAATTGATNTGTTCATCANAAGAACCATTACNTCNNTG<br>CCTAATTATGCATGCCCTTTNATTTTTCCTAAAATTTCCCTTGATACCATTTC<br>AAGTTGCAAAGATGANTTTTTTTTNCTTCGTACTGTTTAATATTTTTGTTAGC<br>CATAAACTTTCAAAANTAGTTCAGTGTCCCATTTTATACATAAATNCTTATGT<br>GTACNTGATGGGTCGNCT |
| 111 | ATTTATGTGCCTYYAGGCGAACCACTTYCATCYGAACCTGGCGAGCCGTTGA<br>GAGTGAACGTGCTMTTCAAGCATATTCAGGCAATGCTGTCYGGCGACA[C]<br>GGCTGTCATCGCAGAGACTGGGGACTCGTGGTTTAACTGCCAGAAGCTGAA<br>GCTACCGGAAGGMTGTGGGTAAGCTCCTCTTTCGAANNNTGRTTTTGCT |
| 112 | GCACAGAACTCTCCCCTGTCCTTTCCTGGGGTTTTGGTTACGTGGTGGTAGTA<br>AGCTTGGATTTGCACATGGATAAAGTTGTTCTAAGCTCCGTGGGTTGCTTGA<br>GATCTTGCTGTTATTGCGTGCCGT[C]CTCACTTTTTTTGCAATCCGAGGAA<br>TGAATTTGTCGTTTACTCGTTTTGGTGGATTATTAGCGCGAAAAAAAAACTC<br>TTTTTTTTTTGTTCTTTTACTACGAAAAGCATCTTCTTGGATTTTGCTATCTTC<br>TTTTACTACGAAAAACTCTTGAGTCTAGGAATTTGAATT |
| 113 | GGCTATTGTACAACAACAAGGCGGCATTGCCATCRCAGTTGCAGTACTASCA<br>ATTGCCWTCGKGATTGCGGTTGCGGTGTTGCAGTAGTAGT[G]CTGTAGTA<br>CTATCAAGTGAGTCTGATGCATGAMCAGAGCAGAYGGAGTAGTTAAACGGA<br>GGCGCCGGTGAGCTTGCCGTTGACGATGTGGTGGTTGTCGT |
| 114 | RGACACGGAGGAGCAGTACGACTTCGACCCGCTGGACGACACCAAGACGTG<br>GCCGGAGGACCTGCTSCCGCTCMGSCCCGTGGGGAGGCTGGTGCTGGAC<br>[C]GGAACGTGGACAACTTCTTCAACGAGAACGAGCAGCTGGCGTTCGGSCCG<br>GGGCTGGTGGTGCCAGGGATCTACTACTCGGACGACAAGATGCTGCAGTG |
| 115 | ATGAACTATGAAGAACCCTATCACTTTGAGCTAGTCTCAAGTCCAAGCAAAG<br>AKAACAATTCACCAGTAGTAATGGAAAGAGAAGATTAGCAATAACT[A]TT<br>GTTTAGTGGAGCAATAAATATCTTTTTCAGTTTCAAGTMTTAAGAGAGAAAA<br>TGATAGATGTAAATGGCAAGCACCTACTGTACTTGACAACGTTAAA |
| 116 | ATAGTAAAAGGTTGGAATGTTAGTTGAAAACAAGGTGTAAGAAATGTATCA<br>TCTTTTGGACTGGACAACAGACCTGAAGTAGAAGCTTCTGGGTTTCCTCANA<br>NNTGGCCCTCAGCTTNNCNCCNAANGNNNNNNNNTCCTNTGAAACGAGGAG<br>TTTGTCATACAGTGNGGCAATGCCAGGATTACCCTTGGNGAACNCCATNTCC<br>NCCAGATCAATAGTCACCCTGAAAAATGGCCACTCATTGTACATTTCCTGGA<br>GCATGTGGAGGTTCCTGATGTCCTTCTGGAGGACAT[T]CTTGAATGCGGCT<br>CCAAATCCTAGCCAGACCGGGAGGTGGAACCGCGTNTGTGTCCAAGCAAAG<br>ATCCATGGGATTGCTCGGAGTGAGTCGATACCTCCGCTCGGCTTTCTCTTGG<br>ATGGCCTGCTTCCTATGTTCATCCTACCATACTCTGTTTCAGGGGTTGCCTGT<br>CAACACAAACATCACAAAGTAAATACTCGCTAAATGTAGGGGTCAAATCGA<br>ATGCTTCAGTAACCATTTTACTTAGGCTTGCAAAAGATAGTTTCTNCAGTAA<br>ATCATTGTGCTAGATTAATATTAAGTATCAGGTCAGANCTATTTCAAAAGTT<br>TGTTTTTGCATCTTATGTTACTGTAGTATCTCTAGACACCACTCAGGTGGNAG<br>CCTCNAGTACTGGTCTACNNNCATCTTTTNATGTTACTGTAGTATGGCAATC<br>GATGGGATCAAGGACTTACAAGGCGGAAATACTCGACAAAGCGTGGCTCTT<br>TGAAGACAATGGACCGATAT |
| 117 | ATGCTCTGGGGTCATCTCATGTCTGAATTCTGATCCAATTGAAGGGTTGTAG<br>CTTTAGTGCAATGTTGCTATNTTTATCATGCAAACCCCTTTACCTTTTGTAAC<br>ATGTCACCAAACAATTCATTTCCATTGGGTTGTTCAAGGATCATGTATTCCC<br>ATGCAATACAACNTGGAGAAGTCANGCTATTCCTTTACTATTTTACGTAGCA<br>GTGTTGGCCCACGATTATATTGTTTTAATATCTGTACTTCAGTTGAGGAAATT<br>ATATTTTCTGAGCGATCAGNTAATCACTTATTTTGGTTCCACTACTTTCCTAT<br>CAGGTTCTTGAGTCTCGGAATATTCAGCTTTTNTTGGGATATTTTGTGAGCNG<br>CATCAAAGAGGCTCCTACATCTGATGANTCAAGTAGCACAGTTACATACTCT<br>GAAGTTGACGGTGATCATAGGGAAACTAATTTTGGACCTTCAACCTGCTGAAA<br>GAGGCCTCAAAGGNCAGACNCTCGATGC[T]GATTTGGTGCTGTGGACAGT |

TABLE 12-continued

| SEQ ID NO. | Sequence (Codominant Marker Position shown in Brackets) |
|---|---|
| | GGGTTCAACATCTCAGATTCCNCGGTTACAGCCTCCTGATGCTCCCTANGTT ATTCCTCTGAATGGTCGNGGACAGGNGGAGACAGAGGAANNNNNNNNNNN NAAA |
| 118 | GCATAGCATACTGCATGCATGGCGCTGTTGCATTGCAGGTTGCAGCTGCAGN NNNNNCNGNNGACCCNGNTGNNNNCGTGCAGACTGNNNNNNNNNNNANNNN NNNNNNNCANNTNNNNNTANNNNNNNNNNGTNNNNNNNNNNNNNANNNNT ANATAAATNTANNNNAGTACANTTTTGCNNNNNCCTGCTGCCTGCCCTAGC ACTAGCAGCCAGGCAGCAGGGCTGGCGCCTNTGCTGCGGTGCATGAAAAGG CGACGAGCAAAGAAGGGGCGCGTGGAAAACTGCCCGTCGCGCGCTGCTACC GCCGTATGATTGGATCGAGTGGAGCGTGCGG[€/T]TGGCTTTTTGGATCCTTT CGGCACGTCAAGAAATAAAAANNTAACCAGTTCCTTTATTTCATCGGTCTCC GACTCTCCAAGGCGGCAGNNNCAGCAAGCTCTCGTAGCTNNGTGTAAAGCT GTGGAGCACACAGCAGCTGTGAGCCTGTGTTGGTGTTGCGAGCAAGAGCAN AGCTGGCAAGCGCAGCANAGGANTTGCACACGGCTTTATACGAATGAGCAG AACANAGGCATCTGTACATGANGACGGGCACGGCACACACAGGCCTTTG GTTCGTTGGANGANNGTGTATTGGCCTCCTACTATACTGANACTGNACACCC CTGGACATCCGCATGNCCGCATCTACTACGCATNGATAGCAGCGNTNTGTAA NNNNNNTGNANTGGNCTCNNANGCAGCCATGCCATGNNANCCAGNANNCC CACAGCAC |
| 119 | CACACATAATTACTCCMATCTTCTCAGTGGAGGTACATCAGCAACCGAGGTT TATAAAGGAACRCTYGAGGACAACACGATGGTGGCGGTGCATAGATTG[C/G] TCTACGAGGGCTCTGAGGAGGCGTTCATCAACGGAGGGATGGTYGTGTCCA AGATCGCCCACARGAACATCGTCAGAGTTCTGGGCTGCTGTCTGGAACC |
| 120 | TGGATCCATCACGGTAGAGCTGACNATGATATGTCCAAANGCTTCTGCTGCT AGTTGTTGGTCGTCCGCAAGAGACTTGACCCNACAGGTTTTTTTCGTTGGGC CTCAAGAACTGTAGGTGCATTTTCCATGGAGGGTTATGATGCTTAACCCCAC TCTGGTTTCTG[A]TGGCTAAAACATTCTCTCCAGTCGGCTTCTACCATGAG CCCTGGCACTTAGT |
| 121 | TGGCTTTATCCGTCCGGATGCCCCGCCATGTGCTCCTTGTCTCGGGACTCGG AGACAGNCTGACAGTCCTGGGTTNTTGTGCTAATGGCCNTGGTTAACTTACG TTAATCNTGCGCCTTATTATCATCATCTAGGTGTAATTACTTCCGT[C]TGTG CTAATCACCTCGTGATTGCCTGCAANNNNNNGGAACCCCAGCCCCCCNACCT TGCTGATGCCGTGCTTTTCTAGAGAAGTACCCTGCCGCGTCACGCTTCGTCCT CGCCTGCTTTGGATTCAACGGNTTTTTGGAGNCNNNGGCCA |
| 122 | GGTGCCGGAAGCCGCCTACAGCGGCCCGCCGCTCAGCTA[T]TACGTCACC AAGTTCCAGCCGGCGGTGGCTGCGCCGGCGCAGACCCTCGAGGCCCCCGCC CCCGNCGAGGCACAAGACGGCGCCGCCGCCNCCGTCGNGNCTCCGGAGGTA CCGGCACCGCAGCTGTCGT |
| 123 | RCATAAAAYATTGCAAATGCTGAGGAATATAAGCACATAGATACTTAGCAT GTGTCCGCCAGATGGAAATACTTTTACCATTCCCCCAC[A]ACTGGATTGCC AGAAAGGTCAATGCCTATGACACCTTGGTCCATYATTTCCAYGGCTAGATTA ACCTGGCCAGGGGAAAYAAATSATTTTGTGCAGATTC |
| 124 | ACGSYGTAAGGGCTCTACTGCATGTTCCTGAGGTTGCTCTTGACACCCTCAA TTTGCTGGAAATCATCCCCATCTRGGGACATAAATGGAGCAAAATTGC[T] GTGAGCTTGAACAAATGGAAGGTCACTGTGATGGTTCTGAATGCCATCAGG CAGATTCTGTGATGTGTTTGCTTCTGATGAAGAAGGGAAGTTCCAGCGG |
| 125 | TCTCAAGCTTATTTAGGTTGACTAAATTTGGAACATCCCCCGAGATGCTATT GCCGGCAAGCGCGAGCTCCGTAAGCATGGCAGCTTTGCCAATCGATGC[T] GGTATGGACCCCTTCAGCTGGTTACTCTGCAACCGAAGAACARTGAGGTTCG AGAATGAGTCAAGCCAGTCTGGCACACTTCCATTGAAGTAGTTACCAT |
| 126 | TACTAGCACACTTTGCCTCCTGATAGCTTGTACCATTGTGACCTTGTTTGGAT TTTGGGATTCCACCCAATGTCAAACATACCCAAACAGTGACCCGTKATCTTT TTCTTCGTATTTCTATGTCAAGCACTYAAGCATAACTCATACA[C]TTGCCT CTACAGGTGTTTCTGAAACACTAGTGCTCAATATGTCAACTCTGACATGGTC AGTTGTTAGCACTGTGGAAGGACGTGTTCCTCTTGCCAGTGAGGTATWTCTC TTGAGCGGTTGAGCAGCATTCCAGTTGTTAAGATG |
| 127 | GCACAGGTAACTCTTGCATGGCACCTGTCCTGAAACAAGTTTCGTGCTAACA AGGGAAATTATCCTTTTTCGTGGCACCAATATCTGTTTTCCATTCAATGATGT ACTGATGTGTTCACGGAGTCGTTACCTAGAAATCTCGCTTACTG[C]GACAT ATCACACCGAGCATCATTTTATATCTGCTGTGYGCCCTCCTTGCTAATGTAG GCACCTG |
| 128 | RYTKCAACMTGCGAGAARTARAAAATCACTAACCTTGGCTTTATCAAGTAT AGCAAGGTGAAMGCGAATGCCARGAAGAAGCAGAGTCCRCCGACGRTGAG GTACGCAAGGCCCAGAAAATCGTTCTTTCCCCCGAGCCAGGTTGCGGT[A] GAAAGCACCAGCTTCTTCTTGCCACCAAAGCTATAGGTGTTGTAGTTGTTGT |

TABLE 12-continued

| SEQ ID NO. | Sequence (Codominant Marker Position shown in Brackets) |
|---|---|
| | CCARCTGGACTGTGATTGTRTCGTTTTCCTTGAGATCAACATATATCCTTCCA TACAGCTTTCTGAATGTCGGAAGTGCTGYAGTCCGCATCCAAACA |
| 129 | GCGCTCGCCATGAATGCGCGTCGTCTCCRTTGGACCATCAACCATTTGCAAT TGATGAGGAGACGAGACAGGAGAAACGGCGAGGGCAGYAGTGTTCTGTAG CTGAAAGCTGCCGCGAATCGACTGCCATTATTGGACGCC[G]TCCCTTGCCC GACTGAGAATCGGGCGGCCGCGTGCACTGCACTRCMCTACCGCCGCCCGCC AGGCGCCAGCCRRCCTCGTGGTACAAAATTCATCCAGAATTCGCACGAGGC CACCAGCTCGGCTCCGGCCTGCGAGGATTTCAA |
| 130 | TCATGGAATTGCTTCAAACCCGAGAGCGGCAAGATAATAGACGAACGATCA GCTCCAGCCACCTGTAAGTACAATCACAAAYRGTAAGAGCAATGGATCACT YGTGGAGGCTTGTGTTTACAAATAATRGCCAACAACA[G]GTTACCTCAGA AATCCTCAAATAATGGCCCTGTTGTTGCTGCCCAGGTCGAAGAAGAACCTT TTCTGATCTGCCCTRATMACCTTAGACATACCCATGCCACTAATTTCTTCTTG AGGAGGCAGATCAACCAAGCGTTCSACATCTA |
| 131 | TAYAAGCAATATTAAGAGATGGAAATGTCGCCTCTGTACCACAAGTTAGTA AGTTACTAACTTGATTGTTAAAACACCATCGAAATGTGTGACATGTAGGACC TGGTCCCACATGTCAGACAAAGCCAATGCTATTTTGGCATTCATGTT[G]CA ATGTAGTGCTATAATTTCCACAAAAAAWACAAGACAGGTCAAATACTGYGT AAACATTCGATCCAAAAAACAGAGATGCTTTGTCATAAAAAATCTAGCCAA AAGAATTGGAGCTATTGAGATACAATGRA |
| 132 | ACGTTCCTTGTCGACCATTATCATTCGCTATCTATTTTTGAACGAACGCATTC GCTATCTATGGCCACATCTCCACTTCGTCTTTGCCGAAGCTTCAGTACGCGGT GCGGGTGTCTCCTGGTGTGTATGCTGTTCTTTTCTCGGTCCAT[A]TTATCCC CCGTTTGACGCGCCTCTGTCAATCTGCTGTACTGTGAATTTTATTTGACGTGC ATAAATYATTCTGGAAACGCTCTTGGTACGTCACGTACCTYGAGAA |
| 133 | ATCSGGCACCTGATCCWGAATGTGAGWCSGAGTGCGACCTATACCCGTCCC CAACCGCCCCCATTGAATCCACCGGTGAATCTATCGCTCCGCCACCACGAGG CCCTATATTAACTCCACAGCATCCATGTGTCCGAG[T]CTGTCTGTATACCT GTCACTCACGCTACCGCCGTGCCGATCGTTCGTTCCTTCCCTCCCTTCGCGGG CCGCGCGCCTATKWTWTTTACTACTSTATTCRTATCATTATAYTKTTTGGTTT CCWTCCCK |
| 134 | TTCTCGTAATCTCTATGGAAATTRCCRTTACTAGAGATAAATGGCATCCTTGC AATGTCCCAAATTCTCACCGAAGAACACAAGKAAAAGARAAGAAAATATTG AGCAAGCACAGCACAGGCAGGCAGCATGAATCCACACAGAACCA[G]TGG TTTTTAGCACAGYASGYTGACAGCCAAGGGTTACAGTACATAATCAGACGG GGCAACACGAACGAAGCAGCCGCATCARCAGCAGCCTASAAACCCATTAATT GACACACAGCGTATATATATATATATRTAGTACTTGTCTTTTAGC |
| 135 | AAGTCCAGATGACTTTCAGAAAGAAAATCGAGAACTTCAGACACCTTCTGA CCGCTGAAGCACGAACGACAATGGCCATAC[T]GCACGATGTTGCACGTTT YGTAGAAGTTTGTATCTTCGTTAAAAATTATAGCAGTACAAATSATAGCRCA TTCTGTAGGTGTAGGATACAGTAACACAGCAGCAGAACATCAAACCCRTCTC CTGCCAGGCTCTGAGCAACGCCAAAGC |
| 136 | CCRTRCAACATTAGSTCGTTYTGTTTCTATTTSTTGACCAAGACATGGTTGYT GTTCTGATGGCAGATTTGAACCTGACATGCTTGCYTTTTCTGGGTGCTATTAT GGTGGTGGAGAAAAGGAGAGGAGAGAATTAGCTGCAATTCGCAG[A]CGA TGGAGAACCTTGCATGTACAAGCTGTGTGATGTGTAATCATTACTCGCTTAC TGAGATAGAATTAYCTTTTGCTAAAAGTTTTCATATTCTAGATACGTGACCC GGAGAAAGGAAGACGGCAAGGCAGGTGTCCACTAACTCCTGAG |
| 137 | NCGCGTGTTCGTGCGGATGCWAYKCATGCAGAGGYAGCARARCTAGCTAGY AAGCACGWACKYACGTAGCACATGATAAGAAGGCTGCRTTGAGACAGTAA GACGAAGAATGGCARGCAGAAGAGCACGTC[A]GCATGCTCCCCGCGGCTT ATAGCTTAGAGGCACTTGAATCCGTGGGCACKCTCTTGCCGCAGTGGTTGA GGATAGGCTGAGGTCGACSGGYAGGTTGAGCTTGATTCCKAGGACCTCTCC CTTGATGGCGGTGCAGAGGCACACGGCG |
| 138 | ATGGATGCTTYTGTAGCATTAAACGTGAGAGTTTAATCTSACCACAACAAGC ATGGGTGATCACAAGAAATACAAAACAGCCAACTAACCAAAMAWKATATT AGCAAATGCAACTTACTTATAACATGGCAACCAAACACAAACACATTG[T] GCACACTTATGCTGGCTTAGTCTATCCTGCATTAGACCCAATGCAGTGAATT GCTAGTGCAAGCAACCAATTGCTCCCGTAGTGTTTCCTTTTGCTTCTATGAAG GCTATGAACTGTCAGGGTTTATTCTAGTGATCTATTTATCTAYCA |
| 139 | TGGAAACCRTTAATAATTGAAGTTTTCTYAGTACAGRTCTGCATAGCATTGA ACTGGACAGCTTGCTG[C]GTTACTCTGTRTAASGAACGATCTACTGCTGAT CTGTACTGTTCCTTGATTTTTYYYYCWCTTTTCTTCTTTTGATGGCAAGCAGG ACTGAAGATAAGATGGCTGCCTTRCCATTGGCCACCGCAGAAGCATGTGAT GCTAATGCTG |

TABLE 12-continued

| SEQ ID NO. | Sequence (Codominant Marker Position shown in Brackets) |
| --- | --- |
| 140 | GGAAATCTTGACAAGGATATGGAGAGAAGGTTTAGCTACGCCCTAAGCAGA<br>GAAGACATCGAGAACGCCATACTCGGAGGACCTTAASCTGAACACATGGCC<br>AAGGGGCTCAKAGCTAGGAATTGCTTAGTCGAGGTTGGCACTGAAGAA[A]<br>TAATCGCTCCAGTGATCTGCGTGCTACCATTACGCCATTGTAAGAGCAAATG<br>GATCATGTGTCGAGAAATAATATTCATGAGCAATAATCTCGAACTAGGCTGG<br>AAATGTTGGAWGCCTCCTGGTGACATGCGYYTGGTTTGTTGGCMTC |
| 141 | MTAGGAAGGTCAAGGTGCCTTTGGACCCCGGCAGCAACTACACCTTCGACC<br>TGAGCTACTACCGCCACGTRCTCGCCACGGGCGGGCTGTTCCAGTCCGACGG<br>CAGCCTCCTGCACGACCCCGTCACCAGAGGCTACGTCGAGAAGGTGG[C]C<br>AAGGCGTCGTCGCCCGACGAGTACTACGCGGACTTCGCCRCGGCGATGGTC<br>AAGATGGGCCGCACCGACGTGCTTGTCGGCGATCATGGGGAGATCAGGCCA<br>ACGTGTGGCATTTTTGTTGACTAGGTTCAGGAKTGGGTTGAARATGC |
| 142 | GTCAACAAGCACCAGACTTTCCAGGACACTCGGTGCTTTTTCGTGGTCTCCA<br>CAGATGGATCCCAGGCAGAYTTCTCCTACCTGAAGTGCCTGGAGAACTTTGT<br>GAGGAAGAGCTACACGGAGGACGYSGACACATTCTGCATGAAGTA[C]TTA<br>AGGCCCCGTCGCAGGCAGGCACCACCAGCTGATGTTGGGACAGCATCAGGC<br>RCCCCGGATGAGGTTCCACCGTCAACCGCAGCTGAGACAGAGCAAGGCACT<br>CCTCCAGCCCCTCAGGCAGAGGTTCCRCAAGAGAYTTGG |
| 143 | ATTACACCWAACTTGTCCTTATAAGTTAGAAYTCCTACAATATTTATTAGAC<br>TCTGTAGGAGAATCTCTTCTAGATACAAACCCACATCCTTTACTGTAAAAAA<br>GGCCCATTGTTAGCTACAATGACTTAACAT[C]TACGGAGGGACCAAATCT<br>CTGGTCTGAAACCCAAACTTTCAAGGTTCACTAGGTTCGTCCACTGGCAGAT<br>AAAACAAATCCTCATTTAYGATCATAAGTTGACATACTGGACAAAGAATAC<br>TTGTAAGACGATCCCTTCTTATCTGATGA |
| 144 | AGTGTAGAGATACTCACAAGAACAATTTTGAACTGCCTTGCAGAGCCAGGT<br>ACCACGAATAAGTGTTCAACCTTACTCTCATGCCTCAATTTCAAGAACACCT<br>GAACACATTTGCTAAATGATGTAAGAAAAAAGTTGCCATCATGGTA[G]CA<br>GATACGAGGTGAGTAGCAACCTGGTGAGGTTTAAATGTGTGCCCMAGCGGT<br>GTGSTTAGTTGAAAAGATAAACRCAGTTTCTGCAGATGGTTTGCAGAAAGAG<br>ACACTTTTGTATCTTTCAGAAGATCTAACCTGAAATGAAGCA |
| 145 | CCATGCGCTACTACCAGGCCGGYTCCTCGGAGATGTTYGGCTCCACGCCGCC<br>GCCGCAGCGCGAGGACACGCCCTTCCACCCGCGCTCGCCCTACGCCGCCGCC<br>AAGGTCGCCGCGCACTGGTACACSGTCAACTACCGCGAGGCCTACG[A]CG<br>TATTCGCCTGCAACGGCGTGCTYTTCAACCACGAGTCCCCGCCCGCGGCGA<br>GAACTTCGTCACGCGCAAGATCACGCGCGCCGTCGGCCGCATCAAGGTCGG<br>GCTGCAGACCAGGGTCTTCCTCGGCAACCTCTCGGCCGCCAGGGA |
| 146 | TACATACCTTGCAGCATGTCAAATGCACAAGGATGAAGAGAGAGGGAAAGT<br>TGCAGCAAAGAAACTTGTTGAGATGGAACCACAAAGCTCATCCACGTACGT<br>GTTCCTDTCAAGCTTRCATGCTGCGGCTGGTAACTGGGTTGAAGCCAA[A]<br>GTAGCCAGAGAAGCAATGCGAGAAAAAGGGGTGATGAAATTTCCAGGGTGT<br>AGTTGGATCACAGTGGGKAACAAACARAGYGTATTGTTGTACAGGACACA<br>CA |
| 147 | ACTCAAATTGAGTCAAGAAATGCTAAGGGAAAGCCCGTGAAACAATATAAT<br>CGAACTTTTACATTTTATTGATGTGGCCTTYTTAAAAATGACGCCATAAACC<br>WCTATACTGAAAACGGCCTCGGCGCTTAAACCAGTAGCATTCGTA[G]GTT<br>CATTTCTGATTTGGGACTTCAAACCAATAGTGTTTGAGACTCACAGGTTTAG<br>AACCGATTGGTGGCTGCCTTCAATCAAGAGCGAAACCAACATGTTATTGCCC<br>ACCTTAAAATCACAGATTTTGTATTATCGTGTACAATAAAAAT |
| 148 | YCAGATCATCACTGGAATCAACAGCAGTTCTCTGGTTCATTTGTTCAGATGC<br>TTCKGTGTCAACTGCTTCTGAAYGATGGTTTAAGCTTATAACATCATCARCA<br>TTTTTGTTAATTATTGCACTGTTCTCGTTGTCCTTTACCACGCTAT[C]CAAA<br>WTTTCTGGCTCCTCAGATACTACAAGATCAGATRTCTGCCCGTTCTGAGTAA<br>GAGTGGTTTCAGGACTGACACCCATACCTTGTGCAAGTGCTACATACCGAAG<br>TACTAGWTGCTTGTACGAATTCAATAGGCTCTCTACATCAGC |
| 149 | CTTTAGTAGCTAGTCYTATAGCTCATAGGTTCTCAGTTCGGTATATRTYGGTG<br>AYATATTTCATGAACTTASTTTTWAAMCMATTTAAAAMGCAMACGCAACA<br>ACGAAGGGAGTGATATTGACCATGGG[C]CTTTCGTAGCTTTTCAATCAAAC<br>GTCACATAAAAAAAGAAACAWCCAAAAGWTCATAATACACAGATTKRAAM<br>SKKKAGACAAAAATACGAGTACAAGACATTGGACCTTCAATWWTTTTTTTK<br>TGTTTTCTGAGACATGAAAA |
| 150 | TTGCACCACCCATAGTTTAAGAGGCAGTTGCTTTCACACACTTTATTTTGCAT<br>GGCACAGCCAACTGTCCCCATCATTCTAAACCAGGCTGCAACTGAGCCACTA<br>CAGAAACTGCTAATATTAGATATTCCAGCAAATAGTCTTGACACTAGAGTGC<br>TA[G]GTCCCTAAACACGAAAGACATTTGTCAGGAGACCCGTATTGAGTAC |

TABLE 12-continued

| SEQ ID NO. | Sequence (Codominant Marker Position shown in Brackets) |
|---|---|
| | TAGCAGAGTATACTACCGCTAGATATTCCAGTATAATCGTGCAGCAGCTCCG GTCAATGGCAGTGGCACTTGAAGTCTGCAACCTCAGCCAACAGATCCACAT GAGAACCAAC |
| 151 | TACACTATACTAATTAGAATGTCTGGAAAGGCTGGGAAGACCACTAAATTTG TCTCATTKTTGGAGGAAATGGTGTCCRAAGGATGTGTTCTTARTCTGATTGCT TATAATACTGTTATTGAGGCTCTTGGTAAGAACAAGATGGTTGAC[G]AGG CGATTTTTATGCTTTCTAAAATGATTGAGAGTGACTGTCGGCCCAATCAATT CACATATAGCATTATGCTGGATGTTTTATCAACAGGGGGACAACTCCACAGG TTGAATGAGATTCTAGATATTTGTA |
| 152 | CCTTTCTCCAGTTGGTAATATGCTTCATGTAAGGTACCTGAA[G]GTGGTAA GCRACATGATAGTCAAACTCCCACTCATTATTCGAGGCCTGCGACACTTAGA GACACTCGAGGTGGATGCAGAARAAGTCGCTGTTCCACTGGATGTTTTCATC TTGAAGAGCCTGTTGCATCTCCGACTTCCGAGCAAGGCT |
| 153 | TGCATATGAGAAACTACAAGGTTGGCAGGGTCCTTTCCTGTGCCCGAGCTGT CATGAAAAGAAAGAAGCAATGGAAGGGAAACGCCGGCCAAAAGGTATCAT TAAATAGTATTTACCTGAACTACATTCTKTAGTTAACCCTCAGAC[A]GCTC ATTCGTTTCTGGGTTCCTATTTGTCTTTCCAGGATCTTCATCAAACGTCTTTG GTCACATGTGCTAGGCCTGCCTACCACTAAAGATTCTTTTATTGATTSTTAGC TGGAAATAATAGKCAGCCCATAACAATTCATTGGCTAGAA |
| 154 | AAGCACCCGCATGCAGACTTCCAAACTATCCAGTGTCCACAAATAGCAGTTT TGCAAACTAAATACATATATGAAATGATGACACAGGCCACCCAAACAACAA GCCCTAGAGAATCAGACCAACCAACCGAGCAATTCGCAGTGCTCCATATCTT CTAGCATTCACAACCTGACGAACG[T]TGTTGCCTTCCAGCGCCCCCAACAT CAATCGTATCAGGAAGATACCTGCAAAAGTTGGTAAAACATAGATCAAGTT ACACCACAAGGCTGCCTGCATGTATGATACATATATGTGAGCTATATACTAT TCAAACTTACATATCTTCTTCTGGCTCATTTTTTACAGCATTCCTCGCTATA |
| 155 | AGAYGCTACTCTGCTACCATTTTGAGAATCTATTGACAAGAACTTTACAGGA GGRGTCTCATCCCCAGGAGCCTTGCTGATAACTGGAGATGGAGAAGATATG CACATATCCACTCGTGAATGCYTTTTCCTGGACTTATTTCTGTCCTT[C]AGC AGTTGTTTTCCCTAGCAAACAAAAGGAGATACACATAGCATGAGAAAGAAG AAASAAACTGAAACATTYTATAATGAGAAAAAAACATGGGGAGTTGGGGAC AAAGCAACTCACCAATGCTTCTACAAATGTTTTGAACCTCCGA |
| 156 | TGCTTCTGTCGAATTGCTGCGGGCAGARCATGCTTTGGTGGYGGCTTTGCAG TGTGAAACGTTATGAATCTGAGAACCTCGATGCATGCYAGGGACAGGGAAT ACCTGAACAGGGGCCAAGATGACATGAACAGGACGCCGGA[C]AGCACGT GCACAACCTTCCTGCTCAAGCTCTGCCTTCATTGATGGCATGGATCAGTACA GAGTTCGGAAGCCAACGACGTGAACARCTGAACATAAGCAAATGTAATGGC CGTTCTAA |
| 157 | AGGTCGACAAGGCTGCTAGTAACATGTCTGAGCCGACATCAGGGGAGATGC AGGATGCTGCTTTCCAGTCTGACGAAGAGGAGGAAGATGAAGATGTTGATG AAACAGTATTCGGTCAAGATTCAGATTCGTCACARAATAGCGGCACCG[A] CGACGATGCAAAGTAGACTCACTGCTGGTATTCATCATTATGGTGATTGTAT TGTTTTTAATTAAATTGCCAAGCTTGATTTTTGTCAAGGCGACGYTGGAAGG TTGCACAGAATTTTGAYAGTGTCTCTGGTTTCATTTTGAAAGCACT |
| 158 | AGAAAACGAGGCCTTCGTCGTCTTAGCGCGCRGGGGCGTAGGACGGCGGCA GCGGCAGCCCCACGACCTTGCCGCAGCGGAGGGCGTTGTCGGGCATGTTGT ACTCGTCGCGCAGTGATCGCGCCGGCGAGACGACGCTGAT[G]TAGAACTG CTCCCCGAGGTAGTACCGCTCCCAGATGTTGGAATGCACGCTCCACATGCCC GCGTTGTCGAACGTCAGCATGATTGCCGTCCATGACCGCGGGTACACCTGGA TCGTGTGCCGGCTCAC |
| 159 | TTCTGGTACTTGCGGATCTCGCGCAGMGCCACSGTSCCGGGCCTGTACCTGT GGGGCTTCTTCACGCCGCCGGTCGTCGGCGCMGACTTCCTCGCCGCCTGCAA CRARAYAACAACCGCCGCCGCGTCAGCRCCGTCTTACAACGGGAAC[C]AT CGAGGGGATCGGAACAKCAGATCGGTACGGGTAGGTAGAGACGAACCTTGG TKGCGAGCTGCTTGCGCGGGGCCTTGCCTCCGGTGGACTTGCGGGCGGTCTG CTTCGTACGAGCCATCTTCTCCTCTCCTTG |
| 160 | CTGCGTTAGTTTCACCCCTTCTAGCTGCGAGTGAAAGAAACWTGATAACAG CTWSCTGCTAGTTTCTATGRYRGCCATCGAATCTGACATGGCTAYCTCCTGT GMCMACGCAGGTCCGCAGGTACTACCAGCCGAGGAAGAGCCA[C]CGGAC GGTGACGGCGGTGATCCACGGCGAGAAGGTGCCGCTGTACGGCGCCGGGG CGGCCTGACGCTGTCSACGAGCGCGGGCGGGGGSGCGGTGCCCCTGACGC |
| 161 | AGCACCACGATTCACACCTACACATATTCAGACACAAAATTGGGCAGCGAT GGGCATGGACATTTCATTGATAGATGGTATTTAGCTGCCTACTYTGGCATTT GATTCGAGCAGCGAAGCTTCAAGAGCTGCAGAATCGCTACAYATATT[T]C TGTGGGTACACATGCTTCTTGTTCTCCACTCGACCCAGATCATTGTGATGGA |

TABLE 12-continued

| SEQ ID NO. | Sequence (Codominant Marker Position shown in Brackets) |
|---|---|
| | CTACTAACTGSCAGTACAAAAGCAGACATCTATCAAACTTACACAAAAGGC GTGCACAACGAGAYAGYCTGCTTGCGCATCTCCAAGTCTAGTCTAG |
| 162 | AWWTTKKWAGYGCARRAATAAACAAGGCACTGTWRATTGTACAGAGCAA GCTCTCTGCATTTTTCAATGCCGCAGCATCTGCAACTGCAAGCAGAGTTTCT A[G]AGGCCAAGGCCGACTGTCCTGCCATCTCTCCTGCGGAGGCCTGCTAT GTAATGTTTCTCCAGGTTGGTGTCGAGCTCCTCCAGTTTCTTGGCTTCTTCCG CCGAGCTCCCGACCTTGTTCTCGACCGTGTTTAA |
| 163 | TCAATTTGTGATTTCATCCACAATTTCTTCATATGTGAGGAATGCCGCACRCA CTTCTATGAAATGTGTTCAARGTTTGGAAAAACTACTCTAGCCATATATTGC CACAGAAATCAASTGCATGTYTAAT[A]GTTACCGTTCACCTGTAGTGTATC AGTCCCCTTCAAATCTGCCCGTGACCTTGCCCTCTGGCTATGGRCCGCGCAT AACAAAGTTAACGAGAGGTTGATGAAAGAAGAAAAGGAGTTAGACAATGC TGATCCTTCATTTCCTAAGAT |
| 164 | TTGCATACAAACTTGATCMAAATGTTTRCAAMCCATGCTTGAACRRATATAC AAACCCGTTGYGGCAGGAACATYTTAGCTTWGKAMMMTYGYWVAGCAAC AATAGCTTCAATAGAGATTGTTGTAAGTGTAGAGTG[T]TGCTGCGATGGA RACTATGCAAATCACAAGGGATGGGAGAAGAGTGACATTCAGAAGGAGGTC CGTGCCGAGATAACCGGCTGCAGTAATCGTGGCATCTGCAACTACACGGGC CAACGTCCCGG |
| 165 | ACAAGTCCAAATCAAAGGTGTTGTCCCGCCAATGCTTACCCCCCATGSCYCC CCRAAATAGCATCTGAATCCATTTTTTTGTCYGATCTTTTTKKCTCCTCTTCT GACAGGGAAATGCTGCTTGAGTTGGACGAGGAACAGACTGGAAT[G]CAA ATGCACGTCAGGTTGCAAATTCTTATGTTRWTTTTTGKGGCCTATCARTRC ACAGTACTCATAGCATGACAAATGGCGTTGCAGGTTTTGGTTTTTACCSGTTT TGGTTTCC |
| 166 | AACCTCGACTCCACTATAASTGCAGGACGCACGRCAYGCACAACTGAAACA TCCGGACCAACAGGCAGAGTAGTAGCCCAAAGGATGACCCGTCTCATGCAA AAACAGTCAGCTTGATAAACTTATCGAGAAGGCAACA[A]CGGYGCCCAA GTACTGGTTGAAATACAGAGCAGACATTGAAGTGCCAAAGAGGGGGG |
| 167 | GTCTAGAAAAGTCAAAACGTCATATACTTGGAACRGGAGTAGATATGACAA AAAGAGCATGCAAGTGATGTTCTTACAGAAGAATATATATATTTCATGGCAA GCTAGTACCTAAACTTCAGATGGAGTCTTTGCATCGATTGACAGGGC[A]T GCAACCCGGTCTTGAGCTCCTCCTGCAGGAGATCATAGACAGCCCTGTGCCT CTTRAGCAAGCTCTTCCCCTCAAACTCCTTGGACACCACCCTCACATTGAAA TGTGTCTCCCCATTGGTCCCAGCCACGCCAGCATGGCCCTTGTGG |
| 168 | ATTTTACCATACTGCATTCAAAGTTTTACAAGATTGGACATTATTAGTATAA AACATGAAACTTTTCAAGTGAACAASAACTATAARCAACGTCCGCAAGCGC AATCCACAGCTTGAGGTTACATTGTGAGTGTAGTAGA[A]AAACTAGGTGG TCCCAAATAGCACAAGATTATCCAAGCTACCCAGTTTTCTACGATTATGGGC ACRACCATAAGAGCATAGMAGTGCTTCGCATCCTGTTGCATTAAGAAAGTA GTATAGGCATCGGAGGTGCTGAATCTAAGCACACGG |
| 169 | TAAACCAGAYTAGATGCCACCTAGKTTTCTGACACAAATCAYGAACAAAAC ACGAGAAGAAAGCYAATCATACACGGATGAYGGATGGACTCAGCGGAGCC CTTATTTGCTACCATTCCTCATGTCTTATTGCAGAAATCCATCTATTGC[C]A CTCAACTTCAMTCAGTCTCTGGAACTCTGTATCAACAGGGGATGGGAAATGT GTCATGTTCAATGTTTAGCYCATGAAACATAGAAGACCMCATTAGAAGCTA TTATGTGCTTACATTTGATTTTTTATCCAAGACTCAAGTGTAT |
| 170 | RRHYTKRTGGAGGTCGGGGAAGAAACCCTAAGAACGATGTCTCACCAAAT TGATTCCTTCCGCCCGAGAGATTTAGAAGCTAGATCTGTCCAGATTAGTGG ATTGATAGGTTTTGTGAATTTGTCATTCTCCAACTAATCTACTTAC[A]GCC AGATTTTACATCAGACCTGATGAAACACTGTTTCCTTGACACGAAACTGGTG GACGCTGCCTTTGCATCAAGAATCAAGAAATTGATTTRCGTTTTATGTYTCT GGTAGCYCCAGACACCTCATACTCTCCTCGTTGCCTGTSATG |
| 171 | AACGGCTAAGAGTCAGGCGATTCTGTTTGTACAGAGACAATCGCAGCACTT GRMTGCTWCGCATGCGSTTCAGAGGGCCTTCAGCTCAGGCTTGACAGATCT AGTTTTGGYCGCCACGCYRCTCTTCGGCGAGCACTGYACTCTGCTGGC[A]T CTTTAGAAGCCCCGATGCTGTGACGATGTGGCCGGGTGGTAGATGTTGCGTT GGTGTTTTTTCCCTCGGGTGTCTGTGGT |
| 172 | AAACAANACTCAGTGGACTCGCNGAAANNNNATAATGAAAGGTGCTCCATC CATACCCATGAGAANGTTCCGATGCTCGCAGTCTCATGTTTCCCAGTCA[A] TCTTCTTTCATTTCCTTCTCCGTATGCACTAATATGCAGATCATGGCGCAGAG AAAGGTTCAGGATTGCTCTCTTGATCTCTTCAAACCCGCCGTCTTCG |
| 173 | AAAATTACTGAAGGCAGGTGGGTTGCAGTTGTGTGTTCGTTACTGTTTACTG TAWYATGTCAAGCTGTCGGCTGCAATTTCTTTGCTGGCAAGCCGCAGGCACT |

TABLE 12-continued

| SEQ ID NO. | Sequence (Codominant Marker Position shown in Brackets) |
|---|---|
| | GGTGAAGTGCTGATAAATACATCATATTCTGTTGACCTGTGAAGAA[A]CT TGTTCWAGGTRGATTCCATTGTACTAGCTCTGTTGCYCAGCATCTCCTTGTTT GGGAACATTAACAACCAGCYCTCRMCCCTCAANNNNNNNNNNNNNNNNNNN NNNNNNNNNNNNNNNNNNNNNNNNNTAAAATAGTCGCATCATGTA |
| 474 | GTGGAGAATGCAGAGCCATGGATCGCATTCATGGAGTAGCCACAGGGTTC[G] AAGTCAAAATCGCAGATCTCCATCTCGGGGATGATTTCAGAGATGCCAGAG AG |
| 475 | CGAGAGACCAGATCAACAGCTTCNGGNGGCATNCCTTTTGTGGAANACCTG AAAGATAAAATGTACAAAAAGTAAATTAGTAANACAACAGTAACAGTTTT[C] TTAGAGTATTGTAACAAAATGTAGAAAGATTTNNGCACCTTGTGCCATGGG TGTGCTTTGATTTGTGGGAACTTAAACTCTGTGTAATTTGGGTTCATGC |
| 476 | GTCTTCAAACTTGCAGTGACGAATTTCAATGTGCGTGATTGGAACCTTTTCG ATGGTGGCCCTTGAACCAGAGTGGATAATCTCTCCAAAATCAGATGTA[A]A GCATCTGGTTGACATACGGAAGACTACTACCTGTTTTCTAGATTTACAATTC ATTGTCAGAAATTATGCTATCTGACTTAATCTTCCAAATACTCCTAT |
| 477 | AGCGTGCCCATGCCGGAGCCGGTGCCGCCGCCGAGAGAGTGGCAGACCTGG AAGCCTGACAGGCGGGCATAAGATCCCAGTCAGCAAACCAA[G]CAACCTTG CAGAAATGGAAGACGAGACGAGACAAGCAAATAACCAACCAACCTTGCAG GCAGTCGCAGTTCTCGGCCTCCTTTCGCACCACG |
| 478 | TCGACCGCAGYGTGGAATGCACTGGCAACATYAATGCTATGATCCAAGCTTT CGAATGTGTTCATGATGTAAGTATATGTATACACTCTCAGCTACTTTC[C]TTC TCCAGGTTCCCTTCATCCAGACATGCATGTTCTAACYGCCGCSCTCGTGATCC AGGGCTGGGGTGTTGCYGTGCTGGTGGGTGTGCCRCATAAGGAC |
| 479 | GCAGTCGAGCGACGACTAGGAAGAGGAGGTGATCGATGAGAACGGCGA[G] ATTGTCAAGAGGAAGAAGAAGGGCCTTAAGGAGAAGGTCAAGGAGAAGCT |
| 480 | CGCTTCCACACCGGGAGCACATTGGACGCCGCGTCACAAGAAGGTATACAC AGCATGGTCAAATTGTTTGCCTCTGTGGTCGTGCACTCGTGCATGCATGCGG ACAGTGCCCATG[A]TTCAGTCATGTTGAGTTGAGTTCTGCTTGCCGGCCTGT GATGTTATTTGTTCTTGTTCAATCATATCGCAACTGGCAGTGCTGTCCGACGA GCGCGACGCCGCGGCCAGCGGCGG |
| 481 | GCGAGCACATACGTCGTGGACACATTCGAAGGCGGATATCATGGCGTTGA[C] GTTACCGGTGCACTCCACGCTGCGGTCGACGCCGCCGTTGGTCAGCTCAA |
| 482 | GGTTGTCACCTTTSARATCGAGTAGACTGCCATCAGTGCCATGACTTATTGG CAARTTGGAGTCTTTTAGGGTCCACTTGTTTTCCTTGAATTCTGCAAG[T]TGA ATTTGCTTTTTTGTTGACTTCAATAMTCCAACCARTTCTCGAAYGACBRCCAT GCYATTCTTCGCCTTGTGCTCTCTGAGATAGAGTGGAGTCATGA |
| 483 | GAATATTCATGGGCGGTTACAAGATGGCAGGTGAGGACAGGCAGGAAGAT GAACAAGACGACAAGAGCCGACGTAGTCGTCCAAGGATTCGATCAGGATAT TCCTCCAAGATGACAAAGACCACAAAAATAGTTGCTTCTTCAGACGTGAACC AATTTTAAAACTAATTGCATAAGAGGTGATTAATTAGCAAGACAAAACTATT AGCTCTAGTTAGCTCTTGAAGGCATATAATAATATAGCATGATATGAACTAA TTATGGGCTACATATTCAGAATTAATAGGTTTGTCTCGTCAATTAATCACTGT TTACTTGCACAGTAGAGCAAGAGCAAGCGCAGAGAACAGGGGCATAATAAA CTGCTGCGGGTGGTGTACCTAAACCATGATCCAATATTCATCCCCTTATGC TGACTCCAGCAGTTCATCAAAACTTTACCC[G]TAAACAATGTTTTACACTAT AGATTGCACTATTCGTAAAATAGAGTTTGAATATGAGTATGAATATGTATAA GCTGTTGGAGATAGTCTTAATACCTAGTTTAATTACTCTAGTATAAACCTCA ATCTACATGTATTAAGGTAGATTGGAGTGTAACTTAAACTAATTTATATCCC AATCCACCTCAACATACATAACTATAGTCTATCGTACAATATCTAAATGAAG CCTAAAGACAACGTTTAGGATAAGGAACGTGTTAAACAGCCCAAAAGCATT ATGACTCCATGAGTCCAACGGCCCAATAGCACGAGACATCGCAACATGCCC GCTCCCCAACAACTGTAGCACCTGATTTGATTGGTACAAAAATTATGATGAC GTCCCATTTGCAGACATCGAGCATATTGCCCAATACCCTTGTTTGAAATTCA AAATTTGAAT |
| 484 | CATATGAAAAATCNCTGGTTCCGCTTTCGTTTTTTNNGCATACCTAATAACC AACCTCTGCATCTGCTTCAGGTTCGTACTTTTGAGGCGCAATGTGGGTCGTT GGCGCAGTATGGGATGAAGCACATGCGGTCCTTCGCAAACATCTGCAACGC TGGCATCCTTCCTGANGCAGTGTCGAAGGTCGCTGCTCAGGCTTGCACCAGC ATTCCTTCCAACCCCTGGAGTTCTATCCACAAGGGTTTTAGCGCCTAAGAAT CATAAGGTGAGGCGAAATATTTCAGCCGCTCCACCGCAACGAACTGGTTTAC ATTACCAGTCCTCAGGGGGGTCCTAGTTCTTGAACCANNNNNNNNNNNNNNN NNNNNNNNCTANTATAGCTGTTCCACCGTNNNTCAGATTACATAGCTATGC NCAATTTCCGGTGTACATATNATAGTCGGAAAGTTATTTGGCAATTGTATTG GTCGTTGCTGTATATATTCCCTATAGTTTGTTAGCAGATGTGTAGTTTGTNAT TCCATAAAAAATGAAG[G]ACGCGTTACTGCTATTTCTATGTAGCCGACTGNTG |

TABLE 12-continued

| SEQ ID NO. | Sequence (Codominant Marker Position shown in Brackets) |
|---|---|
| | CTCATGTGAAACTTTACCCCATTCTTGTTGGGAAATGNACTATCCGTGGTGG<br>AATTCTNGCATCGAAAACAATTCCCGGGNGATCCTTTATTCAANGTGAANCG<br>TCTGTCNATTTCCATTTGAGGNTCGTATTATTTTCANTTGTAGGCTTGTGGCT<br>GGTGGCATCTGTTCCACTATGNTTNCAAACAAGNNCTATGGGCAGTTTCATT<br>TGTTTCGTTCTCTATATNCCTGCAGCACCTACCCATGGAAAAAAT |
| 485 | TCNNGNANGNANGTGTTTATTTNACCTNCAGATTCCACCTTTGTTTCTTCTAT<br>ATTTACATGGTACCTTGNAGGTTCTTGCTCTTTGTGATNATCCGTGCCTCTNG<br>GAAAAAGAGGAAACCAAATCATTGTTCAGGTGAATATCNTCATCNTTCAATT<br>TACAGAACTCCTAAATTCANAGATCTAGTGNGTGATATCNTGCTATTTTNCC<br>CAACTTNAGTGTCAAAGCAACCTAAAAATTCTAAAAAATACAGAGATAGGG<br>CAATCT[A]TCTTCCTTTAAAATCAAAGCTGTGGCATTTTCTTTGAAATTAGTA<br>AACATTTATATAAATAGTAAAATNTCNTGGAGATCNNNNAGGTANTTAACN<br>TTTTTCCCTTCAACTTCCACAGTAATTAAACATACCTAGGAANATAGTTTTNG<br>AGTTCTCATGTTTAATTGATNTGTTCATCANAAGAACCATTACNTCNNTGCC<br>TAATTATGCATGCCCTTTNATTTTTCCTAAAATTTCCCTTGATACCATTTCAA<br>GTTGCAAAGATGANTTTTTTTNCTTCGTACTGTTTAATATTTTTGTTAGCCA<br>TAAACTTTCAAAANTAGTTCAGTGTCCCATTTATACATAAATNCTTATGTGT<br>ACNTGATGGGTCGNCT |
| 486 | ATTTATGTGCCTYYAGGCGAACCACTTYCATCYGAACCTGGCGAGCCGTTGA<br>GAGTGAACGTGCTMTTCAAGCATATTCAGGCAATGCTGTCYGGCGACA[T]G<br>GCTGTCATCGCAGAGACTGGGGACTCGTGGTTTAACTGCCAGAAGCTGAAG<br>CTACCGGAAGGMTGTGGGTAAGCTCCTCTTTCGAANNNTGRTTTTGCT |
| 487 | GCACAGAACTCTCCCCTGTCCTTTCCTGGGGTTTTGGTTACGTGGTGGTAGTA<br>AGCTTGGATTTGCACATGGATAAAGTTGTTCTAAGCTCCGTGGGTTGCTTGA<br>GATCTTGCTGTTATTGCGTGCCGT[G]CTCACTTTTTTTGCAATCCGAGGAATG<br>AATTTGTCGTTTACTCGTTTTGGTGGATTATTAGCGCGAAAAAAAAACTCTTT<br>TTTTTTTGTTCTTTTACTACGAAAAGCATCTTCTTGGATTTTGCTATCTTCTTT<br>TACTACGAAAAACTCTTGAGTCTAGGAATTTGAATT |
| 488 | GGCTATTGTACAACAACAAGGCGGCATTGCCATCRCAGTTGCAGTACTASCA<br>ATTGCCWTCGKGATTGCGGTTGCGGTGTTGCAGTAGTAGT[A]CTGTAGTACT<br>ATCAAGTGAGTCTGATGCATGAMCAGAGCAGAYGGAGTAGTTAAACGGAG<br>GCGCCGGTGAGCTTGCCGTTGACGATGTGGTGGTTGTCGT |
| 489 | RGACACGGAGGAGCAGTACGACTTCGACCCGCTGGACGACACCAAGACGTG<br>GCCGGAGGACCTGCTSCCGCTCMGSCCCGTGGGGAGGCTGGTGCTGGAC[A]<br>GGAACGTGGACAACTTCTTCAACGAGAACGAGCAGCTGGCGTTCGGSCCGG<br>GGCTGGTGGTGCCAGGGATCTACTACTCGGACGACAAGATGCTGCAGTG |
| 490 | ATGAACTATGAAGAACCCTATCACTTTGAGCTAGTCTCAAGTCCAAGCAAAG<br>AKAACAATTCACCAGTAGTAATGGAAAGAGAAGATTAGCAATAACT[G]TTG<br>TTTAGTGGAGCAATAAATATCTTTTTCAGTTTCAAGTMTTAAGAGAGAAAAT<br>GATAGATGTAAATGGCAAGCACCTACTGTACTTGACAACGTTAAA |
| 491 | ATAGTAAAAGGTTGGAATGTTAGTTGAAAACAAGGTGTAAGAAATGTATCA<br>TCTTTTGGACTGGACAACAGACCTGAAGTAGAAGCTTCTGGGTTTCCTCANA<br>NNTGGCCCTCAGCTTNNCNCCNAANGNNNNNNNNTCCTNTGAAACGAGGAG<br>TTTGTCATACAGTGNGGCAATGCCAGGATTACCCTTGGNGAACNCCATNTCC<br>NCCAGATCAATAGTCACCCTGAAAAATGGCCACTCATTGTACATTTCCTGGA<br>GCATGTGGAGGTTCCTGATGTCCTTCTGGAGGACAT[G]CTTGAATGCGGCTC<br>CAAATCCTAGCCAGACCGGGAGGTGGAACCGCGTNTGTGTCCAAGCAAAGA<br>TCCATGGGATTGCTCGGAGTGAGTCGATACCTCCGCTCGGCTTTCTCTTGGA<br>TGGCCTGCTTCCTATGTTCATCCTACCATACTCTGTTTCAGGGGTTGCCTGTC<br>AACACAAACATCACAAAGTAAATACTCGCTAAATGTAGGGGTCAAATCGAA<br>TGCTTCAGTAACCATTTTACTTAGGCTTGCAAAAGATAGTTTCTNCAGTAAA<br>TCATTGTGCTAGATTAATATTAAGTATCAGGTCAGANCTATTTCAAAAGTTT<br>GTTTTTGCATCTTATGTTACTGTAGTATCTCTAGACACCACTCAGGTGGNAGC<br>CTCNAGTACTGGTCTACNNNCATCTTTTNATGTTACTGTAGTATGGCAATCG<br>ATGGGATCAAGGACTTACAAGGCGGAAATACTCGACAAAGCGTGGCTCTTT<br>GAAGACAATGGACCGATAT |
| 492 | ATGCTCTGGGGTCATCTCATGTCTGAATTCTGATCCAATTGAAGGGTTGTAG<br>CTTTAGTGCAATGTTGCTATNTTTATCATGCAAACCCCTTTACCTTTTGTAAC<br>ATGTCACCAAACAATTCATTTCCATTGGGTTGTTCAAGGATCATGTATTCCC<br>ATGCAATACAACNTGGAGAAGTCANGCTATTCCTTTACTATTTTACGTAGCA<br>GTGTTGGCCCACGATTATATTGTTTTAATATCTGTACTTCAGTTGAGGAAATT<br>ATATTTTCTGAGCGATCAGNTAATCACTTATTTTGGTTCCACTACTTTCCTAT<br>CAGGTTCTTGAGTCTCGGAATATTCAGCTTTTNTTGGGATATTTTGTGAGCNG<br>CATCAAAGAGGCTCCTACATCTGATGANTCAAGTAGCACAGTTACATACTCT<br>GAAGTTGACGGTGATCATAGGGAAACTAATTTTGGACCTTCAACCTGCTGAAA<br>GAGGCCTCAAAGGNCAGACNCTCGATGC[C]GATTTGGTGCTGTGGACAGTG |

TABLE 12-continued

| SEQ ID NO. | Sequence (Codominant Marker Position shown in Brackets) |
|---|---|
| | GGTTCAACATCTCAGATTCCNCGGTTACAGCCTCCTGATGCTCCCTANGTTA TTCCTCTGAATGGTCGNGGACAGGNGGAGACAGAGGAANNNNNNNNNNNN AAA |
| 493 | GCATAGCATACTGCATGCATGGCGCTGTTGCATTGCAGGTTGCAGCTGCAGN NNNNNCNGNNGACCCNGNTGNNNNCGTGCAGACTGNNNNNNNNNNANNNN NNNNNNNCANNTNNNNNTANNNNNNNNNGTNNNNNNNNNNNNNANNNNT ANATAAATNTANNNNAGTACANTTTTGCNNNNNCCTGCTGCCTGCCCTAGC ACTAGCAGCCAGGCAGCAGGGCTGGCGCCTNTGCTGCGGTGCATGAAAAGG CGACGAGCAAAGAAGGGGCGCGTGGAAAACTGCCCGTCGCGCGCTGCTACC GCCGTATGATTGGATCGAGTGGAGCGTGCGG[C]TGGCTTTTTGGATCCTTTC GGCACGTCAAGAAATAAAAANNTAACCAGTTCCTTTATTTCATCGGTCTCCG ACTCTCCAAGGCGGCAGNNNCAGCAAGCTCTCGTAGCTNNGTGTAAAGCTG TGGAGCACACAGCAGCTGTGAGCCTGTGTTGGTGTTGCGAGCAAGAGCANA GCTGGCAAGCGCAGCANAGGANTTGCACACGGCTTTATACGAATGAGCAGA ACANAGGCATCTGTACATGANGACGGGCACGGCACACACACAGGCCTTTGG TTCGTTGGANGANNGTGTATTGGCCTCCTACTATACTGANACTGNACACCCC TGGACATCCGCATGNCCGCATCTACTACGCATNGATAGCAGCGNTNTGTAA NNNNNNTGNANTGGNCTCNNANGCAGCCATGCCATGNNANCCAGNANNCC CACAGCAC |
| 494 | CACACATAATTACTCCMATCTTCTCAGTGGAGGTACATCAGCAACCGAGGTT TATAAAGGAACRCTYGAGGACAACACGATGGTGGCGGTGCATAGATTG[C]T CTACGAGGGCTCTGAGGAGGCGTTCATCAACGGAGGGATGGTYGTGTCCAA GATCGCCCACARGAACATCGTCAGAGTTCTGGGCTGCTGTCTGGAACC |
| 495 | TGGATCCATCACGGTAGAGCTGACNATGATATGTCCAAANGCTTCTGCTGCT AGTTGTTGGTCGTCCGCAAGAGACTTGACCCNACAGGTTTTTTTCGTTGGGC CTCAAGAACTGTAGGTGCATTTTCCATGGAGGGTTATGATGCTTAACCCCAC TCTGGTTTCTG[G]TGGCTAAAACATTCTCTCCAGTCGGCTTCTACCATGAGCC CTGGCACTTAGT |
| 496 | TGGCTTTATCCGTCCGGATGCCCCGCCATGTGCTCCTTGTCTCGGGACTCGG AGACAGNCTGACAGTCCTGGGTTNTTGTGCTAATGGCCNTGGTTAACTTACG TTAATCNTGCGCCTTATTATCATCATCTAGGTGTAATTACTTCCGT[T]TGTGC TAATCACCTCGTGATTGCCTGCAANNNNNNGGAACCCCAGCCCCCCNACCTT GCTGATGCCGTGCTTTTCTAGAGAAGTACCCTGCCGCGTCACGCTTCGTCCT CGCCTGCTTTGGATTCAACGGNTTTTTGGAGNCNNNGGCCA |
| 497 | GGTGCCGGAAGCCGCCTACAGCGGCCCGCCGCTCAGCTA[C]TACGTCACCA AGTTCCAGCCGGCGGTGGCTGCGCCGGCGCAGACCCTCGAGGCCCCCGCCC CCGNCGAGGCACAAGACGGCGCCGCCGCCNCCGTCGNGNCTCCGGAGGTAC CGGCACCGCAGCTGTCGT |
| 498 | RCATAAAAYATTGCAAATGCTGAGGAATATAAGCACATAGATACTTAGCAT GTGTCCGCCAGATGGAAATACTTTTACCATTCCCCCAC[G]ACTGGATTGCCA GAAAGGTCAATGCCTATGACACCTTGGTCCATYATTTCCAYGGCTAGATTAA CCTGGCCAGGGGAAAYAAATSATTTTGTGCAGATTC |
| 499 | ACGSYGTAAGGGCTCTACTGCATGTTCCTGAGGTTGCTCTTGACACCCTCAA TTTGCTGGAAATCATCCCCATCTRGGGACATAAATGGAGCAAAATTGC[C]GT GAGCTTGAACAAATGGAAGGTCACTGTGATGGTTCTGAATGCCATCAGGCA GATTCTGTGATGTGTTTGCTTCTGATGAAGAAGGGAAGTTCCAGCGG |
| 500 | TCTCAAGCTTATTTAGGTTGACTAAATTTGGAACATCCCCCGAGATGCTATT GCCGGCAAGCGCGAGCTCCGTAAGCATGGCAGCTTTGCCAATCGATGC[C]G GTATGGACCCCTTCAGCTGGTTACTCTGCAACCGAAGAACARTGAGGTTCGA GAATGAGTCAAGCCAGTCTGGCACACTTCCATTGAAGTAGTTACCAT |
| 501 | TACTAGCACACTTTGCCTCCTGATAGCTTGTACCATTGTGACCTTGTTTGGAT TTTGGGATTCCACCCAATGTCAAACATACCCAAACAGTGACCCGTKATCTTT TTCTTCGTATTTCTATGTCAAGCACTYAAGCATAACTCATACA[T]TTGCCTCT ACAGGTGTTTCTGAAACACTAGTGCTCAATATGTCAACTCTGACATGGTCAG TTGTTAGCACTGTGGAAGGACGTGTTCCTCTTGCCAGTGAGGTATWTCTCTT GAGCGGTTGAGCAGCATTCCAGTTGTTAAGATG |
| 502 | GCACAGGTAACTCTTGCATGGCACCTGTCCTGAAACAAGTTTCGTGCTAACA AGGGAAATTATCCTTTTTCGTGGCACCAATATCTGTTTTCCATTCAATGATGT ACTGATGTGTTCACGGAGTCGTTACCTAGAAATCTCGCTTACTG[T]GACATA TCACACCGAGCATCATTTTATATCTGCTGTGYGCCCTCCTTGCTAATGTAGGC ACCTG |
| 503 | RYTKCAACMTGCGAGAARTARAAAATCACTAACCTTGGCTTTATCAAGTAT AGCAAGGTGAAMGCGAATGCCARGAAGAAGCAGAGTCCRCCGACGRTGAG GTACGCAAGGCCCAGAAAATCGTTCTTTCCCCCGAGCCAGGTTGCGGT[C]GA |

TABLE 12-continued

| SEQ ID NO. | Sequence (Codominant Marker Position shown in Brackets) |
|---|---|
| | AAGCACCAGCTTCTTCTTGCCACCAAAGCTATAGGTGTTGTAGTTGTTGTCC ARCTGGACTGTGATTGTRTCGTTTTCCTTGAGATCAACATATATCCTTCCATA CAGCTTTCTGAATGTCGGAAGTGCTGYAGTCCGCATCCAAACA |
| 504 | GCGCTCGCCATGAATGCGCGTCGTCTCCRTTGGACCATCAACCATTTGCAAT TGATGAGGAGACGAGACAGGAGAAACGGCGAGGGCAGYAGTGTTCTGTAG CTGAAAGCTGCCGCGAATCGACTGCCATTATTGGACGCC[A]TCCCTTGCCCG ACTGAGAATCGGGCGGCCGCGTGCACTGCACTRCMCTACCGCCGCCCGCCA GGCGCCAGCCRRCCTCGTGGTACAAAATTCATCCAGAATTCGCACGAGGCC ACCAGCTCGGCTCCGGCCTGCGAGGATTTCAA |
| 505 | TCATGGAATTGCTTCAAACCCGAGAGCGGCAAGATAATAGACGAACGATCA GCTCCAGCCACCTGTAAGTACAATCACAAAYRGTAAGAGCAATGGATCACT YGTGGAGGCTTGTGTTTACAAATAATRGCCAACAACA[T]GTTACCTCAGAAA TCCTCAAATAATGGCCCCTGTTGTTGCTGCCCAGGTCGAAGAAGAACCTTTT CTGATCTGCCCTRATMACCTTAGACATACCCATGCCACTAATTTCTTCTTGA GGAGGCAGATCAACCAAGCGTTCSACATCTA |
| 506 | TAYAAGCAATATTAAGAGATGGAAATGTCGCCTCTGTACCACAAGTTAGTA AGTTACTAACTTGATTGTTAAAACACCATCGAAATGTGTGACATGTAGGACC TGGTCCCACATGTCAGACAAAGCCAATGCTATTTTGGCATTCATGTT[A]CAA TGTAGTGCTATAATTTCCACAAAAAAWACAAGACAGGTCAAATACTGYGTA AACATTCGATCCAAAAAACAGAGATGCTTTGTCATAAAAAATCTAGCCAAA AGAATTGGAGCTATTGAGATACAATGRA |
| 507 | GCTATCTATGGCCACATCTCCACTTCGTCTTTGCCGAAGCTTCAGTACGCGGT ACGTTCCTTGTCGACCATTATCATTCGCTATCTATTTTTGAACGAACGCATTC GCTATCTATGGCCACATCTCCACTTCGTCTTTGCCGAAGCTTCAGTACGCGGT GCGGGTGTCTCCTGGTGTGATGCTGTTCTTTTCTCGGTCCAT[C]TTATCCCC CGTTTGACGCGCCTCTGTCAATCTGCTGTACTGTGAATTTTATTTGACGTGCA TAAATYATTCTGGAAACGCTCTTGGTACGTCACGTACCTYGAGAA |
| 508 | ATCSGGCACCTGATCCWGAATGTGAGWCSGAGTGCGACCTATACCCGTCCC CAACCGCCCCCATTGAATCCACCGGTGAATCTATCGCTCCGCCACCACGAGG CCCTATATTAACTCCACAGCATCCATGTGTCCGAG[C]CTGTCTGTATACCTGT CACTCACGCTACCGCCGTGCCGATCGTTCGTTCCTTCCCTCCCTTCGCGGGCC GCGCGCCTATKWTWTTTACTACTSTATTCRTATCATTATAYTKTTTGGTTTCC WTCCCK |
| 509 | TTCTCGTAATCTCTATGGAAATTRCCRTTACTAGAGATAAATGGCATCCTTGC AATGTCCCAAATTCTCACCGAAGAACACAAGKAAAAGARAAGAAAATATTG AGCAAGCACAGCACAGGCAGGCAGCATGAATCCACACAGAACCA[A]TGGTT TTTAGCACAGYASGYTGACAGCCAAGGGTTACAGTACATAATCAGACGGGG CAACACGAACGAAGCAGCCGCATCARCAGCAGCCTASAACCCATTAATTGA CACACAGCGTATATATATATATRTAGTACTTGTCTTTTAGC |
| 510 | AAGTCCAGATGACTTTCAGAAAGAAAATCGAGAACTTCAGACACCTTCTGA CCGCTGAAGCACGAACGACAATGGCCATAC[A]GCACGATGTTGCACGTTTY GTAGAAGTTTGTATCTTCGTTAAAAATTATAGCAGTACAAATSATAGCRCAT TCTGTAGGTGTAGGATACAGTAACACAGCAGCAGAACATCAAACCCRTCTC CTGCCAGGCTCTGAGCAACGCCAAAGC |
| 511 | CCRTRCAACATTAGSTCGTTYTGTTTCTATTTSTTGACCAAGACATGGTTGYT GTTCTGATGGCAGATTTGAACCTGACATGCTTGCYTTTTCTGGGTGCTATTAT GGTGGTGGAGAAAAGGAGAGGAGAGAATTAGCTGCAATTCGCAG[G]CGAT GGGAGAACCTTGCATGTACAAGCTGTGTGATGTGTAATCATTACTCGCTTACT GAGATAGAATTAYCTTTTGCTAAAAGTTTTCATATTCTAGATACGTGACCCG GAGAAAGGAAGACGGCAAGGCAGGTGTCCACTAACTCCTGAG |
| 512 | NCGCGTGTTCGTGCGGATGCWAYKCATGCAGAGGYAGCARARCTAGCTAGY AAGCACGWACKYACGTAGCACATGATAAGAAGGCTGCRTTGAGACAGTAA GACGAAGAATGGCARGCAGAAGAGCACGTC[G]GCATGCTCCCCGCGGCTTA TAGCTTAGAGGCACTTGAATCCGGTGGGCACKCTCTTGCCGCAGTGGTTGAG GATRAGGCTGAGGTCGACSGGYAGGTTGAGCTTGATTCCKAGGACCTCTCCC TTGATGGCGGTGCAGAGGCACACGGCG |
| 513 | ATGGATGCTTYTGTAGCATTAAACGTGAGAGTTTAATCTSACCACAACAAGC ATGGGTGATCACAAGAAATACAAAACAGCCAACTAACCAAAMAWKATATT AGCAAATGCAACTTACTTATAACATGGCAACCAAACACAAACACATTG[C]G CACACTTATGCTGGCTTAGTCTATCCTGCATTAGACCCAATGCAGTGAATTG CTAGTGCAAGCAACCAATTGCTCCCGTAGTGTTTCCTTTTGCTTCTATGAAGG CTATGAACTGTCAGGGTTTATTCTAGTGATCTATTTATCTAYCA |
| 514 | TGGAAACCRTTAATAATTGAAGTTTTCTYAGTACAGRTCTGCATAGCATTGA ACTGGACAGCTTGCTG[T]GTTACTCTGTRTAASGAACGATCTACTGCTGATCT GTACTGTTCCTTGATTTTTYYYYCWCTTTTCTCTTTTGATGGCAAGCAGGAC |

TABLE 12-continued

| SEQ ID NO. | Sequence (Codominant Marker Position shown in Brackets) |
|---|---|
| | TGAAGATAAGATGGCTGCCTTRCCATTGGCCACCGCAGAAGCATGTGATGCT AATGCTG |
| 515 | GGAAATCTTGACAAGGATATGGAGAGAAGGTTTAGCTACGCCCTAAGCAGA GAAGACATCGAGAACGCCATACTCGGAGGACCTTAASCTGAACACATGGCC AAGGGGCTCAKAGCTAGGAATTGCTTAGTCGAGGTTGGCACTGAAGAA[G]T AATCGCTCCAGTGATCTGCGTGCTACCATTACGCCATTGTAAGAGCAAATGG ATCATGTGTCGAGAAATAATATTCATGAGCAATAATCTCGAACTAGGCTGGA AATGTTGGAWGCCTCCTGGTGACATGCGYYTGGTTTGTTGGCMTC |
| 516 | MTAGGAAGGTCAAGGTGCCTTTGGACCCCGGCAGCAACTACACCTTCGACC TGAGCTACTACCGCCACGTRCTCGCCACGGGCGGGCTGTTCCAGTCCGACGG CAGCCTCCTGCACGACCCCGTCACCAGAGGCTACGTCGAGAAGGTGG[T]CA AGGCGTCGTCGCCCGACGAGTACTACGCGGACTTCGCCRCGGCGATGGTCA AGATGGGCCGCACCGACGTGCTTGTCGGCGATCATGGGGAGATCAGGCCAA CGTGTGGCATTTTTGTTGACTAGGTTCAGGAKTGGGTTGAARATGC |
| 517 | GTCAACAAGCACCAGACTTTCCAGGACACTCGGTGCTTTTTCGTGGTCTCCA CAGATGGATCCCAGGCAGAYTTCTCCTACCTGAAGTGCCTGGAGAACTTTGT GAGGAAGAGCTACACGGAGGACGYSGACACATTCTGCATGAAGTA[T]TTAA GGCCCCGTCGCAGGCAGGCACCACCAGCTGATGTTGGGACAGCATCAGGCR CCCCGGATGAGGTTCCACCGTCAACCGCAGCTGAGACAGAGCAAGGCACTC CTCCAGCCCCTCAGGCAGAGGTTCCRCAAGAGAYTTGG |
| 518 | ATTACACCWAACTTGTCCTTATAAGTTAGAAYTCCTACAATATTTATTAGAC TCTGTAGGAGAATCTCTTCTAGATACAAACCCACATCCTTTACTGTAAAAAA GGCCCATTGTTAGCTACAATGACTTAACAT[T]TACGGAGGGACCAAATCTCT GGTCTGAAACCCAAACTTTCAAGGTTCACTAGGTTCGTCCACTGGCAGATAA AACAAATCCTCATTTAYGATCATAAGTTGACATACTGGACAAAGAATACTTG TAAGACGATCCCTTCTTATCTGATGA |
| 519 | AGTGTAGAGATACTCACAAGAACAATTTTGAACTGCCTTGCAGAGCCAGGT ACCACGAATAAGTGTTCAACCTTACTCTCATGCCTCAATTTCAAGAACACCT GAACACATTTGCTAAATGATGTAAGAAAAAAGTTGCCATCATGGTA[T]CAG ATACGAGGTGAGTAGCAACCTGGTGAGGTTTAAATGTGTGCCCMAGCGGTG TGSTTAGTTGAAAAGATAAACRCAGTTTCTGCAGATGGTTTGCAGAAAGAGA CACTTTTGTATCTTTCAGAAGATCTAACCTGAAATGAAGCA |
| 520 | CCATGCGCTACTACCAGGCCGGYTCCTCGGAGATGTTYGGCTCCACGCCGCC GCCGCAGCGCGAGGACACGCCCTTCCACCCGCGCTCGCCCTACGCCGCCGCC AAGGTCGCCGCGCACTGGTACACSGTCAACTACCGCGAGGCCTACG[G]CGT ATTCGCCTGCAACGGCGTGCTYTTCAACCACGAGTCCCCGCCGCCGCGGCGAG AACTTCGTCACGCGCAAGATCACGCGCGCCGTCGGCCGCATCAAGGTCGGG CTGCAGACCAGGGTCTTCCTCGGCAACCTCTCGGCCGCCAGGGA |
| 521 | TACATACCTTGCAGCATGTCAAATGCACAAGGATGAAGAGAGAGGGAAAGT TGCAGCAAAGAAACTTGTTGAGATGGAACCACAAAGCTCATCCACGTACGT GTTCCTDTCAAGCTTRCATGCTGCGGCTGGTAACTGGGTTGAAGCCAA[G]GT AGCCAGAGAAGCAATGCGAGAAAAAGGGGTGATGAAATTTCCAGGGTGTA GTTGGATCACAGTGGGKAACAAACARAGYGTATTTGTTGTACAGGACACAC A |
| 522 | ACTCAAATTGAGTCAAGAAATGCTAAGGGAAAGCCCGTGAAACAATATAAT CGAACTTTTACATTTTATTGATGTGGCCTTYTTAAAAATGACGCCATAAACC WCTATACTGAAAACGGCCTCGGCGCTTAAACCAGTAGCATTCGTA[A]GTTC ATTTCTGATTTGGGACTTCAAACCAATAGTGTTTGAGACTCACAGGTTTAGA ACCGATTGGTGGCTGCCTTCAATCAAGAGCGAAACCAACATGTTATTGCCCA CCTTAAAATCACAGATTTTGTATTATCGTGTACAATAAAAAT |
| 523 | YCAGATCATCACTGGAATCAACAGCAGTTCTCTGGTTCATTTGTTCAGATGC TTCKGTGTCAACTGCTTCTGAAYGATGGTTTAAGCTTATAACATCATCARCA TTTTTGTTAATTATTGCACTGTTCTCGTTGTCCTTTACCACGCTAT[T]CAAAW TTTCTGGCTCCTCAGATACTACAAGATCAGATRTCTGCCCGTTCTGAGTAAG AGTGGTTTCAGGACTGACACCCATACCTTGTGCAAGTGCTACATACCGAAGT ACTAGWTGCTTGTACGAATTCAATAGGCTCTCTACATCAGC |
| 524 | CTTTAGTAGCTAGTCYTATAGCTCATAGGTTCTCAGTTCGGTATATRTYGGTG AYATATTTCATGAACTTASTTTTWAAMCMATTTAAAAMGCAMACGCAACA ACGAAGGGAGTGATATTGACCATGGG[T]CTTTCGTAGCTTTTCAATCAAACG TCACATAAAAAAGAAACAWCCAAAAGWTCATAATACACAGATTKRAAMS KKKAGACAAAAATACGAGTACAAGACATTGGACCTTCAATWWTTTTTTTKT GTTTTCTGAGACATGAAAA |
| 525 | TTGCACCACCCATAGTTTAAGAGGCAGTTGCTTTCACACACTTTATTTTGCAT GGCACAGCCAACTGTCCCCATCATTCTAAACCAGGCTGCAACTGAGCCACTA CAGAAACTGCTAATATTAGATATTCCAGCAAATAGTCTTGACACTAGAGTGC |

TABLE 12-continued

| SEQ ID NO. | Sequence (Codominant Marker Position shown in Brackets) |
|---|---|
| | TA[A]GTCCCTAAACACGAAAGACATTTGTCAGGAGACCCGTATTGAGTACTA GCAGAGTATACTACCGCTAGATATTCCAGTATAATCGTGCAGCAGCTCCGGT CAATGGCAGTGGCACTTGAAGTCTGCAACCTCAGCCAACAGATCCACATGA GAACCAAC |
| 526 | TACACTATACTAATTAGAATGTCTGGAAAGGCTGGGAAGACCACTAAATTTG TCTCATTKTTGGAGGAAATGGTGTCCRAAGGATGTGTTCTTARTCTGATTGCT TATAATACTGTTATTGAGGCTCTTGGTAAGAACAAGATGGTTGAC[A]AGGCG ATTTTTATGCTTTCTAAAATGATTGAGAGTGACTGTCGGCCCAATCAATTCA CATATAGCATTATGCTGGATGTTTTATCAACAGGGGGACAACTCCACAGGTT GAATGAGATTCTAGATATTTGTA |
| 527 | CCTTTCTCCAGTTGGTAATATGCTTCATGTAAGGTACCTGAA[A]GTGGTAAG CRACATGATAGTCAAACTCCCACTCATTATTCGAGGCCTGCGACACTTAGAG ACACTCGAGGTGGATGCAGAARAAGTCGCTGTTCCACTGGATGTTTTCATCT TGAAGAGCCTGTTGCATCTCCGACTTCCGAGCAAGGCT |
| 528 | TGCATATGAGAAACTACAAGGTTGGCAGGGTCCTTTCCTGTGCCCGAGCTGT CATGAAAAGAAAGAAGCAATGGAAGGGAAACGCCGGCCAAAAGGTATCAT TAAATAGTATTTACCTGAACTACATTCTKTAGTTAACCCTCAGAC[T]GCTCAT TCGTTTCTGGGTTCCTATTTGTCTTTCCAGGATCTTCATCAAACGTCTTTGGT CACATGTGCTAGGCCTGCCTACCACTAAAGATTCTTTTATTGATTSTTAGCTG GAAATAATAGKCAGCCCATAACAATTCATTGGCTAGAA |
| 529 | AAGCACCCGCATGCAGACTTCCAAACTATCCAGTGTCCACAAATAGCAGTTT TGCAAACTAAATACATATATGAAATGATGACACAGGCCACCCAAACAACAA GCCCTAGAGAATCAGACCAACCAACCGAGCAATTCGCAGTGCTCCATATCTT CTAGCATTCACAACCTGACGAACG[C]TGTTGCCTTCCAGCGCCCCCAACATC AATCGTATCAGGAAGATACCTGCAAAAGTTGGTAAAACATAGATCAAGTTA CACCACAAGGCTGCCTGCATGTATGATACATATATGTGAGCTATATACTATT CAAACTTACATATCTTCTTCTGGCTCATTTTTTACAGCATTCCTCGCTATA |
| 530 | AGAYGCTACTCTGCTACCATTTTGAGAATCTATTGACAAGAACTTTACAGGA GGRGTCTCATCCCCAGGAGCCTTGCTGATAACTGGAGATGGAGAAGATATG CACATATCCACTCGTGAATGCYTTTTCCTGGACTTATTTCTGTCCTT[T]AGCA GTTGTTTTCCCTAGCAAACAAAAGGAGATACACATAGCATGAGAAAGAAGA AASAAACTGAAACATTYTATAATGAGAAAAAAACATGGGGAGTTGGGGACA AAGCAACTCACCAATGCTTCTACAAATGTTTTGAACCTCCGA |
| 531 | TGCTTCTGTCGAATTGCTGCGGGCAGARCATGCTTTGGTGGYGGCTTTGCAG TGTGAAACGTTATGAATCTGAGAACCTCGATGCATGCYAGGGACAGGGAAT ACCTGAACAGGGGCCAAGATGACATGAACAGGACGCCGGA[T]AGCACGTGC ACAACCTTCCTGCTCAAGCTCTGCCTTCATTGATGGCATGGATCAGTACAGA GTTCGGAAGCCAACGACGTGAACARCTGAACATAAGCAAATGTAATGGCCG TTCTAA |
| 532 | AGGTCGACAAGGCTGCTAGTAACATGTCTGAGCCGACATCAGGGGAGATGC AGGATGCTGCTTTCCAGTCTGACGAAGAGGAGGAAGATGAAGATGTTGATG AAACAGTATTCGGTCAAGATTCAGATTCGTCACARAATAGCGGCACCG[G]C GACGATGCAAAGTAGACTCACTGCTGGTATTCATCATTATGGTGATTGTATT GTTTTTAATTAAATTGCCAAGCTTGATTTTTGTCAAGGCGACGYTGGAAGGT TGCACAGAATTTTGAYAGTGTCTCTGGTTTCATTTTGAAAGCACT |
| 533 | AGAAAACGAGGCCTTCGTCGTCTTAGCGCGCRGGGGCGTAGGACGGCGGCA GCGGCAGCCCCACGACCTTGCCGCAGCGGAGGGCGTTGTCGGGCATGTTGT ACTCGTCGCGCAGTGATCGCGCCGGCGAGACGACGCTGAT[A]TAGAACTGC TCCCCGAGGTAGTACCGCTCCCAGATGTTGGAATGCACGCTCCACATGCCCG CGTTGTCGAACGTCAGCATGATTGCCGTCCATGACCGCGGGTACACCTGGAT CGTGTGCCGGCTCAC |
| 534 | TTCTGGTACTTGCGGATCTCGCGCAGMGCCACSGTSCCGGGCCTGTACCTGT GGGGCTTCTTCACGCCGCCGGTCGTCGGCGCMGACTTCCTCGCCGCCTGCAA CRARAYAACAACCGCCGCCGCGTCAGCRCCGTCTTACAACGGGAAC[A]ATC GAGGGGATCGGAACAKCAGATCGGTACGGGTAGGTAGAGACGAACCTTGGT KGCGAGCTGCTTGCGCGGGGCCTTGCCTCCGGTGGACTTGCGGGCGGTCTGC TTCGTACGAGCCATCTTCTCCTCTCCTTG |
| 535 | CTGCGTTAGTTTCACCCCTTCTAGCTGCGAGTGAAAGAAACWTGATAACAG CTWSCTGCTAGTTTCTATGRYRGCCATCGAATCTGACATGGCTAYCTCCTGT GMCMACGCAGGTCCGCAGGTACTACCAGCCGAGGAAGAGCCA[A]CGGACG GTGACGGCGGTGATCCACGGCGAGAAGGTGCCGCTGTACGGCGCGGGGC GGCCTGACGCTGTCSACGAGCGCGGGCGGGGGSGCGGTGCCCCTGACGC |
| 536 | AGCACCACGATTCACACCTACACATATTCAGACACAAAATTGGGCAGCGAT GGGCATGGACATTTCATTGATAGATGGTATTTAGCTGCCTACYTGGCATTT GATTCGAGCAGCGAAGCTTCAAGAGCTGCAGAATCGCTACAYATATT[C]CT |

TABLE 12-continued

| SEQ ID NO. | Sequence (Codominant Marker Position shown in Brackets) |
|---|---|
| | GTGGGTACACATGCTTCTTGTTCTCCACTCGACCCAGATCATTGTGATGGAC TACTAACTGSCAGTACAAAAGCAGACATCTATCAAACTTACACAAAAGGCG TGCACAACGAGAYAGYCTGCTTGCGCATCTCCAAGTCTAGTCTAG |
| 537 | AWWTTKKWAGYGCARRAATAAACAAGGCACTGTWRATTGTACAGAGCAA GCTCTCTGCATTTTTCAATGCCGCAGCATCTGCAACTGCAAGCAGAGTTTCT A[C]AGGCCAAGGCCGACTGTCCTGCCATCTCTCCTGCGGAGGCCTGCTATGT AATGTTTCTCCAGGTTGGTGTCGAGCTCCTCCAGTTTCTTGGCTTCTTCCGCC GAGCTCCCGACCTTGTTCTCGACCGTGTTTAA |
| 538 | TCAATTTGTGATTTCATCCACAATTTCTTCATATGTGAGGAATGCCGCACRCA CTTCTATGAAATGTGTTCAARGTTTGGAAAAACTACTCTAGCCATATATTGC CACAGAAATCAASTGCATGTYTAAT[T]GTTACCGTTCACCTGTAGTGTATCA GTCCCCTTCAAATCTGCCCGTGACCTTGCCCTCTGGCTATGGRCCGCGCATA ACAAAGTTAACGAGAGGTTGATGAAAGAAGAAAAGGAGTTAGACAATGCT GATCCTTCATTTCCTAAGAT |
| 539 | TTGCATACAAACTTGATCMAAATGTTTRCAAMCCATGCTTGAACRRATATAC AAACCCGTTGYGGCAGGAACATYTTAGCTTWGKAMMMTYGYWVAGCAAC AATAGCTTCAATAGAGATTGTTGTAAGTGTAGAGTG|C|TGCTGCGATGGARA CTATGCAAATCACAAGGGATGGGAGAAGAGTGACATTCAGAAGGAGGTCCG TGCCGAGATAACCGGCTGCAGTAATCGTGGCATCTGCAACTACACGGGCCA ACGTCCCGG |
| 540 | ACAAGTCCAAATCAAAGGTGTTGTCCCGCCAATGCTTACCCCCCATGSCYCC CCRAAATAGCATCTGAATCCATTTTTTTGTCYGATCTTTTTKKCTCCTCTTCT GACAGGGAAATGCTGCTTGAGTTGGACGAGGAACAGACTGGAAT[A]CAAAT GCACGTGCAGGTTGCAAATTCTTATGTTRWTTTTTGKGGCCTATCARTRCAC AGTACTCATAGCATGACAAATGGCGTTGCAGGTTTTGGTTTTTACCSGTTTTG GTTTCC |
| 541 | AACCTCGACTCCACTATAASTGCAGGACGCACGRCAYGCACAACTGAAACA TCCGGACCAACAGGCAGAGTAGTAGCCCAAAGGATGACCCGTCTCATGCAA AAACAGTCAGCTTGATAAACTTATCGAGAAGGCAACA[C]CGGYGCCCAAGT ACTGGTTGAAATACAGAGCAGACATTGAAGTGCCAAAGAGGGGGG |
| 542 | GTCTAGAAAAGTCAAAACGTCATATACTTGGAACRGGAGTAGATATGACAA AAAGAGCATGCAAGTGATGTTCTTACAGAAGAATATATATATTTCATGGCAA GCTAGTACCTAAACTTCAGATGGAGTCTTTGCATCGATTGACAGGGC[G]TGC AACCCGGTCTTGAGCTCCTCCTGCAGGAGATCATAGACAGCCCTGTGCCTCT TRAGCAAGCTCTTCCCCTCAAACTCCTTGGACACCACCCTCACATTGAAATG TGTCTCCCCATTGGTCCCAGCCACGCCAGCATGGCCCTTGTGG |
| 543 | ATTTTACCATACTGCATTCAAAGTTTTACAAGATTGGACATTATTAGTATAA AACATGAAACTTTTCAAGTGAACAASAACTATAARCAACGTCCGCAAGCGC AATCCACAGCTTGAGGTTACATTGTGAGTGTAGTAGA[G]AAACTAGGTGGTC CCAAATAGCACAAGATTATCCAAGCTACCCAGTTTTCTACGATTATGGGCAC RACCATAAGAGCATAGMAGTGCTTCGCATCCTGTTGCATTAAGAAAGTAGT ATAGGCATCGGAGGTGCTGAATCTAAGCACACGG |
| 544 | TAAACCAGAYTAGATGCCACCTAGKTTTCTGACACAAATCAYGAACAAAAC ACGAGAAGAAAGCYAATCATACACGGATGAYGGATGGACTCAGCGGAGCC CTTATTTGCTACCATTCCTCATGTCTTATTGCAGAAATCCATCTATTGC[T]AC TCAACTTCAMTCAGTCTCTGGAACTCTGTATCAACAGGGGATGGGAAATGT GTCATGTTCAATGTTTAGCYCATGAAACATAGAAGACCMCATTAGAAGCTA TTATGTGCTTACATTTGATTTTTTATCCAAGACTCAAGTGTAT |
| 545 | RRHYTKRTGGAGGTCGGGGGAAGAAACCCTAAGAACGATGTCTCACCAAAT TGATTCCTTCCGCCCGAGAGATTTAGAAGCTAGATCTGTCCAGATTTAGTGG ATTGATAGGTTTTGTGAATTTGTCATTCTCCAACTAATCTACTTAC[G]GCCAG ATTTTACATCAGACCTGATGAAACACTGTTTCCTTGACACGAAACTGGTGGA CGCTGCCTTTGCATCAAGAATCAAGAAATTGATTTRCGTTTTATGTYTCTGGT AGCYCCAGACACCTCATACTCTCCTCTGTTGCCTGTSATG |
| 546 | AACGGCTAAGAGTCAGGCGATTCTGTTTGTACAGAGACAATCGCAGCACTT GRMTGCTWCGCATGCGSTTCAGAGGGCCTTCAGCTCAGGCTTGACAGATCT AGTTTTGGYCGCCACGCYRCTCTTCGGCGAGCACTGYACTCTGCTGGC[G]TC TTTAGAAGCCCCGATGCTGTGACGATGTGGCCGGGTGGTAGATGTTGCGTTG GTGTTTTTTCCCTCGGGTGTCTGTGGT |
| 547 | AAACAANACTCAGTGGACTCGCNGAAAANNNNATAATGAAAGGTGCTCCATC CATACCCATGAGAANGTTCCGATGCTCGCAGTCTCATGTTTCCCAGTCA[A]T CTTCTTTCATTTCCTTCTCCGTATGCACTAATATGCAGATCATGGCGCAGAGA AAGGTTCAGGATTGCTCTCTTGATCTCTTCAAACCCGCCGTCTTCG |

TABLE 12-continued

| SEQ ID NO. | Sequence (Codominant Marker Position shown in Brackets) |
|---|---|
| 548 | AAAATTACTGAAGGCAGGTGGGTTGCAGTTGTGTGTTCGTTACTGTTTACTG TAWYATGTCAAGCTGTCGGCTGCAATTTCTTTGCTGGCAAGCCGCAGGCACT GGTGAAGTGCTGATAAATACATCATATTCTGTTGACCTGTGAAGAA[G]CTTG TTCWAGGTRGATTCCATTGTACTAGCTCTGTTGCYCAGCATCTCCTTGTTTGG GAACATTAACAACCAGCYCTCRMCCCTCAANNNNNNNNNNNNNNNNNNNNNN NNNNNNNNNNNNNNNNNNNNNNNTAAAATAGTCGCATCATGTA |

Table 13 provides assay primers and probes usable for detecting the codominant markers in Table 12 by Taqman Assay under the conditions described above. F1 and R1 correspond to forward and reverse primers, respectively. Probes are indicated by fluorescent reporter (Fluo Color). The detected male line corresponds to inducer line NP2222. The detected female line corresponds to an inbreed line, line B14.

TABLE 13

| Assay for | SEQ ID NO: | Primer [[/]] or Probe | Seq | Fluocolor | Allele | Sex |
|---|---|---|---|---|---|---|
| SEQ ID NO: 99 and 474 | 174 | F1 | GCCATGGATCGCATTCATG | | | |
| | 175 | R1 | CTCTCTGGCATCTCTGAAATC ATC | | | |
| | 176 | FM | CGATTTTGACTTTGAACC | FM | A | Male |
| | 177 | TT | CGATTTTGACTTCGAAC | TT | G | Female |
| SEQ ID NO: 100 and 475 | 178 | R1 | ACACCCATGGCACAAGGT | | | |
| | 179 | F1 | CGAGAGACCAGATCAACAGC TT | | | |
| | 180 | FM | CAATACTCTAAAAAACTG | FM | A | Male |
| | 181 | TT | CAATACTCTAAGAAACTG | TT | G | Female |
| SEQ ID NO: 101 and 476 | 182 | R1 | CCCTTGAACCAGAGTGGATAA TCTC | | | |
| | 183 | F1 | CAGGTAGTAGTCTTCCGTATG TCAAC | | | |
| | 184 | FM | ATCAGATGTAAAGCATC | FM | A | Female |
| | 185 | VC | AAATCAGATGTAGAGCATC | VC | G | Male |
| SEQ ID NO: 102 and 477 | 186 | F1 | ACTGCCTGCAAGGTTGGTT | | | |
| | 187 | R1 | CGGGCATAAGATCCCAGTCA | | | |
| | 188 | FM | CAAACCAAACAACCTT | FM | A | Male |
| | 189 | TT | AAACCAAGCAACCTT | TT | G | Female |
| SEQ ID NO: 103 and 478 | 190 | R1 | CCCCAGCCCTGGATCAC | | | |
| | 191 | F1 | GCTTTCGAATGTGTTCATGAT GTAAGT | | | |
| | 192 | VC | CCTGGAGAATGAAAGTA | VC | A | Male |
| | 193 | 1FM | CTGGAGAAGGAAAGTA | FM | C | Female |
| SEQ ID NO: 104 and 479 | 194 | F1 | AGCTTCTCCTTGACCTTCTCCT TAA | | | |
| | 195 | R1 | AGGAAGAGGAGGTGATCGAT GAG | | | |
| | 196 | TT | AACGGCGAAATTGTCAA | TT | A | Male |
| | 197 | FM | CGGCGAGATTGTCAA | FM | G | Female |
| SEQ ID NO: 105 and 480 | 198 | R1 | GCGTCACAAGAAGGTA | | | |
| | 199 | F1 | GCAAGCAGAACTCAAC | | | |
| | 200 | TT | TCAACATGACTGAATCA | TT | A | Female |
| | 201 | FM | CAACATGACTGAAGCAT | FM | C | Male |
| SEQ ID NO: 106 and 481 | 202 | R1 | CGCAGCGTGGAGTGC | | | |
| | 203 | F1 | ACACATTCGAAGGCGGATATC ATG | | | |
| | 204 | FM | CCGGTAACATCAACG | FM | A | Male |
| | 205 | TT | CCGGTAACGTCAACG | TT | G | Female |
| SEQ ID NO: 107 and 482 | 206 | F1 | GGAGTCTTTTAGGGTCCACTT GTTT | | | |
| | 207 | R1 | AGAGAGCACAAGGCGAAGAA T | | | |
| | 208 | TT | TTCTGCAAGTTGAATTT | TT | A | Female |
| | 209 | FM | TGCAAGCTGAATTT | FM | G | Male |

TABLE 13-continued

| Assay for | SEQ ID NO: | Primer [[/]] or Probe | Seq | Fluocolor | Allele | Sex |
|---|---|---|---|---|---|---|
| SEQ ID NO: 108 and 483 | 210 | R1 | GAGCAAGCGCAGAGAACAG | | | |
| | 211 | F1 | CGGGCATGTTGCGATGTC | | | |
| | 212 | VC | AAAACTTTACCCATAAACAA | VC | A | Male |
| | 213 | FM | ACTTTACCCGTAAACAA | FM | G | Female |
| SEQ ID NO: 109 and 484 | 214 | R1 | CCCGGGAATTGTTTTCGATGC | | | |
| | 215 | F1 | CCCTATAGTTTGTTAGCAGATGTGTAGTT | | | |
| | 216 | FM | TAACGCGTTCTTCATTT | FM | A | Male |
| | 217 | TT | ACGCGTCCTTCATTT | TT | G | Female |
| SEQ ID NO: 110 and 485 | 218 | F1 | GCAACCTAAAAATTCTAAAAATACAGAGATAGGG | | | |
| | 219 | R1 | ACTAATTTCAAAGAAAATGCCACAGCTTT | | | |
| | 220 | VC | ATTTTAAAGGAAGATAGATTG | VC | A | Female |
| | 221 | FM | TTTAAAGGAAGACAGATTG | FM | G | Male |
| SEQ ID NO: 111 and 486 | 222 | F1 | GCGAGCCGTTGAGAGTGAA | | | |
| | 223 | R1 | CCACGAGTCCCCAGTCTCT | | | |
| | 224 | FM | ACAGCCATGTCGCC | FM | A | Female |
| | 225 | TT | ACAGCCGTGTCGCC | TT | G | Male |
| SEQ ID NO: 112 and 487 | 226 | R1 | CCACCAAAACGAGTAAACGACAAAT | | | |
| | 227 | F1 | GGTTGCTTGAGATCTTGCTGTTATT | | | |
| | 228 | TT | AGTGAGCACGGCACG | TT | G | Female |
| | 229 | FM | AGTGAGGACGGCACG | FM | C | Male |
| SEQ ID NO: 113 and 488 | 230 | R1 | ACAACAAGGCGGCATTGC | | | |
| | 231 | F1 | GGCGCCTCCGTTTAACTACTC | | | |
| | 232 | FM | TTGCAGTAGTAGTACTGTAG | FM | A | Female |
| | 233 | TT | TTGCAGTAGTAGTGCTGTAG | TT | G | Male |
| SEQ ID NO: 114 and 489 | 234 | F1 | GCTGCTCGTTCTCGTTGAAGA | | | |
| | 235 | R1 | CGCTGGACGACACCAAGA | | | |
| | 236 | FM | TCCACGTTCCTGTCCAG | FM | A | Female |
| | 237 | TT | CACGTTCCGGTCCAG | TT | C | Male |
| SEQ ID NO: 115 and 490 | 238 | F1 | GCTAGTCTCAAGTCCAAGCAAAGA | | | |
| | 239 | R1 | AGTAGGTGCTTGCCATTTACATCT | | | |
| | 240 | TT | AAGATTAGCAATAACTATTGTT | TT | A | Male |
| | 241 | FM | AAGATTAGCAATAACTGTTGTT | FM | G | Female |
| SEQ ID NO: 116 and 491 | 242 | R1 | CGGTCTGGCTAGGATTTGGA | | | |
| | 243 | F1 | GAGCATGTGGAGGTTCCTGAT | | | |
| | 244 | FM | CATTCAAGAATGTCCTC | FM | A | Male |
| | 245 | TT | CATTCAAGCATGTCCTC | TT | C | Female |
| SEQ ID NO: 117 and 492 | 246 | R1 | GAATCTGAGATGTTGAACCCACTGT | | | |
| | 247 | F1 | TGCTGAAAGAGGCCTCAAAGG | | | |
| | 248 | FM | CACCAAATCAGCATCG | FM | A | Male |
| | 249 | TT | CACCAAATCGGCATCG | TT | G | Female |
| SEQ ID NO: 118 and 493 | 250 | R1 | TTCTTGACGTGCCGAAAGGAT | | | |
| | 251 | F1 | CCGCCGTATGATTGGATCGA | | | |
| | 252 | FM | AAAAAGCCAACCGCACG | FM | A | Male |
| | 253 | TT | AAAAAGCCAGCCGCACG | TT | G | Female |
| SEQ ID NO: 119 and 494 | 254 | F1 | GGTACATCAGCAACCGAGGTTTATA | | | |
| | 255 | R1 | GTTGATGAACGCCTCCTCAGA | | | |
| | 256 | FM | CTCGTAGAGCAATCT | FM | G | Male |
| | 257 | VC | CCTCGTAGACCAATCT | VC | C | Female |

TABLE 13-continued

| Assay for | SEQ ID NO: | Primer [[/]] or Probe | Seq | Fluocolor | Allele | Sex |
|---|---|---|---|---|---|---|
| SEQ ID NO: 120 and 495 | 258 | R1 | GAAGCCGACTGGAGAGAATGTTT | | | |
| | 259 | F1 | TTTTCCATGGAGGGTTATGATGCTT | | | |
| | 260 | TT | CTCTGGTTTCTGATGGCTA | TT | A | Male |
| | 261 | FM | TCTGGTTTCTGGTGGCTA | FM | G | Female |
| SEQ ID NO: 121 and 496 | 262 | F1 | GCGCCTTATTATCATCATCTAGGTGTA | | | |
| | 263 | R1 | GAAAAGCACGGCATCAGCAA | | | |
| | 264 | FM | ATTAGCACAAACGGAAGT | FM | A | Female |
| | 265 | TT | ATTAGCACAGACGGAAGT | TT | G | Male |
| SEQ ID NO: 122 and 497 | 266 | R1 | CGGCGCCGTCTTGTG | | | |
| | 267 | F1 | CCGGAAGCCGCCTACAG | | | |
| | 268 | TT | AACTTGGTGACGTAATAG | TT | A | Male |
| | 269 | FM | AACTTGGTGACGTAGTAG | FM | G | Female |
| SEQ ID NO: 123 and 498 | 270 | R1 | GACCAAGGTGTCATAGGCATTGA | | | |
| | 271 | F1 | GCAAATGCTGAGGAATATAAGCACAT | | | |
| | 272 | TT | CCCCCACAACTGGAT | TT | A | Male |
| | 273 | FM | CCCCACGACTGGAT | FM | G | Female |
| SEQ ID NO: 124 and 499 | 274 | R1 | CCATCACAGTGACCTTCCATTTGT | | | |
| | 275 | F1 | TGACACCCTCAATTTGCTGGAAA | | | |
| | 276 | FM | AAGCTCACAGCAATT | FM | A | Male |
| | 277 | TT | AAGCTCACGGCAATT | TT | G | Female |
| SEQ ID NO: 125 and 500 | 278 | R1 | GTTGCAGAGTAACCAGCTGAAG | | | |
| | 279 | F1 | CGCGAGCTCCGTAAGCAT | | | |
| | 280 | FM | TCCATACCAGCATCG | FM | A | Male |
| | 281 | TT | TCCATACCGGCATCG | TT | G | Female |
| SEQ ID NO: 126 and 501 | 282 | R1 | CAGAGTTGACATATTGAGCACTAGTGT | | | |
| | 283 | F1 | CCAATGTCAAACATACCCAAACAGT | | | |
| | 284 | FM | TGTAGAGGCAAATGTAT | FM | A | Female |
| | 285 | VC | CTGTAGAGGCAAGTGTAT | VC | G | Male |
| SEQ ID NO: 127 and 502 | 286 | F1 | GGCACCAATATCTGTTTTCCATTCAAT | | | |
| | 287 | R1 | ACAGCAGATATAAAATGATGCTCGGT | | | |
| | 288 | FM | TGATATGTCACAGTAAGC | FM | A | Female |
| | 289 | TT | ATATGTCGCAGTAAGC | TT | G | Male |
| SEQ ID NO: 128 and 503 | 290 | F1 | TCCCCCGAGCCAGGTT | | | |
| | 291 | R1 | CCTATAGCTTTGGTGGCAAGAAGAA | | | |
| | 292 | TT | CTGGTGCTTTCTACCG | TT | A | Male |
| | 293 | FM | CTGGTGCTTTCGACCG | FM | C | Female |
| SEQ ID NO: 129 and 504 | 294 | R1 | GCCGCCCGATTCTCAGT | | | |
| | 295 | F1 | CGCGAATCGACTGCCATT | | | |
| | 296 | TT | ACGCCATCCCTTGC | TT | A | Female |
| | 297 | FM | CGCCGTCCCTTGC | FM | G | Male |
| SEQ ID NO: 130 and 505 | 298 | F1 | AGCCACCTGTAAGTACAATCACAAA | | | |
| | 299 | R1 | CCTGGGCAGCAACAACAG | | | |
| | 300 | FM | CCAACAACATGTTACC | FM | A | Female |
| | 301 | TT | CCAACAACAGGTTACC | TT | C | Male |
| SEQ ID NO: 131 and 506 | 302 | F1 | CATGTCAGACAAAGCCAATGCTATT | | | |
| | 303 | R1 | TGGCTAGATTTTTATGACAAAGCATCTCT | | | |
| | 304 | TT | CATTCATGTTACAATGTAG | TT | A | Female |
| | 305 | FM | TCATGTTGCAATGTAG | FM | G | Male |

TABLE 13-continued

| Assay for | SEQ ID NO: | Primer [[/]] or Probe | Seq | Fluocolor | Allele | Sex |
|---|---|---|---|---|---|---|
| SEQ ID NO: 132 and 507 | 306 | R1 | CAGAGGCGCGTCAAACG | | | |
| | 307 | F1 | CCTGGTGTGTATGCTGTTCTTTTC | | | |
| | 308 | TT | TCGGTCCATATTATC | TT | A | Male |
| | 309 | FM | CGGTCCATCTTATC | FM | C | Female |
| SEQ ID NO: 133 and 508 | 310 | F1 | TTGAATCCACCGGTGAATCTATCG | | | |
| | 311 | R1 | GCGGTAGCGTGAGTGACA | | | |
| | 312 | FM | ATACAGACAGACTCGGAC | FM | A | Male |
| | 313 | TT | ATACAGACAGGCTCGGAC | TT | G | Female |
| SEQ ID NO: 134 and 509 | 314 | R1 | GTACTGTAACCCTTGGCTGTCA | | | |
| | 315 | F1 | GGCAGGCAGCATGAATCC | | | |
| | 316 | VC | ACAGAACCAATGGTTTT | VC | A | Female |
| | 317 | FM | CAGAACCAGTGGTTTT | FM | G | Male |
| SEQ ID NO: 135 and 510 | 318 | R1 | CTGCTGCTGTGTTACTGTATCCT | | | |
| | 319 | F1 | TGACCGCTGAAGCACGAA | | | |
| | 320 | TT | ATGGCCATACAGCACGA | TT | A | Female |
| | 321 | FM | AATGGCCATACTGCACGA | FM | T | Male |
| SEQ ID NO: 136 and 511 | 322 | R1 | CATCACACAGCTTGTACATGCAA | | | |
| | 323 | F | GTGGAGAAAAGGAGAGGAGAGAATT | | | |
| | 324 | TT | CAATTCGCAGACGATGG | TT | A | Male |
| | 325 | FM | ATTCGCAGGCGATGG | FM | G | Female |
| SEQ ID NO: 137 and 512 | 326 | R1 | CGGATTCAAGTGCCTCTAAGCTATA | | | |
| | 327 | F1 | GAGACAGTAAGACGAAGAATGGCA | | | |
| | 328 | TT | CACGTCAGCATGCT | TT | A | Male |
| | 329 | FM | CACGTCGGCATGCT | FM | G | Female |
| SEQ ID NO: 138 and 513 | 330 | F1 | GCAACTTACTTATAACATGGCAACCAA | | | |
| | 331 | R1 | GCAATTCACTGCATTGGGTCTAATG | | | |
| | 332 | FM | ATAAGTGTGCACAATGT | FM | A | Male |
| | 333 | TT | ATAAGTGTGCGCAATGT | TT | G | Female |
| SEQ ID NO: 139 and 514 | 334 | F1 | TCTGCATAGCATTGAACTGGACAG | | | |
| | 335 | R1 | AGGAACAGTACAGATCAGCAGTAGA | | | |
| | 336 | FM | ACAGAGTAACACAGCAAG | FM | A | Female |
| | 337 | TT | CAGAGTAACGCAGCAAG | TT | G | Male |
| SEQ ID NO: 140 and 515 | 338 | R1 | GTAATGGTAGCACGCAGATCACT | | | |
| | 339 | F1 | GCTAGGAATTGCTTAGTCGAGGTT | | | |
| | 340 | TT | ACTGAAGAAATAATCGC | TT | A | Male |
| | 341 | FM | CTGAAGAAGTAATCGC | FM | G | Female |
| SEQ ID NO: 141 and 516 | 342 | R1 | GCGAAGTCCGCGTAGTACTC | | | |
| | 343 | F1 | CGTCACCAGAGGCTACGT | | | |
| | 344 | FM | ACGCCTTGACCACCT | FM | A | Female |
| | 345 | VC | ACGCCTTGGCCACCT | VC | G | Male |
| SEQ ID NO: 142 and 517 | 346 | F1 | AGAACTTTGTGAGGAAGAGCTACAC | | | |
| | 347 | R1 | GCCTGATGCTGTCCCAACAT | | | |
| | 348 | FM | CATGAAGTATTTAAGGCC | FM | A | Female |
| | 349 | TT | CATGAAGTACTTAAGGCC | TT | G | Male |
| SEQ ID NO: 143 and 518 | 350 | F1 | CTGTAAAAAGGCCCATTGTTAGCT | | | |
| | 351 | R1 | TGGGTTTCAGACCAGAGATTTGG | | | |

TABLE 13-continued

| Assay for | SEQ ID NO: | Primer [[/]] or Probe | Seq | Fluocolor | Allele | Sex |
|---|---|---|---|---|---|---|
| | 352 | FM | CCCTCCGTAAATGTTAA | FM | A | Female |
| | 353 | TT | CCCTCCGTAGATGTTAA | TT | G | Male |
| SEQ ID NO: 144 and 519 | 354 | F1 | CAAGAACACCTGAACACATTTGCT | | | |
| | 355 | R1 | ACCTCACCAGGTTGCTACTCA | | | |
| | 356 | FM | CCATCATGGTATCAGATA | FM | A | Female |
| | 357 | TT | CCATCATGGTAGCAGATA | TT | C | Male |
| SEQ ID NO: 145 and 520 | 358 | F1 | CCGCGCACTGGTACAC | | | |
| | 359 | R1 | GCGCGTGACGAAGTTCTC | | | |
| | 360 | VC | CCTACGACGTATTCG | VC | A | Male |
| | 361 | FM | TACGGCGTATTCG | FM | G | Female |
| SEQ ID NO: 146 and 521 | 362 | F1 | TGCTGCGGCTGGTAACTG | | | |
| | 363 | R1 | CCCTGGAAATTTCATCACCCCTTTT | | | |
| | 364 | TT | TTGAAGCCAAAGTAGCCAG | TT | A | Male |
| | 365 | FM | AAGCCAAGGTAGCCAG | FM | G | Female |
| SEQ ID NO: 147 and 522 | 366 | F1 | GCCTCGGCGCTTAAACC | | | |
| | 367 | R1 | CCTGTGAGTCTCAAACACTATTGGT | | | |
| | 368 | TT | TAGCATTCGTAAGTTCATT | TT | A | Female |
| | 369 | FM | CATTCGTAGGTTCATT | FM | G | Male |
| SEQ ID NO: 148 and 523 | 370 | F1 | TTGTTAATTATTGCACTGTTCTCGTTGTC | | | |
| | 371 | R1 | TCAGTCCTGAAACCACTCTTACTCA | | | |
| | 372 | FM | TTACCACGCTATTCAAA | FM | A | Female |
| | 373 | TT | TTTACCACGCTATCCAAA | TT | G | Male |
| SEQ ID NO: 149 and 524 | 374 | F1 | GCAACAACGAAGGGAGTGATATTGA | | | |
| | 375 | R1 | GAAGGTCCAATGTCTTGTACTCGTA | | | |
| | 376 | FM | CCATGGGTCTTTCGT | FM | A | Female |
| | 377 | TT | CCATGGGCCTTTCGT | TT | G | Male |
| SEQ ID NO: 150 and 525 | 378 | F1 | GCTGCTGCACGATTATACTGGAAT | | | |
| | 379 | R1 | CTGAGCCACTACAGAAACTGCTA | | | |
| | 380 | FM | CTAGAGTGCTAAGTCCCT | FM | A | Female |
| | 381 | TT | CTAGAGTGCTAGGTCCCT | TT | G | Male |
| SEQ ID NO: 151 and 526 | 382 | R1 | GAAAGGCTGGGAAGACCACTA | | | |
| | 383 | F1 | GGCCGACAGTCACTCTCAA | | | |
| | 384 | TT | AAAATCGCCTTGTCAAC | TT | A | Female |
| | 385 | FM | AAAATCGCCTCGTCAA | FM | G | Male |
| SEQ ID NO: 152 and 527 | 386 | R1 | CTCCAGTTGGTAATATGCT | | | |
| | 387 | F1 | GAGTGGGAGTTTGACTATC | | | |
| | 388 | TT | CTTACCACTTTCAGGTA | TT | A | Female |
| | 389 | FM | TTACCACCTTCAGGTA | FM | G | Male |
| SEQ ID NO: 153 and 528 | 390 | F1 | CCTGGAAAGACAAATAGGAACCCA | | | |
| | 391 | R1 | GGAAACGCCGGCCAAA | | | |
| | 392 | TT | AACGAATGAGCTGTCTGA | TT | A | Male |
| | 393 | FM | AAACGAATGAGCAGTCTG | FM | T | Female |
| SEQ ID NO: 154 and 529 | 394 | F1 | GTGCTCCATATCTTCTAGCATTCAC | | | |
| | 395 | R1 | GGCAGCCTTGTGGTGTAAC | | | |
| | 396 | TT | AACCTGACGAACGTTGT | TT | A | Male |
| | 397 | FM | CTGACGAACGCTGTT | FM | G | Female |
| SEQ ID NO: 155 and 530 | 398 | F1 | TGCACATATCCACTCGTGAATGC | | | |
| | 399 | R1 | ATCTCCTTTTGTTTGCTAGGGAAA | | | |

TABLE 13-continued

| Assay for | SEQ ID NO: | Primer [[/]] or Probe | Seq | Fluocolor | Allele | Sex |
|---|---|---|---|---|---|---|
| | 400 | TT | TATTTCTGTCCTTTAGCAG | TT | A | Female |
| | 401 | FM | TTCTGTCCTTCAGCAG | FM | G | Male |
| SEQ ID NO: 156 and 531 | 402 | F1 | GGGCCAAGATGACATGAACA | | | |
| | 403 | R1 | CAGAGCTTGAGCAGGAAGGT T | | | |
| | 404 | TT | ACGCCGGATAGCAC | TT | A | Female |
| | 405 | FM | CCGGACAGCACGT | FM | G | Male |
| SEQ ID NO: 157 and 532 | 406 | R1 | CTGACGAAGAGGAGGAAGAT GAAG | | | |
| | 407 | F1 | ACCAGCAGTGAGTCTACTTTG C | | | |
| | 408 | TT | ATCGTCGTCGGTGC | TT | A | Male |
| | 409 | FM | ATCGTCGCCGGTG | FM | G | Female |
| SEQ ID NO: 158 and 533 | 410 | R1 | GAGCGTGCATTCCAACATCTG | | | |
| | 411 | F1 | GTACTCGTCGCGCAGTGAT | | | |
| | 412 | FM | AGACGACGCTGATATAGA | FM | A | Female |
| | 413 | TT | ACGACGCTGATGTAGA | TT | G | Male |
| SEQ ID NO: 159 and 534 | 414 | R1 | ACCAAGGTTCGTCTCTACCTA CC | | | |
| | 415 | F1 | CCTCGCCGCCTGCAAC | | | |
| | 416 | FM | CTTACAACGGGAACAATC | FM | A | Female |
| | 417 | TT | CTTACAACGGGAACCAT | TT | C | Male |
| SEQ ID NO: 160 and 535 | 418 | R1 | GCAGGTCCGCAGGTACTA | | | |
| | 419 | F1 | CCTTCTCGCCGTGGATCAC | | | |
| | 420 | TT | ACCGTCCGTTGGCT | TT | A | Female |
| | 421 | FM | ACCGTCCGGTGGC | FM | C | Male |
| SEQ ID NO: 161 and 536 | 422 | R1 | GCATTTGATTCGAGCAGCGA | | | |
| | 423 | F1 | TGGGTCGAGTGGAGAACAAG | | | |
| | 424 | FM | TGTGTACCCACAGAAAT | FM | A | Male |
| | 425 | TT | ATGTGTACCCACAGGAAT | TT | G | Female |
| SEQ ID NO: 162 and 537 | 426 | F1 | TTTCAATGCCGCAGCATCTG | | | |
| | 427 | R1 | TCGACACCAACCTGGAGAA | | | |
| | 428 | TT | CAGAGTTTCTAGAGGCC | TT | G | Male |
| | 429 | FM | CAAGCAGAGTTTCTACAG | FM | C | Female |
| SEQ ID NO: 163 and 538 | 430 | F1 | GCAAGGTCACGGGCAGAT | | | |
| | 431 | R1 | AGCCATATATTGCCACAGAAA TCA | | | |
| | 432 | TT | CAGGTGAACGGTAACTATT | TT | A | Male |
| | 433 | FM | CAGGTGAACGGTAACAATT | FM | T | Female |
| SEQ ID NO: 164 and 539 | 434 | R1 | GCAACAATAGCTTCAATAGA G | | | |
| | 435 | F1 | CCCTTGTGATTTGCATAGT | | | |
| | 436 | FM | CCATCGCAGCAACA | FM | A | Male |
| | 437 | TT | TCGCAGCAGCACT | TT | G | Female |
| SEQ ID NO: 165 and 540 | 438 | F1 | GTCATGCTATGAGTACTGT | | | |
| | 439 | R1 | ATGCTGCTTGAGTTGGA | | | |
| | 440 | TT | CACGTGCATTTGTATTC | TT | A | Female |
| | 441 | FM | CACGTGCATTTGCAT | FM | G | Male |
| SEQ ID NO: 166 and 541 | 442 | R1 | GGCACTTCAATGTCTGCTCTG T | | | |
| | 443 | F1 | GATGACCCGTCTCATGCAAA | | | |
| | 444 | FM | CGAGAAGGCAACAACG | FM | A | Male |
| | 445 | TT | AGAAGGCAACACCGG | TT | C | Female |
| SEQ ID NO: 167 and 542 | 446 | F1 | TCATGGCAAGCTAGTACCTAA AC | | | |
| | 447 | R1 | CTGCAGGAGGAGCTCAAGAC | | | |
| | 448 | FM | ATCGATTGACAGGGCATG | FM | A | Male |
| | 449 | TT | TTGACAGGGCGTGC | TT | G | Female |

TABLE 13-continued

| Assay for | SEQ ID NO: | Primer [[/]] or Probe | Seq | Fluocolor | Allele | Sex |
|---|---|---|---|---|---|---|
| SEQ ID NO: 168 and 543 | 450 | R1 | CACCTCCGATGCCTATACTAC TTTC | | | |
| | 451 | F1 | GCGCAATCCACAGCTTGA | | | |
| | 452 | FM | TTGTGAGTGTAGTAGAAAA | FM | A | Male |
| | 453 | TT | TTGTGAGTGTAGTAGAGAA | TT | G | Female |
| SEQ ID NO: 169 and 544 | 454 | F1 | CGGAGCCCTTATTTGCTACCA TTC | | | |
| | 455 | R1 | CCCTGTTGATACAGAGTTCCA GA | | | |
| | 456 | TT | AAATCCATCTATTGCTACT | TT | A | Female |
| | 457 | FM | CATCTATTGCCACTCA | FM | G | Male |
| SEQ ID NO: 170 and 545 | 458 | R1 | TTCCGCCCGAGAGATTTAGAA G | | | |
| | 459 | F1 | CACCAGTTTCGTGTCAAGGA | | | |
| | 460 | TT | TGTAAAATCTGGCTGTAAG | TT | A | Male |
| | 461 | FM | TGTAAAATCTGGCCGTA | FM | G | Female |
| SEQ ID NO: 171 and 546 | 462 | F1 | GGCCACATCGTCACAGCAT | | | |
| | 463 | R1 | TCAGCTCAGGCTTGACAGA | | | |
| | 464 | TT | CTTCTAAAGATGCCAGC | TT | A | Male |
| | 465 | FM | TCTAAAGACGCCAGC | FM | G | Female |
| SEQ ID NO: 172 and 547 | 466 | R1 | GCATATTAGTGCATACGGAGA AGGA | | | |
| | 467 | F1 | CGATGCTCGCAGTCTCATGTT | | | |
| | 468 | TT | CCCAGTCAATCTTCTT | TT | A | Female |
| | 469 | FM | CCAGTCAGTCTTCTT | FM | G | Male |
| SEQ ID NO: 173 and 548 | 470 | F1 | CACTGGTGAAGTGCTGATAAA TACATC | | | |
| | 471 | R1 | ATGTTCCCAAACAAGGAGAT GCT | | | |
| | 472 | TT | CCTGTGAAGAAACTTGTT | TT | A | Male |
| | 473 | FM | CTGTGAAGAAGCTTGTT | FM | G | Female |

What is claimed is:

1. A method of testing an edited haploid maize plant progeny for the absence of a first maize plant's genomic material, wherein the first maize plant is an NP2222 haploid inducer line, the method comprising:

isolating a nucleic acid from the edited haploid maize progeny, and detecting in the nucleic acid the presence of a plurality of codominant markers, wherein the codominant markers have a distinct haplotype for a second maize plant, wherein the second maize plant is a B14 line, and wherein the second maize plant comprises the source of genomic DNA in the edited haploid maize plant progeny, wherein the plurality of codominant markers includes SEQ ID NOs 474-548, and wherein the detecting includes the use of at least one set of primers and at least one probe selected from SEQ ID NOs: 174-473, wherein SEQ ID NOs: 174, 175, and 177 are used to detect SEQ ID NO: 474, SEQ ID NOs: 178, 179, and 181 are used to detect SEQ ID NO: 475, SEQ ID NOs: 182, 183, and 184 are used to detect SEQ ID NO: 476, SEQ ID NOs: 186, 187, and 189 are used to detect SEQ ID NO: 477, SEQ ID NOs: 190, 191, and 193 are used to detect SEQ ID NO: 478, SEQ ID NOs: 194, 195, and 197 are used to detect SEQ ID NO: 479, SEQ ID NOs: 198, 199, and 200 are used to detect SEQ ID NO: 480, SEQ ID NOs: 202, 203, and 205 are used to detect SEQ ID NO: 481, SEQ ID NOs: 206, 207, and 208 are used to detect SEQ ID NO: 482, SEQ ID NOs: 210, 211, and 213 are used to detect SEQ ID NO: 483, SEQ ID NOs: 214, 215, and 217 are used to detect SEQ ID NO: 484, SEQ ID NOs: 218, 219, and 220 are used to detect SEQ ID NO: 485, SEQ ID NOs: 222, 223, and 224 are used to detect SEQ ID NO: 486, SEQ ID NOs: 226, 227, and 228 are used to detect SEQ ID NO: 487, SEQ ID NOs: 230, 231, and 232 are used to detect SEQ ID NO: 488, SEQ ID NOs: 234, 235, and 236 are used to detect SEQ ID NO: 489, SEQ ID NOs: 238, 239, and 241 are used to detect SEQ ID NO: 490, SEQ ID NOs: 242, 243, and 245 are used to detect SEQ ID NO: 491, SEQ ID NOs: 246, 247, and 249 are used to detect SEQ ID NO: 492, SEQ ID NOs: 250, 251, and 253 are used to detect SEQ ID NO: 493, SEQ ID NOs: 254, 255, and 257 are used to detect SEQ ID NO: 494, SEQ ID NOs: 258, 259, and 261 are used to detect SEQ ID NO: 495, SEQ ID NOs: 262, 263, and 264 are used to detect SEQ ID NO: 496, SEQ ID NOs: 266, 267, and 269 are used to detect SEQ ID NO: 497, SEQ ID NOs: 270, 271, and 273 are used to detect SEQ ID NO: 498, SEQ ID NOs: 274, 275, and 277 are used to detect SEQ ID NO: 499, SEQ ID NOs: 278, 279, and 281 are used to detect SEQ ID NO: 500, SEQ ID NOs: 282, 283, and 284 are used to detect SEQ ID NO: 501, SEQ ID NOs: 286, 287, and 288 are used to detect SEQ ID NO: 502, SEQ ID NOs: 290, 291, and 293 are used to detect SEQ ID NO: 503, SEQ ID NOs: 294, 295, and 296 are used to detect SEQ ID NO: 504, SEQ ID NOs: 298, 299, and 300 are used to detect SEQ ID NO: 505, SEQ ID NOs: 302, 303, and 304 are used to detect SEQ ID NO: 506, SEQ ID NOs: 306, 307, and 309 are used to detect SEQ ID NO: 507, SEQ ID NOs: 310, 311, and 313 are used to detect SEQ ID NO: 508, SEQ ID NOs: 314, 315, and 316 are used to detect SEQ ID NO: 509, SEQ ID NOs: 318, 319, and 320 are used to detect SEQ ID NO: 510, SEQ ID NOs: 322, 323, and 325 are used to detect SEQ ID NO: 511, SEQ ID NOs: 326, 327, and 329 are used to detect SEQ ID NO: 512, SEQ ID NOs: 330, 331, and 333 are used to detect SEQ ID NO: 513, SEQ ID NOs: 334, 335, and 336 are used to detect SEQ ID NO: 514, SEQ ID NOs: 338, 339, and 341 are used to detect SEQ ID NO: 515, SEQ ID NOs: 342, 343, and 344 are used to detect SEQ ID NO: 516, SEQ ID NOs: 346, 347, and 348 are used to detect SEQ ID NO: 517, SEQ ID NOs: 350, 351, and 352 are used to detect SEQ ID NO: 518, SEQ ID NOs: 354, 355, and 356 are used to detect SEQ ID NO: 519, SEQ ID NOs: 358, 359, and 361 are used to detect SEQ ID NO: 520, SEQ ID NOs: 362, 363, and 365 are used to detect SEQ ID NO: 521, SEQ ID NOs: 366, 367, and 368 are used to detect SEQ ID NO: 522, SEQ ID NOs: 370, 371, and 372 are used to detect SEQ ID NO: 523, SEQ ID NOs: 374, 375, and 376 are used to detect SEQ ID NO: 524, SEQ ID NOs: 378, 379, and 38 are used to detect SEQ ID NO: 525, SEQ ID NOs: 382, 383, and 384 are used to detect SEQ ID NO: 526, SEQ ID NOs: 386, 387, and 388 are used to detect SEQ ID NO: 527, SEQ ID NOs: 390, 391, and 393 are used to detect SEQ ID NO: 528, SEQ ID NOs: 394, 395, and 397 are used to detect SEQ ID NO: 529, SEQ ID NOs: 398, 399, and 400 are used to detect SEQ ID NO: 530, SEQ ID NOS: 402, 403, and 404 are used to detect SEQ ID NO: 531, SEQ ID NOs: 406, 407, and 409 are used to detect SEQ ID NO: 532, SEQ ID NOs: 410, 411, and 412 are used to detect SEQ ID NO: 533, SEQ ID NOs: 414, 415, and 416 are used to detect SEQ ID NO: 534, SEQ ID NOS: 418, 419, and 420 are used to detect SEQ ID NO: 535, SEQ ID NOs: 422, 423, and 425 are used to detect SEQ ID NO: 536, SEQ ID NOs: 426, 427, and 429 are used to detect SEQ ID NO: 537, SEQ ID NOs: 430, 431, and 433 are used to detect SEQ ID NO: 538, SEQ ID NOS: 434, 435, and 437 are used to detect SEQ ID NO: 539, SEQ ID NOs: 438, 439, and 440 are used to detect SEQ ID NO: 540, SEQ ID NOs: 442, 443, and 445 are used to detect SEQ ID NO: 541, SEQ ID NOs: 446, 447, and 449 are used to detect SEQ ID NO: 542, SEQ ID NOS: 450, 451, and 453 are used to detect SEQ ID NO: 543, SEQ ID NOs: 454, 455, and 456 are used to detect SEQ ID NO: 544, SEQ ID NOs: 458, 459, and 461 are used to detect SEQ ID NO: 545, SEQ ID NOs: 462, 463, and 465 are used to detect SEQ ID NO: 546, SEQ ID NOS: 466, 467, and 468 are used to detect SEQ ID NO: 547, and SEQ ID NOs: 470, 471, and 473 are used to detect SEQ ID NO: 548.

2. The method of claim 1, wherein the edited haploid plant is first obtained by a method comprising:
   (a) obtaining the first plant, wherein the first plant is capable of expressing a DNA modification enzyme and optionally at least one guide nucleic acid;
   (b) obtaining the second plant, wherein the second plant comprises the plant genomic DNA which is to be edited;
   (c) pollinating the second plant with pollen from the first plant; and
   (d) selecting at least one haploid progeny produced by the pollination of step (c), wherein the haploid progeny comprises the genome of the second plant but not the first plant, and the genome of the haploid progeny has been modified by the DNA modification enzyme and optionally at least one guide nucleic acid delivered by the first plant.

3. The method of claim 2, wherein the DNA modification enzyme is a site-directed nuclease selected from the group consisting of meganucleases (MNs), zinc-finger nucleases (ZFNs), transcription-activator like effector nucleases (TALENs), Cas9 nuclease, Cpf1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease.

4. The method of claim 2, wherein the at least one guide nucleic acid is a guide RNA.

5. The method of claim 1, wherein the edited haploid progeny is treated with a chromosome doubling agent after testing, thereby creating an edited doubled haploid progeny, optionally wherein the chromosome doubling agent is colchicine, pronamide, dithipyr, or trifluralin.

6. The method of claim 2, wherein the optional guide RNA is 18-21 nucleotides long and is at least 90% identical to a sequence selected from the group consisting of SEQ ID NOs: 2, 4, 8, 21, 23, 25, 29, 32, and 33.

7. The method of claim 1, wherein the first plant expresses a marker gene.

8. The method of claim 7, wherein the marker gene is selected from the group consisting of GUS, PMI, PAT, GFP, RFP, CFP, B1, C1, R1-nj, and anthocyanin pigments.

9. The method of claim 1, wherein the first plant acts as the male and the second plant acts as the female in a cross resulting in the haploid progeny.

\* \* \* \* \*